US009957509B2

(12) United States Patent
Mirsky et al.

(10) Patent No.: US 9,957,509 B2
(45) Date of Patent: May 1, 2018

(54) SYNTHETIC GENE CLUSTERS

(71) Applicant: The Regents of the University of California, Oakland, CA (US)

(72) Inventors: Ethan Mirsky, San Francisco, CA (US); Karsten Temme, San Francisco, CA (US); Christopher A. Voigt, Belmont, MA (US); Dehua Zhao, Allston, MA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days. days.

(21) Appl. No.: 15/288,916

(22) Filed: Oct. 7, 2016

(65) Prior Publication Data

US 2017/0152519 A1 Jun. 1, 2017

Related U.S. Application Data

(63) Continuation of application No. 14/126,307, filed as application No. PCT/US2012/042502 on Jun. 14, 2012, now Pat. No. 9,512,431.

(60) Provisional application No. 61/497,781, filed on Jun. 16, 2011.

(51) Int. Cl.

| | |
|---|---|
| ***C12N 15/63*** | (2006.01) |
| ***G06F 19/22*** | (2011.01) |
| ***G06F 19/20*** | (2011.01) |
| ***C07K 14/26*** | (2006.01) |
| ***C12N 9/02*** | (2006.01) |

(52) U.S. Cl.

CPC ............ *C12N 15/635* (2013.01); *C07K 14/26* (2013.01); *C12N 9/0095* (2013.01); *C12Y 118/06001* (2013.01); *G06F 19/20* (2013.01); *G06F 19/22* (2013.01)

(58) Field of Classification Search

None

See application file for complete search history.

(56) References Cited

U.S. PATENT DOCUMENTS

| | | | |
|---|---|---|---|
| 5,916,029 | A | 6/1999 | Smith et al. |
| 6,548,289 | B1 | 4/2003 | Beynon et al. |
| 7,084,331 | B2 | 8/2006 | Isawa et al. |
| 7,470,427 | B2 | 12/2008 | Cocking |
| 8,076,142 | B2 | 12/2011 | Huang et al. |
| 8,137,665 | B2 | 3/2012 | Cocking |
| 8,268,584 | B1 | 9/2012 | Harwood et al. |
| 8,377,671 | B2 | 2/2013 | Cournac et al. |
| 9,321,697 | B2 | 4/2016 | Kumar et al. |
| 9,487,451 | B2 | 8/2016 | Doty et al. |
| 9,657,298 | B2 | 5/2017 | Soto, Sr. et al. |
| 2004/0241847 | A1 | 12/2004 | Okuyama et al. |
| 2005/0081262 | A1 | 4/2005 | Cook et al. |
| 2006/0127988 | A1 | 6/2006 | Wood et al. |
| 2006/0243011 | A1 | 11/2006 | Someus |
| 2009/0105076 | A1 | 4/2009 | Stewart et al. |
| 2010/0028870 | A1 | 2/2010 | Welch |
| 2012/0015806 | A1 | 1/2012 | Paikray et al. |
| 2014/0011261 | A1 | 1/2014 | Wang et al. |
| 2014/0230504 | A1 | 8/2014 | Finlayson et al. |
| 2014/0336050 | A1 | 11/2014 | Soto, Sr. et al. |
| 2015/0101373 | A1 | 4/2015 | Munusamy et al. |
| 2015/0239789 | A1 | 8/2015 | Kang et al. |
| 2016/0292355 | A1 | 10/2016 | Lou et al. |

FOREIGN PATENT DOCUMENTS

| | | | |
|---|---|---|---|
| WO | 99009834 | A2 | 3/1999 |
| WO | 2001007567 | A1 | 2/2001 |
| WO | 2006005100 | A1 | 1/2006 |
| WO | 2009060012 | A2 | 5/2009 |
| WO | 2009091557 | A1 | 7/2009 |
| WO | 2011099019 | A1 | 8/2011 |
| WO | 2011099024 | A1 | 8/2011 |
| WO | 2011154960 | A1 | 12/2011 |
| WO | 2013076687 | A2 | 5/2013 |
| WO | 2014042517 | A2 | 3/2014 |
| WO | 2014071182 | A1 | 5/2014 |

OTHER PUBLICATIONS

Pfleger et al.; "Combinatorial engineering of intergenic regions in operons tunes expression of multiple genes"; *Nature Biotechnology;* 24(8):1027-1031 (2006).

Sleight et al.; "Designing and engineering evolutionary robust genetic circuits"; *J. Biological Engineering;* 4:12, 2010 (20 pages).

Temme et al.; "Refactoring the nitrogen fixation gene cluster from *Klebsiella oxytoca"; Proc. Natl. Acad. Sci. USA;* 109(18):7085-7090 (2012) ePub Apr. 16, 2021.

"T7 RNA Polymerase Expression System for *Bacillus megaterium*"; T7 RNAP Expression System Handbook, Jan. 2010, © MoBiTec GmbH, 18 pages.

International Search Report and Written Opinion from PCT/US2012/042502, dated Jan. 31, 2013.

Chan et al., "Refactoring bacteriophage T7," *Molecular Systems Biology,* 2005, vol. 1, No. 1, pp. E1-E10 (doi: 10.1038/msb4100025).

Fischbach et al., "Prokaryotic gene clusters: A rich toolbox for synthetic biology," *Biotechnology Journal,* 2010, 15(12): 1277-1296.

Mirsky, Ethan M. (2012) *Refactoring the Salmonella Type III Secretion System.* (Doctoral Dissertation) Apr. 12, 2012 Retrieved from web at Proquest site (media.proquest.com/media/pq/classic/doc/2644519781/fmt/aijrep/NPDF?hl=&cit:auth=Mirsky).

Temme, Karsten Louis. (2011) *Designing and Engineering Complex Behavior in Living Machines.* (Doctoral Dissertation) Oct. 1, 2011. Retrieved from the web at escholarship.org/uc/item/1r41x99s.

Voigt et al., "Genetic parts to program bacteria, " *Current Opinion in Biotechnology,* 2006, 17(5):548-557.

(Continued)

*Primary Examiner* — Channing S Mahatan

(74) *Attorney, Agent, or Firm* — Kilpatrick Townsend & Stockton LLP

(57) ABSTRACT

Methods for making synthetic gene clusters are described.

16 Claims, 93 Drawing Sheets

(56) References Cited

OTHER PUBLICATIONS

Voigt, C. (2011) "Gaining Access: Rebuilding Genetics from the Ground Up". Institute of Medicine Board on Global Health Forum on Microbial Threats. Mar. 14, 2011 (Mar. 14, 2011). Retrieved from the web at iom.edu/~/media/Files/ActivityFiles/PublicHealth/MicrobialThreats/2011-MAR-14/Voigt.pdf.

Extended European Search Report from EP Appl. No. 12800054.4, dated Dec. 19, 2014.

| Promoter Name | Sequence TAATACGACTCACTANNNNNAGA | Strength |
|---|---|---|
| WT | TAATACGACTCACTATAGGGAGA | 13780 |
| Mut1 | TAATACGACTCACTACAGGCAGA | 147 |
| Mut2 | TAATACGACTCACTAGAGAGAGA | 752 |
| Mut3 | TAATACGACTCACTAATGGGAGA | 1346 |
| Mut4 | TAATACGACTCACTATAGGTAGA | 2127 |
| Mut5 | TAATACGACTCACTAAAGGGAGA | 3738 |
| Mut6 | TAATACGACTCACTATTGGGAGA | 6710 |

*FIG. 3*

| Strain Name | E Promoter | N Promoter | Fixation |
|---|---|---|---|
| #1 (N259) | WT | WT | 20% |
| #2 (N438) | Mut 4 | Mut 5 | 9% |
| #3 (N307) | Mut 4 | Mut 2 | 12% |
| Reflection (N319) | WT | Mut 3 | 52% |

FIG. 5

| Gene | Native RBS Strength | Synthetic RBS Strength |
|---|---|---|
| J | 254 | 104 |
| H | 21641 | 9903 |
| D | 446 | 496 |
| K | 23 | 54 |
| T | 303 | Eliminated |
| Y | 62 | 243 |
| E | 85 | 43 |
| N | 95 | 41 |
| X | 558 | Eliminated |
| U | 814 | 2832 |
| S | 686 | 174 |
| V | 11 | 5 |
| W | 39 | 43 |
| Z | 218 | 366 |
| M | 637 | 754 |
| F | 9283 | 46 |
| B | 80 | 221 |
| Q | Not Detectable | Not Detectable |

FIG. 10

| Operon | Error Location | Error |
|---|---|---|
| HDKY | H | Transposon insertion |
| USVWZM | S | Sequencing errors in Arnold NCBI entry (L110M, Q113E, S124G, R290A) |
| USVWZM | V | Sequencing errors in Arnold NCBI entry (L257S, D295H) |
| USVWZM | M | Cloning mutation |
| USVWZM | Ptac | Cloning error yielded constitutive promoter |

FIG. 12

| Operon | Function with Ptac promoter | T7 promoter | Function with T7 promoter |
|---|---|---|---|
| J | 109% | WT | 87% |
| HDKY | 39% | WT | 35% |
| EN | 75% | WT | 71% |
| USVWZM | 29% | Mut 2 | 25% |
| F | 112% | Mut 3 | 98% |
| BQ | 85% | Mut 2 | 80% |

| Gene | SEQ ID NO: | WT Sequence | Synthetic Sequence | % Nucleotide Identity | % Codon Identity |
|---|---|---|---|---|---|
| J | WT Gene J is SEQ ID NO:1<br>Synthetic Gene J is SEQ ID NO:2 | atgaaaacaatggatggcaacgccgcggcggcc<br>tggatctcttatgcctttaccgaggtcgcggcgattt<br>accccataacccccctccacgccgatggcggaaa<br>acgtcgacgagtgggcggcgcaggggaaaaag<br>aacctttttggccagccggtgcgcttaatggagat<br>gcagtcggaggccggcgcggcaggcgcggtcc<br>acggcgcgctgcaggccggggcgctcaccacc<br>acctatacggcctcccaggggctgctgctgatgat<br>ccccaacatgtacaaaatcgccggtgaactgctg<br>ccgggcgtctttcacgtcagcgcccgggcgctgg<br>cgaccaattcgctgaatatttttggcgatcaccagg<br>atgtgatggcggtccgccagaccggctgcgcgat<br>gctggcggagaacaacgtgcagcaggtgatgga<br>tttgtcggcggtggcgcatctggcggcgattaagg<br>gacgcatcccgtttgttaacttcttcgacggttttcg<br>cacctcgcacgaaattcaaaaaatcgaggtgttgg<br>aatatgagcagctggcgacgctgctggaccggc<br>ccgcgctcgacagcttccgccgtaacgcgctgca<br>tccggatcatccggtcatccgcggaacggcgcag<br>aacccggatatctacttccaggagcgggaggcg<br>ggcaaccgtttttatcaggcgctgcccgacattgtc<br>gaaagctatatgacgcaaatcagcgcgctcaccg<br>gccgggagtatcatctgtttaactataccggcgcg<br>gcggatgccgaacgggtgattatcgcaatgggat<br>cggtctgcgataccgttcaggaagtggtggatac<br>gctgaacgcggcgggagagaaggtcgggctgct<br>cagcgtgcatctgtttcgcccttttcgctggcccac<br>ttcttcgcccagctgccgaaaaccgtgcagcggat<br>tgccgtccttgaccgtaccaaagagcccggcgct<br>caggctgaaccgctgtgcctggatgtgaaaaacg<br>ccttctaccaccacgacgatgcgccgctaatcgtc<br>ggcggccgctatgcgcttggcgggaaggatgttc<br>tgcccaacgatatcgcggccgtctttgataacctca<br>ataaaccgctgccgatggacgggtttaccctcgg<br>gattgtcgatgatgtaacctttacttcgttaccgccg<br>gcccagcagacgctggcggtctcgcatgacggc<br>atcaccgcctgtaaattttggggcatgggctcgga<br>cggcaccgtcggggccaataaaagcgcgatcaa<br>aattatcggcgataaaacgccgctctacgcgcag<br>gcctacttttcttatgactcgaaaaaatccggcggc<br>attaccgtttcacatttacgcttcggcgaccggccg<br>atcaattcgccctacctgatccatcgggccgatttt<br>atctcctgttcgcagcagtcctacgttgagcgctac<br>gatctgctggacggattaaagccgggcgggacct<br>ttttactcaactgcagctggtccgatgcggagctg<br>gagcagcatctgccggtcggctttaaacgctatct<br>ggcgcgggaaaatatccatttttataccctgaacg<br>ccgtggatatcgcccgcgagctcgggctgggcg<br>ggcgctttaatatgctgatgcaggcggcgttcttta<br>agctggcggcgattatcgacccgcagaccgcgg<br>cggattacctcaagcaggcggttgaaaaagcta<br>cggcagcaaaggggcggcggtgattgagatgaa | ATGAAAACTATGGACGGTAA<br>CGCTGCGGCTGCATGGATTA<br>GCTACGCCTTTACCGAAGTGG<br>CTGCGATCTACCCGATTACGC<br>CGAGCACCCCGATGGCGGAA<br>AATGTGGACGAATGGGCTGC<br>GCAGGGCAAGAAGAACCTCT<br>TCGGCCAGCCGGTGCGCCTG<br>ATGGAGATGCAGTCGGAAGC<br>GGGTGCAGCAGGTGCTGTGC<br>ATGGCGCCTTGCAAGCTGGC<br>GCACTGACGACCACCTACAC<br>CGCGTCGCAGGGCCTGTTGCT<br>GATGATCCCAAACATGTACA<br>AAATCGCGGGTGAACTGCTG<br>CCGGGTGTCTTTCATGTTTCG<br>GCACGCGCACTGGCCACCAA<br>TAGCCTCAACATCTTTGGCGA<br>TCATCAGGATGTAATGGCGG<br>TGCGCCAAACGGGCTGCGCG<br>ATGTTGGCCGAGAATAACGT<br>CCAGCAAGTTATGGATTTGTC<br>CGCGGTAGCCCACTTGGCAG<br>CGATCAAAGGTCGCATTCCGT<br>TCGTGAACTTCTTCGATGGCT<br>TTCGCACCAGCCACGAAATC<br>CAGAAGATCGAGGTTCTGGA<br>ATATGAACAGCTGGCCACCTT<br>GTTGGATCGTCCGGCCCTGGA<br>CAGCTTCCGCCGTAACGCCCT<br>TCACCCGGACCACCCGGTCAT<br>CCGTGGCACCGCCCAGAACC<br>CGGACATCTACTTCCAGGAA<br>CGTGAGGCCGGTAACCGTTTC<br>TATCAGGCGCTCCCGGATATT<br>GTGGAATCTTACATGACCCA<br>GATTTCTGCCCTGACTGGTCG<br>CGAGTATCACCTGTTTAACTA<br>CACTGGTGCTGCGGATGCGG<br>AGCGCGTGATCATCGCGATG<br>GGCTCTGTCTGTGACACCGTC<br>CAAGAGGTGGTTGACACGCT<br>GAATGCAGCGGGTGAGAAAG<br>TTGGTCTGCTCTCCGTTCATC<br>TTTTCCGCCCGTTTTCGTTAG<br>CGCACTTCTTCGCCCAACTGC<br>CGAAAACTGTACAGCGTATC<br>GCAGTATTGGACCGTACGAA<br>AGAGCCAGGTGCTCAAGCAG<br>AGCCGCTGTGCCTCGATGTGA<br>AGAATGCCTTTTACCACCATG<br>ACGATGCCCCGTTGATTGTGG | 80.8 | 48 |

FIG. 18 (cont)

| Gene | SEQ ID NO: | WT Sequence | Synthetic Sequence | % Nucleotide Identity | % Codon Identity |
|---|---|---|---|---|---|
| | | ccagcgggcgatcgagctgggcatggcctcgct<br>gcatcaggtgacgattccggcgcactgggcgac<br>gctggatgaacccgcggcgcaagcatcagccat<br>gatgccggatttcatccgcgatattctgcagccgat<br>gaaccgccagtgcggcgaccagctgccggtgag<br>cgcgttcgtcggtatggaggacgggacctttcctt<br>cgggcaccgccgcgtgggagaaacgcgggatc<br>gcgctggaagtgccggtctggcagccggagggc<br>tgcacgcagtgtaaccagtgcgcctttatctgccc<br>gcatgcggcgatccgcccggcgctgctcaacgg<br>cgaagagcatgacgccgcgccggttgggctgct<br>gagcaaacccgcgcagggagcgaaggagtatc<br>actaccatctggctatctcgccgctggattgttccg<br>gctgcggcaactgcgtggatatctgtcccgcgcg<br>cggcaaggcgttaaaaatgcagtctctcgatagcc<br>agcgtcagatggcgccggtctgggactatgcgct<br>ggcgctgacgccgaagagcaatccgtttcgtaag<br>acgacggtcaaaggcagccagtttgaaaccccg<br>ctgctggagttttccggcgcctgcgcgggatgcg<br>gtgaaacgccttatgcccgcctgataacccagctg<br>tttggcgaccggatgctgatcgctaacgccaccg<br>gctgctcttctatctggggagccagcgcgccgtcg<br>attccctataccaccaaccaccgcggccatggcc<br>cggcatgggcgaactcgctgtttgaggataatgc<br>ggagtttggcctcggcatgatgctcggcggccag<br>gcggtgcgtcaacaaatcgccgatgatatgaccg<br>ccgcgctggcgctaccggtcagcgacgaacttag<br>cgacgcaatgcgccagtggctggcgaagcagga<br>tgaaggcgagggcacccgcgagcgcgcggacc<br>ggctcagcgaacggctggcggcggaaaaagag<br>ggcgtgccgctgttggagcagctgtggcagaacc<br>gcgactattttgttcgtcgttcgcagtggattttcgg<br>cggcgacggctgggcctacgatatcggcttcggc<br>ggtctcgatcacgtgctggcgagcggggaagac<br>gtcaatattctggtgtttgacaccgaggtttactcca<br>ataccggcggccagtcgtctaaatcgaccccggt<br>ggcggccatcgcgaagtttgccgcgcagggcaa<br>acgcacgcggaaaaagatctcggcatgatggc<br>gatgagctacggcaatgtgtacgtggcccaggtc<br>gcgatgggcgctgataaagatcagaccctacgg<br>gcgatcgccgaggccgaagcctggccgggacc<br>gtcgctggtgattgcctacgccgcctgcattaacc<br>acgggctgaaagccggtatgcgctgcagccagc<br>gcgaggcgaaacgggcggttgaggcgggatact<br>ggcacctgtggcgctatcatccgcagcgggaag<br>cggaaggtaagacgccgtttatgctcgattccgaa<br>gagccggaggagagcttccgcgactttttgcttgg<br>cgaagtgcgctacgcctcgctgcacaaaacgac<br>gccgcatctggcggatgcgctctttagccgaacc<br>gaggaggacgcgcgggcccgctttgcccagtat<br>cggcggctggccggcgaggagtag | GTGGTCGCTATGCCTTGGGCG<br>GTAAGGACGTGTTGCCGAAC<br>GATATTGCGGCCGTGTTTGAT<br>AACCTGAACAAACCGCTGCC<br>GATGGACGGCTTCACGCTGG<br>GTATCGTGGACGATGTTACCT<br>TCACCTCTCTCCCGCCAGCGC<br>AGCAGACCCTGGCGGTTTCTC<br>ACGACGGCATCACGGCATGT<br>AAGTTTTGGGGCATGGGCTCC<br>GACGGCACGGTTGGTGCGAA<br>CAAGTCCGCGATCAAGATTA<br>TCGGCGACAAAACGCCACTG<br>TATGCGCAAGCGTACTTTTCC<br>TACGACTCGAAGAAGAGCGG<br>TGGTATTACCGTCAGCCATCT<br>GCGTTTTGGTGATCGCCCGAT<br>CAACTCCCCGTATTTGATCCA<br>TCGCGCGGATTTCATCTCGTG<br>CAGCCAGCAAAGCTATGTTG<br>AACGCTACGATCTGCTGGAT<br>GGCCTTAAACCGGGTGGCAC<br>CTTTCTGCTGAACTGCTCCTG<br>GAGCGATGCCGAACTGGAGC<br>AACATCTGCCGGTCGGTTTCA<br>AACGTTATCTGGCACGCGAG<br>AATATCCACTTCTACACTCTC<br>AACGCTGTGGACATCGCCCG<br>TGAGCTTGGTTTGGGTGGCCG<br>TTTCAACATGCTGATGCAGGC<br>TGCCTTCTTCAAACTGGCCGC<br>GATCATTGACCCGCAGACTG<br>CTGCGGACTATCTGAAGCAG<br>GCTGTTGAGAAAAGCTATGG<br>CAGCAAAGGTGCGGCGGTCA<br>TCGAGATGAACCAGCGTGCC<br>ATCGAGCTTGGCATGGCCAG<br>CCTGCACCAGGTGACGATCC<br>CGGCACATTGGGCCACCCTG<br>GATGAGCCAGCGGCGCAGGC<br>GTCCGCGATGATGCCGGACTT<br>TATCCGCGACATCCTGCAACC<br>GATGAACCGTCAGTGCGGCG<br>ACCAGCTTCCGGTGTCGGCTT<br>TTGTCGGCATGGAAGATGGC<br>ACCTTCCCGTCCGGCACGGCC<br>GCATGGGAGAAACGTGGCAT<br>CGCCCTTGAGGTGCCAGTCTG<br>GCAGCCGGAAGGCTGCACGC<br>AGTGCAACCAGTGCGCCTTC<br>ATTTGTCCGCACGCCGCGATT<br>CGTCCGGCGTTGTTGAATGGC<br>GAAGAGCATGATGCTGCCCC<br>GGTTGGCCTGCTGAGCAAAC | | |

FIG. 18 (cont)

| Gene | SEQ ID NO: | WT Sequence | Synthetic Sequence | % Nucleotide Identity | % Codon Identity |
|---|---|---|---|---|---|
| | | | CGGCACAAGGCGCTAAAGAA<br>TATCACTATCATCTGGCGATT<br>AGCCCGCTGGACTGCTCCGG<br>CTGTGGCAACTGCGTTGACAT<br>TTGTCCAGCTCGTGGCAAAGC<br>GTTGAAGATGCAGTCTCTGG<br>ATAGCCAACGCCAGATGGCT<br>CCGGTGTGGGATTATGCGCTG<br>GCGCTGACCCCGAAGTCTAA<br>CCCGTTTCGTAAAACCACCGT<br>CAAAGGCTCGCAGTTCGAAA<br>CCCCGCTGCTGGAGTTTAGCG<br>GTGCGTGCGCTGGTTGTGGCG<br>AAACGCCGTATGCGCGCCTC<br>ATTACCCAGCTGTTTGGCGAC<br>CGCATGCTGATTGCCAATGCC<br>ACCGGCTGTTCCAGCATCTGG<br>GGCGCATCTGCGCCGAGCAT<br>CCCGTATACCACCAATCATCG<br>TGGTCATGGTCCGGCCTGGGC<br>GAATAGCCTGTTTGAGGACA<br>ATGCCGAATTTGGTTTAGGTA<br>TGATGCTGGGCGGTCAAGCT<br>GTGCGTCAACAGATCGCGGA<br>CGATATGACGGCTGCGTTAG<br>CGCTCCCGGTTTCCGATGAGC<br>TGAGCGACGCGATGCGCCAG<br>TGGTTGGCGAAACAGGACGA<br>GGGTGAAGGCACGCGTGAGC<br>GTGCGGACCGTCTGAGCGAG<br>CGCTTAGCCGCGGAGAAAGA<br>GGGCGTTCCGCTGTTAGAGC<br>AGCTGTGGCAAAATCGTGAT<br>TACTTTGTGCGTCGCAGCCAG<br>TGGATTTTCGGCGGTGACGGC<br>TGGGCCTATGATATTGGCTTC<br>GGTGGCCTGGACCACGTCCTC<br>GCCAGCGGTGAGGATGTGAA<br>CATTCTGGTATTTGACACCGA<br>AGTCTACTCGAACACCGGCG<br>GTCAAAGCAGCAAATCGACC<br>CCGGTCGCGGCCATCGCCAA<br>GTTCGCGGCTCAGGGCAAGC<br>GCACCCGCAAGAAAGACCTG<br>GGTATGATGGCGATGAGCTA<br>CGGCAACGTCTATGTAGCCC<br>AGGTGGCGATGGGTGCGGAT<br>AAAGATCAAACTCTGCGCGC<br>CATTGCGGAAGCTGAAGCGT<br>GGCCAGGCCCGTCGCTGGTG<br>ATTGCGTATGCGGCCTGCATC<br>AATCATGGCCTGAAGGCCGG<br>TATGCGTTGCAGCCAACGTG<br>AGGCGAAGCGCGCTGTTGAG | | |

FIG. 18 (cont)

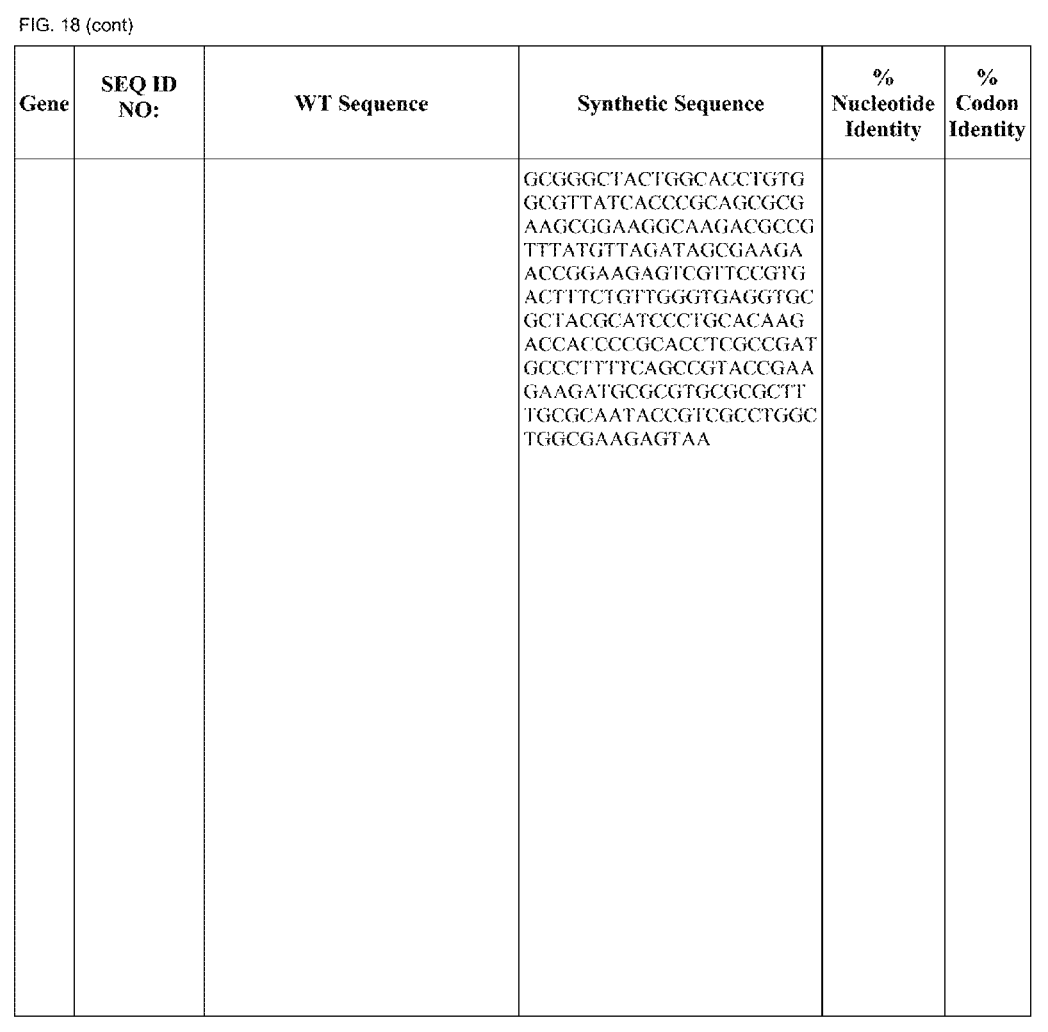

| Gene | SEQ ID NO: | WT Sequence | Synthetic Sequence | % Nucleotide Identity | % Codon Identity |
|---|---|---|---|---|---|
| | | | GCGGGCTACTGGCACCTGTG<br>GCGTTATCACCCGCAGCGCG<br>AAGCGGAAGGCAAGACGCCG<br>TTTATGTTAGATAGCGAAGA<br>ACCGGAAGAGTCGTTCCGTG<br>ACTTTCTGTTGGGTGAGGTGC<br>GCTACGCATCCCTGCACAAG<br>ACCACCCCGCACCTCGCCGAT<br>GCCCTTTTCAGCCGTACCGAA<br>GAAGATGCGCGTGCGCGCTT<br>TGCGCAATACCGTCGCCTGGC<br>TGGCGAAGAGTAA | | |

FIG. 18 (cont)

| Gene | SEQ ID NO: | WT Sequence | Synthetic Sequence | % Nucleotide Identity | % Codon Identity |
|---|---|---|---|---|---|
| **H** | **WT Gene H is SEQ ID NO:3**<br>**Synthetic Gene H is SEQ ID NO:4** | atgaccatgcgtcaatgcgctatttacggtaaagg<br>cggtatcggtaaatccaccaccacgcagaacctc<br>gtcgccgcgctggcggagatgggtaagaaagtg<br>atgatcgtcggctgcgatccgaaggcggactcca<br>cccgtctgattctgcacgccaaagcacagaacac<br>cattatggagatggccgcggaagtcggctcggtc<br>gaggacctcgaactcgaagacgtgctgcaaattg<br>gctacggcgatgtgcgctgcgcggaatccggcg<br>gcccggagccaggcgtcggctgcgcgggacgc<br>ggcgtgatcacggcgatcaactttcttgaagaaga<br>aggcgcctacgaggacgatctcgatttcgtgttcta<br>tgacgtgctcggcgacgtggtctgcggcggcttc<br>gccatgccgatccgcgaaaacaaagcccaggag<br>atctacatcgtctgctccggcgaaatgatggcgat<br>gtacgcggccaacaatatctccaaagggatcgtta<br>aatacgccaaatccggcaaggtgcgcctcggcg<br>gcctgatctgtaactcacgtcagaccgaccgtgaa<br>gacgaactgattattgccctggcggaaaagctcg<br>gtacccagatgatccactttgtgccccgcgacaac<br>atcgtgcagcgcgcggagatccgccgcatgacg<br>gttatcgagtacgaccccgcctgtaaacaggcca<br>acgaataccgcaccctggcgcagaagatcgtcaa<br>caacaccatgaaagtggtgccgacgccctgcacc<br>atggatgagctggaatcgctgctgatggagttcgg<br>catcatggaagaggaagacaccagcatcattggc<br>aaaaccgccgccgaagaaaacgcggcctga | ATGACCATGCGTCAGTGCGC<br>GATTTATGGCAAAGGTGGTA<br>TTGGCAAAAGCACGACGACC<br>CAGAACTTGGTGGCGGCCCT<br>GGCCGAGATGGGTAAAAAGG<br>TTATGATTGTGGGTTGCGACC<br>CGAAGGCCGACAGCACGCGC<br>CTGATTCTGCACGCGAAAGC<br>ACAAAACACGATTATGGAGA<br>TGGCTGCCGAGGTTGGTAGC<br>GTGGAGGATCTGGAGCTGGA<br>GGACGTTCTGCAAATTGGTTA<br>CGGTGATGTTCGTTGCGCAGA<br>GAGCGGTGGTCCGGAACCAG<br>GTGTCGGCTGTGCGGGTCGTG<br>GTGTGATTACCGCTATCAATT<br>TCCTGGAAGAAGAGGGTGCG<br>TACGAAGATGATCTGGATTTC<br>GTTTTCTACGATGTGCTGGGT<br>GATGTCGTGTGCGGTGGTTTT<br>GCAATGCCGATTCGCGAGAA<br>TAAGGCACAAGAAATTTACA<br>TTGTCTGTAGCGGCGAGATG<br>ATGGCAATGTACGCTGCTAA<br>CAACATCAGCAAGGGTATTG<br>TTAAATACGCAAAAAGCGGT<br>AAGGTTCGCTTGGGTGGTTTG<br>ATTTGCAACAGCCGTCAGAC<br>CGACCGTGAGGACGAACTGA<br>TCATCGCCCTGGCTGAGAAA<br>CTGGGCACCCAAATGATCCA<br>CTTCGTGCCACGCGATAATAT<br>TGTTCAACGTGCAGAAATCC<br>GCCGTATGACCGTCATTGAGT<br>ATGACCCGGCATGCAAGCAA<br>GCGAACGAGTACCGCACCTT<br>GGCACAGAAAATCGTGAACA<br>ACACCATGAAGGTTGTTCCG<br>ACGCCGTGTACGATGGACGA<br>GCTGGAGAGCCTGCTGATGG<br>AGTTCGGCATTATGGAGGAG<br>GAGGACACCAGCATTATCGG<br>TAAGACCGCAGCGGAGGAGA<br>ATGCGGCATAA | **79** | **41.8** |

FIG. 18 (cont)

| Gene | SEQ ID NO: | WT Sequence | Synthetic Sequence | % Nucleotide Identity | % Codon Identity |
|---|---|---|---|---|---|
| D | **WT Gene D is SEQ ID NO:5**<br>**Synthetic Gene D is SEQ ID NO:6** | atgatgaccaacgcaacgggcgaacgtaatctgg<br>cgctgatccaggaagtcctggaggtgttcccgga<br>aaccgcgcgaaaagagcgcagaaagcacatgat<br>ggtcagcgatccgaaaatgaagagcgtcggcaa<br>gtgcattatctctaaccgcaaatcacaacccggcg<br>taatgaccgtacgcggctgcgcctacgccggttc<br>caaaggggtggtatttgggccgattaaggatatgg<br>cccatatttcgcacggaccggctggctgcggcca<br>gtattcccgcgccgaacgacgcaactactacacc<br>ggagtcagcggcgtcgatagcttcggcacgctga<br>acttcacctctgattttcaggagcgcgacatcgtctt<br>cggcggcgataaaaagctcagcaagctgattgaa<br>gagatggagttgctgttcccgctcaccaaagggat<br>caccattcagtcggaatgcccggtggggctgatc<br>ggtgatgatatcagcgcggtggccaacgccagc<br>agcaaggcgctggataaaccggtgatcccggtac<br>gctgcgaaggctttcgcggcgtgtcgcagtctctg<br>gggcaccatatcgccaacgacgtggtgcgcgact<br>ggatcctgaacaatcgcgaaggacagccgtttga<br>aaccaccccttacgatgtggcgatcatcggcgact<br>acaacatcggcggcgacgcctgggcctcgcgca<br>ttctgctggaagagatggggctacgggtagtcgc<br>gcagtggtccggcgacggcacgctggtggagat<br>ggagaataccccattcgtcaagctgaacctggttc<br>actgctaccgttcgatgaactatatcgcccgccata<br>tggaggagaaacatcagattccgtggatggagta<br>caacttcttcgggccgaccaaaatcgccgaatcg<br>ctgcgcaaaatcgccgaccagttcgacgatacca<br>ttcgcgcgaacgccgaagcggtgatcgcccggt<br>atgaggggcagatggcggcgattatcgccaaata<br>tcgcccgcgcctggagggggcgtaaggtgctgctc<br>tatatcggaggcctgcggccgcgccacgttattgg<br>cgcctatgaggatctcgggatggagatcatcgcc<br>gccggctacgagtttgcccataacgatgattacga<br>ccgcaccctgccggatctgaaagagggcacgct<br>gctgttcgatgacgccagcagctacgagctggaa<br>gcgttcgtcaaggcgctgaagcccgaccttatcg<br>gctccggcatcaaggaaaaatatatcttccagaaa<br>atgggcgtgccgttccgccagatgcactcgtggg<br>actattccggcccgtaccacggctacgatggtttc<br>gccattttcgcccgcgatatggatatgaccctgaa<br>caacccggcgtggaacgaactgaccgctccgtg<br>gctgaagtctgcgtga | atgatgactaatgctactggcgaacgtaacctgg<br>cactgattcaagaagtactggaagtgttcccgga<br>aaccgcgcgcaaagagcgccgtaaacacatg<br>atggtttctgacccgaaaatgaaatctgtgggta<br>aatgcatcatctctaatcgcaaatctcagccggg<br>tgtcatgactgttcgtggctgtgcgtacgcaggtt<br>ctaaaggtgtcgtattcggcccgatcaaagatat<br>ggcgcatatctctcatggcccggcaggctgtgg<br>ccagtactctcgcgcggaacgtcgtaactacta<br>cacgggcgtttctggcgttgactctttcggcacg<br>ctgaacttcacctctgacttccaggaacgtgaca<br>tcgttttcggtggcgataaaaagctgtccaaact<br>gatcgaagaaatggaactgctgttcccgctgact<br>aaaggcattactatccaaagcgaatgtccggtg<br>ggtctgatcggtgatgacatcagcgcggtcgca<br>aacgcatcttccaaagccctggataagccggtg<br>atcccggttcgttgcgagggcttccgcggcgttt<br>ctcagtctctgggtcatcacatcgcaaacgatgtt<br>gtgcgtgactggattctgaacaaccgtgaaggt<br>cagcctttgaaaccaccccttatgacgttgcgat<br>tattggcgactataacatcggcggcgacgcctg<br>ggcatcccgcatcctgctggaggagatgggtct<br>gcgtgttgtcgcacagtggtctggcgatggcac<br>cctggttgaaatggaaaacaccccgtttgttaaa<br>ctgaacctggttcactgctaccgctccatgaact<br>acattgcccgtcacatggaagaaaaacatcaga<br>tcccttggatggaatacaacttcttcggtccgact<br>aaaatcgcagaatccctgcgtaaaatcgccgat<br>cagtttgatgataccattcgcgcgaacgctgaag<br>cagtaattgcgcgctacgaaggccagatggca<br>gcaatcattgctaagtaccgtccgcgcctggaa<br>ggtcgtaaagtgctgctgtacatgggtggtctgc<br>gtccacgtcatgtgatcggtgcctacgaggacc<br>tgggcatggagatcatcgcagcgggttacgaat<br>ttgcacacaacgacgactatgatcgtacgctgc<br>cagacctgaaagaaggtacgctgctgtttgacg<br>acgccagctcttatgaactggaagccttcgtgaa<br>agcgctgaaaccagacctgatcggctccggca<br>tcaaggaaaaatacattttccagaaaatgggcgt<br>gccgttccgccagatgcactcctgggactactc<br>cggtccgtaccacggctacgacggtttcgctatc<br>ttcgctcgtgacatggatatgaccctgaataacc<br>cagcgtggaatgaactgaccgcaccgtggctg<br>aaatctgcataa | **82.6** | **51.2** |

FIG. 18 (cont)

| Gene | SEQ ID NO: | WT Sequence | Synthetic Sequence | % Nucleotide Identity | % Codon Identity |
|---|---|---|---|---|---|
| **K** | **WT Gene K is SEQ ID NO:7**<br>**Synthetic Gene K is SEQ ID NO:8** | atgagccaaacgattgataaaattaatagctgttat<br>ccgctattcgaacaggatgaataccaggagctgtt<br>ccgcaataagcggcagctggaagaggcgcacg<br>atgcgcagcgcgtgcaggaggtctttgcctggac<br>caccaccgccgagtatgaagcgctgaatttccga<br>cgcgaggcgctgaccgttgacccggcgaaagcc<br>tgccagccgcttggcgcggtgctttgctcgctggg<br>atttgccaacaccctgccgtatgtgcacggctctca<br>ggggtgcgtggcctactttcgcacctattttaaccg<br>ccatttcaaagagccgatcgcctgcgtctccgact<br>cgatgaccgaagacgcggcggtcttcggcggca<br>acaacaatatgaacctgggcctgcagaacgccag<br>cgcgctgtacaaaccggagatcattgcggtgtcc<br>accacctgcatggcggaagttatcggcgatgacc<br>tgcaggcgtttatcgccaacgctaaaaagatggc<br>ttcgtcgacagcagcatcgccgtgccccacgccc<br>atacgccaagctttatcggcagccacgtcaccgg<br>ctgggataacatgtttgaaggcttcgccaaaacctt<br>cactgcggactaccagggggcagccgggcaaatt<br>gccgaagctcaatctggtgaccggctttgaaacct<br>atctcggcaacttccgcgtattaaagcggatgatg<br>gaacagatggcggtgccgtgcagcctgctctccg<br>atccgtcggaagttctcgacacgcccgccgacgg<br>tcactatcggatgtattccggcggcaccacgcagc<br>aggagatgaaagaggcccctgacgccatcgata<br>cgctgctcctgcagccgtggcagctgctgaagag<br>caaaaaagtggtgcaggagatgtggaaccagcc<br>cgccaccgaggtcgccattccgctggggctggc<br>cgccaccgatgaactgctgatgaccgtcagccag<br>cttagcggcaagccgattgccgacgccctcaccc<br>ttgagcgcggccggctggttgacatgatgctcga<br>ctcccacacctggctgcacggcaagaagtttggc<br>ctgtacggcgatccggacttcgtgatgggcctcac<br>ccgcttcctgctggagctgggctgcgagccaacg<br>gtgatcctgagccataacgccaacaaacgctggc<br>aaaaagcgatgaacaaaatgctcgatgcctcgcc<br>gtacgggcgcgatagcgaagtgtttatcaactgcg<br>atttgtggcacttccgttcgctgatgttcacccgtca<br>gccggactttatgatcggcaactcctacggcaagt<br>ttatccagcgcgataccctggcgaagggtaaagc<br>ctttgaagtgccgcttatccgcctcggctttccgct<br>gttcgaccgccaccatctgcaccgccagacaacc<br>tggggttatgaagggggcgatgaacattgtgacga<br>cgctggtgaacgccgtgctggagaaactggatag<br>cgataccagccagctgggcaaaaccgattacagc<br>ttcgatctcgtccgttaa | atgtctcaaactatcgataaaatcaactcttgttac<br>ccgctgttcgagcaggacgaatatcaggaactg<br>ttccgtaacaaacgtcagctggaagaagcgcac<br>gacgcacagcgcgtgcaggaagtgttcgcatg<br>gaccaccaccgcggaatacgaagctctgaactt<br>ccgtcgcgaagccctgacggttgatccggcga<br>aagcgtgccagcctctgggtgcggttctgtgca<br>gcctgggttttgccaacaccctgccgtatgtcca<br>cggttcccagggctgcgtagcctacttccgtacc<br>tatttcaaccgccactttaaagaaccaatcgcgt<br>gcgtgtccgacagcatgacggaggacgcggc<br>agttttcggtggtaacaacaacatgaacctgggc<br>ctgcaaaatgcttccgcactgtacaaaccggaa<br>atcatcgcagtgtctaccacctgcatggcagag<br>gttattggtgatgatctgcaagcatttattgccaac<br>gcaaagaaagacggtttcgttgacagctctatcg<br>cggttccgcacgctcataccccgtccttcatcgg<br>ttctcacgtaactggttgggacaacatgttcgaa<br>ggcttcgcaaaaacttttaccgcagactatcaag<br>gccaaccgggtaaactgccgaagctgaacctg<br>gtgaccggctttgaaacctacctgggcaacttc<br>gtgtcctgaagcgcatgatggagcagatggcg<br>gttccgtgttctctgctgtctgacccgtctgaggtt<br>ctggacactccagcggacggccactatcgcat<br>gtattctggtggcaccactcagcaggaaatgaa<br>agaggccccagacgcgattgacaccctgctgc<br>tgcaaccgtggcagctgctgaaaagcaagaaa<br>gttgttcaggaaatgtggaaccagccggcaacg<br>gaagttgcaatcccgctgggtctggcagctact<br>gacgaactgctgatgaccgtgtcccaactgagc<br>ggcaaaccaatcgcggatgctctgaccctgga<br>acgcggtcgcctggtggacatgatgctggaca<br>gccacacgtggctgcatggcaagaaatttggcc<br>tgtacggtgacccggacttcgtaatgggcctga<br>cccgtttcctgctggaactgggctgcgagccga<br>ctgttatcctgtctcacaacgctaacaaacgttgg<br>cagaaggccatgaacaaaatgctggatgcgag<br>cccatacggccgtgatagcgaagtgttcatcaa<br>ctgcgacctgtggcatttccgctctctgatgtttac<br>gcgtcagccggatttcatgatcggtaactcttac<br>ggcaaattcatccagcgtgacactctggccaaa<br>ggcaaagcgtttgaagtgccgctgattcgtctgg<br>gctttccgctgttcgaccgtcaccacctgcaccg<br>ccagaccacctggggttacgaaggcgcgatga<br>acatcgtaactactctggtaaacgcagtactgga<br>aaagctggacagcgatacttcccagctgggca<br>aaaccgactattctttcgatctggttcgttaa | **82.1** | **51.2** |

FIG. 18

| Gene | SEQ ID NO: | WT Sequence | Synthetic Sequence | % Nucleotide Identity | % Codon Identity |
|---|---|---|---|---|---|
| **Y** | **WT Gene Y is SEQ ID NO:9**<br>**Synthetic Gene Y is SEQ ID NO:10** | atgtccgacaacgataccctattctggcgtatgctg<br>gcgctgtttcagtctctgccggacctacagccggc<br>gcaaatcgtcgactggctggcgcaggagagcgg<br>cgagacgctgacgccagagcgtctggcgaccct<br>gacccagccgcagctggccgccagctttccctcc<br>gcgacggcggtgatgtcccccgctcgctggtcgc<br>gggtgatggcgagcctgcagggcgcgctgcccg<br>cccatttacgcatcgttcgccctgcccagcgcacg<br>ccgcagctgctggcggcattttgctcccaggatgg<br>gctggtgattaacggccatttcggccagggacga<br>ctgtttttatctacgcgttcgatgaacaaggcggct<br>ggttgtacgatctgcgccgctatccctccgccccc<br>caccagcaggaggccaacgaagtgcgcgcccg<br>gcttattgaggactgtcagctgctgttttgccagga<br>gataggcgggcccgccgccgcgcggctgatcc<br>gccatcgcatccacccgatgaaagcgcagcccg<br>ggacgacgattcaggcacagtgcgaggcgatca<br>atacgctgctggccggccgtttgccgccgtggct<br>ggcgaagcggcttaacagggataaccctctggaa<br>gaacgcgtttttaa | ATGTCTGACAATGATACCCTG<br>TTTTGGCGCATGCTGGCGCTG<br>TTTCAGTCGCTGCCGGATTTG<br>CAGCCGGCTCAAATCGTCGA<br>TTGGCTGGCGCAGGAATCCG<br>GCGAAACCCTGACGCCGGAG<br>CGCCTTGCCACCCTGACCCAA<br>CCGCAACTCGCGGCGTCGTTC<br>CCATCCGCGACGGCAGTGAT<br>GAGCCCGGCTCGCTGGAGCC<br>GCGTTATGGCTTCTCTGCAAG<br>GCGCCCTCCCAGCCCACTTGC<br>GCATCGTACGTCCGGCGCAG<br>CGTACCCCGCAACTGCTCGCC<br>GCGTTTTGCAGCCAAGACGG<br>CCTTGTTATCAATGGTCATTT<br>CGGCCAGGGTCGTCTGTTCTT<br>CATTTACGCCTTTGACGAGCA<br>GGGCGGCTGGCTGTATGACTT<br>GCGCCGCTATCCGAGCGCAC<br>CGCACCAGCAGGAAGCGAAT<br>GAGGTGCGTGCTCGTCTGATT<br>GAAGATTGCCAGCTGCTGTTC<br>TGCCAGGAGATTGGCGGTCC<br>GGCAGCAGCGCGTCCGATCC<br>GCCACCGCATCCATCCGATG<br>AAGGCGCAGCCGGGTACTAC<br>GATTCAGGCGCAGTGTGAAG<br>CTATCAACACCCTGCTGGCCG<br>GTCGCCTGCCGCCGTGGCTCG<br>CCAAACGTTTGAACCGTGAT<br>AACCCGCTGGAAGAGCGTGT<br>GTTTTAA | **79.8** | **45.2** |

FIG. 18 (cont)

| Gene | SEQ ID NO: | WT Sequence | Synthetic Sequence | % Nucleotide Identity | % Codon Identity |
|---|---|---|---|---|---|
| E | **WT Gene E is SEQ ID NO:11**<br>**Synthetic Gene E is SEQ ID NO:12** | atgaagggaaatgaaattctggcgctgctggatga<br>accggcctgtgaacacaaccataaacaaaaatcc<br>ggctgcagcgcgcccaaacccggcgccaccgc<br>cgcgggctgcgcgttcgacggcgcgcagataac<br>cctgctgcccatcgccgacgtggcgcatctggtc<br>cacggccccatcggctgcgccggaagctcatgg<br>gataaccgcggcagcgccagctccggccccacc<br>cttaatcggctcgggttcaccaccgatctcaacga<br>acaggacgtgattatgggccgcggcgaacgccg<br>actgtttcacgccgtgcgccatatcgtcacccgcta<br>tcatccggcggcggtctttatctacaacacctgcgt<br>accggccatggagggcgatgacctggaagcggt<br>atgccaggccgcgcagaccgccaccggcgtacc<br>ggttatcgctattgacgccgccggtttctacggca<br>gtaaaaatctcggtaaccggccggcgggcgacg<br>tcatggtcaaacgggtcatcggccagcgcgagcc<br>cgccccctggccggagagcacgctctttgccccg<br>gagcagcgtcacgatattggcctgattggcgaatt<br>caatattgccggcgagttctggcatattcagccgct<br>gctcgacgaactggggatccgcgtgctcggcag<br>cctctccggtgatggccgcttcgccgagatccag<br>accatgcaccgggcgcaggccaatatgctggtct<br>gctcgcgggcgttaattaacgtcgccagagccct<br>ggagcagcgctacggcacgccgtggttcgaagg<br>cagcttttacgggatccgcgccacctctgacgccc<br>tgcgccagctggcggcgctgctgggcgacgacg<br>accttcgccagcgcaccgaagcgctgattgcgcg<br>ggaggaacaggcggcggaactggcgctacagc<br>cgtggcgcgaacagctgcgcggccgcaaagcg<br>ctgctctataccggcggggtgaaatcctggtcggt<br>ggtatcggcgctgcaggatttgggcatgaccgtg<br>gtggcaaccggcacgcgtaaatccaccgaagag<br>gataaacagcggatccgcgagctgatgggcgaa<br>gaggcggtaatgctggaagagggcaacgcccg<br>cacgctgctggatgtggtctatcgctatcaggccg<br>acctgatgattgccggcggacgcaatatgtacacc<br>gcctataaagccaggctgccgtttctcgatatcaat<br>caggagcgcgaacacgccttcgctggctatcagg<br>ggatcgtcaccctcgcccgccagctgtgtcagac<br>catcaacagccccatctggccgcaaacccattctc<br>gcgccccgtggcgctaa | ATGAAGGGTAACGAGATTCT<br>TGCTCTGCTGGACGAACCGG<br>CCTGTGAACACAACCATAAA<br>CAGAAATCCGGCTGTAGCGC<br>CCCAAAGCCGGGTGCGACGG<br>CGGCTGGCTGCGCTTTCGATG<br>GTGCGCAGATCACCCTGCTCC<br>CGATTGCGGACGTTGCCCACC<br>TCGTGCATGGCCCAATCGGTT<br>GCGCAGGTAGCTCTTGGGAC<br>AACCGTGGCAGCGCCTCCAG<br>CGGTCCGACCCTGAATCGTTT<br>GGGCTTTACCACTGACTTGAA<br>TGAACAAGATGTGATCATGG<br>GTCGCGGCGAGCGTCGCCTG<br>TTCCACGCTGTGCGCCATATT<br>GTCACCCGTTACCACCCAGCG<br>GCAGTATTCATCTACAATACG<br>TGCGTGCCGGCTATGGAAGG<br>CGATGACCTGGAGGCCGTGT<br>GTCAGGCAGCCCAGACTGCG<br>ACCGGCGTCCCGGTAATCGC<br>AATTGATGCGGCTGGCTTCTA<br>CGGTTCGAAGAACCTGGGCA<br>ACCGTCCGGCAGGCGATGTC<br>ATGGTTAAACGCGTCATTGGC<br>CAACGTGAGCCAGCGCCGTG<br>GCCGGAGAGCACCCTGTTTG<br>CCCCGGAGCAACGTCATGAC<br>ATTGGCTTGATCGGTGAGTTC<br>AACATTGCGGGCGAGTTTTG<br>GCACATTCAGCCGCTGCTTGA<br>TGAGCTGGGTATCCGCGTTTT<br>GGGTTCGCTCAGCGGCGATG<br>GTCGTTTCGCCGAGATTCAAA<br>CCATGCACCGTGCCCAGGCG<br>AACATGCTGGTGTGCAGCCG<br>TGCTCTGATCAATGTTGCGCG<br>TGCTCTGGAACAGCGCTATG<br>GCACCCCGTGGTTTGAAGGCT<br>CGTTCTATGGTATCCGCGCGA<br>CCAGCGACGCCCTGCGCCAG<br>TTAGCGGCGCTGCTGGGCGA<br>TGACGACCTCCGTCAGCGCA<br>CCGAGGCGCTGATCGCGCGT<br>GAAGAACAGGCGGCTGAGCT<br>GGCCCTGCAACCGTGGCGTG<br>AACAGCTGCGTGGCCGCAAG<br>GCCCTGCTCTACACGGGTGGT<br>GTCAAAAGCTGGTCTGTGGT<br>GTCCGCGCTTCAGGATCTGGG<br>TATGACCGTGGTTGCCACGG<br>GCACGCGTAAGAGCACGGAA<br>GAGGATAAACAGCGCATCCG | **80.8** | **47.6** |

FIG. 18 (cont)

| Gene | SEQ ID NO: | WT Sequence | Synthetic Sequence | % Nucleotide Identity | % Codon Identity |
|---|---|---|---|---|---|
| | | | CGAATTGATGGGCGAAGAGG<br>CCGTGATGCTTGAAGAAGGC<br>AACGCACGTACCTTATTGGAT<br>GTAGTTTATCGCTATCAAGCA<br>GACCTGATGATTGCCGGTGG<br>CCGCAACATGTATACCGCCTA<br>CAAAGCGCGCTTGCCGTTCCT<br>GGACATCAACCAGGAACGCG<br>AGCACGCGTTTGCGGGCTAC<br>CAAGGCATCGTGACCTTAGC<br>GCGCCAGCTGTGCCAAACGA<br>TTAACAGCCCGATCTGGCCGC<br>AGACTCATTCCCGCGCACCGT<br>GGCGCTAA | | |

FIG. 18 (cont)

| Gene | SEQ ID NO: | WT Sequence | Synthetic Sequence | % Nucleotide Identity | % Codon Identity |
|---|---|---|---|---|---|
| N | **WT Gene N is SEQ ID NO:13**<br>**Synthetic Gene N is SEQ ID NO:14** | atggcagacattttccgcaccgataagccgctggc<br>ggtcagccccatcaaaaccggccagccgctcgg<br>cgcaatcctcgccagcctcgggatcgaacacagc<br>atccctctggtccacggcgcgcaggggtgcagc<br>gccttcgccaaagtctttttattcaacatttccacga<br>cccggttcccctgcagtcgacggcgatggacccc<br>acgtcgacgattatgggcgcggacggcaatatttt<br>taccgccctggataccctctgccagcgcaacaatc<br>cgcaggctatcgtactgctcagcaccgggctgtc<br>ggaggcccagggcagcgatatttcccgcgtggtt<br>cgccagtttcgcgaagagtatccccggcataagg<br>gggtggcgatattgacggttaacacgccggatttt<br>atggctccatggagaacggcttcagcgcggtgtta<br>gagagcgtcattgagcagtgggtgccgccggcg<br>ccgcgcccggctcagcgcaatcgccgggtcaat<br>ctgctggtcagccatctctgttcgccgggcgatatc<br>gagtggctgcgccgatgcgtcgaagcctttggtct<br>gcagccgataatcctgccggacctggcgcaatcg<br>atggacggccacctggcgcagggcgatttctcgc<br>cgctgacccagggcgggacgccgctgcgccag<br>atagagcagatggggcaaagcctgtgcagcttcg<br>ccattggcgtctcccttcatcgcgcctcatcgctgc<br>tggccccgcgctgccgcggcgaggttatcgccct<br>gccgcacctgatgaccctcgaacgctgcgacgc<br>ctttattcatcaactggcgaaaatttccggacgcgc<br>cgttcccgagtggctggaacgccagcgcggcca<br>gctacaggatgcgatgatcgactgccatatgtggc<br>tccagggccagcgcatggcgatagcggcggaa<br>ggcgatttgctggcggcgtggtgtgatttcgccaa<br>cagccaggggatgcagcccggcccgctggtgg<br>cccctaccggtcatcccagcctgcgccagctgcc<br>ggtggaacgggtggtgccgggggatctggagga<br>tctgcaaaccctgctgtgcgcgcatcccgccgac<br>ctgctggtggcgaactcgcacgcccgcgacctg<br>gcggagcagtttgcgctgccgctggtgcgcgcg<br>ggttttccgctctttgacaagctcggcgaattccgc<br>cgggtgcgacaggggtatagcgggatgcgcgat<br>acgctgtttgagctggcaaacctgatacgcgagc<br>gtcaccaccacctcgcccactaccgatcgccgct<br>gcgccagaaccccgaatcgtcactctccacagga<br>ggcgcttatgccgccgattaa | ATGGCAGACATTTTCCGCACT<br>GATAAGCCGTTGGCTGTGTCG<br>CCGATCAAGACCGGCCAGCC<br>GCTGGGTGCGATCCTGGCGTC<br>CCTGGGTATCGAGCACTCGAT<br>TCCGCTGGTACATGGCGCGC<br>AGGGCTGTTCGGCTTTTGCCA<br>AGGTTTTCTTTATCCAGCACT<br>TCCACGATCCGGTCCCGCTGC<br>AAAGCACGGCAATGGACCCG<br>ACCAGCACCATCATGGGCGC<br>TGATGGTAACATCTTCACCGC<br>GCTGGACACTCTCTGCCAACG<br>CAATAACCCGCAAGCAATTG<br>TGCTGCTGAGCACCGGCCTCT<br>CCGAGGCGCAGGGCAGCGAC<br>ATTTCCCGTGTAGTGCGTCAG<br>TTCCGTGAAGAATATCCGCGT<br>CATAAAGGCGTGGCGATTCT<br>GACTGTTAACACCCCGGACTT<br>TTACGGTAGCATGGAGAACG<br>GCTTTTCCGCTGTCCTGGAGT<br>CTGTGATTGAACAGTGGGTTC<br>CGCCAGCCCCACGTCCGGCG<br>CAGCGCAATCGTCGCGTCAA<br>TCTTTTGGTGAGCCATCTCTG<br>TAGCCCAGGCGATATTGAGT<br>GGCTGCGCCGTTGCGTCGAG<br>GCCTTCGGTCTGCAACCGATC<br>ATTCTGCCGGATCTGGCTCAG<br>AGCATGGACGGCCACCTTGC<br>TCAGGGTGACTTTTCGCCGCT<br>GACGCAGGGCGGCACGCCGT<br>TGCGCCAAATCGAGCAGATG<br>GGCCAGAGCCTTTGCTCTTTT<br>GCGATTGGCGTCAGCCTGCA<br>CCGTGCGAGCAGCCTGCTGG<br>CTCCGCGTTGTCGTGGCGAAG<br>TCATCGCCTTGCCGCACCTCA<br>TGACCTTGGAACGCTGCGAC<br>GCCTTTATCCATCAGTTGGCG<br>AAAATCAGCGGTCGCGCCGT<br>TCCGGAGTGGCTGGAACGCC<br>AGCGCGGTCAGCTGCAAGAC<br>GCCATGATCGATTGCCACATG<br>TGGCTGCAAGGCCAGCGCAT<br>GGCGATTGCCGCCGAAGGCG<br>ACCTGCTGGCAGCGTGGTGC<br>GATTTCGCGAACTCTCAAGGT<br>ATGCAGCCGGGTCCACTGGTT<br>GCTCCGACGGGTCATCCGAG<br>CCTGCGTCAGTTGCCGGTGGA<br>GCGCGTGGTGCCGGGTGATC<br>TGGAGGATCTTCAGACCCTCT | 79.7 | 47 |

FIG. 18 (cont)

| Gene | SEQ ID NO: | WT Sequence | Synthetic Sequence | % Nucleotide Identity | % Codon Identity |
|---|---|---|---|---|---|
| | | | TATGCGCACATCCGGCCGACT<br>TACTGGTGGCGAACTCCCAC<br>GCCCGTGATTTAGCAGAGCA<br>ATTCGCCCTGCCGCTGGTGCG<br>CGCAGGCTTCCCGCTGTTTGA<br>CAAACTGGGCGAATTTCGTC<br>GTGTTCGCCAGGGTTATAGCG<br>GTATGCGTGATACCCTGTTCG<br>AGTTGGCGAACCTGATCCGT<br>GAACGCCATCATCATCTGGCT<br>CATTATCGCAGCCCGCTGCGC<br>CAGAACCCAGAATCCTCGTT<br>GTCTACGGGTGGCGCGTACG<br>CAGCGGATTAA | | |

FIG. 18 (cont)

| Gene | SEQ ID NO: | WT Sequence | Synthetic Sequence | % Nucleotide Identity | % Codon Identity |
|---|---|---|---|---|---|
| U | **WT Gene U is SEQ ID NO:15**<br>**Synthetic Gene U is SEQ ID NO:16** | atgtggaattactccgagaaagtgaaagaccattttttaacccccgcaatgcgcgcgtggtggacaacgccaacgcggtaggcgacgtcggttcgttaagctgcggcgacgccctgcgcctgatgctgcgcgtcgacccgcaaagcgaaatcattgaggaggcgggcttccagaccttcggctgcggcagcgccatcgcctcctcctccgcgctgacggagctgattatcggccatacc ctcgccgaagccgggcagataaccaatcagcagattgccgattatctcgacggactgccgccggagaaaatgcactgctcggtgatgggccaggaggccctgcgcgcggccatcgccaactttcgcggcgaaagccttgaagaggagcacgacgagggcaagctgatctgcaaatgcttcggcgtcgatgaagggcatattcgccgcgcggtacagaacaacgggctgaccacccttgccgaggtgatcaactacaccaaagcgggcggcggctgcacctcttgccacgaaaaaatcgagctggccctggcggagatcctcgcccagcagccgcagacgacgccagccgtggccagcggcaaagatccgcactggcagagcgtcgtcgataccatcgcagaactgcggccgcatattcaggccgacggcggcgatatggcgctactcagcgtcaccaaccaccaggtgaccgtcagcctctccggcagctgtagcggctgcatgatgaccgatatgaccctggcctggctgcagcaaaaactgatggaacgtaccggctgttatatggaagtggtggcggcctga | ATGTGGAACTACAGCGAGAAAGTCAAGGACCATTTCTTCAATCCGCGCAACGCGCGTGTTGTGGATAACGCAAATGCGGTGGGCGACGTCGGCAGCTTATCTTGTGGCGATGCTCTCCGCTTGATGCTGCGCGTGGACCCGCAGAGCGAAATCATCGAAGAAGCGGGCTTTCAGACCTTCGGCTGCGGCAGCGCGATTGCGTCGTCCAGCGCACTGACGGAGCTGATCATCGGTCACACCCTGGCGGAAGCGGGTCAGATCACCAACCAGCAGATCGCCGACTATCTGGACGGCTTACCGCCGGAAAAGATGCACTGCTCTGTAATGGGCCAGGAAGCTCTTCGTGCGGCCATTGCTAACTTTCGCGGTGAATCGCTGGAAGAGGAGCATGACGAGGGTAAGCTGATCTGCAAGTGCTTCGGCGTCGATGAAGGCCATATTCGCCGTGCTGTCCAGAACAACGGTCTTACGACTCTGGCCGAGGTGATCAATTACACCAAGGCAGGTGGCGGTTGTACCAGCTGCCATGAGAAAATCGAGCTGGCCCTGGCCGAGATTCTCGCCCAACAGCCGCAAACCACCCCGGCAGTTGCGTCCGGTAAAGATCCGCACTGGCAGAGCGTCGTGGATACCATCGCTGAACTGCGTCCACATATCCAAGCGGACGGTGGTGACATGGCGCTGTTGTCCGTGACGAACCACCAAGTGACTGTTTCGCTGTCGGGCAGCTGTTCTGGCTGCATGATGACCGACATGACCCTGGCGTGGCTGCAACAGAAATTGATGGAGCGTACCGGCTGCTATATGGAAGTTGTTGCCGCCTAA | **82.3** | **53.5** |

FIG. 18 (cont)

| Gene | SEQ ID NO: | WT Sequence | Synthetic Sequence | % Nucleotide Identity | % Codon Identity |
|---|---|---|---|---|---|
| **S** | **WT Gene S is SEQ ID NO:17**<br>**Synthetic Gene S is SEQ ID NO:18** | atgaaacaggtttatctcgataacaacgccaccac<br>ccgtctggacccgatggtcctggaagcgatgatg<br>ccctttttgaccgatttttacggcaacccctcgtcga<br>tacacgattttggcattccggcccaggcggctctg<br>gaacgcgcgcatcagcaggctgcggcgctgctg<br>ggcgcggagtatcccagcgagatcatctttacctc<br>ctgcgccaccgaagccaccgccaccgccatcgc<br>ctcggcgatcgccctgctgcctgagcgtcgcgaa<br>atcatcaccagcgtggtcgaacatccggcgacgc<br>tggcggcctgcgagcacatggagcgcgagggct<br>accggattcatcgcatcgcggtagatggcgaggg<br>ggcgctggacatggcgcagttccgcgcggcgct<br>cagcccgcgcgtcgcgttggtcagcgtgatgtgg<br>gcgaataacgaaaccggggtgcttttcccgatcg<br>gcgaaatggcggagctggcccatgaacaaggg<br>gcgctgtttcactgcgatgcggtgcaggtggtcgg<br>gaaaataccgatcgccgtgggccagacccgcat<br>cgatatgctctcctgctcggcgcataagttccacg<br>ggccaaaaggcgtaggctgtctttatctgcggcg<br>gggaacgcgctttcgcccgctgctgcgcggcggt<br>caccaggagtacggtcggcgagccgggacaga<br>aaatatctgcggaatcgtcggcatgggcgcggcc<br>tgcgagctggcgaatattcatctgccgggaatgac<br>gcatatcggccaattgcgcaacaggctggagcat<br>cgcctgctggccagcgtgccgtcggtcatggtga<br>tgggcggcggccagccggcggtgcccggcacg<br>gtgaatctggcctttgagtttattgaaggtgaagcc<br>attctgctgctgttaaaccaggccgggatcgccgc<br>ctccagcggcagcgcctgcacctcaggctcgctg<br>gaaccctcccacgtgatgcgggcgatgaatatcc<br>cctacaccgccgcccacggcaccatccgcttttct<br>ctctcgcgctacacccgggagaaagagatcgatt<br>acgtcgtcgccacgctgccgccgattatcgaccg<br>gctgcgcgcgctgtcgccctactggcagaacgg<br>caagccgcgcccggcggacgccgtattcacgcc<br>ggtttacggctaa | ATGAAACAAGTGTACCTGGA<br>CAACAACGCGACCACCCGCC<br>TGGACCCGATGGTTCTGGAA<br>GCGATGATGCCGTTTCTCACG<br>GATTTCTATGGCAATCCGTCC<br>AGCATCCATGACTTCGGCATC<br>CCGGCACAAGCGGCGCTGGA<br>ACGTGCGCACCAGCAAGCTG<br>CGGCACTGCTGGGCGCAGAG<br>TACCCGTCTGAAATCATTTTC<br>ACGAGCTGTGCGACCGAGGC<br>CACTGCAACCGCCATTGCGTC<br>GGCCATCGCGTTATTGCCGGA<br>ACGCCGCGAAATCATCACCT<br>CGGTAGTGGAGCACCCGGCT<br>ACGCTGGCGGCGTGCGAGCA<br>CATGGAACGCGAAGGCTATC<br>GCATCCATCGCATTGCGGTGG<br>ATGGCGAAGGTGCGCTGGAC<br>ATGGCCCAGTTCCGTGCAGC<br>GCTCtcgCCGCGTGTCGCGTTG<br>GTGAGCGTGATGTGGGCCAA<br>CAACGAAACCGGCGTGCTGT<br>TCCCGATTGGCGAAATGGCC<br>GAGCTTGCCCACGAGCAGGG<br>CGCTCTGTTCCACTGCGATGC<br>CGTTCAGGTCGTTGGCAAAAT<br>CCCAATTGCTGTTGGCCAGAC<br>GCGCATCGACATGCTGTCTTG<br>CTCCGCGCACAAGTTTCATGG<br>TCCGAAGGGTGTTGGTTGCTT<br>GTACTTACGTCGTGGCACGCG<br>CTTTCGTCCGCTGCTTCGCGG<br>TGGCCATCAAGAATATGGTC<br>GCCGTGCCGGCACTGAGAAT<br>ATCTGTGGCATCGTCGGCATG<br>GGCGCTGCGTGCGAACTGGC<br>GAACATCCATCTGCCGGGTAT<br>GACCCATATTGGCCAGTTACG<br>CAATCGCCTGGAGCACCGTCT<br>GCTCGCCAGCGTGCCGTCCGT<br>GATGGTTATGGGCGGTGGTC<br>AGCCGGCTGTACCGGGTACT<br>GTCAACCTGGCGTTCGAGTTT<br>ATCGAAGGTGAAGCGATCCT<br>GCTCTTGCTGAACCAGGCTGG<br>CATTGCCGCAAGCTCCGGCTC<br>CGCGTGTACCTCTGGCAGCTT<br>GGAGCCGAGCCATGTGATGC<br>GCGCCATGAACATTCCATAC<br>ACCGCGGCTCACGGCACCAT<br>TCGTTTTAGCCTGAGCCGTTA<br>TACGCGCGAGAAAGAGATCG<br>ACTACGTCGTTGCGACCCTCC | **79.1** | **43.6** |

FIG. 18 (cont)

| Gene | SEQ ID NO: | WT Sequence | Synthetic Sequence | % Nucleotide Identity | % Codon Identity |
|---|---|---|---|---|---|
| | | | CGCCAATCATTGATCGTCTGC<br>GTGCCTTGTCCCCGTATTGGC<br>AGAATGGTAAGCCGCGTCCG<br>GCAGATGCAGTCTTTACCCCG<br>GTTTACGGTTAA | | |

FIG. 18 (cont)

| Gene | SEQ ID NO: | WT Sequence | Synthetic Sequence | % Nucleotide Identity | % Codon Identity |
|---|---|---|---|---|---|
| **V** | **WT Gene V is SEQ ID NO:19**<br>**Synthetic Gene V is SEQ ID NO:20** | atggaacgcgtgctgattaacgataccaccctgcg<br>cgacggcgagcagagccccggcgtcgcctttcg<br>caccagcgaaaaggtcgccattgccgaggcgctt<br>tacgccgcaggaataacggcgatggaggtcggc<br>accccggcgatgggcgacgaggagatcgcgcg<br>gatccagctggtgcgtcgccagctgcccgacgc<br>gaccctgatgacctggtgtcggatgaacgcgctg<br>gagatccgccagagcgccgatctgggcatcgact<br>gggtggatatctcgattccggcttcggataagctg<br>cggcagtacaaactgcgcgagccgctggcggtg<br>ctgctggagcggctggcgatgtttatccatcttgcg<br>cataccctcggcctgaaggtatgcatcggctgcg<br>aggacgcctcgcgggccagcggccagaccctg<br>cgcgctatcgccgaggtcgcgcagcaatgcgcc<br>gccgcccgcctgcgctatgccgatacggtcggcc<br>tgctcgaccctttaccaccgcggcgcaaatctcg<br>gccctgcgcgacgtctggtccggcgaaatcgaaa<br>tgcatgcccataacgatctgggtatggcgaccgc<br>caatacgctggcggcggtaagcgccggggccac<br>cagcgtgaatacgacggtcctcggtctcggcgag<br>cggggcgggcaacgcggcgctggaaaccgtcgc<br>gctgggccttgaacgctgcctgggcgtggagacc<br>ggcgtgcatttttcggcgctgcccgcgtcctgtca<br>gagggtcgcggaagccgcgcagcgcgccatcg<br>acccgcagcagccgctggtcggcgagctggtgtt<br>tacccatgagtcaggtgtccacgtggcggcgctg<br>ctgcggcacagcgagagctaccagtccatcgcc<br>ccttccctgatgggccgcagctaccggctggtgct<br>gggcaaacactccgggcgtcaggcggtcaacgg<br>cgtttttgaccagatgggctatcacctcaacgccg<br>cgcagattaaccagctgctgcccgccatccgccg<br>cttcgccgagaactggaagcgcagcccgaaaga<br>ttacgagctggtggctatctacgacgagctgtgcg<br>gtgaatccgctctgcgggcgagggggtaa | ATGGAGCGCGTCTTGATCAA<br>CGATACTACCCTGCGTGATGG<br>CGAACAATCTCCGGGCGTAG<br>CGTTTCGTACCTCCGAGAAAG<br>TTGCCATCGCGGAGGCACTGT<br>ACGCTGCGGGTATCACCGCG<br>ATGGAAGTCGGCACTCCGGC<br>GATGGGTGATGAAGAGATCG<br>CCCGCATTCAGCTGGTGCGTC<br>GTCAACTGCCGGACGCGACG<br>CTTATGACCTGGTGCCGTATG<br>AACGCTCTGGAAATCCGTCA<br>GAGCGCGGATCTGGGTATTG<br>ACTGGGTGGATATCTCGATCC<br>CAGCATCCGACAAGCTGCGT<br>CAGTACAAGCTGCGTGAGCC<br>GCTGGCCGTGCTGCTGGAGC<br>GCCTTGCGATGTTTATCCATC<br>TGGCCCACACGTTAGGCCTCA<br>AAGTATGTATTGGTTGCGAG<br>GATGCGAGCCGTGCGTCTGG<br>TCAGACCCTGCGCGCCATTGC<br>CGAGGTGGCCCAGCAATGCG<br>CGGCTGCGCGCTTGCGTTACG<br>CTGACACCGTGGGCCTGCTG<br>GACCCGTTCACCACCGCAGC<br>CCAGATCAGCGCCCTGCGTG<br>ACGTTTGGTCGGGCGAGATC<br>GAGATGCATGCTCACAATGA<br>TCTGGGCATGGCTACCGCGA<br>ACACGCTGGCGGCAGTTTCG<br>GCTGGCGCCACGTCGGTGAA<br>CACTACCGTCCTCGGTCTGGG<br>TGAACGTGCAGGCAACGCAG<br>CCCTGGAAACCGTTGCGCTG<br>GGCCTGGAACGCTGCCTGGG<br>CGTGGAAACCGGCGTCCATTT<br>CAGCGCGCTCCCAGCGAGCT<br>GTCAGCGCGTCGCGGAGGCT<br>GCACAGCGCGCAATCGACCC<br>GCAACAGCCGCTGGTGGGTG<br>AATTGGTTTTCACCCACGAGT<br>CTGGTGTTCACGTTGCGGCGC<br>TGCTGCGCCACAGCGAATCCT<br>ATCAATCTATTGCCCCAAGCC<br>TCATGGGCCGTAGCTACCGTC<br>TGGTGCTCGGCAAGCATTCG<br>GGTCGTCAGGCTGTCAACGG<br>TGTTTTCGACCAGATGGGTTA<br>CCACCTGAATGCGGCGCAGA<br>TCAATCAGTTGCTGCCGGCCA<br>TTCGCCGCTTCGCCGAGAATT<br>GGAAACGCTCTCCGAAAGAC<br>TACGAACTGGTTGCGATCTAT | **80.8** | **48.3** |

FIG. 18 (cont)

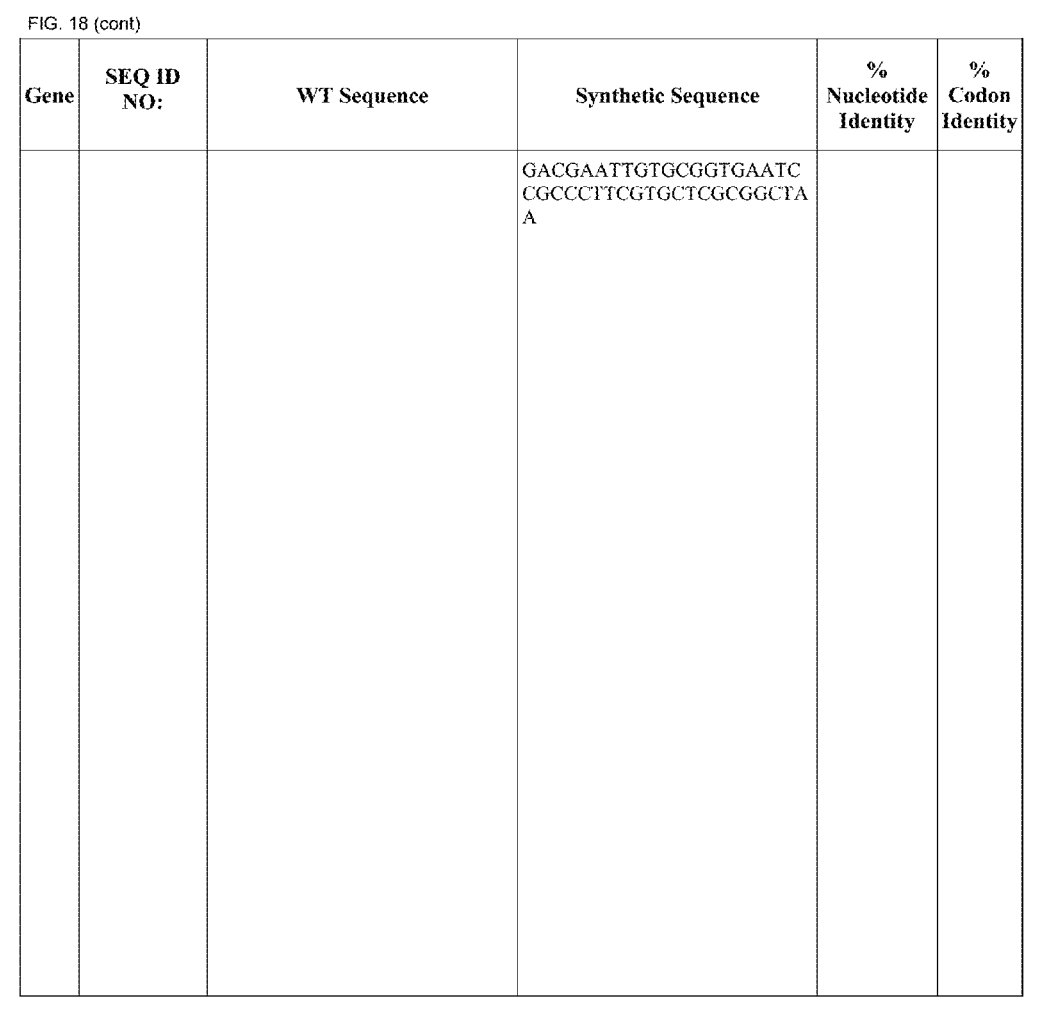

| Gene | SEQ ID NO: | WT Sequence | Synthetic Sequence | % Nucleotide Identity | % Codon Identity |
|---|---|---|---|---|---|
| | | | GACGAATTGTGCGGTGAATCCGCCCTTCGTGCTCGCGGCTAA | | |

FIG. 18 (cont)

| Gene | SEQ ID NO: | WT Sequence | Synthetic Sequence | % Nucleotide Identity | % Codon Identity |
|---|---|---|---|---|---|
| W | **WT Gene W is SEQ ID NO:21**<br>**Synthetic Gene W is SEQ ID NO:22** | atggagtggttttatcaaattcccggcgtggacga<br>acttcgctccgccgaatcttttttcagtttttcgccgt<br>cccctatcagcccgagctgcttggccgctgcagc<br>ctgccggtgctggcaacgtttcatcgcaaactccg<br>cgcggaggtgccgctgcaaaaccggctcgagga<br>taacgaccgcgcgccctggctgctggcgcgaag<br>actgctcgcggagagctatcagcaacagtttcag<br>gagagcggaacatga | ATGGAGTGGTTTTACCAGATT<br>CCGGGTGTAGACGAATTGCG<br>CAGCGCTGAATCCTTCTTTCA<br>GTTCTTCGCGGTTCCATACCA<br>GCCGGAACTGCTGGGCCGCT<br>GCTCGCTTCCGGTGTTAGCGA<br>CGTTCCACCGTAAACTGCGTG<br>CGGAGGTCCCGCTGCAAAAC<br>CGTCTGGAGGACAATGATCG<br>TGCGCCGTGGCTCTTGGCGCG<br>CCGCCTCCTGGCCGAATCTTA<br>TCAGCAGCAATTTCAGGAGA<br>GCGGCACCTAA | 77.9 | 43 |

FIG. 18 (cont)

| Gene | SEQ ID NO: | WT Sequence | Synthetic Sequence | % Nucleotide Identity | % Codon Identity |
|---|---|---|---|---|---|
| **Z** | **WT Gene Z is SEQ ID NO:23**<br>**Synthetic Gene Z is SEQ ID NO:24** | atgagaccgaaattcacctttagcgaagaggtccg<br>cgtcgtacgcgcgattcgtaacgacggcaccgtg<br>gcgggcttcgcgcccggcgcgctgctggtcagg<br>cgcggcagcaccggctttgtgcgcgactggggc<br>gtttttttgcaagatcagattatctaccagatccactt<br>tccggaaaccgatcggatcatcggctgccgcgag<br>caggagctgatccccatcacccagccgtggctgg<br>ccggaaatttgcaatacagggatagcgtgacctg<br>ccagatggcgctcgcggtcaacggcgatgtggtc<br>gtgagcgccggccagcggggacgcgttgaggct<br>accgatcggggagagctcggcgacagctacacc<br>gtcgactttagcggccgctggttcagggtcccggt<br>gcaggccatcgcccttatagaggaaagagaaga<br>atga | ATGCGCCCGAAATTCACCTTC<br>TCTGAAGAGGTCCGCGTAGTT<br>CGCGCGATTCGTAATGATGG<br>CACCGTGGCGGGTTTTGCGCC<br>AGGTGCGCTGCTGGTTCGTCG<br>CGGTTCGACGGGCTTTGTGCG<br>TGACTGGGGTGTGTTCCTGCA<br>AGACCAGATCATCTATCAAA<br>TCCACTTTCCGGAAACCGACC<br>GCATTATCGGCTGTCGCGAGC<br>AGGAGTTAATCCCGATTACCC<br>AGCCGTGGTTGGCTGGTAAC<br>CTCCAGTATCGTGACAGCGTC<br>ACGTGCCAAATGGCACTGGC<br>TGTCAACGGTGACGTGGTTGT<br>GAGCGCCGGTCAACGTGGCC<br>GTGTGGAGGCCACTGATCGT<br>GGCGAACTTGGCGATTCCTAC<br>ACCGTGGACTTCAGCGGCCG<br>TTGGTTCCGCGTTCCGGTCCA<br>GGCCATCGCGCTGATTGAAG<br>AGCGCGAAGAATAA | **80.1** | **48.3** |

FIG. 18 (cont)

| Gene | SEQ ID NO: | WT Sequence | Synthetic Sequence | % Nucleotide Identity | % Codon Identity |
|---|---|---|---|---|---|
| **M** | **WT Gene M is SEQ ID NO:25**<br>**Synthetic Gene M is SEQ ID NO:26** | atgaacccgtggcaacgttttgcccggcagcggctggcgcgcagccgctggaatcgcgatccggcggccctggatccggccgacacgccggcttttgaacaggcctggcaacgccagtgccatatggagcagacgatcgtcgcgcgggtccctgaaggcgatattccggcggcgttgctggagaatatcgctgcctcccttgccatctggctcgacgagggggattttgcgccgcccgagcgcgctgccatcgtgcgccatcacgcccggctggaactcgccttcgccgatatcgcccgccaggcgccgcagccggatctctccacggtacaggcatggtatctgcgccaccagacgcagtttatgcgcccggaacagcgtctgacccgccatttactgctgacggtcgataacgaccgcgaagccgtgcaccagcggatcctcggcctgtatcggcaaatcaacgcctcgcgggacgctttcgcgccgctggcccagcgccattcccactgcccgagcgcgctggaagagggtcgtttaggctggattagccgtggcctgctctatccgcagctcgagaccgcgctgttttcactggcggaaaacgcgctaagccttcccatcgccagcgaactgggctggcatcttttatggtgcgaagcgattcgcccgccgcgcccatggagccgcagcaggcgctggagagcgcgcgcgattatctttggcagcagagccagcagcgccatcagcgccagtggctggaacagatgatttcccgtcagccgggactgtgcgggtag | ATGAATCCGTGGCAGCGCTTTGCCCGTCAACGCCTTGCTCGCAGCCGCTGGAACCGTGATCCGGCTGCTCTCGACCCAGCCGATACCCCAGCGTTCGAGCAGGCGTGGCAGCGTCAATGCCATATGGAACAAACCATCGTAGCGCGTGTCCCGGAAGGCGATATTCCGGCTGCCTTACTGGAAAACATCGCGGCCAGCCTGGCGATCTGGCTGGACGAGGGTGACTTCGCTCCGCCGGAGCGCGCTGCGATTGTGCGTCATCATGCACGTCTGGAGCTGGCGTTTGCCGACATTGCCCGCCAGGCACCGCAACCGGATCTGAGCACGGTTCAAGCGTGGTATCTGCGTCACCAGACTCAATTCATGCGTCCGGAGCAGCGTCTGACCCGTCACCTGCTCCTGACGGTCGATAATGATCGCGAGGCGGTGCATCAACGCATCCTTGGCCTGTATCGTCAGATCAACGCGAGCCGTGACGCCTTCGCCCCACTGGCACAGCGCCACTCTCATTGCCCGTCCGCCTTGGAAGAAGGCCGTCTGGGCTGGATCTCCCGTGGTCTGCTGTACCCGCAGCTCGAAACCGCGTTGTTTAGCCTGGCGGAAAACGCACTGTCGCTGCCGATTGCGTCGGAATTGGGTTGGCACCTGTTATGGTGCGAGGCCATTCGTCCGGCAGCCCCGATGGAGCCGCAACAGGCCCTTGAATCTGCGCGCGACTACTTGTGGCAGCAGAGCCAGCAGCGCCACCAGCGTCAATGGCTGGAGCAGATGATTTCCCGCCAACCGGGCCTGTGTGGTTAA | **79.7** | **45.3** |

FIG. 18 (cont)

| Gene | SEQ ID NO: | WT Sequence | Synthetic Sequence | % Nucleotide Identity | % Codon Identity |
|---|---|---|---|---|---|
| **F** | **WT Gene F is SEQ ID NO:27**<br>**Synthetic Gene F is SEQ ID NO:28** | atggcgaacattggtattttctttggcaccgatacc<br>ggtaaaacccgcaaaatcgcgaaaatgatccata<br>agcaactgggcgagctggcggatgccccggtca<br>acattaaccgcacgacgctggacgactttatggcc<br>tatccggtgctgctgctgggcacgccgacgctcg<br>gcgacggccagctgccggggctggaggccgga<br>tgcgaaagcgagtcatggagcgaatttatcagcg<br>gcctcgacgacgccagcctgaaagggaaaaccg<br>tggcgctgttcggcctcggcgatcagagaggcta<br>tccggacaacttcgtcagcgggatgcgcccgctg<br>ttcgacgccctgagcgcgcgcggcgcgcagatg<br>attggcagctggccaaatgagggttatgaattcag<br>cgcgtcctcggcgctggaaggcgaccgctttgtt<br>gggctggtgctggatcaggataaccagttcgacc<br>agaccgaagcgcgtctggcgagctggcttgagg<br>agattaaacgcaccgtgctgtag | ATGGCGAACATCGGCATCTTC<br>TTTGGTACGGATACCGGCAA<br>AACCCGCAAGATTGCGAAGA<br>TGATTCACAAACAGCTGGGC<br>GAGCTGGCCGATGCCCCGGT<br>TAACATCAATCGTACCACTTT<br>GGATGACTTTATGGCTTACCC<br>AGTCCTGTTGCTCGGCACGCC<br>GACGCTTGGTGATGGTCAACT<br>GCCGGGCTTAGAGGCGGGCT<br>GCGAGAGCGAAAGCTGGTCT<br>GAGTTTATCTCCGGTCTGGAT<br>GACGCTTCCCTGAAGGGCAA<br>AACCGTGGCGCTGTTTGGCCT<br>GGGCGACCAGCGTGGTTACC<br>CGGACAACTTCGTGTCGGGT<br>ATGCGTCCGCTGTTCGACGCG<br>CTGAGCGCCCGTGGCGCCCA<br>GATGATTGGTAGCTGGCCGA<br>ACGAAGGTTATGAGTTTAGC<br>GCATCGTCCGCGCTGGAAGG<br>CGACCGCTTCGTCGGCTTGGT<br>GCTGGATCAAGACAATCAGT<br>TCGACCAGACCGAAGCGCGC<br>CTGGCGTCTTGGCTTGAAGAG<br>ATCAAACGCACCGTTCTGTAA | **81.5** | **51.4** |

FIG. 18 (cont)

| Gene | SEQ ID NO: | WT Sequence | Synthetic Sequence | % Nucleotide Identity | % Codon Identity |
|---|---|---|---|---|---|
| B | **WT Gene B is SEQ ID NO:29**<br><br>**Synthetic Gene B is SEQ ID NO:30** | atgacttcctgctcctcttttctggcggcaaagcct<br>gccgcccggcggatgacagcgcattgacgccgc<br>ttgtggccgataaagctgccgcgcacccctgctac<br>tctcgccatgggcatcaccgtttcgcgcggatgca<br>tctgcccgtcgcgcccgcctgcaatttgcagtgca<br>actactgtaatcgcaaattcgattgcagcaacgagt<br>cccgccccggggtatcgtcaacgctgctgacgcc<br>tgaacaggcggtcgtgaaagtgcgtcaggtcgcg<br>caggcgatcccgcagctttcggtggtgggcatcg<br>ccgggcccggcgatccgctcgccaatatcgccc<br>gcacctttcgcaccctggagctgatccgcgaaca<br>gctgccggacctgaaattatgcctgtcgaccaacg<br>gactggtgctgcctgacgcggtggaccgcctgct<br>ggatgtcggcgttgaccacgtcacggtcaccatta<br>acaccctcgacgcggagattgccgcgcaaatcta<br>cgcctggctatggctggacggcgaacgctacag<br>cgggcgcgaagcgggagagatcctgattgcccg<br>tcagcttgagggcgtacgcaggctgaccgccaaa<br>ggcgtgctggtgaaaataaattcggtgctgatccc<br>cggtatcaacgatagcggcatggccggcgtgag<br>ccgcgcgctgcgggccagcggcgcgtttatccat<br>aatattatgccgctgatcgccaggccggagcacg<br>gcacggtgtttggcctcaacggccagccggagc<br>cggacgccgagacgctcgccgccacccgcagc<br>cggtgcggcgaagtgatgccgcagatgacccac<br>tgccaccagtgtcgcgccgacgccattgggatgc<br>tcggcgaagaccgcagccagcagtttacccagct<br>tccggcgccagagagtctcccggcctggctgcc<br>gatcctccaccagcgcgcgcagctgcacgccag<br>cattgcgacccgcggcgaatctgaagccgatgac<br>gcctgcctggtcgccgtggcgtcaagccgcggg<br>gacgtcattgattgtcactttggtcacgccgaccgg<br>ttctacatttacagcctctcggccgccggtatggtg<br>ctggtcaacgagcgctttacgcccaaatattgtca<br>ggggcgcgatgactgcgagccgcaggataacg<br>cagcccggtttgcggcgatcctcgaactgctggc<br>ggacgttaaagccgtattctgcgtgcgtatcggcc<br>atacgccgtggcaacagctggaacaggaaggca<br>ttgaaccctgcgttgacggcgcgtggcggccggt<br>ctccgaagtgctgcccgcgtggtggcaacagcgt<br>cggggggagctggcctgccgcgttgccgcataag<br>ggggtcgcctga | ATGACCTCTTGTTCGTCGTTT<br>TCTGGCGGTAAAGCGTGCCG<br>TCCGGCCGATGACTCCGCGCT<br>GACTCCGCTGGTGGCCGACA<br>AGGCAGCTGCGCACCCGTGC<br>TATAGCCGCCACGGCCATCA<br>CCGCTTCGCGCGTATGCACCT<br>GCCAGTCGCTCCGGCCTGCA<br>ACTTACAATGCAACTACTGCA<br>ACCGCAAGTTCGATTGCAGC<br>AATGAAAGCCGTCCGGGCGT<br>GTCCTCTACCCTGCTGACGCC<br>GGAACAGGCTGTGGTGAAGG<br>TGCGCCAGGTCGCCCAAGCT<br>ATCCCGCAGCTGtcgGTGGTCG<br>GTATTGCTGGTCCGGGCGATC<br>CGCTTGCGAATATCGCCCGCA<br>CCTTCCGTACCTTGGAGCTTA<br>TTCGCGAACAGTTGCCGGAC<br>CTGAAACTGTGCCTGAGCAC<br>CAACGGCTTGGTGCTGCCAG<br>ATGCCGTTGATCGTCTGCTCG<br>ATGTGGGCGTGGATCACGTT<br>ACCGTCACCATTAACACCCTG<br>GACGCAGAAATCGCAGCGCA<br>AATCTACGCGTGGTTGTGGCT<br>GGATGGCGAACGCTACTCCG<br>GTCGCGAAGCCGGCGAAATT<br>CTCATTGCCCGCCAGCTGGAA<br>GGCGTACGTCGCCTGACCGC<br>GAAAGGTGTGCTCGTCAAGA<br>TCAACAGCGTATTGATTCCGG<br>GCATCAATGACAGCGGCATG<br>GCGGGTGTTAGCCGTGCGCT<br>GCGCGCGTCTGGTGCGTTCAT<br>CCACAACATCATGCCACTGAT<br>TGCGCGTCCGGAGCATGGCA<br>CTGTTTTCGGTCTGAACGGCC<br>AGCCGGAACCGGACGCGGAA<br>ACCCTGGCGGCGACGCGCTC<br>CCGCTGCGGCGAGGTTATGC<br>CACAAATGACCCACTGCCAC<br>CAGTGCCGTGCCGACGCGAT<br>TGGCATGCTTGGTGAGGATC<br>GCTCGCAACAGTTTACGCAAT<br>TACCGGCTCCGGAGTCCCTCC<br>CGGCCTGGCTGCCGATCCTGC<br>ATCAGCGTGCTCAGTTGCATG<br>CGAGCATCGCCACGCGCGGT<br>GAGAGCGAAGCCGATGACGC<br>CTGCCTGGTGGCCGTTGCGTC<br>GAGCCGTGGCGATGTAATTG<br>ACTGCCATTTCGGCCATGCCG<br>ACCGTTTCTATATCTATAGCC | 80.2 | 45.4 |

FIG. 18 (cont)

| Gene | SEQ ID NO: | WT Sequence | Synthetic Sequence | % Nucleotide Identity | % Codon Identity |
|---|---|---|---|---|---|
| | | | TGTCTGCGGCTGGTATGGTTC<br>TGGTTAACGAACGTTTCACCC<br>CGAAATACTGCCAGGGTCGC<br>GATGACTGCGAGCCGCAGGA<br>CAATGCCGCACGCTTTGCTGC<br>CATCCTTGAGTTGCTGGCGGA<br>CGTCAAAGCGGTGTTTTGTGT<br>GCGTATCGGCCATACCCCGTG<br>GCAACAGCTGGAGCAGGAAG<br>GCATCGAACCGTGCGTGGAT<br>GGCGCCTGGCGTCCGGTATCC<br>GAGGTCCTGCCGGCATGGTG<br>GCAGCAGCGCCGTGGTAGCT<br>GGCCGGCTGCATTGCCGCAC<br>AAAGGCGTTGCGTAA | | |

FIG. 18 (cont)

| Gene | SEQ ID NO: | WT Sequence | Synthetic Sequence | % Nucleotide Identity | % Codon Identity |
|---|---|---|---|---|---|
| **Q** | **WT Gene Q is SEQ ID NO:31**<br>**Synthetic Gene Q is SEQ ID NO:32** | atgccgccgctcgactggttgcggcgcttatggct<br>gctgtaccacgcggggaaaggcagctttccgctg<br>cgcatggggcttagcccgcgcgattggcaggcg<br>ctgcggcggcgcctgggcgaggtggaaacgcc<br>gctcgacggcgagacgctcacccgtcgccgcct<br>gatggcggagctcaacgccacccgcgaagagg<br>agcgccagcagctgggcgcctggctggcgggct<br>ggatgcagcaggatgccgggccgatggcgcag<br>attatcgccgaggtttcgctggcgtttaaccatctct<br>ggcaggatcttggtctggcatcgcgcgccgaatt<br>gcgcctgctgatgagcgactgctttccacagctgg<br>tggtgatgaacgaacacaatatgcgctggaaaaa<br>gttcttttatcgtcagcgctgtttgctgcaacagggg<br>gaagttatctgccgttcgccaagctgcgacgagtg<br>ctgggaacgcagcgcctgttttgagtag | ATGCCGCCATTGGACTGGTTG<br>CGTCGTTTGTGGTTACTCTAT<br>CACGCCGGCAAAGGCAGCTT<br>TCCGCTTCGTATGGGCTTGTC<br>GCCGCGTGACTGGCAAGCTC<br>TGCGCCGTCGCCTGGGCGAG<br>GTGGAAACGCCGCTGGATGG<br>CGAAACCCTGACCCGTCGCC<br>GTCTGATGGCGGAGCTGAAT<br>GCGACCCGCGAAGAAGAACG<br>CCAGCAGCTGGGTGCCTGGC<br>TGGCCGGTTGGATGCAACAG<br>GATGCCGGTCCGATGGCGCA<br>GATTATCGCAGAGGTGAGCC<br>TGGCGTTCAACCATCTCTGGC<br>AGGACCTTGGCCTCGCGAGC<br>CGCGCTGAACTGCGTCTGCTG<br>ATGTCTGACTGCTTCCCGCAG<br>CTGGTTGTTATGAACGAGCAC<br>AACATGCGCTGGAAGAAATT<br>CTTTTACCGCCAGCGTTGCCT<br>GCTGCAACAGGGCGAAGTCA<br>TCTGTCGCAGCCCGTCTTGCG<br>ATGAATGCTGGGAACGTTCT<br>GCGTGCTTTGAGTAA | **81.3** | **54.2** |

FIG. 19 Ptac-T7 Synthetic Controller.

Order #8-19: backbone is pincW (KT_96)

| SEQ ID NO: | Order | Name | Sequence |
|---|---|---|---|
| SEQ ID NO:33 | 1 | lacI | caattcgcgctaacttacattaattgcgttgcgctcactgcccgctttccagtcgggaaacctgtcgtgccagctgcattaatgaatcggccaacgcgcggggagaggcggtttgcgtattgggcgccagggtggtttttcttttcaccagtgagacgggcaacagctgattgcccttcaccgcctggccctgagagagttgcagcaagcggtccacgctggtttgccccagcaggcgaaaatcctgtttgatggtggttgacggcgggatataacatgagctgtcttcggtatcgtcgtatcccactaccgagatatccgcaccaacgcgcagcccggactcggtaatggcgcgcattgcgcccagcgccatctgatcgttggcaaccagcatcgcagtgggaacgatgccctcattcagcatttgcatggtttgttgaaaaccggacatggcactccagtcgccttcccgttccgctatcggctgaatttgattgcgagtgagatatttatgccagccagccagacgcagacgcgccgagacagaacttaatgggcccgctaacagcgcgatttgctggtgacccaatgcgaccagatgctccacgcccagtcgcgtaccgtcttcatgggagaaaataatactgttgatgggtgtctggtcagagacatcaagaaataacgccggaacattagtgcaggcagcttccacagcaatggcatcctggtcatccagcggatagttaatgatcagcccactgacgcgttgcgcgagaagattgtgcaccgccgctttacaggcttcgacgccgcttcgttctaccatcgacaccaccacgctggcacccagttgatcggcgcgagatttaatcgccgcgacaatttgcgacggcgcgtgcagggccagactggaggtggcaacgccaatcagcaacgactgtttgcccgccagttgttgtgccacgcggttgggaatgtaattcagctccgccatcgccgcttccactttttcccgcgttttcgcagaaacgtggctggcctggttcaccacgcgggaaacggtctgataagagacaccggcatactctgcgacatcgtataacgttactggtttcac |
| SEQ ID NO:34 | 2 | lacI promoter | attcaccaccctgaattgactctcttccgggcgctatcatgccataccgcgaaaggttttgcaccattcgatggtgtcaacgtaaatgcatgccgcttcgccttcgcgcgcgaattggccgccatgccggcgataatggcctgcttctcgccgaaacgtttggtggcgggaccagtgacgaaggcttgagcgagggcgtgcaagattccgaataccgcaagcgacaggccgatcatcgtcgcgctccagcgaaagcggtcctcgccgaaaatgacccagagcgctgccggcacctgtcctacgagttgcatgataaagaagacagtcataagtgcggcgacgatagtcatgccccgcgcccaccggaaggagctgactgggttgaaggctctcaagggcatcggcggagcttatcgactgcacggtgcaccaatgcttctggcgtcaggcagccatcggaagctgtggtatggctgtgcaggtcgtaaatcactgcataattcgtgtcgctcaaggcgcactcccgttctggataatgttttttgcgccgacatcataacggttctggcaaatattctgaaatgagctg |
| SEQ ID NO:35 | 3 | tac promoter | ttgacaattaatcatcggctcgtataatgtgtggaattgtgagcggataacaatt |
| SEQ ID NO:36 | 4 | insulator 1 | TGCAGTTTTATTCTCTCGCCAGCACTGTAATAGGCACTAA |
| SEQ ID NO:37 | 5 | T7 RNAP rbs | TATCCAAACCAGTAGCTCAATTggagtCGTCTAT |
| SEQ ID NO:38 | 6 | umuD degradation tag | Gtgttgtttatcaagcctgcggatctccgcgaaattgtgacttttccgctatttagcgatcttgttcagtgtggctttccttcaccggcagcagattacgttgaacagcgcatcgatctg |

FIG. 19 (cont)

| SEQ ID NO: | Order | Name | Sequence |
|---|---|---|---|
| SEQ ID NO:39 | 7 | T7 RNAP scaffold | ggtggcAACACGATTAACATCGCTAAGAACGACTTCTCTGACATC<br>GAACTGGCTGCTATCCCGTTCAACACTCTGGCTGACCATTACG<br>GTGAGCGTTTAGCTCGCGAACAGTTGGCCCTTGAGCATGAGTC<br>TTACGAGATGGGTGAAGCACGCTTCCGCAAGATGTTTGAGCGT<br>CAACTTAAAGCTGGTGAGGTTGCGGATAACGCTGCCGCCAAG<br>CCTCTCATCACTACCCTACTCCCTAAGATGATTGCACGCATCA<br>ACGACTGGTTTGAGGAAGTGAAAGCTAAGCGCGGCAAGCGCC<br>CGACAGCCTTCCAGTTCCTGCAAGAAATCAAGCCGGAAGCCGT<br>AGCGTACATCACCATTAAGACCACTCTGGCTTGCCTAACCAGT<br>GCTGACAATACAACCGTTCAGGCTGTAGCAAGCGCAATCGGTC<br>GGGCCATTGAGGACGAGGCTCGCTTCGGTCGTATCCGTGACCT<br>TGAAGCTAAGCACTTCAAGAAAAACGTTGAGGAACAACTCAA<br>CAAGCGCGTAGGGCACGTCTACAAGAAAGCATTTATGCAAGT<br>TGTCGAGGCTGACATGCTCTCTAAGGGTCTACTCGGTGGCGAG<br>GCGTGGTCTTCGTGGCATAAGGAAGACTCTATTCATGTAGGAG<br>TACGCTGCATCGAGATGCTCATTGAGTCAACCGGAATGGTTAG<br>CTTACACCGCCAAAATGCTGGCGTAGTAGGTCAAGACTCTGAG<br>ACTATCGAACTCGCACCTGAATACGCTGAGGCTATCGCAACCC<br>GTGCAGGTGCGCTGGCTGGCATCTCTCCGATGTTCCAACCTTG<br>CGTAGTTCCTCCTAAGCCGTGGACTGGCATTACTGGTGGTGGC<br>TATTGGGCTAACGGTCGTCGTCCTCTGGCGCTGGTGCGTACTC<br>ACAGTAAGAAAGCACTGATGCGCTACGAAGACGTTTACATGC<br>CTGAGGTGTACAAAGCGATTAACATTGCGCAAAACACCGCAT<br>GGAAAATCAACAAGAAAGTCCTAGCGGTCGCCAACGTAATCA<br>CCAAGTGGAAGCATTGTCCGGTCGAGGACATCCCTGCGATTGA<br>GCGTGAAGAACTCCCGATGAAACCGGAAGACATCGACATGAA<br>TCCTGAGGCTCTCACCGCGTGGAAACGTGCTGCCGCTGCTGTG<br>TACCGCAAGGACAAGGCTCGCAAGTCTCGCCGTATCAGCCTTG<br>AGTTCATGCTTGAGCAAGCCAATAAGTTTGCTAACCATAAGGC<br>CATCTGGTTCCCTTACAACATGGACTGGCGCGGTCGTGTTTAC<br>GCTGTGTCAATGTTCAACCCGCAAGGTAACGATATGACCAAAG<br>GACTGCTTACGCTGGCGAAAGGTAAACCAATCGGTAAGGAAG<br>GTTACTACTGGCTGAAAATCCACGGTGCAAACTGTGCGGGTGT<br>CGACAAGGTTCCGTTCCCTGAGCGCATCAAGTTCATTGAGGAA<br>AACCACGAGAACATCATGGCTTGCGCTAAGTCTCCACTGGAGA<br>ACACTTGGTGGGCTGAGCAAGATTCTCCGTTCTGCTTCCTTGC<br>GTTCTGCTTTGAGTACGCTGGGGTACAGCACCACGGCCTGAGC<br>TATAACTGCTCCCTTCCGCTGGCGTTTGACGGGTCTTGCTCTGG<br>CATCCAGCACTTCTCCGCGATGCTCCGAGATGAGGTAGGTGGT<br>CGCGCGGTTAACTTGCTTCCTAGTGAAACCGTTCAGGACATCT<br>ACGGGATTGTTGCTAAGAAAGTCAACGAGATTCTACAAGCAG<br>ACGCAATCAATGGGACCGATAACGAAGTAGTTACCGTGACCG<br>ATGAGAACACTGGTGAAATCTCTGAGAAAGTCAAGCTGGGCA<br>CTAAGGCACTGGCTGGTCAATGGCTGGCTTACGGTGTTACTCG<br>CAGTGTGACTAAGAGTTCAGTCATGACGCTGGCTTACGGGTCC<br>AAAGAGTTCGGCTTCCGTCAACAAGTGCTGGAAGATACCATTC<br>AGCCAGCTATTGATTCCGGCAAGGGTCTGATGTTCACTCAGCC<br>GAATCAGGCTGCTGGATACATGGCTAAGCTGATTTGGGAATCT<br>GTGAGCGTGACGGTGGTAGCTGCGGTTGAAGCAATGAACTGG<br>CTTAAGTCTGCTGCTAAGCTGCTGGCTGCTGAGGTCAAAGATA<br>AGAAGACTGGAGAGATTCTTCGCAAGCGTTGCGCTGTGCATTG<br>GGTAACTCCTGATGGTTTCCCTGTGTGGCAGGAATACAAGAAG<br>CCTATTCAGACGCGCTTGAACCTGATGTTCCTCGGTCAGTTCC<br>GCTTACAGCCTACCATTAACACCAACAAAGATAGCGAGATTG<br>ATGCACACAAACAGGAGTCTGGTATCGCTCCTAACTTTGTACA<br>CAGCCAAGACGGTAGCCACCTTCGTAAGACTGTAGTGTGGGC<br>ACACGAGAAGTACGGAATCGAATCTTTTGCACTGATTCACGAC<br>TCCTTCGGTACGATTCCGGCTGACGCTGCGAACCTGTTCAAAG<br>CAGTGCGCGAAACTATGGTTGACACATATGAGTCTTGTGATGT<br>ACTGGCTGATTTCTACGACCAGTTCGCTGACCAGTTGCACGAG |

FIG. 19 (cont)

| SEQ ID NO: | Order | Name | Sequence |
|---|---|---|---|
| SEQ ID NO:40 | 8 | Biobrick suffix (BBa_G00001) | Tactagtagcggccgctgcag |
| SEQ ID NO:41 | 9 | Translational stop (BBa_B0042) | ttagttagttag |
| SEQ ID NO:42 | 10 | Terminator (BBa_B0054) | attagcagaaagtcaaaagcctccgaccggaggcttttgactaaaacttcccttggggttatcattggg |
| SEQ ID NO:43 | 11 | VR primer sequence (BBa_G00102) | gctcactcaaaggcggtaat |
| SEQ ID NO:44 | 12 | Terminator (BBa_B0062) | cagataaaaaaaatccttagctttcgctaaggatgatttct |

FIG. 19 (cont)

| SEQ ID NO: | Order | Name | Sequence |
|---|---|---|---|
| SEQ ID NO:45 | 13 | pSa origin | gctagagctgtcagaccagagctccaaaccaacgttttatctataccgctacagggtatttaattcctattta<br>atctgcgctagaatgaggcatgtttaaccgaatctgacgttttccctgcaaatgccaaaatactatgcctat<br>ctccgggtttcgcgtgacggccaagacccggaaaaccaaaaatacggtttgctcgaatacgcgaacgc<br>caaaggcttcgcgccgctacagatcgaggaagaaattgccagcagagcaaaggactggcgcaagcg<br>caagctcggagcaatcatcgaaaaggccgagcgtggcgacgtgctactgacgcccggagattacgcgc<br>attgccggttccgccctcgccgccttggaaattctcaaagcggcgagcgagcgcggcctaatcgtccat<br>gtgaccaaacagaagatcatcatggacggcagcctacaaagcgacatcatggcaaccgtgcttggctt<br>ggctgcacagatcgagcggcatttcattcaggcacgtaccaccgaggcgctacaagtcgccagagag<br>cgcggcaagacgctcgggcgacccaagggcagcaaatcgagcgccttgaagctggacagccgtatt<br>gatgaagtacaggcatacgtgaaccttggcttgccgcaaagtcgcgcagccgagttgttaggcgtcag<br>ccctcacaccttgcgcctgttcatcaaacgccggaacatcaaacccacaaacactagaccaaccatcac<br>catgccggggagggaacaacatgcctaagaacaacaaagcccccggccatcgtatcaacgagatcat<br>caagacgagcctcgcgctcgaaatggaggatgcccgcgaagctggcttagtcggctacatggcccgtt<br>gccttgtgcaagcgaccatgccccacaccgaccccaagaccagctactttgagcgcaccaatggcatc<br>gtcaccttgtcgatcatgggcaagccgagcatcggcctgccctacggttctatgccgcgcaccttgcttg<br>cttggatatgcaccgaggccgtgcgaacgaaagaccccgtgttgaaccttggccggtcgcaatcggaa<br>tttctacaaaggctcggaatgcacaccgatggccgttacacggccacccttcgcaatcaggcgcaacg<br>cctgttttcatccatgatttcgcttgccggcgagcaaggcaatgacttcggcattgagaacgtcgtcattgc<br>caagcgcgcttttctattctggaatcccaagcggccagaagatcgggcgctatgggatagcaccctcac<br>cctcacaggcgatttcttcgaggaagtcacccgctcaccggttcctatccgaatcgactacctgcatgcct<br>tgcggcagtctccgcttgcgatggacatttacacgtggctgacctatcgcgtgttcctgttgcgggccaa<br>gggccgccccttcgtgcaaatcccttgggtcgccctgcaagcgcaattcggctcatcctatggcagccg<br>cgcacgcaactcgcccgaactggacgataaggcccgagagcgggcagagcgggcagcactcgcca<br>gcttcaaatacaacttcaaaaagcgcctacgcgaagtgttgattgtctatcccgaggcaagcgactgcat<br>cgaagatgacggcgaatgcctgcgcatcaaatccacacgcctgcatgtcacccgcgcacccggcaag<br>ggcgctcgcatcggccccccctccgacttgaccaggccaacgctacgcttggcttggtcaagccttccca<br>tccaacagcccgccgtcgagcgggctttttatccccggaagcctgtggatagagggtagttatccacgt<br>gaaaccgctaatgccccgcaaagccttgattcacggggctttccggcccgctccaaaaactatccacgt<br>gaaatcgctaatcagggtacgtgaaatcgctaatcggagtacgtgaaatcgctaataaggtcacgtgaa<br>atcgctaatcaaaaaggcacgtgagaacgctaatagccctttcagatcaacagcttgcaaacacccctc<br>gctccggcaagtagttacagcaagtagtatgttcaattagcttttcaattatgaatatatatatcaattattggt<br>cgcccttggcttgtggacaatgcgctacgcgcaccggctccgcccgtggacaaccgcaagcggttgc<br>ccaccgtcgagcgccagcgcctttgcccacaacccggcggccgcaacagatcgttttataaattttttttt<br>tgaaaaagaaaaagcccgaaaggcggcaacctctcgggcttctggatttccgatcaacgcaggagtcg<br>ttcggaaagtagctgttccagaattataggcgcagagacaccagattccaagatggctctgttaaattgtt<br>gtagtatgtagtatcatacaacatactacagtacagaggcccgcaagaatggcaatcactaaacaagac<br>atttggcgagcagccgacgaactggacgccgaaggcatccggcccactttggccgccgtgcgcaaga<br>aactcggaagcggtagcttcacaaccatttccgatgcaatggctgaatggaaaaaccgcaagaccgcc<br>accctgccctcatcagacccattgccggttgcagtcaacgagcatcttgccgagcttggcaatgcgctat<br>gggctatcgccctggcgcacgccaacgcccggtttgacgaagatcggaaacagatcgaggccgaca<br>aagcggccatcagccagcagcttgccgaagcaatcgaactagccgacaccttcacccgcgaaaacga<br>ccagctccgcgaacgagtgaatcagctcgaacctatggaacgcgagcgcgacaagctggccgacca<br>gcttgccgaagtgaaacgccgcagcggcgaagaactaaaccgctgcatggaaaagctcacccaacg<br>cgataacgaggctatcgaggcccgcaaacaggccaaggaggccatcgagcgcgccgccagtctgca<br>aggtcaggtggaagccctcaaagagcaggtcgccaatctcacagccgtcttgaaaacaggaggcaaa<br>caatgaaaagcgcccttgccgcccttcgcgcggtcgcggccgctgtcgtcctaatcgtcagtgtgcccg<br>cttgggccgacttccggggtgaagtcgtccgaatccttgacggtgacactatcgacgttttggtgaaccg<br>tcagaccatccgcgtgagattggccgatattgacgcaccggaaagcggccaagccttcggctcccgtg<br>ctcgccaacggctcgccgacttgacctttcgccaagaggttcaagtgaccgaaaaagaggttgatcggt<br>atggccgcactcttggggtcgtttacgcgccgttgcaataccccggcggccaaacacaactcaccaac<br>atcaatgcgatcatggttcaagaaggcatggcctgggcttaccgttattacggcaaaccaaccgacgcg<br>cagatgtacgagtatgaaaaagaggcccgccgccaacggctcggcctttggtcagacccgaatgctca<br>ggagccttggaaatggcgtcgcgcctcgaaaaatgccacgaactgacaccgggcacgccccttgttcg<br>acgcgccgcaggcacgtcgaatttaccgccgggacg |

FIG. 19 (cont)

| SEQ ID NO: | Order | Name | Sequence |
|---|---|---|---|
| SEQ ID NO:46 | 14 | spectinomycin resistance | cccctcgtcccgacacttccagatcgccatagcgcacagcgcctcgagcggtggtaacggcgcagtg gcggttttcatggcttgttatgactgtttttttggggtacagtctatgcctcgggcatccaagcagcaagcg cgttacgccgtgggtcgatgtttgatgttatggagcagcaacgatgttacgcagcagggcagtcgccct aaaacaaagttaaacatcatgagggaagcggtgatcgccgaagtatcgactcaactatcagaggtagtt ggcgtcatcgagcgccatctcgaaccgacgttgctggccgtacatttgtacggctccgcagtggatggc ggcctgaagccacacagtgatattgatttgctggttacggtgaccgtaaggcttgatgaaacaacgcgg cgagctttgatcaacgaccttttggaaacttcggcttcccctggagagagcgagattctccgcgctgtag aagtcaccattgttgtgcacgacgacatcattccgtggcgttatccagctaagcgcgaactgcaatttgga gaatggcagcgcaatgacattcttgcaggtatcttcgagccagccacgatcgacattgatctggctatctt gctgacaaaagcaagagaacatagcgttgccttggtaggtccagcggcggaggaactctttgatccgg ttcctgaacaggatctatttgaggcgctaaatgaaaccttaacgctatggaactcgccgcccgactgggc tggcgatgagcgaaatgtagtgcttacgttgtcccgcatttggtacagcgcagtaaccggcaaaatcgc gccgaaggatgtcgctgccgactgggcaatggagcgcctgccggcccagtatcagcccgtcatacttg aagctagacaggcttatcttggacaagaagaagatcgcttggcctcgcgcgcagatcagttggaagaat ttgtccactacgtgaaaggcgagatcaccaaggtagtcggcaaataatgtctaacaattcgttcaagccg acgccgcttcgcggcgcggcttaactcaagcgttagatgcactaagcacataattgctcacagccaaac tatcaggtcaagtctgcttttattatttttaagcgtgcataataagccctacacaaatggtaccc |
| SEQ ID NO:47 | 15 | Terminator (BBa_B0053) | tccggcaaaaaaacgggcaaggtgtcaccaccctgccctttttctttaaaaccgaaaagattacttcgcgt t |
| SEQ ID NO:48 | 16 | VF2 primer sequence (BBa_G000101) | tgccacctgacgtctaagaa |
| SEQ ID NO:49 | 17 | Terminator (BBa_B0055) | aaggaatattcagcaatttgcccgtgccgaagaaaggcccacccgtgaaggtgagccagtgagttgatt gctacgtaa |
| SEQ ID NO:50 | 18 | Translational stop (BBa_B0042) | ttagttagttag |
| SEQ ID NO:51 | 19 | Biobrick prefix (Bba_G00000) | gaattcgcggccgcttctagag |

FIG. 20 Parts List of Full Synthetic Cluster

Order # 57-67 have pSB4C5 backbone.

| | Order | Name | Strength (AFU) | Sequence |
|---|---|---|---|---|
| SEQ ID NO:52 | 1 | T7 promoter WT | 9000 | TAATACGACTCACTATAGGGAGA |
| SEQ ID NO:53 | 2 | nifH rbs | 5500 | ACAATAAACTAACATAAGGAGGATAAAT |
| SEQ ID NO:54 | 3 | nifH | | ATGACCATGCGTCAGTGCGCGATTTATGGCAAAGGTGGTATTG<br>GCAAAAGCACGACGACCCAGAACTTGGTGGCGGCCCTGGCCG<br>AGATGGGTAAAAAGGTTATGATTGTGGGTTGCGACCCGAAGG<br>CCGACAGCACGCGCCTGATTCTGCACGCGAAAGCACAAAACA<br>CGATTATGGAGATGGCTGCCGAGGTTGGTAGCGTGGAGGATC<br>TGGAGCTGGAGGACGTTCTGCAAATTGGTTACGGTGATGTTCG<br>TTGCGCAGAGAGCGGTGGTCCGGAACCAGGTGTCGGCTGTGC<br>GGGTCGTGGTGTGATTACCGCTATCAATTTCCTGGAAGAAGAG<br>GGTGCGTACGAAGATGATCTGGATTTCGTTTTCTACGATGTGC<br>TGGGTGATGTCGTGTGCGGTGGTTTTGCAATGCCGATTCGCGA<br>GAATAAGGCACAAGAAATTTACATTGTCTGTAGCGGCGAGAT<br>GATGGCAATGTACGCTGCTAACAACATCAGCAAGGGTATTGT<br>TAAATACGCAAAAAGCGGTAAGGTTCGCTTGGGTGGTTTGATT<br>TGCAACAGCCGTCAGACCGACCGTGAGGACGAACTGATCATC<br>GCCCTGGCTGAGAAACTGGGCACCCAAATGATCCACTTCGTG<br>CCACGCGATAATATTGTTCAACGTGCAGAAATCCGCCGTATGA<br>CCGTCATTGAGTATGACCCGGCATGCAAGCAAGCGAACGAGT<br>ACCGCACCTTGGCACAGAAAATCGTGAACAACACCATGAAGG<br>TTGTTCCGACGCCGTGTACGATGGACGAGCTGGAGAGCCTGCT<br>GATGGAGTTCGGCATTATGGAGGAGGAGGACACCAGCATTAT<br>CGGTAAGACCGCAGCGGAGGAGAATGCGGCATAA |
| SEQ ID NO:55 | 4 | insulator 1 | | GCGTGCGTACACCTTAATCACCGCTTCATGCTAAGGTCCTGGC<br>TGCATGC |
| SEQ ID NO:56 | 5 | nifD rbs | 500 | AAAAATTCACATCCCTATCTAGCGGAGGAGCCGG |
| SEQ ID NO:57 | 6 | nifD | | atgatgactaatgctactggcgaacgtaacctggcactgattcaagaagtactggaagtgttcccggaa<br>accgcgcgcaaagagcgccgtaaacacatgatggtttctgacccgaaaatgaaatctgtgggtaaatg<br>catcatctctaatcgcaaatctcagccgggtgtcatgactgttcgtggctgtgcgtacgcaggttctaaag<br>gtgtcgtattcggcccgatcaaagatatggcgcatatctctcatggcccggcaggctgtggccagtact<br>ctcgcgcggaacgtcgtaactactacacgggcgtttctggcgttgactctttcggcacgctgaacttcac<br>ctctgacttccaggaacgtgacatcgttttcggtggcgataaaaagctgtccaaactgatcgaagaaatg<br>gaactgctgttcccgctgactaaaggcattactatccaaagcgaatgtccggtgggtctgatcggtgatg<br>acatcagcgcggtcgcaaacgcatcttccaaagccctggataagccggtgatcccggttcgttgcgag<br>ggcttccgcggcgtttctcagtctctgggtcatcacatcgcaaacgatgttgtgcgtgactggattctgaa<br>caaccgtgaaggtcagccttttgaaaccaccccttatgacgttgcgattattggcgactataacatcggc<br>ggcgacgcctgggcatcccgcatcctgctggaggagatgggtctgcgtgttgtcgcacagtggtctgg<br>cgatggcaccctggttgaaatggaaaacaccccgtttgttaaactgaacctggttcactgctaccgctcc<br>atgaactacattgcccgtcacatggaagaaaaacatcagatcccttggatggaatacaacttcttcggtc<br>cgactaaaatcgcagaatccctgcgtaaaatcgccgatcagtttgatgataccattcgcgcgaacgctg<br>aagcagtaattgcgcgctacgaaggccagatggcagcaatcattgctaagtaccgtccgcgcctggaa<br>ggtcgtaaagtgctgctgtacatgggtggtctgcgtccacgtcatgtgatcggtgcctacgaggacctg<br>ggcatggagatcatcgcagcgggttacgaatttgcacacaacgacgactatgatcgtacgctgccaga<br>cctgaaagaaggtacgctgctgtttgacgacgccagctcttatgaactggaagccttcgtgaaagcgct<br>gaaaccagacctgatcggctccggcatcaaggaaaaatacattttccagaaaatgggcgtgccgttcc<br>gccagatgcactcctgggactactccggtccgtaccacggctacgacggtttcgctatcttcgctcgtga |

FIG. 20 (cont)

| | | | | |
|---|---|---|---|---|
| | | | | catggatatgaccctgaataacccagcgtggaatgaactgaccgcaccgtggctgaaatctgcataa |
| SEQ ID NO:58 | 7 | insulator 2 | | CAAACACCCCATGTCGATACTGAACGAATCGACGCACACTCC CTTCCTTG |
| SEQ ID NO:59 | 8 | nifK rbs | 50 | CAATCTCATACTCTCAAAAATTAGGCGAGGTAAC |
| SEQ ID NO:60 | 9 | nifK | | atgtctcaaactatcgataaaatcaactcttgttacccgctgttcgagcaggacgaatatcaggaactgtt ccgtaacaaacgtcagctggaagaagcgcacgacgcacagcgcgtgcaggaagtgttcgcatggac caccaccgcggaatacgaagctctgaacttccgtcgcgaagccctgacggttgatccggcgaaagcg tgccagcctctgggtgcggttctgtgcagcctgggttttgccaacaccctgccgtatgtccacggttccc agggctgcgtagcctacttccgtacctatttcaaccgccactttaaagaaccaatcgcgtgcgtgtccga cagcatgacggaggacgcggcagttttcggtggtaacaacaacatgaacctgggcctgcaaaatgctt ccgcactgtacaaaccggaaatcatcgcagtgtctaccacctgcatggcagaggttattggtgatgatct gcaagcatttattgccaacgcaaagaaagacggtttcgttgacagctctatcgcggttccgcacgctcat accccgtccttcatcggttctcacgtaactggttgggacaacatgttcgaaggcttcgcaaaaactttac cgcagactatcaaggccaaccgggtaaactgccgaagctgaacctggtgaccggctttgaaacctacc tgggcaactttcgtgtcctgaagcgcatgatggagcagatggcggttccgtgttctctgctgtctgaccc gtctgaggttctggacactccagcggacggccactatcgcatgtattctggtggcaccactcagcagga aatgaaagaggccccagacgcgattgacaccctgctgctgcaaccgtggcagctgctgaaaagcaag aaagttgttcaggaaatgtggaaccagccggcaacggaagttgcaatcccgctgggtctggcagctac tgacgaactgctgatgaccgtgtcccaactgagcggcaaaccaatcgcggatgctctgaccctggaac gcggtcgcctggtggacatgatgctggacagccacacgtggctgcatggcaagaaatttggcctgtac ggtgacccggacttcgtaatgggcctgacccgtttcctgctggaactgggctgcgagccgactgttatc ctgtctcacaacgctaacaaacgttggcagaaggccatgaacaaaatgctggatgcgagcccatacgg ccgtgatagcgaagtgttcatcaactgcgacctgtggcatttccgctctctgatgtttacgcgtcagccgg atttcatgatcggtaactcttacggcaaattcatccagcgtgacactctggccaaaggcaaagcgtttga agtgccgctgattcgtctgggctttccgctgttcgaccgtcaccacctgcaccgccagaccacctgggg ttacgaaggcgcgatgaacatcgtaactactctggtaaacgcagtactggaaaagctggacagcgata cttcccagctgggcaaaaccgactattctttcgatctggttcgttaa |
| SEQ ID NO:61 | 10 | insulator 3 | | CCTGATTGTATCCGCATCTGATGCTACCGTGGTTGAGTTA |
| SEQ ID NO:62 | 11 | nifY rbs | 240 | CCATACTCACTCCCGGAGGTACTTCT |
| SEQ ID NO:63 | 12 | nifY | | ATGTCTGACAATGATACCCTGTTTTGGCGCATGCTGGCGCTGT TTCAGTCGCTGCCGGATTTGCAGCCGGCTCAAATCGTCGATTG GCTGGCGCAGGAATCCGGCGAAACCCTGACGCCGGAGCGCCT TGCCACCCTGACCCAACCGCAACTCGCGGCGTCGTTCCCATCC GCGACGGCAGTGATGAGCCCGGCTCGCTGGAGCCGCGTTATG GCTTCTCTGCAAGGCGCCCTCCCAGCCCACTTGCGCATCGTAC GTCCGGCGCAGCGTACCCCGCAACTGCTCGCCGCGTTTTGCAG CCAAGACGGCCTTGTTATCAATGGTCATTTCGGCCAGGGTCGT CTGTTCTTCATTTACGCCTTTGACGAGCAGGGCGGCTGGCTGT ATGACTTGCGCCGCTATCCGAGCGCACCGCACCAGCAGGAAG CGAATGAGGTGCGTGCTCGTCTGATTGAAGATTGCCAGCTGCT GTTCTGCCAGGAGATTGGCGGTCCGGCAGCAGCGCGTCCGAT CCGCCACCGCATCCATCCGATGAAGGCGCAGCCGGGTACTAC GATTCAGGCGCAGTGTGAAGCTATCAACACCCTGCTGGCCGG TCGCCTGCCGCCGTGGCTCGCCAAACGTTTGAACCGTGATAAC CCGCTGGAAGAGCGTGTGTTTTAA |
| SEQ ID NO:64 | 13 | insulator 4 | | CATTTTTGCCTTGCGACAGACCTCCTACTTAGATTGCCAC |
| SEQ ID NO:65 | 14 | nifE rbs | 40 | ACTATTCAATACATCACTGGAGGTTATTACAA |

FIG. 20 (cont)

| | | | | |
|---|---|---|---|---|
| SEQ ID NO:66 | 15 | nifE | | ATGAAGGGTAACGAGATTCTTGCTCTGCTGGACGAACCGGCC TGTGAACACAACCATAAACAGAAATCCGGCTGTAGCGCCCCA AAGCCGGGTGCGACGGCGGCTGGCTGCGCTTTCGATGGTGCG CAGATCACCCTGCTCCCGATTGCGGACGTTGCCCACCTCGTGC ATGGCCCAATCGGTTGCGCAGGTAGCTCTTGGGACAACCGTG GCAGCGCCTCCAGCGGTCCGACCCTGAATCGTTTGGGCTTTAC CACTGACTTGAATGAACAAGATGTGATCATGGGTCGCGGCGA GCGTCGCCTGTTCCACGCTGTGCGCCATATTGTCACCCGTTAC CACCCAGCGGCAGTATTCATCTACAATACGTGCGTGCCGGCTA TGGAAGGCGATGACCTGGAGGCCGTGTGTCAGGCAGCCCAGA CTGCGACCGGCGTCCCGGTAATCGCAATTGATGCGGCTGGCTT CTACGGTTCGAAGAACCTGGGCAACCGTCCGGCAGGCGATGT CATGGTTAAACGCGTCATTGGCCAACGTGAGCCAGCGCCGTG GCCGGAGAGCACCCTGTTTGCCCCGGAGCAACGTCATGACAT TGGCTTGATCGGTGAGTTCAACATTGCGGGCGAGTTTTGGCAC ATTCAGCCGCTGCTTGATGAGCTGGGTATCCGCGTTTTGGGTT CGCTCAGCGGCGATGGTCGTTTCGCCGAGATTCAAACCATGCA CCGTGCCCAGGCGAACATGCTGGTGTGCAGCCGTGCTCTGATC AATGTTGCGCGTGCTCTGGAACAGCGCTATGGCACCCCGTGGT TTGAAGGCTCGTTCTATGGTATCCGCGCGACCAGCGACGCCCT GCGCCAGTTAGCGGCGCTGCTGGGCGATGACGACCTCCGTCA GCGCACCGAGGCGCTGATCGCGCGTGAAGAACAGGCGGCTGA GCTGGCCCTGCAACCGTGGCGTGAACAGCTGCGTGGCCGCAA GGCCCTGCTCTACACGGGTGGTGTCAAAAGCTGGTCTGTGGTG TCCGCGCTTCAGGATCTGGGTATGACCGTGGTTGCCACGGGCA CGCGTAAGAGCACGGAAGAGGATAAACAGCGCATCCGCGAAT TGATGGGCGAAGAGGCCGTGATGCTTGAAGAAGGCAACGCAC GTACCTTATTGGATGTAGTTTATCGCTATCAAGCAGACCTGAT GATTGCCGGTGGCCGCAACATGTATACCGCCTACAAAGCGCG CTTGCCGTTCCTGGACATCAACCAGGAACGCGAGCACGCGTTT GCGGGCTACCAAGGCATCGTGACCTTAGCGCGCCAGCTGTGC CAAACGATTAACAGCCCGATCTGGCCGCAGACTCATTCCCGC GCACCGTGGCGCTAA |
| SEQ ID NO:67 | 16 | insulator 5 | | TGTCACGCTAGGAGGCAATTCTATAAGAATGCACACTGCA |
| SEQ ID NO:68 | 17 | infN rbs | 40 | CCTAAACCTACCACACCTGGAAGAAGTAATT |
| SEQ ID NO:69 | 18 | nifN | | ATGGCAGACATTTTCCGCACTGATAAGCCGTTGGCTGTGTCGC CGATCAAGACCGGCCAGCCGCTGGGTGCGATCCTGGCGTCCC TGGGTATCGAGCACTCGATTCCGCTGGTACATGGCGCGCAGG GCTGTTCGGCTTTTGCCAAGGTTTTCTTTATCCAGCACTTCCAC GATCCGGTCCCGCTGCAAAGCACGGCAATGGACCCGACCAGC ACCATCATGGGCGCTGATGGTAACATCTTCACCGCGCTGGACA CTCTCTGCCAACGCAATAACCCGCAAGCAATTGTGCTGCTGAG CACCGGCCTCTCCGAGGCGCAGGGCAGCGACATTTCCCGTGT AGTGCGTCAGTTCCGTGAAGAATATCCGCGTCATAAAGGCGT GGCGATTCTGACTGTTAACACCCCGGACTTTTACGGTAGCATG GAGAACGGCTTTTCCGCTGTCCTGGAGTCTGTGATTGAACAGT GGGTTCCGCCAGCCCCACGTCCGGCGCAGCGCAATCGTCGCG TCAATCTTTTGGTGAGCCATCTCTGTAGCCCAGGCGATATTGA GTGGCTGCGCCGTTGCGTCGAGGCCTTCGGTCTGCAACCGATC ATTCTGCCGGATCTGGCTCAGAGCATGGACGGCCACCTTGCTC AGGGTGACTTTTCGCCGCTGACGCAGGGCGGCACGCCGTTGC GCCAAATCGAGCAGATGGGCCAGAGCCTTTGCTCTTTTGCGAT TGGCGTCAGCCTGCACCGTGCGAGCAGCCTGCTGGCTCCGCGT TGTCGTGGCGAAGTCATCGCCTTGCCGCACCTCATGACCTTGG AACGCTGCGACGCCTTTATCCATCAGTTGGCGAAAATCAGCG |

FIG. 20 (cont)

| | | | | |
|---|---|---|---|---|
| | | | | GTCGCGCCGTTCCGGAGTGGCTGGAACGCCAGCGCGGTCAGC<br>TGCAAGACGCCATGATCGATTGCCACATGTGGCTGCAAGGCC<br>AGCGCATGGCGATTGCCGCCGAAGGCGACCTGCTGGCAGCGT<br>GGTGCGATTTCGCGAACTCTCAAGGTATGCAGCCGGGTCCACT<br>GGTTGCTCCGACGGGTCATCCGAGCCTGCGTCAGTTGCCGGTG<br>GAGCGCGTGGTGCCGGGTGATCTGGAGGATCTTCAGACCCTCT<br>TATGCGCACATCCGGCCGACTTACTGGTGGCGAACTCCCACGC<br>CCGTGATTTAGCAGAGCAATTCGCCCTGCCGCTGGTGCGCGCA<br>GGCTTCCCGCTGTTTGACAAACTGGGCGAATTTCGTCGTGTTC<br>GCCAGGGTTATAGCGGTATGCGTGATACCCTGTTCGAGTTGGC<br>GAACCTGATCCGTGAACGCCATCATCATCTGGCTCATTATCGC<br>AGCCCGCTGCGCCAGAACCCAGAATCCTCGTTGTCTACGGGTG<br>GCGCGTACGCAGCGGATTAA |
| SEQ ID NO:70 | 19 | nifJ rbs | 100 | ctagagattaaagaggagaaattaagc |
| SEQ ID NO:71 | 20 | nifJ | | ATGAAAACTATGGACGGTAACGCTGCGGCTGCATGGATTAGC<br>TACGCCTTTACCGAAGTGGCTGCGATCTACCCGATTACGCCGA<br>GCACCCCGATGGCGGAAAATGTGGACGAATGGGCTGCGCAGG<br>GCAAGAAGAACCTCTTCGGCCAGCCGGTGCGCCTGATGGAGA<br>TGCAGTCGGAAGCGGGTGCAGCAGGTGCTGTGCATGGCGCCT<br>TGCAAGCTGGCGCACTGACGACCACCTACACCGCGTCGCAGG<br>GCCTGTTGCTGATGATCCCAAACATGTACAAAATCGCGGGTG<br>AACTGCTGCCGGGTGTCTTTCATGTTTCGGCACGCGCACTGGC<br>CACCAATAGCCTCAACATCTTTGGCGATCATCAGGATGTAATG<br>GCGGTGCGCCAAACGGGCTGCGCGATGTTGGCCGAGAATAAC<br>GTCCAGCAAGTTATGGATTTGTCCGCGGTAGCCCACTTGGCAG<br>CGATCAAAGGTCGCATTCCGTTCGTGAACTTCTTCGATGGCTT<br>TCGCACCAGCCACGAAATCCAGAAGATCGAGGTTCTGGAATA<br>TGAACAGCTGGCCACCTTGTTGGATCGTCCGGCCCTGGACAGC<br>TTCCGCCGTAACGCCCTTCACCCGGACCACCCGGTCATCCGTG<br>GCACCGCCCAGAACCCGGACATCTACTTCCAGGAACGTGAGG<br>CCGGTAACCGTTTCTATCAGGCGCTCCCGGATATTGTGGAATC<br>TTACATGACCCAGATTTCTGCCCTGACTGGTCGCGAGTATCAC<br>CTGTTTAACTACACTGGTGCTGCGGATGCGGAGCGCGTGATCA<br>TCGCGATGGGCTCTGTCTGTGACACCGTCCAAGAGGTGGTTGA<br>CACGCTGAATGCAGCGGGTGAGAAAGTTGGTCTGCTCTCCGTT<br>CATCTTTTCCGCCCGTTTTCGTTAGCGCACTTCTTCGCCCAACT<br>GCCGAAAACTGTACAGCGTATCGCAGTATTGGACCGTACGAA<br>AGAGCCAGGTGCTCAAGCAGAGCCGCTGTGCCTCGATGTGAA<br>GAATGCCTTTTACCACCATGACGATGCCCCGTTGATTGTGGGT<br>GGTCGCTATGCCTTGGGCGGTAAGGACGTGTTGCCGAACGAT<br>ATTGCGGCCGTGTTTGATAACCTGAACAAACCGCTGCCGATGG<br>ACGGCTTCACGCTGGGTATCGTGGACGATGTTACCTTCACCTC<br>TCTCCCGCCAGCGCAGCAGACCCTGGCGGTTTCTCACGACGGC<br>ATCACGGCATGTAAGTTTTGGGGCATGGGCTCCGACGGCACG<br>GTTGGTGCGAACAAGTCCGCGATCAAGATTATCGGCGACAAA<br>ACGCCACTGTATGCGCAAGCGTACTTTTCCTACGACTCGAAGA<br>AGAGCGGTGGTATTACCGTCAGCCATCTGCGTTTTGGTGATCG<br>CCCGATCAACTCCCCGTATTTGATCCATCGCGCGGATTTCATC<br>TCGTGCAGCCAGCAAAGCTATGTTGAACGCTACGATCTGCTGG<br>ATGGCCTTAAACCGGGTGGCACCTTTCTGCTGAACTGCTCCTG<br>GAGCGATGCCGAACTGGAGCAACATCTGCCGGTCGGTTTCAA<br>ACGTTATCTGGCACGCGAGAATATCCACTTCTACACTCTCAAC<br>GCTGTGGACATCGCCCGTGAGCTTGGTTTGGGTGGCCGTTTCA<br>ACATGCTGATGCAGGCTGCCTTCTTCAAACTGGCCGCGATCAT<br>TGACCCGCAGACTGCTGCGGACTATCTGAAGCAGGCTGTTGA<br>GAAAAGCTATGGCAGCAAAGGTGCGGCGGTCATCGAGATGAA<br>CCAGCGTGCCATCGAGCTTGGCATGGCCAGCCTGCACCAGGT |

FIG. 20 (cont)

| | | | | |
|---|---|---|---|---|
| | | | | GACGATCCCGGCACATTGGGCCACCCTGGATGAGCCAGCGGC GCAGGCGTCCGCGATGATGCCGGACTTTATCCGCGACATCCTG CAACCGATGAACCGTCAGTGCGGCGACCAGCTTCCGGTGTCG GCTTTTGTCGGCATGGAAGATGGCACCTTCCCGTCCGGCACGG CCGCATGGGAGAAACGTGGCATCGCCCTTGAGGTGCCAGTCT GGCAGCCGGAAGGCTGCACGCAGTGCAACCAGTGCGCCTTCA TTTGTCCGCACGCCGCGATTCGTCCGGCGTTGTTGAATGGCGA AGAGCATGATGCTGCCCCGGTTGGCCTGCTGAGCAAACCGGC ACAAGGCGCTAAAGAATATCACTATCATCTGGCGATTAGCCC GCTGGACTGCTCCGGCTGTGGCAACTGCGTTGACATTTGTCCA GCTCGTGGCAAAGCGTTGAAGATGCAGTCTCTGGATAGCCAA CGCCAGATGGCTCCGGTGTGGGATTATGCGCTGGCGCTGACCC CGAAGTCTAACCCGTTTCGTAAAACCACCGTCAAAGGCTCGC AGTTCGAAACCCCGCTGCTGGAGTTTAGCGGTGCGTGCGCTGG TTGTGGCGAAACGCCGTATGCGCGCCTCATTACCCAGCTGTTT GGCGACCGCATGCTGATTGCCAATGCCACCGGCTGTTCCAGCA TCTGGGGCGCATCTGCGCCGAGCATCCCGTATACCACCAATCA TCGTGGTCATGGTCCGGCCTGGGCGAATAGCCTGTTTGAGGAC AATGCCGAATTTGGTTTAGGTATGATGCTGGGCGGTCAAGCTG TGCGTCAACAGATCGCGGACGATATGACGGCTGCGTTAGCGC TCCCGGTTTCCGATGAGCTGAGCGACGCGATGCGCCAGTGGTT GGCGAAACAGGACGAGGGTGAAGGCACGCGTGAGCGTGCGG ACCGTCTGAGCGAGCGCTTAGCCGCGGAGAAAGAGGGCGTTC CGCTGTTAGAGCAGCTGTGGCAAAATCGTGATTACTTTGTGCG TCGCAGCCAGTGGATTTTCGGCGGTGACGGCTGGGCCTATGAT ATTGGCTTCGGTGGCCTGGACCACGTCCTCGCCAGCGGTGAGG ATGTGAACATTCTGGTATTTGACACCGAAGTCTACTCGAACAC CGGCGGTCAAAGCAGCAAATCGACCCCGGTCGCGGCCATCGC CAAGTTCGCGGCTCAGGGCAAGCGCACCCGCAAGAAAGACCT GGGTATGATGGCGATGAGCTACGGCAACGTCTATGTAGCCCA GGTGGCGATGGGTGCGGATAAAGATCAAACTCTGCGCGCCAT TGCGGAAGCTGAAGCGTGGCCAGGCCCGTCGCTGGTGATTGC GTATGCGGCCTGCATCAATCATGGCCTGAAGGCCGGTATGCGT TGCAGCCAACGTGAGGCGAAGCGCGCTGTTGAGGCGGGCTAC TGGCACCTGTGGCGTTATCACCCGCAGCGCGAAGCGGAAGGC AAGACGCCGTTTATGTTAGATAGCGAAGAACCGGAAGAGTCG TTCCGTGACTTTCTGTTGGGTGAGGTGCGCTACGCATCCCTGC ACAAGACCACCCCGCACCTCGCCGATGCCCTTTTCAGCCGTAC CGAAGAAGATGCGCGTGCGCGCTTTGCGCAATACCGTCGCCT GGCTGGCGAAGAGTAATAA |
| SEQ ID NO:72 | 21 | T7 terminator 25 | 1600 | TACTCTAACCCCATCGGCCGTCTTAGGGGTTTTTTGT |
| SEQ ID NO:73 | 22 | insulator 6 | | CCGTGGTTGAGTCAGCGTCGAGCACGCGGC |
| SEQ ID NO:74 | 23 | T7 promoter mut 2 | 1500 | TAATACGACTCACTAGAGAGAGA |
| SEQ ID NO:75 | 24 | insulator 7 | | CGCGACTTCCAGAGAAGAAGACTACTGACTTGAGCGTTCC |
| SEQ ID NO:76 | 25 | nifB rbs | 220 | CTCTCTGTAATACATCAAATCAATCATAGGAGGGCTAAA |
| SEQ ID NO:77 | 26 | nifB | | ATGACCTCTTGTTCGTCGTTTTCTGGCGGTAAAGCGTGCCGTC CGGCCGATGACTCCGCGCTGACTCCGCTGGTGGCCGACAAGG CAGCTGCGCACCCGTGCTATAGCCGCCACGGCCATCACCGCTT CGCGCGTATGCACCTGCCAGTCGCTCCGGCCTGCAACTTACAA TGCAACTACTGCAACCGCAAGTTCGATTGCAGCAATGAAAGC |

FIG. 20 (cont)

| | | | | |
|---|---|---|---|---|
| | | | | CGTCCGGGCGTGTCCTCTACCCTGCTGACGCCGGAACAGGCTG<br>TGGTGAAGGTGCGCCAGGTCGCCCAAGCTATCCCGCAGCTGtcg<br>GTGGTCGGTATTGCTGGTCCGGGCGATCCGCTTGCGAATATCG<br>CCCGCACCTTCCGTACCTTGGAGCTTATTCGCGAACAGTTGCC<br>GGACCTGAAACTGTGCCTGAGCACCAACGGCTTGGTGCTGCC<br>AGATGCCGTTGATCGTCTGCTCGATGTGGGCGTGGATCACGTT<br>ACCGTCACCATTAACACCCTGGACGCAGAAATCGCAGCGCAA<br>ATCTACGCGTGGTTGTGGCTGGATGGCGAACGCTACTCCGGTC<br>GCGAAGCCGGCGAAATTCTCATTGCCCGCCAGCTGGAAGGCG<br>TACGTCGCCTGACCGCGAAAGGTGTGCTCGTCAAGATCAACA<br>GCGTATTGATTCCGGGCATCAATGACAGCGGCATGGCGGGTG<br>TTAGCCGTGCGCTGCGCGCGTCTGGTGCGTTCATCCACAACAT<br>CATGCCACTGATTGCGCGTCCGGAGCATGGCACTGTTTTCGGT<br>CTGAACGGCCAGCCGGAACCGGACGCGGAAACCCTGGCGGCG<br>ACGCGCTCCCGCTGCGGCGAGGTTATGCCACAAATGACCCAC<br>TGCCACCAGTGCCGTGCCGACGCGATTGGCATGCTTGGTGAG<br>GATCGCTCGCAACAGTTTACGCAATTACCGGCTCCGGAGTCCC<br>TCCCGGCCTGGCTGCCGATCCTGCATCAGCGTGCTCAGTTGCA<br>TGCGAGCATCGCCACGCGCGGTGAGAGCGAAGCCGATGACGC<br>CTGCCTGGTGGCCGTTGCGTCGAGCCGTGGCGATGTAATTGAC<br>TGCCATTTCGGCCATGCCGACCGTTTCTATATCTATAGCCTGTC<br>TGCGGCTGGTATGGTTCTGGTTAACGAACGTTTCACCCCGAAA<br>TACTGCCAGGGTCGCGATGACTGCGAGCCGCAGGACAATGCC<br>GCACGCTTTGCTGCCATCCTTGAGTTGCTGGCGGACGTCAAAG<br>CGGTGTTTTGTGTGCGTATCGGCCATACCCCGTGGCAACAGCT<br>GGAGCAGGAAGGCATCGAACCGTGCGTGGATGGCGCCTGGCG<br>TCCGGTATCCGAGGTCCTGCCGGCATGGTGGCAGCAGCGCCG<br>TGGTAGCTGGCCGGCTGCATTGCCGCACAAAGGCGTTGCGTA<br>A |
| SEQ ID NO:78 | 27 | insulator 8 | | ACTACGAGATTTGAGGTAAACCAAATAAGCACGTAGTGGC |
| SEQ ID NO:79 | 28 | nifQ rbs | 5 | TGCGTTTAGCAGTTCCCGTAGGAATATTTCCTT |
| SEQ ID NO:80 | 29 | nifQ | | ATGCCGCCATTGGACTGGTTGCGTCGTTTGTGGTTACTCTATC<br>ACGCCGGCAAAGGCAGCTTTCCGCTTCGTATGGGCTTGTCGCC<br>GCGTGACTGGCAAGCTCTGCGCCGTCGCCTGGGCGAGGTGGA<br>AACGCCGCTGGATGGCGAAACCCTGACCCGTCGCCGTCTGAT<br>GGCGGAGCTGAATGCGACCCGCGAAGAAGAACGCCAGCAGCT<br>GGGTGCCTGGCTGGCCGGTTGGATGCAACAGGATGCCGGTCC<br>GATGGCGCAGATTATCGCAGAGGTGAGCCTGGCGTTCAACCA<br>TCTCTGGCAGGACCTTGGCCTCGCGAGCCGCGCTGAACTGCGT<br>CTGCTGATGTCTGACTGCTTCCCGCAGCTGGTTGTTATGAACG<br>AGCACAACATGCGCTGGAAGAAATTCTTTTACCGCCAGCGTTG<br>CCTGCTGCAACAGGGCGAAGTCATCTGTCGCAGCCCGTCTTGC<br>GATGAATGCTGGGAACGTTCTGCGTGCTTTGAGTAA |
| SEQ ID NO:81 | 30 | T7 terminator 1 | 1300 | TACATATCGGGGGGGTAGGGGTTTTTTGT |
| SEQ ID NO:82 | 31 | insulator 9 | | GTCTGTAGCACGTGCATC |
| SEQ ID NO:83 | 32 | T7 promoter mut 3 | 2750 | TAATACGACTCACTAATGGGAGA |
| SEQ ID NO:84 | 33 | nifF rbs | 45 | GACAAGAGTCTCAATTATAAGGAGGCTTTACTAC |

FIG. 20 (cont)

| | | | | |
|---|---|---|---|---|
| SEQ ID NO:85 | 34 | nifF | | ATGGCGAACATCGGCATCTTCTTTGGTACGGATACCGGCAAA ACCCGCAAGATTGCGAAGATGATTCACAAACAGCTGGGCGAG CTGGCCGATGCCCCGGTTAACATCAATCGTACCACTTTGGATG ACTTTATGGCTTACCCAGTCCTGTTGCTCGGCACGCCGACGCT TGGTGATGGTCAACTGCCGGGCTTAGAGGCGGGCTGCGAGAG CGAAAGCTGGTCTGAGTTTATCTCCGGTCTGGATGACGCTTCC CTGAAGGGCAAAACCGTGGCGCTGTTTGGCCTGGGCGACCAG CGTGGTTACCCGGACAACTTCGTGTCGGGTATGCGTCCGCTGT TCGACGCGCTGAGCGCCCGTGGCGCCCAGATGATTGGTAGCT GGCCGAACGAAGGTTATGAGTTTAGCGCATCGTCCGCGCTGG AAGGCGACCGCTTCGTCGGCTTGGTGCTGGATCAAGACAATC AGTTCGACCAGACCGAAGCGCGCCTGGCGTCTTGGCTTGAAG AGATCAAACGCACCGTTCTGTAATAA |
| SEQ ID NO:86 | 35 | T7 terminator 1 | 1300 | TACATATCGGGGGGGTAGGGGTTTTTTGT |
| SEQ ID NO:87 | 36 | insulator 10 | | GGTCATTACAACGGTTAT |
| SEQ ID NO:88 | 37 | T7 promoter mut 2 | 1500 | TAATACGACTCACTAGAGAGAGA |
| SEQ ID NO:89 | 38 | insulator 11 | | AACATAGCGTTCCATGAGGGCTAGAATTACCTACCGGCCT |
| SEQ ID NO:90 | 39 | nifU rbs | 2800 | CAGATACTGACAAATAAACCAGCGAAGGAGGTTCCTA |
| SEQ ID NO:91 | 40 | nifU | | ATGTGGAACTACAGCGAGAAAGTCAAGGACCATTTCTTCAAT CCGCGCAACGCGCGTGTTGTGGATAACGCAAATGCGGTGGGC GACGTCGGCAGCTTATCTTGTGGCGATGCTCTCCGCTTGATGC TGCGCGTGGACCCGCAGAGCGAAATCATCGAAGAAGCGGGCT TTCAGACCTTCGGCTGCGGCAGCGCGATTGCGTCGTCCAGCGC ACTGACGGAGCTGATCATCGGTCACACCCTGGCGGAAGCGGG TCAGATCACCAACCAGCAGATCGCCGACTATCTGGACGGCTT ACCGCCGGAAAAGATGCACTGCTCTGTAATGGGCCAGGAAGC TCTTCGTGCGGCCATTGCTAACTTTCGCGGTGAATCGCTGGAA GAGGAGCATGACGAGGGTAAGCTGATCTGCAAGTGCTTCGGC GTCGATGAAGGCCATATTCGCCGTGCTGTCCAGAACAACGGT CTTACGACTCTGGCCGAGGTGATCAATTACACCAAGGCAGGT GGCGGTTGTACCAGCTGCCATGAGAAAATCGAGCTGGCCCTG GCCGAGATTCTCGCCCAACAGCCGCAAACCACCCCGGCAGTT GCGTCCGGTAAAGATCCGCACTGGCAGAGCGTCGTGGATACC ATCGCTGAACTGCGTCCACATATCCAAGCGGACGGTGGTGAC ATGGCGCTGTTGTCCGTGACGAACCACCAAGTGACTGTTTCGC TGTCGGGCAGCTGTTCTGGCTGCATGATGACCGACATGACCCT GGCGTGGCTGCAACAGAAATTGATGGAGCGTACCGGCTGCTA TATGGAAGTTGTTGCCGCCTAA |
| SEQ ID NO:92 | 41 | insulator 12 | | CATTGTAATAGCCACCAAAAGAGTGATGATAGTCATGGGT |
| SEQ ID NO:93 | 42 | nifS rbs | 175 | GATACCCGTAGACCATTCTGAAATCGAAGGAGGTTTTCC |
| SEQ ID NO:94 | 43 | nifS | | ATGAAACAAGTGTACCTGGACAACAACGCGACCACCCGCCTG GACCCGATGGTTCTGGAAGCGATGATGCCGTTTCTCACGGATT TCTATGGCAATCCGTCCAGCATCCATGACTTCGGCATCCCGGC ACAAGCGGCGCTGGAACGTGCGCACCAGCAAGCTGCGGCACT GCTGGGCGCAGAGTACCCGTCTGAAATCATTTTCACGAGCTGT GCGACCGAGGCCACTGCAACCGCCATTGCGTCGGCCATCGCG |

FIG. 20 (cont)

| | | | | |
|---|---|---|---|---|
| | | | | TTATTGCCGGAACGCCGCGAAATCATCACCTCGGTAGTGGAG CACCCGGCTACGCTGGCGGCGTGCGAGCACCTGGAACGCCAA GGCTATCGCATCCATCGCATTGCGGTGGATAGCGAAGGTGCG CTGGACATGGCCCAGTTCCGTGCAGCGCTCtcgCCGCGTGTCGC GTTGGTGAGCGTGATGTGGGCCAACAACGAAACCGGCGTGCT GTTCCCGATTGGCGAAATGGCCGAGCTTGCCCACGAGCAGGG CGCTCTGTTCCACTGCGATGCCGTTCAGGTCGTTGGCAAAATC CCAATTGCTGTTGGCCAGACGCGCATCGACATGCTGTCTTGCT CCGCGCACAAGTTTCATGGTCCGAAGGGTGTTGGTTGCTTGTA CTTACGTCGTGGCACGCGCTTTCGTCCGCTGCTTCGCGGTGGC CATCAAGAATATGGTCGCCGTGCCGGCACTGAGAATATCTGT GGCATCGTCGGCATGGGCGCTGCGTGCGAACTGGCGAACATC CATCTGCCGGGTATGACCCATATTGGCCAGTTACGCAATCGCC TGGAGCACCGTCTGCTCGCCAGCGTGCCGTCCGTGATGGTTAT GGGCGGTGGTCAGCCGcgTGTACCGGGTACTGTCAACCTGGCG TTCGAGTTTATCGAAGGTGAAGCGATCCTGCTCTTGCTGAACC AGGCTGGCATTGCCGCAAGCTCCGGCTCCGCGTGTACCTCTGG CAGCTTGGAGCCGAGCCATGTGATGCGCGCCATGAACATTCC ATACACCGCGGCTCACGGCACCATTCGTTTTAGCCTGAGCCGT TATACGCGCGAGAAAGAGATCGACTACGTCGTTGCGACCCTC CCGCCAATCATTGATCGTCTGCGTGCCTTGTCCCCGTATTGGC AGAATGGTAAGCCGCGTCCGGCAGATGCAGTCTTTACCCCGG TTTACGGTTAA |
| SEQ ID NO:95 | 44 | insulator 13 | | GAGTTACTGGCCCTGATTTCTCCGCTTCTAATACCGCACA |
| SEQ ID NO:96 | 45 | nifV rbs | 5 | GCGACTAGGAGCCTAACTCGCCACAAGGAAACAT |
| SEQ ID NO:97 | 46 | nifV | | ATGGAGCGCGTCTTGATCAACGATACTACCCTGCGTGATGGCG AACAATCTCCGGGCGTAGCGTTTCGTACCTCCGAGAAAGTTGC CATCGCGGAGGCACTGTACGCTGCGGGTATCACCGCGATGGA AGTCGGCACTCCGGCGATGGGTGATGAAGAGATCGCCCCGCAT TCAGCTGGTGCGTCGTCAACTGCCGGACGCGACGCTTATGACC TGGTGCCGTATGAACGCTCTGGAAATCCGTCAGAGCGCGGAT CTGGGTATTGACTGGGTGGATATCTCGATCCCAGCATCCGACA AGCTGCGTCAGTACAAGCTGCGTGAGCCGCTGGCCGTGCTGCT GGAGCGCCTTGCGATGTTTATCCATCTGGCCCACACGTTAGGC CTCAAAGTATGTATTGGTTGCGAGGATGCGAGCCGTGCGTCTG GTCAGACCCTGCGCGCCATTGCCGAGGTGGCCCAGCAATGCG CGGCTGCGCGCTTGCGTTACGCTGACACCGTGGGCCTGCTGGA CCCGTTCACCACCGCAGCCCAGATCAGCGCCCTGCGTGACGTT TGGTCGGGCGAGATCGAGATGCATGCTCACAATGATCTGGGC ATGGCTACCGCGAACACGCTGGCGGCAGTTTCGGCTGGCGCC ACGTCGGTGAACACTACCGTCCTCGGTCTGGGTGAACGTGCA GGCAACGCAGCCCTGGAAACCGTTGCGCTGGGCCTGGAACGC TGCCTGGGCGTGGAAACCGGCGTCCATTTCAGCGCGCTCCCAG CGAGCTGTCAGCGCGTCGCGGAGGCTGCACAGCGCGCAATCG ACCCGCAACAGCCGCTGGTGGGTGAATTGGTTTTCACCCACGA GTCTGGTGTTCACGTTGCGGCGCTGCTGCGCCACAGCGAATCC TATCAATCTATTGCCCCAAGCCTCATGGGCCGTAGCTACCGTC TGGTGCTCGGCAAGCATTCGGGTCGTCAGGCTGTCAACGGTGT TTTCGACCAGATGGGTTACCACCTGAATGCGGCGCAGATCAAT CAGTTGCTGCCGGCCATTCGCCGCTTCGCCGAGAATTGGAAAC GCTCTCCGAAAGACTACGAACTGGTTGCGATCTATGACGAATT GTGCGGTGAATCCGCCCTTCGTGCTCGCGGCTAA |
| SEQ ID NO:98 | 47 | insulator 14 | | GACTCAACACGCTAGGGACGTGAAGTCGATTCCTTCGATG |

FIG. 20 (cont)

| | | | | |
|---|---|---|---|---|
| SEQ ID NO:99 | 48 | nifW rbs | 40 | CAGAAGGCGAGAACTAGATTTAAGGGCCATTATAG |
| SEQ ID NO:100 | 49 | nifW | | ATGGAGTGGTTTTACCAGATTCCGGGTGTAGACGAATTGCGCAGCGCTGAATCCTTCTTTCAGTTCTTCGCGGTTCCATACCAGCCGGAACTGCTGGGCCGCTGCTCGCTTCCGGTGTTAGCGACGTTCCACCGTAAACTGCGTGCGGAGGTCCCGCTGCAAAACCGTCTGGAGGACAATGATCGTGCGCCGTGGCTCTTGGCGCGCCGCCTCCTGGCCGAATCTTATCAGCAGCAATTTCAGGAGAGCGGCACCTAA |
| SEQ ID NO:101 | 50 | insulator 15 | | TCGAGAAACAAGGCAGTTCCGGGCTGAAAGTAGCGCCGGG |
| SEQ ID NO:102 | 51 | nifZ rbs | 365 | ACAAGTCCCGTATTATAACCGCCTAGGAGGTGTTGG |
| SEQ ID NO:103 | 52 | nifZ | | ATGCGCCCGAAATTCACCTTCTCTGAAGAGGTCCGCGTAGTTCGCGCGATTCGTAATGATGGCACCGTGGCGGGTTTGCGCCAGGTGCGCTGCTGGTTCGTCGCGGTTCGACGGGCTTTGTGCGTGACTGGGGTGTGTTCCTGCAAGACCAGATCATCTATCAAATCCACTTTCCGGAAACCGACCGCATTATCGGCTGTCGCGAGCAGGAGTTAATCCCGATTACCCAGCCGTGGTTGGCTGGTAACCTCCAGTATCGTGACAGCGTCACGTGCCAAATGGCACTGGCTGTCAACGGTGACGTGGTTGTGAGCGCCGGTCAACGTGGCCGTGTGGAGGCCACTGATCGTGGCGAACTTGGCGATTCCTACACCGTGGACTTCAGCGGCCGTTGGTTCCGCGTTCCGGTCCAGGCCATCGCGCTGATTGAAGAGCGCGAAGAATAA |
| SEQ ID NO:104 | 53 | insulator 16 | | ACGCCACGCGTAGTGAGACATACACGTTCGTTGGGTTCAC |
| SEQ ID NO:105 | 54 | nifM rbs | 750 | TCAGAGACTGAAGTTATTACCCAGGAGGTCTATA |
| SEQ ID NO:106 | 55 | nifM | | ATGAATCCGTGGCAGCGCTTTGCCCGTCAACGCCTTGCTCGCAGCCGCTGGAACCGTGATCCGGCTGCTCTCGACCCAGCCGATACCCCAGCGTTCGAGCAGGCGTGGCAGCGTCAATGCCATATGGAACAAACCATCGTAGCGCGTGTCCCGGAAGGCGATATTCCGGCTGCCTTACTGGAAAACATCGCGGCCAGCCTGGCGATCTGGCTGGACGAGGGTGACTTCGCTCCGCCGGAGCGCGCTGCGATTGTGCGTCATCATGCACGTCTGGAGCTGGCGTTTGCCGACATTGCCCGCCAGGCACCGCAACCGGATCTGAGCACGGTTCAAGCGTGGTATCTGCGTCACCAGACTCAATTCATGCGTCCGGAGCAGCGTCTGACCCGTCACCTGCTCCTGACGGTCGATAATGATCGCGAGGCGGTGCATCAACGCATCCTTGGCCTGTATCGTCAGATCAACGCGAGCCGTGACGCCTTCGCCCCACTGGCACAGCGCCACTCTCATTGCCCGTCCGCCTTGGAAGAAGGCCGTCTGGGCTGGATCTCCCGTGGTCTGCTGTACCCGCAGCTCGAAACCGCGTTGTTTAGCCTGGCGGAAAACGCACTGTCGCTGCCGATTGCGTCGGAATTGGGTTGGCACCTGTTATGGTGCGAGGCCATTCGTCCGGCAGCCCCGATGGAGCCGCAACAGGCCCTTGAATCTGCGCGCGACTACTTGTGGCAGCAGAGCCAGCAGCGCCACCAGCGTCAATGGCTGGAGCAGATGATTTCCCGCCAACCGGGCCTGTGTGGTTAA |
| SEQ ID NO:107 | 56 | T7 terminator WT | 1400 | TAGCATAACCCCTTGGGGCCTCTAAACGGGTCTTGAGGGGTTTTTTG |
| SEQ ID NO:108 | 57 | Biobrick suffix (BBa_G00001) | | Tactagtagcggccgctgcag |
| SEQ ID | 58 | Translational | | ttagttagttag |

FIG. 20 (cont)

| | | | | |
|---|---|---|---|---|
| NO:109 | | stop (BBa_B0042) | | |
| SEQ ID NO:110 | 59 | Terminator (BBa_B0054) | | attagcagaaagtcaaaagcctccgaccggaggcttttgactaaaacttcccttggggttatcattggg |
| SEQ ID NO:111 | 60 | VR primer sequence (BBa_G00102) | | gctcactcaaaggcggtaat |
| SEQ ID NO:112 | 61 | Terminator (BBa_B0062) | | cagataaaaaaaatccttagctttcgctaaggatgatttct |
| SEQ ID NO:113 | 62 | pSC101 origin (BBa_I50042) | | ctgtcagaccaagtttacgagctcgcttggactcctgttgatagatccagtaatgacctcagaactccatc<br>tggatttgttcagaacgctcggttgccgccgggcgttttttattggtgagaatccaagcactagggacagt<br>aagacgggtaagcctgttgatgataccgctgccttactgggtgcattagccagtctgaatgacctgtcac<br>gggataatccgaagtggtcagactggaaaatcagagggcaggaactgctgaacagcaaaaagtcag<br>atagcaccacatagcagacccgccataaaacgccctgagaagcccgtgacgggcttttcttgtattatg<br>ggtagtttccttgcatgaatccataaaaggcgcctgtagtgccatttacccccattcactgccagagccgt<br>gagcgcagcgaactgaatgtcacgaaaaagacagcgactcaggtgcctgatggtcggagacaaaag<br>gaatattcagcgatttgcccgagcttgcgagggtgctacttaagcctttagggttttaaggtctgttttgtag<br>aggagcaaacagcgtttgcgacatccttttgtaatactgcggaactgactaaagtagtgagttatacaca<br>gggctgggatctattctttttatctttttttattctttctttattctataaattataaccacttgaatataaacaaaaa<br>aaacacacaaaggtctagcggaatttacagagggtctagcagaatttacaagttttccagcaaaggtcta<br>gcagaatttacagatacccacaactcaaaggaaaaggacatgtaattatcattgactagcccatctcaatt<br>ggtatagtgattaaaatcacctagaccaattgagatgtatgtctgaattagttgttttcaaagcaaatgaact<br>agcgattagtcgctatgacttaacggagcatgaaaccaagctaattttatgctgtgtggcactactcaacc<br>ccacgattgaaaaccctacaaggaaagaacggacggtatcgttcacttataaccaatacgctcagatga<br>tgaacatcagtagggaaaatgcttatggtgtattagctaaagcaaccagagagctgatgacgagaactg<br>tggaaatcaggaatcctttggttaaaggctttgagattttccagtggacaaactatgccaagttctcaagc<br>gaaaaattagaattagtttttagtgaagagatattgccttatcttttccagttaaaaaaattcataaaatataat<br>ctggaacatgttaagtcttttgaaaacaaatactctatgaggatttatgagtggttattaaaagaactaacac<br>aaaagaaaactcacaaggcaaatatagagattagccttgatgaatttaagttcatgttaatgcttgaaaata<br>actaccatgagtttaaaaggcttaaccaatgggttttgaaaccaataagtaaagatttaaacacttacagc<br>aatatgaaattggtggttgataagcgaggccgcccgactgatacgttgattttccaagttgaactagatag<br>acaaatggatctcgtaaccgaacttgagaacaaccagataaaaatgaatggtgacaaataccaacaa<br>ccattacatcagattcctacctacgtaacggactaagaaaaacactacacgatgctttaactgcaaaaatt<br>cagctcaccagttttgaggcaaaatttttgagtgacatgcaaagtaagcatgatctcaatggttcgttctca<br>tggctcacgcaaaaacaacgaaccacactagagaacatactggctaaatacggaaggatctgaggttc<br>ttatggctcttgtatctatcagtgaagcatcaagactaacaaacaaaagtagaacaactgttcaccgttag<br>atatcaaagggaaaactgtccatatgcacagatgaaaacggtgtaaaaaagatagatacatcagagctt<br>ttacgagtttttggtgcatttaaagctgttcaccatgaacagatcgacaatgtaac |
| SEQ ID NO:114 | 63 | chloramphenic ol resistance (BBa_P1004) | | gttgatcgggcacgtaagaggttccaactttcaccataatgaaataagatcactaccgggcgtattttttg<br>agttatcgagattttcaggagctaaggaagctaaaatggagaaaaaaatcacgggatataccaccgttg<br>atatatcccaatggcatcgtaaagaacattttgaggcatttcagtcagttgctcaatgtacctataaccaga<br>ccgttcagctggatattacggcctttttaaagaccgtaaagaaaaataagcacaagttttatccggccttta<br>ttcacattcttgcccgcctgatgaacgctcacccggagtttcgtatggccatgaaagacggtgagctggt<br>gatctgggatagtgttcacccttgttacaccgttttccatgagcaaactgaaacgttttcgtccctctggagt<br>gaataccacgacgatttccggcagtttctccacatatattcgcaagatgtggcgtgttacggtgaaaacct<br>ggcctatttccctaaagggtttattgagaatatgtttttgtctcagccaatccctgggtgagtttcaccagtt<br>ttgatttaaacgtggccaatatggacaacttcttcgcccccgttttcacgatgggcaaatattatacgcaag<br>gcgacaaggtgctgatgccgctggcgatccaggttcatcatgccgtttgtgatggcttccatgtcggcc<br>gcatgcttaatgaattacaacagtactgtgatgagtggcagggcggggcgtaataa |
| SEQ ID NO:115 | 64 | Terminator (BBa_B0053) | | tccggcaaaaaaacgggcaaggtgtcaccaccctgccctttttctttaaaaccgaaaagattacttcgcg<br>tt |
| SEQ ID NO:116 | 65 | VF2 primer sequence (BBa_G00101) | | tgccacctgacgtctaagaa |

FIG. 20 (cont)

| | | | | |
|---|---|---|---|---|
| SEQ ID NO:117 | 66 | Terminator (BBa_B0055) | | aaggaatattcagcaatttgcccgtgccgaagaaaggcccacccgtgaaggtgagccagtgagttgattgctacgtaa |
| SEQ ID NO:118 | 67 | Translational stop (BBa_B0042) | | ttagttagttag |

FIG. 24

| SEQ ID NO: | Name | Sequence |
|---|---|---|
| SEQ ID NO:119 | SynPrgH_RBS | ATTAAACAGGATAATAAGC |
| SEQ ID NO:120 | SynPrgH | ATGGAAACTAGCAAGGAGAAAACGATTACGTCCCCTGGTCCGTATATCGTT<br>CGTCTGTTGAACTCGTCCCTGAACGGTTGTGAATTTCCGCTGCTGACTGGTC<br>GTACGCTGTTCGTCGTGGGTCAGAGCGATGCTCTGACCGCGTCTGGTCAGCT<br>GCCGGACATTCCTGCCGACTCCTTCTTCATCCCGCTGGATCATGGCGGTGTT<br>AATTTCGAGATTCAAGTGGACACTGACGCGACGGAAATCATCCTGCACGAA<br>CTGAAAGAGGGCAACTCCGAGAGCCGCTCCGTGCAACTGAACACCCCGATC<br>CAAGTTGGTGAACTGCTGATTTTGATTCGTCCGGAGAGCGAGCCGTGGGTG<br>CCGGAACAGCCGGAGAAGTTGGAAACTTCTGCGAAAAAGAACGAACCGCG<br>CTTTAAAAACGGCATCGTCGCGGCACTGGCGGGTTTCTTTATCCTGGGTATC<br>GGCACGGTTGGCACCCTGTGGATTCTGAACTCGCCGCAACGTCAAGCAGCC<br>GAATTGGACAGCCTGTTGGGTCAGGAGAAGGAGCGTTTTCAGGTGCTGCCG<br>GGTCGCGACAAGATGCTGTATGTCGCCGCGCAAAACGAACGCGACACCCTG<br>TGGGCACGTCAAGTCCTGGCACGCGGCGATTACGATAAAAACGCACGCGTT<br>ATTAATGAAAATGAGGAGAATAAACGTATCAGCATCTGGCTGGACACGTAT<br>TATCCACAACTGGCATATTACCGTATCCATTTTGATGAACCACGTAAGCCGG<br>TGTTTTGGCTGTCCCGTCAACGCAACACGATGAGCAAGAAAGAGCTGGAGG<br>TGCTGTCCCAGAAATTGCGTGCGCTGATGCCGTACGCCGACAGCGTCAATAT<br>TACTCTGATGGATGACGTGACCGCAGCAGGCCAAGCCGAGGCAGGTCTGAA<br>ACAACAGGCGCTGCCATACAGCCGCCGTAACCACAAAGGTGGTGTTACGTT<br>CGTTATTCAGGGCGCCTTGGACGACGTTGAGATTCTGCGTGCGCGCCAGTTT<br>GTCGACTCCTATTATCGTACCTGGGGTGGTCGTTACGTTCAATTCGCAATTG<br>AATTGAAAGACGATTGGCTGAAAGGCCGCTCGTTCCAATACGGTGCGGAAG<br>GCTACATTAAGATGAGCCCAGGTCATTGGTATTTTCCGTCTCCTCTGTAATA<br>G |
| SEQ ID NO:121 | SynPrgI_RBS | ATTAAAGAGGAGAAATTAAGC |
| SEQ ID NO:122 | SynPrgJ_RBS | ATTAAGGAGGATAAATTAAGC |
| SEQ ID NO:123 | SynPrgJ | ATGTCTATCGCGACTATCGTGCCTGAAAATGCCGTTATTGGTCAAGCGGTGA<br>ATATTCGCAGCATGGAAACGGACATCGTCAGCTTGGACGACCGTTTGCTGC<br>AAGCATTTTCGGGCAGCGCCATCGCTACCGCCGTCGATAAGCAGACCATTA<br>CCAATCGCATTGAAGACCCTAATCTGGTTACCGATCCGAAGGAGCTGGCGA<br>TTAGCCAGGAAATGATTTCCGACTACAATCTGTACGTCAGCATGGTTAGCAC<br>CCTGACGCGTAAGGGCGTTGGCGCTGTTGAGACTTTGCTGCGTTCCTGATAG |
| SEQ ID NO:124 | SynPrgK_RBS | ATTAAACAGGATAATAAGC |
| SEQ ID NO:125 | SynPrgK | ATGATCCGCCGTTACCTGTATACCTTCTTGCTGGTTATGACTTTGGCCGGCTG<br>TAAAGATAAGGATCTGCTGAAAGGCTTGGACCAAGAGCAAGCGAATGAGG<br>TCATTGCGGTTCTGCAAATGCACAACATTGAGGCTAACAAGATTGATAGCG<br>GCAAGCTGGGTTACAGCATTACCGTCGCGGAACCGGATTTCACCGCGGCAG<br>TGTATTGGATTAAGACCTACCAGTTGCCGCCTCGCCCGCGTGTCGAAATCGC<br>CCAAATGTTTCCGGCAGACAGCCTGGTTAGCTCTCCGCGTGCGGAGAAAGC<br>ACGTCTGTACTCGGCGATTGAACAGCGCCTGGAGCAGTCGCTGCAAACGAT<br>GGAAGGTGTTCTGTCGGCCCGTGTCCACATCAGCTATGATATTGATGCGGGC<br>GAGAACGGTCGTCCGCCTAAGCCGGTGCACCTGTCGGCTTTGGCGGTGTAT<br>GAACGCGGTTCCCCTCTGGCCCATCAGATTTCGGATATTAAGCGCTTCCTGA<br>AAAACAGCTTCGCGGATGTTGACTATGATAACATCAGCGTGGTTCTGTCCGA |

FIG. 24 (cont)

| SEQ ID NO: | Name | Sequence |
| --- | --- | --- |
| | | GCGTAGCGACGCACAGTTGCAGGCGCCGGGCACGCCGGTCAAGCGCAATAG<br>CTTCGCTACCTCCTGGATTGTGCTGATTATCCTGTTGTCTGTTATGAGCGCGG<br>GTTTCGGTGTCTGGTACTACAAAAATCACTATGCGCGTAATAAGAAAGGCA<br>TTACTGCCGATGACAAGGCAAAGTCCAGCAACGAGTAATAA |
| SEQ ID NO:126 | SynOrgA_RBS | GAAAGAAGGGACAGACTAG |
| SEQ ID NO:127 | SynOrgA | ATGATTCGTCGTAACCGTCAAATGAACCGTCAACCACTGCCAATTATCTGGC<br>AACGCATTATTTTCGACCCACTGTCCTATATTCACCCACAACGTCTGCAAAT<br>CGCGCCGGAGATGATCGTGCGTCCGGCAGCGCGTGCGGCAGCGAATGAGCT<br>GATTTTGGCGGCGTGGCGTTTGAAGAACGGTGAGAAGGAGTGCATTCAGAA<br>TAGCCTGACGCAGCTGTGGTTGCGTCAATGGCGCCGTCTGCCGCAGGTTGCT<br>TACCTGCTGGGTTGCCACAAGTTGCGTGCTGACCTGGCCCGTCAAGGTGCTT<br>TATTGGGCCTGCCGGACTGGGCGCAGGCATTCTTGGCGATGCACCAGGGTA<br>CGTCCTTGTCGGTTTGTAATAAGGCGCCGAACCACCGTTTCCTGCTGTCCGT<br>TGGTTACGCCCAACTGAACGCGCTGAATGAGTTCCTGCCGGAGAGCTTGGC<br>CCAACGCTTTCCTCTGCTGTTTCCACCGTTCATCGAGGAGGCACTGAAACAA<br>GATGCAGTGGAGATGAGCATCCTGCTGCTGGCCCTGCAATACGCGCAAAAG<br>TATCCTAACACCGTCCCGGCGTTTGCGTGCTAATAA |
| SEQ ID NO:128 | SynOrgB_RBS | GAAAGAAGGGACAGACTAG |
| SEQ ID NO:129 | SynOrgB | ATGTTGAAAAATATCCCGATTCCATCCCCTCTGTCTCCGGTTGAAGGTATCC<br>TGATTAAACGCAAGACGTTGGAGCGTTACTTCTCGATTGAGCGCCTGGAAC<br>AACAGGCGCATCAGCGTGCAAAGCGCATTTTGCGTGAGGCAGAAGAAGAA<br>GCCAAGACCCTGCGCATGTATGCGTACCAGGAGGGCTACGAGCAGGGCATG<br>ATTGACGCACTGCAACAGGTGGCCGCCTATTTGACCGACAACCAGACGATG<br>GCTTGGAAATGGATGGAGAAAATTCAAATCTATGCGCGTGAGTTGTTCAGC<br>GCGGCTGTCGATCACCCGGAAACGTTGTTGACGGTGCTGGACGAGTGGCTG<br>CGTGATTTCGATAAGCCGGAAGGTCAGCTGTTTTTGACCCTGCCGGTGAACG<br>CAAAGAAAGATCATCAGAAACTGATGGTGCTGCTGATGGAAAATTGGCCGG<br>GCACCTTCAATCTGAAGTATCATCAGGAGCAACGTTTTATCATGTCCTGTGG<br>CGATCAGATTGCCGAGTTTTCGCCGGAACAATTTGTTGAAACGGCGGTTGGT<br>GTTATCAAGCACCATCTGGATGAGCTGCCTCAGGACTGTCGCACCATTTCGG<br>ACAATGCGATTAACGCGCTGATTGATGAATGGAAGACGAAAACCCAAGCTG<br>AAGTTATTCGCTGATAA |
| SEQ ID NO:130 | SynInvA_RBS | CTTGGGCACGCGTCCATTAAACAGGAGTAATTAAGC |
| SEQ ID NO:131 | SynInvA | ATGCTGCTGTCCCTGCTGAATAGCGCGCGTCTGCGTCCTGAGCTGCTGATTC<br>TGGTTCTGATGGTTATGATCATCAGCATGTTCGTTATCCCGTTGCCGACCTAT<br>TTGGTTGACTTCTTGATCGCTTTGAACATTGTCCTGGCAATTCTGGTGTTCAT<br>GGGCTCCTTCTACATCGACCGCATTCTGAGCTTCAGCACCTTTCCGGCGGTT<br>CTGCTGATCACGACTCTGTTCCGTTTGGCACTGAGCATCAGCACCAGCCGCC<br>TGATCCTGATTGAAGCAGATGCGGGTGAGATCATCGCGACCTTTGGTCAGTT<br>TGTGATCGGTGACAGCCTGGCGGTTGGTTTCGTCGTATTCTCCATCGTGACG<br>GTGGTGCAGTTTATCGTTATTACCAAGGGCAGCGAACGTGTGGCGGAGGTC<br>GCCGCTCGCTTCAGCCTGGACGGCATGCCGGGTAAACAGATGTCTATTGAT<br>GCAGACCTGAAAGCCGGCATTATTGATGCTGATGCAGCGCGCGAGCGCCGC<br>AGCGTCCTGGAGCGTGAAAGCCAACTGTACGGTTCCTTCGACGGTGCCATG<br>AAGTTCATTAAAGGTGATGCGATTGCGGGCATCATTATCATCTTCGTTAACT<br>TCATTGGCGGTATCAGCGTCGGTATGACCCGTCATGGTATGGATCTGAGCAG<br>CGCCCTGAGCACCTACACCATGCTGACGATTGGTGATGGTCTGGTTGCCCAA<br>ATTCCGGCGTTGCTGATCGCGATTTCTGCGGGCTTCATCGTTACCCGCGTCA |

FIG. 24 (cont)

| SEQ ID NO: | Name | Sequence |
|---|---|---|
| | | ACGGTGATAGCGATAACATGGGTCGTAACATTATGACCCAGCTGCTGAATA<br>ATCCGTTTGTCCTGGTTGTAACGGCGATTTTGACCATCAGCATGGGCACGCT<br>GCCGGGCTTTCCGTTGCCGGTTTTCGTTATTCTGTCTGTTGTGCTGTCCGTCC<br>TGTTTTACTTTAAGTTCCGCGAGGCGAAACGTAGCGCTGCGAAACCAAAAA<br>CGAGCAAGGGCGAGCAACCGTTGTCCATCGAGGAGAAGGAAGGTAGCAGC<br>CTGGGCCTGATTGGCGACCTGGATAAGGTTAGCACGGAAACCGTCCCGCTG<br>ATTTTGCTGGTGCCGAAATCGCGTCGTGAGGATCTGGAGAAAGCGCAGCTG<br>GCGGAACGTCTGCGCAGCCAATTCTTTATTGATTATGGTGTGCGTCTGCCAG<br>AAGTACTGCTGCGTGACGGTGAGGGTCTGGATGACAACTCTATCGTCCTGCT<br>GATTAATGAGATTCGCGTTGAACAGTTTACTGTCTATTTTGACCTGATGCGT<br>GTGGTTAACTACAGCGACGAGGTGGTGAGCTTTGGCATCAACCCGACCATT<br>CACCAGCAAGGTTCCAGCCAGTACTTTTGGGTGACCCATGAGGAAGGCGAA<br>AAGCTGCGCGAGCTGGGCTACGTCCTGCGTAATGCACTGGACGAACTGTAC<br>CACTGTCTGGCGGTGACGCTGGCACGCAATGTGAACGAGTATTTCGGTATCC<br>AAGAAACGAAACACATGCTGGACCAACTGGAAGCAAAGTTTCCTGACCTGC<br>TGAAGGAGGTTTTGCGCCACGCCACCGTGCAGCGCATTTCGGAAGTGCTGC<br>AACGTCTGCTGTCCGAACGCGTGAGCGTCCGTAACATGAAGCTGATCATGG<br>AAGCCCTGGCACTGTGGGCTCCGCGTGAGAAAGATGTGATCAATCTGGTGG<br>AGCACATCCGTGGTGCGATGGCGCGTTATATCTGCCACAAGTTCGCAAATG<br>GTGGTGAACTGCGTGCCGTTATGGTTTCCGCCGAAGTTGAGGATGTCATTCG<br>TAAAGGCATTCGTCAAACTTCTGGCTCCACCTTTTTGAGCTTGGACCCGGAG<br>GCTTCGGCAAATCTGATGGACCTGATCACGCTGAAGCTGGACGACCTGTTG<br>ATTGCGCATAAGGACCTGGTCCTGTTGACCAGCGTTGACGTGCGTCGTTTTA<br>TCAAGAAAATGATTGAAGGTCGTTTTCCGGATCTGGAGGTCCTGTCCTTCGG<br>TGAGATTGCAGATAGCAAAAGCGTGAATGTCATCAAAACCATCTGA |
| SEQ ID NO:132 | SynInvC_RBS | CTTGGGCACGCGTCCATTAAAGAGGACCAATTAAGC |
| SEQ ID NO:133 | SynInvC | ATGAAAACCCCACGTCTGCTGCAATACCTGGCCTACCCGCAGAAAATCACT<br>GGCCCTATCATTGAAGCAGAACTGCGTGATGTTGCAATTGGTGAATTGTGCG<br>AGATCCGTCGCGGCTGGCACCAGAAGCAGGTTGTGGCCCGTGCGCAAGTGG<br>TTGGTTTGCAGCGCGAACGTACCGTCCTGAGCCTGATCGGCAATGCCCAAG<br>GCCTGAGCCGTGATGTGGTCTTGTACCCGACCGGCCGTGCTCTGAGCGCGTG<br>GGTTGGTTACAGCGTTCTGGGCGCAGTACTGGACCCGACGGGTAAAATCGT<br>TGAACGTTTCACCCCGGAAGTCGCACCGATTTCCGAGGAGCGCGTTATCGA<br>CGTGGCACCGCCGAGCTACGCAAGCCGTGTCGGTGTGCGCGAACCGCTGAT<br>CACGGGTGTCCGCGCAATTGATGGTCTGCTGACGTGTGGTGTGGGCCAGCG<br>TATGGGTATTTTCGCAAGCGCGGGTTGTGGTAAGACCATGTTGATGCACATG<br>CTGATCGAGCAAACCGAAGCGGATGTCTTTGTTATTGGCCTGATTGGCGAGC<br>GTGGTCGTGAAGTTACCGAATTTGTAGACATGTTGCGTGCATCTCATAAGAA<br>AGAAAAATGTGTGCTGGTTTTTGCCACGTCCGACTTCCCAAGCGTTGACCGC<br>TGCAACGCTGCCCAGCTGGCAACGACGGTCGCCGAGTATTTCCGCGACCAG<br>GGTAAACGTGTTGTCCTGTTTATCGACAGCATGACCCGTTATGCACGCGCGT<br>TGCGTGATGTCGCGCTGGCGAGCGGCGAGCGTCCGGCTCGCCGTGGTTATC<br>CGGCGTCTGTGTTCGACAATCTGCCGCGTTTGCTGGAGCGTCCGGGTGCGAC<br>GAGCGAGGGTAGCATTACCGCCTTCTATACCGTCCTGCTGGAGTCGGAAGA<br>AGAAGCGGACCCGATGGCGGACGAGATCCGTTCTATTCTGGACGGTCACCT<br>GTACCTGTCCCGCAAACTGGCGGGTCAGGGTCATTACCCGGCTATCGATGTG<br>CTGAAGAGCGTGAGCCGTGTGTTTGGTCAAGTGACCACCCCGACTCACGCG<br>GAGCAAGCGAGCGCGGTCCGTAAGCTGATGACCCGTCTGGAAGAGCTGCAA<br>CTGTTCATTGACCTGGGCGAGTATCGTCCGGGCGAGAACATTGACAATGAT<br>CGTGCGATGCAAATGCGCGATAGCCTGAAGGCGTGGCTGTGTCAGCCTGTT<br>GCGCAATACAGCAGCTTCGATGATACGCTGTCCGGCATGAACGCCTTTGCG<br>GATCAGAACTGA |

FIG. 24 (cont)

| SEQ ID NO: | Name | Sequence |
|---|---|---|
| SEQ ID NO:134 | SynInvE_RBS | TACTTGGGCACGCGTCCATTAATTAGGATCAATAGC |
| SEQ ID NO:135 | SynInvE | ATGATTCCGGGCAGCACCTCCGGTATTTCCTTTAGCCGTATCCTGAGCCGTC AGACCTCCCACCAGGATGCAACCCAGCATACCGACGCACAACAAGCGGAA ATTCAACAAGCGGCGGAAGATAGCTCGCCGGGTGCGGAGGTTCAGAAATTC GTCCAGAGCACGGACGAGATGTCTGCTGCGTTGGCGCAGTTCCGCAATCGC CGTGACTATGAGAAAAAGAGCAGCAATTTGTCTAACTCCTTCGAGCGCGTT CTGGAGGACGAGGCACTGCCGAAAGCGAAGCAGATTCTGAAACTGATCAGC GTGCATGGCGGTGCGTTGGAGGATTTCCTGCGTCAGGCGCGCAGCCTGTTCC CGGACCCAAGCGATCTGGTGCTGGTTCTGCGCGAGCTGTTGCGTCGTAAGG ACCTGGAGGAGATCGTGCGTAAGAAGCTGGAGAGCCTGCTGAAGCACGTGG AGGAACAAACCGACCCGAAAACCCTGAAGGCCGGTATTAACTGCGCGCTGA AGGCGCGTCTGTTTGGCAAGACGCTGTCTCTGAAACCTGGTCTGCTGCGTGC CAGCTACCGCCAGTTCATCCAAAGCGAAAGCCACGAAGTCGAGATTTACAG CGATTGGATCGCCAGCTACGGTTATCAGCGTCGCCTGGTTGTTCTGGATTTC ATTGAAGGCAGCCTGCTGACTGACATCGATGCTAACGATGCAAGCTGCTCC CGTCTGGAGTTTGGCCAACTGCTGCGCCGTCTGACCCAGCTGAAAATGTTGC GTAGCGCCGACCTGCTGTTTGTCTCGACGTTGCTGTCTTACAGCTTCACGAA AGCATTTAACGCTGAGGAGAGCAGCTGGCTGTTGCTGATGCTGTCTTTGCTG CAACAGCCGCACGAAGTGGATAGCCTGCTGGCGGACATTATCGGTCTGAAT GCGCTGCTGTTGTCCCACAAAGAGCACGCCAGCTTCCTGCAAATCTTCTATC AGGTCTGTAAGGCAATCCCGTCTAGCCTGTTTATGAAGAGTACTGGCAAG AAGAACTGCTGATGGCACTGCGCTCCATGACGGACATTGCTTACAAACACG AAATGGCCGAACAACGTCGTACCATCGAAAAGCTGTCCTAA |
| SEQ ID NO:136 | SynInvF_RBS | CTTGGGCACGCGTCCATTAAAAAGGAGTAATTAAGC |
| SEQ ID NO:137 | SynInvF | ATGAGCTTCAGCGAGAGCCGCCACAATGAAAACTGTCTGATTCAAGAAGGC GCACTGCTGTTTGTGAGCAAGCAGTCGTGGCGCCTGTCAGCGGTGATCTGG TTTTTCGTCCGCTGAAAATCGAGGTCCTGAGCAAGCTGCTGGCGTTCATCGA CGGCGCAGGTCTGGTGGATACGACCTACGCGGAGTCGGACAAATGGGTTCT GCTGTCTCCGGAGTTCCGTGCTATTTGGCAAGACCGTAAACGTTGCGAATAT TGGTTTTTGCAGCAGATTATCACCCCATCTCCGGCGTTCAACAAGGTTCTGG CACTGTTGCGTAAGAGCGAAAGCTATTGGTTGGTCGGCTACTTGCTGGCCCA AAGCACCAGCGGCAATACTATGCGTATGTTGGGTGAGGATTACGGTGTTAG CTACACGCATTTCCGCCGTCTGTGCAGCCGCGCTCTGGGCGGTAAGGCGAA AAGCGAGCTGCGCAATTGGCGCATGGCCCAGTCCCTGCTGAATAGCGTGGA AGGTCATGAAAACATCACCCAGCTGGCGGTCAACCACGGTTATAGCAGCCC GTCCCACTTTAGCTCTGAAATCAAGGAGCTGATTGGTGTTTCCCCGCGTAAG CTGTCTAACATCATTCAGCTGGCCGACAAATGA |
| SEQ ID NO:138 | SynInvG_RBS | TGGGCACGCGTCCATTAATGAGGAAAAATTATTAGC |
| SEQ ID NO:139 | SynInvG | ATGAAAACGCACATTCTGTTGGCCCGTGTGCTGGCTTGCGCAGCTCTGGTGC TGGTCACCCCAGGTTATAGCTCCGAGAAGATCCCGGTTACGGGCAGCGGCT TCGTTGCAAAGGACGATTCTCTGCGCACCTTTTTCGATGCGATGGCACTGCA ATTGAAGGAGCCGGTGATTGTCAGCAAGATGGCGGCTCGCAAAAAGATTAC CGGCAATTTCGAGTTCCACGATCCAAACGCGCTGCTGGAGAAACTGTCCCT GCAACTGGGTCTGATCTGGTACTTTGATGGTCAGGCGATCTACATCTACGAC GCGAGCGAAATGCGTAATGCGGTTGTGAGCCTGCGTAATGTCAGCCTGAAC GAGTTCAACAATTTTCTGAAGCGCAGCGGCCTGTACAATAAGAACTACCCT CTGCGTGGTGATAATCGTAAAGGCACCTTCTATGTCAGCGGTCCGCCGGTGT ATGTTGATATGGTTGTAAATGCGGCCACCATGATGGACAAACAGAATGATG |

FIG. 24 (cont)

| SEQ ID NO: | Name | Sequence |
|---|---|---|
| | | GCATCGAGCTGGGTCGCCAAAAGATCGGTGTTATGCGCCTGAACAACACTT TTGTGGGCGACCGCACCTACAACCTGCGTGATCAAAAGATGGTCATTCCGG GTATTGCTACGGCAATTGAACGCCTGTTGCAAGGCGAAGAACAACCGCTGG GTAACATTGTAAGCTCCGAGCCTCCGGCCATGCCGGCCTTTAGCGCAAACG GCGAGAAAGGTAAGGCAGCGAATTACGCGGGTGGTATGAGCCTGCAAGAA GCGCTGAAACAGAACGCAGCGGCAGGCAACATCAAAATTGTGGCCTATCCG GACACCAACAGCCTGCTGGTGAAAGGTACGGCGGAGCAGGTGCATTTCATC GAGATGCTGGTTAAAGCCCTGGACGTGGCGAAACGTCACGTTGAATTGAGC CTGTGGATTGTGGATTTGAATAAGAGCGACCTGGAACGCTTGGGCACCAGC TGGAGCGGTAGCATCACCATCGGCGACAAGCTGGGTGTGAGCCTGAACCAG AGCAGCATCTCCACGCTGGACGGTAGCCGCTTTATTGCGGCGGTCAACGCTC TGGAGGAAAAGAAACAGGCCACTGTTGTCAGCCGTCCGGTTCTGCTGACCC AGGAGAATGTCCCGGCGATTTTTGACAATAATCGTACTTTCTATACCAAACT GATCGGTGAACGTAATGTTGCATTGGAACACGTGACCTATGGCACCATGAT CCGTGTCCTGCCGCGTTTCAGCGCGGACGGCCAGATTGAGATGAGCCTGGA CATCGAAGATGGTAATGACAAAACCCCGCAGTCTGATACGACCACCTCCGT TGATGCGCTGCCAGAAGTGGGTCGTACCCTGATCTCGACGATTGCACGTGTC CCGCATGGTAAATCTCTGCTGGTTGGTGGCTACACGCGTGATGCAAACACG GACACGGTCCAAAGCATCCCGTTCCTGGGTAAGCTGCCGCTGATTGGCTCGT TGTTTCGCTACAGCAGCAAAAACAAGTCTAATGTCGTCCGTGTCTTTATGAT TGAGCCGAAAGAAATCGTTGACCCGCTGACCCCGGATGCCAGCGAGAGCGT TAACAACATTCTGAAACAGTCCGGTGCGTGGAGCGGTGACGATAAGCTGCA AAAGTGGGTTCGTGTGTATTTGGACCGTGGTCAGGAGGCCATTAAGTAA |
| SEQ ID NO:140 | SynInvI_RBS | CTTGGGCACGCGTCCATTAAAAAGGACCAATTAAGC |
| SEQ ID NO:141 | SynInvI | ATGCACTCTCTGACTCGTATCAAGGTCCTGCAACGTCGTTGTACCGTGTTCC ATTCTCAGTGCGAGTCCATTCTGTTGCGTTATCAGGACGAAGATCGCGGCTT GCAGGCGGAGGAGGAGGCCATCCTGGAACAGATCGCAGGTCTGAAACTGCT GTTGGACACCCTGCGTGCTGAAAATCGTCAACTGAGCCGTGAAGAAATCTA TACGCTGCTGCGCAAACAGAGCATTGTTCGTCGCCAGATTAAGGATCTGGA GCTGCAAATCATTCAGATTCAAGAAAAGCGTAGCGAGCTGGAAAAGAAAC GTGAGGAATTTCAAAAGAAAAGCAAATACTGGCTGCGTAAAGAAGGTAACT ACCAGCGCTGGATTATCCGTCAAAAACGCTTCTACATTCAACGTGAGATCCA GCAAGAGGAGGCGGAGAGCGAAGAGATCATTTAA |
| SEQ ID NO:142 | SynInvJ_RBS | AAAAAAAAGCTCTAAAAGATTAAGAGGGGGTAACAT |
| SEQ ID NO:143 | SynInvJ | ATGGGTGACGTGAGCGCGGTGAGCAGCAGCGGTAACATTCTGCTGCCGCAG CAGGACGAGGTTGGTGGCCTGTCCGAAGCGCTGAAGAAAGCGGTTGAAAA ACACAAAACCGAATACAGCGGTGACAAGAAAGATCGTGATTATGGTGACGC CTTTGTTATGCACAAGGAAACCGCGCTGCCGTTGTTGCTGGCAGCTTGGCGC CACGGCGCACCGGCGAAAAGCGAGCACCATAACGGTAACGTAAGCGGTCT GCATCACAACGGTAAGAGCGAGCTGCGTATTGCTGAGAAACTGCTGAAGGT GACGGCGGAGAAGAGCGTTGGTCTGATTAGCGCTGAAGCGAAGGTGGATA AATCTGCGGCGCTGCTGTCTAGCAAGAATCGTCCGCTGGAATCGGTCAGCG GCAAAAAGTTGTCCGCCGATCTGAAAGCAGTGGAGTCCGTGTCCGAGGTCA CGGATAACGCCACCGGCATTTCGGATGACAACATCAAAGCATTGCCGGGTG ACAATAAGGCCATCGCCGGTGAGGGTGTGCGTAAAGAAGGTGCGCCCGCTGG CGCGTGACGTGGCTCCGGCACGCATGGCGGCAGCAAATACGGGCAAGCCGG AGGATAAAGACCACAAGAAGGTCAAGGACGTTAGCCAGCTGCCGCTGCAA CCGACTACCATCGCCGATCTGTCTCAACTGACGGGTGGCGATGAAAAGATG CCGCTGGCAGCGCAGTCCAAACCGATGATGACCATTTTCCCAACCGCCGAC GGCGTTAAAGGTGAGGACAGCTCTCTGACCTATCGTTTCCAGCGCTGGGGC |

FIG. 24 (cont)

| SEQ ID NO: | Name | Sequence |
|---|---|---|
| | | AACGATTACTCCGTCAATATCCAGGCACGCCAAGCGGGCGAATTTAGCCTG ATTCCTAGCAATACCCAGGTTGAACATCGTCTGCACGACCAATGGCAAAAT GGCAATCCACAACGCTGGCATTTGACGCGTGATGACCAGCAAAACCCGCAA CAGCAACAGCATCGTCAGCAGTCCGGTGAAGAGGACGACGCGTAA |
| SEQ ID NO:144 | SynSpaO_RBS | CTTGGGCACGCGTCCATGAAAGACAGGACCCACTAG |
| SEQ ID NO:145 | SynSpaO | ATGAGCTTGCGCGTACGCCAAATTGACCGCCGTGAATGGCTGCTGGCCCAG ACTGCGACCGAATGTCAGCGTCACGGTCGTGAGGCCACCCTGGAGTATCCG ACCCGTCAGGGTATGTGGGTCCGCCTGTCTGATGCCGAAAAACGCTGGTCT GCGTGGATCAAACCGGGTGATTGGTTGGAACACGTTAGCCCAGCACTGGCG GGTGCCGCGGTCAGCGCAGGCGCGGAGCACCTGGTGGTTCCGTGGCTGGCG GCAACCGAACGCCCGTTCGAGCTGCCGGTCCCGCACTTGAGCTGCCGTCGTC TGTGCGTGGAGAACCCGGTTCCGGGTTCCGCACTGCCTGAGGGCAAGCTGC TGCACATCATGTCGGATCGTGGTGGCCTGTGGTTTGAGCATCTGCCGGAGCT GCCGGCTGTTGGCGGTGGCCGTCCGAAGATGCTGCGTTGGCCGCTGCGTTTC GTTATTGGCAGCAGCGACACCCAGCGCAGCCTGCTGGGTCGTATCGGTATC GGTGATGTTCTGCTGATCCGCACCAGCCGTGCTGAGGTTTACTGTTACGCGA AGAAACTGGGCCACTTTAATCGTGTGGAAGGTGGCATTATTGTCGAAACGC TGGACATTCAACATATCGAGGAGGAGAACAACACGACGGAAACGGCGGAA ACCCTGCCGGGTCTGAATCAACTGCCGGTGAAGCTGGAGTTCGTTCTGTATC GTAAAAACGTGACGTTGGCCGAACTGGAAGCAATGGGTCAGCAACAACTGC TGTCCTTGCCAACCAATGCGGAACTGAACGTCGAAATCATGGCGAATGGCG TGCTGCTGGGTAACGGCGAACTGGTGCAGATGAATGACACCCTGGGTGTCG AGATTCATGAGTGGTTGTCCGAGAGCGGTAATGGCGAGTAG |
| SEQ ID NO:146 | SynSpaP_RBS | CTTGGGCACGCGTCCATGAAAGAAACGACATACTAG |
| SEQ ID NO:147 | SynSpaP | ATGGGTAACGATATTAGCTTGATTGCATTGCTGGCGTTTTCCACCCTGCTGC CGTTCATCATCGCGTCTGGTACTTGCTTCGTCAAATTCAGCATCGTCTTTGTG ATGGTGCGCAACGCGCTGGGTCTGCAACAAATTCCAAGCAATATGACCCTG AATGGCGTCGCACTGCTGCTGTCGATGTTTGTTATGTGGCCGATTATGCACG ACGCGTATGTGTATTTCGAGGATGAAGATGTGACCTTTAACGACATCTCCAG CCTGAGCAAGCATGTTGATGAGGGCCTGGACGGTTATCGCGACTACCTGAT CAAGTATTCCGACCGTGAGCTGGTGCAGTTCTTTGAGAATGCCCAGTTGAAA CGTCAGTACGGTGAAGAAACGGAAACCGTTAAACGTGACAAGGACGAGAT TGAAAAGCCGAGCATTTTCGCACTGTTGCCTGCTTACGCCTTGAGCGAGATT AAGAGCGCATTCAAAATTGGTTTTTACCTGTACCTGCCGTTCGTTGTGGTCG ATCTGGTTGTCTCCAGCGTTCTGCTGGCCCTGGGCATGATGATGATGTCCCC GGTTACCATCAGCACGCCGATCAAACTGGTCCTGTTTGTGGCCCTGGATGGT TGGACGCTGCTGTCTAAAGGCCTGATCCTGCAATACATGGACATCGCGACCT AA |
| SEQ ID NO:148 | SynSpaQ_RBS | CTTGGGCACGCGTCCATTAAGAAGGAGGAATTAAGC |
| SEQ ID NO:149 | SynSpaQ | ATGGACGATCTGGTTTTCGCCGGCAACAAAGCCCTGTACTTGGTGCTGATTC TGTCCGGTTGGCCGACGATTGTCGCAACCATTATCGGTCTGCTGGTTGGTCT GTTTCAAACCGTGACGCAGTTGCAGGAGCAAACCCTGCCGTTCGGTATCAA GCTGCTGGGTGTGTGTCTGTGCCTGTTTTTGCTGTCTGGCTGGTATGGCGAA GTTCTGCTGTCCTACGGCCGTCAGGTCATCTTCCTGGCTCTGGCGAAAGGTT AA |
| SEQ ID NO:150 | SynSpaR_RBS | CTTGGGCACGCGTCCATGAAAGACAGGACCCACTAG |

FIG. 24 (cont)

| SEQ ID NO: | Name | Sequence |
|---|---|---|
| SEQ ID NO:151 | SynSpaR | ATGTTCTATGCATTGTATTTTGAGATCCACCATCTGGTGGCGTCCGCGGCTC TGGGTTTTGCGCGTGTTGCTCCGATCTTTTTCTTTCTGCCGTTCCTGAATAGC GGTGTCCTGAGCGGTGCTCCGCGCAACGCGATCATCATTCTGGTGGCGCTGG GTGTATGGCCGCACGCCCTGAATGAGGCGCCACCGTTTCTGTCTGTGGCAAT GATTCCGCTGGTCCTGCAAGAGGCAGCCGTGGGTGTTATGCTGGGTTGCCTG TTGTCCTGGCCGTTTTGGGTTATGCACGCGTTGGGCTGTATCATTGATAACC AACGCGGTGCAACCCTGTCCAGCAGCATTGATCCTGCGAATGGCATCGACA CCAGCGAGATGGCCAATTTCCTGAACATGTTCGCGGCTGTCGTGTATTTGCA GAACGGTGGCTTGGTCACGATGGTGGACGTGCTGAATAAGTCTTACCAGCT GTGTGATCCGATGAACGAGTGTACGCCGAGCCTGCCTCCGTTGCTGACCTTC ATTAATCAAGTGGCCCAGAACGCACTGGTGCTGGCGTCCCCGGTCGTTCTGG TTCTGCTGCTGTCGGAAGTTTTCCTGGGCCTGCTGTCTCGTTTTGCACCGCAA ATGAACGCGTTCGCCATTAGCCTGACTGTTAAAAGCGGTATTGCGGTTTTGA TCATGCTGCTGTATTTCAGCCCGGTCCTGCCGGACAATGTTCTGCGTCTGAG CTTTCAGGCGACCGGCCTGAGCAGCTGGTTCTACGAACGTGGCGCAACGCA TGTGCTGGAATAA |
| SEQ ID NO:152 | SynSpaS_RBS | CTTGGGCACGCGTCCATGAAAGACAGGACCCACTAG |
| SEQ ID NO:153 | SynSpaS | ATGTCCAGCAACAAAACCGAAAAACCGACTAAGAAACGTCTGGAGGATAG CGCAAAGAAAGGTCAGAGCTTCAAGAGCAAGGACCTGATTATCGCGTGCCT GACCCTGGGTGGTATCGCTTATTTGGTGAGCTACGGCAGCTTCAATGAGTTT ATGGGTATCATTAAGATTATCATCGCTGATAACTTTGATCAGTCGATGGCAG ATTATAGCCTGGCCGTGTTTGGTATTGGCCTGAAATACCTGATTCCGTTCAT GCTGCTGTGTTTGGTTTGTTCCGCACTGCCGGCACTGCTGCAAGCGGGCTTC GTTCTGGCAACCGAGGCCCTGAAGCCGAATCTGTCCGCCCTGAACCCGGTT GAAGGCGCGAAGAAACTGTTTTCCATGCGCACCGTCAAAGACACGGTCAAG ACGCTGCTGTATCTGTCGAGCTTTGTGGTTGCGGCAATCATTTGCTGGAAAA AGTATAAAGTCGAGATTTTCAGCCAACTGAACGGTAATATCGTGGGTATTG CGGTTATCTGGCGTGAATTGCTGCTGGCGTTGGTTCTGACCTGTCTGGCGTG CGCGCTGATCGTGCTGTTGCTGGATGCTATTGCCGAGTACTTTCTGACCATG AAAGATATGAAGATGGACAAAGAAGAAGTTAAACGCGAGATGAAAGAGCA GGAGGGTAACCCGGAGGTGAAGTCTAAACGTCGTGAAGTCCACATGGAAAT CCTGAGCGAACAAGTCAAGTCTGACATTGAAAATAGCCGTCTGATTGTGGC AAACCCTACGCATATTACCATCGGCATCTACTTCAAACCGGAACTGATGCCG ATTCCAATGATTAGCGTCTATGAAACCAATCAACGCGCGCTGGCGGTCCGT GCGTACGCCGAGAAAGTGGGTGTTCCGGTTATTGTAGACATCAAGCTGGCG CGCAGCCTGTTCAAAACGCACCGTCGTTACGACCTGGTGAGCCTGGAGGAG ATCGACGAGGTTTTGCGCCTGCTGGTTTGGTTGGAAGAGGTCGAAAACGCA GGCAAGGATGTGATCCAACCGCAGGAGAATGAAGTGCGTCATTAA |
| SEQ ID NO:154 | Syn_PrgOrg_Operon | GCATGCATTAAAGAGGAGAAATTAAGCATGGCTACTCCGTGGTCTGGTTAT CTGGATGATGTTTCTGCAAAATTTGACACGGGTGTTGACAACTTGCAAACCC AAGTTACCGAAGCCCTGGACAAGCTGGCTGCGAAGCCGTCCGATCCGGCGC TGCTGGCGGCGTATCAATCCAAACTGTCTGAGTATAACTTGTACCGTAATGC GCAGTCGAACACGGTCAAGGTCTTCAAAGATATTGATGCAGCGATTATTCA GAACTTTCGTTAGTAACCTAGGATTAAGGAGGATAAATTAAGCATGTCTATC GCGACTATCGTGCCTGAAAATGCCGTTATTGGTCAAGCGGTGAATATTCGCA GCATGGAAACGGACATCGTCAGCTTGGACGACCGTTTGCTGCAAGCATTTTC GGGCAGCGCCATCGCTACCGCCGTCGATAAGCAGACCATTACCAATCGCAT TGAAGACCCTAATCTGGTTACCGATCCGAAGGAGCTGGCGATTAGCCAGGA AATGATTTCCGACTACAATCTGTACGTCAGCATGGTTAGCACCCTGACGCGT AAGGGCGTTGGCGCTGTTGAGACTTTGCTGCGTTCCTGATAGGCTAGCATTA AACAGGATAATAAGCATGGAAACTAGCAAGGAGAAAACGATTACGTCCCCT GGTCCGTATATCGTTCGTCTGTTGAACTCGTCCCTGAACGGTTGTGAATTTC |

FIG. 24 (cont)

| SEQ ID NO: | Name | Sequence |
|---|---|---|
| | | CGCTGCTGACTGGTCGTACGCTGTTCGTCGTGGGTCAGAGCGATGCTCTGAC<br>CGCGTCTGGTCAGCTGCCGGACATTCCTGCCGACTCCTTCTTCATCCCGCTG<br>GATCATGGCGGTGTTAATTTCGAGATTCAAGTGGACACTGACGCGACGGAA<br>ATCATCCTGCACGAACTGAAAGAGGGCAACTCCGAGAGCCGCTCCGTGCAA<br>CTGAACACCCCGATCCAAGTTGGTGAACTGCTGATTTTGATTCGTCCGGAGA<br>GCGAGCCGTGGGTGCCGGAACAGCCGGAGAAGTTGGAAACTTCTGCGAAA<br>AAGAACGAACCGCGCTTTAAAAACGGCATCGTCGCGGCACTGGCGGGTTTC<br>TTTATCCTGGGTATCGGCACGGTTGGCACCCTGTGGATTCTGAACTCGCCGC<br>AACGTCAAGCAGCCGAATTGGACAGCCTGTTGGGTCAGGAGAAGGAGCGTT<br>TTCAGGTGCTGCCGGGTCGCGACAAGATGCTGTATGTCGCCGCGCAAAACG<br>AACGCGACACCCTGTGGGCACGTCAAGTCCTGGCACGCGGCGATTACGATA<br>AAAACGCACGCGTTATTAATGAAAATGAGGAGAATAAACGTATCAGCATCT<br>GGCTGGACACGTATTATCCACAACTGGCATATTACCGTATCCATTTTGATGA<br>ACCACGTAAGCCGGTGTTTTGGCTGTCCCGTCAACGCAACACGATGAGCAA<br>GAAAGAGCTGGAGGTGCTGTCCCAGAAATTGCGTGCGCTGATGCCGTACGC<br>CGACAGCGTCAATATTACTCTGATGGATGACGTGACCGCAGCAGGCCAAGC<br>CGAGGCAGGTCTGAAACAACAGGCGCTGCCATACAGCCGCCGTAACCACAA<br>AGGTGGTGTTACGTTCGTTATTCAGGGCGCCTTGGACGACGTTGAGATTCTG<br>CGTGCGCGCCAGTTTGTCGACTCCTATTATCGTACCTGGGGTGGTCGTTACG<br>TTCAATTCGCAATTGAATTGAAAGACGATTGGCTGAAAGGCCGCTCGTTCCA<br>ATACGGTGCGGAAGGCTACATTAAGATGAGCCCAGGTCATTGGTATTTTCC<br>GTCTCCTCTGTAATAGAAGCTTATTAAACAGGATAATAAGCATGATCCGCCG<br>TTACCTGTATACCTTCTTGCTGGTTATGACTTTGGCCGGCTGTAAAGATAAG<br>GATCTGCTGAAAGGCTTGGACCAAGAGCAAGCGAATGAGGTCATTGCGGTT<br>CTGCAAATGCACAACATTGAGGCTAACAAGATTGATAGCGGCAAGCTGGGT<br>TACAGCATTACCGTCGCGGAACCGGATTTCACCGCGGCAGTGTATTGGATTA<br>AGACCTACCAGTTGCCGCCTCGCCCGCGTGTCGAAATCGCCCAAATGTTTCC<br>GGCAGACAGCCTGGTTAGCTCTCCGCGTGCGGAGAAAGCACGTCTGTACTC<br>GGCGATTGAACAGCGCCTGGAGCAGTCGCTGCAAACGATGGAAGGTGTTCT<br>GTCGGCCCGTGTCCACATCAGCTATGATATTGATGCGGGCGAGAACGGTCG<br>TCCGCCTAAGCCGGTGCACCTGTCGGCTTTGGCGGTGTATGAACGCGGTTCC<br>CCTCTGGCCCATCAGATTTCGGATATTAAGCGCTTCCTGAAAAACAGCTTCG<br>CGGATGTTGACTATGATAACATCAGCGTGGTTCTGTCCGAGCGTAGCGACG<br>CACAGTTGCAGGCGCCGGGCACGCCGGTCAAGCGCAATAGCTTCGCTACCT<br>CCTGGATTGTGCTGATTATCCTGTTGTCTGTTATGAGCGCGGGTTTCGGTGTC<br>TGGTACTACAAAAATCACTATGCGCGTAATAAGAAAGGCATTACTGCCGAT<br>GACAAGGCAAAGTCCAGCAACGAGTAATAAGGTACCGAAAGAAGGGACAG<br>ACTAGATGATTCGTCGTAACCGTCAAATGAACCGTCAACCACTGCCAATTAT<br>CTGGCAACGCATTATTTTCGACCCACTGTCCTATATTCACCCACAACGTCTG<br>CAAATCGCGCCGGAGATGATCGTGCGTCCGGCAGCGCGTGCGGCAGCGAAT<br>GAGCTGATTTTGGCGGCGTGGCGTTTGAAGAACGGTGAGAAGGAGTGCATT<br>CAGAATAGCCTGACGCAGCTGTGGTTGCGTCAATGGCGCCGTCTGCCGCAG<br>GTTGCTTACCTGCTGGGTTGCCACAAGTTGCGTGCTGACCTGGCCCGTCAAG<br>GTGCTTTATTGGGCCTGCCGGACTGGGCGCAGGCATTCTTGGCGATGCACCA<br>GGGTACGTCCTTGTCGGTTTGTAATAAGGCGCCGAACCACCGTTTCCTGCTG<br>TCCGTTGGTTACGCCCAACTGAACGCGCTGAATGAGTTCCTGCCGGAGAGCT<br>TGGCCCAACGCTTTCCTCTGCTGTTTCCACCGTTCATCGAGGAGGCACTGAA<br>ACAAGATGCAGTGGAGATGAGCATCCTGCTGCTGGCCCTGCAATACGCGCA<br>AAAGTATCCTAACACCGTCCCGGCGTTTGCGTGCTAATAAAGATCTGAAAG<br>AAGGGACAGACTAGATGTTGAAAAATATCCCGATTCCATCCCCTCTGTCTCC<br>GGTTGAAGGTATCCTGATTAAACGCAAGACGTTGGAGCGTTACTTCTCGATT<br>GAGCGCCTGGAACAACAGGCGCATCAGCGTGCAAAGCGCATTTTGCGTGAG<br>GCAGAAGAAGAAGCCAAGACCCTGCGCATGTATGCGTACCAGGAGGGCTA<br>CGAGCAGGGCATGATTGACGCACTGCAACAGGTGGCCGCCTATTTGACCGA<br>CAACCAGACGATGGCTTGGAAATGGATGGAGAAAATTCAAATCTATGCGCG<br>TGAGTTGTTCAGCGCGGCTGTCGATCACCCGGAAACGTTGTTGACGGTGCTG |

FIG. 24 (cont)

| SEQ ID NO: | Name | Sequence |
|---|---|---|
| | | GACGAGTGGCTGCGTGATTTCGATAAGCCGGAAGGTCAGCTGTTTTTGACCC<br>TGCCGGTGAACGCAAAGAAAGATCATCAGAAACTGATGGTGCTGCTGATGG<br>AAAATTGGCCGGGCACCTTCAATCTGAAGTATCATCAGGAGCAACGTTTTAT<br>CATGTCCTGTGGCGATCAGATTGCCGAGTTTTCGCCGGAACAATTTGTTGAA<br>ACGGCGGTTGGTGTTATCAAGCACCATCTGGATGAGCTGCCTCAGGACTGTC<br>GCACCATTTCGGACAATGCGATTAACGCGCTGATTGATGAATGGAAGACGA<br>AAACCCAAGCTGAAGTTATTCGCTGATAAGGATCCGGCATCAAATAAAACG<br>AAAGGCTCAGTCGAAAGACTGGGCCTTTCGTTTTATCTGTTGTTTGTCGGTG<br>AACGCTCTCCTGAGTAGGACAAATCCGCCGCCCTAGAACTAGTccataagaatGC<br>GGCCGC |
| SEQ ID NO:155 | Syn_InvSpa_ Operon | CTCGAGAAAAAAAAGCTCTAAAAGATTAAGAGGGGGTAACATATGGGTGA<br>CGTGAGCGCGGTGAGCAGCAGCGGTAACATTCTGCTGCCGCAGCAGGACGA<br>GGTTGGTGGCCTGTCCGAAGCGCTGAAGAAAGCGGTTGAAAAACACAAAAC<br>CGAATACAGCGGTGACAAGAAAGATCGTGATTATGGTGACGCCTTTGTTAT<br>GCACAAGGAAACCGCGCTGCCGTTGTTGCTGGCAGCTTGGCGCCACGGCGC<br>ACCGGCGAAAAGCGAGCACCATAACGGTAACGTAAGCGGTCTGCATCACAA<br>CGGTAAGAGCGAGCTGCGTATTGCTGAGAAACTGCTGAAGGTGACGGCGGA<br>GAAGAGCGTTGGTCTGATTAGCGCTGAAGCGAAGGTGGATAAATCTGCGGC<br>GCTGCTGTCTAGCAAGAATCGTCCGCTGGAATCGGTCAGCGGCAAAAAGTT<br>GTCCGCCGATCTGAAAGCAGTGGAGTCCGTGTCCGAGGTCACGGATAACGC<br>CACCGGCATTTCGGATGACAACATCAAAGCATTGCCGGGTGACAATAAGGC<br>CATCGCCGGTGAGGGTGTGCGTAAAGAAGGTGCGCCGCTGGCGCGTGACGT<br>GGCTCCGGCACGCATGGCGGCAGCAAATACGGGCAAGCCGGAGGATAAAG<br>ACCACAAGAAGGTCAAGGACGTTAGCCAGCTGCCGCTGCAACCGACTACCA<br>TCGCCGATCTGTCTCAACTGACGGGTGGCGATGAAAAGATGCCGCTGGCAG<br>CGCAGTCCAAACCGATGATGACCATTTTCCCAACCGCCGACGGCGTTAAAG<br>GTGAGGACAGCTCTCTGACCTATCGTTTCCAGCGCTGGGGCAACGATTACTC<br>CGTCAATATCCAGGCACGCCAAGCGGGCGAATTTAGCCTGATTCCTAGCAA<br>TACCCAGGTTGAACATCGTCTGCACGACCAATGGCAAAATGGCAATCCACA<br>ACGCTGGCATTTGACGCGTGATGACCAGCAAAACCCGCAACAGCAACAGCA<br>TCGTCAGCAGTCCGGTGAAGAGGACGACGCGTAACTTGGGCACGCGTCCAT<br>TAAGAAGGAGGAATTAAGCATGGACGATCTGGTTTTCGCCGGCAACAAAGC<br>CCTGTACTTGGTGCTGATTCTGTCCGGTTGGCCGACGATTGTCGCAACCATT<br>ATCGGTCTGCTGGTTGGTCTGTTTCAAACCGTGACGCAGTTGCAGGAGCAAA<br>CCCTGCCGTTCGGTATCAAGCTGCTGGGTGTGTGTCTGTGCCTGTTTTTGCTG<br>TCTGGCTGGTATGGCGAAGTTCTGCTGTCCTACGGCCGTCAGGTCATCTTCC<br>TGGCTCTGGCGAAAGGTTAAGACGTCCTTGGGCACGCGTCCATTAAACAGG<br>AGTAATTAAGCATGCTGCTGTCCCTGCTGAATAGCGCGCGTCTGCGTCCTGA<br>GCTGCTGATTCTGGTTCTGATGGTTATGATCATCAGCATGTTCGTTATCCCGT<br>TGCCGACCTATTTGGTTGACTTCTTGATCGCTTTGAACATTGTCCTGGCAATT<br>CTGGTGTTCATGGGCTCCTTCTACATCGACCGCATTCTGAGCTTCAGCACCT<br>TTCCGGCGGTTCTGCTGATCACGACTCTGTTCCGTTTGGCACTGAGCATCAG<br>CACCAGCCGCCTGATCCTGATTGAAGCAGATGCGGGTGAGATCATCGCGAC<br>CTTTGGTCAGTTTGTGATCGGTGACAGCCTGGCGGTTGGTTTCGTCGTATTCT<br>CCATCGTGACGGTGGTGCAGTTTATCGTTATTACCAAGGGCAGCGAACGTGT<br>GGCGGAGGTCGCCGCTCGCTTCAGCCTGGACGGCATGCCGGGTAAACAGAT<br>GTCTATTGATGCAGACCTGAAAGCCGGCATTATTGATGCTGATGCAGCGCG<br>CGAGCGCCGCAGCGTCCTGGAGCGTGAAAGCCAACTGTACGGTTCCTTCGA<br>CGGTGCCATGAAGTTCATTAAAGGTGATGCGATTGCGGGCATCATTATCATC<br>TTCGTTAACTTCATTGGCGGTATCAGCGTCGGTATGACCCGTCATGGTATGG<br>ATCTGAGCAGCGCCCTGAGCACCTACACCATGCTGACGATTGGTGATGGTCT<br>GGTTGCCCAAATTCCGGCGTTGCTGATCGCGATTTCTGCGGGCTTCATCGTT<br>ACCCGCGTCAACGGTGATAGCGATAACATGGGTCGTAACATTATGACCCAG<br>CTGCTGAATAATCCGTTTGTCCTGGTTGTAACGGCGATTTTGACCATCAGCA<br>TGGGCACGCTGCCGGGCTTTCCGTTGCCGGTTTTCGTTATTCTGTCTGTTGTG |

FIG. 24 (cont)

| SEQ ID NO: | Name | Sequence |
|---|---|---|
| | | CTGTCCGTCCTGTTTTACTTTAAGTTCCGCGAGGCGAAACGTAGCGCTGCGA<br>AACCAAAAACGAGCAAGGGCGAGCAACCGTTGTCCATCGAGGAGAAGGAA<br>GGTAGCAGCCTGGGCCTGATTGGCGACCTGGATAAGGTTAGCACGGAAACC<br>GTCCCGCTGATTTTGCTGGTGCCGAAATCGCGTCGTGAGGATCTGGAGAAA<br>GCGCAGCTGGCGGAACGTCTGCGCAGCCAATTCTTTATTGATTATGGTGTGC<br>GTCTGCCAGAAGTACTGCTGCGTGACGGTGAGGGTCTGGATGACAACTCTA<br>TCGTCCTGCTGATTAATGAGATTCGCGTTGAACAGTTTACTGTCTATTTTGAC<br>CTGATGCGTGTGGTTAACTACAGCGACGAGGTGGTGAGCTTTGGCATCAAC<br>CCGACCATTCACCAGCAAGGTTCCAGCCAGTACTTTTGGGTGACCCATGAG<br>GAAGGCGAAAAGCTGCGCGAGCTGGGCTACGTCCTGCGTAATGCACTGGAC<br>GAACTGTACCACTGTCTGGCGGTGACGCTGGCACGCAATGTGAACGAGTAT<br>TTCGGTATCCAAGAAACGAAACACATGCTGGACCAACTGGAAGCAAAGTTT<br>CCTGACCTGCTGAAGGAGGTTTTGCGCCACGCCACCGTGCAGCGCATTTCGG<br>AAGTGCTGCAACGTCTGCTGTCCGAACGCGTGAGCGTCCGTAACATGAAGC<br>TGATCATGGAAGCCCTGGCACTGTGGGCTCCGCGTGAGAAAGATGTGATCA<br>ATCTGGTGGAGCACATCCGTGGTGCGATGGCGCGTTATATCTGCCACAAGTT<br>CGCAAATGGTGGTGAACTGCGTGCCGTTATGGTTTCCGCCGAAGTTGAGGA<br>TGTCATTCGTAAAGGCATTCGTCAAACTTCTGGCTCCACCTTTTTGAGCTTG<br>GACCCGGAGGCTTCGGCAAATCTGATGGACCTGATCACGCTGAAGCTGGAC<br>GACCTGTTGATTGCGCATAAGGACCTGGTCCTGTTGACCAGCGTTGACGTGC<br>GTCGTTTTATCAAGAAAATGATTGAAGGTCGTTTTCCGGATCTGGAGGTCCT<br>GTCCTTCGGTGAGATTGCAGATAGCAAAAGCGTGAATGTCATCAAAACCAT<br>CTGAATTTAAATCTTGGGCACGCGTCCATTAAAAAGGAGTAATTAAGCATG<br>AGCTTCAGCGAGAGCCGCCACAATGAAAACTGTCTGATTCAAGAAGGCGCA<br>CTGCTGTTTTGTGAGCAAGCAGTCGTGGCGCCTGTCAGCGGTGATCTGGTTT<br>TTCGTCCGCTGAAAATCGAGGTCCTGAGCAAGCTGCTGGCGTTCATCGACG<br>GCGCAGGTCTGGTGGATACGACCTACGCGGAGTCGGACAAATGGGTTCTGC<br>TGTCTCCGGAGTTCCGTGCTATTTGGCAAGACCGTAAACGTTGCGAATATTG<br>GTTTTTGCAGCAGATTATCACCCCATCTCCGGCGTTCAACAAGGTTCTGGCA<br>CTGTTGCGTAAGAGCGAAAGCTATTGGTTGGTCGGCTACTTGCTGGCCCAAA<br>GCACCAGCGGCAATACTATGCGTATGTTGGGTGAGGATTACGGTGTTAGCT<br>ACACGCATTTCCGCCGTCTGTGCAGCCGCGCTCTGGGCGGTAAGGCGAAAA<br>GCGAGCTGCGCAATTGGCGCATGGCCCAGTCCCTGCTGAATAGCGTGGAAG<br>GTCATGAAAACATCACCCAGCTGGCGGTCAACCACGGTTATAGCAGCCCGT<br>CCCACTTTAGCTCTGAAATCAAGGAGCTGATTGGTGTTTCCCCGCGTAAGCT<br>GTCTAACATCATTCAGCTGGCCGACAAATGAATTTAAATGCTAGCCTTGGGC<br>ACGCGTCCATTAAAGAGGACCAATTAAGCATGAAAACCCCACGTCTGCTGC<br>AATACCTGGCCTACCCGCAGAAAATCACTGGCCCTATCATTGAAGCAGAAC<br>TGCGTGATGTTGCAATTGGTGAATTGTGCGAGATCCGTCGCGGCTGGCACCA<br>GAAGCAGGTTGTGGCCCGTGCGCAAGTGGTTGGTTTGCAGCGCGAACGTAC<br>CGTCCTGAGCCTGATCGGCAATGCCCAAGGCCTGAGCCGTGATGTGGTCTTG<br>TACCCGACCGGCCGTGCTCTGAGCGCGTGGGTTGGTTACAGCGTTCTGGGCG<br>CAGTACTGGACCCGACGGGTAAAATCGTTGAACGTTTCACCCCGGAAGTCG<br>CACCGATTTCCGAGGAGCGCGTTATCGACGTGGCACCGCCGAGCTACGCAA<br>GCCGTGTCGGTGTGCGCGAACCGCTGATCACGGGTGTCCGCGCAATTGATG<br>GTCTGCTGACGTGTGGTGTGGGCCAGCGTATGGGTATTTTCGCAAGCGCGG<br>GTTGTGGTAAGACCATGTTGATGCACATGCTGATCGAGCAAACCGAAGCGG<br>ATGTCTTTGTTATTGGCCTGATTGGCGAGCGTGGTCGTGAAGTTACCGAATT<br>TGTAGACATGTTGCGTGCATCTCATAAGAAAGAAAAATGTGTGCTGGTTTTT<br>GCCACGTCCGACTTCCCAAGCGTTGACCGCTGCAACGCTGCCCAGCTGGCA<br>ACGACGGTCGCCGAGTATTTCCGCGACCAGGGTAAACGTGTTGTCCTGTTTA<br>TCGACAGCATGACCCGTTATGCACGCGCGTTGCGTGATGTCGCGCTGGCGA<br>GCGGCGAGCGTCCGGCTCGCCGTGGTTATCCGGCGTCTGTGTTCGACAATCT<br>GCCGCGTTTGCTGGAGCGTCCGGGTGCGACGAGCGAGGGTAGCATTACCGC<br>CTTCTATACCGTCCTGCTGGAGTCGGAAGAAGAAGCGGACCCGATGGCGGA<br>CGAGATCCGTTCTATTCTGGACGGTCACCTGTACCTGTCCCGCAAACTGGCG |

FIG. 24 (cont)

| SEQ ID NO: | Name | Sequence |
|---|---|---|
| | | GGTCAGGGTCATTACCCGGCTATCGATGTGCTGAAGAGCGTGAGCCGTGTG TTTGGTCAAGTGACCACCCCGACTCACGCGGAGCAAGCGAGCGCGGTCCGT AAGCTGATGACCCGTCTGGAAGAGCTGCAACTGTTCATTGACCTGGGCGAG TATCGTCCGGGCGAGAACATTGACAATGATCGTGCGATGCAAATGCGCGAT AGCCTGAAGGCGTGGCTGTGTCAGCCTGTTGCGCAATACAGCAGCTTCGAT GATACGCTGTCCGGCATGAACGCCTTTGCGGATCAGAACTGACTTGGGCAC GCGTCCATGAAAGAAACGACATACTAGATGGGTAACGATATTAGCTTGATT GCATTGCTGGCGTTTTCCACCCTGCTGCCGTTCATCATCGCGTCTGGTACTTG CTTCGTCAAATTCAGCATCGTCTTTGTGATGGTGCGCAACGCGCTGGGTCTG CAACAAATTCCAAGCAATATGACCCTGAATGGCGTCGCACTGCTGCTGTCG ATGTTTGTTATGTGGCCGATTATGCACGACGCGTATGTGTATTTCGAGGATG AAGATGTGACCTTTAACGACATCTCCAGCCTGAGCAAGCATGTTGATGAGG GCCTGGACGGTTATCGCGACTACCTGATCAAGTATTCCGACCGTGAGCTGGT GCAGTTCTTTGAGAATGCCCAGTTGAAACGTCAGTACGGTGAAGAAACGGA AACCGTTAAACGTGACAAGGACGAGATTGAAAAGCCGAGCATTTTCGCACT GTTGCCTGCTTACGCCTTGAGCGAGATTAAGAGCGCATTCAAAATTGGTTTT TACCTGTACCTGCCGTTCGTTGTGGTCGATCTGGTTGTCTCCAGCGTTCTGCT GGCCCTGGGCATGATGATGATGTCCCCGGTTACCATCAGCACGCCGATCAA ACTGGTCCTGTTTGTGGCCCTGGATGGTTGGACGCTGCTGTCTAAAGGCCTG ATCCTGCAATACATGGACATCGCGACCTAAGAGCTCTGGGCACGCGTCCAT TAATGAGGAAAAATTATTAGCATGAAAACGCACATTCTGTTGGCCCGTGTG CTGGCTTGCGCAGCTCTGGTGCTGGTCACCCCAGGTTATAGCTCCGAGAAGA TCCCGGTTACGGGCAGCGGCTTCGTTGCAAAGGACGATTCTCTGCGCACCTT TTTCGATGCGATGGCACTGCAATTGAAGGAGCCGGTGATTGTCAGCAAGAT GGCGGCTCGCAAAAAGATTACCGGCAATTTCGAGTTCCACGATCCAAACGC GCTGCTGGAGAAACTGTCCCTGCAACTGGGTCTGATCTGGTACTTTGATGGT CAGGCGATCTACATCTACGACGCGAGCGAAATGCGTAATGCGGTTGTGAGC CTGCGTAATGTCAGCCTGAACGAGTTCAACAATTTTCTGAAGCGCAGCGGC CTGTACAATAAGAACTACCCTCTGCGTGGTGATAATCGTAAAGGCACCTTCT ATGTCAGCGGTCCGCCGGTGTATGTTGATATGGTTGTAAATGCGGCCACCAT GATGGACAAACAGAATGATGGCATCGAGCTGGGTCGCCAAAAGATCGGTGT TATGCGCCTGAACAACACTTTTGTGGGCGACCGCACCTACAACCTGCGTGAT CAAAAGATGGTCATTCCGGGTATTGCTACGGCAATTGAACGCCTGTTGCAA GGCGAAGAACAACCGCTGGGTAACATTGTAAGCTCCGAGCCTCCGGCCATG CCGGCCTTTAGCGCAAACGGCGAGAAAGGTAAGGCAGCGAATTACGCGGGT GGTATGAGCCTGCAAGAAGCGCTGAAACAGAACGCAGCGGCAGGCAACAT CAAAATTGTGGCCTATCCGGACACCAACAGCCTGCTGGTGAAAGGTACGGC GGAGCAGGTGCATTTCATCGAGATGCTGGTTAAAGCCCTGGACGTGGCGAA ACGTCACGTTGAATTGAGCCTGTGGATTGTGGATTTGAATAAGAGCGACCT GGAACGCTTGGGCACCAGCTGGAGCGGTAGCATCACCATCGGCGACAAGCT GGGTGTGAGCCTGAACCAGAGCAGCATCTCCACGCTGGACGGTAGCCGCTT TATTGCGGCGGTCAACGCTCTGGAGGAAAAGAAACAGGCCACTGTTGTCAG CCGTCCGGTTCTGCTGACCCAGGAGAATGTCCCGGCGATTTTTGACAATAAT CGTACTTTCTATACCAAACTGATCGGTGAACGTAATGTTGCATTGGAACACG TGACCTATGGCACCATGATCCGTGTCCTGCCGCGTTTCAGCGCGGACGGCCA GATTGAGATGAGCCTGGACATCGAAGATGGTAATGACAAAACCCCGCAGTC TGATACGACCACCTCCGTTGATGCGCTGCCAGAAGTGGGTCGTACCCTGATC TCGACGATTGCACGTGTCCCGCATGGTAAATCTCTGCTGGTTGGTGGCTACA CGCGTGATGCAAACACGGACACGGTCCAAAGCATCCCGTTCCTGGGTAAGC TGCCGCTGATTGGCTCGTTGTTTCGCTACAGCAGCAAAAACAAGTCTAATGT CGTCCGTGTCTTTATGATTGAGCCGAAAGAAATCGTTGACCCGCTGACCCCG GATGCCAGCGAGAGCGTTAACAACATTCTGAAACAGTCCGGTGCGTGGAGC GGTGACGATAAGCTGCAAAAGTGGGTTCGTGTGTATTTGGACCGTGGTCAG GAGGCCATTAAGTAACTTGGGCACGCGTCCATGAAAGACAGGACCCACTAG ATGTCCAGCAACAAAACCGAAAAACCGACTAAGAAACGTCTGGAGGATAG CGCAAAGAAAGGTCAGAGCTTCAAGAGCAAGGACCTGATTATCGCGTGCCT |

FIG. 24 (cont)

| SEQ ID NO: | Name | Sequence |
|---|---|---|
| | | GACCCTGGGTGGTATCGCTTATTTGGTGAGCTACGGCAGCTTCAATGAGTTT<br>ATGGGTATCATTAAGATTATCATCGCTGATAACTTTGATCAGTCGATGGCAG<br>ATTATAGCCTGGCCGTGTTTGGTATTGGCCTGAAATACCTGATTCCGTTCAT<br>GCTGCTGTGTTTGGTTTGTTCCGCACTGCCGGCACTGCTGCAAGCGGGCTTC<br>GTTCTGGCAACCGAGGCCCTGAAGCCGAATCTGTCCGCCCTGAACCCGGTT<br>GAAGGCGCGAAGAAACTGTTTTCCATGCGCACCGTCAAAGACACGGTCAAG<br>ACGCTGCTGTATCTGTCGAGCTTTGTGGTTGCGGCAATCATTTGCTGGAAAA<br>AGTATAAAGTCGAGATTTTCAGCCAACTGAACGGTAATATCGTGGGTATTG<br>CGGTTATCTGGCGTGAATTGCTGCTGGCGTTGGTTCTGACCTGTCTGGCGTG<br>CGCGCTGATCGTGCTGTTGCTGGATGCTATTGCCGAGTACTTTCTGACCATG<br>AAAGATATGAAGATGGACAAAGAAGAAGTTAAACGCGAGATGAAAGAGCA<br>GGAGGGTAACCCGGAGGTGAAGTCTAAACGTCGTGAAGTCCACATGGAAAT<br>CCTGAGCGAACAAGTCAAGTCTGACATTGAAAATAGCCGTCTGATTGTGGC<br>AAACCCTACGCATATTACCATCGGCATCTACTTCAAACCGGAACTGATGCCG<br>ATTCCAATGATTAGCGTCTATGAAACCAATCAACGCGCGCTGGCGGTCCGT<br>GCGTACGCCGAGAAAGTGGGTGTTCCGGTTATTGTAGACATCAAGCTGGCG<br>CGCAGCCTGTTCAAAACGCACCGTCGTTACGACCTGGTGAGCCTGGAGGAG<br>ATCGACGAGGTTTTGCGCCTGCTGGTTTGGTTGGAAGAGGTCGAAAACGCA<br>GGCAAGGATGTGATCCAACCGCAGGAGAATGAAGTGCGTCATTAACTGCAG<br>GTTTAAACTACTTGGGCACGCGTCCATTAATTAGGATCAATAGCATGATTCC<br>GGGCAGCACCTCCGGTATTTCCTTTAGCCGTATCCTGAGCCGTCAGACCTCC<br>CACCAGGATGCAACCCAGCATACCGACGCACAACAAGCGGAAATTCAACA<br>AGCGGCGGAAGATAGCTCGCCGGGTGCGGAGGTTCAGAAATTCGTCCAGAG<br>CACGGACGAGATGTCTGCTGCGTTGGCGCAGTTCCGCAATCGCCGTGACTAT<br>GAGAAAAAGAGCAGCAATTTGTCTAACTCCTTCGAGCGCGTTCTGGAGGAC<br>GAGGCACTGCCGAAAGCGAAGCAGATTCTGAAACTGATCAGCGTGCATGGC<br>GGTGCGTTGGAGGATTTCCTGCGTCAGGCGCGCAGCCTGTTCCCGGACCCA<br>AGCGATCTGGTGCTGGTTCTGCGCGAGCTGTTGCGTCGTAAGGACCTGGAG<br>GAGATCGTGCGTAAGAAGCTGGAGAGCCTGCTGAAGCACGTGGAGGAACA<br>AACCGACCCGAAAACCCTGAAGGCCGGTATTAACTGCGCGCTGAAGGCGCG<br>TCTGTTTGGCAAGACGCTGTCTCTGAAACCTGGTCTGCTGCGTGCCAGCTAC<br>CGCCAGTTCATCCAAAGCGAAAGCCACGAAGTCGAGATTTACAGCGATTGG<br>ATCGCCAGCTACGGTTATCAGCGTCGCCTGGTTGTTCTGGATTTCATTGAAG<br>GCAGCCTGCTGACTGACATCGATGCTAACGATGCAAGCTGCTCCCGTCTGG<br>AGTTTGGCCAACTGCTGCGCCGTCTGACCCAGCTGAAAATGTTGCGTAGCGC<br>CGACCTGCTGTTTGTCTCGACGTTGCTGTCTTACAGCTTCACGAAAGCATTT<br>AACGCTGAGGAGAGCAGCTGGCTGTTGCTGATGCTGTCTTTGCTGCAACAG<br>CCGCACGAAGTGGATAGCCTGCTGGCGGACATTATCGGTCTGAATGCGCTG<br>CTGTTGTCCCACAAAGAGCACGCCAGCTTCCTGCAAATCTTCTATCAGGTCT<br>GTAAGGCAATCCCGTCTAGCCTGTTTTATGAAGAGTACTGGCAAGAAGAAC<br>TGCTGATGGCACTGCGCTCCATGACGGACATTGCTTACAAACACGAAATGG<br>CCGAACAACGTCGTACCATCGAAAAGCTGTCCTAAGTTTAAACCTTGGGCA<br>CGCGTCCATGAAAGACAGGACCCACTAGATGAGCTTGCGCGTACGCCAAAT<br>TGACCGCCGTGAATGGCTGCTGGCCCAGACTGCGACCGAATGTCAGCGTCA<br>CGGTCGTGAGGCCACCCTGGAGTATCCGACCCGTCAGGGTATGTGGGTCCG<br>CCTGTCTGATGCCGAAAAACGCTGGTCTGCGTGGATCAAACCGGGTGATTG<br>GTTGGAACACGTTAGCCCAGCACTGGCGGGTGCCGCGGTCAGCGCAGGCGC<br>GGAGCACCTGGTGGTTCCGTGGCTGGCGGCAACCGAACGCCCGTTCGAGCT<br>GCCGGTCCCGCACTTGAGCTGCCGTCGTCTGTGCGTGGAGAACCCGGTTCCG<br>GGTTCCGCACTGCCTGAGGGCAAGCTGCTGCACATCATGTCGGATCGTGGT<br>GGCCTGTGGTTTGAGCATCTGCCGGAGCTGCCGGCTGTTGGCGGTGGCCGTC<br>CGAAGATGCTGCGTTGGCCGCTGCGTTTCGTTATTGGCAGCAGCGACACCCA<br>GCGCAGCCTGCTGGGTCGTATCGGTATCGGTGATGTTCTGCTGATCCGCACC<br>AGCCGTGCTGAGGTTTACTGTTACGCGAAGAAACTGGGCCACTTTAATCGTG<br>TGGAAGGTGGCATTATTGTCGAAACGCTGGACATTCAACATATCGAGGAGG<br>AGAACAACACGACGGAAACGGCGGAAACCCTGCCGGGTCTGAATCAACTG |

FIG. 24 (cont)

| SEQ ID NO: | Name | Sequence |
|---|---|---|
| | | CCGGTGAAGCTGGAGTTCGTTCTGTATCGTAAAAACGTGACGTTGGCCGAA<br>CTGGAAGCAATGGGTCAGCAACAACTGCTGTCCTTGCCAACCAATGCGGAA<br>CTGAACGTCGAAATCATGGCGAATGGCGTGCTGCTGGGTAACGGCGAACTG<br>GTGCAGATGAATGACACCCTGGGTGTCGAGATTCATGAGTGGTTGTCCGAG<br>AGCGGTAATGGCGAGTAGAGATCTCTTGGGCACGCGTCCATTAAAAAGGAC<br>CAATTAAGCATGCACTCTCTGACTCGTATCAAGGTCCTGCAACGTCGTTGTA<br>CCGTGTTCCATTCTCAGTGCGAGTCCATTCTGTTGCGTTATCAGGACGAAGA<br>TCGCGGCTTGCAGGCGGAGGAGGAGGCCATCCTGGAACAGATCGCAGGTCT<br>GAAACTGCTGTTGGACACCCTGCGTGCTGAAAATCGTCAACTGAGCCGTGA<br>AGAAATCTATACGCTGCTGCGCAAACAGAGCATTGTTCGTCGCCAGATTAA<br>GGATCTGGAGCTGCAAATCATTCAGATTCAAGAAAAGCGTAGCGAGCTGGA<br>AAAGAAACGTGAGGAATTTCAAAAGAAAAGCAAATACTGGCTGCGTAAAG<br>AAGGTAACTACCAGCGCTGGATTATCCGTCAAAAACGCTTCTACATTCAAC<br>GTGAGATCCAGCAAGAGGAGGCGGAGAGCGAAGAGATCATTTAACTTGGG<br>CACGCGTCCATGAAAGACAGGACCCACTAGATGTTCTATGCATTGTATTTG<br>AGATCCACCATCTGGTGGCGTCCGCGGCTCTGGGTTTTGCGCGTGTTGCTCC<br>GATCTTTTTCTTTCTGCCGTTCCTGAATAGCGGTGTCCTGAGCGGTGCTCCGC<br>GCAACGCGATCATCATTCTGGTGGCGCTGGGTGTATGGCCGCACGCCCTGA<br>ATGAGGCGCCACCGTTTCTGTCTGTGGCAATGATTCCGCTGGTCCTGCAAGA<br>GGCAGCCGTGGGTGTTATGCTGGGTTGCCTGTTGTCCTGGCCGTTTTGGGTT<br>ATGCACGCGTTGGGCTGTATCATTGATAACCAACGCGGTGCAACCCTGTCCA<br>GCAGCATTGATCCTGCGAATGGCATCGACACCAGCGAGATGGCCAATTTCC<br>TGAACATGTTCGCGGCTGTCGTGTATTTGCAGAACGGTGGCTTGGTCACGAT<br>GGTGGACGTGCTGAATAAGTCTTACCAGCTGTGTGATCCGATGAACGAGTG<br>TACGCCGAGCCTGCCTCCGTTGCTGACCTTCATTAATCAAGTGGCCCAGAAC<br>GCACTGGTGCTGGCGTCCCCGGTCGTTCTGGTTCTGCTGCTGTCGGAAGTTT<br>TCCTGGGCCTGCTGTCTCGTTTTGCACCGCAAATGAACGCGTTCGCCATTAG<br>CCTGACTGTTAAAAGCGGTATTGCGGTTTTGATCATGCTGCTGTATTTCAGC<br>CCGGTCCTGCCGGACAATGTTCTGCGTCTGAGCTTTCAGGCGACCGGCCTGA<br>GCAGCTGGTTCTACGAACGTGGCGCAACGCATGTGCTGGAATAAGGATCCG<br>GCATCAAATAAAACGAAAGGCTCAGTCGAAAGACTGGGCCTTTCGTTTTAT<br>CTGTTGTTTGTCGGTGAACGCTCTCCTGAGTAGGACAAATCCGCCGCCCTAG<br>AACTAGTccataagaatGCGGCCGC |

FIG. 27A
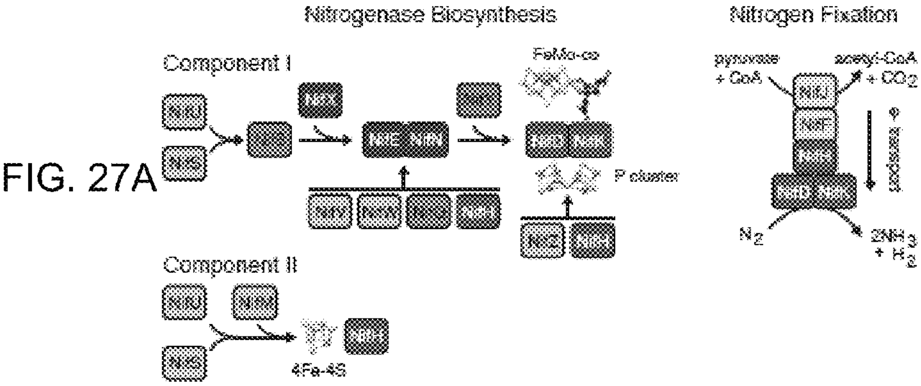
FIG. 27B
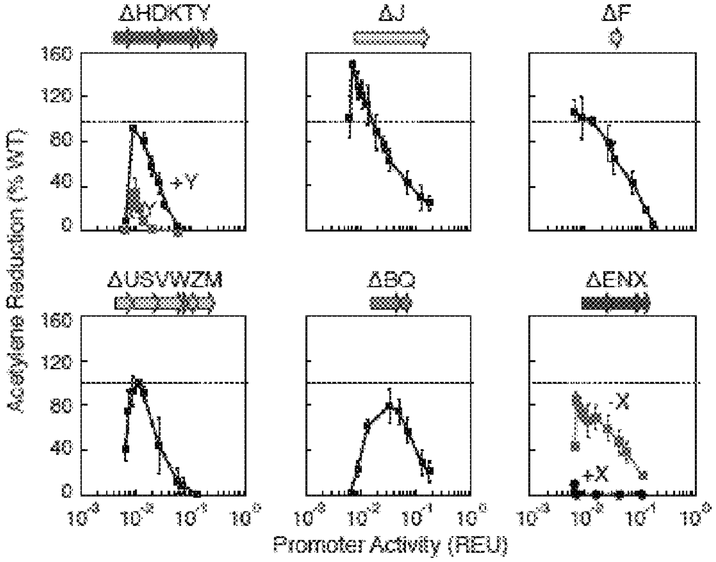
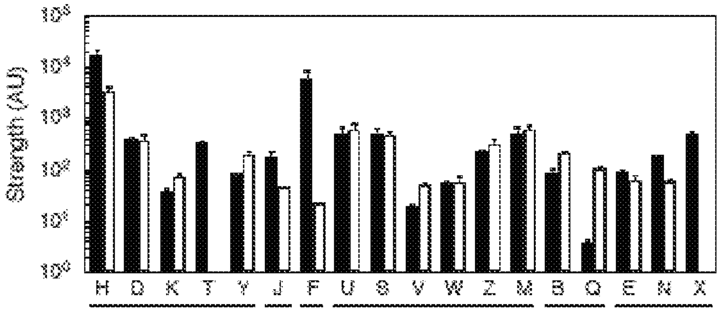
FIG. 27C

*FIG. 32*

**Table. Construction and verification of all *K.oxytoca nif* gene deletion mutants**

| Name | Genotype | Note | Parental Strain | Allelic Exchange Plasmid[4] | DNA sequence of the deletion region[5] |
|---|---|---|---|---|---|
| NF8 | Δ*nifJ, Km* | operon deletion | M5aL | pNif16 | gcaggagaactaaaggcccg**GCATGC**<br>(Km cassette)**GCATGC**aagcgcccatggcccggca |
| UC12 | Δ*nifHDK* | in-frame deletion | M5aL | pRHB296 | cataaacaggcacggctggt**GGTACC**ccatcaggtgccccgcgtca |
| NF9 | Δ*nifHDKTY* | operon deletion | M5aL | pNif9 | atggccccggcaggcgcaat**GCATGC**gacgctcttccccacgttac |
| UC14 | Δ*nifENX* | operon deletion | M5aL | pRHB294 | gacgctcttccccacgttac**GCATGC**gatccggacccgcgccgcta |
| UC15 | Δ*nifENX* | operon deletion | M5aL | pRHB295 | ctcttccccacgttacgctc**GCATGC**gatccggacccgcgccgcta |
| NF10 | Δ*nifUSVWZM* | operon deletion[1] | M5aL | pNif10 | cggacccgcgccgctagccg**GCATGC**atctttggcagcagagccag |
| NF11 | Δ*nifUSVWZM* | operon deletion | M5aL | pNif11 | cggacccgcgccgctagccg**GCATGC**agcctcggcggctacccgtt |
| NF12 | Δ*nifF* | operon deletion[2] | M5aL | pNif12 | actggttatcctgatccagc**GCATGC**ctttgcactaccgcggccca |
| NF13 | Δ*nifF* | operon deletion | M5aL | pNif13 | ccgttaacgcctacagcacg**GCATGC**ctttgcactaccgcggccca |
| NF14 | Δ*nifBQ* | operon deletion | M5aL | pNif14 | attcagggacgcgggttgcc------atgtgattatgcgacgtctt |
| NF24 | Δ*nifJ,HDKTY, ENX* | operon deletion[3] | M5aL | pNif32 | gtcaaacaccagaatattga**GAGCTC**tgtcgtttctgtgacaagc |
| NF25 | Δ*nifUSVWZM,F,BQ* | operon deletion | NF14 | pNif51 | cggacccgcgccgctagccg**GCATGC**ctttgcactaccgcggccca |
| NF26 | Δ*nifJ,HDKTY,ENX, USVWZM,F,LA,BQ* | whole *nif* deletion[3] | NF24 | pNif54 | gtcaaacaccagaatattga**CTCGAG**atgtgattatgcgacgtctt |

1) 83bp of *nifM* 3' retained
2) 82bp of *nifF* 3' retained
3) 500bp of *nifJ* 3' retained
4) The backbone for all allelic exchange plasmids is pDS132(1).
5) The bold region shows the restriction site sequence that replaces the deletion region. The 20 nucleotides flanking each site of the deletion region are shown.

FIG. 33A
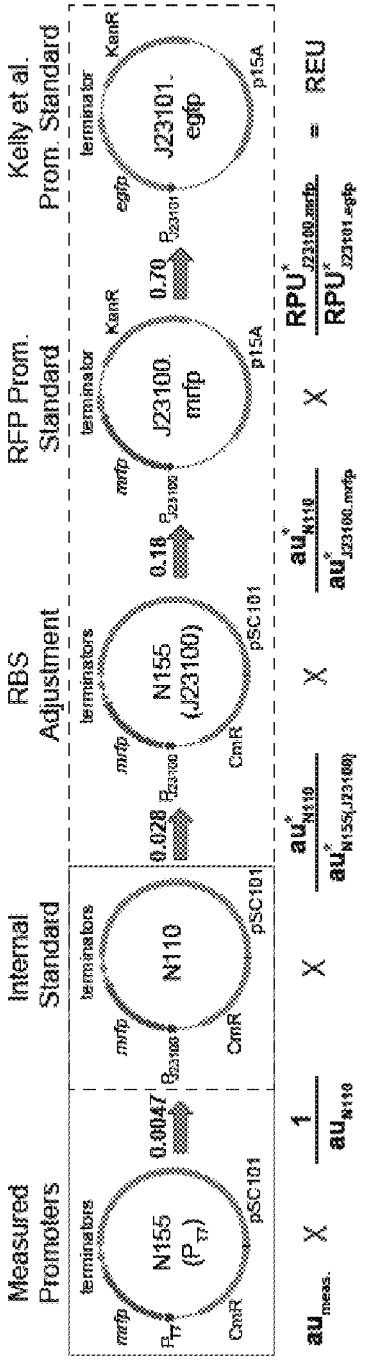
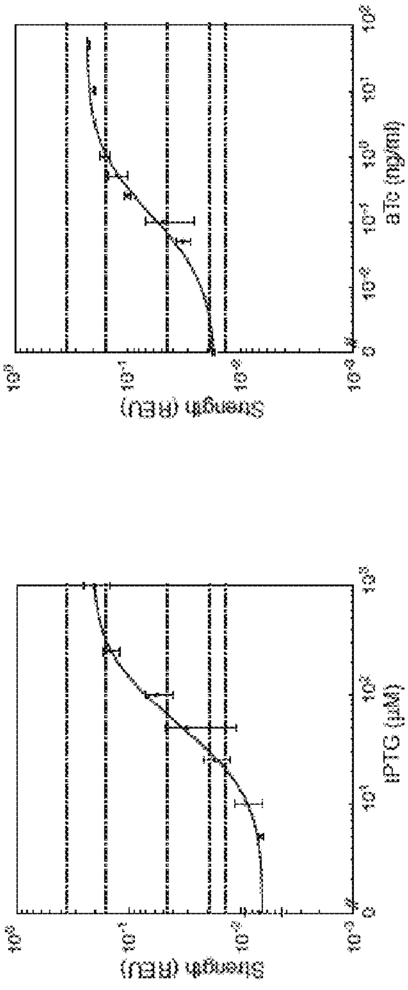
FIG. 33B

*FIG. 35*

**Table: DNA sequence errors in *nif* cluster sequence X13303.1**

| Location | X13303.1 | This Study | Impact |
|---|---|---|---|
| 5187 | a | g | NifD K39E |
| 5193 | a | g | NifD K41E |
| 5332 | ct | tc | NifD A87V |
| 5359 | a | g | NifD E96G |
| 6137 | c | g | NifD I355M |
| 6140 | a | c | silent |
| 6749 | ga | ag | NifK R57Q |
| 7371 | t | c | silent |
| 7371 | t | c | silent |
| 8168 | cgg | ggc | *nifT* 5' UTR |
| 8919 | c | t | NifY P170L |
| 9341 | - | insert t | *nifE* 5' UTR |
| 9498 | cg | gc | NifE A35G |
| 9697 | ac | ct | silent |
| 9891 | c | t | NifE P166L |
| 12541 | ca | ac | NifX Q131T |
| 12770 | t | c | *nifU* 5' UTR |
| 13646 | gc | cg | *nifS* 5' UTR |
| 13999 | a | c | NifS M110L |
| 14008 | g | c | NifS E113Q |
| 14037 | a | g | silent |
| 14041 | g | a | NifS G124S |
| 14539 | gc | cg | NifS A290R |
| 15657 | tc | ct | NifV S257L |
| 15770 | gc | cg | NifV H295D |
| 16739 | g | a | silent |
| 16814 | c | t | silent |
| 22050 | g | a | NifB V141M |
| 22309 | g | a | NifB G227D |

*FIG. 38*

Table. DNA sequences of synthetic parts

| Part Number | Part Type | Sequence |
|---|---|---|
| SBa_000443 | T7 Promoter WT | taatacgactcactatagggaga |
| SBa_000444 | T7 Promoter 1 | taatacgactcactacaggcaga |
| SBa_000445 | T7 Promoter 2 | taatacgactcactagagagaga |
| SBa_000446 | T7 Promoter 3 | taatacgactcactaatgggaga |
| SBa_000447 | T7 Promoter 4 | taatacgactcactattgggaga |
| SBa_000450 | WT T7 Terminator | tagcataaccccttggggcctctaaacgggtcttgaggggttttttgt |
| SBa_000451 | T7 Terminator | tacatatcgggggggtaggggttttttgt |
| SBa_000452 | T7 Terminator | tactctaaccccatcggccgtcttaggggttttttgt |
| SBa_000453 | Insulator | gcgtgcgtacaccttaatcaccgcttcatgctaaggtcctggctgcatgc |
| SBa_000454 | Insulator | caaacaccccatgtcgatactgaacgaatcgacgcacactcccttccttg |
| SBa_000455 | Insulator | cctgattgtatccgcatctgatgctaccgtggttgagtta |
| SBa_000456 | Insulator | catttttgccttgcgacagacctcctacttagattgccac |
| SBa_000457 | Insulator | tgtcacgctaggaggcaattctataagaatgcacactgca |
| SBa_000458 | Insulator | ccgtggttgagtcagcgtcgagcacgcggc |
| SBa_000459 | Insulator | cgcgacttccagagaagaagactactgacttgagcgttcc |
| SBa_000460 | Insulator | actacgagatttgaggtaaaccaaataagcacgtagtggc |
| SBa_000461 | Insulator | gtctgtagcacgtgcatc |
| SBa_000462 | Insulator | ggtcattacaacggttat |
| SBa_000463 | Insulator | aacatagcgttccatgagggctagaattacctacggcct |
| SBa_000464 | Insulator | cattgtaatagccaccaaaagagtgatgatagtcatgggt |
| SBa_000465 | Insulator | gagttactggccctgatttctccgcttctaataccgcaca |
| SBa_000466 | Insulator | gactcaacacgctagggacgtgaagtcgattccttcgatg |
| SBa_000467 | Insulator | tcgagaaacaaggcagttccgggctgaaagtagcgccggg |
| SBa_000468 | Insulator | acgccacgcgtagtgagacatacacgttcgttgggttcac |
| SBa_000508 | Insulator | tgcagttttattctctcgccagcactgtaataggcactaa |
| SBa_000475 | Synthetic RBS | ttaaagaggagaaattaagcATGaaaactatggacggtaacgctgcggctgcatggattagcta<br>cgcctttaccgaagtggctgcgatctacccgattacgccgagcacc |
| SBa_000469 | Synthetic RBS | tactagagacaataaactaacataaggaggataaatATGaccatgcgtcagtgcgcgatttatg<br>gcaaaggtggtattggcaaaagcacgacgacccagaacttggtggcggccctggccgagatg |
| SBa_000470 | Synthetic RBS | gcgtgcgtacaccttaatcaccgcttcatgctaaggtcctggctgcatgcaaaaattcacatcc<br>ctatctaggggaggagcagcATGatgactaatgctactggcgaacgtaacctggcactgatcca<br>agaagtactggaagtgttcccggaaaccgcgcgcaaagagcgccgt |
| SBa_000471 | Synthetic RBS | caaacaccccatgtcgatactgaacgaatcgacgcacactcccttccttgcattcacatactct<br>caaaattaaggaggttaacATGtctcaaactatcgataaaatcaactcttgttacccgctgtt<br>cgagcaggacgaatatcaggaactgttccgtaacaaacgtcagctg |
| SBa_000472 | Synthetic RBS | cctgattgtatccgcatctgatgctaccgtggttgagttaccatacctcattcccggaggtactt<br>ctATGcctgacaatgataccctgtttttggcgcatgctggcgctgtttcagtcgctgccggattt<br>gcagccggctcaaatcgtcgattggctg |
| SBa_000473 | Synthetic RBS | catttttgccttgcgacagacctcctacttagattgccacacattcaatacatcactggaggt<br>tattacaaATGaaggcgtaacgagattcttgctctgctggacgaaccggcctgtgaacacaacca<br>taaacagaaatccggctgtagcgccccaaagccg |
| SBa_000474 | Synthetic RBS | tgtcacgctaggaggcaattctataagaatgcacactgcacctaaacctaccacatctgaggag<br>agtaattATGgcagacattttccgcactgataagcccttggctgtgtcgccgatcaagaccgcc<br>cagccgctgggtgcgatcctggcgtccctgggt |
| SBa_000476 | Synthetic RBS | aacatagcgttccatgagggctagaattacctacggccttagatacgacaataaacgagcg<br>aaggaggttcctaATGtggaactacagcgagaaagtcaaggaccatttcttcaatccgcgcaac<br>gcgcgtgttgtggataacgcaaatgcggtggcgacgtc |
| SBa_000477 | Synthetic RBS | cattgtaatagccaccaaaagagtgatgatagtcatgggtgataacgtagacattttgaaa<br>cgaaggaggtttcctATGaaacaagtgtacctggacaacaacgcgaccacccgcctggacccga<br>tggttctggaagcgatgatgccgtttctcacggatttcgat |
| SBa_000478 | Synthetic RBS | gagttactggccctgatttctccgcttctaatacgcacaggactaggagccaacttcgcac<br>aaggaaacaATGgagcgcgtcttgatcaacgataccaccctgcgtgatggcgaacaatctccg<br>ggcgtaagcgttcgtacctccgagaaagttgccatc |
| SBa_000479 | Synthetic RBS | gactcaacacgctagggacgtgaagtcgattccttcgatgcaagaaggcgagaactagattaag<br>ggaattatagATGagtggtttaaccagattcgggtgtagacgaattgcgcagcgctgaatc<br>cttctttcagttcttcgcggttccatacccagccggaa |
| SBa_000480 | Synthetic RBS | tcgagaaacaaggcagttccgggctgaaagtagcgccgggacaagtcccgtattataaccgcct<br>aggaggtgtaggATGcgcccgaaattcaccttctctgaagaggtccgcgtagttcgcgcgattc<br>gtaatgatggcaccgtggcgggttttgcgccaggtgcg |
| SBa_000481 | Synthetic RBS | acgccacgcgtagtgagacatacacgttcgttgggttcactcagagactgaagttattacccag<br>gaggtctataATGaatccgtggcagcgctttgcccgtcaacgccttgctcgcagccgctggaac<br>cgtgatccggctgctctcgacccagccgataccca |
| SBa_000482 | Synthetic RBS | gacaagaggtctcaattataaggaggctttactacATGgcgaacatcggcatcttctttggtacg<br>gataccggcaaaacccgcaagattgcgaagatgattcacaaacagctgggcgagctggcc |
| SBa_000483 | Synthetic RBS | cgcgacttccagagaagaagactactgacttgagcgttccctctctgtaatacatcaatcaat<br>cataggagggctaaaATGacctcttgttcgtcgttttctggcggtaaagcgtgccgtccggccg<br>atgactccgcgctgactccgctggtggccgacaaggcagct |
| SBa_000475 | Synthetic RBS | aactacgagatttgaggtaaaccaaataagcacgtagtggcattaaagaggagaaattaagcAT<br>Gccgccattggactggttgcgtcgtttgtggttactctatcaggccggcaaaggcagctttccg<br>cttcgtatgggcttgtcgccgcgt |
| SBa_000561 | $P_{tac}$ Promoter and | caattcgcgctaacttacattaattgcgttgcgctcactgcccgctttccagtcgggaaacctg |

FIG. 38 (cont)

| | | |
|---|---|---|
| | lacI cassette | tcgtgccagctgcattaatgaatcggccaacgcgcggggagaggcggtttgcgtattgggcgcc<br>agggtggtttttcttttcaccagtgagacgggcaacagctgattgcccttcaccgcctggccct<br>gagagagttgcagcaagcggtccacgctggtttgccccagcaggcgaaaatcctgtttgatggt<br>ggttgacggcgggatataacatgagctgtcttcggtatcgtcgtatcccactaccgagatatcc<br>gcaccaacgcgcagcccggactcggtaatggcgcgcattgcgcccagcgccatctgatcgttgg<br>caaccagcatcgcagtgggaacgatgccctcattcagcatttgcatggtttgttgaaaaccgga<br>catggcactccagtcgccttcccgttccgctatcggctgaatttgattgcgagtgagatattta<br>tgccagccagccagacgcagacgcgccgagacagaacttaatgggcccgctaacagcgcgattt<br>gctggtgacccaatgcgaccagatgctccacgcccagtcgcgtaccgtcttcatgggagaaaat<br>aatactgttgatgggtgtctggtcagagacatcaagaaataacgccggaacattagtgcaggca<br>gcttccacagcaatggcatcctggtcatccagcggatagttaatgatcagcccactgacgcgtt<br>gcgcgagaagattgtgcaccgccgctttacaggcttcgacgccgcttcgttctaccatcgacac<br>caccacgctggcacccagttgatcggcgcgagatttaatcgccgcgacaatttgcgacggcgcg<br>tgcagggccagactggaggtggcaacgccaatcagcaacgactgtttgcccgccagttgttgtg<br>ccacgcggttgggaatgtaattcagctccgccatcgccgcttccactttttcccgcgttttcgc<br>agaaacgtggctggcctggttcaccacgcgggaaacggtctgataagagacaccggcatactct<br>gcgacatcgtataacgttactggtttcacattcaccaccctgaattgactctcttccgggcgct<br>atcatgccataccgcgaaaggttttgcaccattcgatggtgtcaacgtaaatgcatgccgcttc<br>gccttcgcgcgcgaattggccgccatgccggcgataatggcctgcttctcgccgaaacgtttgg<br>tggcgggaccagtgacgaaggcttgagcgagggcgtgcaagattccgaataccgcaagcgacag<br>gccgatcatcgtcgcgctccagcgaaagcggtcctcgccgaaaatgacccagagcgctgccggc<br>acctgtcctacgagttgcatgataaagaagacagtcataagtgcggcgacgatagtcatgcccc<br>gcgcccaccggaaggagctgactgggttgaaggctctcaagggcatcggcggagcttatcgact<br>gcacggtgcaccaatgcttctggcgtcaggcagccatcggaagctgtggtatggctgtgcaggt<br>cgtaaatcactgcataattcgtgtcgctcaaggcgcactcccgttctggataatgttttttgcg<br>ccgacatcataacggttctggcaaatattctgaaatgagctgttgacaattaatcatcggctcg<br>tataatgtgtggaattgtgagcggataacaatt |
| SBa_000562 | $P_{tet}$ Promoter and tetR cassette | ttattaggacccactttcacatttaagttgtttttctaatccgcatatgatcaattcaaggccg<br>aataagaaggctggctctgcaccttggtgatcaaataattcgatagcttgtcgtaataatggcg<br>gcatactatcagtagtaggtgtttccctttcttctttagcgacttgatgctcttgatcttccaa<br>tacgcaacctaaagtaaaatgccccacagcgctgagtgcatataatgcattctctagtgaaaaa<br>ccttgttggcataaaaaggctaattgattttcgagagtttcatactgtttttctgtaggccgtg<br>tacctaaatgtacttttgctccatcgcgatgacttagtaaagcacatctaaaacttttagcgtt<br>attacgtaaaaaatcttgccagctttccccttctaaagggcaaaagtgagtatggtgcctatct<br>aacatctcaatggctaaggcgtcgagcaaagcccgcttattttttacatgccaatacaatgtag<br>gctgctctacacctagcttctgggcgagtttacgggttgttaaaccttcgattccgacctcatt<br>aagcagctctaatgcgctgttaatcactttacttttatctaatctggacatcgaggcctttcct<br>gtgtgagctagcactgtacctaggactgagctagccgtcaatttttccctatcagtgatagag<br>attgacatccctatcagtgatagatataatgagcac |
| SBa_000484 | mRFP Fluorescent Reporter | atgtccagattagataaaagtaaagttgcgagctctgaagacgttatcaaagagttcatgcgtt<br>tcaaagttcgtatggaaggttccgttaacggtcacgagttcgaaatcgaaggtgaaggtgaagg<br>tcgtccgtacgaaggtacccagaccgctaaactgaaagttaccaaaggtggtccgctgccgttc<br>gcttgggacatcctgtccccgcagttccagtacggttccaaagcttacgttaaacacccggctg<br>acatcccggactacctgaaactgtccttcccggaaggtttcaaatgggaacgtgttatgaactt<br>cgaagacggtggtgttgttaccgttacccaggactcctccctgcaagacggtgagttcatctac<br>aaagttaaactgcgtggtaccaacttcccgtccgacggtccggttatgcagaaaaaaaccatgg<br>gttgggaagcttccaccgaacgtatgtacccggaagacggtgctctgaaaggtgaaatcaaaat<br>gcgtctgaaactgaaagacggtggtcactacgacgctgaagttaaaaccacctacatggctaaa<br>aaaccggttcagctgccgggtgcttacaaaaccgacatcaaactggacatcacctcccacaacg<br>aagactacaccatcgttgaacagtacgaacgtgctgaaggtcgtcactccaccggtgcttaa |
| SBa_000514 | T7* RNAP | atgaacacgattaacatcgctaagaacgacttctctgacatcgaactggctgctatcccgttca<br>acactctggctgaccattacggtgagcgtttagctcgcgaacagttggcccttgagcatgagtc<br>ttacgagatgggtgaagcacgcttccgcaagatgtttgagcgtcaacttaaagctggtgaggtt<br>gcggataacgctgccgccaagcctctcatcactaccctactccctaagatgattgcacgcatca<br>acgactggtttgaggaagtgaaagctaagcgcggcaagcgcccgacagccttccagttcctgca<br>agaaatcaagccggaagccgtagcgtacatcaccattaagaccactctggcttgcctaaccagt<br>gctgacaatacaaccgttcaggctgtagcaagcgcaatcggtcgggccattgaggacgaggctc<br>gcttcggtcgtatccgtgaccttgaagctaagcacttcaagaaaaacgttgaggaacaactcaa<br>caagcgcgtagggcacgtctacaagaaagcatttatgcaagttgtcgaggctgacatgctctct<br>aagggtctactcggtggcgaggcgtggtcttcgtggcataaggaagactctattcatgtaggag<br>tacgctgcatcgagatgctcattgagtcaaccggaatggttagcttacaccgccaaaatgctgg<br>cgtagtaggtcaagactctgagactatcgaactcgcacctgaatacgctgaggctatcgcaacc<br>cgtgcaggtgcgctggctggcatctctccgatgttccaaccttgcgtagttcctcctaagccgt<br>ggactggcattactggtggtggctattgggctaacggtcgtcgtcctctggcgctggtgcgtac<br>tcacagtaagaaagcactgatgcgctacgaagacgtttacatgcctgaggtgtacaaagcgatt<br>aacattgcgcaaaacaccgcatggaaaatcaacaagaaagtcctagcggtcgccaacgtaatca<br>ccaagtggaagcattgtccggtcgaggacatccctgcgattgagcgtgaagaactcccgatgaa<br>accggaagacatcgacatgaatcctgaggctctcaccgcgtggaaacgtgctgccgctgctgtg<br>taccgcaaggacaaggctcgcaagtctcgccgtatcagccttgagttcatgcttgagcaagcca<br>ataagtttgctaaccataaggccatctggttcccttacaacatggactggcgcggtcgtgttta<br>cgctgtgtcaatgttcaacccgcaaggtaacgatatgaccaaaggactgcttacgctggcgaaa<br>ggtaaaccaatcggtaaggaaggttactactggctgaaaatccacggtgcaaactgtgcgggtg<br>tcgacaaggttccgttccctgagcgcatcaagttcattgaggaaaaccacgagaacatcatggc<br>ttgcgctaagtctccactggagaacacttggtgggctgagcaagattctccgttctgcttcctt<br>gcgttctgctttgagtacgctggggtacagcaccacggcctgagctataactgctcccttccgc<br>tggcgtttgacgggtcttgctctggcatccagcacttctccgcgatgctccgagatgaggtagg<br>tggtcgcgcggttaacttgcttcctagtgaaaccgttcaggacatctacgggattgttgctaag<br>aaagtcaacgagattctacaagcagacgcaatcaatgggaccgataacgaagtagttaccgtga<br>ccgatgagaacactggtgaaatctctgagaaagtcaagctgggcactaaggcactggctggtca<br>atggctggcttacggtgttactcgcagtgtgactaagagttcagtcatgacgctggcttacggg<br>tccaaagagttcggcttccgtcaacaagtgctggaagataccattcagccagctattgattccg |

FIG. 38 (cont)

gcaagggtctgatgttcactcagccgaatcaggctgctggatacatggctaagctgatttggga
atctgtgagcgtgacggtggtagctgcggttgaagcaatgaactggcttaagtctgctgctaag
ctgctggctgctgaggtcaaagataagaagactggagagattcttcgcaagcgttgcgctgtgc
attgggtaactcctgatggtttccctgtgtgccaggaatacaagaagcctattcagacgcgctt
gaacctgatgttcctcggtcagttccgcttacagcctaccattaacaccaacaaagatagcgag
attgatgcacacaaacaggagtctggtatcgctcctaactttgtacacagccaagacggtagcc
accttcgtaagactgtagtgtgggcacacgagaagtacggaatcgaatcttttgcactgattca
cgactccttcggtacgattccggctgacgctgcgaacctgttcaaagcagtgcgcgaaactatg
gttgacacatatgagtcttgtgatgtactggctgatttctacgaccagttcgctgaccagttgc
acgagtctcaattggacaaaatgccagcacttccggctaaaggtaacttgaacctccgtgacat
cttagagtcggacttcgcgttcgcgtaa Synthetic *nifJ* atgaaaactatggacggtaacgctgcggctgcatggattagctacgcctttaccgaagtggctg
cgatctacccgattacgccgagcaccccgatggcggaaaatgtggacgaatgggctgcgcaggg
caagaagaacctcttcggccagccggtgcgcctgatggagatgcagtcggaagcgggtgcagca
ggtgctgtgcatggcgccttgcaagctggcgcactgacgaccacctacaccgcgtcgcagggcc
tgttgctgatgatcccaaacatgtacaaaatcgcgggtgaactgctgccgggtgtctttcatgt
ttcggcacgcgcactggccaccaatagcctcaacatctttggcgatcatcaggatgtaatggcg
gtgcgccaaacgggctgcgcgatgttggccgagaataacgtccagcaagttatggatttgtccg
cggtagcccacttggcagcgatcaaaggtcgcattccgttcgtgaacttcttcgatggctttcg
caccagccacgaaatccagaagatcgaggttctggaatatgaacagctggccaccttgttggat
cgtccggccctggacagcttccgccgtaacgcccttcacccggaccacccggtcatccgtggca
ccgcccagaacccggacatctacttccaggaacgtgaggccggtaaccgtttctatcaggcgct
cccggatattgtggaatcttacatgacccagatttctgccctgactggtcgcgagtatcacctg
tttaactacactggtgctgcggatgcggagcgcgtgatcatcgcgatgggctctgtctgtgaca
ccgtccaagaggtggttgacacgctgaatgcagcgggtgagaaagttggtctgctctccgttca
tctttccgcccgtttcgttagcgcacttcttcgcccaactgccgaaaactgtacagcgtatc
gcagtattggaccgtacgaaagagccaggtgctcaagcagagccgctgtgcctcgatgtgaaga
atgccttttaccaccatgacgatgccccgttgattgtgggtggtcgctatgccttgggcggtaa
ggacgtgttgccgaacgatattgcggccgtgtttgataacctgaacaaaccgctgccgatggac
ggcttcacgctgggtatcgtggacgatgttaccttcacctctctcccgccagcgcagcagaccc
tggcggtttctcacgacggcatcacggcatgtaagttttggggcatgggctccgacggcacggt
tggtgcgaacaagtccgcgatcaagattatcggcgacaaaacgccactgtatgcgcaagcgtac
ttttcctacgactcgaagaagagcggtggtattaccgtcagccatctgcgttttggtgatcgcc
cgatcaactccccgtatttgatccatcgcgcggatttcatctcgtgcagccagcaaagctatgt
tgaacgctacgatctgctggatggccttaaaccgggtggcacctttctgctgaactgctcctgg
agcgatgccgaactggagcaacatctgccggtcggtttcaaacgttatctggcacgcgagaata
tccacttctacactctcaacgctgtggacatcgcccgtgagcttggtttgggtggccgtttcaa
catgctgatgcaggctgccttcttcaaactggccgcgatcattgacccgcagactgctgcggac
tatctgaagcaggctgttgagaaaagctatggcagcaaaggtgcggcggtcatcgagatgaacc
agcgtgccatcgagcttggcatggccagcctgcaccaggtgacgatcccggcacattgggccac
cctggatgagccagcggcgcaggcgtccgcgatgatgccggactttatccgcgacatcctgcaa
ccgatgaaccgtcagtgcggcgaccagcttccggtgtcggctttgtcggcatggaagatggca
cctttcccgtcccggcacggccgcatggagaaacgtggcatcgcccttgaggtgccagtctggca
gccggaaggctgcacgcagtgcaaccagtgcgccttcatttgtccgcacgccgcgattcgtccg
gcgttgttgaatggcgaagagcatgatgctgccccggttggcctgctgagcaaaccggcacaag
gcgctaaagaatatcactatcatctggcgattagcccgctggactgctccggctgtggcaactg
cgttgacatttgtccagctcgtggcaaagcgttgaagatgcagtctctggatagccaacgccag
atggctccggtgtgggattatgcgctggcgctgaccccgaagtctaacccgtttcgtaaaacca
ccgtcaaaggctcgcagttcgaaaccccgctgctggagtttagcggtgcgtgcgctggttgtgg
cgaaacgccgtatgcgcgcctcattacccagctgtttggcgaccgcatgctgattgccaatgcc
accggctgttccagcatctggggcgcatctgcgccgagcatcccgtataccaccaatcatcgtg
gtcatggtccggcctgggcgaatagcctgtttgaggacaatgccgaatttggtttaggtatgat
gctgggcggtcaagctgtgcgtcaacagatcgcggacgatatgacggctgcgttagcgctcccg
gtttccgatgagctgagcgacgcgatgcgccagtggttggcgaaacaggacgagggtgaaggca
cgcgtgagcgtgcggaccgtctgagcgagcgcttagccgcggagaaagagggcgttccgctgtt
agagcagctgtggcaaaatcgtgattactttgtgcgtcgcagccagtggatttcggcggtgac
ggctgggccgatgatattggcttcggtggcctggaccacgtcctcgccagcggtgaggatgtga
acattctggtatttgacaccgaagtctactcgaacaccggcggtcaaagcagcaaatcgacccc
ggtcgcggccatcgccaagttcgcggctcagggcaagcgcacccgcaagaaagacctgggtatg
atggcgatgagctacggcaacgtctatgtagcccaggtggcgatgggtgcggataaagatcaaa
ctctgcgcgccattgcggaagctgaagcgtggccaggcccgtcgctggtgattgcgtatgcggc
ctgcatcaatcatggcctgaaggccggtatgcgttgcagccaacgtgaggcgaagcgcgctgtt
gaggcgggctactggcacctgtggcgttatcacccgcagcgcgaagcggaaggcaagacgccgt
ttatgttagatagcgaagaaccggaagagtcgttccgtgactttctgttggctgaggtgcgcta
cgcatccctgcacaagaccaccccgcacctcgccgatgcccttttcagccgtaccgaagaagat
gcgcgtgcgcgctttgcgcaataccgtcgcctggctggcgaagagtaa Synthetic *nifH* atgaccatgcgtcagtgcgcgatttatggcaaaggtggtattggcaaaagcacgacgacccaga
acttggtggcggccctggccgagatgggtaaaaaggttatgattgtgggttgcgacccgaaggc
cgacagcacgcgcctgattctgcacgcgaaagcacaaaacacgattatggagatggctgccgag
gttggtagcgtggaggatctggagctggaggacgttctgcaaattggttacggtgatgttcgtt
gcgcagagagcggtggtccggaaccaggtgtcggctgtgcgggtcgtggtgtgattaccgctat
caatttcctggaagaagagggtgcgtacgaagatgatctggatttcgtttttctacgatgtgctg
ggtgatgtcgtgtgcggtggttttgcaatgccgattcgcgagaataaggcacaagaaatttaca
ttgtctgtagcggcgagatgatggcaatgtacgctgctaacaacatcagcaagggtattgttaa
atacgcaaaaagcggtaaggttcgcttgggtggtttgatttgcaacagccgtcagaccgaccgt
gaggacgaactgatcatcgccctggctgagaaactgggcacccaaatgatccacttcgtgcccac
gcgataatattgttcaacgtgcagaaatccgccgtatgaccgtcattgagtatgacccggcatg
caagcaagcgaacgagtaccgcaccttggcacagaaaatcgtgaacaacaccatgaaggttgtt
ccgacgccgtgtacgatggacgagctggagagcctgctgatggagttcggcattatggaggagg
aggacaccagcattatcggtaagaccgcagcggaggagaatgcggcataa Synthetic *nifD* atgatgactaatgctactggcgaacgtaacctggcactgattcaagaagtactggaagtgttcc

FIG. 38 (cont)

cggaaaccgcgcgcaaagagcgccgtaaacacatgatggtttctgacccgGaaatgGaatctgt
gggtaaatgcatcatctctaatcgcaaatctcagccgggtgtcatgactgttcgtggctgtgcg
tacgcaggttctaaaggtgtcgtattcggcccgatcaaagatatggcgcatatctctcatggcc
cggTaggctgtggccagtactctcgcgcggGacgtcgtaactactacacgggcgtttctggcgt
tgactctttggcaacgctgaacttcacctctgacttccaggaacgtgacatcgttttcggtggc
gataaaaagctgtccaaactgatcgaagaaatggaactgctgttcccgctgactaaaggcatta
ctatccaaagcgaatgtccggtgggtctgatcggtgatgacatcagcgcggtcgcaaacgcatc
ttccaaagccctggataagccggtgatcccggttcgttgcgagggcttccgcggcgtttctcag
tctctgggtcatcacatcgcaaacgatgttgtgcgtgactggattctgaacaaccgtgaaggtc
agccttttgaaaccaccccttatgacgttgcgattattggcgactataacatcggcggcgacgc
ctgggcatcccgcatcctgctggaggagatgggtctgcgtgttgtcgcacagtggtctggcgat
ggcaccctggttgaaatggaaaacaccccgtttgttaaactgaacctggttcactgctaccgct
ccatgaactacattgcccgtcacatggaagaaaaacatcagatcccttggatggaatacaactt
cttcggtccgactaaaatcgcagaatccctgcgtaaaatcgccgatcagtttgatgataccatt
cgcgcgaacgctgaagcagtaattgcgcgctacgaaggccagatggcagcaatcattgctaagt
accgtccgcgcctggaaggtcgtaaagtgctgctgtacatgggtggtctgcgtccacgtcatgt
gatcggtgcctacgaggacctgggcatggagatcatcgcagcgggttacgaatttgcacacaac
gacgactatgatcgtacgctgccagacctgaaagaaggtacgctgctgtttgacgacgccagct
cttatgaactggaagccttcgtgaaagcgctgaaaccagacctgatcggctccggcatcaagga
aaaatacatttttccagaaaatgggcgtgccgttccgccagatgcactcctgggactactccggt
ccgtaccacggctacgacggtttcgctatcttcgctcgtgacatggatatgaccctgaataacc
cagcgtggaatgaactgaccgcaccgtggctgaaatctgcataa Synthetic *nifK* atgtctcaaactatcgataaaatcaactctgttacccgctgttcgagcaggacgaatatcagg
aactgttccgtaacaaacgtcagctggaagaagcgcacgacgcacagcgcgtgcaggaagtgtt
cgcatggaccaccaccgcggaatacgaagctctgaacttccagcgcgaagccctgacggttgat
ccggcgaaagcgtgccagcctctgggtgcggttctgtgcagcctgggttttgccaacaccctgc
cgtatgtccacggttcccagggctgcgtagcctacttccgtacctatttcaaccgccactttaa
agaaccaatcgcgtgcgtgtccgacagcatgacggaggacgcggcagttttcggtggtaacaac
aacatgaacctgggcctgcaaaatgcttccgcactgtacaaaccggaaatcatcgcagtgtcta
ccacctgcatggcagaggttattggtgatgatctgcaagcatttattgccaacgcaaagaaaga
cggtttcgttgacagctctatcgcggttccgcacgctcataccccgtccttcatcggttctcac
gtaactggttgggacaacatgttcgaaggcttcgcaaaaactttaccgcagactatcaaggcc
aaccgggtaaactgccgaagctgaacctggtgaccggctttgaaacctacctgggcaactttcg
tgtcctgaagcgcatgatggagcagatggcggttccgtgttctctgctgtctgacccgtctgag
gttctggacactccagcggacggccactatcgcatgtattctggtggcaccactcagcaggaaa
tgaaagaggccccagacgcgattgacaccctgctgctgcaaccgtggcagctgctgaaaagcaa
gaaagttgttcaggaaatgtggaaccagccggcaacggaagttgcaatcccgctgggtctggca
gctactgacgaactgctgatgaccgtgtcccaactgagcggcaaaccaatcgcggatgctctga
ccctggaacgcggtcgcctggtggacatgatgctggacagccacacgtggctgcatggcaagaa
atttggcctgtacggtgacccggacttcgtaatgggcctgacccgtttcctgctggaactgggc
tgcgagccgactgttatcctgtctcacaacgctaacaaacgttggcagaaggccatgaacaaaa
tgctggatgcgagcccatacggccgtgatagcgaagtgttcatcaactgcgacctgtggcattt
ccgctctctgatgtttacgcgtcagccggatttcatgatcggtaactcttacggcaaattcatc
cagcgtgacactctggccaaaggcaaagcgtttgaagtgccgctgattcgtctgggctttccgc
tgttcgaccgtcaccacctgcaccgccagaccacctggggttacgaaggcgcgatgaacatcgt
aactactctggtaaacgcagtactggaaaagctggacagcgatacttcccagctgggcaaaacc
gactattctttcgatctggttcgttaa Synthetic *nifY* atgtctgacaatgataccctgttttggcgcatgctggcgctgtttcagtcgctgccggatttgc
agccggctcaaatcgtcgattggctggcgcaggaatccggcgaaaccctgacgccggagcgcct
tgccaccctgacccaaccgcaactcgcggcgtcgttcccatccgcgacggcagtgatgagcccg
gctcgctggagccgcgttatggcttctctgcaaggcgccctcccagcccacttgcgcatcgtac
gtccggcgcagcgtaccccgcaactgctcgccgcgttttgcagccaagacggcgttgttatcaa
tggtcatttcggccagggtcgtctgttcttcatttacgcctttgacgagcagggcggctggctg
tatgacttgcgccgctatccgagcgcaccgcaccagcaggaagcgaatgaggtgcgtgctcgtc
tgattgaagattgccagctgctgttctgccaggagattggcggtccggcagcagcgcgtctgat
ccgccaccgcatccatccgatgaaggcgcagccgggtactacgattcaggcgcagtgtgaagct
atcaacaccctgctggccggtcgcctgccgccgtggctcgccaaacgtttgaaccgtgataacc
cgctggaagagcgtgtgttttaa Synthetic *nifE* atgaagggtaacgagattcttgctctgctggacgaaccggcctgtgaacacaaccataaacaga
aatccggctgtagcgccccaaagccgggtgcgacggcggctggctgcgctttcgatggtgcgca
gatcaccctgctcccgattgcggacgttgcccacctcgtgcatggcccaatcggttgcgcaggt
agctcttgggacaaccgtggcagcgcctccagcggtccgaccctgaatcgtttgggctttacca
ctgacttgaatgaacaagatgtgatcatgggtcgcggcgagcgtcgcctgttccacgctgtgcg
ccatattgtcacccgttaccacccagcggcagtattcatctacaatacgtgcgtgccggctatg
gaaggcgatgacctggaggccgtgtgtcaggcagcccagactgcgaccggcgtcccggtaatcg
caattgatgcgggctggcttctacggttcgaagaacctgggcaaccgtccggcaggcgatgtcat
ggttaaacgcgtcattggccaacgtgagccagcgccgtggccggagagcacccctgtttgcccg
gagcaacgtcatgacattggcttgatcggtgagttcaacattgcgggcgagtttttggcacattc
agccgctgcttgatgagctgggtatccgcgtttttgggttcgctcagcggcgatggtcgtttcgc
cgagattcaaaccatgcaccgtgcccaggcgaacatgctggtgtgcagccgtgctctgatcaat
gtggcgcgtgctctggaacgcgctatggcacccgtggtttgaaggctcgttctatggtatcc
gcgcgaccagcgacgcccctgcgccagttagcggcgctgctgggcgatgacgacctcgtcagcg
caccgaggcgctgatcgcgcgtgaagaacaggcggctgagctggccctgcaaccgcggcgtgaa
cagctgcgtggcgcaaggccctgctctacacgggtggtgtcaaaagctggtctgtggtgtccg
cgcttcaggatctgggtatgaccgtggttgccacgggcacgcgtaagagcacggaagaggataa
acagcgcatccgcgaattgatgggcgaagagccggtgatgctgaagaaggcaacgcacgtacc
ttattggatgtagtttatcgctatcaagcagactgatgattgccggtggcgcaacatgtata
ccgcctacaaagcgcgcttgccgttcctggacatcaaccaggaacgcgagcacgcgtttgcggg
ctacaaggcatcgtgaccttagcgcgcagctgtgccaaacgattaacagcccggatctggccg
cagactcattcccgcgcaccgtggcgctaa Synthetic *nifN* atggcagacatttcgcactgataagccgttggctgtgtcgccgatcaagaccggccagccgc

FIG. 38 (cont)

| | |
|---|---|
| | tgggtgcgatcctggcgtccctgggtatcgagcactcgattccgctggtacatggcgcgcaggg<br>ctgttcggcttttgccaaggttttctttatccagcacttccacgatccggtcccgctgcaaagc<br>acggcaatggacccgaccagcaccatcatgggcgctgatggtaacatcttcaccgcgctggaca<br>ctctctgccaacgcaataacccgcaagcaattgtgctgctgagcaccggcctctccgaggcgca<br>gggcagcgacatttcccgtgtagtgcgtcagttccgtgaagaatatccgcgtcataaaggcgtg<br>gcgattctgactgttaacacccggactttacggtagcatgagaacggctttccgctgtcc<br>tggagtctgtgattgaacagtgggttccgccagccccacgtccggcgcagcgcaatcgtcgcgt<br>caatcttttggtgagccatctctgtagcccaggcgatattgagtggctgcgccgttgcgtcgag<br>gccttcggtctgcaaccgatcattctgccggatctggctcagagcatggacggccaccttgctc<br>agggtgactttcgccgctgacgcaggcggcacgccgttgcgccaaatcgagcagatgggcca<br>gagcctttgctcttttgcgattggcgtcagcctgcaccgtgcgagcagcctgctggctccgcgt<br>tgtcgtggcgaagtcatcgccttgccgcacctcatgaccttggaacgctgcgacgcctttatcc<br>atcagttggcgaaaatcagcggtcgcgccgttccggagtggctggaacgccagcgcggtcagct<br>gcaagacgccatgatcgattgccacatgtggctgcaaggccagcgcatggcgattgccgccgaa<br>ggcgacctgctggcagcgtggtgcgatttcgcgaactctcaaggtatgcagccgggtccactgg<br>ttgctccgacgggtcatccgagcctgcgtcagttgccggtggagcgcgtggtgccgggtgatct<br>ggaggatcttcagaccctcttatgcgcacatccggccgacttactggtggcgaactcccacgcc<br>cgtgatttagcagagcaattcgccctgccgctggtgcgcgcaggcttcccgctgtttgacaaac<br>tgggcgaatttcctcgtgttcgccagggttatagcggtatgcgtgataccctgttcgagttggc<br>gaacctgatccgtgaacgccatcatcatctggctcattatcgcagcccgctgcgccagaaccca<br>gaatcctcgttgtctacgggtggcgcgtacgcagcggattaa |
| Synthetic *nifU* | atgtggaactacagcgagaaagtcaaggaccatttcttcaatccgcgcaacgcgcgtgttgtgg<br>ataacgcaaatgcggtgggcgacgtcggcagcttatcttgtggcgatgctctccgcttgatgct<br>gcgcgtggacccgcagagcgaaatcatcgaagaagcgggctttcagaccttcggctgcggcagc<br>gcgattgcgtcgtccagcgcactgacggagctgatcatcggtcacaccctggcggaagcgggtc<br>agatcaccaaccagcagatcgccgactatctggacggcttaccgccggaaaagatgcactgctc<br>tgtaatgggccaggaagctcttcgtgcggccattgctaactttcgcggtgaatcgctggaagag<br>gagcatgacgagggtaagctgatctgcaagtgcttcggcgtcgatgaaggccatattcgccgtg<br>ctgtccagaacaacggtcttacgactctggccgaggtgatcaattacaccaaggcaggtggcgg<br>ttgtaccagctgccatgagaaaatcgagctggccctggccgagattctcgcccaacagccgcaa<br>accacccggcagttgcgtccggtaaagatcgacactggaagaggtcgtggataccatcgctg<br>aactgcgtccacatatccaagcggacggtggtgacatggcgctgttgtccgtgacgaaccacca<br>agtgactgtttcgctgtcgggcagcgttctggctgcatgatgaccgacatgaccctggcgtgg<br>ctgcaacagaaattgatggagcgtaccggctgctatatggaagttgttgccgcctaa |
| Synthetic *nifS* | atgaaacaagtgtacctggacaacaacgcgaccacccgcctggacccgatggttctggaagcga<br>tgatgccgtttctcacggatttctatggcaatccgtccagcatccatgacttcggcatcccggc<br>acaagcggcgctggaacgtacgcaccagcaagctgcggcactgctgggcgcagagtacccgtct<br>gaaatcattttcacgagctgtgcgaccgaggccactgcaaccgccattgcgtcggccatcgcgt<br>tattgcggaagcgcgcgaaatcatcacctcggtagtggagcaccggctacgctggcggcgtg<br>cgagcacctggaacgccaaggctatcgcatcatcgcattgcggtggataagcgaaggtgcgctg<br>gacatggcccagttccgtgcagcgctctcgccgcgtgtcgcgttggtgagcgtgatgtgggcca<br>acaacgaaaccggcgtgctgttcccgattggcgaaatggccgagcttgcccacgagcagggcgc<br>tctgttccactgcgatgccgttcaggtcgttggcaaaatcccaattgctgttggccagacgcgc<br>atcgacatgctgtcttgctccgcacaagttcatggtccgaagggtattggtgctttgtact<br>tacgtcgtggcacgcgctttcgtccgctgcttcgcggtggccatcaagaatatggtcgccgtgc<br>cggcactgagaatatctgtggcatcgtcggcatgggcgctgcgtgcgaactggcgaacatccat<br>ctgccgggtatgacccatattggccagttacgcaatcgcctggagcaccgtctgctcgccagcg<br>tgccgtccgtgatggttatgggcggtggtcagcgcgtgtacccgggtactgtcaacctggcgtt<br>cgagtttatcgaaggtgaagcgatcctgctctctgctgaacaggctggatgccgcaagctcc<br>ggctccgcgtgtacctctggcagcttggagccgagccaagtgatgcgcgcgatgaacattccat<br>acaccgcggctcacggcaccattcgtttttagcctgagccgttatacgcgcgagaaagagatcga<br>ctacgtcgttgcgaccctcccgccaatcattgatcgtctgcgtgccttgtcccgtattggcag<br>aatggtaagcgcgtccggcagatgcagtctttacccgggtttacggttaa |
| Synthetic *nifV* | atggagcgcgtcttgatcaacgatactaccctgcgtgatggcgaacaatctccgggcgtagcgt<br>ttcgtacctccgagaaagttgccatcgcggaggcactgtacgctgcgggtatcaccgcgatgga<br>agtcggcacctccggcgatgggtgatgaagagatcgcccgcattcagctggtgcgtcgtcaactg<br>ccggacgcgacgctatgacctggtgcgtatgaacgctctggaaatccgtcagagcgcggatc<br>tggtattgacctggtggatatctcgatcccagcatccgacaagctgcgtcagtacaagctgcg<br>tgagccgctggccgtgctgctggagcgcctttgcgatgtttatccatctggcccacacgttaggc<br>ctcaaagtatgtattggttgcgaggatgcgagccgtgcgtctggtcagaccctgcgcgccattg<br>ccgaggtggcccagcaatgcgcggctgcgcgcttgcgttacgctgaaccgtgggctgctgga<br>cccgttcaccaccgcagcccagatcagcgccctgcgtgacgtttggtcgggcgagatcgagatg<br>catgctcacaatgatctgggcatggctaccgcgaacacgctggcggcagtttcggctggcgcca<br>cgtcggtgaacactaccgtcctcggtctgggtgaacgtgcaggcaacgcagccctggaaaccgt<br>tgcgctgggcctggaacgctgcctgggcgtggaaaccggcgtccatttcagcgcgctcccagcg<br>ctctgtcagcgcgtcgcggaggctgcacagcgcgcaatcgacccgcaacagccgctggtgggtg<br>aattggttttcacccacgagtctggtgttcacgttgcggcgctgctgcgcgacagcgaatccta<br>tcaatctattgccccaagcctcatgggccgtagctaccgtctggtgctcggcaagcattcgggt<br>cgtcaggctgtcaacggtgtttcgaccagatgggttaccacctgaatgcggcgcagatcaatc<br>agttgctgccggccattcgccgcttcgccgagaattggaaacgctctccgaaagattacgaact<br>ggttgcgatctatgacgaattgtgcggtgaatccgcccttcgtgctcgcggctaa |
| Synthetic *nifW* | atggagtggttttaccagattccgggtgtagacgaattgcgcagcgctgaatcctttctttcagt<br>tcttcgcggttccataccagccggaactgctgggccgctgctcgcttccggtgttagcgacgtt<br>ccacccgtaaactgcgtgcggaggtcccgctgcaaaaccgtctggaggacaatgatcgtgcgccg<br>tggctcttggcgcgccgcctcctggccgaatcttatcagcagcaatttcaggagagcggcacct<br>aa |
| Synthetic *nifZ* | atgcgcccgaaattcaccttctctgaagaggtccgcgtagttcgcgcgattcgtaatgatggca<br>ccgtggcgggttttgcgccaggtgcgctgctggttcgtcgcggttcgacgggctttgtgcgtga<br>ctggggtgtgttcctgcaagaccagatcatctatcaaatccactttccggaaaccgaccgcatt<br>atcggctgtcgccagcaggagttaatcccgattacccagccgtggttggctggtaacctccagt<br>atcgtgacagcgtcacgtgccaaatggcactggctgtcaacggtgacgtggttgtgagcgccgg |

FIG. 38 (cont)

| | |
|---|---|
| | tcaacgtggccgtgtggaggccactgatcgtggcgaacttggcgattcctacaccgtggacttc<br>agcggccgttggttccgcgttccggtccaggccatcgcgctgattgaagagcgcgaagaataa |
| Synthetic *nifM* | atgaatccgtggcagcgctttgcccgtcaacgccttgctcgcagccgctggaaccgtgatccgg<br>ctgctctcgacccagccgataccccagcgttcgagcaggcgtggcagcgtcaatgccatatgga<br>acaaaccatcgtagcgcgtgtcccggaaggcgatattccggctgccttactggaaaacatcgcg<br>gccagcctggcgatctggctggacgagggtgacttcgctccgccggagcgcgctgcgattgtgc<br>gtcatcatgcacgtctggagctggcgtttgccgacattgcccgccaggcaccgcaaccggatct<br>gagcacggttcaagcgtggtatctgcgtcaccagactcaattcatgcgtccggagcagcgtctg<br>accgtcacctgctcctgacggtcgataatgatcgcgaggcggtgcatcaacgcatccttggcc<br>tgtatcgtcagatcaacgcgagccgtgacgccttcgccccactggcacagcgccactctcattg<br>cccgtccgccttggaagaaggccgtctgggctggatctcccgtggtctgctgtacccgcagctc<br>gaaaccgcgttgtttagcctggcggaaaacgcactgtcgctgccgattgcgtcggaattgggtt<br>ggcacctgttatggtgcgaggccattcgtccggcagccccgatggagccgcaacaggcccttga<br>atctgcgcgcgactacttgtggcagcagagccagcagcgccaccagcgtcaatggctggagcag<br>atgatttcccgccaaccgggcctgtgtggttaa |
| Synthetic *nifF* | atggcgaacatcggcatcttctttggtacggataccggcaaaacccgcaagattgcgaagatga<br>ttcacaaacagctgggcgagctggccgatgccccggttaacatcaatcgtaccactttggatga<br>ctttatggcttacccagtcctgttgctcggcacgccgacgcttggtgatggtcaactgccgggc<br>ttagaggcgggctgcgagagcgaaagctggtctgagtttatctccggtctggatgacgcttccc<br>tgaagggcaaaaccgtggcgctgtttggcctgggcgaccagcgtggttacccggacaacttcgt<br>gtcgggtatgcgtccgctgttcgacgcgctgagcgcccgtggcgcccagatgattggtagctgg<br>ccgaacgaaggttatgagtttagcgcatcgtccgcgctggaaggcgaccgcttcgtcggcttgg<br>tgctggatcaagacaatcagttcgaccagaccgaagcgcgcctggcgtcttggcttgaagagat<br>caaacgcaccgttctgtaa |
| Synthetic *nifB* | atgacctcttgttcgtcgttttctggcggtaaagcgtgccgtccggccgatgactccgcgctga<br>ctccgctggtggccgacaaggcagctgcgcaccccgtgctatagccgccacggccatcaccgctt<br>cgcgcgtatgcacctgccagtcgctccggcctgcaacttacaatgcaactactgcaaccgcaag<br>ttcgattgcagcaatgaaagccgtccgggcgtgtcctctaccctgctgacgccggaacaggctg<br>tggtgaaggtgcgccaggtcgcccaagctatcccgcagctgtcggtggtcggtattgctggtcc<br>gggcgatccgcttgcgaatatcgcccgcaccttccgtaccttggagcttattcgcgaacagttg<br>ccggacctgaaactgtgcctgagcaccaacggcttggtgctgccagatgccgttgatcgtctgc<br>tcgatgtgggcgtggatcacgttaccgtcaccattaacaccctggacgcagaaatcgcagcgca<br>aatctacgcgtggttgtggctggatggcgaacgctactccggtcgcgaagccggcgaaattctc<br>attgcccgccagctggaaggcgtacgtcgcctgaccgcgaaaggtgtgctcgtcaagatcaaca<br>gcgtattgattccgggcatcaatgacagcggcatggcgggtgttagccgtgcgctgcgcgcgtc<br>tggtgcgttcatccacaacatcatgccactgattgcgcgtccggagcatggcactgttttcggt<br>ctgaacggccagccggaaccggacgcggaaaccctggcggcgacgcgctcccgctgcggcgagg<br>ttatgccacaaatgacccactgccaccagtgccgtgccgacgcgattggcatgcttggtgagga<br>tcgctcgcaacagtttacgcaattaccggctccggagtccctcccggcctggctgccgatcctg<br>catcagcgtgctcagttgcatgcgagcatcgccacgcgcggtgagagcgaagccgatgacgcct<br>gcctcgtggccgttgcgtcgagccgtggcgatgtaattgactgccatttcggccatgccgaccg<br>tttctatatctatagcctgtctgcggctggtatggttctggttaacgaacgtttcaccccgaaa<br>tactgccagggtcgcgatgactgcgagccgcaggacaatgccgcacgctttgctgccatccttg<br>agttgctggcggacgtcaaagcggtgttttgtgtgcgtatcggccataccccgtggcaacagct<br>ggagcaggaaggcatcgaaccgtgcgtggatggcgcctggcgtccggtatccgaggtcctgccg<br>gcatggtggcagcagcgccgtggtagctggccggctgcattgccgcacaaaggcgttgcgtaa |
| Synthetic *nifQ* | atgccgccattggactggttgcgtcgtttgtggttactctatcacgccggcaaaggcagctttc<br>cgcttcgtatgggcttgtcgccgcgtgactggcaagctctgcgccgtcgcctgggcgaggtgga<br>aacgccgctggatggcgaaaccctgacccgtcgccgtctgatggcggagctgaatgcgacccgc<br>gaagaagaacgccagcagctgggtgcctggctggccggttggatgcaacaggatgccggtccga<br>tggcgcagattatcgcagaggtgagcctggcgttcaaccatctctggcaggaccttggcctcgc<br>gagccgcgctgaactgcgtctgctgatgtctgactgcttcccgcagctggttgttatgaacgag<br>cacaacatgcgctggaagaaattctttacccgccagcgttgcctgctgcaacagggcgaagtca<br>tctgtcgcagcccgtcttgcgatgaatgctgggaacgttctgcgtgctttgagtaa |

SEQUENCE LISTING

```
<160> NUMBER OF SEQ ID NOS: 345

<210> SEQ ID NO 1
<211> LENGTH: 3504
<212> TYPE: DNA
<213> ORGANISM: Klebsiella pneumoniae
<220> FEATURE:
<223> OTHER INFORMATION: wild type Gene J, nifJ

<400> SEQUENCE: 1

atgaaaacaa tggatggcaa cgccgcggcg gcctggatct cttatgcctt taccgaggtc     60

gcggcgattt accccataac cccctccacg ccgatggcgg aaaacgtcga cgagtgggcg    120

gcgcagggga aaaagaacct ttttggccag ccggtgcgct taatggagat gcagtcggag    180

gccggcgcgg caggcgcggt ccacggcgcg ctgcaggccg gggcgctcac caccacctat    240

acggcctccc aggggctgct gctgatgatc cccaacatgt acaaaatcgc cggtgaactg    300

ctgccgggcg tctttcacgt cagcgcccgg gcgctggcga ccaattcgct gaatattttt    360

ggcgatcacc aggatgtgat ggcggtccgc cagaccggct gcgcgatgct ggcggagaac    420

aacgtgcagc aggtgatgga tttgtcggcg gtggcgcatc tggcggcgat taagggacgc    480

atcccgtttg ttaacttctt cgacggtttt cgcacctcgc acgaaattca aaaaatcgag    540

gtgttggaat atgagcagct ggcgacgctg ctggaccggc ccgcgctcga cagcttccgc    600
```

-continued

```
cgtaacgcgc tgcatccgga tcatccggtc atccgcggaa cggcgcagaa cccggatatc    660
tacttccagg agcgggaggc gggcaaccgt ttttatcagg cgctgcccga cattgtcgaa    720
agctatatga cgcaaatcag cgcgctcacc ggccgggagt atcatctgtt taactatacc    780
ggcgcggcgg atgccgaacg ggtgattatc gcaatgggat cggtctgcga taccgttcag    840
gaagtggtgg atacgctgaa cgcggcggga gagaaggtcg ggctgctcag cgtgcatctg    900
tttcgccctt tttcgctggc ccacttcttc gcccagctgc cgaaaaccgt gcagcggatt    960
gccgtccttg accgtaccaa agagcccggc gctcaggctg aaccgctgtg cctggatgtg   1020
aaaaacgcct tctaccacca cgacgatgcg ccgctaatcg tcggcggccg ctatgcgctt   1080
ggcgggaagg atgttctgcc caacgatatc gcggccgtct ttgataacct caataaaccg   1140
ctgccgatgg acgggtttac cctcgggatt gtcgatgatg taacctttac ttcgttaccg   1200
ccggcccagc agacgctggc ggtctcgcat gacggcatca ccgcctgtaa attttggggc   1260
atgggctcgg acggcaccgt cggggccaat aaaagcgcga tcaaaattat cggcgataaa   1320
acgccgctct acgcgcaggc ctacttttct tatgactcga aaaaatccgg cggcattacc   1380
gtttcacatt tacgcttcgg cgaccggccg atcaattcgc cctacctgat ccatcgggcc   1440
gattttatct cctgttcgca gcagtcctac gttgagcgct acgatctgct ggacggatta   1500
aagccgggcg ggaccttttt actcaactgc agctggtccg atgcggagct ggagcagcat   1560
ctgccggtcg gctttaaacg ctatctggcg cgggaaaata tccattttta taccctgaac   1620
gccgtggata tcgcccgcga gctcgggctg ggcgggcgct ttaatatgct gatgcaggcg   1680
gcgttcttta agctggcggc gattatcgac ccgcagaccg cggcggatta cctcaagcag   1740
gcggttgaaa aaagctacgg cagcaaaggg gcggcggtga ttgagatgaa ccagcgggcg   1800
atcgagctgg gcatggcctc gctgcatcag gtgacgattc cggcgcactg ggcgacgctg   1860
gatgaacccg cggcgcaagc atcagccatg atgccggatt tcatccgcga tattctgcag   1920
ccgatgaacc gccagtgcgg cgaccagctg ccggtgagcg cgttcgtcgg tatggaggac   1980
gggacctttc cttcgggcac cgccgcgtgg gagaaacgcg ggatcgcgct ggaagtgccg   2040
gtctggcagc cggagggctg cacgcagtgt aaccagtgcg cctttatctg cccgcatgcg   2100
gcgatccgcc cggcgctgct caacggcgaa gagcatgacg ccgcgccggt tgggctgctg   2160
agcaaacccg cgcagggagc gaaggagtat cactaccatc tggctatctc gccgctggat   2220
tgttccggct gcggcaactg cgtggatatc tgtcccgcgc gcggcaaggc gttaaaaatg   2280
cagtctctcg atagccagcg tcagatggcg ccggtctggg actatgcgct ggcgctgacg   2340
ccgaagagca atccgtttcg taagacgacg gtcaaaggca gccagtttga aaccccgctg   2400
ctggagtttt ccggcgcctg cgcgggatgc ggtgaaacgc cttatgcccg cctgataacc   2460
cagctgtttg gcgaccggat gctgatcgct aacgccaccg gctgctcttc tatctgggga   2520
gccagcgcgc cgtcgattcc ctataccacc aaccaccgcg gccatggccc ggcatgggcg   2580
aactcgctgt ttgaggataa tgcggagttt ggcctcggca tgatgctcgg cggccaggcg   2640
gtgcgtcaac aaatcgccga tgatatgacc gccgcgctgg cgctaccggt cagcgacgaa   2700
cttagcgacg caatgcgcca gtggctggcg aagcaggatg aaggcgaggg cacccgcgag   2760
cgcgcggacc ggctcagcga acggctggcg gcggaaaaag agggcgtgcc gctgttggag   2820
cagctgtggc agaaccgcga ctattttgtt cgtcgttcgc agtggatttt cggcggcgac   2880
ggctgggcct acgatatcgg cttcggcggt ctcgatcacg tgctggcgag cggggaagac   2940
gtcaatattc tggtgtttga caccgaggtt tactccaata ccggcggcca gtcgtctaaa   3000
```

```
tcgaccccgg tggcggccat cgcgaagttt gccgcgcagg gcaaacgcac gcggaaaaaa   3060
gatctcggca tgatggcgat gagctacggc aatgtgtacg tggcccaggt cgcgatgggc   3120
gctgataaag atcagaccct acgggcgatc gccgaggccg aagcctggcc gggaccgtcg   3180
ctggtgattg cctacgccgc ctgcattaac cacgggctga aagccggtat gcgctgcagc   3240
cagcgcgagg cgaaacgggc ggttgaggcg ggatactggc acctgtggcg ctatcatccg   3300
cagcgggaag cggaaggtaa gacgccgttt atgctcgatt ccgaagagcc ggaggagagc   3360
ttccgcgact ttttgcttgg cgaagtgcgc tacgcctcgc tgcacaaaac gacgccgcat   3420
ctggcggatg cgctctttag ccgaaccgag gaggacgcgc gggcccgctt tgcccagtat   3480
cggcggctgg ccggcgagga gtag                                          3504
```

<210> SEQ ID NO 2
<211> LENGTH: 3504
<212> TYPE: DNA
<213> ORGANISM: Artificial Sequence
<220> FEATURE:
<223> OTHER INFORMATION: synthetic Gene J

<400> SEQUENCE: 2

```
atgaaaacta tggacggtaa cgctgcggct gcatggatta gctacgcctt taccgaagtg     60
gctgcgatct acccgattac gccgagcacc ccgatggcgg aaaatgtgga cgaatgggct    120
gcgcagggca agaagaacct cttcggccag ccggtgcgcc tgatggagat gcagtcggaa    180
gcgggtgcag caggtgctgt gcatggcgcc ttgcaagctg gcgcactgac gaccacctac    240
accgcgtcgc agggcctgtt gctgatgatc ccaaacatgt acaaaatcgc gggtgaactg    300
ctgccgggtg tctttcatgt ttcggcacgc gcactggcca ccaatagcct caacatcttt    360
ggcgatcatc aggatgtaat ggcggtgcgc caaacgggct gcgcgatgtt ggccgagaat    420
aacgtccagc aagttatgga tttgtccgcg gtagcccact tggcagcgat caaaggtcgc    480
attccgttcg tgaacttctt cgatggcttt cgcaccagcc acgaaatcca gaagatcgag    540
gttctggaat atgaacagct ggccaccttg ttggatcgtc cggccctgga cagcttccgc    600
cgtaacgccc ttcacccgga ccacccggtc atccgtggca ccgcccagaa cccggacatc    660
tacttccagg aacgtgaggc cggtaaccgt ttctatcagg cgctcccgga tattgtggaa    720
tcttacatga cccagatttc tgccctgact ggtcgcgagt atcacctgtt taactacact    780
ggtgctgcgg atgcggagcg cgtgatcatc gcgatgggct ctgtctgtga caccgtccaa    840
gaggtggttg acacgctgaa tgcagcgggt gagaaagttg gtctgctctc cgttcatctt    900
ttccgcccgt tttcgttagc gcacttcttc gcccaactgc cgaaaactgt acagcgtatc    960
gcagtattgg accgtacgaa agagccaggt gctcaagcag agccgctgtg cctcgatgtg   1020
aagaatgcct tttaccacca tgacgatgcc ccgttgattg tgggtggtcg ctatgccttg   1080
ggcggtaagg acgtgttgcc gaacgatatt gcggccgtgt ttgataacct gaacaaaccg   1140
ctgccgatgg acggcttcac gctgggtatc gtggacgatg ttaccttcac ctctctcccg   1200
ccagcgcagc agaccctggc ggtttctcac gacggcatca cggcatgtaa gttttggggc   1260
atgggctccg acggcacggt tggtgcgaac aagtccgcga tcaagattat cggcgacaaa   1320
acgccactgt atgcgcaagc gtacttttcc tacgactcga agaagagcgg tggtattacc   1380
gtcagccatc tgcgttttgg tgatcgcccg atcaactccc cgtatttgat ccatcgcgcg   1440
gatttcatct cgtgcagcca gcaaagctat gttgaacgct acgatctgct ggatggcctt   1500
```

-continued

```
aaaccgggtg gcacctttct gctgaactgc tcctggagcg atgccgaact ggagcaacat   1560

ctgccggtcg gtttcaaacg ttatctggca cgcgagaata tccacttcta cactctcaac   1620

gctgtggaca tcgcccgtga gcttggtttg ggtggccgtt tcaacatgct gatgcaggct   1680

gccttcttca aactggccgc gatcattgac ccgcagactg ctgcggacta tctgaagcag   1740

gctgttgaga aaagctatgg cagcaaaggt gcggcggtca tcgagatgaa ccagcgtgcc   1800

atcgagcttg gcatggccag cctgcaccag gtgacgatcc cggcacattg ggccaccctg   1860

gatgagccag cggcgcaggc gtccgcgatg atgccggact ttatccgcga catcctgcaa   1920

ccgatgaacc gtcagtgcgg cgaccagctt ccggtgtcgg cttttgtcgg catggaagat   1980

ggcaccttcc cgtccggcac ggccgcatgg gagaaacgtg gcatcgccct tgaggtgcca   2040

gtctggcagc cggaaggctg cacgcagtgc aaccagtgcg ccttcatttg tccgcacgcc   2100

gcgattcgtc cggcgttgtt gaatggcgaa gagcatgatg ctgcccccggt tggcctgctg   2160

agcaaaccgg cacaaggcgc taaagaatat cactatcatc tggcgattag cccgctggac   2220

tgctccggct gtggcaactg cgttgacatt tgtccagctc gtggcaaagc gttgaagatg   2280

cagtctctgg atagccaacg ccagatggct ccggtgtggg attatgcgct ggcgctgacc   2340

ccgaagtcta acccgtttcg taaaaccacc gtcaaaggct cgcagttcga aaccccgctg   2400

ctggagttta gcggtgcgtg cgctggttgt ggcgaaacgc cgtatgcgcg cctcattacc   2460

cagctgtttg gcgaccgcat gctgattgcc aatgccaccg gctgttccag catctggggc   2520

gcatctgcgc cgagcatccc gtataccacc aatcatcgtg gtcatggtcc ggcctgggcg   2580

aatagcctgt ttgaggacaa tgccgaattt ggtttaggta tgatgctggg cggtcaagct   2640

gtgcgtcaac agatcgcgga cgatatgacg gctgcgttag cgctcccggt ttccgatgag   2700

ctgagcgacg cgatgcgcca gtggttggcg aaacaggacg agggtgaagg cacgcgtgag   2760

cgtgcggacc gtctgagcga gcgcttagcc gcggagaaag agggcgttcc gctgttagag   2820

cagctgtggc aaaatcgtga ttactttgtg cgtcgcagcc agtggatttt cggcggtgac   2880

ggctgggcct atgatattgg cttcggtggc ctggaccacg tcctcgccag cggtgaggat   2940

gtgaacattc tggtatttga caccgaagtc tactcgaaca ccggcggtca aagcagcaaa   3000

tcgaccccgg tcgcggccat cgccaagttc gcggctcagg gcaagcgcac ccgcaagaaa   3060

gacctgggta tgatggcgat gagctacggc aacgtctatg tagcccaggt ggcgatgggt   3120

gcggataaag atcaaactct gcgcgccatt gcggaagctg aagcgtggcc aggcccgtcg   3180

ctggtgattg cgtatgcggc ctgcatcaat catggcctga aggccggtat gcgttgcagc   3240

caacgtgagg cgaagcgcgc tgttgaggcg ggctactggc acctgtggcg ttatcacccg   3300

cagcgcgaag cggaaggcaa gacgccgttt atgttagata gcgaagaacc ggaagagtcg   3360

ttccgtgact ttctgttggg tgaggtgcgc tacgcatccc tgcacaagac caccccgcac   3420

ctcgccgatg cccttttcag ccgtaccgaa gaagatgcgc gtgcgcgctt tgcgcaatac   3480

cgtcgcctgg ctggcgaaga gtaa                                          3504
```

<210> SEQ ID NO 3
<211> LENGTH: 882
<212> TYPE: DNA
<213> ORGANISM: Klebsiella pneumoniae
<220> FEATURE:
<223> OTHER INFORMATION: wild type Gene H, nifH

<400> SEQUENCE: 3

```
atgaccatgc gtcaatgcgc tatttacggt aaaggcggta tcggtaaatc caccaccacg     60
```

```
cagaacctcg tcgccgcgct ggcggagatg ggtaagaaag tgatgatcgt cggctgcgat    120

ccgaaggcgg actccacccg tctgattctg cacgccaaag cacagaacac cattatggag    180

atggccgcgg aagtcggctc ggtcgaggac ctcgaactcg aagacgtgct gcaaattggc    240

tacggcgatg tgcgctgcgc ggaatccggc ggcccggagc caggcgtcgg ctgcgcggga    300

cgcggcgtga tcacggcgat caactttctt gaagaagaag gcgcctacga ggacgatctc    360

gatttcgtgt tctatgacgt gctcggcgac gtggtctgcg gcggcttcgc catgccgatc    420

cgcgaaaaca aagcccagga gatctacatc gtctgctccg gcgaaatgat ggcgatgtac    480

gcggccaaca atatctccaa agggatcgtt aaatacgcca aatccggcaa ggtgcgcctc    540

ggcggcctga tctgtaactc acgtcagacc gaccgtgaag acgaactgat tattgccctg    600

gcggaaaagc tcggtaccca gatgatccac tttgtgcccc gcgacaacat cgtgcagcgc    660

gcggagatcc gccgcatgac ggttatcgag tacgaccccg cctgtaaaca ggccaacgaa    720

taccgcaccc tggcgcagaa gatcgtcaac aacaccatga aagtggtgcc gacgccctgc    780

accatggatg agctggaatc gctgctgatg gagttcggca tcatggaaga ggaagacacc    840

agcatcattg gcaaaaccgc cgccgaagaa aacgcggcct ga                       882
```

<210> SEQ ID NO 4
<211> LENGTH: 882
<212> TYPE: DNA
<213> ORGANISM: Artificial Sequence
<220> FEATURE:
<223> OTHER INFORMATION: synthetic Gene H

<400> SEQUENCE: 4

```
atgaccatgc gtcagtgcgc gatttatggc aaaggtggta ttggcaaaag cacgacgacc     60

cagaacttgg tggcggccct ggccgagatg ggtaaaaagg ttatgattgt gggttgcgac    120

ccgaaggccg acagcacgcg cctgattctg cacgcgaaag cacaaaacac gattatggag    180

atggctgccg aggttggtag cgtggaggat ctggagctgg aggacgttct gcaaattggt    240

tacggtgatg ttcgttgcgc agagagcggt ggtccggaac caggtgtcgg ctgtgcgggt    300

cgtggtgtga ttaccgctat caatttcctg gaagaagagg gtgcgtacga agatgatctg    360

gatttcgttt tctacgatgt gctgggtgat gtcgtgtgcg gtggttttgc aatgccgatt    420

cgcgagaata aggcacaaga aatttacatt gtctgtagcg gcgagatgat ggcaatgtac    480

gctgctaaca acatcagcaa gggtattgtt aaatacgcaa aagcggtaa ggttcgcttg     540

ggtggtttga tttgcaacag ccgtcagacc gaccgtgagg acgaactgat catcgccctg    600

gctgagaaac tgggcaccca aatgatccac ttcgtgccac gcgataatat tgttcaacgt    660

gcagaaatcc gccgtatgac cgtcattgag tatgacccgg catgcaagca agcgaacgag    720

taccgcacct tggcacagaa aatcgtgaac aacaccatga aggttgttcc gacgccgtgt    780

acgatggacg agctggagag cctgctgatg gagttcggca ttatggagga ggaggacacc    840

agcattatcg gtaagaccgc agcggaggag aatgcggcat aa                       882
```

<210> SEQ ID NO 5
<211> LENGTH: 1452
<212> TYPE: DNA
<213> ORGANISM: Klebsiella pneumoniae
<220> FEATURE:
<223> OTHER INFORMATION: wild type Gene D, nifD

<400> SEQUENCE: 5

```
atgatgacca acgcaacggg cgaacgtaat ctggcgctga tccaggaagt cctggaggtg     60
ttcccggaaa ccgcgcgaaa agagcgcaga aagcacatga tggtcagcga tccgaaaatg    120
aagagcgtcg gcaagtgcat tatctctaac cgcaaatcac aacccggcgt aatgaccgta    180
cgcggctgcg cctacgccgg ttccaaaggg gtggtatttg ggccgattaa ggatatggcc    240
catatttcgc acggaccggc tggctgcggc cagtattccc gcgccgaacg acgcaactac    300
tacaccggag tcagcggcgt cgatagcttc ggcacgctga acttcacctc tgattttcag    360
gagcgcgaca tcgtcttcgg cggcgataaa aagctcagca agctgattga agagatggag    420
ttgctgttcc cgctcaccaa agggatcacc attcagtcgg aatgcccggt ggggctgatc    480
ggtgatgata tcagcgcggt ggccaacgcc agcagcaagg cgctggataa accggtgatc    540
ccggtacgct gcgaaggctt tcgcggcgtg tcgcagtctc tggggcacca tatcgccaac    600
gacgtggtgc gcgactggat cctgaacaat cgcgaaggac agccgtttga aaccacccct    660
tacgatgtgg cgatcatcgg cgactacaac atcggcggcg acgcctgggc ctcgcgcatt    720
ctgctggaag agatggggct acgggtagtc gcgcagtggt ccggcgacgg cacgctggtg    780
gagatggaga ataccccatt cgtcaagctg aacctggttc actgctaccg ttcgatgaac    840
tatatcgccc gccatatgga ggagaaacat cagattccgt ggatggagta caacttcttc    900
gggccgacca aaatcgccga atcgctgcgc aaaatcgccg accagttcga cgataccatt    960
cgcgcgaacg ccgaagcggt gatcgcccgg tatgaggggc agatggcggc gattatcgcc   1020
aaatatcgcc cgcgcctgga ggggcgtaag gtgctgctct atatcggagg cctgcggccg   1080
cgccacgtta ttggcgccta tgaggatctc gggatggaga tcatcgccgc cggctacgag   1140
tttgcccata acgatgatta cgaccgcacc ctgccggatc tgaaagaggg cacgctgctg   1200
ttcgatgacg ccagcagcta cgagctggaa gcgttcgtca aggcgctgaa gcccgacctt   1260
atcggctccg gcatcaagga aaaatatatc ttccagaaaa tgggcgtgcc gttccgccag   1320
atgcactcgt gggactattc cggcccgtac cacggctacg atggtttcgc cattttcgcc   1380
cgcgatatgg atatgaccct gaacaacccg gcgtggaacg aactgaccgc tccgtggctg   1440
aagtctgcgt ga                                                       1452
```

<210> SEQ ID NO 6
<211> LENGTH: 1452
<212> TYPE: DNA
<213> ORGANISM: Artificial Sequence
<220> FEATURE:
<223> OTHER INFORMATION: synthetic Gene D

<400> SEQUENCE: 6

```
atgatgacta atgctactgg cgaacgtaac ctggcactga ttcaagaagt actggaagtg     60
ttcccggaaa ccgcgcgcaa agagcgccgt aaacacatga tggtttctga cccgaaaatg    120
aaatctgtgg gtaaatgcat catctctaat cgcaaatctc agccgggtgt catgactgtt    180
cgtggctgtg cgtacgcagg ttctaaaggt gtcgtattcg gcccgatcaa agatatggcg    240
catatctctc atggcccggc aggctgtggc cagtactctc gcgcggaacg tcgtaactac    300
tacacgggcg tttctggcgt tgactctttc ggcacgctga acttcacctc tgacttccag    360
gaacgtgaca tcgttttcgg tggcgataaa aagctgtcca aactgatcga agaaatggaa    420
ctgctgttcc cgctgactaa aggcattact atccaaagcg aatgtccggt gggtctgatc    480
ggtgatgaca tcagcgcggt cgcaaacgca tcttccaaag ccctggataa gccggtgatc    540
ccggttcgtt gcgagggctt ccgcggcgtt tctcagtctc tgggtcatca catcgcaaac    600
```

gatgttgtgc gtgactggat tctgaacaac cgtgaaggtc agccttttga aaccacccct 660
tatgacgttg cgattattgg cgactataac atcggcggcg acgcctgggc atcccgcatc 720
ctgctggagg agatgggtct gcgtgttgtc gcacagtggt ctggcgatgg caccctggtt 780
gaaatggaaa acaccccgtt tgttaaactg aacctggttc actgctaccg ctccatgaac 840
tacattgccc gtcacatgga agaaaaacat cagatccctt ggatggaata caacttcttc 900
ggtccgacta aaatcgcaga atccctgcgt aaaatcgccg atcagtttga tgataccatt 960
cgcgcgaacg ctgaagcagt aattgcgcgc tacgaaggcc agatggcagc aatcattgct 1020
aagtaccgtc cgcgcctgga aggtcgtaaa gtgctgctgt acatgggtgg tctgcgtcca 1080
cgtcatgtga tcggtgccta cgaggacctg ggcatggaga tcatcgcagc gggttacgaa 1140
tttgcacaca acgacgacta tgatcgtacg ctgccagacc tgaaagaagg tacgctgctg 1200
tttgacgacg ccagctctta tgaactggaa gccttcgtga aagcgctgaa accagacctg 1260
atcggctccg gcatcaagga aaaatacatt ttccagaaaa tgggcgtgcc gttccgccag 1320
atgcactcct gggactactc cggtccgtac cacggctacg acggtttcgc tatcttcgct 1380
cgtgacatgg atatgaccct gaataaccca gcgtggaatg aactgaccgc accgtggctg 1440
aaatctgcat aa 1452

<210> SEQ ID NO 7
<211> LENGTH: 1563
<212> TYPE: DNA
<213> ORGANISM: Klebsiella pneumoniae
<220> FEATURE:
<223> OTHER INFORMATION: wild type Gene K, nifK

<400> SEQUENCE: 7
atgagccaaa cgattgataa aattaatagc tgttatccgc tattcgaaca ggatgaatac 60
caggagctgt tccgcaataa gcggcagctg gaagaggcgc acgatgcgca gcgcgtgcag 120
gaggtctttg cctggaccac caccgccgag tatgaagcgc tgaatttccg acgcgaggcg 180
ctgaccgttg acccggcgaa agcctgccag ccgcttggcg cggtgctttg ctcgctggga 240
tttgccaaca ccctgccgta tgtgcacggc tctcaggggt gcgtggccta ctttcgcacc 300
tattttaacc gccatttcaa agagccgatc gcctgcgtct ccgactcgat gaccgaagac 360
gcggcggtct tcggcggcaa caacaatatg aacctgggcc tgcagaacgc cagcgcgctg 420
tacaaaccgg agatcattgc ggtgtccacc acctgcatgg cggaagttat cggcgatgac 480
ctgcaggcgt ttatcgccaa cgctaaaaaa gatggcttcg tcgacagcag catcgccgtg 540
ccccacgccc atacgccaag ctttatcggc agccacgtca ccggctggga taacatgttt 600
gaaggcttcg ccaaaacctt cactgcggac taccaggggc agccgggcaa attgccgaag 660
ctcaatctgg tgaccggctt tgaaacctat ctcggcaact tccgcgtatt aaagcggatg 720
atggaacaga tggcggtgcc gtgcagcctg ctctccgatc cgtcggaagt tctcgacacg 780
cccgccgacg gtcactatcg gatgtattcc ggcggcacca cgcagcagga gatgaaagag 840
gcccctgacg ccatcgatac gctgctcctg cagccgtggc agctgctgaa gagcaaaaaa 900
gtggtgcagg agatgtggaa ccagcccgcc accgaggtcg ccattccgct ggggctggcc 960
gccaccgatg aactgctgat gaccgtcagc cagcttagcg gcaagccgat tgccgacgcc 1020
ctcacccttg agcgcggccg gctggttgac atgatgctcg actcccacac ctggctgcac 1080
ggcaagaagt ttggcctgta cggcgatccg gacttcgtga tgggcctcac ccgcttcctg 1140

-continued

```
ctggagctgg gctgcgagcc aacggtgatc ctgagccata acgccaacaa acgctggcaa   1200

aaagcgatga acaaaatgct cgatgcctcg ccgtacgggc gcgatagcga agtgtttatc   1260

aactgcgatt tgtggcactt ccgttcgctg atgttcaccc gtcagccgga ctttatgatc   1320

ggcaactcct acggcaagtt tatccagcgc gataccctgg cgaagggtaa agcctttgaa   1380

gtgccgctta tccgcctcgg ctttccgctg ttcgaccgcc accatctgca ccgccagaca   1440

acctggggtt atgaaggggc gatgaacatt gtgacgacgc tggtgaacgc cgtgctggag   1500

aaactggata gcgataccag ccagctgggc aaaaccgatt acagcttcga tctcgtccgt   1560

taa                                                                 1563
```

<210> SEQ ID NO 8
<211> LENGTH: 1563
<212> TYPE: DNA
<213> ORGANISM: Artificial Sequence
<220> FEATURE:
<223> OTHER INFORMATION: synthetic Gene K

<400> SEQUENCE: 8

```
atgtctcaaa ctatcgataa aatcaactct tgttacccgc tgttcgagca ggacgaatat     60

caggaactgt tccgtaacaa acgtcagctg gaagaagcgc acgacgcaca gcgcgtgcag    120

gaagtgttcg catggaccac caccgcggaa tacgaagctc tgaacttccg tcgcgaagcc    180

ctgacggttg atccggcgaa agcgtgccag cctctgggtg cggttctgtg cagcctgggt    240

tttgccaaca ccctgccgta tgtccacggt tcccagggct gcgtagccta cttccgtacc    300

tatttcaacc gccactttaa agaaccaatc gcgtgcgtgt ccgacagcat gacggaggac    360

gcggcagttt tcggtggtaa caacaacatg aacctgggcc tgcaaaatgc ttccgcactg    420

tacaaaccgg aaatcatcgc agtgtctacc acctgcatgg cagaggttat tggtgatgat    480

ctgcaagcat ttattgccaa cgcaaagaaa gacggtttcg ttgacagctc tatcgcggtt    540

ccgcacgctc ataccccgtc cttcatcggt tctcacgtaa ctggttggga caacatgttc    600

gaaggcttcg caaaaacttt taccgcagac tatcaaggcc aaccgggtaa actgccgaag    660

ctgaacctgg tgaccggctt tgaaacctac ctgggcaact ttcgtgtcct gaagcgcatg    720

atggagcaga tggcggttcc gtgttctctg ctgtctgacc cgtctgaggt tctggacact    780

ccagcggacg gccactatcg catgtattct ggtggcacca ctcagcagga aatgaaagag    840

gccccagacg cgattgacac cctgctgctg caaccgtggc agctgctgaa aagcaagaaa    900

gttgttcagg aaatgtggaa ccagccggca acggaagttg caatcccgct gggtctggca    960

gctactgacg aactgctgat gaccgtgtcc caactgagcg gcaaaccaat cgcggatgct   1020

ctgaccctgg aacgcggtcg cctggtggac atgatgctgg acagccacac gtggctgcat   1080

ggcaagaaat ttggcctgta cggtgacccg gacttcgtaa tgggcctgac ccgtttcctg   1140

ctggaactgg gctgcgagcc gactgttatc ctgtctcaca acgctaacaa acgttggcag   1200

aaggccatga acaaaatgct ggatgcgagc ccatacggcc gtgatagcga agtgttcatc   1260

aactgcgacc tgtggcattt ccgctctctg atgtttacgc gtcagccgga tttcatgatc   1320

ggtaactctt acggcaaatt catccagcgt gacactctgg ccaaaggcaa agcgtttgaa   1380

gtgccgctga ttcgtctggg ctttccgctg ttcgaccgtc accacctgca ccgccagacc   1440

acctggggtt acgaaggcgc gatgaacatc gtaactactc tggtaaacgc agtactggaa   1500

aagctggaca gcgatacttc ccagctgggc aaaaccgact attctttcga tctggttcgt   1560

taa                                                                 1563
```

<210> SEQ ID NO 9
<211> LENGTH: 663
<212> TYPE: DNA
<213> ORGANISM: Klebsiella pneumoniae
<220> FEATURE:
<223> OTHER INFORMATION: wild type Gene Y, nifY

<400> SEQUENCE: 9
atgtccgaca acgataccct attctggcgt atgctggcgc tgtttcagtc tctgccggac 60
ctacagccgg cgcaaatcgt cgactggctg gcgcaggaga gcggcgagac gctgacgcca 120
gagcgtctgg cgaccctgac ccagccgcag ctggccgcca gctttccctc cgcgacggcg 180
gtgatgtccc ccgctcgctg gtcgcgggtg atggcgagcc tgcagggcgc gctgcccgcc 240
catttacgca tcgttcgccc tgcccagcgc acgccgcagc tgctggcggc attttgctcc 300
caggatgggc tggtgattaa cggccatttc ggccagggac gactgttttt tatctacgcg 360
ttcgatgaac aaggcggctg gttgtacgat ctgcgccgct atccctccgc cccccaccag 420
caggaggcca acgaagtgcg cgcccggctt attgaggact gtcagctgct gttttgccag 480
gagataggcg ggcccgccgc cgcgcggctg atccgccatc gcatccaccc gatgaaagcg 540
cagcccggga cgacgattca ggcacagtgc gaggcgatca atacgctgct ggccggccgt 600
ttgccgccgt ggctggcgaa gcggcttaac agggataacc ctctggaaga acgcgttttt 660
taa 663

<210> SEQ ID NO 10
<211> LENGTH: 663
<212> TYPE: DNA
<213> ORGANISM: Artificial Sequence
<220> FEATURE:
<223> OTHER INFORMATION: synthetic Gene Y

<400> SEQUENCE: 10
atgtctgaca atgataccct gttttggcgc atgctggcgc tgtttcagtc gctgccggat 60
ttgcagccgg ctcaaatcgt cgattggctg gcgcaggaat ccggcgaaac cctgacgccg 120
gagcgccttg ccaccctgac ccaaccgcaa ctcgcggcgt cgttcccatc cgcgacggca 180
gtgatgagcc cggctcgctg gagccgcgtt atggcttctc tgcaaggcgc cctcccagcc 240
cacttgcgca tcgtacgtcc ggcgcagcgt accccgcaac tgctcgccgc gttttgcagc 300
caagacggcc ttgttatcaa tggtcatttc ggccagggtc gtctgttctt catttacgcc 360
tttgacgagc agggcggctg gctgtatgac ttgcgccgct atccgagcgc accgcaccag 420
caggaagcga atgaggtgcg tgctcgtctg attgaagatt gccagctgct gttctgccag 480
gagattggcg gtccggcagc agcgcgtccg atccgccacc gcatccatcc gatgaaggcg 540
cagccgggta ctacgattca ggcgcagtgt gaagctatca acaccctgct ggccggtcgc 600
ctgccgccgt ggctcgccaa acgtttgaac cgtgataacc cgctggaaga gcgtgtgttt 660
taa 663

<210> SEQ ID NO 11
<211> LENGTH: 1374
<212> TYPE: DNA
<213> ORGANISM: Klebsiella pneumoniae
<220> FEATURE:
<223> OTHER INFORMATION: wild type Gene E, nifE

<400> SEQUENCE: 11

-continued

```
atgaagggaa atgaaattct ggcgctgctg gatgaaccgg cctgtgaaca caaccataaa      60
caaaaatccg gctgcagcgc gcccaaaccc ggcgccaccg ccgcgggctg cgcgttcgac     120
ggcgcgcaga taaccctgct gcccatcgcc gacgtggcgc atctggtcca cggccccatc     180
ggctgcgccg gaagctcatg ggataaccgc ggcagcgcca gctccggccc caccccttaat    240
cggctcgggt tcaccaccga tctcaacgaa caggacgtga ttatgggccg cggcgaacgc     300
cgactgtttc acgccgtgcg ccatatcgtc acccgctatc atccggcggc ggtctttatc     360
tacaacacct gcgtaccggc catggagggc gatgacctgg aagcggtatg ccaggccgcg     420
cagaccgcca ccggcgtacc ggttatcgct attgacgccg ccggtttcta cggcagtaaa     480
aatctcggta accggccggc gggcgacgtc atggtcaaac gggtcatcgg ccagcgcgag     540
cccgcccccct ggccggagag cacgctcttt gccccggagc agcgtcacga tattggcctg    600
attggcgaat tcaatattgc cggcgagttc tggcatattc agccgctgct cgacgaactg     660
gggatccgcg tgctcggcag cctctccggt gatggccgct tcgccgagat ccagaccatg     720
caccgggcgc aggccaatat gctggtctgc tcgcgggcgt taattaacgt cgccagagcc     780
ctggagcagc gctacggcac gccgtggttc gaaggcagct tttacgggat ccgcgccacc     840
tctgacgccc tgcgccagct ggcggcgctg ctgggcgacg acgaccttcg ccagcgcacc     900
gaagcgctga ttgcgcggga ggaacaggcg gcggaactgg cgctacagcc gtggcgcgaa     960
cagctgcgcg gccgcaaagc gctgctctat accggcgggg tgaaatcctg gtcggtggta    1020
tcggcgctgc aggatttggg catgaccgtg gtggcaaccg gcacgcgtaa atccaccgaa    1080
gaggataaac agcggatccg cgagctgatg ggcgaagagg cggtaatgct ggaagagggc    1140
aacgcccgca cgctgctgga tgtggtctat cgctatcagg ccgacctgat gattgccggc    1200
ggacgcaata tgtacaccgc ctataaagcc aggctgccgt ttctcgatat caatcaggag    1260
cgcgaacacg ccttcgctgg ctatcagggg atcgtcaccc tcgcccgcca gctgtgtcag    1320
accatcaaca gccccatctg gccgcaaacc cattctcgcg ccccgtggcg ctaa          1374
```

<210> SEQ ID NO 12
<211> LENGTH: 1374
<212> TYPE: DNA
<213> ORGANISM: Artificial Sequence
<220> FEATURE:
<223> OTHER INFORMATION: synthetic Gene E

<400> SEQUENCE: 12

```
atgaagggta acgagattct tgctctgctg gacgaaccgg cctgtgaaca caaccataaa      60
cagaaatccg gctgtagcgc cccaaagccg ggtgcgacgg cggctggctg cgctttcgat     120
ggtgcgcaga tcaccctgct cccgattgcg gacgttgccc acctcgtgca tggcccaatc     180
ggttgcgcag gtagctcttg ggacaaccgt ggcagcgcct ccagcggtcc gaccctgaat     240
cgtttgggct ttaccactga cttgaatgaa caagatgtga tcatgggtcg cggcgagcgt     300
cgcctgttcc acgctgtgcg ccatattgtc acccgttacc acccagcggc agtattcatc     360
tacaatacgt gcgtgccggc tatggaaggc gatgacctgg aggccgtgtg tcaggcagcc     420
cagactgcga ccggcgtccc ggtaatcgca attgatgcgg ctggcttcta cggttcgaag     480
aacctgggca accgtccggc aggcgatgtc atggttaaac gcgtcattgg ccaacgtgag     540
ccagcgccgt ggccggagag caccctgttt gccccggagc aacgtcatga cattggcttg     600
atcggtgagt tcaacattgc gggcgagttt tggcacattc agccgctgct tgatgagctg     660
ggtatccgcg ttttgggttc gctcagcggc gatggtcgtt tcgccgagat tcaaaccatg     720
```

caccgtgccc aggcgaacat gctggtgtgc agccgtgctc tgatcaatgt tgcgcgtgct 780
ctggaacagc gctatggcac cccgtggttt gaaggctcgt tctatggtat ccgcgcgacc 840
agcgacgccc tgcgccagtt agcggcgctg ctgggcgatg acgacctccg tcagcgcacc 900
gaggcgctga tcgcgcgtga agaacaggcg gctgagctgg ccctgcaacc gtggcgtgaa 960
cagctgcgtg gccgcaaggc cctgctctac acgggtggtg tcaaaagctg gtctgtggtg 1020
tccgcgcttc aggatctggg tatgaccgtg gttgccacgg gcacgcgtaa gagcacggaa 1080
gaggataaac agcgcatccg cgaattgatg ggcgaagagg ccgtgatgct tgaagaaggc 1140
aacgcacgta ccttattgga tgtagtttat cgctatcaag cagacctgat gattgccggt 1200
ggccgcaaca tgtataccgc ctacaaagcg cgcttgccgt tcctggacat caaccaggaa 1260
cgcgagcacg cgtttgcggg ctaccaaggc atcgtgacct tagcgcgcca gctgtgccaa 1320
acgattaaca gcccgatctg gccgcagact cattcccgcg caccgtggcg ctaa 1374

<210> SEQ ID NO 13
<211> LENGTH: 1386
<212> TYPE: DNA
<213> ORGANISM: Klebsiella pneumoniae
<220> FEATURE:
<223> OTHER INFORMATION: wild type Gene N, nifN

<400> SEQUENCE: 13
atggcagaca ttttccgcac cgataagccg ctggcggtca gccccatcaa aaccggccag 60
ccgctcggcg caatcctcgc cagcctcggg atcgaacaca gcatccctct ggtccacggc 120
gcgcaggggt gcagcgcctt cgccaaagtc ttttttattc aacatttcca cgacccggtt 180
cccctgcagt cgacggcgat ggaccccacg tcgacgatta tgggcgcgga cggcaatatt 240
tttaccgccc tggataccct ctgccagcgc aacaatccgc aggctatcgt actgctcagc 300
accgggctgt cggaggccca gggcagcgat atttcccgcg tggttcgcca gtttcgcgaa 360
gagtatcccc ggcataaggg ggtggcgata ttgacggtta acacgccgga tttttatggc 420
tccatggaga acggcttcag cgcggtgtta gagagcgtca ttgagcagtg ggtgccgccg 480
gcgccgcgcc cggctcagcg caatcgccgg gtcaatctgc tggtcagcca tctctgttcg 540
ccgggcgata tcgagtggct gcgccgatgc gtcgaagcct ttggtctgca gccgataatc 600
ctgccggacc tggcgcaatc gatggacggc cacctggcgc agggcgattt ctcgccgctg 660
acccagggcg ggacgccgct gcgccagata gagcagatgg ggcaaagcct gtgcagcttc 720
gccattggcg tctcccttca tcgcgcctca tcgctgctgg ccccgcgctg ccgcggcgag 780
gttatcgccc tgccgcacct gatgaccctc gaacgctgcg acgcctttat tcatcaactg 840
gcgaaaattt ccggacgcgc cgttcccgag tggctggaac gccagcgcgg ccagctacag 900
gatgcgatga tcgactgcca tatgtggctc cagggccagc gcatggcgat agcggcggaa 960
ggcgatttgc tggcggcgtg gtgtgatttc gccaacagcc aggggatgca gcccggcccg 1020
ctggtggccc ctaccggtca tcccagcctg cgccagctgc cggtggaacg ggtggtgccg 1080
ggggatctgg aggatctgca aaccctgctg tgcgcgcatc ccgccgacct gctggtggcg 1140
aactcgcacg cccgcgacct ggcggagcag tttgcgctgc cgctggtgcg cgcgggtttt 1200
ccgctctttg acaagctcgg cgaattccgc cgggtgcgac aggggtatag cgggatgcgc 1260
gatacgctgt ttgagctggc aaacctgata cgcgagcgtc accaccacct cgcccactac 1320
cgatcgccgc tgcgccagaa ccccgaatcg tcactctcca caggaggcgc ttatgccgcc 1380
gattaa 1386

<210> SEQ ID NO 14
<211> LENGTH: 1386
<212> TYPE: DNA
<213> ORGANISM: Artificial Sequence
<220> FEATURE:
<223> OTHER INFORMATION: synthetic Gene N

<400> SEQUENCE: 14
atggcagaca ttttccgcac tgataagccg ttggctgtgt cgccgatcaa gaccggccag 60
ccgctgggtg cgatcctggc gtccctgggt atcgagcact cgattccgct ggtacatggc 120
gcgcagggct gttcggcttt tgccaaggtt ttctttatcc agcacttcca cgatccggtc 180
ccgctgcaaa gcacggcaat ggacccgacc agcaccatca tgggcgctga tggtaacatc 240
ttcaccgcgc tggacactct ctgccaacgc aataacccgc aagcaattgt gctgctgagc 300
accggcctct ccgaggcgca gggcagcgac atttcccgtg tagtgcgtca gttccgtgaa 360
gaatatccgc gtcataaagg cgtggcgatt ctgactgtta acaccccgga cttttacggt 420
agcatggaga acggcttttc cgctgtcctg gagtctgtga ttgaacagtg ggttccgcca 480
gccccacgtc cggcgcagcg caatcgtcgc gtcaatcttt tggtgagcca tctctgtagc 540
ccaggcgata ttgagtggct gcgccgttgc gtcgaggcct tcggtctgca accgatcatt 600
ctgccggatc tggctcagag catggacggc caccttgctc agggtgactt ttcgccgctg 660
acgcagggcg gcacgccgtt gcgccaaatc gagcagatgg gccagagcct ttgctctttt 720
gcgattggcg tcagcctgca ccgtgcgagc agcctgctgg ctccgcgttg tcgtggcgaa 780
gtcatcgcct tgccgcacct catgaccttg gaacgctgcg acgcctttat ccatcagttg 840
gcgaaaatca gcggtcgcgc cgttccggag tggctggaac gccagcgcgg tcagctgcaa 900
gacgccatga tcgattgcca catgtggctg caaggccagc gcatggcgat tgccgccgaa 960
ggcgacctgc tggcagcgtg gtgcgatttc gcgaactctc aaggtatgca gccgggtcca 1020
ctggttgctc cgacgggtca tccgagcctg cgtcagttgc cggtggagcg cgtggtgccg 1080
ggtgatctgg aggatcttca gaccctctta tgcgcacatc cggccgactt actggtggcg 1140
aactcccacg cccgtgattt agcagagcaa ttcgccctgc cgctggtgcg cgcaggcttc 1200
ccgctgtttg acaaactggg cgaatttcgt cgtgttcgcc agggttatag cggtatgcgt 1260
gataccctgt tcgagttggc gaacctgatc cgtgaacgcc atcatcatct ggctcattat 1320
cgcagcccgc tgcgccagaa cccagaatcc tcgttgtcta cgggtggcgc gtacgcagcg 1380
gattaa 1386

<210> SEQ ID NO 15
<211> LENGTH: 825
<212> TYPE: DNA
<213> ORGANISM: Klebsiella pneumoniae
<220> FEATURE:
<223> OTHER INFORMATION: wild type Gene U, nifU

<400> SEQUENCE: 15
atgtggaatt actccgagaa agtgaaagac catttttta acccccgcaa tgcgcgcgtg 60
gtggacaacg ccaacgcggt aggcgacgtc ggttcgttaa gctgcggcga cgccctgcgc 120
ctgatgctgc gcgtcgaccc gcaaagcgaa atcattgagg aggcgggctt ccagaccttc 180
ggctgcggca gcgccatcgc ctcctcctcc gcgctgacgg agctgattat cggccatacc 240
ctcgccgaag ccgggcagat aaccaatcag cagattgccg attatctcga cggactgccg 300

```
ccggagaaaa tgcactgctc ggtgatgggc caggaggccc tgcgcgcggc catcgccaac    360

tttcgcggcg aaagccttga agaggagcac gacgagggca agctgatctg caaatgcttc    420

ggcgtcgatg aagggcatat tcgccgcgcg gtacagaaca acgggctgac cacccttgcc    480

gaggtgatca actacaccaa agcgggcggc ggctgcacct cttgccacga aaaaatcgag    540

ctggccctgg cggagatcct cgcccagcag ccgcagacga cgccagccgt ggccagcggc    600

aaagatccgc actggcagag cgtcgtcgat accatcgcag aactgcggcc gcatattcag    660

gccgacggcg gcgatatggc gctactcagc gtcaccaacc accaggtgac cgtcagcctc    720

tccggcagct gtagcggctg catgatgacc gatatgaccc tggcctggct gcagcaaaaa    780

ctgatggaac gtaccggctg ttatatggaa gtggtggcgg cctga                    825
```

<210> SEQ ID NO 16
<211> LENGTH: 825
<212> TYPE: DNA
<213> ORGANISM: Artificial Sequence
<220> FEATURE:
<223> OTHER INFORMATION: synthetic Gene U

<400> SEQUENCE: 16

```
atgtggaact acagcgagaa agtcaaggac catttcttca atccgcgcaa cgcgcgtgtt     60

gtggataacg caaatgcggt gggcgacgtc ggcagcttat cttgtggcga tgctctccgc    120

ttgatgctgc gcgtggaccc gcagagcgaa atcatcgaag aagcgggctt tcagaccttc    180

ggctgcggca gcgcgattgc gtcgtccagc gcactgacgg agctgatcat cggtcacacc    240

ctggcggaag cgggtcagat caccaaccag cagatcgccg actatctgga cggcttaccg    300

ccggaaaaga tgcactgctc tgtaatgggc caggaagctc ttcgtgcggc cattgctaac    360

tttcgcggtg aatcgctgga agaggagcat gacgagggta agctgatctg caagtgcttc    420

ggcgtcgatg aaggccatat tcgccgtgct gtccagaaca acggtcttac gactctggcc    480

gaggtgatca attacaccaa ggcaggtggc ggttgtacca gctgccatga gaaaatcgag    540

ctggccctgg ccgagattct cgcccaacag ccgcaaacca ccccggcagt tgcgtccggt    600

aaagatccgc actggcagag cgtcgtggat accatcgctg aactgcgtcc acatatccaa    660

gcggacggtg gtgacatggc gctgttgtcc gtgacgaacc accaagtgac tgtttcgctg    720

tcgggcagct gttctggctg catgatgacc gacatgaccc tggcgtggct gcaacagaaa    780

ttgatggagc gtaccggctg ctatatggaa gttgttgccg cctaa                    825
```

<210> SEQ ID NO 17
<211> LENGTH: 1203
<212> TYPE: DNA
<213> ORGANISM: Klebsiella pneumoniae
<220> FEATURE:
<223> OTHER INFORMATION: wild type Gene S, nifS

<400> SEQUENCE: 17

```
atgaaacagg tttatctcga taacaacgcc accacccgtc tggacccgat ggtcctggaa     60

gcgatgatgc cctttttgac cgatttttac ggcaacccct cgtcgataca cgattttggc    120

attccggccc aggcggctct ggaacgcgcg catcagcagg ctgcggcgct gctgggcgcg    180

gagtatccca gcgagatcat ctttacctcc tgcgccaccg aagccaccgc caccgccatc    240

gcctcggcga tcgccctgct gcctgagcgt cgcgaaatca tcaccagcgt ggtcgaacat    300

ccggcgacgc tggcggcctg cgagcacatg gagcgcgagg gctaccggat tcatcgcatc    360
```

gcggtagatg gcgagggggc gctggacatg gcgcagttcc gcgcggcgct cagcccgcgc 420
gtcgcgttgg tcagcgtgat gtgggcgaat aacgaaaccg gggtgctttt cccgatcggc 480
gaaatggcgg agctggccca tgaacaaggg gcgctgtttc actgcgatgc ggtgcaggtg 540
gtcgggaaaa taccgatcgc cgtgggccag acccgcatcg atatgctctc ctgctcggcg 600
cataagttcc acgggccaaa aggcgtaggc tgtctttatc tgcggcgggg aacgcgcttt 660
cgcccgctgc tgcgcggcgg tcaccaggag tacggtcggc gagccgggac agaaaatatc 720
tgcggaatcg tcggcatggg cgcggcctgc gagctggcga atattcatct gccgggaatg 780
acgcatatcg gccaattgcg caacaggctg gagcatcgcc tgctggccag cgtgccgtcg 840
gtcatggtga tgggcggcgg ccagccggcg gtgcccggca cggtgaatct ggcctttgag 900
tttattgaag gtgaagccat tctgctgctg ttaaaccagg ccgggatcgc cgcctccagc 960
ggcagcgcct gcacctcagg ctcgctggaa ccctcccacg tgatgcgggc gatgaatatc 1020
ccctacaccg ccgcccacgg caccatccgc ttttctctct cgcgctacac ccgggagaaa 1080
gagatcgatt acgtcgtcgc cacgctgccg ccgattatcg accggctgcg cgcgctgtcg 1140
ccctactggc agaacggcaa gccgcgcccg gcggacgccg tattcacgcc ggtttacggc 1200
taa 1203

<210> SEQ ID NO 18
<211> LENGTH: 1203
<212> TYPE: DNA
<213> ORGANISM: Artificial Sequence
<220> FEATURE:
<223> OTHER INFORMATION: synthetic Gene S

<400> SEQUENCE: 18
atgaaacaag tgtacctgga caacaacgcg accacccgcc tggacccgat ggttctggaa 60
gcgatgatgc cgtttctcac ggatttctat ggcaatccgt ccagcatcca tgacttcggc 120
atcccggcac aagcggcgct ggaacgtgcg caccagcaag ctgcggcact gctgggcgca 180
gagtacccgt ctgaaatcat tttcacgagc tgtgcgaccg aggccactgc aaccgccatt 240
gcgtcggcca tcgcgttatt gccggaacgc cgcgaaatca tcacctcggt agtggagcac 300
ccggctacgc tggcggcgtg cgagcacatg gaacgcgaag gctatcgcat ccatcgcatt 360
gcggtggatg gcgaaggtgc gctggacatg gcccagttcc gtgcagcgct ctcgccgcgt 420
gtcgcgttgg tgagcgtgat gtgggccaac aacgaaaccg gcgtgctgtt cccgattggc 480
gaaatggccg agcttgccca cgagcagggc gctctgttcc actgcgatgc cgttcaggtc 540
gttggcaaaa tcccaattgc tgttggccag acgcgcatcg acatgctgtc ttgctccgcg 600
cacaagtttc atggtccgaa gggtgttggt tgcttgtact tacgtcgtgg cacgcgcttt 660
cgtccgctgc ttcgcggtgg ccatcaagaa tatggtcgcc gtgccggcac tgagaatatc 720
tgtggcatcg tcggcatggg cgctgcgtgc gaactggcga acatccatct gccgggtatg 780
acccatattg gccagttacg caatcgcctg gagcaccgtc tgctcgccag cgtgccgtcc 840
gtgatggtta tgggcggtgg tcagccggct gtaccgggta ctgtcaacct ggcgttcgag 900
tttatcgaag gtgaagcgat cctgctcttg ctgaaccagg ctggcattgc cgcaagctcc 960
ggctccgcgt gtacctctgg cagcttggag ccgagccatg tgatgcgcgc catgaacatt 1020
ccatacaccg cggctcacgg caccattcgt tttagcctga gccgttatac gcgcgagaaa 1080
gagatcgact acgtcgttgc gaccctcccg ccaatcattg atcgtctgcg tgccttgtcc 1140
ccgtattggc agaatggtaa gccgcgtccg gcagatgcag tctttacccc ggtttacggt 1200
taa 1203

<210> SEQ ID NO 19
<211> LENGTH: 1143
<212> TYPE: DNA
<213> ORGANISM: Klebsiella pneumoniae
<220> FEATURE:
<223> OTHER INFORMATION: wild type Gene V, nifV

<400> SEQUENCE: 19
atggaacgcg tgctgattaa cgataccacc ctgcgcgacg gcgagcagag ccccggcgtc 60
gcctttcgca ccagcgaaaa ggtcgccatt gccgaggcgc tttacgccgc aggaataacg 120
gcgatggagg tcggcacccc ggcgatgggc gacgaggaga tcgcgcggat ccagctggtg 180
cgtcgccagc tgcccgacgc gaccctgatg acctggtgtc ggatgaacgc gctggagatc 240
cgccagagcg ccgatctggg catcgactgg gtggatatct cgattccggc ttcggataag 300
ctgcggcagt acaaactgcg cgagccgctg gcggtgctgc tggagcggct ggcgatgttt 360
atccatcttg cgcataccct cggcctgaag gtatgcatcg gctgcgagga cgcctcgcgg 420
gccagcggcc agaccctgcg cgctatcgcc gaggtcgcgc agcaatgcgc cgccgcccgc 480
ctgcgctatg ccgatacggt cggcctgctc gaccctttta ccaccgcggc gcaaatctcg 540
gccctgcgcg acgtctggtc cggcgaaatc gaaatgcatg cccataacga tctgggtatg 600
gcgaccgcca atacgctggc ggcggtaagc gccggggcca ccagcgtgaa tacgacggtc 660
ctcggtctcg gcgagcgggc gggcaacgcg gcgctggaaa ccgtcgcgct gggccttgaa 720
cgctgcctgg gcgtggagac cggcgtgcat ttttcggcgc tgcccgcgtc ctgtcagagg 780
gtcgcggaag ccgcgcagcg cgccatcgac ccgcagcagc cgctggtcgg cgagctggtg 840
tttacccatg agtcaggtgt ccacgtggcg gcgctgctgc ggcacagcga gagctaccag 900
tccatcgccc cttccctgat gggccgcagc taccggctgg tgctgggcaa acactccggg 960
cgtcaggcgg tcaacggcgt ttttgaccag atgggctatc acctcaacgc cgcgcagatt 1020
aaccagctgc tgcccgccat ccgccgcttc gccgagaact ggaagcgcag cccgaaagat 1080
tacgagctgg tggctatcta cgacgagctg tgcggtgaat ccgctctgcg ggcgaggggg 1140
taa 1143

<210> SEQ ID NO 20
<211> LENGTH: 1143
<212> TYPE: DNA
<213> ORGANISM: Artificial Sequence
<220> FEATURE:
<223> OTHER INFORMATION: synthetic Gene V

<400> SEQUENCE: 20
atggagcgcg tcttgatcaa cgatactacc ctgcgtgatg gcgaacaatc tccgggcgta 60
gcgtttcgta cctccgagaa agttgccatc gcggaggcac tgtacgctgc gggtatcacc 120
gcgatggaag tcggcactcc ggcgatgggt gatgaagaga tcgcccgcat tcagctggtg 180
cgtcgtcaac tgccggacgc gacgcttatg acctggtgcc gtatgaacgc tctggaaatc 240
cgtcagagcg cggatctggg tattgactgg gtggatatct cgatcccagc atccgacaag 300
ctgcgtcagt acaagctgcg tgagccgctg gccgtgctgc tggagcgcct tgcgatgttt 360
atccatctgg cccacacgtt aggcctcaaa gtatgtattg gttgcgagga tgcgagccgt 420
gcgtctggtc agaccctgcg cgccattgcc gaggtggccc agcaatgcgc ggctgcgcgc 480

```
ttgcgttacg ctgacaccgt gggcctgctg gacccgttca ccaccgcagc ccagatcagc    540

gccctgcgtg acgtttggtc gggcgagatc gagatgcatg ctcacaatga tctgggcatg    600

gctaccgcga acacgctggc ggcagtttcg gctggcgcca cgtcggtgaa cactaccgtc    660

ctcggtctgg gtgaacgtgc aggcaacgca gccctggaaa ccgttgcgct gggcctggaa    720

cgctgcctgg gcgtggaaac cggcgtccat ttcagcgcgc tcccagcgag ctgtcagcgc    780

gtcgcggagg ctgcacagcg cgcaatcgac ccgcaacagc cgctggtggg tgaattggtt    840

ttcacccacg agtctggtgt tcacgttgcg gcgctgctgc gccacagcga atcctatcaa    900

tctattgccc caagcctcat gggccgtagc taccgtctgg tgctcggcaa gcattcgggt    960

cgtcaggctg tcaacggtgt tttcgaccag atgggttacc acctgaatgc ggcgcagatc   1020

aatcagttgc tgccggccat tcgccgcttc gccgagaatt ggaaacgctc tccgaaagac   1080

tacgaactgg ttgcgatcta tgacgaattg tgcggtgaat ccgcccttcg tgctcgcggc   1140

taa                                                                 1143
```

<210> SEQ ID NO 21
<211> LENGTH: 258
<212> TYPE: DNA
<213> ORGANISM: Klebsiella pneumoniae
<220> FEATURE:
<223> OTHER INFORMATION: wild type Gene W, nifW

<400> SEQUENCE: 21

```
atggagtggt tttatcaaat tcccggcgtg gacgaacttc gctccgccga atcttttttt     60

cagtttttcg ccgtccccta tcagcccgag ctgcttggcc gctgcagcct gccggtgctg    120

gcaacgtttc atcgcaaact ccgcgcggag gtgccgctgc aaaaccggct cgaggataac    180

gaccgcgcgc cctggctgct ggcgcgaaga ctgctcgcgg agagctatca gcaacagttt    240

caggagagcg gaacatga                                                  258
```

<210> SEQ ID NO 22
<211> LENGTH: 258
<212> TYPE: DNA
<213> ORGANISM: Artificial Sequence
<220> FEATURE:
<223> OTHER INFORMATION: synthetic Gene W

<400> SEQUENCE: 22

```
atggagtggt tttaccagat tccgggtgta gacgaattgc gcagcgctga atccttcttt     60

cagttcttcg cggttccata ccagccggaa ctgctgggcc gctgctcgct tccggtgtta    120

gcgacgttcc accgtaaact gcgtgcggag gtcccgctgc aaaaccgtct ggaggacaat    180

gatcgtgcgc cgtggctctt ggcgcgccgc ctcctggccg aatcttatca gcagcaattt    240

caggagagcg gcacctaa                                                  258
```

<210> SEQ ID NO 23
<211> LENGTH: 447
<212> TYPE: DNA
<213> ORGANISM: Klebsiella pneumoniae
<220> FEATURE:
<223> OTHER INFORMATION: wild type Gene Z, nifZ

<400> SEQUENCE: 23

```
atgagaccga aattcacctt tagcgaagag gtccgcgtcg tacgcgcgat tcgtaacgac     60

ggcaccgtgg cgggcttcgc gcccggcgcg ctgctggtca ggcgcggcag caccggcttt    120

gtgcgcgact ggggcgtttt tttgcaagat cagattatct accagatcca ctttccggaa    180
```

accgatcgga tcatcggctg ccgcgagcag gagctgatcc ccatcaccca gccgtggctg 240
gccggaaatt tgcaatacag ggatagcgtg acctgccaga tggcgctcgc ggtcaacggc 300
gatgtggtcg tgagcgccgg ccagcgggga cgcgttgagg ctaccgatcg gggagagctc 360
ggcgacagct acaccgtcga ctttagcggc cgctggttca gggtcccggt gcaggccatc 420
gcccttatag aggaaagaga agaatga 447

<210> SEQ ID NO 24
<211> LENGTH: 447
<212> TYPE: DNA
<213> ORGANISM: Artificial Sequence
<220> FEATURE:
<223> OTHER INFORMATION: synthetic Gene Z

<400> SEQUENCE: 24
atgcgcccga aattcacctt ctctgaagag gtccgcgtag ttcgcgcgat tcgtaatgat 60
ggcaccgtgg cgggttttgc gccaggtgcg ctgctggttc gtcgcggttc gacgggcttt 120
gtgcgtgact ggggtgtgtt cctgcaagac cagatcatct atcaaatcca ctttccggaa 180
accgaccgca ttatcggctg tcgcgagcag gagttaatcc cgattaccca gccgtggttg 240
gctggtaacc tccagtatcg tgacagcgtc acgtgccaaa tggcactggc tgtcaacggt 300
gacgtggttg tgagcgccgg tcaacgtggc cgtgtggagg ccactgatcg tggcgaactt 360
ggcgattcct acaccgtgga cttcagcggc cgttggttcc gcgttccggt ccaggccatc 420
gcgctgattg aagagcgcga agaataa 447

<210> SEQ ID NO 25
<211> LENGTH: 801
<212> TYPE: DNA
<213> ORGANISM: Klebsiella pneumoniae
<220> FEATURE:
<223> OTHER INFORMATION: wild type Gene M, nifM

<400> SEQUENCE: 25
atgaacccgt ggcaacgttt tgcccggcag cggctggcgc gcagccgctg gaatcgcgat 60
ccggcggccc tggatccggc cgacacgccg gcttttgaac aggcctggca acgccagtgc 120
catatggagc agacgatcgt cgcgcgggtc cctgaaggcg atattccggc ggcgttgctg 180
gagaatatcg ctgcctccct tgccatctgg ctcgacgagg gggattttgc gccgcccgag 240
cgcgctgcca tcgtgcgcca tcacgcccgg ctggaactcg ccttcgccga tatcgcccgc 300
caggcgccgc agccggatct ctccacggta caggcatggt atctgcgcca ccagacgcag 360
tttatgcgcc cggaacagcg tctgacccgc catttactgc tgacggtcga taacgaccgc 420
gaagccgtgc accagcggat cctcggcctg tatcggcaaa tcaacgcctc gcgggacgct 480
ttcgcgccgc tggcccagcg ccattcccac tgcccgagcg cgctggaaga gggtcgttta 540
ggctggatta gccgtggcct gctctatccg cagctcgaga ccgcgctgtt ttcactggcg 600
gaaaacgcgc taagccttcc catcgccagc gaactgggct ggcatctttt atggtgcgaa 660
gcgattcgcc ccgccgcgcc catggagccg cagcaggcgc tggagagcgc gcgcgattat 720
ctttggcagc agagccagca gcgccatcag cgccagtggc tggaacagat gatttcccgt 780
cagccgggac tgtgcgggta g 801

<210> SEQ ID NO 26
<211> LENGTH: 801
<212> TYPE: DNA

<213> ORGANISM: Artificial Sequence
<220> FEATURE:
<223> OTHER INFORMATION: synthetic Gene M

<400> SEQUENCE: 26
atgaatccgt ggcagcgctt tgcccgtcaa cgccttgctc gcagccgctg gaaccgtgat 60
ccggctgctc tcgacccagc cgatacccca gcgttcgagc aggcgtggca gcgtcaatgc 120
catatggaac aaaccatcgt agcgcgtgtc ccggaaggcg atattccggc tgccttactg 180
gaaaacatcg cggccagcct ggcgatctgg ctggacgagg gtgacttcgc tccgccggag 240
cgcgctgcga ttgtgcgtca tcatgcacgt ctggagctgg cgtttgccga cattgcccgc 300
caggcaccgc aaccggatct gagcacggtt caagcgtggt atctgcgtca ccagactcaa 360
ttcatgcgtc cggagcagcg tctgacccgt cacctgctcc tgacggtcga taatgatcgc 420
gaggcggtgc atcaacgcat ccttggcctg tatcgtcaga tcaacgcgag ccgtgacgcc 480
ttcgccccac tggcacagcg ccactctcat tgcccgtccg ccttggaaga aggccgtctg 540
ggctggatct cccgtggtct gctgtacccg cagctcgaaa ccgcgttgtt tagcctggcg 600
gaaaacgcac tgtcgctgcc gattgcgtcg gaattgggtt ggcacctgtt atggtgcgag 660
gccattcgtc cggcagcccc gatggagccg caacaggccc ttgaatctgc gcgcgactac 720
ttgtggcagc agagccagca gcgccaccag cgtcaatggc tggagcagat gatttcccgc 780
caaccgggcc tgtgtggtta a 801

<210> SEQ ID NO 27
<211> LENGTH: 531
<212> TYPE: DNA
<213> ORGANISM: Klebsiella pneumoniae
<220> FEATURE:
<223> OTHER INFORMATION: wild type Gene F, nifF

<400> SEQUENCE: 27
atggcgaaca ttggtatttt ctttggcacc gataccggta aaacccgcaa aatcgcgaaa 60
atgatccata agcaactggg cgagctggcg gatgccccgg tcaacattaa ccgcacgacg 120
ctggacgact ttatggccta tccggtgctg ctgctgggca cgccgacgct cggcgacggc 180
cagctgccgg ggctggaggc cggatgcgaa agcgagtcat ggagcgaatt tatcagcggc 240
ctcgacgacg ccagcctgaa agggaaaacc gtggcgctgt tcggcctcgg cgatcagaga 300
ggctatccgg acaacttcgt cagcgggatg cgcccgctgt tcgacgccct gagcgcgcgc 360
ggcgcgcaga tgattggcag ctggccaaat gagggttatg aattcagcgc gtcctcggcg 420
ctggaaggcg accgctttgt tgggctggtg ctggatcagg ataaccagtt cgaccagacc 480
gaagcgcgtc tggcgagctg gcttgaggag attaaacgca ccgtgctgta g 531

<210> SEQ ID NO 28
<211> LENGTH: 531
<212> TYPE: DNA
<213> ORGANISM: Artificial Sequence
<220> FEATURE:
<223> OTHER INFORMATION: synthetic Gene F

<400> SEQUENCE: 28
atggcgaaca tcggcatctt ctttggtacg gataccggca aaacccgcaa gattgcgaag 60
atgattcaca aacagctggg cgagctggcc gatgccccgg ttaacatcaa tcgtaccact 120
ttggatgact ttatggctta cccagtcctg ttgctcggca cgccgacgct tggtgatggt 180
caactgccgg gcttagaggc gggctgcgag agcgaaagct ggtctgagtt tatctccggt 240
ctggatgacg cttccctgaa gggcaaaacc gtggcgctgt ttggcctggg cgaccagcgt 300
ggttacccgg acaacttcgt gtcgggtatg cgtccgctgt tcgacgcgct gagcgcccgt 360
ggcgcccaga tgattggtag ctggccgaac gaaggttatg agtttagcgc atcgtccgcg 420
ctggaaggcg accgcttcgt cggcttggtg ctggatcaag acaatcagtt cgaccagacc 480
gaagcgcgcc tggcgtcttg gcttgaagag atcaaacgca ccgttctgta a 531

<210> SEQ ID NO 29
<211> LENGTH: 1407
<212> TYPE: DNA
<213> ORGANISM: Klebsiella pneumoniae
<220> FEATURE:
<223> OTHER INFORMATION: wild type Gene B, nifB

<400> SEQUENCE: 29
atgacttcct gctcctcttt ttctggcggc aaagcctgcc gcccggcgga tgacagcgca 60
ttgacgccgc ttgtggccga taaagctgcc gcgcacccct gctactctcg ccatgggcat 120
caccgtttcg cgcggatgca tctgcccgtc gcgcccgcct gcaatttgca gtgcaactac 180
tgtaatcgca aattcgattg cagcaacgag tcccgccccg gggtatcgtc aacgctgctg 240
acgcctgaac aggcggtcgt gaaagtgcgt caggtcgcgc aggcgatccc gcagctttcg 300
gtggtgggca tcgccgggcc cggcgatccg ctcgccaata tcgcccgcac ctttcgcacc 360
ctggagctga tccgcgaaca gctgccggac ctgaaattat gcctgtcgac caacggactg 420
gtgctgcctg acgcggtgga ccgcctgctg gatgtcggcg ttgaccacgt cacggtcacc 480
attaacaccc tcgacgcgga gattgccgcg caaatctacg cctggctatg gctggacggc 540
gaacgctaca gcgggcgcga agcgggagag atcctgattg cccgtcagct tgagggcgta 600
cgcaggctga ccgccaaagg cgtgctggtg aaaataaatt cggtgctgat ccccggtatc 660
aacgatagcg gcatggccgg cgtgagccgc gcgctgcggg ccagcggcgc gtttatccat 720
aatattatgc cgctgatcgc caggccggag cacggcacgg tgtttggcct caacggccag 780
ccggagccgg acgccgagac gctcgccgcc acccgcagcc ggtgcggcga agtgatgccg 840
cagatgaccc actgccacca gtgtcgcgcc gacgccattg ggatgctcgg cgaagaccgc 900
agccagcagt ttacccagct tccggcgcca gagagtctcc cggcctggct gccgatcctc 960
caccagcgcg cgcagctgca cgccagcatt gcgacccgcg gcgaatctga agccgatgac 1020
gcctgcctgg tcgccgtggc gtcaagccgc ggggacgtca ttgattgtca ctttggtcac 1080
gccgaccggt tctacattta cagcctctcg gccgccggta tggtgctggt caacgagcgc 1140
tttacgccca aatattgtca ggggcgcgat gactgcgagc cgcaggataa cgcagcccgg 1200
tttgcggcga tcctcgaact gctggcggac gttaaagccg tattctgcgt gcgtatcggc 1260
catacgccgt ggcaacagct ggaacaggaa ggcattgaac cctgcgttga cggcgcgtgg 1320
cggccggtct ccgaagtgct gcccgcgtgg tggcaacagc gtcgggggag ctggcctgcc 1380
gcgttgccgc ataagggggt cgcctga 1407

<210> SEQ ID NO 30
<211> LENGTH: 1407
<212> TYPE: DNA
<213> ORGANISM: Artificial Sequence
<220> FEATURE:
<223> OTHER INFORMATION: synthetic Gene B

<400> SEQUENCE: 30

-continued

```
atgacctctt gttcgtcgtt ttctggcggt aaagcgtgcc gtccggccga tgactccgcg     60
ctgactccgc tggtggccga caaggcagct gcgcacccgt gctatagccg ccacggccat    120
caccgcttcg cgcgtatgca cctgccagtc gctccggcct gcaacttaca atgcaactac    180
tgcaaccgca agttcgattg cagcaatgaa agccgtccgg gcgtgtcctc taccctgctg    240
acgccggaac aggctgtggt gaaggtgcgc caggtcgccc aagctatccc gcagctgtcg    300
gtggtcggta ttgctggtcc gggcgatccg cttgcgaata tcgcccgcac cttccgtacc    360
ttggagctta ttcgcgaaca gttgccggac ctgaaactgt gcctgagcac caacggcttg    420
gtgctgccag atgccgttga tcgtctgctc gatgtgggcg tggatcacgt taccgtcacc    480
attaacaccc tggacgcaga aatcgcagcg caaatctacg cgtggttgtg gctggatggc    540
gaacgctact ccggtcgcga agccggcgaa attctcattg cccgccagct ggaaggcgta    600
cgtcgcctga ccgcgaaagg tgtgctcgtc aagatcaaca gcgtattgat tccgggcatc    660
aatgacagcg gcatggcggg tgttagccgt gcgctgcgcg cgtctggtgc gttcatccac    720
aacatcatgc cactgattgc gcgtccggag catggcactg ttttcggtct gaacggccag    780
ccggaaccgg acgcggaaac cctggcggcg acgcgctccc gctgcggcga ggttatgcca    840
caaatgaccc actgccacca gtgccgtgcc gacgcgattg gcatgcttgg tgaggatcgc    900
tcgcaacagt ttacgcaatt accggctccg gagtccctcc cggcctggct gccgatcctg    960
catcagcgtg ctcagttgca tgcgagcatc gccacgcgcg gtgagagcga agccgatgac   1020
gcctgcctgg tggccgttgc gtcgagccgt ggcgatgtaa ttgactgcca tttcggccat   1080
gccgaccgtt tctatatcta tagcctgtct gcggctggta tggttctggt taacgaacgt   1140
ttcaccccga aatactgcca gggtcgcgat gactgcgagc cgcaggacaa tgccgcacgc   1200
tttgctgcca tccttgagtt gctggcggac gtcaaagcgg tgttttgtgt gcgtatcggc   1260
cataccccgt ggcaacagct ggagcaggaa ggcatcgaac cgtgcgtgga tggcgcctgg   1320
cgtccggtat ccgaggtcct gccggcatgg tggcagcagc gccgtggtag ctggccggct   1380
gcattgccgc acaaaggcgt tgcgtaa                                       1407
```

<210> SEQ ID NO 31
<211> LENGTH: 504
<212> TYPE: DNA
<213> ORGANISM: Klebsiella pneumoniae
<220> FEATURE:
<223> OTHER INFORMATION: wild type Gene Q, nifQ

<400> SEQUENCE: 31

```
atgccgccgc tcgactggtt gcggcgctta tggctgctgt accacgcggg gaaaggcagc     60
tttccgctgc gcatggggct tagcccgcgc gattggcagg cgctgcggcg gcgcctgggc    120
gaggtggaaa cgccgctcga cggcgagacg ctcacccgtc gccgcctgat ggcggagctc    180
aacgccaccc gcgaagagga gcgccagcag ctgggcgcct ggctggcggg ctggatgcag    240
caggatgccg ggccgatggc gcagattatc gccgaggttt cgctggcgtt taaccatctc    300
tggcaggatc ttggtctggc atcgcgcgcc gaattgcgcc tgctgatgag cgactgcttt    360
ccacagctgg tggtgatgaa cgaacacaat atgcgctgga aaaagttctt ttatcgtcag    420
cgctgtttgc tgcaacaggg ggaagttatc tgccgttcgc caagctgcga cgagtgctgg    480
gaacgcagcg cctgttttga gtag                                           504
```

<210> SEQ ID NO 32
<211> LENGTH: 504

<212> TYPE: DNA
<213> ORGANISM: Artificial Sequence
<220> FEATURE:
<223> OTHER INFORMATION: synthetic Gene Q

<400> SEQUENCE: 32
atgccgccat tggactggtt gcgtcgtttg tggttactct atcacgccgg caaaggcagc 60
tttccgcttc gtatgggctt gtcgccgcgt gactggcaag ctctgcgccg tcgcctgggc 120
gaggtggaaa cgccgctgga tggcgaaacc ctgacccgtc gccgtctgat ggcggagctg 180
aatgcgaccc gcgaagaaga acgccagcag ctgggtgcct ggctggccgg ttggatgcaa 240
caggatgccg gtccgatggc gcagattatc gcagaggtga gcctggcgtt caaccatctc 300
tggcaggacc ttggcctcgc gagccgcgct gaactgcgtc tgctgatgtc tgactgcttc 360
ccgcagctgg ttgttatgaa cgagcacaac atgcgctgga agaaattctt ttaccgccag 420
cgttgcctgc tgcaacaggg cgaagtcatc tgtcgcagcc cgtcttgcga tgaatgctgg 480
gaacgttctg cgtgctttga gtaa 504

<210> SEQ ID NO 33
<211> LENGTH: 1117
<212> TYPE: DNA
<213> ORGANISM: Artificial Sequence
<220> FEATURE:
<223> OTHER INFORMATION: synthetic lacI sequence of Ptac-T7 synthetic
      controller

<400> SEQUENCE: 33
caattcgcgc taacttacat taattgcgtt gcgctcactg cccgctttcc agtcgggaaa 60
cctgtcgtgc cagctgcatt aatgaatcgg ccaacgcgcg gggagaggcg gtttgcgtat 120
tgggcgccag ggtggttttt cttttcacca gtgagacggg caacagctga ttgcccttca 180
ccgcctggcc ctgagagagt tgcagcaagc ggtccacgct ggtttgcccc agcaggcgaa 240
aatcctgttt gatggtggtt gacggcggga tataacatga gctgtcttcg gtatcgtcgt 300
atcccactac cgagatatcc gcaccaacgc gcagcccgga ctcggtaatg gcgcgcattg 360
cgcccagcgc catctgatcg ttggcaacca gcatcgcagt gggaacgatg ccctcattca 420
gcatttgcat ggtttgttga aaaccggaca tggcactcca gtcgccttcc cgttccgcta 480
tcggctgaat ttgattgcga gtgagatatt tatgccagcc agccagacgc agacgcgccg 540
agacagaact taatgggccc gctaacagcg cgatttgctg gtgacccaat gcgaccagat 600
gctccacgcc cagtcgcgta ccgtcttcat gggagaaaat aatactgttg atgggtgtct 660
ggtcagagac atcaagaaat aacgccggaa cattagtgca ggcagcttcc acagcaatgg 720
catcctggtc atccagcgga tagttaatga tcagcccact gacgcgttgc gcgagaagat 780
tgtgcaccgc cgctttacag gcttcgacgc cgcttcgttc taccatcgac accaccacgc 840
tggcacccag ttgatcggcg cgagatttaa tcgccgcgac aatttgcgac ggcgcgtgca 900
gggccagact ggaggtggca acgccaatca gcaacgactg tttgcccgcc agttgttgtg 960
ccacgcggtt gggaatgtaa ttcagctccg ccatcgccgc ttccactttt tcccgcgttt 1020
tcgcagaaac gtggctggcc tggttcacca cgcgggaaac ggtctgataa gagacaccgg 1080
catactctgc gacatcgtat aacgttactg gtttcac 1117

<210> SEQ ID NO 34
<211> LENGTH: 589
<212> TYPE: DNA
<213> ORGANISM: Artificial Sequence
<220> FEATURE:
<223> OTHER INFORMATION: synthetic lacI promoter sequence of Ptac-T7
synthetic controller

<400> SEQUENCE: 34

```
attcaccacc ctgaattgac tctcttccgg gcgctatcat gccataccgc gaaaggtttt     60

gcaccattcg atggtgtcaa cgtaaatgca tgccgcttcg ccttcgcgcg cgaattggcc    120

gccatgccgg cgataatggc ctgcttctcg ccgaaacgtt tggtggcggg accagtgacg    180

aaggcttgag cgagggcgtg caagattccg aataccgcaa gcgacaggcc gatcatcgtc    240

gcgctccagc gaaagcggtc ctcgccgaaa atgacccaga gcgctgccgg cacctgtcct    300

acgagttgca tgataaagaa gacagtcata agtgcggcga cgatagtcat gccccgcgcc    360

caccggaagg agctgactgg gttgaaggct ctcaagggca tcggcggagc ttatcgactg    420

cacggtgcac caatgcttct ggcgtcaggc agccatcgga agctgtggta tggctgtgca    480

ggtcgtaaat cactgcataa ttcgtgtcgc tcaaggcgca ctcccgttct ggataatgtt    540

ttttgcgccg acatcataac ggttctggca aatattctga aatgagctg                589
```

<210> SEQ ID NO 35
<211> LENGTH: 55
<212> TYPE: DNA
<213> ORGANISM: Artificial Sequence
<220> FEATURE:
<223> OTHER INFORMATION: synthetic tac promoter sequence of Ptac-T7
synthetic controller

<400> SEQUENCE: 35

```
ttgacaatta atcatcggct cgtataatgt gtggaattgt gagcggataa caatt          55
```

<210> SEQ ID NO 36
<211> LENGTH: 40
<212> TYPE: DNA
<213> ORGANISM: Artificial Sequence
<220> FEATURE:
<223> OTHER INFORMATION: synthetic insulator 1 sequence of Ptac-T7
synthetic controller

<400> SEQUENCE: 36

```
tgcagtttta ttctctcgcc agcactgtaa taggcactaa                          40
```

<210> SEQ ID NO 37
<211> LENGTH: 34
<212> TYPE: DNA
<213> ORGANISM: Artificial Sequence
<220> FEATURE:
<223> OTHER INFORMATION: synthetic Enterobacteria phage T7 RNA
polymerase (RNAP) ribosome binding site (rbs, RBS) sequence of
Ptac-T7 synthetic controller

<400> SEQUENCE: 37

```
tatccaaacc agtagctcaa ttggagtcgt ctat                                34
```

<210> SEQ ID NO 38
<211> LENGTH: 120
<212> TYPE: DNA
<213> ORGANISM: Artificial Sequence
<220> FEATURE:
<223> OTHER INFORMATION: synthetic umuD degradatiobn tag sequence of
Ptac-T7 synthetic controller

<400> SEQUENCE: 38

```
gtgttgttta tcaagcctgc ggatctccgc gaaattgtga cttttccgct atttagcgat     60
```

cttgttcagt gtggctttcc ttcaccggca gcagattacg ttgaacagcg catcgatctg 120

<210> SEQ ID NO 39
<211> LENGTH: 2568
<212> TYPE: DNA
<213> ORGANISM: Artificial Sequence
<220> FEATURE:
<223> OTHER INFORMATION: synthetic Enterobacteria phage T7 RNA polymerase (RNAP) scaffold sequence of Ptac-T7 synthetic controller

<400> SEQUENCE: 39
ggtggcaaca cgattaacat cgctaagaac gacttctctg acatcgaact ggctgctatc 60
ccgttcaaca ctctggctga ccattacggt gagcgtttag ctcgcgaaca gttggccctt 120
gagcatgagt cttacgagat gggtgaagca cgcttccgca agatgtttga gcgtcaactt 180
aaagctggtg aggttgcgga taacgctgcc gccaagcctc tcatcactac cctactccct 240
aagatgattg cacgcatcaa cgactggttt gaggaagtga aagctaagcg cggcaagcgc 300
ccgacagcct tccagttcct gcaagaaatc aagccggaag ccgtagcgta catcaccatt 360
aagaccactc tggcttgcct aaccagtgct gacaatacaa ccgttcaggc tgtagcaagc 420
gcaatcggtc gggccattga ggacgaggct cgcttcggtc gtatccgtga ccttgaagct 480
aagcacttca agaaaaacgt tgaggaacaa ctcaacaagc gcgtagggca cgtctacaag 540
aaagcattta tgcaagttgt cgaggctgac atgctctcta agggtctact cggtggcgag 600
gcgtggtctt cgtggcataa ggaagactct attcatgtag gagtacgctg catcgagatg 660
ctcattgagt caaccggaat ggttagctta caccgccaaa atgctggcgt agtaggtcaa 720
gactctgaga ctatcgaact cgcacctgaa tacgctgagg ctatcgcaac ccgtgcaggt 780
gcgctggctg gcatctctcc gatgttccaa ccttgcgtag ttcctcctaa gccgtggact 840
ggcattactg gtggtggcta ttgggctaac ggtcgtcgtc ctctggcgct ggtgcgtact 900
cacagtaaga aagcactgat gcgctacgaa gacgtttaca tgcctgaggt gtacaaagcg 960
attaacattg cgcaaaacac cgcatggaaa atcaacaaga aagtcctagc ggtcgccaac 1020
gtaatcacca agtggaagca ttgtccggtc gaggacatcc ctgcgattga gcgtgaagaa 1080
ctcccgatga aaccggaaga catcgacatg aatcctgagg ctctcaccgc gtggaaacgt 1140
gctgccgctg ctgtgtaccg caaggacaag gctcgcaagt ctcgccgtat cagccttgag 1200
ttcatgcttg agcaagccaa taagtttgct aaccataagg ccatctggtt cccttacaac 1260
atggactggc gcggtcgtgt ttacgctgtg tcaatgttca acccgcaagg taacgatatg 1320
accaaaggac tgcttacgct ggcgaaaggt aaaccaatcg gtaaggaagg ttactactgg 1380
ctgaaaatcc acggtgcaaa ctgtgcgggt gtcgacaagg ttccgttccc tgagcgcatc 1440
aagttcattg aggaaaacca cgagaacatc atggcttgcg ctaagtctcc actggagaac 1500
acttggtggg ctgagcaaga ttctccgttc tgcttccttg cgttctgctt tgagtacgct 1560
ggggtacagc accacggcct gagctataac tgctcccttc cgctggcgtt tgacgggtct 1620
tgctctggca tccagcactt ctccgcgatg ctccgagatg aggtaggtgg tcgcgcggtt 1680
aacttgcttc ctagtgaaac cgttcaggac atctacggga ttgttgctaa gaaagtcaac 1740
gagattctac aagcagacgc aatcaatggg accgataacg aagtagttac cgtgaccgat 1800
gagaacactg gtgaaatctc tgagaaagtc aagctgggca ctaaggcact ggctggtcaa 1860
tggctggctt acggtgttac tcgcagtgtg actaagagtt cagtcatgac gctggcttac 1920
gggtccaaag agttcggctt ccgtcaacaa gtgctggaag ataccattca gccagctatt 1980
gattccggca agggtctgat gttcactcag ccgaatcagg ctgctggata catggctaag 2040
ctgatttggg aatctgtgag cgtgacggtg gtagctgcgg ttgaagcaat gaactggctt 2100
aagtctgctg ctaagctgct ggctgctgag gtcaaagata agaagactgg agagattctt 2160
cgcaagcgtt gcgctgtgca ttgggtaact cctgatggtt tccctgtgtg gcaggaatac 2220
aagaagccta ttcagacgcg cttgaacctg atgttcctcg gtcagttccg cttacagcct 2280
accattaaca ccaacaaaga tagcgagatt gatgcacaca aacaggagtc tggtatcgct 2340
cctaactttg tacacagcca agacggtagc caccttcgta agactgtagt gtgggcacac 2400
gagaagtacg gaatcgaatc ttttgcactg attcacgact ccttcggtac gattccggct 2460
gacgctgcga acctgttcaa agcagtgcgc gaaactatgg ttgacacata tgagtcttgt 2520
gatgtactgg ctgatttcta cgaccagttc gctgaccagt tgcacgag 2568

<210> SEQ ID NO 40
<211> LENGTH: 21
<212> TYPE: DNA
<213> ORGANISM: Artificial Sequence
<220> FEATURE:
<223> OTHER INFORMATION: synthetic Biobrick suffix (BBa_G00001) sequence of Ptac-T7 synthetic controller

<400> SEQUENCE: 40
tactagtagc ggccgctgca g 21

<210> SEQ ID NO 41
<211> LENGTH: 12
<212> TYPE: DNA
<213> ORGANISM: Artificial Sequence
<220> FEATURE:
<223> OTHER INFORMATION: synthetic translational stop (BBa_B0042) sequence of Ptac-T7 synthetic controller

<400> SEQUENCE: 41
ttagttagtt ag 12

<210> SEQ ID NO 42
<211> LENGTH: 69
<212> TYPE: DNA
<213> ORGANISM: Artificial Sequence
<220> FEATURE:
<223> OTHER INFORMATION: synthetic terminator (BBa_B0054) sequence of Ptac-T7 synthetic controller

<400> SEQUENCE: 42
attagcagaa agtcaaaagc ctccgaccgg aggcttttga ctaaaacttc ccttggggtt 60
atcattggg 69

<210> SEQ ID NO 43
<211> LENGTH: 20
<212> TYPE: DNA
<213> ORGANISM: Artificial Sequence
<220> FEATURE:
<223> OTHER INFORMATION: synthetic VR primer (BBa_G00102) sequence of Ptac-T7 synthetic controller

<400> SEQUENCE: 43
gctcactcaa aggcggtaat 20

<210> SEQ ID NO 44
<211> LENGTH: 41
<212> TYPE: DNA

<213> ORGANISM: Artificial Sequence
<220> FEATURE:
<223> OTHER INFORMATION: synthetic terminator (BBa_B0062) sequence of Ptac-T7 synthetic controller

<400> SEQUENCE: 44
cagataaaaa aaatccttag ctttcgctaa ggatgatttc t 41

<210> SEQ ID NO 45
<211> LENGTH: 3671
<212> TYPE: DNA
<213> ORGANISM: Artificial Sequence
<220> FEATURE:
<223> OTHER INFORMATION: synthetic pSa origin sequence of Ptac-T7 synthetic controller

<400> SEQUENCE: 45
gctagagctg tcagaccaga gctccaaacc aacgttttat ctataccgct acagggtatt 60
taattcctat ttaatctgcg ctagaatgag gcatgtttaa ccgaatctga cgttttccct 120
gcaaatgcca aaatactatg cctatctccg ggtttcgcgt gacggccaag acccggaaaa 180
ccaaaaatac ggtttgctcg aatacgcgaa cgccaaaggc ttcgcgccgc tacagatcga 240
ggaagaaatt gccagcagag caaaggactg gcgcaagcgc aagctcggag caatcatcga 300
aaaggccgag cgtggcgacg tgctactgac gccggagatt acgcgcattg ccggttccgc 360
cctcgccgcc ttggaaattc tcaaagcggc gagcgagcgc ggcctaatcg tccatgtgac 420
caaacagaag atcatcatgg acggcagcct acaaagcgac atcatggcaa ccgtgcttgg 480
cttggctgca cagatcgagc ggcatttcat tcaggcacgt accaccgagg cgctacaagt 540
cgccagagag cgcggcaaga cgctcgggcg acccaagggc agcaaatcga gcgccttgaa 600
gctggacagc cgtattgatg aagtacaggc atacgtgaac cttggcttgc cgcaaagtcg 660
cgcagccgag ttgttaggcg tcagccctca caccttgcgc ctgttcatca aacgccggaa 720
catcaaaccc acaaacacta gaccaaccat caccatgccg gggagggaac aacatgccta 780
agaacaacaa agcccccggc catcgtatca acgagatcat caagacgagc ctcgcgctcg 840
aaatggagga tgcccgcgaa gctggcttag tcggctacat ggcccgttgc cttgtgcaag 900
cgaccatgcc ccacaccgac cccaagacca gctactttga gcgcaccaat ggcatcgtca 960
ccttgtcgat catgggcaag ccgagcatcg gcctgcccta cggttctatg ccgcgcacct 1020
tgcttgcttg gatatgcacc gaggccgtgc gaacgaaaga ccccgtgttg aaccttggcc 1080
ggtcgcaatc ggaatttcta caaaggctcg gaatgcacac cgatggccgt tacacggcca 1140
cccttcgcaa tcaggcgcaa cgcctgtttt catccatgat ttcgcttgcc ggcgagcaag 1200
gcaatgactt cggcattgag aacgtcgtca ttgccaagcg cgcttttcta ttctggaatc 1260
ccaagcggcc agaagatcgg gcgctatggg atagcaccct caccctcaca ggcgatttct 1320
tcgaggaagt cacccgctca ccggttccta tccgaatcga ctacctgcat gccttgcggc 1380
agtctccgct tgcgatggac atttacacgt ggctgaccta tcgcgtgttc ctgttgcggg 1440
ccaagggccg ccccttcgtg caaatccctt gggtcgccct gcaagcgcaa ttcggctcat 1500
cctatggcag ccgcgcacgc aactcgcccg aactggacga taaggcccga gagcgggcag 1560
agcgggcagc actcgccagc ttcaaataca acttcaaaaa gcgcctacgc gaagtgttga 1620
ttgtctatcc cgaggcaagc gactgcatcg aagatgacgg cgaatgcctg cgcatcaaat 1680
ccacacgcct gcatgtcacc cgcgcacccg gcaagggcgc tcgcatcggc ccccctccga 1740
cttgaccagg ccaacgctac gcttggcttg gtcaagcctt cccatccaac agcccgccgt 1800
cgagcgggct tttttatccc cggaagcctg tggatagagg gtagttatcc acgtgaaacc 1860
gctaatgccc cgcaaagcct tgattcacgg ggctttccgg cccgctccaa aaactatcca 1920
cgtgaaatcg ctaatcaggg tacgtgaaat cgctaatcgg agtacgtgaa atcgctaata 1980
aggtcacgtg aaatcgctaa tcaaaaaggc acgtgagaac gctaatagcc ctttcagatc 2040
aacagcttgc aaacacccct cgctccggca agtagttaca gcaagtagta tgttcaatta 2100
gcttttcaat tatgaatata tatatcaatt attggtcgcc cttggcttgt ggacaatgcg 2160
ctacgcgcac cggctccgcc cgtggacaac cgcaagcggt tgcccaccgt cgagcgccag 2220
cgcctttgcc cacaacccgg cggccgcaac agatcgtttt ataaattttt ttttttgaaa 2280
aagaaaaagc ccgaaaggcg gcaacctctc gggcttctgg atttccgatc aacgcaggag 2340
tcgttcggaa agtagctgtt ccagaattat aggcgcagag acaccagatt ccaagatggc 2400
tctgttaaat tgttgtagta tgtagtatca tacaacatac tacagtacag aggcccgcaa 2460
gaatggcaat cactaaacaa gacatttggc gagcagccga cgaactggac gccgaaggca 2520
tccggcccac tttggccgcc gtgcgcaaga aactcggaag cggtagcttc acaaccattt 2580
ccgatgcaat ggctgaatgg aaaaaccgca agaccgccac cctgccctca tcagacccat 2640
tgccggttgc agtcaacgag catcttgccg agcttggcaa tgcgctatgg gctatcgccc 2700
tggcgcacgc caacgcccgg tttgacgaag atcggaaaca gatcgaggcc gacaaagcgg 2760
ccatcagcca gcagcttgcc gaagcaatcg aactagccga caccttcacc cgcgaaaacg 2820
accagctccg cgaacgagtg aatcagctcg aacctatgga acgcgagcgc gacaagctgg 2880
ccgaccagct tgccgaagtg aaacgccgca gcggcgaaga actaaaccgc tgcatggaaa 2940
agctcaccca acgcgataac gaggctatcg aggcccgcaa acaggccaag gaggccatcg 3000
agcgcgccgc cagtctgcaa ggtcaggtgg aagccctcaa agagcaggtc gccaatctca 3060
cagccgtctt gaaaacagga ggcaaacaat gaaaagcgcc cttgccgccc ttcgcgcggt 3120
cgcggccgct gtcgtcctaa tcgtcagtgt gcccgcttgg gccgacttcc ggggtgaagt 3180
cgtccgaatc cttgacggtg acactatcga cgttttggtg aaccgtcaga ccatccgcgt 3240
gagattggcc gatattgacg caccggaaag cggccaagcc ttcggctccc gtgctcgcca 3300
acggctcgcc gacttgacct ttcgccaaga ggttcaagtg accgaaaaag aggttgatcg 3360
gtatggccgc actcttgggg tcgtttacgc gccgttgcaa taccccggcg gccaaacaca 3420
actcaccaac atcaatgcga tcatggttca agaaggcatg gcctgggctt accgttatta 3480
cggcaaacca accgacgcgc agatgtacga gtatgaaaaa gaggcccgcc gccaacggct 3540
cggcctttgg tcagacccga atgctcagga gccttggaaa tggcgtcgcg cctcgaaaaa 3600
tgccacgaac tgacaccggg cacgcccctt gttcgacgcg ccgcaggcac gtcgaattta 3660
ccgccgggac g 3671

<210> SEQ ID NO 46
<211> LENGTH: 1175
<212> TYPE: DNA
<213> ORGANISM: Artificial Sequence
<220> FEATURE:
<223> OTHER INFORMATION: synthetic spectinomycin resistance sequence of Ptac-T7 synthetic controller

<400> SEQUENCE: 46
cccctcgtcc cgacacttcc agatcgccat agcgcacagc gcctcgagcg gtggtaacgg 60
cgcagtggcg gttttcatgg cttgttatga ctgttttttt ggggtacagt ctatgcctcg 120

```
ggcatccaag cagcaagcgc gttacgccgt gggtcgatgt ttgatgttat ggagcagcaa    180

cgatgttacg cagcagggca gtcgccctaa aacaaagtta aacatcatga gggaagcggt    240

gatcgccgaa gtatcgactc aactatcaga ggtagttggc gtcatcgagc gccatctcga    300

accgacgttg ctggccgtac atttgtacgg ctccgcagtg gatggcggcc tgaagccaca    360

cagtgatatt gatttgctgg ttacggtgac cgtaaggctt gatgaaacaa cgcggcgagc    420

tttgatcaac gaccttttgg aaacttcggc ttcccctgga gagagcgaga ttctccgcgc    480

tgtagaagtc accattgttg tgcacgacga catcattccg tggcgttatc cagctaagcg    540

cgaactgcaa tttggagaat ggcagcgcaa tgacattctt gcaggtatct tcgagccagc    600

cacgatcgac attgatctgg ctatcttgct gacaaaagca agagaacata gcgttgcctt    660

ggtaggtcca gcggcggagg aactctttga tccggttcct gaacaggatc tatttgaggc    720

gctaaatgaa accttaacgc tatggaactc gccgcccgac tgggctggcg atgagcgaaa    780

tgtagtgctt acgttgtccc gcatttggta cagcgcagta accggcaaaa tcgcgccgaa    840

ggatgtcgct gccgactggg caatggagcg cctgccggcc cagtatcagc ccgtcatact    900

tgaagctaga caggcttatc ttggacaaga agaagatcgc ttggcctcgc gcgcagatca    960

gttggaagaa tttgtccact acgtgaaagg cgagatcacc aaggtagtcg gcaaataatg   1020

tctaacaatt cgttcaagcc gacgccgctt cgcggcgcgg cttaactcaa gcgttagatg   1080

cactaagcac ataattgctc acagccaaac tatcaggtca agtctgcttt tattattttt   1140

aagcgtgcat aataagccct acacaaatgg taccc                              1175
```

<210> SEQ ID NO 47
<211> LENGTH: 72
<212> TYPE: DNA
<213> ORGANISM: Artificial Sequence
<220> FEATURE:
<223> OTHER INFORMATION: synthetic terminator (BBa_B0053) sequence of Ptac-T7 synthetic controller

<400> SEQUENCE: 47

```
tccggcaaaa aaacgggcaa ggtgtcacca ccctgccctt tttctttaaa accgaaaaga     60

ttacttcgcg tt                                                         72
```

<210> SEQ ID NO 48
<211> LENGTH: 20
<212> TYPE: DNA
<213> ORGANISM: Artificial Sequence
<220> FEATURE:
<223> OTHER INFORMATION: synthetic VF2 primer (BBa_G000101) sequence of Ptac-T7 synthetic controller

<400> SEQUENCE: 48

```
tgccacctga cgtctaagaa                                                 20
```

<210> SEQ ID NO 49
<211> LENGTH: 78
<212> TYPE: DNA
<213> ORGANISM: Artificial Sequence
<220> FEATURE:
<223> OTHER INFORMATION: synthetic terminator (BBa_B0055) sequence of Ptac-T7 synthetic controller

<400> SEQUENCE: 49

```
aaggaatatt cagcaatttg cccgtgccga agaaaggccc acccgtgaag gtgagccagt     60

gagttgattg ctacgtaa                                                   78
```

<210> SEQ ID NO 50
<211> LENGTH: 12
<212> TYPE: DNA
<213> ORGANISM: Artificial Sequence
<220> FEATURE:
<223> OTHER INFORMATION: synthetic translational stop (BBa_B0042) sequence of Ptac-T7 synthetic controller

<400> SEQUENCE: 50
ttagttagtt ag 12

<210> SEQ ID NO 51
<211> LENGTH: 22
<212> TYPE: DNA
<213> ORGANISM: Artificial Sequence
<220> FEATURE:
<223> OTHER INFORMATION: synthetic Biobrick prefix (BBa_G00000) sequence of Ptac-T7 synthetic controller

<400> SEQUENCE: 51
gaattcgcgg ccgcttctag ag 22

<210> SEQ ID NO 52
<211> LENGTH: 23
<212> TYPE: DNA
<213> ORGANISM: Artificial Sequence
<220> FEATURE:
<223> OTHER INFORMATION: synthetic Enterobacteria phage T7 wild type (WT) promoter of full synthetic cluster

<400> SEQUENCE: 52
taatacgact cactataggg aga 23

<210> SEQ ID NO 53
<211> LENGTH: 28
<212> TYPE: DNA
<213> ORGANISM: Artificial Sequence
<220> FEATURE:
<223> OTHER INFORMATION: synthetic nifH ribosome binding site (rbs, RBS) of full synthetic cluster

<400> SEQUENCE: 53
acaataaact aacataagga ggataaat 28

<210> SEQ ID NO 54
<211> LENGTH: 882
<212> TYPE: DNA
<213> ORGANISM: Artificial Sequence
<220> FEATURE:
<223> OTHER INFORMATION: synthetic nifH of full synthetic cluster

<400> SEQUENCE: 54
atgaccatgc gtcagtgcgc gatttatggc aaaggtggta ttggcaaaag cacgacgacc 60
cagaacttgg tggcggccct ggccgagatg ggtaaaaagg ttatgattgt gggttgcgac 120
ccgaaggccg acagcacgcg cctgattctg cacgcgaaag cacaaaacac gattatggag 180
atggctgccg aggttggtag cgtggaggat ctggagctgg aggacgttct gcaaattggt 240
tacggtgatg ttcgttgcgc agagagcggt ggtccggaac caggtgtcgg ctgtgcgggt 300
cgtggtgtga ttaccgctat caatttcctg gaagaagagg gtgcgtacga agatgatctg 360
gatttcgttt tctacgatgt gctgggtgat gtcgtgtgcg gtggttttgc aatgccgatt 420
cgcgagaata aggcacaaga aatttacatt gtctgtagcg gcgagatgat ggcaatgtac 480
gctgctaaca acatcagcaa gggtattgtt aaatacgcaa aaagcggtaa ggttcgcttg 540
ggtggtttga tttgcaacag ccgtcagacc gaccgtgagg acgaactgat catcgccctg 600
gctgagaaac tgggcaccca aatgatccac ttcgtgccac gcgataatat tgttcaacgt 660
gcagaaatcc gccgtatgac cgtcattgag tatgacccgg catgcaagca agcgaacgag 720
taccgcacct tggcacagaa aatcgtgaac aacaccatga aggttgttcc gacgccgtgt 780
acgatggacg agctggagag cctgctgatg gagttcggca ttatggagga ggaggacacc 840
agcattatcg gtaagaccgc agcggaggag aatgcggcat aa 882

<210> SEQ ID NO 55
<211> LENGTH: 50
<212> TYPE: DNA
<213> ORGANISM: Artificial Sequence
<220> FEATURE:
<223> OTHER INFORMATION: synthetic insulator 1 of full synthetic cluster

<400> SEQUENCE: 55
gcgtgcgtac accttaatca ccgcttcatg ctaaggtcct ggctgcatgc 50

<210> SEQ ID NO 56
<211> LENGTH: 34
<212> TYPE: DNA
<213> ORGANISM: Artificial Sequence
<220> FEATURE:
<223> OTHER INFORMATION: synthetic nifD ribosome binding site (rbs, RBS) of full synthetic cluster

<400> SEQUENCE: 56
aaaaattcac atccctatct agcggaggag ccgg 34

<210> SEQ ID NO 57
<211> LENGTH: 1452
<212> TYPE: DNA
<213> ORGANISM: Artificial Sequence
<220> FEATURE:
<223> OTHER INFORMATION: synthetic nifD of full synthetic cluster

<400> SEQUENCE: 57
atgatgacta atgctactgg cgaacgtaac ctggcactga ttcaagaagt actggaagtg 60
ttcccggaaa ccgcgcgcaa agagcgccgt aaacacatga tggtttctga cccgaaaatg 120
aaatctgtgg gtaaatgcat catctctaat cgcaaatctc agccgggtgt catgactgtt 180
cgtggctgtg cgtacgcagg ttctaaaggt gtcgtattcg gcccgatcaa agatatggcg 240
catatctctc atggcccggc aggctgtggc cagtactctc gcgcggaacg tcgtaactac 300
tacacgggcg tttctggcgt tgactctttc ggcacgctga acttcacctc tgacttccag 360
gaacgtgaca tcgttttcgg tggcgataaa aagctgtcca aactgatcga agaaatggaa 420
ctgctgttcc cgctgactaa aggcattact atccaaagcg aatgtccggt gggtctgatc 480
ggtgatgaca tcagcgcggt cgcaaacgca tcttccaaag ccctggataa gccggtgatc 540
ccggttcgtt gcgagggctt ccgcggcgtt tctcagtctc tgggtcatca catcgcaaac 600
gatgttgtgc gtgactggat tctgaacaac cgtgaaggtc agccttttga aaccacccct 660
tatgacgttg cgattattgg cgactataac atcggcggcg acgcctgggc atcccgcatc 720
ctgctggagg agatgggtct gcgtgttgtc gcacagtggt ctggcgatgg caccctggtt 780
gaaatggaaa acaccccgtt tgttaaactg aacctggttc actgctaccg ctccatgaac 840
tacattgccc gtcacatgga agaaaaacat cagatccctt ggatggaata caacttcttc 900
ggtccgacta aaatcgcaga atccctgcgt aaaatcgccg atcagtttga tgataccatt 960
cgcgcgaacg ctgaagcagt aattgcgcgc tacgaaggcc agatggcagc aatcattgct 1020
aagtaccgtc cgcgcctgga aggtcgtaaa gtgctgctgt acatgggtgg tctgcgtcca 1080
cgtcatgtga tcggtgccta cgaggacctg ggcatggaga tcatcgcagc gggttacgaa 1140
tttgcacaca acgacgacta tgatcgtacg ctgccagacc tgaaagaagg tacgctgctg 1200
tttgacgacg ccagctctta tgaactggaa gccttcgtga aagcgctgaa accagacctg 1260
atcggctccg gcatcaagga aaaatacatt ttccagaaaa tgggcgtgcc gttccgccag 1320
atgcactcct gggactactc cggtccgtac cacggctacg acggtttcgc tatcttcgct 1380
cgtgacatgg atatgaccct gaataaccca gcgtggaatg aactgaccgc accgtggctg 1440
aaatctgcat aa 1452

<210> SEQ ID NO 58
<211> LENGTH: 50
<212> TYPE: DNA
<213> ORGANISM: Artificial Sequence
<220> FEATURE:
<223> OTHER INFORMATION: synthetic insulator 2 of full synthetic cluster

<400> SEQUENCE: 58
caaacacccc atgtcgatac tgaacgaatc gacgcacact cccttccttg 50

<210> SEQ ID NO 59
<211> LENGTH: 34
<212> TYPE: DNA
<213> ORGANISM: Artificial Sequence
<220> FEATURE:
<223> OTHER INFORMATION: synthetic nifK ribosome binding site (rbs, RBS) of full synthetic cluster

<400> SEQUENCE: 59
caatctcata ctctcaaaaa ttaggcgagg taac 34

<210> SEQ ID NO 60
<211> LENGTH: 1563
<212> TYPE: DNA
<213> ORGANISM: Artificial Sequence
<220> FEATURE:
<223> OTHER INFORMATION: synthetic nifK of full synthetic cluster

<400> SEQUENCE: 60
atgtctcaaa ctatcgataa aatcaactct tgttacccgc tgttcgagca ggacgaatat 60
caggaactgt tccgtaacaa acgtcagctg gaagaagcgc acgacgcaca gcgcgtgcag 120
gaagtgttcg catggaccac caccgcggaa tacgaagctc tgaacttccg tcgcgaagcc 180
ctgacggttg atccggcgaa agcgtgccag cctctgggtg cggttctgtg cagcctgggt 240
tttgccaaca ccctgccgta tgtccacggt tcccagggct gcgtagccta cttccgtacc 300
tatttcaacc gccactttaa agaaccaatc gcgtgcgtgt ccgacagcat gacggaggac 360
gcggcagttt tcggtggtaa caacaacatg aacctgggcc tgcaaaatgc ttccgcactg 420
tacaaaccgg aaatcatcgc agtgtctacc acctgcatgg cagaggttat tggtgatgat 480
ctgcaagcat ttattgccaa cgcaaagaaa gacggtttcg ttgacagctc tatcgcggtt 540
ccgcacgctc ataccccgtc cttcatcggt tctcacgtaa ctggttggga caacatgttc 600
gaaggcttcg caaaaacttt taccgcagac tatcaaggcc aaccgggtaa actgccgaag 660
ctgaacctgg tgaccggctt tgaaacctac ctgggcaact ttcgtgtcct gaagcgcatg 720

```
atggagcaga tggcggttcc gtgttctctg ctgtctgacc cgtctgaggt tctggacact    780

ccagcggacg gccactatcg catgtattct ggtggcacca ctcagcagga aatgaaagag    840

gccccagacg cgattgacac cctgctgctg caaccgtggc agctgctgaa aagcaagaaa    900

gttgttcagg aaatgtggaa ccagccggca acggaagttg caatcccgct gggtctggca    960

gctactgacg aactgctgat gaccgtgtcc caactgagcg gcaaaccaat cgcggatgct   1020

ctgaccctgg aacgcggtcg cctggtggac atgatgctgg acagccacac gtggctgcat   1080

ggcaagaaat ttggcctgta cggtgacccg gacttcgtaa tgggcctgac ccgtttcctg   1140

ctggaactgg gctgcgagcc gactgttatc ctgtctcaca acgctaacaa acgttggcag   1200

aaggccatga acaaaatgct ggatgcgagc ccatacggcc gtgatagcga agtgttcatc   1260

aactgcgacc tgtggcattt ccgctctctg atgtttacgc gtcagccgga tttcatgatc   1320

ggtaactctt acggcaaatt catccagcgt gacactctgg ccaaaggcaa agcgtttgaa   1380

gtgccgctga ttcgtctggg ctttccgctg ttcgaccgtc accacctgca ccgccagacc   1440

acctggggtt acgaaggcgc gatgaacatc gtaactactc tggtaaacgc agtactggaa   1500

aagctggaca gcgatacttc ccagctgggc aaaaccgact attctttcga tctggttcgt   1560

taa                                                                 1563
```

<210> SEQ ID NO 61
<211> LENGTH: 40
<212> TYPE: DNA
<213> ORGANISM: Artificial Sequence
<220> FEATURE:
<223> OTHER INFORMATION: synthetic insulator 3 of full synthetic cluster

<400> SEQUENCE: 61

```
cctgattgta tccgcatctg atgctaccgt ggttgagtta                           40
```

<210> SEQ ID NO 62
<211> LENGTH: 26
<212> TYPE: DNA
<213> ORGANISM: Artificial Sequence
<220> FEATURE:
<223> OTHER INFORMATION: synthetic nifY ribosome binding site (rbs, RBS) of full synthetic cluster

<400> SEQUENCE: 62

```
ccatactcac tcccggaggt acttct                                          26
```

<210> SEQ ID NO 63
<211> LENGTH: 663
<212> TYPE: DNA
<213> ORGANISM: Artificial Sequence
<220> FEATURE:
<223> OTHER INFORMATION: synthetic nifY of full synthetic cluster

<400> SEQUENCE: 63

```
atgtctgaca atgataccct gttttggcgc atgctggcgc tgtttcagtc gctgccggat     60

ttgcagccgg ctcaaatcgt cgattggctg gcgcaggaat ccggcgaaac cctgacgccg    120

gagcgccttg ccaccctgac ccaaccgcaa ctcgcggcgt cgttcccatc cgcgacggca    180

gtgatgagcc cggctcgctg gagccgcgtt atggcttctc tgcaaggcgc cctcccagcc    240

cacttgcgca tcgtacgtcc ggcgcagcgt accccgcaac tgctcgccgc gttttgcagc    300

caagacggcc ttgttatcaa tggtcatttc ggccagggtc gtctgttctt catttacgcc    360

tttgacgagc agggcggctg gctgtatgac ttgcgccgct atccgagcgc accgcaccag    420
```

caggaagcga atgaggtgcg tgctcgtctg attgaagatt gccagctgct gttctgccag 480
gagattggcg gtccggcagc agcgcgtccg atccgccacc gcatccatcc gatgaaggcg 540
cagccgggta ctacgattca ggcgcagtgt gaagctatca acaccctgct ggccggtcgc 600
ctgccgccgt ggctcgccaa acgtttgaac cgtgataacc cgctggaaga gcgtgtgttt 660
taa 663

<210> SEQ ID NO 64
<211> LENGTH: 40
<212> TYPE: DNA
<213> ORGANISM: Artificial Sequence
<220> FEATURE:
<223> OTHER INFORMATION: synthetic insulator 4 of full synthetic cluster

<400> SEQUENCE: 64
catttttgcc ttgcgacaga cctcctactt agattgccac 40

<210> SEQ ID NO 65
<211> LENGTH: 32
<212> TYPE: DNA
<213> ORGANISM: Artificial Sequence
<220> FEATURE:
<223> OTHER INFORMATION: synthetic nifE ribosome binding site (rbs, RBS) of full synthetic cluster

<400> SEQUENCE: 65
actattcaat acatcactgg aggttattac aa 32

<210> SEQ ID NO 66
<211> LENGTH: 1374
<212> TYPE: DNA
<213> ORGANISM: Artificial Sequence
<220> FEATURE:
<223> OTHER INFORMATION: synthetic nifE of full synthetic cluster

<400> SEQUENCE: 66
atgaagggta acgagattct tgctctgctg gacgaaccgg cctgtgaaca caaccataaa 60
cagaaatccg gctgtagcgc cccaaagccg ggtgcgacgg cggctggctg cgctttcgat 120
ggtgcgcaga tcaccctgct cccgattgcg gacgttgccc acctcgtgca tggcccaatc 180
ggttgcgcag gtagctcttg ggacaaccgt ggcagcgcct ccagcggtcc gaccctgaat 240
cgtttgggct ttaccactga cttgaatgaa caagatgtga tcatgggtcg cggcgagcgt 300
cgcctgttcc acgctgtgcg ccatattgtc acccgttacc acccagcggc agtattcatc 360
tacaatacgt gcgtgccggc tatggaaggc gatgacctgg aggccgtgtg tcaggcagcc 420
cagactgcga ccggcgtccc ggtaatcgca attgatgcgg ctggcttcta cggttcgaag 480
aacctgggca accgtccggc aggcgatgtc atggttaaac gcgtcattgg ccaacgtgag 540
ccagcgccgt ggccggagag caccctgttt gccccggagc aacgtcatga cattggcttg 600
atcggtgagt tcaacattgc gggcgagttt tggcacattc agccgctgct tgatgagctg 660
ggtatccgcg ttttgggttc gctcagcggc gatggtcgtt tcgccgagat tcaaaccatg 720
caccgtgccc aggcgaacat gctggtgtgc agccgtgctc tgatcaatgt tgcgcgtgct 780
ctggaacagc gctatggcac cccgtggttt gaaggctcgt tctatggtat ccgcgcgacc 840
agcgacgccc tgcgccagtt agcggcgctg ctgggcgatg acgacctccg tcagcgcacc 900
gaggcgctga tcgcgcgtga agaacaggcg gctgagctgg ccctgcaacc gtggcgtgaa 960
cagctgcgtg gccgcaaggc cctgctctac acgggtggtg tcaaaagctg gtctgtggtg 1020
tccgcgcttc aggatctggg tatgaccgtg gttgccacgg gcacgcgtaa gagcacggaa 1080
gaggataaac agcgcatccg cgaattgatg ggcgaagagg ccgtgatgct tgaagaaggc 1140
aacgcacgta ccttattgga tgtagtttat cgctatcaag cagacctgat gattgccggt 1200
ggccgcaaca tgtataccgc ctacaaagcg cgcttgccgt tcctggacat caaccaggaa 1260
cgcgagcacg cgtttgcggg ctaccaaggc atcgtgacct tagcgcgcca gctgtgccaa 1320
acgattaaca gcccgatctg gccgcagact cattcccgcg caccgtggcg ctaa 1374

<210> SEQ ID NO 67
<211> LENGTH: 40
<212> TYPE: DNA
<213> ORGANISM: Artificial Sequence
<220> FEATURE:
<223> OTHER INFORMATION: synthetic insulator 5 of full synthetic cluster

<400> SEQUENCE: 67
tgtcacgcta ggaggcaatt ctataagaat gcacactgca 40

<210> SEQ ID NO 68
<211> LENGTH: 31
<212> TYPE: DNA
<213> ORGANISM: Artificial Sequence
<220> FEATURE:
<223> OTHER INFORMATION: synthetic nifN ribosome binding site (rbs, RBS) of full synthetic cluster

<400> SEQUENCE: 68
cctaaaccta ccacacctgg aagaagtaat t 31

<210> SEQ ID NO 69
<211> LENGTH: 1386
<212> TYPE: DNA
<213> ORGANISM: Artificial Sequence
<220> FEATURE:
<223> OTHER INFORMATION: synthetic nifN of full synthetic cluster

<400> SEQUENCE: 69
atggcagaca ttttccgcac tgataagccg ttggctgtgt cgccgatcaa gaccggccag 60
ccgctgggtg cgatcctggc gtccctgggt atcgagcact cgattccgct ggtacatggc 120
gcgcagggct gttcggcttt tgccaaggtt ttctttatcc agcacttcca cgatccggtc 180
ccgctgcaaa gcacggcaat ggacccgacc agcaccatca tgggcgctga tggtaacatc 240
ttcaccgcgc tggacactct ctgccaacgc aataacccgc aagcaattgt gctgctgagc 300
accggcctct ccgaggcgca gggcagcgac atttcccgtg tagtgcgtca gttccgtgaa 360
gaatatccgc gtcataaagg cgtggcgatt ctgactgtta acaccccgga cttttacggt 420
agcatggaga acggcttttc cgctgtcctg gagtctgtga ttgaacagtg ggttccgcca 480
gccccacgtc cggcgcagcg caatcgtcgc gtcaatcttt tggtgagcca tctctgtagc 540
ccaggcgata ttgagtggct gcgccgttgc gtcgaggcct tcggtctgca accgatcatt 600
ctgccggatc tggctcagag catggacggc caccttgctc agggtgactt ttcgccgctg 660
acgcagggcg gcacgccgtt gcgccaaatc gagcagatgg gccagagcct ttgctctttt 720
gcgattggcg tcagcctgca ccgtgcgagc agcctgctgg ctccgcgttg tcgtggcgaa 780
gtcatcgcct tgccgcacct catgaccttg gaacgctgcg acgcctttat ccatcagttg 840
gcgaaaatca gcggtcgcgc cgttccggag tggctggaac gccagcgcgg tcagctgcaa 900
gacgccatga tcgattgcca catgtggctg caaggccagc gcatggcgat tgccgccgaa 960
ggcgacctgc tggcagcgtg gtgcgatttc gcgaactctc aaggtatgca gccgggtcca 1020
ctggttgctc cgacgggtca tccgagcctg cgtcagttgc cggtggagcg cgtggtgccg 1080
ggtgatctgg aggatcttca gaccctctta tgcgcacatc cggccgactt actggtggcg 1140
aactcccacg cccgtgattt agcagagcaa ttcgccctgc cgctggtgcg cgcaggcttc 1200
ccgctgtttg acaaactggg cgaatttcgt cgtgttcgcc agggttatag cggtatgcgt 1260
gataccctgt tcgagttggc gaacctgatc cgtgaacgcc atcatcatct ggctcattat 1320
cgcagcccgc tgcgccagaa cccagaatcc tcgttgtcta cgggtggcgc gtacgcagcg 1380
gattaa 1386

<210> SEQ ID NO 70
<211> LENGTH: 27
<212> TYPE: DNA
<213> ORGANISM: Artificial Sequence
<220> FEATURE:
<223> OTHER INFORMATION: synthetic nifJ ribosome binding site (rbs, RBS) of full synthetic cluster

<400> SEQUENCE: 70
ctagagatta aagaggagaa attaagc 27

<210> SEQ ID NO 71
<211> LENGTH: 3507
<212> TYPE: DNA
<213> ORGANISM: Artificial Sequence
<220> FEATURE:
<223> OTHER INFORMATION: synthetic nifJ of full synthetic cluster

<400> SEQUENCE: 71
atgaaaacta tggacggtaa cgctgcggct gcatggatta gctacgcctt taccgaagtg 60
gctgcgatct acccgattac gccgagcacc ccgatggcgg aaaatgtgga cgaatgggct 120
gcgcagggca agaagaacct cttcggccag ccggtgcgcc tgatggagat gcagtcggaa 180
gcgggtgcag caggtgctgt gcatggcgcc ttgcaagctg gcgcactgac gaccacctac 240
accgcgtcgc agggcctgtt gctgatgatc ccaaacatgt acaaaatcgc gggtgaactg 300
ctgccgggtg tctttcatgt ttcggcacgc gcactggcca ccaatagcct caacatcttt 360
ggcgatcatc aggatgtaat ggcggtgcgc caaacgggct gcgcgatgtt ggccgagaat 420
aacgtccagc aagttatgga tttgtccgcg gtagcccact tggcagcgat caaaggtcgc 480
attccgttcg tgaacttctt cgatggcttt cgcaccagcc acgaaatcca gaagatcgag 540
gttctggaat atgaacagct ggccaccttg ttggatcgtc cggccctgga cagcttccgc 600
cgtaacgccc ttcacccgga ccacccggtc atccgtggca ccgcccagaa cccggacatc 660
tacttccagg aacgtgaggc cggtaaccgt ttctatcagg cgctcccgga tattgtggaa 720
tcttacatga cccagatttc tgccctgact ggtcgcgagt atcacctgtt taactacact 780
ggtgctgcgg atgcggagcg cgtgatcatc gcgatgggct ctgtctgtga caccgtccaa 840
gaggtggttg acacgctgaa tgcagcgggt gagaaagttg gtctgctctc cgttcatctt 900
ttccgcccgt tttcgttagc gcacttcttc gcccaactgc cgaaaactgt acagcgtatc 960
gcagtattgg accgtacgaa agagccaggt gctcaagcag agccgctgtg cctcgatgtg 1020
aagaatgcct tttaccacca tgacgatgcc ccgttgattg tgggtggtcg ctatgccttg 1080
ggcggtaagg acgtgttgcc gaacgatatt gcggccgtgt ttgataacct gaacaaaccg 1140
ctgccgatgg acggcttcac gctgggtatc gtggacgatg ttaccttcac ctctctcccg 1200

-continued

```
ccagcgcagc agaccctggc ggtttctcac gacggcatca cggcatgtaa gttttggggc   1260
atgggctccg acggcacggt tggtgcgaac aagtccgcga tcaagattat cggcgacaaa   1320
acgccactgt atgcgcaagc gtacttttcc tacgactcga agaagagcgg tggtattacc   1380
gtcagccatc tgcgttttgg tgatcgcccg atcaactccc cgtatttgat ccatcgcgcg   1440
gatttcatct cgtgcagcca gcaaagctat gttgaacgct acgatctgct ggatggcctt   1500
aaaccgggtg gcacctttct gctgaactgc tcctggagcg atgccgaact ggagcaacat   1560
ctgccggtcg gtttcaaacg ttatctggca cgcgagaata tccacttcta cactctcaac   1620
gctgtggaca tcgcccgtga gcttggtttg ggtggccgtt tcaacatgct gatgcaggct   1680
gccttcttca aactggccgc gatcattgac ccgcagactg ctgcggacta tctgaagcag   1740
gctgttgaga aaagctatgg cagcaaaggt gcggcggtca tcgagatgaa ccagcgtgcc   1800
atcgagcttg gcatggccag cctgcaccag gtgacgatcc cggcacattg ggccaccctg   1860
gatgagccag cggcgcaggc gtccgcgatg atgccggact ttatccgcga catcctgcaa   1920
ccgatgaacc gtcagtgcgg cgaccagctt ccggtgtcgg cttttgtcgg catggaagat   1980
ggcaccttcc cgtccggcac ggccgcatgg gagaaacgtg gcatcgccct tgaggtgcca   2040
gtctggcagc cggaaggctg cacgcagtgc aaccagtgcg ccttcatttg tccgcacgcc   2100
gcgattcgtc cggcgttgtt gaatggcgaa gagcatgatg ctgccccggt tggcctgctg   2160
agcaaaccgg cacaaggcgc taaagaatat cactatcatc tggcgattag cccgctggac   2220
tgctccggct gtggcaactg cgttgacatt tgtccagctc gtggcaaagc gttgaagatg   2280
cagtctctgg atagccaacg ccagatggct ccggtgtggg attatgcgct ggcgctgacc   2340
ccgaagtcta acccgtttcg taaaaccacc gtcaaaggct cgcagttcga aaccccgctg   2400
ctggagttta gcggtgcgtg cgctggttgt ggcgaaacgc cgtatgcgcg cctcattacc   2460
cagctgtttg gcgaccgcat gctgattgcc aatgccaccg gctgttccag catctggggc   2520
gcatctgcgc cgagcatccc gtataccacc aatcatcgtg gtcatggtcc ggcctgggcg   2580
aatagcctgt ttgaggacaa tgccgaattt ggtttaggta tgatgctggg cggtcaagct   2640
gtgcgtcaac agatcgcgga cgatatgacg gctgcgttag cgctcccggt ttccgatgag   2700
ctgagcgacg cgatgcgcca gtggttggcg aaacaggacg agggtgaagg cacgcgtgag   2760
cgtgcggacc gtctgagcga gcgcttagcc gcggagaaag agggcgttcc gctgttagag   2820
cagctgtggc aaaatcgtga ttactttgtg cgtcgcagcc agtggatttt cggcggtgac   2880
ggctgggcct atgatattgg cttcggtggc ctggaccacg tcctcgccag cggtgaggat   2940
gtgaacattc tggtatttga caccgaagtc tactcgaaca ccggcggtca aagcagcaaa   3000
tcgaccccgg tcgcggccat cgccaagttc gcggctcagg gcaagcgcac ccgcaagaaa   3060
gacctgggta tgatggcgat gagctacggc aacgtctatg tagcccaggt ggcgatgggt   3120
gcggataaag atcaaactct gcgcgccatt gcggaagctg aagcgtggcc aggcccgtcg   3180
ctggtgattg cgtatgcggc ctgcatcaat catggcctga aggccggtat gcgttgcagc   3240
caacgtgagg cgaagcgcgc tgttgaggcg ggctactggc acctgtggcg ttatcacccg   3300
cagcgcgaag cggaaggcaa gacgccgttt atgttagata gcgaagaacc ggaagagtcg   3360
ttccgtgact ttctgttggg tgaggtgcgc tacgcatccc tgcacaagac caccccgcac   3420
ctcgccgatg ccctttttcag ccgtaccgaa gaagatgcgc gtgcgcgctt tgcgcaatac   3480
cgtcgcctgg ctggcgaaga gtaataa                                        3507
```

<210> SEQ ID NO 72
<211> LENGTH: 37
<212> TYPE: DNA
<213> ORGANISM: Artificial Sequence
<220> FEATURE:
<223> OTHER INFORMATION: synthetic Enterobacteria phage T7 terminator 25 of full synthetic cluster

<400> SEQUENCE: 72
tactctaacc ccatcggccg tcttaggggt tttttgt 37

<210> SEQ ID NO 73
<211> LENGTH: 30
<212> TYPE: DNA
<213> ORGANISM: Artificial Sequence
<220> FEATURE:
<223> OTHER INFORMATION: synthetic insulator 6 of full synthetic cluster

<400> SEQUENCE: 73
ccgtggttga gtcagcgtcg agcacgcggc 30

<210> SEQ ID NO 74
<211> LENGTH: 23
<212> TYPE: DNA
<213> ORGANISM: Artificial Sequence
<220> FEATURE:
<223> OTHER INFORMATION: synthetic Enterobacteria phage T7 promoter mut 2 of full synthetic cluster

<400> SEQUENCE: 74
taatacgact cactagagag aga 23

<210> SEQ ID NO 75
<211> LENGTH: 40
<212> TYPE: DNA
<213> ORGANISM: Artificial Sequence
<220> FEATURE:
<223> OTHER INFORMATION: synthetic insulator 7 of full synthetic cluster

<400> SEQUENCE: 75
cgcgacttcc agagaagaag actactgact tgagcgttcc 40

<210> SEQ ID NO 76
<211> LENGTH: 39
<212> TYPE: DNA
<213> ORGANISM: Artificial Sequence
<220> FEATURE:
<223> OTHER INFORMATION: synthetic nifB ribosome binding site (rbs, RBS) of full synthetic cluster

<400> SEQUENCE: 76
ctctctgtaa tacatcaaat caatcatagg agggctaaa 39

<210> SEQ ID NO 77
<211> LENGTH: 1407
<212> TYPE: DNA
<213> ORGANISM: Artificial Sequence
<220> FEATURE:
<223> OTHER INFORMATION: synthetic nifB of full synthetic cluster

<400> SEQUENCE: 77
atgacctctt gttcgtcgtt ttctggcggt aaagcgtgcc gtccggccga tgactccgcg 60
ctgactccgc tggtggccga caaggcagct gcgcacccgt gctatagccg ccacggccat 120
caccgcttcg cgcgtatgca cctgccagtc gctccggcct gcaacttaca atgcaactac 180
tgcaaccgca agttcgattg cagcaatgaa agccgtccgg gcgtgtcctc taccctgctg 240

-continued

```
acgccggaac aggctgtggt gaaggtgcgc caggtcgccc aagctatccc gcagctgtcg    300
gtggtcggta ttgctggtcc gggcgatccg cttgcgaata tcgcccgcac cttccgtacc    360
ttggagctta ttcgcgaaca gttgccggac ctgaaactgt gcctgagcac caacggcttg    420
gtgctgccag atgccgttga tcgtctgctc gatgtgggcg tggatcacgt taccgtcacc    480
attaacaccc tggacgcaga aatcgcagcg caaatctacg cgtggttgtg gctggatggc    540
gaacgctact ccggtcgcga agccggcgaa attctcattg cccgccagct ggaaggcgta    600
cgtcgcctga ccgcgaaagg tgtgctcgtc aagatcaaca gcgtattgat tccgggcatc    660
aatgacagcg gcatggcggg tgttagccgt gcgctgcgcg cgtctggtgc gttcatccac    720
aacatcatgc cactgattgc gcgtccggag catggcactg ttttcggtct gaacggccag    780
ccggaaccgg acgcggaaac cctggcggcg acgcgctccc gctgcggcga ggttatgcca    840
caaatgaccc actgccacca gtgccgtgcc gacgcgattg gcatgcttgg tgaggatcgc    900
tcgcaacagt ttacgcaatt accggctccg gagtccctcc cggcctggct gccgatcctg    960
catcagcgtg ctcagttgca tgcgagcatc gccacgcgcg gtgagagcga agccgatgac   1020
gcctgcctgg tggccgttgc gtcgagccgt ggcgatgtaa ttgactgcca tttcggccat   1080
gccgaccgtt tctatatcta tagcctgtct gcggctggta tggttctggt taacgaacgt   1140
ttcaccccga aatactgcca gggtcgcgat gactgcgagc cgcaggacaa tgccgcacgc   1200
tttgctgcca tccttgagtt gctggcggac gtcaaagcgg tgttttgtgt gcgtatcggc   1260
cataccccgt ggcaacagct ggagcaggaa ggcatcgaac cgtgcgtgga tggcgcctgg   1320
cgtccggtat ccgaggtcct gccggcatgg tggcagcagc gccgtggtag ctggccggct   1380
gcattgccgc acaaaggcgt tgcgtaa                                       1407
```

<210> SEQ ID NO 78
<211> LENGTH: 40
<212> TYPE: DNA
<213> ORGANISM: Artificial Sequence
<220> FEATURE:
<223> OTHER INFORMATION: synthetic insulator 8 of full synthetic cluster

<400> SEQUENCE: 78

```
actacgagat ttgaggtaaa ccaaataagc acgtagtggc                           40
```

<210> SEQ ID NO 79
<211> LENGTH: 33
<212> TYPE: DNA
<213> ORGANISM: Artificial Sequence
<220> FEATURE:
<223> OTHER INFORMATION: synthetic nifQ ribosome binding site (rbs, RBS) of full synthetic cluster

<400> SEQUENCE: 79

```
tgcgtttagc agttcccgta ggaatatttc ctt                                  33
```

<210> SEQ ID NO 80
<211> LENGTH: 504
<212> TYPE: DNA
<213> ORGANISM: Artificial Sequence
<220> FEATURE:
<223> OTHER INFORMATION: synthetic nifQ of full synthetic cluster

<400> SEQUENCE: 80

```
atgccgccat tggactggtt gcgtcgtttg tggttactct atcacgccgg caaaggcagc     60
tttccgcttc gtatgggctt gtcgccgcgt gactggcaag ctctgcgccg tcgcctgggc    120
```

gaggtggaaa cgccgctgga tggcgaaacc ctgacccgtc gccgtctgat ggcggagctg 180
aatgcgaccc gcgaagaaga acgccagcag ctgggtgcct ggctggccgg ttggatgcaa 240
caggatgccg gtccgatggc gcagattatc gcagaggtga gcctggcgtt caaccatctc 300
tggcaggacc ttggcctcgc gagccgcgct gaactgcgtc tgctgatgtc tgactgcttc 360
ccgcagctgg ttgttatgaa cgagcacaac atgcgctgga agaaattctt ttaccgccag 420
cgttgcctgc tgcaacaggg cgaagtcatc tgtcgcagcc cgtcttgcga tgaatgctgg 480
gaacgttctg cgtgctttga gtaa 504

<210> SEQ ID NO 81
<211> LENGTH: 29
<212> TYPE: DNA
<213> ORGANISM: Artificial Sequence
<220> FEATURE:
<223> OTHER INFORMATION: synthetic Enterobacteria phage T7 terminator 1 of full synthetic cluster

<400> SEQUENCE: 81
tacatatcgg gggggtaggg gttttttgt 29

<210> SEQ ID NO 82
<211> LENGTH: 18
<212> TYPE: DNA
<213> ORGANISM: Artificial Sequence
<220> FEATURE:
<223> OTHER INFORMATION: synthetic insulator 9 of full synthetic cluster

<400> SEQUENCE: 82
gtctgtagca cgtgcatc 18

<210> SEQ ID NO 83
<211> LENGTH: 23
<212> TYPE: DNA
<213> ORGANISM: Artificial Sequence
<220> FEATURE:
<223> OTHER INFORMATION: synthetic Enterobacteria phage T7 promoter mut 3 of full synthetic cluster

<400> SEQUENCE: 83
taatacgact cactaatggg aga 23

<210> SEQ ID NO 84
<211> LENGTH: 34
<212> TYPE: DNA
<213> ORGANISM: Artificial Sequence
<220> FEATURE:
<223> OTHER INFORMATION: synthetic nifF ribosome binding site (rbs, RBS) of full synthetic cluster

<400> SEQUENCE: 84
gacaagagtc tcaattataa ggaggcttta ctac 34

<210> SEQ ID NO 85
<211> LENGTH: 534
<212> TYPE: DNA
<213> ORGANISM: Artificial Sequence
<220> FEATURE:
<223> OTHER INFORMATION: synthetic nifF of full synthetic cluster

<400> SEQUENCE: 85
atggcgaaca tcggcatctt ctttggtacg gataccggca aaacccgcaa gattgcgaag 60
atgattcaca aacagctggg cgagctggcc gatgccccgg ttaacatcaa tcgtaccact 120
ttggatgact ttatggctta cccagtcctg ttgctcggca cgccgacgct tggtgatggt 180
caactgccgg gcttagaggc gggctgcgag agcgaaagct ggtctgagtt tatctccggt 240
ctggatgacg cttccctgaa gggcaaaacc gtggcgctgt ttggcctggg cgaccagcgt 300
ggttacccgg acaacttcgt gtcgggtatg cgtccgctgt tcgacgcgct gagcgcccgt 360
ggcgcccaga tgattggtag ctggccgaac gaaggttatg agtttagcgc atcgtccgcg 420
ctggaaggcg accgcttcgt cggcttggtg ctggatcaag acaatcagtt cgaccagacc 480
gaagcgcgcc tggcgtcttg gcttgaagag atcaaacgca ccgttctgta ataa 534

<210> SEQ ID NO 86
<211> LENGTH: 29
<212> TYPE: DNA
<213> ORGANISM: Artificial Sequence
<220> FEATURE:
<223> OTHER INFORMATION: synthetic Enterobacteria phage T7 terminator 1 of full synthetic cluster

<400> SEQUENCE: 86
tacatatcgg gggggtaggg gttttttgt 29

<210> SEQ ID NO 87
<211> LENGTH: 18
<212> TYPE: DNA
<213> ORGANISM: Artificial Sequence
<220> FEATURE:
<223> OTHER INFORMATION: synthetic insulator 10 of full synthetic cluster

<400> SEQUENCE: 87
ggtcattaca acggttat 18

<210> SEQ ID NO 88
<211> LENGTH: 23
<212> TYPE: DNA
<213> ORGANISM: Artificial Sequence
<220> FEATURE:
<223> OTHER INFORMATION: synthetic Enterobacteria phage T7 promoter mut 2 of full synthetic cluster

<400> SEQUENCE: 88
taatacgact cactagagag aga 23

<210> SEQ ID NO 89
<211> LENGTH: 40
<212> TYPE: DNA
<213> ORGANISM: Artificial Sequence
<220> FEATURE:
<223> OTHER INFORMATION: synthetic insulator 11 of full synthetic cluster

<400> SEQUENCE: 89
aacatagcgt tccatgaggg ctagaattac ctaccggcct 40

<210> SEQ ID NO 90
<211> LENGTH: 37
<212> TYPE: DNA
<213> ORGANISM: Artificial Sequence
<220> FEATURE:
<223> OTHER INFORMATION: synthetic nifU ribosome binding site (rbs, RBS) of full synthetic cluster

<400> SEQUENCE: 90
cagatactga caaataaacc agcgaaggag gttccta 37

<210> SEQ ID NO 91
<211> LENGTH: 825
<212> TYPE: DNA
<213> ORGANISM: Artificial Sequence
<220> FEATURE:
<223> OTHER INFORMATION: synthetic nifU of full synthetic cluster

<400> SEQUENCE: 91
atgtggaact acagcgagaa agtcaaggac catttcttca atccgcgcaa cgcgcgtgtt 60
gtggataacg caaatgcggt gggcgacgtc ggcagcttat cttgtggcga tgctctccgc 120
ttgatgctgc gcgtggaccc gcagagcgaa atcatcgaag aagcgggctt tcagaccttc 180
ggctgcggca gcgcgattgc gtcgtccagc gcactgacgg agctgatcat cggtcacacc 240
ctggcggaag cgggtcagat caccaaccag cagatcgccg actatctgga cggcttaccg 300
ccggaaaaga tgcactgctc tgtaatgggc caggaagctc ttcgtgcggc cattgctaac 360
tttcgcggtg aatcgctgga agaggagcat gacgagggta agctgatctg caagtgcttc 420
ggcgtcgatg aaggccatat tcgccgtgct gtccagaaca acggtcttac gactctggcc 480
gaggtgatca attacaccaa ggcaggtggc ggttgtacca gctgccatga gaaaatcgag 540
ctggccctgg ccgagattct cgcccaacag ccgcaaacca ccccggcagt tgcgtccggt 600
aaagatccgc actggcagag cgtcgtggat accatcgctg aactgcgtcc acatatccaa 660
gcggacggtg gtgacatggc gctgttgtcc gtgacgaacc accaagtgac tgtttcgctg 720
tcgggcagct gttctggctg catgatgacc gacatgaccc tggcgtggct gcaacagaaa 780
ttgatggagc gtaccggctg ctatatggaa gttgttgccg cctaa 825

<210> SEQ ID NO 92
<211> LENGTH: 40
<212> TYPE: DNA
<213> ORGANISM: Artificial Sequence
<220> FEATURE:
<223> OTHER INFORMATION: synthetic insulator 12 of full synthetic cluster

<400> SEQUENCE: 92
cattgtaata gccaccaaaa gagtgatgat agtcatgggt 40

<210> SEQ ID NO 93
<211> LENGTH: 39
<212> TYPE: DNA
<213> ORGANISM: Artificial Sequence
<220> FEATURE:
<223> OTHER INFORMATION: synthetic nifS ribosome binding site (rbs, RBS) of full synthetic cluster

<400> SEQUENCE: 93
gatacccgta gaccattctg aaatcgaagg aggttttcc 39

<210> SEQ ID NO 94
<211> LENGTH: 1203
<212> TYPE: DNA
<213> ORGANISM: Artificial Sequence
<220> FEATURE:
<223> OTHER INFORMATION: synthetic nifS of full synthetic cluster

<400> SEQUENCE: 94
atgaaacaag tgtacctgga caacaacgcg accacccgcc tggacccgat ggttctggaa 60
gcgatgatgc cgtttctcac ggatttctat ggcaatccgt ccagcatcca tgacttcggc 120
atcccggcac aagcggcgct ggaacgtgcg caccagcaag ctgcggcact gctgggcgca 180
gagtacccgt ctgaaatcat tttcacgagc tgtgcgaccg aggccactgc aaccgccatt 240
gcgtcggcca tcgcgttatt gccggaacgc cgcgaaatca tcacctcggt agtggagcac 300
ccggctacgc tggcggcgtg cgagcacctg gaacgccaag gctatcgcat ccatcgcatt 360
gcggtggata gcgaaggtgc gctggacatg gcccagttcc gtgcagcgct ctcgccgcgt 420
gtcgcgttgg tgagcgtgat gtgggccaac aacgaaaccg gcgtgctgtt cccgattggc 480
gaaatggccg agcttgccca cgagcagggc gctctgttcc actgcgatgc cgttcaggtc 540
gttggcaaaa tcccaattgc tgttggccag acgcgcatcg acatgctgtc ttgctccgcg 600
cacaagtttc atggtccgaa gggtgttggt tgcttgtact tacgtcgtgg cacgcgcttt 660
cgtccgctgc ttcgcggtgg ccatcaagaa tatggtcgcc gtgccggcac tgagaatatc 720
tgtggcatcg tcggcatggg cgctgcgtgc gaactggcga acatccatct gccgggtatg 780
acccatattg gccagttacg caatcgcctg gagcaccgtc tgctcgccag cgtgccgtcc 840
gtgatggtta tgggcggtgg tcagccgcgt gtaccgggta ctgtcaacct ggcgttcgag 900
tttatcgaag gtgaagcgat cctgctcttg ctgaaccagg ctggcattgc cgcaagctcc 960
ggctccgcgt gtacctctgg cagcttggag ccgagccatg tgatgcgcgc catgaacatt 1020
ccatacaccg cggctcacgg caccattcgt tttagcctga gccgttatac gcgcgagaaa 1080
gagatcgact acgtcgttgc gaccctcccg ccaatcattg atcgtctgcg tgccttgtcc 1140
ccgtattggc agaatggtaa gccgcgtccg gcagatgcag tctttacccc ggtttacggt 1200
taa 1203

<210> SEQ ID NO 95
<211> LENGTH: 40
<212> TYPE: DNA
<213> ORGANISM: Artificial Sequence
<220> FEATURE:
<223> OTHER INFORMATION: synthetic insulator 13 of full synthetic cluster

<400> SEQUENCE: 95
gagttactgg ccctgatttc tccgcttcta ataccgcaca 40

<210> SEQ ID NO 96
<211> LENGTH: 34
<212> TYPE: DNA
<213> ORGANISM: Artificial Sequence
<220> FEATURE:
<223> OTHER INFORMATION: synthetic nifV ribosome binding site (rbs, RBS) of full synthetic cluster

<400> SEQUENCE: 96
gcgactagga gcctaactcg ccacaaggaa acat 34

<210> SEQ ID NO 97
<211> LENGTH: 1143
<212> TYPE: DNA
<213> ORGANISM: Artificial Sequence
<220> FEATURE:
<223> OTHER INFORMATION: synthetic nifV of full synthetic cluster

<400> SEQUENCE: 97
atggagcgcg tcttgatcaa cgatactacc ctgcgtgatg gcgaacaatc tccgggcgta 60
gcgtttcgta cctccgagaa agttgccatc gcggaggcac tgtacgctgc gggtatcacc 120
gcgatggaag tcggcactcc ggcgatgggt gatgaagaga tcgcccgcat tcagctggtg 180

```
cgtcgtcaac tgccggacgc gacgcttatg acctggtgcc gtatgaacgc tctggaaatc    240

cgtcagagcg cggatctggg tattgactgg gtggatatct cgatcccagc atccgacaag    300

ctgcgtcagt acaagctgcg tgagccgctg gccgtgctgc tggagcgcct tgcgatgttt    360

atccatctgg cccacacgtt aggcctcaaa gtatgtattg gttgcgagga tgcgagccgt    420

gcgtctggtc agaccctgcg cgccattgcc gaggtggccc agcaatgcgc ggctgcgcgc    480

ttgcgttacg ctgacaccgt gggcctgctg gacccgttca ccaccgcagc ccagatcagc    540

gccctgcgtg acgtttggtc gggcgagatc gagatgcatg ctcacaatga tctgggcatg    600

gctaccgcga acacgctggc ggcagtttcg gctggcgcca cgtcggtgaa cactaccgtc    660

ctcggtctgg gtgaacgtgc aggcaacgca gccctggaaa ccgttgcgct gggcctggaa    720

cgctgcctgg gcgtggaaac cggcgtccat ttcagcgcgc tcccagcgag ctgtcagcgc    780

gtcgcggagg ctgcacagcg cgcaatcgac ccgcaacagc cgctggtggg tgaattggtt    840

ttcacccacg agtctggtgt tcacgttgcg gcgctgctgc gccacagcga atcctatcaa    900

tctattgccc caagcctcat gggccgtagc taccgtctgg tgctcggcaa gcattcgggt    960

cgtcaggctg tcaacggtgt tttcgaccag atgggttacc acctgaatgc ggcgcagatc   1020

aatcagttgc tgccggccat tcgccgcttc gccgagaatt ggaaacgctc tccgaaagac   1080

tacgaactgg ttgcgatcta tgacgaattg tgcggtgaat ccgcccttcg tgctcgcggc   1140

taa                                                                 1143
```

```
<210> SEQ ID NO 98
<211> LENGTH: 40
<212> TYPE: DNA
<213> ORGANISM: Artificial Sequence
<220> FEATURE:
<223> OTHER INFORMATION: synthetic insulator 14 of full synthetic
      cluster

<400> SEQUENCE: 98

gactcaacac gctagggacg tgaagtcgat tccttcgatg                          40


<210> SEQ ID NO 99
<211> LENGTH: 35
<212> TYPE: DNA
<213> ORGANISM: Artificial Sequence
<220> FEATURE:
<223> OTHER INFORMATION: synthetic nifW ribosome binding site (rbs, RBS)
      of full synthetic cluster

<400> SEQUENCE: 99

cagaaggcga gaactagatt taagggccat tatag                               35


<210> SEQ ID NO 100
<211> LENGTH: 258
<212> TYPE: DNA
<213> ORGANISM: Artificial Sequence
<220> FEATURE:
<223> OTHER INFORMATION: synthetic nifW of full synthetic cluster

<400> SEQUENCE: 100

atggagtggt tttaccagat tccgggtgta gacgaattgc gcagcgctga atccttcttt     60

cagttcttcg cggttccata ccagccggaa ctgctgggcc gctgctcgct tccggtgtta    120

gcgacgttcc accgtaaact gcgtgcggag gtcccgctgc aaaaccgtct ggaggacaat    180

gatcgtgcgc cgtggctctt ggcgcgccgc ctcctggccg aatcttatca gcagcaattt    240
```

caggagagcg gcacctaa 258

<210> SEQ ID NO 101
<211> LENGTH: 40
<212> TYPE: DNA
<213> ORGANISM: Artificial Sequence
<220> FEATURE:
<223> OTHER INFORMATION: synthetic insulator 15 of full synthetic cluster

<400> SEQUENCE: 101
tcgagaaaca aggcagttcc gggctgaaag tagcgccggg 40

<210> SEQ ID NO 102
<211> LENGTH: 36
<212> TYPE: DNA
<213> ORGANISM: Artificial Sequence
<220> FEATURE:
<223> OTHER INFORMATION: synthetic nifZ ribosome binding site (rbs, RBS) of full synthetic cluster

<400> SEQUENCE: 102
acaagtcccg tattataacc gcctaggagg tgttgg 36

<210> SEQ ID NO 103
<211> LENGTH: 447
<212> TYPE: DNA
<213> ORGANISM: Artificial Sequence
<220> FEATURE:
<223> OTHER INFORMATION: synthetic nifZ of full synthetic cluster

<400> SEQUENCE: 103
atgcgcccga aattcacctt ctctgaagag gtccgcgtag ttcgcgcgat tcgtaatgat 60
ggcaccgtgg cgggttttgc gccaggtgcg ctgctggttc gtcgcggttc gacgggcttt 120
gtgcgtgact ggggtgtgtt cctgcaagac cagatcatct atcaaatcca ctttccggaa 180
accgaccgca ttatcggctg tcgcgagcag gagttaatcc cgattaccca gccgtggttg 240
gctggtaacc tccagtatcg tgacagcgtc acgtgccaaa tggcactggc tgtcaacggt 300
gacgtggttg tgagcgccgg tcaacgtggc cgtgtggagg ccactgatcg tggcgaactt 360
ggcgattcct acaccgtgga cttcagcggc cgttggttcc gcgttccggt ccaggccatc 420
gcgctgattg aagagcgcga agaataa 447

<210> SEQ ID NO 104
<211> LENGTH: 40
<212> TYPE: DNA
<213> ORGANISM: Artificial Sequence
<220> FEATURE:
<223> OTHER INFORMATION: synthetic insulator 16 of full synthetic cluster

<400> SEQUENCE: 104
acgccacgcg tagtgagaca tacacgttcg ttgggttcac 40

<210> SEQ ID NO 105
<211> LENGTH: 34
<212> TYPE: DNA
<213> ORGANISM: Artificial Sequence
<220> FEATURE:
<223> OTHER INFORMATION: synthetic nifM ribosome binding site (rbs, RBS) of full synthetic cluster

<400> SEQUENCE: 105
tcagagactg aagttattac ccaggaggtc tata 34

<210> SEQ ID NO 106
<211> LENGTH: 801
<212> TYPE: DNA
<213> ORGANISM: Artificial Sequence
<220> FEATURE:
<223> OTHER INFORMATION: synthetic nifM of full synthetic cluster

<400> SEQUENCE: 106
atgaatccgt ggcagcgctt tgcccgtcaa cgccttgctc gcagccgctg gaaccgtgat 60
ccggctgctc tcgacccagc cgatacccca gcgttcgagc aggcgtggca gcgtcaatgc 120
catatggaac aaaccatcgt agcgcgtgtc ccggaaggcg atattccggc tgccttactg 180
gaaaacatcg cggccagcct ggcgatctgg ctggacgagg gtgacttcgc tccgccggag 240
cgcgctgcga ttgtgcgtca tcatgcacgt ctggagctgg cgtttgccga cattgcccgc 300
caggcaccgc aaccggatct gagcacggtt caagcgtggt atctgcgtca ccagactcaa 360
ttcatgcgtc cggagcagcg tctgacccgt cacctgctcc tgacggtcga taatgatcgc 420
gaggcggtgc atcaacgcat ccttggcctg tatcgtcaga tcaacgcgag ccgtgacgcc 480
ttcgccccac tggcacagcg ccactctcat tgcccgtccg ccttggaaga aggccgtctg 540
ggctggatct cccgtggtct gctgtacccg cagctcgaaa ccgcgttgtt tagcctggcg 600
gaaaacgcac tgtcgctgcc gattgcgtcg gaattgggtt ggcacctgtt atggtgcgag 660
gccattcgtc cggcagcccc gatggagccg caacaggccc ttgaatctgc gcgcgactac 720
ttgtggcagc agagccagca gcgccaccag cgtcaatggc tggagcagat gatttcccgc 780
caaccgggcc tgtgtggtta a 801

<210> SEQ ID NO 107
<211> LENGTH: 47
<212> TYPE: DNA
<213> ORGANISM: Artificial Sequence
<220> FEATURE:
<223> OTHER INFORMATION: synthetic Enterobacteria phage T7 wild type (WT) terminator of full synthetic cluster

<400> SEQUENCE: 107
tagcataacc ccttggggcc tctaaacggg tcttgagggg ttttttg 47

<210> SEQ ID NO 108
<211> LENGTH: 21
<212> TYPE: DNA
<213> ORGANISM: Artificial Sequence
<220> FEATURE:
<223> OTHER INFORMATION: synthetic Biobrick suffix (BBa_G000001) of full synthetic cluster

<400> SEQUENCE: 108
tactagtagc ggccgctgca g 21

<210> SEQ ID NO 109
<211> LENGTH: 12
<212> TYPE: DNA
<213> ORGANISM: Artificial Sequence
<220> FEATURE:
<223> OTHER INFORMATION: synthetic translational stop (BBa_B0042) of full synthetic cluster

<400> SEQUENCE: 109
ttagttagtt ag 12

<210> SEQ ID NO 110
<211> LENGTH: 69
<212> TYPE: DNA
<213> ORGANISM: Artificial Sequence
<220> FEATURE:
<223> OTHER INFORMATION: synthetic terminator (BBa_B0054) of full synthetic cluster

<400> SEQUENCE: 110
attagcagaa agtcaaaagc ctccgaccgg aggcttttga ctaaaacttc ccttggggtt 60
atcattggg 69

<210> SEQ ID NO 111
<211> LENGTH: 20
<212> TYPE: DNA
<213> ORGANISM: Artificial Sequence
<220> FEATURE:
<223> OTHER INFORMATION: synthetic VR primer (BBa_G00102) of full synthetic cluster

<400> SEQUENCE: 111
gctcactcaa aggcggtaat 20

<210> SEQ ID NO 112
<211> LENGTH: 41
<212> TYPE: DNA
<213> ORGANISM: Artificial Sequence
<220> FEATURE:
<223> OTHER INFORMATION: synthetic terminator (BBa_B0062) of full synthetic cluster

<400> SEQUENCE: 112
cagataaaaa aaatccttag ctttcgctaa ggatgatttc t 41

<210> SEQ ID NO 113
<211> LENGTH: 2037
<212> TYPE: DNA
<213> ORGANISM: Artificial Sequence
<220> FEATURE:
<223> OTHER INFORMATION: synthetic pSC101 origin (BBa_150042) of full synthetic cluster

<400> SEQUENCE: 113
ctgtcagacc aagtttacga gctcgcttgg actcctgttg atagatccag taatgacctc 60
agaactccat ctggatttgt tcagaacgct cggttgccgc cgggcgtttt ttattggtga 120
gaatccaagc actagggaca gtaagacggg taagcctgtt gatgataccg ctgccttact 180
gggtgcatta gccagtctga atgacctgtc acgggataat ccgaagtggt cagactggaa 240
aatcagaggg caggaactgc tgaacagcaa aaagtcagat agcaccacat agcagacccg 300
ccataaaacg ccctgagaag cccgtgacgg gcttttcttg tattatgggt agtttccttg 360
catgaatcca taaaaggcgc ctgtagtgcc atttaccccc attcactgcc agagccgtga 420
gcgcagcgaa ctgaatgtca cgaaaaagac agcgactcag gtgcctgatg gtcggagaca 480
aaaggaatat tcagcgattt gcccgagctt gcgagggtgc tacttaagcc tttagggttt 540
taaggtctgt tttgtagagg agcaaacagc gtttgcgaca tccttttgta atactgcgga 600
actgactaaa gtagtgagtt atacacaggg ctgggatcta ttcttttttat cttttttttat 660 tctttcttta ttctataaat tataaccact tgaatataaa caaaaaaaac acacaaaggt 720
ctagcggaat ttacagaggg tctagcagaa tttacaagtt ttccagcaaa ggtctagcag 780
aatttacaga tacccacaac tcaaaggaaa aggacatgta attatcattg actagcccat 840

```
ctcaattggt atagtgatta aaatcaccta gaccaattga gatgtatgtc tgaattagtt    900

gttttcaaag caaatgaact agcgattagt cgctatgact taacggagca tgaaaccaag    960

ctaattttat gctgtgtggc actactcaac cccacgattg aaaaccctac aaggaaagaa   1020

cggacggtat cgttcactta taaccaatac gctcagatga tgaacatcag tagggaaaat   1080

gcttatggtg tattagctaa agcaaccaga gagctgatga cgagaactgt ggaaatcagg   1140

aatcctttgg ttaaaggctt tgagattttc cagtggacaa actatgccaa gttctcaagc   1200

gaaaaattag aattagtttt tagtgaagag atattgcctt atcttttcca gttaaaaaaa   1260

ttcataaaat ataatctgga acatgttaag tcttttgaaa acaaatactc tatgaggatt   1320

tatgagtggt tattaaaaga actaacacaa aagaaaactc acaaggcaaa tatagagatt   1380

agccttgatg aatttaagtt catgttaatg cttgaaaata actaccatga gtttaaaagg   1440

cttaaccaat gggttttgaa accaataagt aaagatttaa acacttacag caatatgaaa   1500

ttggtggttg ataagcgagg ccgcccgact gatacgttga ttttccaagt tgaactagat   1560

agacaaatgg atctcgtaac cgaacttgag aacaaccaga taaaaatgaa tggtgacaaa   1620

ataccaacaa ccattacatc agattcctac ctacgtaacg gactaagaaa aacactacac   1680

gatgctttaa ctgcaaaaat tcagctcacc agttttgagg caaaattttt gagtgacatg   1740

caaagtaagc atgatctcaa tggttcgttc tcatggctca cgcaaaaaca acgaaccaca   1800

ctagagaaca tactggctaa atacggaagg atctgaggtt cttatggctc ttgtatctat   1860

cagtgaagca tcaagactaa caaacaaaag tagaacaact gttcaccgtt agatatcaaa   1920

gggaaaactg tccatatgca cagatgaaaa cggtgtaaaa aagatagata catcagagct   1980

tttacgagtt tttggtgcat ttaaagctgt tcaccatgaa cagatcgaca atgtaac      2037
```

<210> SEQ ID NO 114
<211> LENGTH: 769
<212> TYPE: DNA
<213> ORGANISM: Artificial Sequence
<220> FEATURE:
<223> OTHER INFORMATION: synthetic chloramphenicol resistance
(BBa_P1004) of full synthetic cluster

<400> SEQUENCE: 114

```
gttgatcggg cacgtaagag gttccaactt tcaccataat gaaataagat cactaccggg     60

cgtatttttt gagttatcga gattttcagg agctaaggaa gctaaaatgg agaaaaaaat    120

cacgggatat accaccgttg atatatccca atggcatcgt aaagaacatt ttgaggcatt    180

tcagtcagtt gctcaatgta cctataacca gaccgttcag ctggatatta cggccttttt    240

aaagaccgta aagaaaaata agcacaagtt ttatccggcc tttattcaca ttcttgcccg    300

cctgatgaac gctcacccgg agtttcgtat ggccatgaaa gacggtgagc tggtgatctg    360

ggatagtgtt cacccttgtt acaccgtttt ccatgagcaa actgaaacgt tttcgtccct    420

ctggagtgaa taccacgacg atttccggca gtttctccac atatattcgc aagatgtggc    480

gtgttacggt gaaaacctgg cctatttccc taaagggttt attgagaata tgtttttcgt    540

ctcagccaat ccctgggtga gtttcaccag ttttgattta aacgtggcca atatggacaa    600

cttcttcgcc cccgttttca cgatgggcaa atattatacg caaggcgaca aggtgctgat    660

gccgctggcg atccaggttc atcatgccgt ttgtgatggc ttccatgtcg gccgcatgct    720

taatgaatta caacagtact gtgatgagtg gcagggcggg gcgtaataa                769
```

<210> SEQ ID NO 115

<211> LENGTH: 72
<212> TYPE: DNA
<213> ORGANISM: Artificial Sequence
<220> FEATURE:
<223> OTHER INFORMATION: synthetic terminator (BBa_B0053) of full synthetic cluster

<400> SEQUENCE: 115
tccggcaaaa aaacgggcaa ggtgtcacca ccctgccctt tttctttaaa accgaaaaga 60
ttacttcgcg tt 72

<210> SEQ ID NO 116
<211> LENGTH: 20
<212> TYPE: DNA
<213> ORGANISM: Artificial Sequence
<220> FEATURE:
<223> OTHER INFORMATION: synthetic VF2 primer (BBa_G00101) of full synthetic cluster

<400> SEQUENCE: 116
tgccacctga cgtctaagaa 20

<210> SEQ ID NO 117
<211> LENGTH: 78
<212> TYPE: DNA
<213> ORGANISM: Artificial Sequence
<220> FEATURE:
<223> OTHER INFORMATION: synthetic terminator (BBa_B0055) of full synthetic cluster

<400> SEQUENCE: 117
aaggaatatt cagcaatttg cccgtgccga agaaaggccc acccgtgaag gtgagccagt 60
gagttgattg ctacgtaa 78

<210> SEQ ID NO 118
<211> LENGTH: 12
<212> TYPE: DNA
<213> ORGANISM: Artificial Sequence
<220> FEATURE:
<223> OTHER INFORMATION: synthetic translational stop (BBa_B0042) of full synthetic cluster

<400> SEQUENCE: 118
ttagttagtt ag 12

<210> SEQ ID NO 119
<211> LENGTH: 19
<212> TYPE: DNA
<213> ORGANISM: Artificial Sequence
<220> FEATURE:
<223> OTHER INFORMATION: synthetic SynPrgH ribosome binding site (rbs, RBS) of bacterial type III secretion system (T3SS)

<400> SEQUENCE: 119
attaaacagg ataataagc 19

<210> SEQ ID NO 120
<211> LENGTH: 1182
<212> TYPE: DNA
<213> ORGANISM: Artificial Sequence
<220> FEATURE:
<223> OTHER INFORMATION: synthetic SynPrgH of bacterial type III secretion system (T3SS)

<400> SEQUENCE: 120
atggaaacta gcaaggagaa aacgattacg tcccctggtc cgtatatcgt tcgtctgttg 60
aactcgtccc tgaacggttg tgaatttccg ctgctgactg gtcgtacgct gttcgtcgtg 120
ggtcagagcg atgctctgac cgcgtctggt cagctgccgg acattcctgc cgactccttc 180
ttcatcccgc tggatcatgg cggtgttaat ttcgagattc aagtggacac tgacgcgacg 240
gaaatcatcc tgcacgaact gaaagagggc aactccgaga gccgctccgt gcaactgaac 300
accccgatcc aagttggtga actgctgatt ttgattcgtc cggagagcga gccgtgggtg 360
ccggaacagc cggagaagtt ggaaacttct gcgaaaaaga acgaaccgcg ctttaaaaac 420
ggcatcgtcg cggcactggc gggtttcttt atcctgggta tcggcacggt tggcaccctg 480
tggattctga actcgccgca acgtcaagca gccgaattgg acagcctgtt gggtcaggag 540
aaggagcgtt ttcaggtgct gccgggtcgc gacaagatgc tgtatgtcgc cgcgcaaaac 600
gaacgcgaca ccctgtgggc acgtcaagtc ctggcacgcg gcgattacga taaaaacgca 660
cgcgttatta atgaaaatga ggagaataaa cgtatcagca tctggctgga cacgtattat 720
ccacaactgg catattaccg tatccatttt gatgaaccac gtaagccggt gttttggctg 780
tcccgtcaac gcaacacgat gagcaagaaa gagctggagg tgctgtccca gaaattgcgt 840
gcgctgatgc cgtacgccga cagcgtcaat attactctga tggatgacgt gaccgcagca 900
ggccaagccg aggcaggtct gaaacaacag gcgctgccat acagccgccg taaccacaaa 960
ggtggtgtta cgttcgttat tcagggcgcc ttggacgacg ttgagattct gcgtgcgcgc 1020
cagtttgtcg actcctatta tcgtacctgg ggtggtcgtt acgttcaatt cgcaattgaa 1080
ttgaaagacg attggctgaa aggccgctcg ttccaatacg gtgcggaagg ctacattaag 1140
atgagcccag gtcattggta ttttccgtct cctctgtaat ag 1182

<210> SEQ ID NO 121
<211> LENGTH: 21
<212> TYPE: DNA
<213> ORGANISM: Artificial Sequence
<220> FEATURE:
<223> OTHER INFORMATION: synthetic SynPrgI ribosome binding site (rbs, RBS) of bacterial type III secretion system (T3SS)

<400> SEQUENCE: 121
attaaagagg agaaattaag c 21

<210> SEQ ID NO 122
<211> LENGTH: 21
<212> TYPE: DNA
<213> ORGANISM: Artificial Sequence
<220> FEATURE:
<223> OTHER INFORMATION: synthetic SynPrgJ ribosome binding site (rbs, RBS) of bacterial type III secretion system (T3SS)

<400> SEQUENCE: 122
attaaggagg ataaattaag c 21

<210> SEQ ID NO 123
<211> LENGTH: 309
<212> TYPE: DNA
<213> ORGANISM: Artificial Sequence
<220> FEATURE:
<223> OTHER INFORMATION: synthetic SynPrgJ of bacterial type III secretion system (T3SS)

<400> SEQUENCE: 123
atgtctatcg cgactatcgt gcctgaaaat gccgttattg gtcaagcggt gaatattcgc 60
agcatggaaa cggacatcgt cagcttggac gaccgtttgc tgcaagcatt ttcgggcagc 120
gccatcgcta ccgccgtcga taagcagacc attaccaatc gcattgaaga ccctaatctg 180
gttaccgatc cgaaggagct ggcgattagc caggaaatga tttccgacta caatctgtac 240
gtcagcatgg ttagcaccct gacgcgtaag ggcgttggcg ctgttgagac tttgctgcgt 300
tcctgatag 309

<210> SEQ ID NO 124
<211> LENGTH: 19
<212> TYPE: DNA
<213> ORGANISM: Artificial Sequence
<220> FEATURE:
<223> OTHER INFORMATION: synthetic SynPrgK ribosome binding site (rbs, RBS) of bacterial type III secretion system (T3SS)

<400> SEQUENCE: 124
attaaacagg ataataagc 19

<210> SEQ ID NO 125
<211> LENGTH: 762
<212> TYPE: DNA
<213> ORGANISM: Artificial Sequence
<220> FEATURE:
<223> OTHER INFORMATION: synthetic SynPrgK of bacterial type III secretion system (T3SS)

<400> SEQUENCE: 125
atgatccgcc gttacctgta taccttcttg ctggttatga ctttggccgg ctgtaaagat 60
aaggatctgc tgaaaggctt ggaccaagag caagcgaatg aggtcattgc ggttctgcaa 120
atgcacaaca ttgaggctaa caagattgat agcggcaagc tgggttacag cattaccgtc 180
gcggaaccgg atttcaccgc ggcagtgtat tggattaaga cctaccagtt gccgcctcgc 240
ccgcgtgtcg aaatcgccca aatgtttccg gcagacagcc tggttagctc tccgcgtgcg 300
gagaaagcac gtctgtactc ggcgattgaa cagcgcctgg agcagtcgct gcaaacgatg 360
gaaggtgttc tgtcggcccg tgtccacatc agctatgata ttgatgcggg cgagaacggt 420
cgtccgccta agccggtgca cctgtcggct ttggcggtgt atgaacgcgg ttcccctctg 480
gcccatcaga tttcggatat taagcgcttc ctgaaaaaca gcttcgcgga tgttgactat 540
gataacatca gcgtggttct gtccgagcgt agcgacgcac agttgcaggc gccgggcacg 600
ccggtcaagc gcaatagctt cgctacctcc tggattgtgc tgattatcct gttgtctgtt 660
atgagcgcgg gtttcggtgt ctggtactac aaaaatcact atgcgcgtaa taagaaaggc 720
attactgccg atgacaaggc aaagtccagc aacgagtaat aa 762

<210> SEQ ID NO 126
<211> LENGTH: 19
<212> TYPE: DNA
<213> ORGANISM: Artificial Sequence
<220> FEATURE:
<223> OTHER INFORMATION: synthetic SynOrgA ribosome binding site (rbs, RBS) of bacterial type III secretion system (T3SS)

<400> SEQUENCE: 126
gaaagaaggg acagactag 19

<210> SEQ ID NO 127
<211> LENGTH: 603
<212> TYPE: DNA
<213> ORGANISM: Artificial Sequence
<220> FEATURE:
<223> OTHER INFORMATION: synthetic SynOrgA of bacterial type III secretion system (T3SS)

<400> SEQUENCE: 127

```
atgattcgtc gtaaccgtca aatgaaccgt caaccactgc caattatctg gcaacgcatt     60
attttcgacc cactgtccta tattcaccca caacgtctgc aaatcgcgcc ggagatgatc    120
gtgcgtccgg cagcgcgtgc ggcagcgaat gagctgattt tggcggcgtg gcgtttgaag    180
aacggtgaga aggagtgcat tcagaatagc ctgacgcagc tgtggttgcg tcaatggcgc    240
cgtctgccgc aggttgctta cctgctgggt tgccacaagt tgcgtgctga cctggcccgt    300
caaggtgctt tattgggcct gccggactgg gcgcaggcat tcttggcgat gcaccagggt    360
acgtccttgt cggtttgtaa taaggcgccg aaccaccgtt tcctgctgtc cgttggttac    420
gcccaactga acgcgctgaa tgagttcctg ccggagagct tggcccaacg ctttcctctg    480
ctgtttccac cgttcatcga ggaggcactg aaacaagatg cagtggagat gagcatcctg    540
ctgctggccc tgcaatacgc gcaaaagtat cctaacaccg tcccggcgtt tgcgtgctaa    600
taa                                                                  603
```

<210> SEQ ID NO 128
<211> LENGTH: 19
<212> TYPE: DNA
<213> ORGANISM: Artificial Sequence
<220> FEATURE:
<223> OTHER INFORMATION: synthetic SynOrgB ribosome binding site (rbs, RBS) of bacterial type III secretion system (T3SS)

<400> SEQUENCE: 128

```
gaaagaaggg acagactag                                                  19
```

<210> SEQ ID NO 129
<211> LENGTH: 684
<212> TYPE: DNA
<213> ORGANISM: Artificial Sequence
<220> FEATURE:
<223> OTHER INFORMATION: synthetic SynOrgB of bacterial type III secretion system (T3SS)

<400> SEQUENCE: 129

```
atgttgaaaa atatcccgat tccatcccct ctgtctccgg ttgaaggtat cctgattaaa     60
cgcaagacgt tggagcgtta cttctcgatt gagcgcctgg aacaacaggc gcatcagcgt    120
gcaaagcgca ttttgcgtga ggcagaagaa gaagccaaga ccctgcgcat gtatgcgtac    180
caggagggct acgagcaggg catgattgac gcactgcaac aggtggccgc ctatttgacc    240
gacaaccaga cgatggcttg gaaatggatg gagaaaattc aaatctatgc gcgtgagttg    300
ttcagcgcgg ctgtcgatca cccggaaacg ttgttgacgg tgctggacga gtggctgcgt    360
gatttcgata agccggaagg tcagctgttt ttgaccctgc cggtgaacgc aaagaaagat    420
catcagaaac tgatggtgct gctgatggaa aattggccgg gcaccttcaa tctgaagtat    480
catcaggagc aacgttttat catgtcctgt ggcgatcaga ttgccgagtt ttcgccggaa    540
caatttgttg aaacggcggt tggtgttatc aagcaccatc tggatgagct gcctcaggac    600
tgtcgcacca tttcggacaa tgcgattaac gcgctgattg atgaatggaa gacgaaaacc    660
caagctgaag ttattcgctg ataa                                          684
```

<210> SEQ ID NO 130
<211> LENGTH: 36
<212> TYPE: DNA
<213> ORGANISM: Artificial Sequence
<220> FEATURE:
<223> OTHER INFORMATION: synthetic SynInvA ribosome binding site (rbs, RBS) of bacterial type III secretion system (T3SS)

<400> SEQUENCE: 130
cttgggcacg cgtccattaa acaggagtaa ttaagc 36

<210> SEQ ID NO 131
<211> LENGTH: 2058
<212> TYPE: DNA
<213> ORGANISM: Artificial Sequence
<220> FEATURE:
<223> OTHER INFORMATION: synthetic SynInvA of bacterial type III secretion system (T3SS)

<400> SEQUENCE: 131
atgctgctgt ccctgctgaa tagcgcgcgt ctgcgtcctg agctgctgat tctggttctg 60
atggttatga tcatcagcat gttcgttatc ccgttgccga cctatttggt tgacttcttg 120
atcgctttga acattgtcct ggcaattctg gtgttcatgg gctccttcta catcgaccgc 180
attctgagct tcagcacctt tccggcggtt ctgctgatca cgactctgtt ccgtttggca 240
ctgagcatca gcaccagccg cctgatcctg attgaagcag atgcgggtga gatcatcgcg 300
acctttggtc agtttgtgat cggtgacagc ctggcggttg gtttcgtcgt attctccatc 360
gtgacggtgg tgcagtttat cgttattacc aagggcagcg aacgtgtggc ggaggtcgcc 420
gctcgcttca gcctggacgg catgccgggt aaacagatgt ctattgatgc agacctgaaa 480
gccggcatta ttgatgctga tgcagcgcgc gagcgccgca gcgtcctgga gcgtgaaagc 540
caactgtacg gttccttcga cggtgccatg aagttcatta aaggtgatgc gattgcgggc 600
atcattatca tcttcgttaa cttcattggc ggtatcagcg tcggtatgac ccgtcatggt 660
atggatctga gcagcgccct gagcacctac accatgctga cgattggtga tggtctggtt 720
gcccaaattc cggcgttgct gatcgcgatt tctgcgggct tcatcgttac ccgcgtcaac 780
ggtgatagcg ataacatggg tcgtaacatt atgacccagc tgctgaataa tccgtttgtc 840
ctggttgtaa cggcgatttt gaccatcagc atgggcacgc tgccgggctt tccgttgccg 900
gttttcgtta ttctgtctgt tgtgctgtcc gtcctgtttt actttaagtt ccgcgaggcg 960
aaacgtagcg ctgcgaaacc aaaaacgagc aagggcgagc aaccgttgtc catcgaggag 1020
aaggaaggta gcagcctggg cctgattggc gacctggata aggttagcac ggaaaccgtc 1080
ccgctgattt tgctggtgcc gaaatcgcgt cgtgaggatc tggagaaagc gcagctggcg 1140
gaacgtctgc gcagccaatt ctttattgat tatggtgtgc gtctgccaga agtactgctg 1200
cgtgacggtg agggtctgga tgacaactct atcgtcctgc tgattaatga gattcgcgtt 1260
gaacagttta ctgtctattt tgacctgatg cgtgtggtta actacagcga cgaggtggtg 1320
agctttggca tcaacccgac cattcaccag caaggttcca gccagtactt ttgggtgacc 1380
catgaggaag gcgaaaagct gcgcgagctg ggctacgtcc tgcgtaatgc actggacgaa 1440
ctgtaccact gtctggcggt gacgctggca cgcaatgtga acgagtattt cggtatccaa 1500
gaaacgaaac acatgctgga ccaactggaa gcaaagtttc ctgacctgct gaaggaggtt 1560
ttgcgccacg ccaccgtgca gcgcatttcg gaagtgctgc aacgtctgct gtccgaacgc 1620
gtgagcgtcc gtaacatgaa gctgatcatg gaagccctgg cactgtgggc tccgcgtgag 1680
aaagatgtga tcaatctggt ggagcacatc cgtggtgcga tggcgcgtta tatctgccac 1740
aagttcgcaa atggtggtga actgcgtgcc gttatggttt ccgccgaagt tgaggatgtc 1800

-continued attcgtaaag gcattcgtca aacttctggc tccacctttt tgagcttgga cccggaggct 1860
tcggcaaatc tgatggacct gatcacgctg aagctggacg acctgttgat tgcgcataag 1920
gacctggtcc tgttgaccag cgttgacgtg cgtcgtttta tcaagaaaat gattgaaggt 1980
cgttttccgg atctggaggt cctgtccttc ggtgagattg cagatagcaa aagcgtgaat 2040
gtcatcaaaa ccatctga 2058

<210> SEQ ID NO 132
<211> LENGTH: 36
<212> TYPE: DNA
<213> ORGANISM: Artificial Sequence
<220> FEATURE:
<223> OTHER INFORMATION: synthetic SynInvC ribosome binding site (rbs, RBS) of bacterial type III secretion system (T3SS)

<400> SEQUENCE: 132
cttgggcacg cgtccattaa agaggaccaa ttaagc 36

<210> SEQ ID NO 133
<211> LENGTH: 1296
<212> TYPE: DNA
<213> ORGANISM: Artificial Sequence
<220> FEATURE:
<223> OTHER INFORMATION: synthetic SynInvC of bacterial type III secretion system (T3SS)

<400> SEQUENCE: 133
atgaaaaccc cacgtctgct gcaatacctg gcctacccgc agaaaatcac tggccctatc 60
attgaagcag aactgcgtga tgttgcaatt ggtgaattgt gcgagatccg tcgcggctgg 120
caccagaagc aggttgtggc ccgtgcgcaa gtggttggtt tgcagcgcga acgtaccgtc 180
ctgagcctga tcggcaatgc ccaaggcctg agccgtgatg tggtcttgta cccgaccggc 240
cgtgctctga gcgcgtgggt tggttacagc gttctgggcg cagtactgga cccgacgggt 300
aaaatcgttg aacgtttcac cccggaagtc gcaccgattt ccgaggagcg cgttatcgac 360
gtggcaccgc cgagctacgc aagccgtgtc ggtgtgcgcg aaccgctgat cacgggtgtc 420
cgcgcaattg atggtctgct gacgtgtggt gtgggccagc gtatgggtat tttcgcaagc 480
gcgggttgtg gtaagaccat gttgatgcac atgctgatcg agcaaaccga agcggatgtc 540
tttgttattg gcctgattgg cgagcgtggt cgtgaagtta ccgaatttgt agacatgttg 600
cgtgcatctc ataagaaaga aaaatgtgtg ctggtttttg ccacgtccga cttcccaagc 660
gttgaccgct gcaacgctgc ccagctggca acgacggtcg ccgagtattt ccgcgaccag 720
ggtaaacgtg ttgtcctgtt tatcgacagc atgacccgtt atgcacgcgc gttgcgtgat 780
gtcgcgctgg cgagcggcga gcgtccggct cgccgtggtt atccggcgtc tgtgttcgac 840
aatctgccgc gtttgctgga gcgtccgggt gcgacgagcg agggtagcat taccgccttc 900
tataccgtcc tgctggagtc ggaagaagaa gcggacccga tggcggacga gatccgttct 960
attctggacg gtcacctgta cctgtcccgc aaactggcgg gtcagggtca ttacccggct 1020
atcgatgtgc tgaagagcgt gagccgtgtg tttggtcaag tgaccacccc gactcacgcg 1080
gagcaagcga gcgcggtccg taagctgatg acccgtctgg aagagctgca actgttcatt 1140
gacctgggcg agtatcgtcc gggcgagaac attgacaatg atcgtgcgat gcaaatgcgc 1200
gatagcctga aggcgtggct gtgtcagcct gttgcgcaat acagcagctt cgatgatacg 1260
ctgtccggca tgaacgcctt tgcggatcag aactga 1296

<210> SEQ ID NO 134
<211> LENGTH: 36
<212> TYPE: DNA
<213> ORGANISM: Artificial Sequence
<220> FEATURE:
<223> OTHER INFORMATION: synthetic SynInvE ribosome binding site (rbs, RBS) of bacterial type III secretion system (T3SS)

<400> SEQUENCE: 134
tacttgggca cgcgtccatt aattaggatc aatagc 36

<210> SEQ ID NO 135
<211> LENGTH: 1119
<212> TYPE: DNA
<213> ORGANISM: Artificial Sequence
<220> FEATURE:
<223> OTHER INFORMATION: synthetic SynInvE of bacterial type III secretion system (T3SS)

<400> SEQUENCE: 135
atgattccgg gcagcacctc cggtatttcc tttagccgta tcctgagccg tcagacctcc 60
caccaggatg caacccagca taccgacgca caacaagcgg aaattcaaca agcggcggaa 120
gatagctcgc cgggtgcgga ggttcagaaa ttcgtccaga gcacggacga gatgtctgct 180
gcgttggcgc agttccgcaa tcgccgtgac tatgagaaaa agagcagcaa tttgtctaac 240
tccttcgagc gcgttctgga ggacgaggca ctgccgaaag cgaagcagat tctgaaactg 300
atcagcgtgc atggcggtgc gttggaggat ttcctgcgtc aggcgcgcag cctgttcccg 360
gacccaagcg atctggtgct ggttctgcgc gagctgttgc gtcgtaagga cctggaggag 420
atcgtgcgta agaagctgga gagcctgctg aagcacgtgg aggaacaaac cgacccgaaa 480
accctgaagg ccggtattaa ctgcgcgctg aaggcgcgtc tgtttggcaa gacgctgtct 540
ctgaaacctg gtctgctgcg tgccagctac cgccagttca tccaaagcga aagccacgaa 600
gtcgagattt acagcgattg gatcgccagc tacggttatc agcgtcgcct ggttgttctg 660
gatttcattg aaggcagcct gctgactgac atcgatgcta acgatgcaag ctgctcccgt 720
ctggagtttg gccaactgct gcgccgtctg acccagctga aaatgttgcg tagcgccgac 780
ctgctgtttg tctcgacgtt gctgtcttac agcttcacga aagcatttaa cgctgaggag 840
agcagctggc tgttgctgat gctgtctttg ctgcaacagc cgcacgaagt ggatagcctg 900
ctggcggaca ttatcggtct gaatgcgctg ctgttgtccc acaaagagca cgccagcttc 960
ctgcaaatct tctatcaggt ctgtaaggca atcccgtcta gcctgtttta tgaagagtac 1020
tggcaagaag aactgctgat ggcactgcgc tccatgacgg acattgctta caaacacgaa 1080
atggccgaac aacgtcgtac catcgaaaag ctgtcctaa 1119

<210> SEQ ID NO 136
<211> LENGTH: 36
<212> TYPE: DNA
<213> ORGANISM: Artificial Sequence
<220> FEATURE:
<223> OTHER INFORMATION: synthetic SynInvF ribosome binding site (rbs, RBS) of bacterial type III secretion system (T3SS)

<400> SEQUENCE: 136
cttgggcacg cgtccattaa aaaggagtaa ttaagc 36

<210> SEQ ID NO 137
<211> LENGTH: 651
<212> TYPE: DNA
<213> ORGANISM: Artificial Sequence
<220> FEATURE:
<223> OTHER INFORMATION: synthetic SynInvF of bacterial type III secretion system (T3SS)

<400> SEQUENCE: 137

```
atgagcttca gcgagagccg ccacaatgaa aactgtctga ttcaagaagg cgcactgctg     60
ttttgtgagc aagcagtcgt ggcgcctgtc agcggtgatc tggtttttcg tccgctgaaa    120
atcgaggtcc tgagcaagct gctggcgttc atcgacggcg caggtctggt ggatacgacc    180
tacgcggagt cggacaaatg ggttctgctg tctccggagt tccgtgctat ttggcaagac    240
cgtaaacgtt gcgaatattg gtttttgcag cagattatca ccccatctcc ggcgttcaac    300
aaggttctgg cactgttgcg taagagcgaa agctattggt tggtcggcta cttgctggcc    360
caaagcacca gcggcaatac tatgcgtatg ttgggtgagg attacggtgt tagctacacg    420
catttccgcc gtctgtgcag ccgcgctctg ggcggtaagg cgaaaagcga gctgcgcaat    480
tggcgcatgg cccagtccct gctgaatagc gtggaaggtc atgaaaacat cacccagctg    540
gcggtcaacc acggttatag cagcccgtcc cactttagct ctgaaatcaa ggagctgatt    600
ggtgtttccc cgcgtaagct gtctaacatc attcagctgg ccgacaaatg a             651
```

<210> SEQ ID NO 138
<211> LENGTH: 36
<212> TYPE: DNA
<213> ORGANISM: Artificial Sequence
<220> FEATURE:
<223> OTHER INFORMATION: synthetic SynInvG ribosome binding site (rbs, RBS) of bacterial type III secretion system (T3SS)

<400> SEQUENCE: 138

```
tgggcacgcg tccattaatg aggaaaaatt attagc                               36
```

<210> SEQ ID NO 139
<211> LENGTH: 1689
<212> TYPE: DNA
<213> ORGANISM: Artificial Sequence
<220> FEATURE:
<223> OTHER INFORMATION: synthetic SynInvG of bacterial type III secretion system (T3SS)

<400> SEQUENCE: 139

```
atgaaaacgc acattctgtt ggcccgtgtg ctggcttgcg cagctctggt gctggtcacc     60
ccaggttata gctccgagaa gatcccggtt acgggcagcg gcttcgttgc aaaggacgat    120
tctctgcgca cctttttcga tgcgatggca ctgcaattga aggagccggt gattgtcagc    180
aagatggcgg ctcgcaaaaa gattaccggc aatttcgagt tccacgatcc aaacgcgctg    240
ctggagaaac tgtccctgca actgggtctg atctggtact ttgatggtca ggcgatctac    300
atctacgacg cgagcgaaat gcgtaatgcg gttgtgagcc tgcgtaatgt cagcctgaac    360
gagttcaaca attttctgaa gcgcagcggc ctgtacaata agaactaccc tctgcgtggt    420
gataatcgta aaggcacctt ctatgtcagc ggtccgccgg tgtatgttga tatggttgta    480
aatgcggcca ccatgatgga caaacagaat gatggcatcg agctgggtcg ccaaaagatc    540
ggtgttatgc gcctgaacaa cacttttgtg ggcgaccgca cctacaacct gcgtgatcaa    600
aagatggtca ttccgggtat tgctacggca attgaacgcc tgttgcaagg cgaagaacaa    660
ccgctgggta acattgtaag ctccgagcct ccggccatgc cggcctttag cgcaaacggc    720
gagaaaggta aggcagcgaa ttacgcgggt ggtatgagcc tgcaagaagc gctgaaacag    780
aacgcagcgg caggcaacat caaaattgtg gcctatccgg acaccaacag cctgctggtg    840
```

```
aaaggtacgg cggagcaggt gcatttcatc gagatgctgg ttaaagccct ggacgtggcg    900

aaacgtcacg ttgaattgag cctgtggatt gtggatttga ataagagcga cctggaacgc    960

ttgggcacca gctggagcgg tagcatcacc atcggcgaca agctgggtgt gagcctgaac   1020

cagagcagca tctccacgct ggacggtagc cgctttattg cggcggtcaa cgctctggag   1080

gaaaagaaac aggccactgt tgtcagccgt ccggttctgc tgacccagga gaatgtcccg   1140

gcgatttttg acaataatcg tactttctat accaaactga tcggtgaacg taatgttgca   1200

ttggaacacg tgacctatgg caccatgatc cgtgtcctgc cgcgtttcag cgcggacggc   1260

cagattgaga tgagcctgga catcgaagat ggtaatgaca aaaccccgca gtctgatacg   1320

accacctccg ttgatgcgct gccagaagtg ggtcgtaccc tgatctcgac gattgcacgt   1380

gtcccgcatg gtaaatctct gctggttggt ggctacacgc gtgatgcaaa cacggacacg   1440

gtccaaagca tcccgttcct gggtaagctg ccgctgattg gctcgttgtt tcgctacagc   1500

agcaaaaaca agtctaatgt cgtccgtgtc tttatgattg agccgaaaga aatcgttgac   1560

ccgctgaccc cggatgccag cgagagcgtt aacaacattc tgaaacagtc cggtgcgtgg   1620

agcggtgacg ataagctgca aaagtgggtt cgtgtgtatt tggaccgtgg tcaggaggcc   1680

attaagtaa                                                            1689
```

<210> SEQ ID NO 140
<211> LENGTH: 36
<212> TYPE: DNA
<213> ORGANISM: Artificial Sequence
<220> FEATURE:
<223> OTHER INFORMATION: synthetic SynInvI ribosome binding site (rbs, RBS) of bacterial type III secretion system (T3SS)

<400> SEQUENCE: 140

```
cttgggcacg cgtccattaa aaaggaccaa ttaagc                                36
```

<210> SEQ ID NO 141
<211> LENGTH: 444
<212> TYPE: DNA
<213> ORGANISM: Artificial Sequence
<220> FEATURE:
<223> OTHER INFORMATION: synthetic SynInvI of bacterial type III secretion system (T3SS)

<400> SEQUENCE: 141

```
atgcactctc tgactcgtat caaggtcctg caacgtcgtt gtaccgtgtt ccattctcag     60

tgcgagtcca ttctgttgcg ttatcaggac gaagatcgcg gcttgcaggc ggaggaggag    120

gccatcctgg aacagatcgc aggtctgaaa ctgctgttgg acaccctgcg tgctgaaaat    180

cgtcaactga gccgtgaaga aatctatacg ctgctgcgca aacagagcat tgttcgtcgc    240

cagattaagg atctggagct gcaaatcatt cagattcaag aaaagcgtag cgagctggaa    300

aagaaacgtg aggaatttca aaagaaaagc aaatactggc tgcgtaaaga aggtaactac    360

cagcgctgga ttatccgtca aaaacgcttc tacattcaac gtgagatcca gcaagaggag    420

gcggagagcg aagagatcat ttaa                                           444
```

<210> SEQ ID NO 142
<211> LENGTH: 36
<212> TYPE: DNA
<213> ORGANISM: Artificial Sequence
<220> FEATURE:
<223> OTHER INFORMATION: synthetic SynInvJ ribosome binding site (rbs, RBS) of bacterial type III secretion system (T3SS)

<400> SEQUENCE: 142
aaaaaaaagc tctaaaagat taagaggggg taacat 36

<210> SEQ ID NO 143
<211> LENGTH: 1011
<212> TYPE: DNA
<213> ORGANISM: Artificial Sequence
<220> FEATURE:
<223> OTHER INFORMATION: synthetic SynInvJ of bacterial type III secretion system (T3SS)

<400> SEQUENCE: 143
atgggtgacg tgagcgcggt gagcagcagc ggtaacattc tgctgccgca gcaggacgag 60
gttggtggcc tgtccgaagc gctgaagaaa gcggttgaaa aacacaaaac cgaatacagc 120
ggtgacaaga aagatcgtga ttatggtgac gcctttgtta tgcacaagga aaccgcgctg 180
ccgttgttgc tggcagcttg gcgccacggc gcaccggcga aaagcgagca ccataacggt 240
aacgtaagcg gtctgcatca caacggtaag agcgagctgc gtattgctga gaaactgctg 300
aaggtgacgg cggagaagag cgttggtctg attagcgctg aagcgaaggt ggataaatct 360
gcggcgctgc tgtctagcaa gaatcgtccg ctggaatcgg tcagcggcaa aaagttgtcc 420
gccgatctga aagcagtgga gtccgtgtcc gaggtcacgg ataacgccac cggcatttcg 480
gatgacaaca tcaaagcatt gccgggtgac aataaggcca tcgccggtga gggtgtgcgt 540
aaagaaggtg cgccgctggc gcgtgacgtg gctccggcac gcatggcggc agcaaatacg 600
ggcaagccgg aggataaaga ccacaagaag gtcaaggacg ttagccagct gccgctgcaa 660
ccgactacca tcgccgatct gtctcaactg acgggtggcg atgaaaagat gccgctggca 720
gcgcagtcca aaccgatgat gaccattttc ccaaccgccg acggcgttaa aggtgaggac 780
agctctctga cctatcgttt ccagcgctgg ggcaacgatt actccgtcaa tatccaggca 840
cgccaagcgg gcgaatttag cctgattcct agcaataccc aggttgaaca tcgtctgcac 900
gaccaatggc aaaatggcaa tccacaacgc tggcatttga cgcgtgatga ccagcaaaac 960
ccgcaacagc aacagcatcg tcagcagtcc ggtgaagagg acgacgcgta a 1011

<210> SEQ ID NO 144
<211> LENGTH: 36
<212> TYPE: DNA
<213> ORGANISM: Artificial Sequence
<220> FEATURE:
<223> OTHER INFORMATION: synthetic SynSpaO ribosome binding site (rbs, RBS) of bacterial type III secretion system (T3SS)

<400> SEQUENCE: 144
cttgggcacg cgtccatgaa agacaggacc cactag 36

<210> SEQ ID NO 145
<211> LENGTH: 912
<212> TYPE: DNA
<213> ORGANISM: Artificial Sequence
<220> FEATURE:
<223> OTHER INFORMATION: synthetic SynSpaO of bacterial type III secretion system (T3SS)

<400> SEQUENCE: 145
atgagcttgc gcgtacgcca aattgaccgc cgtgaatggc tgctggccca gactgcgacc 60
gaatgtcagc gtcacggtcg tgaggccacc ctggagtatc cgacccgtca gggtatgtgg 120
gtccgcctgt ctgatgccga aaaacgctgg tctgcgtgga tcaaaccggg tgattggttg 180

```
gaacacgtta gcccagcact ggcgggtgcc gcggtcagcg caggcgcgga gcacctggtg    240

gttccgtggc tggcggcaac cgaacgcccg ttcgagctgc cggtcccgca cttgagctgc    300

cgtcgtctgt gcgtggagaa cccggttccg ggttccgcac tgcctgaggg caagctgctg    360

cacatcatgt cggatcgtgg tggcctgtgg tttgagcatc tgccggagct gccggctgtt    420

ggcggtggcc gtccgaagat gctgcgttgg ccgctgcgtt tcgttattgg cagcagcgac    480

acccagcgca gcctgctggg tcgtatcggt atcggtgatg ttctgctgat ccgcaccagc    540

cgtgctgagg tttactgtta cgcgaagaaa ctgggccact ttaatcgtgt ggaaggtggc    600

attattgtcg aaacgctgga cattcaacat atcgaggagg agaacaacac gacggaaacg    660

gcggaaaccc tgccgggtct gaatcaactg ccggtgaagc tggagttcgt tctgtatcgt    720

aaaaacgtga cgttggccga actggaagca atgggtcagc aacaactgct gtccttgcca    780

accaatgcgg aactgaacgt cgaaatcatg gcgaatggcg tgctgctggg taacggcgaa    840

ctggtgcaga tgaatgacac cctgggtgtc gagattcatg agtggttgtc cgagagcggt    900

aatggcgagt ag                                                        912
```

<210> SEQ ID NO 146
<211> LENGTH: 36
<212> TYPE: DNA
<213> ORGANISM: Artificial Sequence
<220> FEATURE:
<223> OTHER INFORMATION: synthetic SynSpaP ribosome binding site (rbs, RBS) of bacterial type III secretion system (T3SS)

<400> SEQUENCE: 146

```
cttgggcacg cgtccatgaa agaaacgaca tactag                               36
```

<210> SEQ ID NO 147
<211> LENGTH: 675
<212> TYPE: DNA
<213> ORGANISM: Artificial Sequence
<220> FEATURE:
<223> OTHER INFORMATION: synthetic SynSpaP of bacterial type III secretion system (T3SS)

<400> SEQUENCE: 147

```
atgggtaacg atattagctt gattgcattg ctggcgtttt ccaccctgct gccgttcatc     60

atcgcgtctg gtacttgctt cgtcaaattc agcatcgtct ttgtgatggt gcgcaacgcg    120

ctgggtctgc aacaaattcc aagcaatatg accctgaatg gcgtcgcact gctgctgtcg    180

atgtttgtta tgtggccgat tatgcacgac gcgtatgtgt atttcgagga tgaagatgtg    240

acctttaacg acatctccag cctgagcaag catgttgatg agggcctgga cggttatcgc    300

gactacctga tcaagtattc cgaccgtgag ctggtgcagt tctttgagaa tgcccagttg    360

aaacgtcagt acggtgaaga aacggaaacc gttaaacgtg acaaggacga gattgaaaag    420

ccgagcattt tcgcactgtt gcctgcttac gccttgagcg agattaagag cgcattcaaa    480

attggttttt acctgtacct gccgttcgtt gtggtcgatc tggttgtctc cagcgttctg    540

ctggccctgg gcatgatgat gatgtccccg gttaccatca gcacgccgat caaactggtc    600

ctgtttgtgg ccctggatgg ttggacgctg ctgtctaaag gcctgatcct gcaatacatg    660

gacatcgcga cctaa                                                     675
```

<210> SEQ ID NO 148
<211> LENGTH: 36
<212> TYPE: DNA

<213> ORGANISM: Artificial Sequence
<220> FEATURE:
<223> OTHER INFORMATION: synthetic SynSpaQ ribosome binding site (rbs, RBS) of bacterial type III secretion system (T3SS)

<400> SEQUENCE: 148
cttgggcacg cgtccattaa gaaggaggaa ttaagc 36

<210> SEQ ID NO 149
<211> LENGTH: 261
<212> TYPE: DNA
<213> ORGANISM: Artificial Sequence
<220> FEATURE:
<223> OTHER INFORMATION: synthetic SynSpaQ of bacterial type III secretion system (T3SS)

<400> SEQUENCE: 149
atggacgatc tggttttcgc cggcaacaaa gccctgtact tggtgctgat tctgtccggt 60
tggccgacga ttgtcgcaac cattatcggt ctgctggttg gtctgtttca aaccgtgacg 120
cagttgcagg agcaaaccct gccgttcggt atcaagctgc tgggtgtgtg tctgtgcctg 180
tttttgctgt ctggctggta tggcgaagtt ctgctgtcct acggccgtca ggtcatcttc 240
ctggctctgg cgaaaggtta a 261

<210> SEQ ID NO 150
<211> LENGTH: 36
<212> TYPE: DNA
<213> ORGANISM: Artificial Sequence
<220> FEATURE:
<223> OTHER INFORMATION: synthetic SynSpaR ribosome binding site (rbs, RBS) of bacterial type III secretion system (T3SS)

<400> SEQUENCE: 150
cttgggcacg cgtccatgaa agacaggacc cactag 36

<210> SEQ ID NO 151
<211> LENGTH: 792
<212> TYPE: DNA
<213> ORGANISM: Artificial Sequence
<220> FEATURE:
<223> OTHER INFORMATION: synthetic SynSpaR of bacterial type III secretion system (T3SS)

<400> SEQUENCE: 151
atgttctatg cattgtattt tgagatccac catctggtgg cgtccgcggc tctgggtttt 60
gcgcgtgttg ctccgatctt tttctttctg ccgttcctga atagcggtgt cctgagcggt 120
gctccgcgca acgcgatcat cattctggtg gcgctgggtg tatggccgca cgccctgaat 180
gaggcgccac cgtttctgtc tgtggcaatg attccgctgg tcctgcaaga ggcagccgtg 240
ggtgttatgc tgggttgcct gttgtcctgg ccgttttggg ttatgcacgc gttgggctgt 300
atcattgata accaacgcgg tgcaaccctg tccagcagca ttgatcctgc gaatggcatc 360
gacaccagcg agatggccaa tttcctgaac atgttcgcgg ctgtcgtgta tttgcagaac 420
ggtggcttgg tcacgatggt ggacgtgctg aataagtctt accagctgtg tgatccgatg 480
aacgagtgta cgccgagcct gcctccgttg ctgaccttca ttaatcaagt ggcccagaac 540
gcactggtgc tggcgtcccc ggtcgttctg gttctgctgc tgtcggaagt tttcctgggc 600
ctgctgtctc gttttgcacc gcaaatgaac gcgttcgcca ttagcctgac tgttaaaagc 660
ggtattgcgg ttttgatcat gctgctgtat ttcagcccgg tcctgccgga caatgttctg 720
cgtctgagct ttcaggcgac cggcctgagc agctggttct acgaacgtgg cgcaacgcat 780
gtgctggaat aa 792

<210> SEQ ID NO 152
<211> LENGTH: 36
<212> TYPE: DNA
<213> ORGANISM: Artificial Sequence
<220> FEATURE:
<223> OTHER INFORMATION: synthetic SynSpaS ribosome binding site (rbs, RBS) of bacterial type III secretion system (T3SS)

<400> SEQUENCE: 152
cttgggcacg cgtccatgaa agacaggacc cactag 36

<210> SEQ ID NO 153
<211> LENGTH: 1071
<212> TYPE: DNA
<213> ORGANISM: Artificial Sequence
<220> FEATURE:
<223> OTHER INFORMATION: synthetic SynSpaS of bacterial type III secretion system (T3SS)

<400> SEQUENCE: 153
atgtccagca acaaaaccga aaaaccgact aagaaacgtc tggaggatag cgcaaagaaa 60
ggtcagagct tcaagagcaa ggacctgatt atcgcgtgcc tgaccctggg tggtatcgct 120
tatttggtga gctacggcag cttcaatgag tttatgggta tcattaagat tatcatcgct 180
gataactttg atcagtcgat ggcagattat agcctggccg tgtttggtat tggcctgaaa 240
tacctgattc cgttcatgct gctgtgtttg gtttgttccg cactgccggc actgctgcaa 300
gcgggcttcg ttctggcaac cgaggccctg aagccgaatc tgtccgccct gaacccggtt 360
gaaggcgcga agaaactgtt ttccatgcgc accgtcaaag acacggtcaa gacgctgctg 420
tatctgtcga gctttgtggt tgcggcaatc atttgctgga aaaagtataa agtcgagatt 480
ttcagccaac tgaacggtaa tatcgtgggt attgcggtta tctggcgtga attgctgctg 540
gcgttggttc tgacctgtct ggcgtgcgcg ctgatcgtgc tgttgctgga tgctattgcc 600
gagtactttc tgaccatgaa agatatgaag atggacaaag aagaagttaa acgcgagatg 660
aaagagcagg agggtaaccc ggaggtgaag tctaaacgtc gtgaagtcca catggaaatc 720
ctgagcgaac aagtcaagtc tgacattgaa aatagccgtc tgattgtggc aaaccctacg 780
catattacca tcggcatcta cttcaaaccg gaactgatgc cgattccaat gattagcgtc 840
tatgaaacca atcaacgcgc gctggcggtc cgtgcgtacg ccgagaaagt gggtgttccg 900
gttattgtag acatcaagct ggcgcgcagc ctgttcaaaa cgcaccgtcg ttacgacctg 960
gtgagcctgg aggagatcga cgaggttttg cgcctgctgg tttggttgga agaggtcgaa 1020
aacgcaggca aggatgtgat ccaaccgcag gagaatgaag tgcgtcatta a 1071

<210> SEQ ID NO 154
<211> LENGTH: 4075
<212> TYPE: DNA
<213> ORGANISM: Artificial Sequence
<220> FEATURE:
<223> OTHER INFORMATION: synthetic Syn_PrgOrg operon of bacterial type III secretion system (T3SS)

<400> SEQUENCE: 154
gcatgcatta aagaggagaa attaagcatg gctactccgt ggtctggtta tctggatgat 60
gtttctgcaa aatttgacac gggtgttgac aacttgcaaa cccaagttac cgaagccctg 120
gacaagctgg ctgcgaagcc gtccgatccg gcgctgctgg cggcgtatca atccaaactg 180

-continued

```
tctgagtata acttgtaccg taatgcgcag tcgaacacgg tcaaggtctt caaagatatt    240
gatgcagcga ttattcagaa ctttcgttag taacctagga ttaaggagga taaattaagc    300
atgtctatcg cgactatcgt gcctgaaaat gccgttattg gtcaagcggt gaatattcgc    360
agcatggaaa cggacatcgt cagcttggac gaccgtttgc tgcaagcatt ttcgggcagc    420
gccatcgcta ccgccgtcga taagcagacc attaccaatc gcattgaaga ccctaatctg    480
gttaccgatc cgaaggagct ggcgattagc caggaaatga tttccgacta caatctgtac    540
gtcagcatgg ttagcaccct gacgcgtaag ggcgttggcg ctgttgagac tttgctgcgt    600
tcctgatagg ctagcattaa acaggataat aagcatggaa actagcaagg agaaaacgat    660
tacgtcccct ggtccgtata tcgttcgtct gttgaactcg tccctgaacg gttgtgaatt    720
tccgctgctg actggtcgta cgctgttcgt cgtgggtcag agcgatgctc tgaccgcgtc    780
tggtcagctg ccggacattc ctgccgactc cttcttcatc ccgctggatc atggcggtgt    840
taatttcgag attcaagtgg acactgacgc gacggaaatc atcctgcacg aactgaaaga    900
gggcaactcc gagagccgct ccgtgcaact gaacaccccg atccaagttg gtgaactgct    960
gattttgatt cgtccggaga gcgagccgtg ggtgccggaa cagccggaga agttggaaac   1020
ttctgcgaaa aagaacgaac cgcgctttaa aaacggcatc gtcgcggcac tggcgggttt   1080
ctttatcctg ggtatcggca cggttggcac cctgtggatt ctgaactcgc cgcaacgtca   1140
agcagccgaa ttggacagcc tgttgggtca ggagaaggag cgttttcagg tgctgccggg   1200
tcgcgacaag atgctgtatg tcgccgcgca aaacgaacgc gacaccctgt gggcacgtca   1260
agtcctggca cgcggcgatt acgataaaaa cgcacgcgtt attaatgaaa atgaggagaa   1320
taaacgtatc agcatctggc tggacacgta ttatccacaa ctggcatatt accgtatcca   1380
ttttgatgaa ccacgtaagc cggtgttttg gctgtcccgt caacgcaaca cgatgagcaa   1440
gaaagagctg gaggtgctgt cccagaaatt gcgtgcgctg atgccgtacg ccgacagcgt   1500
caatattact ctgatggatg acgtgaccgc agcaggccaa gccgaggcag gtctgaaaca   1560
acaggcgctg ccatacagcc gccgtaacca caaaggtggt gttacgttcg ttattcaggg   1620
cgccttggac gacgttgaga ttctgcgtgc gcgccagttt gtcgactcct attatcgtac   1680
ctggggtggt cgttacgttc aattcgcaat tgaattgaaa gacgattggc tgaaaggccg   1740
ctcgttccaa tacggtgcgg aaggctacat taagatgagc ccaggtcatt ggtattttcc   1800
gtctcctctg taatagaagc ttattaaaca ggataataag catgatccgc cgttacctgt   1860
ataccttctt gctggttatg actttggccg gctgtaaaga taaggatctg ctgaaaggct   1920
tggaccaaga gcaagcgaat gaggtcattg cggttctgca aatgcacaac attgaggcta   1980
acaagattga tagcggcaag ctgggttaca gcattaccgt cgcggaaccg gatttcaccg   2040
cggcagtgta ttggattaag acctaccagt tgccgcctcg cccgcgtgtc gaaatcgccc   2100
aaatgtttcc ggcagacagc ctggttagct ctccgcgtgc ggagaaagca cgtctgtact   2160
cggcgattga acagcgcctg gagcagtcgc tgcaaacgat ggaaggtgtt ctgtcggccc   2220
gtgtccacat cagctatgat attgatgcgg gcgagaacgg tcgtccgcct aagccggtgc   2280
acctgtcggc tttggcggtg tatgaacgcg gttcccctct ggcccatcag atttcggata   2340
ttaagcgctt cctgaaaaac agcttcgcgg atgttgacta tgataacatc agcgtggttc   2400
tgtccgagcg tagcgacgca cagttgcagg cgccgggcac gccggtcaag cgcaatagct   2460
tcgctacctc ctggattgtg ctgattatcc tgttgtctgt tatgagcgcg ggtttcggtg   2520
```

-continued

```
tctggtacta caaaaatcac tatgcgcgta ataagaaagg cattactgcc gatgacaagg   2580

caaagtccag caacgagtaa taaggtaccg aaagaaggga cagactagat gattcgtcgt   2640

aaccgtcaaa tgaaccgtca accactgcca attatctggc aacgcattat tttcgaccca   2700

ctgtcctata ttcacccaca acgtctgcaa atcgcgccgg agatgatcgt gcgtccggca   2760

gcgcgtgcgg cagcgaatga gctgattttg gcggcgtggc gtttgaagaa cggtgagaag   2820

gagtgcattc agaatagcct gacgcagctg tggttgcgtc aatggcgccg tctgccgcag   2880

gttgcttacc tgctgggttg ccacaagttg cgtgctgacc tggcccgtca aggtgcttta   2940

ttgggcctgc cggactgggc gcaggcattc ttggcgatgc accagggtac gtccttgtcg   3000

gtttgtaata aggcgccgaa ccaccgtttc ctgctgtccg ttggttacgc ccaactgaac   3060

gcgctgaatg agttcctgcc ggagagcttg gcccaacgct ttcctctgct gtttccaccg   3120

ttcatcgagg aggcactgaa acaagatgca gtggagatga gcatcctgct gctggccctg   3180

caatacgcgc aaaagtatcc taacaccgtc ccggcgtttg cgtgctaata aagatctgaa   3240

agaagggaca gactagatgt tgaaaaatat cccgattcca tcccctctgt ctccggttga   3300

aggtatcctg attaaacgca agacgttgga gcgttacttc tcgattgagc gcctggaaca   3360

acaggcgcat cagcgtgcaa agcgcatttt gcgtgaggca gaagaagaag ccaagaccct   3420

gcgcatgtat gcgtaccagg agggctacga gcagggcatg attgacgcac tgcaacaggt   3480

ggccgcctat ttgaccgaca accagacgat ggcttggaaa tggatggaga aaattcaaat   3540

ctatgcgcgt gagttgttca gcgcggctgt cgatcacccg gaaacgttgt tgacggtgct   3600

ggacgagtgg ctgcgtgatt tcgataagcc ggaaggtcag ctgtttttga ccctgccggt   3660

gaacgcaaag aaagatcatc agaaactgat ggtgctgctg atggaaaatt ggccgggcac   3720

cttcaatctg aagtatcatc aggagcaacg ttttatcatg tcctgtggcg atcagattgc   3780

cgagttttcg ccggaacaat ttgttgaaac ggcggttggt gttatcaagc accatctgga   3840

tgagctgcct caggactgtc gcaccatttc ggacaatgcg attaacgcgc tgattgatga   3900

atggaagacg aaaacccaag ctgaagttat tcgctgataa ggatccggca tcaaataaaa   3960

cgaaaggctc agtcgaaaga ctgggccttt cgttttatct gttgtttgtc ggtgaacgct   4020

ctcctgagta ggacaaatcc gccgccctag aactagtcca taagaatgcg gccgc        4075
```

```
<210> SEQ ID NO 155
<211> LENGTH: 12614
<212> TYPE: DNA
<213> ORGANISM: Artificial Sequence
<220> FEATURE:
<223> OTHER INFORMATION: synthetic Syn_InvSpa operon of bacterial type
      III secretion system (T3SS)

<400> SEQUENCE: 155

ctcgagaaaa aaaagctcta aaagattaag agggggtaac atatgggtga cgtgagcgcg     60

gtgagcagca gcggtaacat tctgctgccg cagcaggacg aggttggtgg cctgtccgaa    120

gcgctgaaga aagcggttga aaaacacaaa accgaataca gcggtgacaa gaaagatcgt    180

gattatggtg acgcctttgt tatgcacaag gaaaccgcgc tgccgttgtt gctggcagct    240

tggcgccacg gcgcaccggc gaaaagcgag caccataacg gtaacgtaag cggtctgcat    300

cacaacggta agagcgagct gcgtattgct gagaaactgc tgaaggtgac ggcggagaag    360

agcgttggtc tgattagcgc tgaagcgaag gtggataaat ctgcggcgct gctgtctagc    420

aagaatcgtc cgctggaatc ggtcagcggc aaaaagttgt ccgccgatct gaaagcagtg    480
```

```
gagtccgtgt ccgaggtcac ggataacgcc accggcattt cggatgacaa catcaaagca    540
ttgccgggtg acaataaggc catcgccggt gagggtgtgc gtaaagaagg tgcgccgctg    600
gcgcgtgacg tggctccggc acgcatggcg gcagcaaata cgggcaagcc ggaggataaa    660
gaccacaaga aggtcaagga cgttagccag ctgccgctgc aaccgactac catcgccgat    720
ctgtctcaac tgacgggtgg cgatgaaaag atgccgctgg cagcgcagtc caaaccgatg    780
atgaccattt tcccaaccgc cgacggcgtt aaaggtgagg acagctctct gacctatcgt    840
ttccagcgct ggggcaacga ttactccgtc aatatccagg cacgccaagc gggcgaattt    900
agcctgattc ctagcaatac ccaggttgaa catcgtctgc acgaccaatg gcaaaatggc    960
aatccacaac gctggcattt gacgcgtgat gaccagcaaa acccgcaaca gcaacagcat   1020
cgtcagcagt ccggtgaaga ggacgacgcg taacttgggc acgcgtccat taagaaggag   1080
gaattaagca tggacgatct ggttttcgcc ggcaacaaag ccctgtactt ggtgctgatt   1140
ctgtccggtt ggccgacgat tgtcgcaacc attatcggtc tgctggttgg tctgtttcaa   1200
accgtgacgc agttgcagga gcaaaccctg ccgttcggta tcaagctgct gggtgtgtgt   1260
ctgtgcctgt ttttgctgtc tggctggtat ggcgaagttc tgctgtccta cggccgtcag   1320
gtcatcttcc tggctctggc gaaaggttaa gacgtccttg ggcacgcgtc cattaaacag   1380
gagtaattaa gcatgctgct gtccctgctg aatagcgcgc gtctgcgtcc tgagctgctg   1440
attctggttc tgatggttat gatcatcagc atgttcgtta tcccgttgcc gacctatttg   1500
gttgacttct tgatcgcttt gaacattgtc ctggcaattc tggtgttcat gggctccttc   1560
tacatcgacc gcattctgag cttcagcacc tttccggcgg ttctgctgat cacgactctg   1620
ttccgtttgg cactgagcat cagcaccagc cgcctgatcc tgattgaagc agatgcgggt   1680
gagatcatcg cgacctttgg tcagtttgtg atcggtgaca gcctggcggt tggtttcgtc   1740
gtattctcca tcgtgacggt ggtgcagttt atcgttatta ccaagggcag cgaacgtgtg   1800
gcggaggtcg ccgctcgctt cagcctggac ggcatgccgg gtaaacagat gtctattgat   1860
gcagacctga aagccggcat tattgatgct gatgcagcgc gcgagcgccg cagcgtcctg   1920
gagcgtgaaa gccaactgta cggttccttc gacggtgcca tgaagttcat taaaggtgat   1980
gcgattgcgg gcatcattat catcttcgtt aacttcattg gcggtatcag cgtcggtatg   2040
acccgtcatg gtatggatct gagcagcgcc ctgagcacct acaccatgct gacgattggt   2100
gatggtctgg ttgcccaaat tccggcgttg ctgatcgcga tttctgcggg cttcatcgtt   2160
acccgcgtca acggtgatag cgataacatg ggtcgtaaca ttatgaccca gctgctgaat   2220
aatccgtttg tcctggttgt aacggcgatt ttgaccatca gcatgggcac gctgccgggc   2280
tttccgttgc cggttttcgt tattctgtct gttgtgctgt ccgtcctgtt ttactttaag   2340
ttccgcgagg cgaaacgtag cgctgcgaaa ccaaaaacga gcaagggcga gcaaccgttg   2400
tccatcgagg agaaggaagg tagcagcctg ggcctgattg gcgacctgga taaggttagc   2460
acggaaaccg tcccgctgat tttgctggtg ccgaaatcgc gtcgtgagga tctggagaaa   2520
gcgcagctgg cggaacgtct gcgcagccaa ttctttattg attatggtgt gcgtctgcca   2580
gaagtactgc tgcgtgacgg tgagggtctg gatgacaact ctatcgtcct gctgattaat   2640
gagattcgcg ttgaacagtt tactgtctat tttgacctga tgcgtgtggt taactacagc   2700
gacgaggtgg tgagctttgg catcaacccg accattcacc agcaaggttc cagccagtac   2760
ttttgggtga cccatgagga aggcgaaaag ctgcgcgagc tgggctacgt cctgcgtaat   2820
gcactggacg aactgtacca ctgtctggcg gtgacgctgg cacgcaatgt gaacgagtat   2880
```

ttcggtatcc aagaaacgaa acacatgctg gaccaactgg aagcaaagtt tcctgacctg 2940
ctgaaggagg ttttgcgcca cgccaccgtg cagcgcattt cggaagtgct gcaacgtctg 3000
ctgtccgaac gcgtgagcgt ccgtaacatg aagctgatca tggaagccct ggcactgtgg 3060
gctccgcgtg agaaagatgt gatcaatctg gtggagcaca tccgtggtgc gatggcgcgt 3120
tatatctgcc acaagttcgc aaatggtggt gaactgcgtg ccgttatggt ttccgccgaa 3180
gttgaggatg tcattcgtaa aggcattcgt caaacttctg gctccacctt tttgagcttg 3240
gacccggagg cttcggcaaa tctgatggac ctgatcacgc tgaagctgga cgacctgttg 3300
attgcgcata aggacctggt cctgttgacc agcgttgacg tgcgtcgttt tatcaagaaa 3360
atgattgaag gtcgttttcc ggatctggag gtcctgtcct tcggtgagat tgcagatagc 3420
aaaagcgtga atgtcatcaa aaccatctga atttaaatct tgggcacgcg tccattaaaa 3480
aggagtaatt aagcatgagc ttcagcgaga gccgccacaa tgaaaactgt ctgattcaag 3540
aaggcgcact gctgttttgt gagcaagcag tcgtggcgcc tgtcagcggt gatctggttt 3600
ttcgtccgct gaaaatcgag gtcctgagca agctgctggc gttcatcgac ggcgcaggtc 3660
tggtggatac gacctacgcg gagtcggaca aatgggttct gctgtctccg gagttccgtg 3720
ctatttggca agaccgtaaa cgttgcgaat attggttttt gcagcagatt atcaccccat 3780
ctccggcgtt caacaaggtt ctggcactgt tgcgtaagag cgaaagctat tggttggtcg 3840
gctacttgct ggcccaaagc accagcggca atactatgcg tatgttgggt gaggattacg 3900
gtgttagcta cacgcatttc cgccgtctgt gcagccgcgc tctgggcggt aaggcgaaaa 3960
gcgagctgcg caattggcgc atggcccagt ccctgctgaa tagcgtggaa ggtcatgaaa 4020
acatcaccca gctggcggtc aaccacggtt atagcagccc gtcccacttt agctctgaaa 4080
tcaaggagct gattggtgtt tccccgcgta agctgtctaa catcattcag ctggccgaca 4140
aatgaattta aatgctagcc ttgggcacgc gtccattaaa gaggaccaat taagcatgaa 4200
aaccccacgt ctgctgcaat acctggccta cccgcagaaa atcactggcc ctatcattga 4260
agcagaactg cgtgatgttg caattggtga attgtgcgag atccgtcgcg gctggcacca 4320
gaagcaggtt gtggcccgtg cgcaagtggt tggtttgcag cgcgaacgta ccgtcctgag 4380
cctgatcggc aatgcccaag gcctgagccg tgatgtggtc ttgtacccga ccggccgtgc 4440
tctgagcgcg tgggttggtt acagcgttct gggcgcagta ctggacccga cgggtaaaat 4500
cgttgaacgt ttcaccccgg aagtcgcacc gatttccgag gagcgcgtta tcgacgtggc 4560
accgccgagc tacgcaagcc gtgtcggtgt gcgcgaaccg ctgatcacgg gtgtccgcgc 4620
aattgatggt ctgctgacgt gtggtgtggg ccagcgtatg ggtattttcg caagcgcggg 4680
ttgtggtaag accatgttga tgcacatgct gatcgagcaa accgaagcgg atgtctttgt 4740
tattggcctg attggcgagc gtggtcgtga agttaccgaa tttgtagaca tgttgcgtgc 4800
atctcataag aaagaaaaat gtgtgctggt ttttgccacg tccgacttcc caagcgttga 4860
ccgctgcaac gctgcccagc tggcaacgac ggtcgccgag tatttccgcg accagggtaa 4920
acgtgttgtc ctgtttatcg acagcatgac ccgttatgca cgcgcgttgc gtgatgtcgc 4980
gctggcgagc ggcgagcgtc cggctcgccg tggttatccg gcgtctgtgt tcgacaatct 5040
gccgcgtttg ctggagcgtc cgggtgcgac gagcgagggt agcattaccg ccttctatac 5100
cgtcctgctg gagtcggaag aagaagcgga cccgatggcg gacgagatcc gttctattct 5160
ggacggtcac ctgtacctgt cccgcaaact ggcgggtcag ggtcattacc cggctatcga 5220

```
tgtgctgaag agcgtgagcc gtgtgtttgg tcaagtgacc accccgactc acgcggagca   5280
agcgagcgcg gtccgtaagc tgatgacccg tctggaagag ctgcaactgt tcattgacct   5340
gggcgagtat cgtccgggcg agaacattga caatgatcgt gcgatgcaaa tgcgcgatag   5400
cctgaaggcg tggctgtgtc agcctgttgc gcaatacagc agcttcgatg atacgctgtc   5460
cggcatgaac gcctttgcgg atcagaactg acttgggcac gcgtccatga aagaaacgac   5520
atactagatg ggtaacgata ttagcttgat tgcattgctg gcgttttcca ccctgctgcc   5580
gttcatcatc gcgtctggta cttgcttcgt caaattcagc atcgtctttg tgatggtgcg   5640
caacgcgctg ggtctgcaac aaattccaag caatatgacc ctgaatggcg tcgcactgct   5700
gctgtcgatg tttgttatgt ggccgattat gcacgacgcg tatgtgtatt tcgaggatga   5760
agatgtgacc tttaacgaca tctccagcct gagcaagcat gttgatgagg gcctggacgg   5820
ttatcgcgac tacctgatca agtattccga ccgtgagctg gtgcagttct ttgagaatgc   5880
ccagttgaaa cgtcagtacg gtgaagaaac ggaaaccgtt aaacgtgaca aggacgagat   5940
tgaaaagccg agcattttcg cactgttgcc tgcttacgcc ttgagcgaga ttaagagcgc   6000
attcaaaatt ggtttttacc tgtacctgcc gttcgttgtg gtcgatctgg ttgtctccag   6060
cgttctgctg gccctgggca tgatgatgat gtccccggtt accatcagca cgccgatcaa   6120
actggtcctg tttgtggccc tggatggttg gacgctgctg tctaaaggcc tgatcctgca   6180
atacatggac atcgcgacct aagagctctg ggcacgcgtc cattaatgag gaaaaattat   6240
tagcatgaaa acgcacattc tgttggcccg tgtgctggct tgcgcagctc tggtgctggt   6300
caccccaggt tatagctccg agaagatccc ggttacgggc agcggcttcg ttgcaaagga   6360
cgattctctg cgcacctttt tcgatgcgat ggcactgcaa ttgaaggagc cggtgattgt   6420
cagcaagatg gcggctcgca aaaagattac cggcaatttc gagttccacg atccaaacgc   6480
gctgctggag aaactgtccc tgcaactggg tctgatctgg tactttgatg gtcaggcgat   6540
ctacatctac gacgcgagcg aaatgcgtaa tgcggttgtg agcctgcgta atgtcagcct   6600
gaacgagttc aacaattttc tgaagcgcag cggcctgtac aataagaact accctctgcg   6660
tggtgataat cgtaaaggca ccttctatgt cagcggtccg ccggtgtatg ttgatatggt   6720
tgtaaatgcg gccaccatga tggacaaaca gaatgatggc atcgagctgg gtcgccaaaa   6780
gatcggtgtt atgcgcctga acaacacttt tgtgggcgac cgcacctaca acctgcgtga   6840
tcaaaagatg gtcattccgg gtattgctac ggcaattgaa cgcctgttgc aaggcgaaga   6900
acaaccgctg ggtaacattg taagctccga gcctccggcc atgccggcct ttagcgcaaa   6960
cggcgagaaa ggtaaggcag cgaattacgc gggtggtatg agcctgcaag aagcgctgaa   7020
acagaacgca gcggcaggca acatcaaaat tgtggcctat ccggacacca acagcctgct   7080
ggtgaaaggt acggcggagc aggtgcattt catcgagatg ctggttaaag ccctggacgt   7140
ggcgaaacgt cacgttgaat tgagcctgtg gattgtggat ttgaataaga gcgacctgga   7200
acgcttgggc accagctgga gcggtagcat caccatcggc gacaagctgg gtgtgagcct   7260
gaaccagagc agcatctcca cgctggacgg tagccgcttt attgcggcgg tcaacgctct   7320
ggaggaaaag aaacaggcca ctgttgtcag ccgtccggtt ctgctgaccc aggagaatgt   7380
cccggcgatt tttgacaata atcgtacttt ctataccaaa ctgatcggtg aacgtaatgt   7440
tgcattggaa cacgtgacct atggcaccat gatccgtgtc ctgccgcgtt tcagcgcgga   7500
cggccagatt gagatgagcc tggacatcga agatggtaat gacaaaaccc cgcagtctga   7560
tacgaccacc tccgttgatg cgctgccaga agtgggtcgt accctgatct cgacgattgc   7620
```

acgtgtcccg catggtaaat ctctgctggt tggtggctac acgcgtgatg caaacacgga 7680
cacggtccaa agcatcccgt tcctgggtaa gctgccgctg attggctcgt tgtttcgcta 7740
cagcagcaaa aacaagtcta atgtcgtccg tgtctttatg attgagccga aagaaatcgt 7800
tgacccgctg accccggatg ccagcgagag cgttaacaac attctgaaac agtccggtgc 7860
gtggagcggt gacgataagc tgcaaaagtg ggttcgtgtg tatttggacc gtggtcagga 7920
ggccattaag taacttgggc acgcgtccat gaaagacagg acccactaga tgtccagcaa 7980
caaaaccgaa aaaccgacta agaaacgtct ggaggatagc gcaaagaaag gtcagagctt 8040
caagagcaag gacctgatta tcgcgtgcct gaccctgggt ggtatcgctt atttggtgag 8100
ctacggcagc ttcaatgagt ttatgggtat cattaagatt atcatcgctg ataactttga 8160
tcagtcgatg gcagattata gcctggccgt gtttggtatt ggcctgaaat acctgattcc 8220
gttcatgctg ctgtgtttgg tttgttccgc actgccggca ctgctgcaag cgggcttcgt 8280
tctggcaacc gaggccctga agccgaatct gtccgccctg aacccggttg aaggcgcgaa 8340
gaaactgttt tccatgcgca ccgtcaaaga cacggtcaag acgctgctgt atctgtcgag 8400
ctttgtggtt gcggcaatca tttgctggaa aaagtataaa gtcgagattt tcagccaact 8460
gaacggtaat atcgtgggta ttgcggttat ctggcgtgaa ttgctgctgg cgttggttct 8520
gacctgtctg gcgtgcgcgc tgatcgtgct gttgctggat gctattgccg agtactttct 8580
gaccatgaaa gatatgaaga tggacaaaga agaagttaaa cgcgagatga aagagcagga 8640
gggtaacccg gaggtgaagt ctaaacgtcg tgaagtccac atggaaatcc tgagcgaaca 8700
agtcaagtct gacattgaaa atagccgtct gattgtggca aaccctacgc atattaccat 8760
cggcatctac ttcaaaccgg aactgatgcc gattccaatg attagcgtct atgaaaccaa 8820
tcaacgcgcg ctggcggtcc gtgcgtacgc cgagaaagtg ggtgttccgg ttattgtaga 8880
catcaagctg gcgcgcagcc tgttcaaaac gcaccgtcgt tacgacctgg tgagcctgga 8940
ggagatcgac gaggttttgc gcctgctggt ttggttggaa gaggtcgaaa acgcaggcaa 9000
ggatgtgatc caaccgcagg agaatgaagt gcgtcattaa ctgcaggttt aaactacttg 9060
ggcacgcgtc cattaattag gatcaatagc atgattccgg gcagcacctc cggtatttcc 9120
tttagccgta tcctgagccg tcagacctcc caccaggatg caacccagca taccgacgca 9180
caacaagcgg aaattcaaca agcggcggaa gatagctcgc cgggtgcgga ggttcagaaa 9240
ttcgtccaga gcacggacga gatgtctgct gcgttggcgc agttccgcaa tcgccgtgac 9300
tatgagaaaa agagcagcaa tttgtctaac tccttcgagc gcgttctgga ggacgaggca 9360
ctgccgaaag cgaagcagat tctgaaactg atcagcgtgc atggcggtgc gttggaggat 9420
ttcctgcgtc aggcgcgcag cctgttcccg gacccaagcg atctggtgct ggttctgcgc 9480
gagctgttgc gtcgtaagga cctggaggag atcgtgcgta agaagctgga gagcctgctg 9540
aagcacgtgg aggaacaaac cgacccgaaa accctgaagg ccggtattaa ctgcgcgctg 9600
aaggcgcgtc tgtttggcaa gacgctgtct ctgaaacctg gtctgctgcg tgccagctac 9660
cgccagttca tccaaagcga aagccacgaa gtcgagattt acagcgattg gatcgccagc 9720
tacggttatc agcgtcgcct ggttgttctg gatttcattg aaggcagcct gctgactgac 9780
atcgatgcta acgatgcaag ctgctcccgt ctggagtttg gccaactgct gcgccgtctg 9840
acccagctga aaatgttgcg tagcgccgac ctgctgtttg tctcgacgtt gctgtcttac 9900
agcttcacga aagcatttaa cgctgaggag agcagctggc tgttgctgat gctgtctttg 9960

-continued

```
ctgcaacagc cgcacgaagt ggatagcctg ctggcggaca ttatcggtct gaatgcgctg  10020
ctgttgtccc acaaagagca cgccagcttc ctgcaaatct tctatcaggt ctgtaaggca  10080
atcccgtcta gcctgtttta tgaagagtac tggcaagaag aactgctgat ggcactgcgc  10140
tccatgacgg acattgctta caaacacgaa atggccgaac aacgtcgtac catcgaaaag  10200
ctgtcctaag tttaaacctt gggcacgcgt ccatgaaaga caggacccac tagatgagct  10260
tgcgcgtacg ccaaattgac cgccgtgaat ggctgctggc ccagactgcg accgaatgtc  10320
agcgtcacgg tcgtgaggcc accctggagt atccgacccg tcagggtatg tgggtccgcc  10380
tgtctgatgc cgaaaaacgc tggtctgcgt ggatcaaacc gggtgattgg ttggaacacg  10440
ttagcccagc actggcgggt gccgcggtca gcgcaggcgc ggagcacctg gtggttccgt  10500
ggctggcggc aaccgaacgc ccgttcgagc tgccggtccc gcacttgagc tgccgtcgtc  10560
tgtgcgtgga gaacccggtt ccgggttccg cactgcctga gggcaagctg ctgcacatca  10620
tgtcggatcg tggtggcctg tggtttgagc atctgccgga gctgccggct gttggcggtg  10680
gccgtccgaa gatgctgcgt tggccgctgc gtttcgttat tggcagcagc gacacccagc  10740
gcagcctgct gggtcgtatc ggtatcggtg atgttctgct gatccgcacc agccgtgctg  10800
aggtttactg ttacgcgaag aaactgggcc actttaatcg tgtggaaggt ggcattattg  10860
tcgaaacgct ggacattcaa catatcgagg aggagaacaa cacgacggaa acggcggaaa  10920
ccctgccggg tctgaatcaa ctgccggtga agctggagtt cgttctgtat cgtaaaaacg  10980
tgacgttggc cgaactggaa gcaatgggtc agcaacaact gctgtccttg ccaaccaatg  11040
cggaactgaa cgtcgaaatc atggcgaatg gcgtgctgct gggtaacggc gaactggtgc  11100
agatgaatga caccctgggt gtcgagattc atgagtggtt gtccgagagc ggtaatggcg  11160
agtagagatc tcttgggcac gcgtccatta aaaaggacca attaagcatg cactctctga  11220
ctcgtatcaa ggtcctgcaa cgtcgttgta ccgtgttcca ttctcagtgc gagtccattc  11280
tgttgcgtta tcaggacgaa gatcgcggct tgcaggcgga ggaggaggcc atcctggaac  11340
agatcgcagg tctgaaactg ctgttggaca ccctgcgtgc tgaaaatcgt caactgagcc  11400
gtgaagaaat ctatacgctg ctgcgcaaac agagcattgt tcgtcgccag attaaggatc  11460
tggagctgca aatcattcag attcaagaaa agcgtagcga gctggaaaag aaacgtgagg  11520
aatttcaaaa gaaaagcaaa tactggctgc gtaaagaagg taactaccag cgctggatta  11580
tccgtcaaaa acgcttctac attcaacgtg agatccagca agaggaggcg gagagcgaag  11640
agatcattta acttgggcac gcgtccatga aagacaggac ccactagatg ttctatgcat  11700
tgtattttga gatccaccat ctggtggcgt ccgcggctct gggttttgcg cgtgttgctc  11760
cgatcttttt ctttctgccg ttcctgaata gcggtgtcct gagcggtgct ccgcgcaacg  11820
cgatcatcat tctggtggcg ctgggtgtat ggccgcacgc cctgaatgag gcgccaccgt  11880
ttctgtctgt ggcaatgatt ccgctggtcc tgcaagaggc agccgtgggt gttatgctgg  11940
gttgcctgtt gtcctggccg ttttgggtta tgcacgcgtt gggctgtatc attgataacc  12000
aacgcggtgc aaccctgtcc agcagcattg atcctgcgaa tggcatcgac accagcgaga  12060
tggccaattt cctgaacatg ttcgcggctg tcgtgtattt gcagaacggt ggcttggtca  12120
cgatggtgga cgtgctgaat aagtcttacc agctgtgtga tccgatgaac gagtgtacgc  12180
cgagcctgcc tccgttgctg accttcatta atcaagtggc ccagaacgca ctggtgctgg  12240
cgtccccggt cgttctggtt ctgctgctgt cggaagtttt cctgggcctg ctgtctcgtt  12300
ttgcaccgca aatgaacgcg ttcgccatta gcctgactgt taaaagcggt attgcggttt  12360
```

tgatcatgct gctgtatttc agcccggtcc tgccggacaa tgttctgcgt ctgagctttc 12420
aggcgaccgg cctgagcagc tggttctacg aacgtggcgc aacgcatgtg ctggaataag 12480
gatccggcat caaataaaac gaaaggctca gtcgaaagac tgggcctttc gttttatctg 12540
ttgtttgtcg gtgaacgctc tcctgagtag gacaaatccg ccgccctaga actagtccat 12600
aagaatgcgg ccgc 12614

<210> SEQ ID NO 156
<211> LENGTH: 23
<212> TYPE: DNA
<213> ORGANISM: Artificial Sequence
<220> FEATURE:
<223> OTHER INFORMATION: synthetic Enterobacteria phage T7 promoter seed sequence
<220> FEATURE:
<221> NAME/KEY: modified_base
<222> LOCATION: (16)...(20)
<223> OTHER INFORMATION: n = g, a, c or t

<400> SEQUENCE: 156
taatacgact cactannnnn aga 23

<210> SEQ ID NO 157
<211> LENGTH: 23
<212> TYPE: DNA
<213> ORGANISM: Artificial Sequence
<220> FEATURE:
<223> OTHER INFORMATION: synthetic Enterobacteria phage T7 wild type (WT) promoter

<400> SEQUENCE: 157
taatacgact cactataggg aga 23

<210> SEQ ID NO 158
<211> LENGTH: 23
<212> TYPE: DNA
<213> ORGANISM: Artificial Sequence
<220> FEATURE:
<223> OTHER INFORMATION: synthetic mutant Enterobacteria phage T7 promoter Mut1

<400> SEQUENCE: 158
taatacgact cactacaggc aga 23

<210> SEQ ID NO 159
<211> LENGTH: 23
<212> TYPE: DNA
<213> ORGANISM: Artificial Sequence
<220> FEATURE:
<223> OTHER INFORMATION: synthetic mutant Enterobacteria phage T7 promoter Mut2

<400> SEQUENCE: 159
taatacgact cactagagag aga 23

<210> SEQ ID NO 160
<211> LENGTH: 23
<212> TYPE: DNA
<213> ORGANISM: Artificial Sequence
<220> FEATURE:
<223> OTHER INFORMATION: synthetic mutant Enterobacteria phage T7 promoter Mut3

<400> SEQUENCE: 160
taatacgact cactaatggg aga 23

<210> SEQ ID NO 161
<211> LENGTH: 23
<212> TYPE: DNA
<213> ORGANISM: Artificial Sequence
<220> FEATURE:
<223> OTHER INFORMATION: synthetic mutant Enterobacteria phage T7
promoter Mut4

<400> SEQUENCE: 161
taatacgact cactataggt aga 23

<210> SEQ ID NO 162
<211> LENGTH: 23
<212> TYPE: DNA
<213> ORGANISM: Artificial Sequence
<220> FEATURE:
<223> OTHER INFORMATION: synthetic mutant Enterobacteria phage T7
promoter Mut5

<400> SEQUENCE: 162
taatacgact cactaaaggg aga 23

<210> SEQ ID NO 163
<211> LENGTH: 23
<212> TYPE: DNA
<213> ORGANISM: Artificial Sequence
<220> FEATURE:
<223> OTHER INFORMATION: synthetic mutant Enterobacteria phage T7
promoter Mut6

<400> SEQUENCE: 163
taatacgact cactattggg aga 23

<210> SEQ ID NO 164
<211> LENGTH: 26
<212> TYPE: DNA
<213> ORGANISM: Artificial Sequence
<220> FEATURE:
<223> OTHER INFORMATION: synthetic Klebsiella oxytoca nif operon
deletion mutant NF8 deletion region
<220> FEATURE:
<221> NAME/KEY: modified_base
<222> LOCATION: (26)...(26)
<223> OTHER INFORMATION: c modified by Km cassette and SEQ ID NO:163

<400> SEQUENCE: 164
gcaggagaac taaaggcccg gcatgc 26

<210> SEQ ID NO 165
<211> LENGTH: 26
<212> TYPE: DNA
<213> ORGANISM: Artificial Sequence
<220> FEATURE:
<223> OTHER INFORMATION: synthetic Klebsiella oxytoca nif operon
deletion mutant NF8 deletion region
<220> FEATURE:
<221> NAME/KEY: modified_base
<222> LOCATION: (1)...(1)
<223> OTHER INFORMATION: g modified by Km cassette and SEQ ID NO:164

<400> SEQUENCE: 165
gcatgcaagc gcccatggcc ccggca 26

<210> SEQ ID NO 166
<211> LENGTH: 46
<212> TYPE: DNA
<213> ORGANISM: Artificial Sequence
<220> FEATURE:
<223> OTHER INFORMATION: synthetic Klebsiella oxytoca nif in-frame
      deletion mutant UC12 deletion region

<400> SEQUENCE: 166
cataaacagg cacggctggt ggtaccccat caggtgcccc gcgtca 46

<210> SEQ ID NO 167
<211> LENGTH: 46
<212> TYPE: DNA
<213> ORGANISM: Artificial Sequence
<220> FEATURE:
<223> OTHER INFORMATION: synthetic Klebsiella oxytoca nif operon
      deletion mutant NF9 deletion region

<400> SEQUENCE: 167
atggccccgg caggcgcaat gcatgcgacg ctcttcccca cgttac 46

<210> SEQ ID NO 168
<211> LENGTH: 46
<212> TYPE: DNA
<213> ORGANISM: Artificial Sequence
<220> FEATURE:
<223> OTHER INFORMATION: synthetic Klebsiella oxytoca nif operon
      deletion mutant UC14 deletion region

<400> SEQUENCE: 168
gacgctcttc cccacgttac gcatgcgatc cggacccgcg ccgcta 46

<210> SEQ ID NO 169
<211> LENGTH: 46
<212> TYPE: DNA
<213> ORGANISM: Artificial Sequence
<220> FEATURE:
<223> OTHER INFORMATION: synthetic Klebsiella oxytoca nif operon
      deletion mutant UC15 deletion region

<400> SEQUENCE: 169
ctcttcccca cgttacgctc gcatgcgatc cggacccgcg ccgcta 46

<210> SEQ ID NO 170
<211> LENGTH: 46
<212> TYPE: DNA
<213> ORGANISM: Artificial Sequence
<220> FEATURE:
<223> OTHER INFORMATION: synthetic Klebsiella oxytoca nif operon
      deletion mutant NF10 deletion region

<400> SEQUENCE: 170
cggacccgcg ccgctagccg gcatgcatct ttggcagcag agccag 46

<210> SEQ ID NO 171
<211> LENGTH: 46
<212> TYPE: DNA
<213> ORGANISM: Artificial Sequence
<220> FEATURE:
<223> OTHER INFORMATION: synthetic Klebsiella oxytoca nif operon
      deletion mutant NF11 deletion region

<400> SEQUENCE: 171
cggacccgcg ccgctagccg gcatgcagcc tcggcggcta cccgtt 46

<210> SEQ ID NO 172
<211> LENGTH: 46
<212> TYPE: DNA
<213> ORGANISM: Artificial Sequence
<220> FEATURE:

<223> OTHER INFORMATION: synthetic Klebsiella oxytoca nif operon deletion mutant NF12 deletion region

<400> SEQUENCE: 172
actggttatc ctgatccagc gcatgccttt gcactaccgc ggccca 46

<210> SEQ ID NO 173
<211> LENGTH: 46
<212> TYPE: DNA
<213> ORGANISM: Artificial Sequence
<220> FEATURE:
<223> OTHER INFORMATION: synthetic Klebsiella oxytoca nif operon deletion mutant NF13 deletion region

<400> SEQUENCE: 173
ccgttaacgc ctacagcacg gcatgccttt gcactaccgc ggccca 46

<210> SEQ ID NO 174
<211> LENGTH: 40
<212> TYPE: DNA
<213> ORGANISM: Artificial Sequence
<220> FEATURE:
<223> OTHER INFORMATION: synthetic Klebsiella oxytoca nif operon deletion mutant NF14 deletion region

<400> SEQUENCE: 174
attcagggac gcgggttgcc atgtgattat gcgacgtctt 40

<210> SEQ ID NO 175
<211> LENGTH: 46
<212> TYPE: DNA
<213> ORGANISM: Artificial Sequence
<220> FEATURE:
<223> OTHER INFORMATION: synthetic Klebsiella oxytoca nif operon deletion mutant NF24 deletion region

<400> SEQUENCE: 175
gtcaaacacc agaatattga gagctctgtc gtttctgtga caaagc 46

<210> SEQ ID NO 176
<211> LENGTH: 46
<212> TYPE: DNA
<213> ORGANISM: Artificial Sequence
<220> FEATURE:
<223> OTHER INFORMATION: synthetic Klebsiella oxytoca nif operon deletion mutant NF25 deletion region

<400> SEQUENCE: 176
cggacccgcg ccgctagccg gcatgccttt gcactaccgc ggccca 46

<210> SEQ ID NO 177
<211> LENGTH: 46
<212> TYPE: DNA
<213> ORGANISM: Artificial Sequence
<220> FEATURE:
<223> OTHER INFORMATION: synthetic Klebsiella oxytoca whole nif deletion mutant NF26 deletion region

<400> SEQUENCE: 177
gtcaaacacc agaatattga ctcgagatgt gattatgcga cgtctt 46

<210> SEQ ID NO 178
<211> LENGTH: 23
<212> TYPE: DNA
<213> ORGANISM: Artificial Sequence
<220> FEATURE:
<223> OTHER INFORMATION: synthetic wild type (WT) Enterobacteria phage T7 promoter part number SBa_000443

<400> SEQUENCE: 178
taatacgact cactataggg aga 23

<210> SEQ ID NO 179
<211> LENGTH: 23
<212> TYPE: DNA
<213> ORGANISM: Artificial Sequence
<220> FEATURE:
<223> OTHER INFORMATION: synthetic Enterobacteria phage T7 promoter 1 part number SBa_000444

<400> SEQUENCE: 179
taatacgact cactacaggc aga 23

<210> SEQ ID NO 180
<211> LENGTH: 23
<212> TYPE: DNA
<213> ORGANISM: Artificial Sequence
<220> FEATURE:
<223> OTHER INFORMATION: synthetic Enterobacteria phage T7 promoter 2 part number SBa_000445

<400> SEQUENCE: 180
taatacgact cactagagag aga 23

<210> SEQ ID NO 181
<211> LENGTH: 23
<212> TYPE: DNA
<213> ORGANISM: Artificial Sequence
<220> FEATURE:
<223> OTHER INFORMATION: synthetic Enterobacteria phage T7 promoter 3 part number SBa_000446

<400> SEQUENCE: 181
taatacgact cactaatggg aga 23

<210> SEQ ID NO 182
<211> LENGTH: 23
<212> TYPE: DNA
<213> ORGANISM: Artificial Sequence
<220> FEATURE:
<223> OTHER INFORMATION: synthetic Enterobacteria phage T7 promoter 4 part number SBa_000447

<400> SEQUENCE: 182
taatacgact cactattggg aga 23

<210> SEQ ID NO 183
<211> LENGTH: 48
<212> TYPE: DNA
<213> ORGANISM: Artificial Sequence
<220> FEATURE:
<223> OTHER INFORMATION: synthetic Enterobacteria phage T7 wild type (WT) terminator part number SBa_000450

<400> SEQUENCE: 183
tagcataacc ccttggggcc tctaaacggg tcttgagggg ttttttgt 48

<210> SEQ ID NO 184
<211> LENGTH: 29
<212> TYPE: DNA
<213> ORGANISM: Artificial Sequence
<220> FEATURE:
<223> OTHER INFORMATION: synthetic Enterobacteria phage T7 terminator part number SBa_000451

<400> SEQUENCE: 184
tacatatcgg gggggtaggg gttttttgt 29

<210> SEQ ID NO 185
<211> LENGTH: 37
<212> TYPE: DNA
<213> ORGANISM: Artificial Sequence
<220> FEATURE:
<223> OTHER INFORMATION: synthetic Enterobacteria phage T7 terminator part number SBa_000452

<400> SEQUENCE: 185
tactctaacc ccatcggccg tcttaggggt tttttgt 37

<210> SEQ ID NO 186
<211> LENGTH: 50
<212> TYPE: DNA
<213> ORGANISM: Artificial Sequence
<220> FEATURE:
<223> OTHER INFORMATION: synthetic insulator part number SBa_000453

<400> SEQUENCE: 186
gcgtgcgtac accttaatca ccgcttcatg ctaaggtcct ggctgcatgc 50

<210> SEQ ID NO 187
<211> LENGTH: 50
<212> TYPE: DNA
<213> ORGANISM: Artificial Sequence
<220> FEATURE:
<223> OTHER INFORMATION: synthetic insulator part number SBa_000454

<400> SEQUENCE: 187
caaacacccc atgtcgatac tgaacgaatc gacgcacact cccttccttg 50

<210> SEQ ID NO 188
<211> LENGTH: 40
<212> TYPE: DNA
<213> ORGANISM: Artificial Sequence
<220> FEATURE:
<223> OTHER INFORMATION: synthetic insulator part number SBa_000455

<400> SEQUENCE: 188
cctgattgta tccgcatctg atgctaccgt ggttgagtta 40

<210> SEQ ID NO 189
<211> LENGTH: 40
<212> TYPE: DNA
<213> ORGANISM: Artificial Sequence
<220> FEATURE:
<223> OTHER INFORMATION: synthetic insulator part number SBa_000456

<400> SEQUENCE: 189
catttttgcc ttgcgacaga cctcctactt agattgccac 40

<210> SEQ ID NO 190
<211> LENGTH: 40
<212> TYPE: DNA
<213> ORGANISM: Artificial Sequence
<220> FEATURE:
<223> OTHER INFORMATION: synthetic insulator part number SBa_000457

<400> SEQUENCE: 190
tgtcacgcta ggaggcaatt ctataagaat gcacactgca 40

<210> SEQ ID NO 191
<211> LENGTH: 30
<212> TYPE: DNA
<213> ORGANISM: Artificial Sequence
<220> FEATURE:
<223> OTHER INFORMATION: synthetic insulator part number SBa_000458

<400> SEQUENCE: 191
ccgtggttga gtcagcgtcg agcacgcggc 30

<210> SEQ ID NO 192
<211> LENGTH: 40
<212> TYPE: DNA
<213> ORGANISM: Artificial Sequence
<220> FEATURE:
<223> OTHER INFORMATION: synthetic insulator part number SBa_000459

<400> SEQUENCE: 192
cgcgacttcc agagaagaag actactgact tgagcgttcc 40

<210> SEQ ID NO 193
<211> LENGTH: 40
<212> TYPE: DNA
<213> ORGANISM: Artificial Sequence
<220> FEATURE:
<223> OTHER INFORMATION: synthetic insulator part number SBa_000460

<400> SEQUENCE: 193
actacgagat ttgaggtaaa ccaaataagc acgtagtggc 40

<210> SEQ ID NO 194
<211> LENGTH: 18
<212> TYPE: DNA
<213> ORGANISM: Artificial Sequence
<220> FEATURE:
<223> OTHER INFORMATION: synthetic insulator part number SBa_000461

<400> SEQUENCE: 194
gtctgtagca cgtgcatc 18

<210> SEQ ID NO 195
<211> LENGTH: 18
<212> TYPE: DNA
<213> ORGANISM: Artificial Sequence
<220> FEATURE:
<223> OTHER INFORMATION: synthetic insulator part number SBa_000462

<400> SEQUENCE: 195
ggtcattaca acggttat 18

<210> SEQ ID NO 196
<211> LENGTH: 40
<212> TYPE: DNA
<213> ORGANISM: Artificial Sequence
<220> FEATURE:
<223> OTHER INFORMATION: synthetic insulator part number SBa_000463

<400> SEQUENCE: 196
aacatagcgt tccatgaggg ctagaattac ctaccggcct 40

<210> SEQ ID NO 197
<211> LENGTH: 40
<212> TYPE: DNA
<213> ORGANISM: Artificial Sequence
<220> FEATURE:
<223> OTHER INFORMATION: synthetic insulator part number SBa_000464

<400> SEQUENCE: 197
cattgtaata gccaccaaaa gagtgatgat agtcatgggt 40

<210> SEQ ID NO 198
<211> LENGTH: 40
<212> TYPE: DNA
<213> ORGANISM: Artificial Sequence
<220> FEATURE:
<223> OTHER INFORMATION: synthetic insulator part number SBa_000465

<400> SEQUENCE: 198
gagttactgg ccctgatttc tccgcttcta ataccgcaca 40

<210> SEQ ID NO 199
<211> LENGTH: 40
<212> TYPE: DNA
<213> ORGANISM: Artificial Sequence
<220> FEATURE:
<223> OTHER INFORMATION: synthetic insulator part number SBa_000466

<400> SEQUENCE: 199
gactcaacac gctagggacg tgaagtcgat tccttcgatg 40

<210> SEQ ID NO 200
<211> LENGTH: 40
<212> TYPE: DNA
<213> ORGANISM: Artificial Sequence
<220> FEATURE:
<223> OTHER INFORMATION: synthetic insulator part number SBa_000467

<400> SEQUENCE: 200
tcgagaaaca aggcagttcc gggctgaaag tagcgccggg 40

<210> SEQ ID NO 201
<211> LENGTH: 40
<212> TYPE: DNA
<213> ORGANISM: Artificial Sequence
<220> FEATURE:
<223> OTHER INFORMATION: synthetic insulator part number SBa_000468

<400> SEQUENCE: 201
acgccacgcg tagtgagaca tacacgttcg ttgggttcac 40

<210> SEQ ID NO 202
<211> LENGTH: 40
<212> TYPE: DNA
<213> ORGANISM: Artificial Sequence
<220> FEATURE:
<223> OTHER INFORMATION: synthetic insulator part number SBa_000508

<400> SEQUENCE: 202
tgcagtttta ttctctcgcc agcactgtaa taggcactaa 40

<210> SEQ ID NO 203
<211> LENGTH: 110
<212> TYPE: DNA
<213> ORGANISM: Artificial Sequence
<220> FEATURE:
<223> OTHER INFORMATION: synthetic ribosome binding site (RBS) part
      number SBa_000475

<400> SEQUENCE: 203
ttaaagagga gaaattaagc atgaaaacta tggacggtaa cgctgcggct gcatggatta 60
gctacgcctt taccgaagtg gctgcgatct acccgattac gccgagcacc 110

<210> SEQ ID NO 204
<211> LENGTH: 126
<212> TYPE: DNA
<213> ORGANISM: Artificial Sequence
<220> FEATURE:
<223> OTHER INFORMATION: synthetic ribosome binding site (RBS) part number SBa_000469

<400> SEQUENCE: 204
tactagagac aataaactaa cataaggagg ataaatatga ccatgcgtca gtgcgcgatt 60
tatggcaaag gtggtattgg caaaagcacg acgacccaga acttggtggc ggccctggcc 120
gagatg 126

<210> SEQ ID NO 205
<211> LENGTH: 174
<212> TYPE: DNA
<213> ORGANISM: Artificial Sequence
<220> FEATURE:
<223> OTHER INFORMATION: synthetic ribosome binding site (RBS) part number SBa_000470

<400> SEQUENCE: 205
gcgtgcgtac accttaatca ccgcttcatg ctaaggtcct ggctgcatgc aaaaattcac 60
atccctatct agcggaggag ccggatgatg actaatgcta ctggcgaacg taacctggca 120
ctgattcaag aagtactgga agtgttcccg gaaaccgcgc gcaaagagcg ccgt 174

<210> SEQ ID NO 206
<211> LENGTH: 174
<212> TYPE: DNA
<213> ORGANISM: Artificial Sequence
<220> FEATURE:
<223> OTHER INFORMATION: synthetic ribosome binding site (RBS) part number SBa_000471

<400> SEQUENCE: 206
caaacacccc atgtcgatac tgaacgaatc gacgcacact cccttccttg caatctcata 60
ctctcaaaaa ttaggcgagg taacatgtct caaactatcg ataaaatcaa ctcttgttac 120
ccgctgttcg agcaggacga atatcaggaa ctgttccgta acaaacgtca gctg 174

<210> SEQ ID NO 207
<211> LENGTH: 156
<212> TYPE: DNA
<213> ORGANISM: Artificial Sequence
<220> FEATURE:
<223> OTHER INFORMATION: synthetic ribosome binding site (RBS) part number SBa_000472

<400> SEQUENCE: 207
cctgattgta tccgcatctg atgctaccgt ggttgagtta ccatactcac tcccggaggt 60
acttctatgt ctgacaatga taccctgttt tggcgcatgc tggcgctgtt tcagtcgctg 120
ccggatttgc agccggctca aatcgtcgat tggctg 156

<210> SEQ ID NO 208
<211> LENGTH: 162
<212> TYPE: DNA
<213> ORGANISM: Artificial Sequence
<220> FEATURE:
<223> OTHER INFORMATION: synthetic ribosome binding site (RBS) part number SBa_000473

<400> SEQUENCE: 208

```
catttttgcc ttgcgacaga cctcctactt agattgccac actattcaat acatcactgg     60

aggttattac aaatgaaggg taacgagatt cttgctctgc tggacgaacc ggcctgtgaa    120

cacaaccata aacagaaatc cggctgtagc gcccccaaagc cg                      162


<210> SEQ ID NO 209
<211> LENGTH: 161
<212> TYPE: DNA
<213> ORGANISM: Artificial Sequence
<220> FEATURE:
<223> OTHER INFORMATION: synthetic ribosome binding site (RBS) part
      number SBa_000474

<400> SEQUENCE: 209

tgtcacgcta ggaggcaatt ctataagaat gcacactgca cctaaaccta ccacacctga     60

ggagagtaat tatggcagac attttccgca ctgataagcc gttggctgtg tcgccgatca    120

agaccggcca gccgctgggt gcgatcctgg cgtccctggg t                        161


<210> SEQ ID NO 210
<211> LENGTH: 167
<212> TYPE: DNA
<213> ORGANISM: Artificial Sequence
<220> FEATURE:
<223> OTHER INFORMATION: synthetic ribosome binding site (RBS) part
      number SBa_000476

<400> SEQUENCE: 210

aacatagcgt tccatgaggg ctagaattac ctaccggcct cagatactga caaataaacc     60

agcgaaggag gttcctaatg tggaactaca gcgagaaagt caaggaccat ttcttcaatc    120

cgcgcaacgc gcgtgttgtg gataacgcaa atgcggtggg cgacgtc                  167


<210> SEQ ID NO 211
<211> LENGTH: 169
<212> TYPE: DNA
<213> ORGANISM: Artificial Sequence
<220> FEATURE:
<223> OTHER INFORMATION: synthetic ribosome binding site (RBS) part
      number SBa_000477

<400> SEQUENCE: 211

cattgtaata gccaccaaaa gagtgatgat agtcatgggt gatacccgta gaccattctg     60

aaatcgaagg aggttttcca tgaaacaagt gtacctggac aacaacgcga ccacccgcct    120

ggacccgatg gttctggaag cgatgatgcc gtttctcacg gatttctat                169


<210> SEQ ID NO 212
<211> LENGTH: 164
<212> TYPE: DNA
<213> ORGANISM: Artificial Sequence
<220> FEATURE:
<223> OTHER INFORMATION: synthetic ribosome binding site (RBS) part
      number SBa_000478

<400> SEQUENCE: 212

gagttactgg ccctgatttc tccgcttcta ataccgcaca gcgactagga gcctaactcg     60

ccacaaggaa acatatggag cgcgtcttga tcaacgatac taccctgcgt gatggcgaac    120

aatctccggg cgtagcgttt cgtacctccg agaaagttgc catc                     164


<210> SEQ ID NO 213
<211> LENGTH: 165
<212> TYPE: DNA
<213> ORGANISM: Artificial Sequence
```

<220> FEATURE:
<223> OTHER INFORMATION: synthetic ribosome binding site (RBS) part number SBa_000479

<400> SEQUENCE: 213
gactcaacac gctagggacg tgaagtcgat tccttcgatg cagaaggcga gaactagatt 60
taagggccat tatagatgga gtggttttac cagattccgg gtgtagacga attgcgcagc 120
gctgaatcct tctttcagtt cttcgcggtt ccataccagc cggaa 165

<210> SEQ ID NO 214
<211> LENGTH: 166
<212> TYPE: DNA
<213> ORGANISM: Artificial Sequence
<220> FEATURE:
<223> OTHER INFORMATION: synthetic ribosome binding site (RBS) part number SBa_000480

<400> SEQUENCE: 214
tcgagaaaca aggcagttcc gggctgaaag tagcgccggg acaagtcccg tattataacc 60
gcctaggagg tgttggatgc gcccgaaatt caccttctct gaagaggtcc gcgtagttcg 120
cgcgattcgt aatgatggca ccgtggcggg ttttgcgcca ggtgcg 166

<210> SEQ ID NO 215
<211> LENGTH: 164
<212> TYPE: DNA
<213> ORGANISM: Artificial Sequence
<220> FEATURE:
<223> OTHER INFORMATION: synthetic ribosome binding site (RBS) part number SBa_000481

<400> SEQUENCE: 215
acgccacgcg tagtgagaca tacacgttcg ttgggttcac tcagagactg aagttattac 60
ccaggaggtc tataatgaat ccgtggcagc gctttgcccg tcaacgcctt gctcgcagcc 120
gctggaaccg tgatccggct gctctcgacc cagccgatac ccca 164

<210> SEQ ID NO 216
<211> LENGTH: 124
<212> TYPE: DNA
<213> ORGANISM: Artificial Sequence
<220> FEATURE:
<223> OTHER INFORMATION: synthetic ribosome binding site (RBS) part number SBa_000482

<400> SEQUENCE: 216
gacaagagtc tcaattataa ggaggcttta ctacatggcg aacatcggca tcttctttgg 60
tacggatacc ggcaaaaccc gcaagattgc gaagatgatt cacaaacagc tgggcgagct 120
ggcc 124

<210> SEQ ID NO 217
<211> LENGTH: 169
<212> TYPE: DNA
<213> ORGANISM: Artificial Sequence
<220> FEATURE:
<223> OTHER INFORMATION: synthetic ribosome binding site (RBS) part number SBa_000483

<400> SEQUENCE: 217
cgcgacttcc agagaagaag actactgact tgagcgttcc ctctctgtaa tacatcaaat 60
caatcatagg agggctaaaa tgacctcttg ttcgtcgttt tctggcggta aagcgtgccg 120
tccggccgat gactccgcgc tgactccgct ggtggccgac aaggcagct 169

<210> SEQ ID NO 218
<211> LENGTH: 152
<212> TYPE: DNA
<213> ORGANISM: Artificial Sequence
<220> FEATURE:
<223> OTHER INFORMATION: synthetic ribosome binding site (RBS) part number SBa_000475

<400> SEQUENCE: 218
aactacgaga tttgaggtaa accaaataag cacgtagtgg cattaaagag gagaaattaa 60
gcatgccgcc attggactgg ttgcgtcgtt tgtggttact ctatcacgcc ggcaaaggca 120
gctttccgct tcgtatgggc ttgtcgccgc gt 152

<210> SEQ ID NO 219
<211> LENGTH: 1761
<212> TYPE: DNA
<213> ORGANISM: Artificial Sequence
<220> FEATURE:
<223> OTHER INFORMATION: synthetic P-tac promoter and lacI cassette part number SBa_000561

<400> SEQUENCE: 219
caattcgcgc taacttacat taattgcgtt gcgctcactg cccgctttcc agtcgggaaa 60
cctgtcgtgc cagctgcatt aatgaatcgg ccaacgcgcg gggagaggcg gtttgcgtat 120
tgggcgccag ggtggttttt cttttcacca gtgagacggg caacagctga ttgcccttca 180
ccgcctggcc ctgagagagt tgcagcaagc ggtccacgct ggtttgcccc agcaggcgaa 240
aatcctgttt gatggtggtt gacggcggga tataacatga gctgtcttcg gtatcgtcgt 300
atcccactac cgagatatcc gcaccaacgc gcagcccgga ctcggtaatg gcgcgcattg 360
cgcccagcgc catctgatcg ttggcaacca gcatcgcagt gggaacgatg ccctcattca 420
gcatttgcat ggtttgttga aaaccggaca tggcactcca gtcgccttcc cgttccgcta 480
tcggctgaat ttgattgcga gtgagatatt tatgccagcc agccagacgc agacgcgccg 540
agacagaact taatgggccc gctaacagcg cgatttgctg gtgacccaat gcgaccagat 600
gctccacgcc cagtcgcgta ccgtcttcat gggagaaaat aatactgttg atgggtgtct 660
ggtcagagac atcaagaaat aacgccggaa cattagtgca ggcagcttcc acagcaatgg 720
catcctggtc atccagcgga tagttaatga tcagcccact gacgcgttgc gcgagaagat 780
tgtgcaccgc cgctttacag gcttcgacgc cgcttcgttc taccatcgac accaccacgc 840
tggcacccag ttgatcggcg cgagatttaa tcgccgcgac aatttgcgac ggcgcgtgca 900
gggccagact ggaggtggca acgccaatca gcaacgactg tttgcccgcc agttgttgtg 960
ccacgcggtt gggaatgtaa ttcagctccg ccatcgccgc ttccactttt tcccgcgttt 1020
tcgcagaaac gtggctggcc tggttcacca cgcgggaaac ggtctgataa gagacaccgg 1080
catactctgc gacatcgtat aacgttactg gtttcacatt caccaccctg aattgactct 1140
cttccgggcg ctatcatgcc ataccgcgaa aggttttgca ccattcgatg gtgtcaacgt 1200
aaatgcatgc cgcttcgcct tcgcgcgcga attggccgcc atgccggcga taatggcctg 1260
cttctcgccg aaacgtttgg tggcgggacc agtgacgaag gcttgagcga gggcgtgcaa 1320
gattccgaat accgcaagcg acaggccgat catcgtcgcg ctccagcgaa agcggtcctc 1380
gccgaaaatg acccagagcg ctgccggcac ctgtcctacg agttgcatga taaagaagac 1440
agtcataagt gcggcgacga tagtcatgcc ccgcgcccac cggaaggagc tgactgggtt 1500
gaaggctctc aagggcatcg gcggagctta tcgactgcac ggtgcaccaa tgcttctggc 1560
gtcaggcagc catcggaagc tgtggtatgg ctgtgcaggt cgtaaatcac tgcataattc 1620
gtgtcgctca aggcgcactc ccgttctgga taatgttttt tgcgccgaca tcataacggt 1680
tctggcaaat attctgaaat gagctgttga caattaatca tcggctcgta taatgtgtgg 1740
aattgtgagc ggataacaat t 1761

<210> SEQ ID NO 220
<211> LENGTH: 740
<212> TYPE: DNA
<213> ORGANISM: Artificial Sequence
<220> FEATURE:
<223> OTHER INFORMATION: synthetic P-tet promoter and tetR cassette part number SBa_000562

<400> SEQUENCE: 220
ttattaggac ccactttcac atttaagttg tttttctaat ccgcatatga tcaattcaag 60
gccgaataag aaggctggct ctgcaccttg gtgatcaaat aattcgatag cttgtcgtaa 120
taatggcggc atactatcag tagtaggtgt ttccctttct tctttagcga cttgatgctc 180
ttgatcttcc aatacgcaac ctaaagtaaa atgccccaca gcgctgagtg catataatgc 240
attctctagt gaaaaacctt gttggcataa aaaggctaat tgattttcga gagtttcata 300
ctgtttttct gtaggccgtg tacctaaatg tacttttgct ccatcgcgat gacttagtaa 360
agcacatcta aaacttttag cgttattacg taaaaaatct tgccagcttt ccccttctaa 420
agggcaaaag tgagtatggt gcctatctaa catctcaatg gctaaggcgt cgagcaaagc 480
ccgcttattt tttacatgcc aatacaatgt aggctgctct acacctagct tctgggcgag 540
tttacgggtt gttaaacctt cgattccgac ctcattaagc agctctaatg cgctgttaat 600
cactttactt ttatctaatc tggacatcga ggcctttcct gtgtgagcta gcactgtacc 660
taggactgag ctagccgtca atttttttccc tatcagtgat agagattgac atccctatca 720
gtgatagata taatgagcac 740

<210> SEQ ID NO 221
<211> LENGTH: 702
<212> TYPE: DNA
<213> ORGANISM: Artificial Sequence
<220> FEATURE:
<223> OTHER INFORMATION: synthetic red fluorescent protein (mRFP) fluorescsnt reporter part number SBa_000484

<400> SEQUENCE: 221
atgtccagat tagataaaag taaagttgcg agctctgaag acgttatcaa agagttcatg 60
cgtttcaaag ttcgtatgga aggttccgtt aacggtcacg agttcgaaat cgaaggtgaa 120
ggtgaaggtc gtccgtacga aggtacccag accgctaaac tgaaagttac caaaggtggt 180
ccgctgccgt tcgcttggga catcctgtcc ccgcagttcc agtacggttc caaagcttac 240
gttaaacacc cggctgacat cccggactac ctgaaactgt ccttcccgga aggtttcaaa 300
tgggaacgtg ttatgaactt cgaagacggt ggtgttgtta ccgttaccca ggactcctcc 360
ctgcaagacg gtgagttcat ctacaaagtt aaactgcgtg gtaccaactt cccgtccgac 420
ggtccggtta tgcagaaaaa aaccatgggt tgggaagctt ccaccgaacg tatgtacccg 480
gaagacggtg ctctgaaagg tgaaatcaaa atgcgtctga aactgaaaga cggtggtcac 540
tacgacgctg aagttaaaac cacctacatg gctaaaaaac cggttcagct gccgggtgct 600
tacaaaaccg acatcaaact ggacatcacc tcccacaacg aagactacac catcgttgaa 660
cagtacgaac gtgctgaagg tcgtcactcc accggtgctt aa 702

<210> SEQ ID NO 222
<211> LENGTH: 2652
<212> TYPE: DNA
<213> ORGANISM: Artificial Sequence
<220> FEATURE:
<223> OTHER INFORMATION: synthetic Enterobacteria phage T7* variant RNA polymerase (RNAP) part number SBa_000514

<400> SEQUENCE: 222
atgaacacga ttaacatcgc taagaacgac ttctctgaca tcgaactggc tgctatcccg 60
ttcaacactc tggctgacca ttacggtgag cgtttagctc gcgaacagtt ggcccttgag 120
catgagtctt acgagatggg tgaagcacgc ttccgcaaga tgtttgagcg tcaacttaaa 180
gctggtgagg ttgcggataa cgctgccgcc aagcctctca tcactaccct actccctaag 240
atgattgcac gcatcaacga ctggtttgag gaagtgaaag ctaagcgcgg caagcgcccg 300
acagccttcc agttcctgca agaaatcaag ccggaagccg tagcgtacat caccattaag 360
accactctgg cttgcctaac cagtgctgac aatacaaccg ttcaggctgt agcaagcgca 420
atcggtcggg ccattgagga cgaggctcgc ttcggtcgta tccgtgacct tgaagctaag 480
cacttcaaga aaaacgttga ggaacaactc aacaagcgcg tagggcacgt ctacaagaaa 540
gcatttatgc aagttgtcga ggctgacatg ctctctaagg gtctactcgg tggcgaggcg 600
tggtcttcgt ggcataagga agactctatt catgtaggag tacgctgcat cgagatgctc 660
attgagtcaa ccggaatggt tagcttacac cgccaaaatg ctggcgtagt aggtcaagac 720
tctgagacta tcgaactcgc acctgaatac gctgaggcta tcgcaacccg tgcaggtgcg 780
ctggctggca tctctccgat gttccaacct tgcgtagttc ctcctaagcc gtggactggc 840
attactggtg gtggctattg ggctaacggt cgtcgtcctc tggcgctggt gcgtactcac 900
agtaagaaag cactgatgcg ctacgaagac gtttacatgc ctgaggtgta caaagcgatt 960
aacattgcgc aaaacaccgc atggaaaatc aacaagaaag tcctagcggt cgccaacgta 1020
atcaccaagt ggaagcattg tccggtcgag gacatccctg cgattgagcg tgaagaactc 1080
ccgatgaaac cggaagacat cgacatgaat cctgaggctc tcaccgcgtg gaaacgtgct 1140
gccgctgctg tgtaccgcaa ggacaaggct cgcaagtctc gccgtatcag ccttgagttc 1200
atgcttgagc aagccaataa gtttgctaac cataaggcca tctggttccc ttacaacatg 1260
gactggcgcg gtcgtgttta cgctgtgtca atgttcaacc cgcaaggtaa cgatatgacc 1320
aaaggactgc ttacgctggc gaaaggtaaa ccaatcggta aggaaggtta ctactggctg 1380
aaaatccacg gtgcaaactg tgcgggtgtc gacaaggttc cgttccctga gcgcatcaag 1440
ttcattgagg aaaaccacga gaacatcatg gcttgcgcta agtctccact ggagaacact 1500
tggtgggctg agcaagattc tccgttctgc ttccttgcgt tctgctttga gtacgctggg 1560
gtacagcacc acggcctgag ctataactgc tcccttccgc tggcgtttga cgggtcttgc 1620
tctggcatcc agcacttctc cgcgatgctc cgagatgagg taggtggtcg cgcggttaac 1680
ttgcttccta gtgaaaccgt tcaggacatc tacgggattg ttgctaagaa agtcaacgag 1740
attctacaag cagacgcaat caatgggacc gataacgaag tagttaccgt gaccgatgag 1800
aacactggtg aaatctctga gaaagtcaag ctgggcacta aggcactggc tggtcaatgg 1860
ctggcttacg gtgttactcg cagtgtgact aagagttcag tcatgacgct ggcttacggg 1920
tccaaagagt tcggcttccg tcaacaagtg ctggaagata ccattcagcc agctattgat 1980

```
tccggcaagg gtctgatgtt cactcagccg aatcaggctg ctggatacat ggctaagctg   2040

atttgggaat ctgtgagcgt gacggtggta gctgcggttg aagcaatgaa ctggcttaag   2100

tctgctgcta agctgctggc tgctgaggtc aaagataaga agactggaga gattcttcgc   2160

aagcgttgcg ctgtgcattg ggtaactcct gatggtttcc ctgtgtggca ggaatacaag   2220

aagcctattc agacgcgctt gaacctgatg ttcctcggtc agttccgctt acagcctacc   2280

attaacacca acaaagatag cgagattgat gcacacaaac aggagtctgg tatcgctcct   2340

aactttgtac acagccaaga cggtagccac cttcgtaaga ctgtagtgtg ggcacacgag   2400

aagtacggaa tcgaatcttt tgcactgatt cacgactcct tcggtacgat tccggctgac   2460

gctgcgaacc tgttcaaagc agtgcgcgaa actatggttg acacatatga gtcttgtgat   2520

gtactggctg atttctacga ccagttcgct gaccagttgc acgagtctca attggacaaa   2580

atgccagcac ttccggctaa aggtaacttg aacctccgtg acatcttaga gtcggacttc   2640

gcgttcgcgt aa                                                        2652
```

<210> SEQ ID NO 223
<211> LENGTH: 3504
<212> TYPE: DNA
<213> ORGANISM: Artificial Sequence
<220> FEATURE:
<223> OTHER INFORMATION: synthetic Klebsiella pneumoniae nifJ

<400> SEQUENCE: 223

```
atgaaaacta tggacggtaa cgctgcggct gcatggatta gctacgcctt taccgaagtg     60

gctgcgatct acccgattac gccgagcacc ccgatggcgg aaaatgtgga cgaatgggct    120

gcgcagggca agaagaacct cttcggccag ccggtgcgcc tgatggagat gcagtcggaa    180

gcgggtgcag caggtgctgt gcatggcgcc ttgcaagctg gcgcactgac gaccacctac    240

accgcgtcgc agggcctgtt gctgatgatc ccaaacatgt acaaaatcgc gggtgaactg    300

ctgccgggtg tctttcatgt ttcggcacgc gcactggcca ccaatagcct caacatcttt    360

ggcgatcatc aggatgtaat ggcggtgcgc caaacgggct gcgcgatgtt ggccgagaat    420

aacgtccagc aagttatgga tttgtccgcg gtagcccact tggcagcgat caaaggtcgc    480

attccgttcg tgaacttctt cgatggcttt cgcaccagcc acgaaatcca gaagatcgag    540

gttctggaat atgaacagct ggccaccttg ttggatcgtc cggccctgga cagcttccgc    600

cgtaacgccc ttcacccgga ccacccggtc atccgtggca ccgcccagaa cccggacatc    660

tacttccagg aacgtgaggc cggtaaccgt ttctatcagg cgctcccgga tattgtggaa    720

tcttacatga cccagatttc tgccctgact ggtcgcgagt atcacctgtt taactacact    780

ggtgctgcgg atgcggagcg cgtgatcatc gcgatgggct ctgtctgtga caccgtccaa    840

gaggtggttg acacgctgaa tgcagcgggt gagaaagttg gtctgctctc cgttcatctt    900

ttccgcccgt tttcgttagc gcacttcttc gcccaactgc cgaaaactgt acagcgtatc    960

gcagtattgg accgtacgaa agagccaggt gctcaagcag agccgctgtg cctcgatgtg   1020

aagaatgcct tttaccacca tgacgatgcc ccgttgattg tgggtggtcg ctatgccttg   1080

ggcggtaagg acgtgttgcc gaacgatatt gcggccgtgt ttgataacct gaacaaaccg   1140

ctgccgatgg acggcttcac gctgggtatc gtggacgatg ttaccttcac ctctctcccg   1200

ccagcgcagc agaccctggc ggtttctcac gacggcatca cggcatgtaa gttttggggc   1260

atgggctccg acggcacggt tggtgcgaac aagtccgcga tcaagattat cggcgacaaa   1320
```

acgccactgt atgcgcaagc gtacttttcc tacgactcga agaagagcgg tggtattacc 1380
gtcagccatc tgcgttttgg tgatcgcccg atcaactccc cgtatttgat ccatcgcgcg 1440
gatttcatct cgtgcagcca gcaaagctat gttgaacgct acgatctgct ggatggcctt 1500
aaaccgggtg gcacctttct gctgaactgc tcctggagcg atgccgaact ggagcaacat 1560
ctgccggtcg gtttcaaacg ttatctggca cgcgagaata tccacttcta cactctcaac 1620
gctgtggaca tcgcccgtga gcttggtttg ggtggccgtt tcaacatgct gatgcaggct 1680
gccttcttca aactggccgc gatcattgac ccgcagactg ctgcggacta tctgaagcag 1740
gctgttgaga aaagctatgg cagcaaaggt gcggcggtca tcgagatgaa ccagcgtgcc 1800
atcgagcttg gcatggccag cctgcaccag gtgacgatcc cggcacattg ggccaccctg 1860
gatgagccag cggcgcaggc gtccgcgatg atgccggact ttatccgcga catcctgcaa 1920
ccgatgaacc gtcagtgcgg cgaccagctt ccggtgtcgg cttttgtcgg catggaagat 1980
ggcaccttcc cgtccggcac ggccgcatgg gagaaacgtg gcatcgccct tgaggtgcca 2040
gtctggcagc cggaaggctg cacgcagtgc aaccagtgcg ccttcatttg tccgcacgcc 2100
gcgattcgtc cggcgttgtt gaatggcgaa gagcatgatg ctgccccggt tggcctgctg 2160
agcaaaccgg cacaaggcgc taaagaatat cactatcatc tggcgattag cccgctggac 2220
tgctccggct gtggcaactg cgttgacatt tgtccagctc gtggcaaagc gttgaagatg 2280
cagtctctgg atagccaacg ccagatggct ccggtgtggg attatgcgct ggcgctgacc 2340
ccgaagtcta acccgtttcg taaaaccacc gtcaaaggct cgcagttcga aaccccgctg 2400
ctggagttta gcggtgcgtg cgctggttgt ggcgaaacgc cgtatgcgcg cctcattacc 2460
cagctgtttg gcgaccgcat gctgattgcc aatgccaccg gctgttccag catctggggc 2520
gcatctgcgc cgagcatccc gtataccacc aatcatcgtg gtcatggtcc ggcctgggcg 2580
aatagcctgt ttgaggacaa tgccgaattt ggtttaggta tgatgctggg cggtcaagct 2640
gtgcgtcaac agatcgcgga cgatatgacg gctgcgttag cgctcccggt ttccgatgag 2700
ctgagcgacg cgatgcgcca gtggttggcg aaacaggacg agggtgaagg cacgcgtgag 2760
cgtgcggacc gtctgagcga gcgcttagcc gcggagaaag agggcgttcc gctgttagag 2820
cagctgtggc aaaatcgtga ttactttgtg cgtcgcagcc agtggatttt cggcggtgac 2880
ggctgggcct atgatattgg cttcggtggc ctggaccacg tcctcgccag cggtgaggat 2940
gtgaacattc tggtatttga caccgaagtc tactcgaaca ccggcggtca aagcagcaaa 3000
tcgaccccgg tcgcggccat cgccaagttc gcggctcagg gcaagcgcac ccgcaagaaa 3060
gacctgggta tgatggcgat gagctacggc aacgtctatg tagcccaggt ggcgatgggt 3120
gcggataaag atcaaactct gcgcgccatt gcggaagctg aagcgtggcc aggcccgtcg 3180
ctggtgattg cgtatgcggc ctgcatcaat catggcctga aggccggtat gcgttgcagc 3240
caacgtgagg cgaagcgcgc tgttgaggcg ggctactggc acctgtggcg ttatcacccg 3300
cagcgcgaag cggaaggcaa gacgccgttt atgttagata gcgaagaacc ggaagagtcg 3360
ttccgtgact ttctgttggg tgaggtgcgc tacgcatccc tgcacaagac cacccccgcac 3420 ctcgccgatg cccttttcag ccgtaccgaa gaagatgcgc gtgcgcgctt tgcgcaatac 3480
cgtcgcctgg ctggcgaaga gtaa 3504

<210> SEQ ID NO 224
<211> LENGTH: 882
<212> TYPE: DNA
<213> ORGANISM: Artificial Sequence
<220> FEATURE:
<223> OTHER INFORMATION: synthetic Klebsiella pneumoniae nifH

<400> SEQUENCE: 224
atgaccatgc gtcagtgcgc gatttatggc aaaggtggta ttggcaaaag cacgacgacc 60
cagaacttgg tggcggccct ggccgagatg ggtaaaaagg ttatgattgt gggttgcgac 120
ccgaaggccg acagcacgcg cctgattctg cacgcgaaag cacaaaacac gattatggag 180
atggctgccg aggttggtag cgtggaggat ctggagctgg aggacgttct gcaaattggt 240
tacggtgatg ttcgttgcgc agagagcggt ggtccggaac caggtgtcgg ctgtgcgggt 300
cgtggtgtga ttaccgctat caatttcctg gaagaagagg gtgcgtacga agatgatctg 360
gatttcgttt tctacgatgt gctgggtgat gtcgtgtgcg gtggttttgc aatgccgatt 420
cgcgagaata aggcacaaga aatttacatt gtctgtagcg gcgagatgat ggcaatgtac 480
gctgctaaca acatcagcaa gggtattgtt aaatacgcaa aaagcggtaa ggttcgcttg 540
ggtggtttga tttgcaacag ccgtcagacc gaccgtgagg acgaactgat catcgccctg 600
gctgagaaac tgggcaccca aatgatccac ttcgtgccac gcgataatat tgttcaacgt 660
gcagaaatcc gccgtatgac cgtcattgag tatgacccgg catgcaagca agcgaacgag 720
taccgcacct tggcacagaa aatcgtgaac aacaccatga aggttgttcc gacgccgtgt 780
acgatggacg agctggagag cctgctgatg gagttcggca ttatggagga ggaggacacc 840
agcattatcg gtaagaccgc agcggaggag aatgcggcat aa 882

<210> SEQ ID NO 225
<211> LENGTH: 1452
<212> TYPE: DNA
<213> ORGANISM: Artificial Sequence
<220> FEATURE:
<223> OTHER INFORMATION: synthetic Klebsiella pneumoniae nifI

<400> SEQUENCE: 225
atgatgacta atgctactgg cgaacgtaac ctggcactga ttcaagaagt actggaagtg 60
ttcccggaaa ccgcgcgcaa agagcgccgt aaacacatga tggtttctga cccggaaatg 120
gaatctgtgg gtaaatgcat catctctaat cgcaaatctc agccgggtgt catgactgtt 180
cgtggctgtg cgtacgcagg ttctaaaggt gtcgtattcg gcccgatcaa agatatggcg 240
catatctctc atggcccggt aggctgtggc cagtactctc gcgcgggacg tcgtaactac 300
tacacgggcg tttctggcgt tgactctttc ggcacgctga acttcacctc tgacttccag 360
gaacgtgaca tcgttttcgg tggcgataaa aagctgtcca aactgatcga agaaatggaa 420
ctgctgttcc cgctgactaa aggcattact atccaaagcg aatgtccggt gggtctgatc 480
ggtgatgaca tcagcgcggt cgcaaacgca tcttccaaag ccctggataa gccggtgatc 540
ccggttcgtt gcgagggctt ccgcggcgtt tctcagtctc tgggtcatca catcgcaaac 600
gatgttgtgc gtgactggat tctgaacaac cgtgaaggtc agccttttga aaccacccct 660
tatgacgttg cgattattgg cgactataac atcggcggcg acgcctgggc atcccgcatc 720
ctgctggagg agatgggtct gcgtgttgtc gcacagtggt ctggcgatgg caccctggtt 780
gaaatggaaa acaccccgtt tgttaaactg aacctggttc actgctaccg ctccatgaac 840
tacattgccc gtcacatgga agaaaaacat cagatccctt ggatggaata caacttcttc 900
ggtccgacta aaatcgcaga atccctgcgt aaaatcgccg atcagtttga tgataccatt 960
cgcgcgaacg ctgaagcagt aattgcgcgc tacgaaggcc agatggcagc aatcattgct 1020

-continued

```
aagtaccgtc cgcgcctgga aggtcgtaaa gtgctgctgt acatgggtgg tctgcgtcca   1080

cgtcatgtga tcggtgccta cgaggacctg ggcatggaga tcatcgcagc gggttacgaa   1140

tttgcacaca acgacgacta tgatcgtacg ctgccagacc tgaaagaagg tacgctgctg   1200

tttgacgacg ccagctctta tgaactggaa gccttcgtga aagcgctgaa accagacctg   1260

atcggctccg gcatcaagga aaaatacatt ttccagaaaa tgggcgtgcc gttccgccag   1320

atgcactcct gggactactc cggtccgtac cacggctacg acggtttcgc tatcttcgct   1380

cgtgacatgg atatgaccct gaataaccca gcgtggaatg aactgaccgc accgtggctg   1440

aaatctgcat aa                                                          1452
```

<210> SEQ ID NO 226
<211> LENGTH: 1563
<212> TYPE: DNA
<213> ORGANISM: Artificial Sequence
<220> FEATURE:
<223> OTHER INFORMATION: synthetic Klebsiella pneumoniae nifK

<400> SEQUENCE: 226

```
atgtctcaaa ctatcgataa aatcaactct tgttacccgc tgttcgagca ggacgaatat     60

caggaactgt tccgtaacaa acgtcagctg gaagaagcgc acgacgcaca gcgcgtgcag    120

gaagtgttcg catggaccac caccgcggaa tacgaagctc tgaacttcca gcgcgaagcc    180

ctgacggttg atccggcgaa agcgtgccag cctctgggtg cggttctgtg cagcctgggt    240

tttgccaaca ccctgccgta tgtccacggt tcccagggct gcgtagccta cttccgtacc    300

tatttcaacc gccactttaa agaaccaatc gcgtgcgtgt ccgacagcat gacggaggac    360

gcggcagttt tcggtggtaa caacaacatg aacctgggcc tgcaaaatgc ttccgcactg    420

tacaaaccgg aaatcatcgc agtgtctacc acctgcatgg cagaggttat tggtgatgat    480

ctgcaagcat ttattgccaa cgcaaagaaa gacggtttcg ttgacagctc tatcgcggtt    540

ccgcacgctc ataccccgtc cttcatcggt tctcacgtaa ctggttggga caacatgttc    600

gaaggcttcg caaaaacttt taccgcagac tatcaaggcc aaccgggtaa actgccgaag    660

ctgaacctgg tgaccggctt tgaaacctac ctgggcaact ttcgtgtcct gaagcgcatg    720

atggagcaga tggcggttcc gtgttctctg ctgtctgacc cgtctgaggt tctggacact    780

ccagcggacg gccactatcg catgtattct ggtggcacca ctcagcagga aatgaaagag    840

gccccagacg cgattgacac cctgctgctg caaccgtggc agctgctgaa aagcaagaaa    900

gttgttcagg aaatgtggaa ccagccggca acggaagttg caatcccgct gggtctggca    960

gctactgacg aactgctgat gaccgtgtcc caactgagcg gcaaaccaat cgcggatgct   1020

ctgaccctgg aacgcggtcg cctggtggac atgatgctgg acagccacac gtggctgcat   1080

ggcaagaaat ttggcctgta cggtgacccg gacttcgtaa tgggcctgac ccgtttcctg   1140

ctggaactgg gctgcgagcc gactgttatc ctgtctcaca acgctaacaa acgttggcag   1200

aaggccatga acaaaatgct ggatgcgagc ccatacggcc gtgatagcga agtgttcatc   1260

aactgcgacc tgtggcattt ccgctctctg atgtttacgc gtcagccgga tttcatgatc   1320

ggtaactctt acggcaaatt catccagcgt gacactctgg ccaaaggcaa agcgtttgaa   1380

gtgccgctga ttcgtctggg ctttccgctg ttcgaccgtc accacctgca ccgccagacc   1440

acctggggtt acgaaggcgc gatgaacatc gtaactactc tggtaaacgc agtactggaa   1500

aagctggaca gcgatacttc ccagctgggc aaaaccgact attctttcga tctggttcgt   1560

taa                                                                   1563
```

<210> SEQ ID NO 227
<211> LENGTH: 663
<212> TYPE: DNA
<213> ORGANISM: Artificial Sequence
<220> FEATURE:
<223> OTHER INFORMATION: synthetic Klebsiella pneumoniae nifY

<400> SEQUENCE: 227
atgtctgaca atgataccct gttttggcgc atgctggcgc tgtttcagtc gctgccggat 60
ttgcagccgg ctcaaatcgt cgattggctg gcgcaggaat ccggcgaaac cctgacgccg 120
gagcgccttg ccaccctgac ccaaccgcaa ctcgcggcgt cgttcccatc cgcgacggca 180
gtgatgagcc cggctcgctg gagccgcgtt atggcttctc tgcaaggcgc cctcccagcc 240
cacttgcgca tcgtacgtcc ggcgcagcgt accccgcaac tgctcgccgc gttttgcagc 300
caagacggcc ttgttatcaa tggtcatttc ggccagggtc gtctgttctt catttacgcc 360
tttgacgagc agggcggctg gctgtatgac ttgcgccgct atccgagcgc accgcaccag 420
caggaagcga atgaggtgcg tgctcgtctg attgaagatt gccagctgct gttctgccag 480
gagattggcg gtccggcagc agcgcgtctg atccgccacc gcatccatcc gatgaaggcg 540
cagccgggta ctacgattca ggcgcagtgt gaagctatca acaccctgct ggccggtcgc 600
ctgccgccgt ggctcgccaa acgtttgaac cgtgataacc cgctggaaga gcgtgtgttt 660
taa 663

<210> SEQ ID NO 228
<211> LENGTH: 1374
<212> TYPE: DNA
<213> ORGANISM: Artificial Sequence
<220> FEATURE:
<223> OTHER INFORMATION: synthetic Klebsiella pneumoniae nifE

<400> SEQUENCE: 228
atgaagggta acgagattct tgctctgctg gacgaaccgg cctgtgaaca caaccataaa 60
cagaaatccg gctgtagcgc cccaaagccg ggtgcgacgg cggctggctg cgctttcgat 120
ggtgcgcaga tcaccctgct cccgattgcg gacgttgccc acctcgtgca tggcccaatc 180
ggttgcgcag gtagctcttg ggacaaccgt ggcagcgcct ccagcggtcc gaccctgaat 240
cgtttgggct ttaccactga cttgaatgaa caagatgtga tcatgggtcg cggcgagcgt 300
cgcctgttcc acgctgtgcg ccatattgtc acccgttacc acccagcggc agtattcatc 360
tacaatacgt gcgtgccggc tatggaaggc gatgacctgg aggccgtgtg tcaggcagcc 420
cagactgcga ccggcgtccc ggtaatcgca attgatgcgg ctggcttcta cggttcgaag 480
aacctgggca accgtccggc aggcgatgtc atggttaaac gcgtcattgg ccaacgtgag 540
ccagcgccgt ggccggagag caccctgttt gccccggagc aacgtcatga cattggcttg 600
atcggtgagt tcaacattgc gggcgagttt tggcacattc agccgctgct tgatgagctg 660
ggtatccgcg ttttgggttc gctcagcggc gatggtcgtt tcgccgagat tcaaaccatg 720
caccgtgccc aggcgaacat gctggtgtgc agccgtgctc tgatcaatgt tgcgcgtgct 780
ctggaacagc gctatggcac cccgtggttt gaaggctcgt tctatggtat ccgcgcgacc 840
agcgacgccc tgcgccagtt agcggcgctg ctgggcgatg acgacctccg tcagcgcacc 900
gaggcgctga tcgcgcgtga agaacaggcg gctgagctgg ccctgcaacc gtggcgtgaa 960
cagctgcgtg gccgcaaggc cctgctctac acgggtggtg tcaaaagctg gtctgtggtg 1020
tccgcgcttc aggatctggg tatgaccgtg gttgccacgg gcacgcgtaa gagcacggaa 1080
gaggataaac agcgcatccg cgaattgatg ggcgaagagg ccgtgatgct tgaagaaggc 1140
aacgcacgta ccttattgga tgtagtttat cgctatcaag cagacctgat gattgccggt 1200
ggccgcaaca tgtataccgc ctacaaagcg cgcttgccgt tcctggacat caaccaggaa 1260
cgcgagcacg cgtttgcggg ctaccaaggc atcgtgacct tagcgcgcca gctgtgccaa 1320
acgattaaca gcccgatctg gccgcagact cattcccgcg caccgtggcg ctaa 1374

<210> SEQ ID NO 229
<211> LENGTH: 1386
<212> TYPE: DNA
<213> ORGANISM: Artificial Sequence
<220> FEATURE:
<223> OTHER INFORMATION: synthetic Klebsiella pneumoniae nifN

<400> SEQUENCE: 229
atggcagaca ttttccgcac tgataagccg ttggctgtgt cgccgatcaa gaccggccag 60
ccgctgggtg cgatcctggc gtccctgggt atcgagcact cgattccgct ggtacatggc 120
gcgcagggct gttcggcttt tgccaaggtt ttctttatcc agcacttcca cgatccggtc 180
ccgctgcaaa gcacggcaat ggacccgacc agcaccatca tgggcgctga tggtaacatc 240
ttcaccgcgc tggacactct ctgccaacgc aataacccgc aagcaattgt gctgctgagc 300
accggcctct ccgaggcgca gggcagcgac atttcccgtg tagtgcgtca gttccgtgaa 360
gaatatccgc gtcataaagg cgtggcgatt ctgactgtta acaccccgga cttttacggt 420
agcatggaga acggcttttc cgctgtcctg gagtctgtga ttgaacagtg ggttccgcca 480
gccccacgtc cggcgcagcg caatcgtcgc gtcaatcttt tggtgagcca tctctgtagc 540
ccaggcgata ttgagtggct gcgccgttgc gtcgaggcct tcggtctgca accgatcatt 600
ctgccggatc tggctcagag catggacggc caccttgctc agggtgactt ttcgccgctg 660
acgcagggcg gcacgccgtt gcgccaaatc gagcagatgg gccagagcct ttgctctttt 720
gcgattggcg tcagcctgca ccgtgcgagc agcctgctgg ctccgcgttg tcgtggcgaa 780
gtcatcgcct tgccgcacct catgaccttg gaacgctgcg acgcctttat ccatcagttg 840
gcgaaaatca gcggtcgcgc cgttccggag tggctggaac gccagcgcgg tcagctgcaa 900
gacgccatga tcgattgcca catgtggctg caaggccagc gcatggcgat tgccgccgaa 960
ggcgacctgc tggcagcgtg gtgcgatttc gcgaactctc aaggtatgca gccgggtcca 1020
ctggttgctc cgacgggtca tccgagcctg cgtcagttgc cggtggagcg cgtggtgccg 1080
ggtgatctgg aggatcttca gaccctctta tgcgcacatc cggccgactt actggtggcg 1140
aactcccacg cccgtgattt agcagagcaa ttcgccctgc cgctggtgcg cgcaggcttc 1200
ccgctgtttg acaaactggg cgaatttcgt cgtgttcgcc agggttatag cggtatgcgt 1260
gataccctgt tcgagttggc gaacctgatc cgtgaacgcc atcatcatct ggctcattat 1320
cgcagcccgc tgcgccagaa cccagaatcc tcgttgtcta cgggtggcgc gtacgcagcg 1380
gattaa 1386

<210> SEQ ID NO 230
<211> LENGTH: 825
<212> TYPE: DNA
<213> ORGANISM: Artificial Sequence
<220> FEATURE:
<223> OTHER INFORMATION: synthetic Klebsiella pneumoniae nifU

<400> SEQUENCE: 230

```
atgtggaact acagcgagaa agtcaaggac catttcttca atccgcgcaa cgcgcgtgtt     60

gtggataacg caaatgcggt gggcgacgtc ggcagcttat cttgtggcga tgctctccgc    120

ttgatgctgc gcgtggaccc gcagagcgaa atcatcgaag aagcgggctt tcagaccttc    180

ggctgcggca gcgcgattgc gtcgtccagc gcactgacgg agctgatcat cggtcacacc    240

ctggcggaag cgggtcagat caccaaccag cagatcgccg actatctgga cggcttaccg    300

ccggaaaaga tgcactgctc tgtaatgggc caggaagctc ttcgtgcggc cattgctaac    360

tttcgcggtg aatcgctgga agaggagcat gacgagggta agctgatctg caagtgcttc    420

ggcgtcgatg aaggccatat tcgccgtgct gtccagaaca acggtcttac gactctggcc    480

gaggtgatca attacaccaa ggcaggtggc ggttgtacca gctgccatga gaaaatcgag    540

ctggccctgg ccgagattct cgcccaacag ccgcaaacca ccccggcagt tgcgtccggt    600

aaagatccgc actggcagag cgtcgtggat accatcgctg aactgcgtcc acatatccaa    660

gcggacggtg gtgacatggc gctgttgtcc gtgacgaacc accaagtgac tgtttcgctg    720

tcgggcagct gttctggctg catgatgacc gacatgaccc tggcgtggct gcaacagaaa    780

ttgatggagc gtaccggctg ctatatggaa gttgttgccg cctaa                    825
```

<210> SEQ ID NO 231
<211> LENGTH: 1203
<212> TYPE: DNA
<213> ORGANISM: Artificial Sequence
<220> FEATURE:
<223> OTHER INFORMATION: synthetic Klebsiella pneumoniae nifS

<400> SEQUENCE: 231

```
atgaaacaag tgtacctgga caacaacgcg accacccgcc tggacccgat ggttctggaa     60

gcgatgatgc cgtttctcac ggatttctat ggcaatccgt ccagcatcca tgacttcggc    120

atcccggcac aagcggcgct ggaacgtgcg caccagcaag ctgcggcact gctgggcgca    180

gagtacccgt ctgaaatcat tttcacgagc tgtgcgaccg aggccactgc aaccgccatt    240

gcgtcggcca tcgcgttatt gccggaacgc cgcgaaatca tcacctcggt agtggagcac    300

ccggctacgc tggcggcgtg cgagcacctg gaacgccaag gctatcgcat ccatcgcatt    360

gcggtggata gcgaaggtgc gctggacatg gcccagttcc gtgcagcgct ctcgccgcgt    420

gtcgcgttgg tgagcgtgat gtgggccaac aacgaaaccg gcgtgctgtt cccgattggc    480

gaaatggccg agcttgccca cgagcagggc gctctgttcc actgcgatgc cgttcaggtc    540

gttggcaaaa tcccaattgc tgttggccag acgcgcatcg acatgctgtc ttgctccgcg    600

cacaagtttc atggtccgaa gggtgttggt tgcttgtact tacgtcgtgg cacgcgcttt    660

cgtccgctgc ttcgcggtgg ccatcaagaa tatggtcgcc gtgccggcac tgagaatatc    720

tgtggcatcg tcggcatggg cgctgcgtgc gaactggcga acatccatct gccgggtatg    780

acccatattg gccagttacg caatcgcctg gagcaccgtc tgctcgccag cgtgccgtcc    840

gtgatggtta tgggcggtgg tcagccgcgt gtaccgggta ctgtcaacct ggcgttcgag    900

tttatcgaag gtgaagcgat cctgctcttg ctgaaccagg ctggcattgc cgcaagctcc    960

ggctccgcgt gtacctctgg cagcttggag ccgagccatg tgatgcgcgc catgaacatt   1020

ccatacaccg cggctcacgg caccattcgt tttagcctga gccgttatac gcgcgagaaa   1080

gagatcgact acgtcgttgc gaccctcccg ccaatcattg atcgtctgcg tgccttgtcc   1140

ccgtattggc agaatggtaa gccgcgtccg gcagatgcag tctttacccc ggtttacggt   1200
```

taa 1203

<210> SEQ ID NO 232
<211> LENGTH: 1143
<212> TYPE: DNA
<213> ORGANISM: Artificial Sequence
<220> FEATURE:
<223> OTHER INFORMATION: synthetic Klebsiella pneumoniae nifV

<400> SEQUENCE: 232
atggagcgcg tcttgatcaa cgatactacc ctgcgtgatg gcgaacaatc tccgggcgta 60
gcgtttcgta cctccgagaa agttgccatc gcggaggcac tgtacgctgc gggtatcacc 120
gcgatggaag tcggcactcc ggcgatgggt gatgaagaga tcgcccgcat tcagctggtg 180
cgtcgtcaac tgccggacgc gacgcttatg acctggtgcc gtatgaacgc tctggaaatc 240
cgtcagagcg cggatctggg tattgactgg gtggatatct cgatcccagc atccgacaag 300
ctgcgtcagt acaagctgcg tgagccgctg gccgtgctgc tggagcgcct tgcgatgttt 360
atccatctgg cccacacgtt aggcctcaaa gtatgtattg gttgcgagga tgcgagccgt 420
gcgtctggtc agaccctgcg cgccattgcc gaggtggccc agcaatgcgc ggctgcgcgc 480
ttgcgttacg ctgacaccgt gggcctgctg gacccgttca ccaccgcagc ccagatcagc 540
gccctgcgtg acgtttggtc gggcgagatc gagatgcatg ctcacaatga tctgggcatg 600
gctaccgcga acacgctggc ggcagtttcg gctggcgcca cgtcggtgaa cactaccgtc 660
ctcggtctgg gtgaacgtgc aggcaacgca gccctggaaa ccgttgcgct gggcctggaa 720
cgctgcctgg gcgtggaaac cggcgtccat ttcagcgcgc tcccagcgct ctgtcagcgc 780
gtcgcggagg ctgcacagcg cgcaatcgac ccgcaacagc cgctggtggg tgaattggtt 840
ttcacccacg agtctggtgt tcacgttgcg gcgctgctgc gcgacagcga atcctatcaa 900
tctattgccc caagcctcat gggccgtagc taccgtctgg tgctcggcaa gcattcgggt 960
cgtcaggctg tcaacggtgt tttcgaccag atgggttacc acctgaatgc ggcgcagatc 1020
aatcagttgc tgccggccat tcgccgcttc gccgagaatt ggaaacgctc tccgaaagac 1080
tacgaactgg ttgcgatcta tgacgaattg tgcggtgaat ccgcccttcg tgctcgcggc 1140
taa 1143

<210> SEQ ID NO 233
<211> LENGTH: 258
<212> TYPE: DNA
<213> ORGANISM: Artificial Sequence
<220> FEATURE:
<223> OTHER INFORMATION: synthetic Klebsiella pneumoniae nifW

<400> SEQUENCE: 233
atggagtggt tttaccagat tccgggtgta gacgaattgc gcagcgctga atccttcttt 60
cagttcttcg cggttccata ccagccggaa ctgctgggcc gctgctcgct tccggtgtta 120
gcgacgttcc accgtaaact gcgtgcggag gtcccgctgc aaaaccgtct ggaggacaat 180
gatcgtgcgc cgtggctctt ggcgcgccgc ctcctggccg aatcttatca gcagcaattt 240
caggagagcg gcacctaa 258

<210> SEQ ID NO 234
<211> LENGTH: 447
<212> TYPE: DNA
<213> ORGANISM: Artificial Sequence
<220> FEATURE:
<223> OTHER INFORMATION: synthetic Klebsiella pneumoniae nifZ

<400> SEQUENCE: 234
atgcgcccga aattcacctt ctctgaagag gtccgcgtag ttcgcgcgat tcgtaatgat 60
ggcaccgtgg cgggttttgc gccaggtgcg ctgctggttc gtcgcggttc gacgggcttt 120
gtgcgtgact ggggtgtgtt cctgcaagac cagatcatct atcaaatcca ctttccggaa 180
accgaccgca ttatcggctg tcgcgagcag gagttaatcc cgattaccca gccgtggttg 240
gctggtaacc tccagtatcg tgacagcgtc acgtgccaaa tggcactggc tgtcaacggt 300
gacgtggttg tgagcgccgg tcaacgtggc cgtgtggagg ccactgatcg tggcgaactt 360
ggcgattcct acaccgtgga cttcagcggc cgttggttcc gcgttccggt ccaggccatc 420
gcgctgattg aagagcgcga agaataa 447

<210> SEQ ID NO 235
<211> LENGTH: 801
<212> TYPE: DNA
<213> ORGANISM: Artificial Sequence
<220> FEATURE:
<223> OTHER INFORMATION: synthetic Klebsiella pneumoniae nifM

<400> SEQUENCE: 235
atgaatccgt ggcagcgctt tgcccgtcaa cgccttgctc gcagccgctg gaaccgtgat 60
ccggctgctc tcgacccagc cgatacccca gcgttcgagc aggcgtggca gcgtcaatgc 120
catatggaac aaaccatcgt agcgcgtgtc ccggaaggcg atattccggc tgccttactg 180
gaaaacatcg cggccagcct ggcgatctgg ctggacgagg gtgacttcgc tccgccggag 240
cgcgctgcga ttgtgcgtca tcatgcacgt ctggagctgg cgtttgccga cattgcccgc 300
caggcaccgc aaccggatct gagcacggtt caagcgtggt atctgcgtca ccagactcaa 360
ttcatgcgtc cggagcagcg tctgacccgt cacctgctcc tgacggtcga taatgatcgc 420
gaggcggtgc atcaacgcat ccttggcctg tatcgtcaga tcaacgcgag ccgtgacgcc 480
ttcgccccac tggcacagcg ccactctcat tgcccgtccg ccttggaaga aggccgtctg 540
ggctggatct cccgtggtct gctgtacccg cagctcgaaa ccgcgttgtt tagcctggcg 600
gaaaacgcac tgtcgctgcc gattgcgtcg gaattgggtt ggcacctgtt atggtgcgag 660
gccattcgtc cggcagcccc gatggagccg caacaggccc ttgaatctgc gcgcgactac 720
ttgtggcagc agagccagca gcgccaccag cgtcaatggc tggagcagat gatttcccgc 780
caaccgggcc tgtgtggtta a 801

<210> SEQ ID NO 236
<211> LENGTH: 531
<212> TYPE: DNA
<213> ORGANISM: Artificial Sequence
<220> FEATURE:
<223> OTHER INFORMATION: synthetic Klebsiella pneumoniae nifF

<400> SEQUENCE: 236
atggcgaaca tcggcatctt ctttggtacg gataccggca aaacccgcaa gattgcgaag 60
atgattcaca aacagctggg cgagctggcc gatgccccgg ttaacatcaa tcgtaccact 120
ttggatgact ttatggctta cccagtcctg ttgctcggca cgccgacgct tggtgatggt 180
caactgccgg gcttagaggc gggctgcgag agcgaaagct ggtctgagtt tatctccggt 240
ctggatgacg cttccctgaa gggcaaaacc gtggcgctgt ttggcctggg cgaccagcgt 300
ggttacccgg acaacttcgt gtcgggtatg cgtccgctgt tcgacgcgct gagcgcccgt 360
ggcgcccaga tgattggtag ctggccgaac gaaggttatg agtttagcgc atcgtccgcg 420
ctggaaggcg accgcttcgt cggcttggtg ctggatcaag acaatcagtt cgaccagacc 480
gaagcgcgcc tggcgtcttg gcttgaagag atcaaacgca ccgttctgta a 531

<210> SEQ ID NO 237
<211> LENGTH: 1407
<212> TYPE: DNA
<213> ORGANISM: Artificial Sequence
<220> FEATURE:
<223> OTHER INFORMATION: synthetic Klebsiella pneumoniae nifB

<400> SEQUENCE: 237
atgacctctt gttcgtcgtt ttctggcggt aaagcgtgcc gtccggccga tgactccgcg 60
ctgactccgc tggtggccga caaggcagct gcgcacccgt gctatagccg ccacggccat 120
caccgcttcg cgcgtatgca cctgccagtc gctccggcct gcaacttaca atgcaactac 180
tgcaaccgca agttcgattg cagcaatgaa agccgtccgg gcgtgtcctc taccctgctg 240
acgccggaac aggctgtggt gaaggtgcgc caggtcgccc aagctatccc gcagctgtcg 300
gtggtcggta ttgctggtcc gggcgatccg cttgcgaata tcgcccgcac cttccgtacc 360
ttggagctta ttcgcgaaca gttgccggac ctgaaactgt gcctgagcac caacggcttg 420
gtgctgccag atgccgttga tcgtctgctc gatgtgggcg tggatcacgt taccgtcacc 480
attaacaccc tggacgcaga aatcgcagcg caaatctacg cgtggttgtg gctggatggc 540
gaacgctact ccggtcgcga agccggcgaa attctcattg cccgccagct ggaaggcgta 600
cgtcgcctga ccgcgaaagg tgtgctcgtc aagatcaaca gcgtattgat tccgggcatc 660
aatgacagcg gcatggcggg tgttagccgt gcgctgcgcg cgtctggtgc gttcatccac 720
aacatcatgc cactgattgc gcgtccggag catggcactg ttttcggtct gaacggccag 780
ccggaaccgg acgcggaaac cctggcggcg acgcgctccc gctgcggcga ggttatgcca 840
caaatgaccc actgccacca gtgccgtgcc gacgcgattg gcatgcttgg tgaggatcgc 900
tcgcaacagt ttacgcaatt accggctccg gagtccctcc cggcctggct gccgatcctg 960
catcagcgtg ctcagttgca tgcgagcatc gccacgcgcg gtgagagcga agccgatgac 1020
gcctgcctgg tggccgttgc gtcgagccgt ggcgatgtaa ttgactgcca tttcggccat 1080
gccgaccgtt tctatatcta tagcctgtct gcggctggta tggttctggt taacgaacgt 1140
ttcaccccga aatactgcca gggtcgcgat gactgcgagc cgcaggacaa tgccgcacgc 1200
tttgctgcca tccttgagtt gctggcggac gtcaaagcgg tgttttgtgt gcgtatcggc 1260
cataccccgt ggcaacagct ggagcaggaa ggcatcgaac cgtgcgtgga tggcgcctgg 1320
cgtccggtat ccgaggtcct gccggcatgg tggcagcagc gccgtggtag ctggccggct 1380
gcattgccgc acaaaggcgt tgcgtaa 1407

<210> SEQ ID NO 238
<211> LENGTH: 504
<212> TYPE: DNA
<213> ORGANISM: Artificial Sequence
<220> FEATURE:
<223> OTHER INFORMATION: synthetic Klebsiella pneumoniae nifQ

<400> SEQUENCE: 238
atgccgccat tggactggtt gcgtcgtttg tggttactct atcacgccgg caaaggcagc 60
tttccgcttc gtatgggctt gtcgccgcgt gactggcaag ctctgcgccg tcgcctgggc 120
gaggtggaaa cgccgctgga tggcgaaacc ctgacccgtc gccgtctgat ggcggagctg 180

```
aatgcgaccc gcgaagaaga acgccagcag ctgggtgcct ggctggccgg ttggatgcaa    240

caggatgccg gtccgatggc gcagattatc gcagaggtga gcctggcgtt caaccatctc    300

tggcaggacc ttggcctcgc gagccgcgct gaactgcgtc tgctgatgtc tgactgcttc    360

ccgcagctgg ttgttatgaa cgagcacaac atgcgctgga agaaattctt ttaccgccag    420

cgttgcctgc tgcaacaggg cgaagtcatc tgtcgcagcc cgtcttgcga tgaatgctgg    480

gaacgttctg cgtgctttga gtaa                                           504
```

<210> SEQ ID NO 239
<211> LENGTH: 206
<212> TYPE: PRT
<213> ORGANISM: Artificial Sequence
<220> FEATURE:
<223> OTHER INFORMATION: synthetic chimeric sigma factor ECF11_ECF02

<400> SEQUENCE: 239

```
Met Arg Ile Thr Ala Ser Leu Arg Thr Phe Cys His Leu Ser Thr Pro
 1               5                  10                  15

His Ser Asp Ser Thr Thr Ser Arg Leu Trp Ile Asp Glu Val Thr Ala
            20                  25                  30

Val Ala Arg Gln Arg Asp Arg Asp Ser Phe Met Arg Ile Tyr Asp His
        35                  40                  45

Phe Ala Pro Arg Leu Leu Arg Tyr Leu Thr Gly Leu Asn Val Pro Glu
    50                  55                  60

Gly Gln Ala Glu Glu Leu Val Gln Glu Val Leu Leu Lys Leu Trp His
65                  70                  75                  80

Lys Ala Glu Ser Phe Asp Pro Ser Lys Ala Ser Leu Gly Thr Trp Leu
                85                  90                  95

Phe Arg Ile Ala Arg Asn Leu Tyr Ile Asp Ser Val Arg Lys Asp Arg
            100                 105                 110

Gly Trp Val Gln Val Gln Asn Ser Leu Glu Gln Leu Glu Arg Leu Glu
        115                 120                 125

Ala Ile Ser Asn Pro Glu Asn Leu Met Leu Ser Glu Glu Leu Arg Gln
    130                 135                 140

Ile Val Phe Arg Thr Ile Glu Ser Leu Pro Glu Asp Leu Arg Met Ala
145                 150                 155                 160

Ile Thr Leu Arg Glu Leu Asp Gly Leu Ser Tyr Glu Glu Ile Ala Ala
                165                 170                 175

Ile Met Asp Cys Pro Val Gly Thr Val Arg Ser Arg Ile Phe Arg Ala
            180                 185                 190

Arg Glu Ala Ile Asp Asn Lys Val Gln Pro Leu Ile Arg Arg
        195                 200                 205
```

<210> SEQ ID NO 240
<211> LENGTH: 187
<212> TYPE: PRT
<213> ORGANISM: Artificial Sequence
<220> FEATURE:
<223> OTHER INFORMATION: synthetic chimeric sigma factor ECF02_ECF11

<400> SEQUENCE: 240

```
Met Ser Glu Gln Leu Thr Asp Gln Val Leu Val Glu Arg Val Gln Lys
 1               5                  10                  15

Gly Asp Gln Lys Ala Phe Asn Leu Leu Val Val Arg Tyr Gln His Lys
            20                  25                  30

Val Ala Ser Leu Val Ser Arg Tyr Val Pro Ser Gly Asp Val Pro Asp
```

```
        35                  40                  45

Val Val Gln Glu Ala Phe Ile Lys Ala Tyr Arg Ala Leu Asp Ser Phe
    50                  55                  60

Arg Gly Asp Ser Ala Phe Tyr Thr Trp Leu Tyr Arg Ile Ala Val Asn
65                  70                  75                  80

Thr Ala Lys Asn Tyr Leu Val Ala Gln Gly Arg Arg Pro Pro Ser Ser
                85                  90                  95

Asp Val Asp Ala Ile Glu Ala Glu Asn Phe Glu Gln Leu Glu Arg Leu
            100                 105                 110

Glu Ala Pro Val Asp Arg Thr Leu Asp Tyr Ser Gln Arg Gln Glu Gln
        115                 120                 125

Gln Leu Asn Ser Ala Ile Gln Asn Leu Pro Thr Asp Gln Ala Lys Val
    130                 135                 140

Leu Arg Met Ser Tyr Phe Glu Ala Leu Ser His Arg Glu Ile Ser Glu
145                 150                 155                 160

Arg Leu Asp Met Pro Leu Gly Thr Val Lys Ser Cys Leu Arg Leu Ala
                165                 170                 175

Phe Gln Lys Leu Arg Ser Arg Ile Glu Glu Ser
            180                 185


<210> SEQ ID NO 241
<211> LENGTH: 883
<212> TYPE: PRT
<213> ORGANISM: Enterobacteria phage T7
<220> FEATURE:
<223> OTHER INFORMATION: Enterobacteria phage T7 RNA polymerase (RNAP)

<400> SEQUENCE: 241

Met Asn Thr Ile Asn Ile Ala Lys Asn Asp Phe Ser Asp Ile Glu Leu
 1              5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
```

```
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Ala Val
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
    450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
    530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640
```

```
Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala


<210> SEQ ID NO 242
<211> LENGTH: 48
<212> TYPE: DNA
<213> ORGANISM: Artificial Sequence
<220> FEATURE:
<223> OTHER INFORMATION: synthetic Enterobacteria phage T7 stem loop
      terminator seed sequence
<220> FEATURE:
<221> NAME/KEY: modified_base
<222> LOCATION: (3)...(6)
<223> OTHER INFORMATION: n = g, a, c or t

<400> SEQUENCE: 242

tannnnaacc sswwssssss tcwwwwcgss sssswwssgg ttttttgt                  48


<210> SEQ ID NO 243
<211> LENGTH: 29
<212> TYPE: DNA
<213> ORGANISM: Artificial Sequence
<220> FEATURE:
<223> OTHER INFORMATION: synthetic Enterobacteria phage T7 terminator 52

<400> SEQUENCE: 243

tataaaacgg ggggctaggg gttttttgt                                       29


<210> SEQ ID NO 244
```

<210> SEQ ID NO 244
<211> LENGTH: 48
<212> TYPE: DNA
<213> ORGANISM: Artificial Sequence
<220> FEATURE:
<223> OTHER INFORMATION: synthetic Enterobacteria phage T7 terminator 23

<400> SEQUENCE: 244
tactcgaacc cctagcccgc tcttatcggg cggctagggg ttttttgt                48

<210> SEQ ID NO 245
<211> LENGTH: 37
<212> TYPE: DNA
<213> ORGANISM: Artificial Sequence
<220> FEATURE:
<223> OTHER INFORMATION: synthetic Enterobacteria phage T7 terminator 72

<400> SEQUENCE: 245
tagcagaacc gctaacgggg gcgaaggggt tttttgt                             37

<210> SEQ ID NO 246
<211> LENGTH: 48
<212> TYPE: DNA
<213> ORGANISM: Artificial Sequence
<220> FEATURE:
<223> OTHER INFORMATION: synthetic Enterobacteria phage T7 terminator 48

<400> SEQUENCE: 246
tactcgaacc cctagcccgc tcttatcggg cggctagggg ttttttgt                48

<210> SEQ ID NO 247
<211> LENGTH: 29
<212> TYPE: DNA
<213> ORGANISM: Artificial Sequence
<220> FEATURE:
<223> OTHER INFORMATION: synthetic Enterobacteria phage T7 terminator 1

<400> SEQUENCE: 247
tacatatcgg gggggtaggg gttttttgt                                      29

<210> SEQ ID NO 248
<211> LENGTH: 29
<212> TYPE: DNA
<213> ORGANISM: Artificial Sequence
<220> FEATURE:
<223> OTHER INFORMATION: synthetic Enterobacteria phage T7 terminator 2

<400> SEQUENCE: 248
tacatatcgg gggggtaggg gttttttgt                                      29

<210> SEQ ID NO 249
<211> LENGTH: 48
<212> TYPE: DNA
<213> ORGANISM: Artificial Sequence
<220> FEATURE:
<223> OTHER INFORMATION: synthetic Enterobacteria phage T7 wild type
      (WT) terminator

<400> SEQUENCE: 249
tagcataacc ccttggggcc tctaaacggg tcttgagggg ttttttgt                48

<210> SEQ ID NO 250
<211> LENGTH: 47
<212> TYPE: DNA
<213> ORGANISM: Artificial Sequence
<220> FEATURE:
<223> OTHER INFORMATION: synthetic Enterobacteria phage T7 terminator 31

```
<400> SEQUENCE: 250

taccctaacc ccttccccgg tcaatcgggg cggatggggt tttttgt          47

<210> SEQ ID NO 251
<211> LENGTH: 47
<212> TYPE: DNA
<213> ORGANISM: Artificial Sequence
<220> FEATURE:
<223> OTHER INFORMATION: synthetic Enterobacteria phage T7 terminator 58

<400> SEQUENCE: 251

tagaccaacc ccttgcggcc tcaatcgggg gggatggggt tttttgt          47

<210> SEQ ID NO 252
<211> LENGTH: 37
<212> TYPE: DNA
<213> ORGANISM: Artificial Sequence
<220> FEATURE:
<223> OTHER INFORMATION: synthetic Enterobacteria phage T7 terminator 25

<400> SEQUENCE: 252

tactctaacc ccatcggccg tcttaggggt tttttgt                     37

<210> SEQ ID NO 253
<211> LENGTH: 48
<212> TYPE: DNA
<213> ORGANISM: Artificial Sequence
<220> FEATURE:
<223> OTHER INFORMATION: synthetic Enterobacteria phage T7 terminator 17

<400> SEQUENCE: 253

tacctcaacc ccttccgccc tcatatcgcg gggcatgcgg ttttttgt         48

<210> SEQ ID NO 254
<211> LENGTH: 39
<212> TYPE: PRT
<213> ORGANISM: Artificial Sequence
<220> FEATURE:
<223> OTHER INFORMATION: synthetic Enterobacteria phage T7 RNA
      polymerase (RNAP) specificity loop sequence

<400> SEQUENCE: 254

Val Trp Gln Glu Tyr Lys Lys Pro Ile Gln Thr Arg Leu Asn Leu Met
 1               5                  10                  15

Phe Leu Gly Gln Phe Arg Leu Gln Pro Thr Ile Asn Thr Asn Lys Asp
             20                  25                  30

Ser Glu Ile Asp Ala His Lys
         35

<210> SEQ ID NO 255
<211> LENGTH: 39
<212> TYPE: PRT
<213> ORGANISM: Artificial Sequence
<220> FEATURE:
<223> OTHER INFORMATION: synthetic Enterobacteria phage T3 RNA
      polymerase (RNAP) specificity loop sequence

<400> SEQUENCE: 255

Val Trp Gln Glu Tyr Lys Lys Pro Ile Gln Lys Arg Leu Asp Met Ile
 1               5                  10                  15

Phe Leu Gly Gln Phe Arg Leu Gln Pro Thr Ile Asn Thr Asn Lys Asp
             20                  25                  30

Ser Glu Ile Asp Ala His Lys
         35
```

<210> SEQ ID NO 256
<211> LENGTH: 23
<212> TYPE: DNA
<213> ORGANISM: Artificial Sequence
<220> FEATURE:
<223> OTHER INFORMATION: synthetic Enterobacteria phage T3 RNA polymerase (RNAP) promoter sequence

<400> SEQUENCE: 256
taataaccct cactataggg aga 23

<210> SEQ ID NO 257
<211> LENGTH: 39
<212> TYPE: PRT
<213> ORGANISM: Artificial Sequence
<220> FEATURE:
<223> OTHER INFORMATION: synthetic Enterobacteria phage K1F RNA polymerase (RNAP) specificity loop sequence

<400> SEQUENCE: 257

```
Val Trp Gln Glu Tyr Lys Lys Pro Ile Gln Thr Arg Leu Asn Leu Met
 1               5                  10                  15

Phe Leu Gly Ser Phe Asn Leu Gln Pro Thr Val Asn Thr Asn Lys Asp
            20                  25                  30

Ser Glu Ile Asp Ala His Lys
        35
```

<210> SEQ ID NO 258
<211> LENGTH: 23
<212> TYPE: DNA
<213> ORGANISM: Artificial Sequence
<220> FEATURE:
<223> OTHER INFORMATION: synthetic Enterobacteria phage K1F RNA polymerase (RNAP) promoter sequence

<400> SEQUENCE: 258
taataactat cactataggg aga 23

<210> SEQ ID NO 259
<211> LENGTH: 39
<212> TYPE: PRT
<213> ORGANISM: Artificial Sequence
<220> FEATURE:
<223> OTHER INFORMATION: synthetic Enterobacteria phage N4 RNA polymerase (RNAP) specificity loop sequence

<400> SEQUENCE: 259

```
Val Trp Gln Glu Tyr Lys Lys Pro Ile Gln Thr Arg Ile Asp Cys Val
 1               5                  10                  15

Ile Leu Gly Thr His Arg Met Ala Leu Thr Ile Asn Thr Asn Lys Asp
            20                  25                  30

Ser Glu Ile Asp Ala His Lys
        35
```

<210> SEQ ID NO 260
<211> LENGTH: 23
<212> TYPE: DNA
<213> ORGANISM: Artificial Sequence
<220> FEATURE:
<223> OTHER INFORMATION: synthetic Enterobacteria phage N4 RNA polymerase (RNAP) promoter sequence

<400> SEQUENCE: 260
taataaccca cactataggg aga 23

<210> SEQ ID NO 261
<211> LENGTH: 498
<212> TYPE: DNA
<213> ORGANISM: Salmonella typhimurium
<220> FEATURE:
<223> OTHER INFORMATION: transcriptional activator sicA

<400> SEQUENCE: 261
atggattatc aaaataatgt cagcgaagaa cgtgttgcgg aaatgatttg ggatgccgtt 60
agtgaaggcg ccacgctaaa agacgttcat gggatccctc aagatatgat ggacggttta 120
tatgctcatg cttatgagtt ttataaccag ggacgactgg atgaagctga gacgttcttt 180
cgtttcttat gcatttatga tttttacaat cccgattaca ccatgggact ggcggcagta 240
tgccaactga aaaaacaatt tcagaaagca tgtgaccttt atgcagtagc gtttacgtta 300
cttaaaaatg attatcgccc cgtttttttt accgggcagt gtcaattatt aatgcgtaag 360
gcagcaaaag ccagacagtg ttttgaactt gtcaatgaac gtactgaaga tgagtctctg 420
cgggcaaaag cgttggtcta tctggaggcg ctaaaaacgg cggagacaga gcagcacagt 480
gaacaagaaa aggaataa 498

<210> SEQ ID NO 262
<211> LENGTH: 498
<212> TYPE: DNA
<213> ORGANISM: Artificial Sequence
<220> FEATURE:
<223> OTHER INFORMATION: synthetic Salmonella typhimurium mutant
transcriptional activator sicA*

<400> SEQUENCE: 262
atggattatc aaaataatgt cagcgaagaa cgtgttgcgg aaatgatttg ggatgccgtt 60
agtgaaggcg ccacgctaaa agacgttcat gggatccctc aagatatgat ggacggttta 120
tatgctcatg cttatgagtt ttataaccag ggacgactgg atgaagctga gacgttcttt 180
cgttacttat gcatttatga tttttacaat cccgattaca ccatgggact ggcggcagta 240
tgccaactga aaaaacaatt tcagaaagca tgtgaccttt atgcagtagc gtttacgtta 300
cttaaaaatg attatcgccc cgtttttttt accgggcagt gtcaattatt aatgcgtaag 360
gcagcaaaag ccagacagtg ttttgaactt gtcaatgaac gtactgaaga tgagtctctg 420
cgggcaaaag cgttggtcta tctggaggcg ctaaaaacgg cggagacaga gcagcacagt 480
gaacaagaaa aggaataa 498

<210> SEQ ID NO 263
<211> LENGTH: 750
<212> TYPE: DNA
<213> ORGANISM: Salmonella typhimurium
<220> FEATURE:
<223> OTHER INFORMATION: transcriptional activator invF with new start
codon

<400> SEQUENCE: 263
atgctaaata cgcaggaagt acttaaagaa ggagagaagc ggaaaatccg cagcccggaa 60
gcatggttta tacagacgtg ttccgcgcaa aagctgcata tgtcattttc tgaaagccga 120
cacaatgaaa attgcctgat tcaggaaggc gcgctgcttt tttgcgagca ggccgttgtc 180
gcaccagtat caggagacct ggtttttcga ccgttaaaaa ttgaagtact cagcaaatta 240
ctggcattta tcgatggcgc aggattagtg gacacgacat atgctgaatc cgataaatgg 300
gttttgctga gtcctgagtt tcgcgctatt tggcaagatc gtaaacgctg cgagtactgg 360
tttttgcagc aaattattac gccttctccg gccttcaata aggtactggc gctgttacga 420
aaaagcgaga gttactggtt ggttggctat ttactcgctc agtcaaccag cggcaacacg 480
atgagaatgc tgggagaaga ctatggcgtt tcttataccc attttcgtcg tttgtgcagc 540
agagcgttgg gcggaaaagc gaagagtgaa ttacgaaact ggcgtatggc gcaatcgctg 600
ctgaatagtg tagaaggcca cgagaacatc acccaattag ccgttaatca tggttactca 660
tcgccttcac atttttctag tgagatcaaa gagctgatcg gcgtttcgcc gcggaaatta 720
tcaaatatta ttcaattggc agacaaatga 750

<210> SEQ ID NO 264
<211> LENGTH: 163
<212> TYPE: DNA
<213> ORGANISM: Artificial Sequence
<220> FEATURE:
<223> OTHER INFORMATION: synthetic promoter psicA

<400> SEQUENCE: 264
ccacaagaaa cgaggtacgg cattgagccg cgtaaggcag tagcgatgta ttcattgggc 60 gtttttgaa tgttcactaa ccaccgtcgg ggtttaataa ctgcatcaga taaacgcagt 120
cgttaagttc tacaaagtcg gtgacagata acaggagtaa gta 163

<210> SEQ ID NO 265
<211> LENGTH: 468
<212> TYPE: DNA
<213> ORGANISM: Shigella flexneri
<220> FEATURE:
<223> OTHER INFORMATION: transcriptional activator ipgC

<400> SEQUENCE: 265
atgtctttaa atatcaccga aaatgaaagc atctctactg cagtaattga tgcaattaac 60
tctggcgcta cactgaaaga tattaatgca attcctgatg atatgatgga tgacatttat 120
tcatatgctt atgactttta caacaaagga agaatagagg aagctgaagt tttcttcagg 180
tttttatgta tatacgactt ttacaatgta gactacatta tgggactcgc agctatttat 240
cagataaaag aacagttcca acaagcagca gacctttatg ctgtcgcttt tgcattagga 300
aaaaatgact atacaccagt attccatact ggacaatgtc agcttcggtt gaaagccccc 360
ttaaaagcta aagagtgctt cgaactcgta attcaacaca gcaatgatga aaaattaaaa 420
ataaaagcac aatcatactt ggacgcaatt caggatatca aggagtaa 468

<210> SEQ ID NO 266
<211> LENGTH: 756
<212> TYPE: DNA
<213> ORGANISM: Artificial Sequence
<220> FEATURE:
<223> OTHER INFORMATION: synthetic codon optimized Shigella flexneri
mxiE

<400> SEQUENCE: 266
atgagtaaat ataaaggcct gaacaccagc aacatgttct acatctacag ctctggtcat 60
gaaccggtga acgttgaact ggtgaaagat aaagaacgta acatcatcga actggcaccg 120
gcgtggaaag gctttttctt tgtgcgtaac cagaacatca aattcagcga taacgttaac 180
taccactacc gcttcaacat caactcttgc gcaaaattcc tggcgttttg ggattatttt 240
agcggcgccc tggttgaaca ttctcacgca gaaaaatgca tccatttcta ccacgaaaac 300

-continued

```
gatctgcgtg atagctgtaa tacggaatct atgctggata aactgatgct gcgcttcatt    360

tttagtagcg atcagaacgt gtctaatgcc ctggcaatga tccgtatgac cgaaagttat    420

catctggttc tgtacctgct gcgtacgatt gaaaaagaaa aagaagtgcg catcaaaagc    480

ctgaccgaac actatggcgt ttctgaagcg tactttcgta gtctgtgtcg caaagcgctg    540

ggtgccaaag tgaaagaaca gctgaacacg tggcgcctgg tgaatggcct gctggatgtt    600

ttcctgcata accagaccat tacgagcgcg gccatgaaca atggttatgc gtctaccagt    660

cacttcagca atgaaattaa aacgcgtctg ggctttagtg cccgcgaact gagcaacatc    720

accttcctgg tgaagaaaat taatgaaaaa atctaa                              756
```

```
<210> SEQ ID NO 267
<211> LENGTH: 350
<212> TYPE: DNA
<213> ORGANISM: Artificial Sequence
<220> FEATURE:
<223> OTHER INFORMATION: synthetic promoter pipaH9.8

<400> SEQUENCE: 267

gcgaaaatga catcaaaaac gccattaacc tgatgttctg gggaatataa atgtcaggct     60

agggtcaaaa atcgtggcgt tgacaaaatg gctgcgttac gtcattgagc atatccagga    120

ctggccggca aaccgggtac gcgatctgtt gccttggaaa gttgatctga cctctcagta    180

aatatcaata cggttctgac gagccgctta ccgttcaaat atgaagtacg atgtttaact    240

aaccgaaaaa caagaacaat acggtgcaaa caggccattc acggttaact gaaacagtat    300

cgttttttta cagccaattt tgtttatcct tattataata aaaaagtgct               350
```

```
<210> SEQ ID NO 268
<211> LENGTH: 350
<212> TYPE: DNA
<213> ORGANISM: Artificial Sequence
<220> FEATURE:
<223> OTHER INFORMATION: synthetic promoter pipaH9.8* with mutation

<400> SEQUENCE: 268

gcgaaaatga catcaaaaac gccattaacc tgatgttctg gggaatataa atgtcaggct     60

agggtcaaaa atcgtggcgt tgacaaaatg gctgcgttac gtcattgagc atatccagga    120

ctggccggca aaccgggtac gcgatctgtt gccttggaaa gttgatctga cctctcagta    180

aatatcaata cggttctgac gagccgctta ccgttcaaat atgaagtacg atgtttaact    240

aaccgaaaaa caagaacaat acggtgcaaa caggccattc acggttaact gaaacagtat    300

cgttttttta cagccaattt tgtttatcct tattaagata aaaaagtgct               350
```

```
<210> SEQ ID NO 269
<211> LENGTH: 438
<212> TYPE: DNA
<213> ORGANISM: Pseudomonas aeruginosa
<220> FEATURE:
<223> OTHER INFORMATION: transcriptional activator exsC

<400> SEQUENCE: 269

atggatttaa cgagcaaggt caaccgactg cttgccgagt tcgcaggccg tatcggtttg     60

ccttccctgt ccctcgacga ggagggcatg gcgagcctcc tgttcgacga acaggtgggc    120

gtcaccctgt tgctgctcgc cgagcgcgag cgtctgttgc tggaggccga tgtggcgggc    180

atcgatgtgc tgggcgaggg gatctttcgc cagctcgcca gcttcaaccg ccattggcac    240

cgtttcgatc tgcatttcgg cttcgacgag ctgaccggca aggtccagtt gtatgcgcag    300
```

attctcgcag cgcaactgac cctcgaatgc ttcgaggcga ccttggccaa tctgctcgat 360
cacgccgagt tctggcagcg cctgctgccg tgcgacagtg atcgcgaggc ggtcgctgcg 420
gtcggcatga gggtttga 438

<210> SEQ ID NO 270
<211> LENGTH: 831
<212> TYPE: DNA
<213> ORGANISM: Pseudomonas aeruginosa
<220> FEATURE:
<223> OTHER INFORMATION: transcriptional activator exsD

<400> SEQUENCE: 270
atggagcagg aagacgataa gcagtactcc cgagaagcgg tgttcgctgg caggcgggta 60
tccgtggtgg gctcggacgc ccgctcgcgg ggtcgggtgc cgggttacgc atcgagcagt 120
ttgtatcgtg agtccggaat catcagtgcg cggcaactgg cgttgctgca gcggatgctg 180
ccgcgcctgc ggctggagca actgttccgc tgcgagtggt tgcagcagcg cctggcgcgc 240
ggcctggcgc tggggcgcga agaggtgcgg cagattctcc tctgcgcggc gcaggacgac 300
gacggctggt gctccgaact gggcgaccgg gtcaacctcg ccgtgccgca gtcgatgatc 360
gactgggtcc tgctgccggt ctatggctgg tgggaaagcc tgctcgacca ggcgatcccc 420
ggctggcgcc tgtcgctggt ggagctggag acccagtccc ggcaactgcg agtcaagtcc 480
gaattctggt cccgcgtggc cgagctggag ccggagcagg cccgcgagga actggccagg 540
gtcgccaagt gccaggcgcg cacccaggaa caggtggccg aactggccgg caagctggag 600
acggcttcgg cactggcgaa gagcgcctgg ccgaactggc agcggggcat ggcgacgctg 660
ctcgccagcg gcgggctggc cggcttcgag ccgatccccg aggtcctcga atgcctctgg 720
caacctctct gccggctgga cgacgacgtc ggcgcggcgg acgccgtcca ggcctggctg 780
cacgaacgca acctgtgcca ggcacaggat cacttctact ggcagagctg a 831

<210> SEQ ID NO 271
<211> LENGTH: 837
<212> TYPE: DNA
<213> ORGANISM: Pseudomonas aeruginosa
<220> FEATURE:
<223> OTHER INFORMATION: transcriptional activator exsA

<400> SEQUENCE: 271
atgcaaggag ccaaatctct tggccgaaag cagataacgt cttgtcattg gaacattcca 60
actttcgaat acagggtaaa caaggaagag ggcgtatatg ttctgctcga gggcgaactg 120
accgtccagg acatcgattc cactttttgc ctggcgcctg gcgagttgct tttcgtccgc 180
cgcggaagct atgtcgtaag taccaaggga aaggacagcc gaatactctg gattccatta 240
tctgcccagt ttctacaagg cttcgtccag cgcttcggcg cgctgttgag tgaagtcgag 300
cgttgcgacg agcccgtgcc gggcatcatc gcgttcgctg ccacgcctct gctggccggt 360
tgcgtcaagg ggttgaagga attgcttgtg catgagcatc cgccgatgct cgcctgcctg 420
aagatcgagg agttgctgat gctcttcgcg ttcagtccgc aggggccgct gctgatgtcg 480
gtcctgcggc aactgagcaa ccggcatgtc gagcgtctgc agctattcat ggagaagcac 540
tacctcaacg agtggaagct gtccgacttc tcccgcgagt tcggcatggg gctgaccacc 600
ttcaaggagc tgttcggcag tgtctatggg gtttcgccgc gcgcctggat cagcgagcgg 660
agaatcctct atgcccatca gttgctgctc aacagcgaca tgagcatcgt cgacatcgcc 720

-continued atggaggcgg gcttttccag tcagtcctat ttcacccaga gctatcgccg ccgtttcggc 780
tgcacgccga gccgctcgcg gcaggggaag gacgaatgcc gggctaaaaa taactga 837

<210> SEQ ID NO 272
<211> LENGTH: 80
<212> TYPE: DNA
<213> ORGANISM: Artificial Sequence
<220> FEATURE:
<223> OTHER INFORMATION: synthetic pesxD promoter

<400> SEQUENCE: 272
gaaggacgaa tgccgggcta aaaataactg acgtttttttg aaagcccggt agcggctgca 60
tgagtagaat cggcccaaat 80

<210> SEQ ID NO 273
<211> LENGTH: 80
<212> TYPE: DNA
<213> ORGANISM: Artificial Sequence
<220> FEATURE:
<223> OTHER INFORMATION: synthetic pexsC promoter

<400> SEQUENCE: 273
gatgtggctt ttttcttaaa agaaaagtct ctcagtgaca aaagcgatgc atagcccggt 60
gctagcatgc gctgagcttt 80

<210> SEQ ID NO 274
<211> LENGTH: 702
<212> TYPE: DNA
<213> ORGANISM: Artificial Sequence
<220> FEATURE:
<223> OTHER INFORMATION: synthetic red fluorescence protein (rfp, RFP)

<400> SEQUENCE: 274
atggcttcct ccgaagacgt tatcaaagag ttcatgcgtt tcaaagttcg tatggaaggt 60
tccgttaacg gtcacgagtt cgaaatcgaa ggtgaaggtg aaggtcgtcc gtacgaaggt 120
acgcagaccg ctaaactgaa agttaccaaa ggtggtccgc tgccgttcgc ttgggacatc 180
ctgtccccgc agttccagta cggttccaaa gcttacgtta aacacccggc tgacatcccg 240
gactacctga aactgtcctt cccggaaggt ttcaaatggg aacgtgttat gaacttcgaa 300
gacggtggtg ttgttaccgt tacccaggac tcctccctgc aagacggtga gttcatctac 360
aaagttaaac tgcgtggtac taacttcccg tccgacggtc cggttatgca gaaaaaaacc 420
atgggttggg aagcttccac cgaacgtatg tacccggaag acggtgctct gaaaggtgaa 480
atcaaaatgc gtctgaaact gaaagacggt ggtcactacg acgctgaagt taaaaccacc 540
tacatggcta aaaaaccggt tcagctgccg ggtgcttaca aaaccgacat caaactggac 600
atcacctccc acaacgaaga ctacaccatc gttgaacagt acgaacgtgc tgaaggtcgt 660
cactccaccg gtgctgcagc aaacgacgaa aactacgctt aa 702

<210> SEQ ID NO 275
<211> LENGTH: 43
<212> TYPE: DNA
<213> ORGANISM: Artificial Sequence
<220> FEATURE:
<223> OTHER INFORMATION: synthetic T5 phage buffer sequence

<400> SEQUENCE: 275
agttcgatga gagcgataac cctctacaaa taattttgtt taa 43

-continued

<210> SEQ ID NO 276
<211> LENGTH: 42
<212> TYPE: DNA
<213> ORGANISM: Artificial Sequence
<220> FEATURE:
<223> OTHER INFORMATION: synthetic T5 phage buffer sequence

<400> SEQUENCE: 276
ataaattgat aaacaaaaac ctctacaaat aattttgttt aa 42

<210> SEQ ID NO 277
<211> LENGTH: 43
<212> TYPE: DNA
<213> ORGANISM: Artificial Sequence
<220> FEATURE:
<223> OTHER INFORMATION: synthetic T5 phage buffer sequence

<400> SEQUENCE: 277
ataaatttga gagaggagtt cctctacaaa taattttgtt taa 43

<210> SEQ ID NO 278
<211> LENGTH: 43
<212> TYPE: DNA
<213> ORGANISM: Artificial Sequence
<220> FEATURE:
<223> OTHER INFORMATION: synthetic T5 phage buffer sequence

<400> SEQUENCE: 278
attaaagagg agaaattaac cctctacaaa taattttgtt taa 43

<210> SEQ ID NO 279
<211> LENGTH: 43
<212> TYPE: DNA
<213> ORGANISM: Artificial Sequence
<220> FEATURE:
<223> OTHER INFORMATION: synthetic T7 phage buffer sequence

<400> SEQUENCE: 279
aaacctaatg gatcgacctt cctctacaaa taattttgtt taa 43

<210> SEQ ID NO 280
<211> LENGTH: 42
<212> TYPE: DNA
<213> ORGANISM: Artificial Sequence
<220> FEATURE:
<223> OTHER INFORMATION: synthetic T7 phage buffer sequence

<400> SEQUENCE: 280
atcgagaggg acacggcgac ctctacaaat aattttgttt aa 42

<210> SEQ ID NO 281
<211> LENGTH: 42
<212> TYPE: DNA
<213> ORGANISM: Artificial Sequence
<220> FEATURE:
<223> OTHER INFORMATION: synthetic T7 phage buffer sequence

<400> SEQUENCE: 281
gctaggtaac actagcagcc ctctacaaat aattttgttt aa 42

<210> SEQ ID NO 282
<211> LENGTH: 42
<212> TYPE: DNA
<213> ORGANISM: Artificial Sequence
<220> FEATURE:
<223> OTHER INFORMATION: synthetic T7 phage buffer sequence

<400> SEQUENCE: 282
atgaaacgac agtgagtcac ctctacaaat aattttgttt aa 42

<210> SEQ ID NO 283
<211> LENGTH: 43
<212> TYPE: DNA
<213> ORGANISM: Artificial Sequence
<220> FEATURE:
<223> OTHER INFORMATION: synthetic T7 phage buffer sequence

<400> SEQUENCE: 283
agggagacca caacggtttc cctctacaaa taattttgtt taa 43

<210> SEQ ID NO 284
<211> LENGTH: 43
<212> TYPE: DNA
<213> ORGANISM: Artificial Sequence
<220> FEATURE:
<223> OTHER INFORMATION: synthetic high-transcription escape buffer sequence

<400> SEQUENCE: 284
attaaaaaac ctgctaggat cctctacaaa taattttgtt taa 43

<210> SEQ ID NO 285
<211> LENGTH: 43
<212> TYPE: DNA
<213> ORGANISM: Artificial Sequence
<220> FEATURE:
<223> OTHER INFORMATION: synthetic high-transcription escape buffer sequence

<400> SEQUENCE: 285
ataaaggaaa acggtcaggt cctctacaaa taattttgtt taa 43

<210> SEQ ID NO 286
<211> LENGTH: 43
<212> TYPE: DNA
<213> ORGANISM: Artificial Sequence
<220> FEATURE:
<223> OTHER INFORMATION: synthetic high-transcription escape buffer sequence

<400> SEQUENCE: 286
ataggttaaa agcctgtcat cctctacaaa taattttgtt taa 43

<210> SEQ ID NO 287
<211> LENGTH: 48
<212> TYPE: DNA
<213> ORGANISM: Artificial Sequence
<220> FEATURE:
<223> OTHER INFORMATION: synthetic carbon utilization buffer sequence

<400> SEQUENCE: 287
acaataaaaa atcatttaca tgtttcctct acaaataatt ttgtttaa 48

<210> SEQ ID NO 288
<211> LENGTH: 48
<212> TYPE: DNA
<213> ORGANISM: Artificial Sequence
<220> FEATURE:
<223> OTHER INFORMATION: synthetic carbon utilization buffer sequence

<400> SEQUENCE: 288
agaagcagcg cgcaaaaatc agctgcctct acaaataatt ttgtttaa 48

<210> SEQ ID NO 289
<211> LENGTH: 48
<212> TYPE: DNA
<213> ORGANISM: Artificial Sequence
<220> FEATURE:
<223> OTHER INFORMATION: synthetic carbon utilization buffer sequence

<400> SEQUENCE: 289
atgagttcat ttcagacagg caaatcctct acaaataatt ttgtttaa 48

<210> SEQ ID NO 290
<211> LENGTH: 48
<212> TYPE: DNA
<213> ORGANISM: Artificial Sequence
<220> FEATURE:
<223> OTHER INFORMATION: synthetic carbon utilization buffer sequence

<400> SEQUENCE: 290
aacttgcagt tatttactgt gattacctct acaaataatt ttgtttaa 48

<210> SEQ ID NO 291
<211> LENGTH: 48
<212> TYPE: DNA
<213> ORGANISM: Artificial Sequence
<220> FEATURE:
<223> OTHER INFORMATION: synthetic carbon utilization buffer sequence

<400> SEQUENCE: 291
agccacaaaa aaagtcatgt tggttcctct acaaataatt ttgtttaa 48

<210> SEQ ID NO 292
<211> LENGTH: 53
<212> TYPE: DNA
<213> ORGANISM: Artificial Sequence
<220> FEATURE:
<223> OTHER INFORMATION: synthetic carbon utilization buffer sequence

<400> SEQUENCE: 292
acacagtcac ttatctttta gttaaaaggt cctctacaaa taattttgtt taa 53

<210> SEQ ID NO 293
<211> LENGTH: 43
<212> TYPE: DNA
<213> ORGANISM: Artificial Sequence
<220> FEATURE:
<223> OTHER INFORMATION: synthetic anti-escaping buffer sequence

<400> SEQUENCE: 293
atccggaatc ctcttcccgg cctctacaaa taattttgtt taa 43

<210> SEQ ID NO 294
<211> LENGTH: 48
<212> TYPE: DNA
<213> ORGANISM: Artificial Sequence
<220> FEATURE:
<223> OTHER INFORMATION: synthetic anti-escaping buffer sequence

<400> SEQUENCE: 294
aacaaaataa aaaggagtcg ctcaccctct acaaataatt ttgtttaa 48

<210> SEQ ID NO 295
<211> LENGTH: 43
<212> TYPE: DNA
<213> ORGANISM: Artificial Sequence
<220> FEATURE:
<223> OTHER INFORMATION: synthetic T5 phage buffer sequence

<400> SEQUENCE: 295
agttcgatga gagcgataac agttccagat tcaggaacta taa 43

<210> SEQ ID NO 296
<211> LENGTH: 42
<212> TYPE: DNA
<213> ORGANISM: Artificial Sequence
<220> FEATURE:
<223> OTHER INFORMATION: synthetic T5 phage buffer sequence

<400> SEQUENCE: 296
ataaattgat aaacaaaaaa gttccagatt caggaactat aa 42

<210> SEQ ID NO 297
<211> LENGTH: 43
<212> TYPE: DNA
<213> ORGANISM: Artificial Sequence
<220> FEATURE:
<223> OTHER INFORMATION: synthetic T5 phage buffer sequence

<400> SEQUENCE: 297
ataaatttga gagaggagtt agttccagat tcaggaacta taa 43

<210> SEQ ID NO 298
<211> LENGTH: 43
<212> TYPE: DNA
<213> ORGANISM: Artificial Sequence
<220> FEATURE:
<223> OTHER INFORMATION: synthetic T5 phage buffer sequence

<400> SEQUENCE: 298
attaaagagg agaaattaac agttccagat tcaggaacta taa 43

<210> SEQ ID NO 299
<211> LENGTH: 43
<212> TYPE: DNA
<213> ORGANISM: Artificial Sequence
<220> FEATURE:
<223> OTHER INFORMATION: synthetic T5 phage buffer sequence

<400> SEQUENCE: 299
aaacctaatg gatcgacctt agttccagat tcaggaacta taa 43

<210> SEQ ID NO 300
<211> LENGTH: 42
<212> TYPE: DNA
<213> ORGANISM: Artificial Sequence
<220> FEATURE:
<223> OTHER INFORMATION: synthetic T7 phage buffer sequence

<400> SEQUENCE: 300
atcgagaggg acacggcgaa gttccagatt caggaactat aa 42

<210> SEQ ID NO 301
<211> LENGTH: 42
<212> TYPE: DNA
<213> ORGANISM: Artificial Sequence
<220> FEATURE:
<223> OTHER INFORMATION: synthetic T7 phage buffer sequence

<400> SEQUENCE: 301
gctaggtaac actagcagca gttccagatt caggaactat aa 42

<210> SEQ ID NO 302

<211> LENGTH: 42
<212> TYPE: DNA
<213> ORGANISM: Artificial Sequence
<220> FEATURE:
<223> OTHER INFORMATION: synthetic T7 phage buffer sequence

<400> SEQUENCE: 302
atgaaacgac agtgagtcaa gttccagatt caggaactat aa 42

<210> SEQ ID NO 303
<211> LENGTH: 43
<212> TYPE: DNA
<213> ORGANISM: Artificial Sequence
<220> FEATURE:
<223> OTHER INFORMATION: synthetic T7 phage buffer sequence

<400> SEQUENCE: 303
agggagacca caacggtttc agttccagat tcaggaacta taa 43

<210> SEQ ID NO 304
<211> LENGTH: 43
<212> TYPE: DNA
<213> ORGANISM: Artificial Sequence
<220> FEATURE:
<223> OTHER INFORMATION: synthetic high-transcription escape buffer sequence

<400> SEQUENCE: 304
attaaaaaac ctgctaggat agttccagat tcaggaacta taa 43

<210> SEQ ID NO 305
<211> LENGTH: 43
<212> TYPE: DNA
<213> ORGANISM: Artificial Sequence
<220> FEATURE:
<223> OTHER INFORMATION: synthetic high-transcription escape buffer sequence

<400> SEQUENCE: 305
ataaaggaaa acggtcaggt agttccagat tcaggaacta taa 43

<210> SEQ ID NO 306
<211> LENGTH: 43
<212> TYPE: DNA
<213> ORGANISM: Artificial Sequence
<220> FEATURE:
<223> OTHER INFORMATION: synthetic high-transcription escape buffer sequence

<400> SEQUENCE: 306
ataggttaaa agcctgtcat agttccagat tcaggaacta taa 43

<210> SEQ ID NO 307
<211> LENGTH: 48
<212> TYPE: DNA
<213> ORGANISM: Artificial Sequence
<220> FEATURE:
<223> OTHER INFORMATION: synthetic carbon utilization buffer sequence

<400> SEQUENCE: 307
acaataaaaa atcatttaca tgtttagttc cagattcagg aactataa 48

<210> SEQ ID NO 308
<211> LENGTH: 48
<212> TYPE: DNA
<213> ORGANISM: Artificial Sequence
<220> FEATURE:

<223> OTHER INFORMATION: synthetic carbon utilization buffer sequence

<400> SEQUENCE: 308
agaagcagcg cgcaaaaatc agctgagttc cagattcagg aactataa 48

<210> SEQ ID NO 309
<211> LENGTH: 48
<212> TYPE: DNA
<213> ORGANISM: Artificial Sequence
<220> FEATURE:
<223> OTHER INFORMATION: synthetic carbon utilization buffer sequence

<400> SEQUENCE: 309
atgagttcat ttcagacagg caaatagttc cagattcagg aactataa 48

<210> SEQ ID NO 310
<211> LENGTH: 48
<212> TYPE: DNA
<213> ORGANISM: Artificial Sequence
<220> FEATURE:
<223> OTHER INFORMATION: synthetic carbon utilization buffer sequence

<400> SEQUENCE: 310
aacttgcagt tatttactgt gattaagttc cagattcagg aactataa 48

<210> SEQ ID NO 311
<211> LENGTH: 48
<212> TYPE: DNA
<213> ORGANISM: Artificial Sequence
<220> FEATURE:
<223> OTHER INFORMATION: synthetic carbon utilization buffer sequence

<400> SEQUENCE: 311
agccacaaaa aaagtcatgt tggttagttc cagattcagg aactataa 48

<210> SEQ ID NO 312
<211> LENGTH: 53
<212> TYPE: DNA
<213> ORGANISM: Artificial Sequence
<220> FEATURE:
<223> OTHER INFORMATION: synthetic carbon utilization buffer sequence

<400> SEQUENCE: 312
acacagtcac ttatctttta gttaaaaggt agttccagat tcaggaacta taa 53

<210> SEQ ID NO 313
<211> LENGTH: 43
<212> TYPE: DNA
<213> ORGANISM: Artificial Sequence
<220> FEATURE:
<223> OTHER INFORMATION: synthetic anti-escaping buffer sequence

<400> SEQUENCE: 313
atccggaatc ctcttcccgg agttccagat tcaggaacta taa 43

<210> SEQ ID NO 314
<211> LENGTH: 48
<212> TYPE: DNA
<213> ORGANISM: Artificial Sequence
<220> FEATURE:
<223> OTHER INFORMATION: synthetic anti-escaping buffer sequence

<400> SEQUENCE: 314
aacaaaataa aaaggagtcg ctcacagttc cagattcagg aactataa 48

<210> SEQ ID NO 315
<211> LENGTH: 30
<212> TYPE: DNA
<213> ORGANISM: Artificial Sequence
<220> FEATURE:
<223> OTHER INFORMATION: synthetic stem loops buffer sequence

<400> SEQUENCE: 315
gatcaccagg gggatccccc ggtgaaggat 30

<210> SEQ ID NO 316
<211> LENGTH: 38
<212> TYPE: DNA
<213> ORGANISM: Artificial Sequence
<220> FEATURE:
<223> OTHER INFORMATION: synthetic stem loops buffer sequence

<400> SEQUENCE: 316
gatcgcccac cggcagctgc cggtgggcga tcaaggat 38

<210> SEQ ID NO 317
<211> LENGTH: 45
<212> TYPE: DNA
<213> ORGANISM: Artificial Sequence
<220> FEATURE:
<223> OTHER INFORMATION: synthetic stem loops buffer sequence

<400> SEQUENCE: 317
gatcatcggt agagttaata ttgagcagat cccccggtga aggat 45

<210> SEQ ID NO 318
<211> LENGTH: 36
<212> TYPE: DNA
<213> ORGANISM: Artificial Sequence
<220> FEATURE:
<223> OTHER INFORMATION: synthetic stem loops buffer sequence

<400> SEQUENCE: 318
attgatctgg ttattaaagg taatcgggtc atttta 36

<210> SEQ ID NO 319
<211> LENGTH: 41
<212> TYPE: DNA
<213> ORGANISM: Artificial Sequence
<220> FEATURE:
<223> OTHER INFORMATION: synthetic stem loops buffer sequence

<400> SEQUENCE: 319
gttctccacg ggtgggatga gcccctcgtg gtggaaatgc g 41

<210> SEQ ID NO 320
<211> LENGTH: 27
<212> TYPE: DNA
<213> ORGANISM: Artificial Sequence
<220> FEATURE:
<223> OTHER INFORMATION: synthetic stem loops buffer sequence

<400> SEQUENCE: 320
agcatgaggt aaagtgtcat gcaccaa 27

<210> SEQ ID NO 321
<211> LENGTH: 38
<212> TYPE: DNA
<213> ORGANISM: Artificial Sequence
<220> FEATURE:
<223> OTHER INFORMATION: synthetic stem loops buffer sequence

<400> SEQUENCE: 321
acgtcgactt atctcgagtg agatattgtt gacggtac 38

<210> SEQ ID NO 322
<211> LENGTH: 37
<212> TYPE: DNA
<213> ORGANISM: Artificial Sequence
<220> FEATURE:
<223> OTHER INFORMATION: synthetic stem loops buffer sequence

<400> SEQUENCE: 322
acgtcgactt atctcgagtg agataagttg acggtac 37

<210> SEQ ID NO 323
<211> LENGTH: 51
<212> TYPE: DNA
<213> ORGANISM: Artificial Sequence
<220> FEATURE:
<223> OTHER INFORMATION: synthetic stem loops buffer sequence

<400> SEQUENCE: 323
acgtcgactt atctcgagac tgcagttcaa tagagatatt gttgacggta c 51

<210> SEQ ID NO 324
<211> LENGTH: 52
<212> TYPE: DNA
<213> ORGANISM: Artificial Sequence
<220> FEATURE:
<223> OTHER INFORMATION: synthetic stem loops (ribozyme) buffer sequence

<400> SEQUENCE: 324
gactgtcacc ggatgtgctt tccggtctga tgagtccgtg aggacgaaac ag 52

<210> SEQ ID NO 325
<211> LENGTH: 53
<212> TYPE: DNA
<213> ORGANISM: Artificial Sequence
<220> FEATURE:
<223> OTHER INFORMATION: synthetic stem loops buffer sequence

<400> SEQUENCE: 325
gatcaccagg gggatccccc ggtgaaggat cctctacaaa taattttgtt taa 53

<210> SEQ ID NO 326
<211> LENGTH: 61
<212> TYPE: DNA
<213> ORGANISM: Artificial Sequence
<220> FEATURE:
<223> OTHER INFORMATION: synthetic stem loops buffer sequence

<400> SEQUENCE: 326
gatcgcccac cggcagctgc cggtgggcga tcaaggatcc tctacaaata attttgttta 60
a 61

<210> SEQ ID NO 327
<211> LENGTH: 68
<212> TYPE: DNA
<213> ORGANISM: Artificial Sequence
<220> FEATURE:
<223> OTHER INFORMATION: synthetic stem loops buffer sequence

<400> SEQUENCE: 327
gatcatcggt agagttaata ttgagcagat cccccggtga aggatcctct acaaataatt 60
ttgtttaa 68

<210> SEQ ID NO 328
<211> LENGTH: 59
<212> TYPE: DNA
<213> ORGANISM: Artificial Sequence
<220> FEATURE:
<223> OTHER INFORMATION: synthetic stem loops buffer sequence

<400> SEQUENCE: 328
attgatctgg ttattaaagg taatcgggtc attttacctc tacaaataat tttgtttaa 59

<210> SEQ ID NO 329
<211> LENGTH: 64
<212> TYPE: DNA
<213> ORGANISM: Artificial Sequence
<220> FEATURE:
<223> OTHER INFORMATION: synthetic stem loops buffer sequence

<400> SEQUENCE: 329
gttctccacg ggtgggatga gcccctcgtg gtggaaatgc gcctctacaa ataattttgt 60
ttaa 64

<210> SEQ ID NO 330
<211> LENGTH: 50
<212> TYPE: DNA
<213> ORGANISM: Artificial Sequence
<220> FEATURE:
<223> OTHER INFORMATION: synthetic stem loops buffer sequence

<400> SEQUENCE: 330
agcatgaggt aaagtgtcat gcaccaacct ctacaaataa ttttgtttaa 50

<210> SEQ ID NO 331
<211> LENGTH: 61
<212> TYPE: DNA
<213> ORGANISM: Artificial Sequence
<220> FEATURE:
<223> OTHER INFORMATION: synthetic stem loops buffer sequence

<400> SEQUENCE: 331
acgtcgactt atctcgagtg agatattgtt gacggtaccc tctacaaata attttgttta 60
a 61

<210> SEQ ID NO 332
<211> LENGTH: 60
<212> TYPE: DNA
<213> ORGANISM: Artificial Sequence
<220> FEATURE:
<223> OTHER INFORMATION: synthetic stem loops buffer sequence

<400> SEQUENCE: 332
acgtcgactt atctcgagtg agataagttg acggtaccct ctacaaataa ttttgtttaa 60

<210> SEQ ID NO 333
<211> LENGTH: 74
<212> TYPE: DNA
<213> ORGANISM: Artificial Sequence
<220> FEATURE:
<223> OTHER INFORMATION: synthetic stem loops buffer sequence

<400> SEQUENCE: 333
acgtcgactt atctcgagac tgcagttcaa tagagatatt gttgacggta ccctctacaa 60
ataattttgt ttaa 74

<210> SEQ ID NO 334
<211> LENGTH: 75
<212> TYPE: DNA
<213> ORGANISM: Artificial Sequence
<220> FEATURE:
<223> OTHER INFORMATION: synthetic stem loops (ribozyme) buffer sequence

<400> SEQUENCE: 334
gactgtcacc ggatgtgctt tccggtctga tgagtccgtg aggacgaaac agcctctaca 60
aataattttg tttaa 75

<210> SEQ ID NO 335
<211> LENGTH: 72
<212> TYPE: DNA
<213> ORGANISM: Artificial Sequence
<220> FEATURE:
<223> OTHER INFORMATION: synthetic Ptac controller #1 promoter sequence,
Ptac (SBa_00512 sequence

<400> SEQUENCE: 335
tattctgaaa tgagctgttg acaattaatc atcggctcgt ataatgtgtg gaattgtgag 60
cggataacaa tt 72

<210> SEQ ID NO 336
<211> LENGTH: 75
<212> TYPE: DNA
<213> ORGANISM: Artificial Sequence
<220> FEATURE:
<223> OTHER INFORMATION: synthetic controller #3 promoter sequence, Ptac
plus OR1 and OR2 (SBa_000506) sequence

<400> SEQUENCE: 336
tattaacacc gtgcgtgttg acagctatac ctctggcggt tataatgcta gcggaattgt 60
gagcggataa caatt 75

<210> SEQ ID NO 337
<211> LENGTH: 36
<212> TYPE: DNA
<213> ORGANISM: Artificial Sequence
<220> FEATURE:
<223> OTHER INFORMATION: synthetic randomized sequence
<220> FEATURE:
<221> NAME/KEY: modified_base
<222> LOCATION: (21)...(28)
<223> OTHER INFORMATION: n = g, a, c or t

<400> SEQUENCE: 337
cttgggcacg cgtccattaa nnaggannaa ttaagc 36

<210> SEQ ID NO 338
<211> LENGTH: 36
<212> TYPE: DNA
<213> ORGANISM: Artificial Sequence
<220> FEATURE:
<223> OTHER INFORMATION: synthetic randomized sequence
<220> FEATURE:
<221> NAME/KEY: modified_base
<222> LOCATION: (19)...(26)
<223> OTHER INFORMATION: n = g, a, c or t

<400> SEQUENCE: 338
tgggcacgcg tccattaann aggannaatt attagc 36

<210> SEQ ID NO 339
<211> LENGTH: 36

<212> TYPE: DNA
<213> ORGANISM: Artificial Sequence
<220> FEATURE:
<223> OTHER INFORMATION: synthetic randomized sequence
<220> FEATURE:
<221> NAME/KEY: modified_base
<222> LOCATION: (23)...(30)
<223> OTHER INFORMATION: n = g, a, c or t

<400> SEQUENCE: 339
tacttgggca cgcgtccatt aannaggann aatagc 36

<210> SEQ ID NO 340
<211> LENGTH: 36
<212> TYPE: DNA
<213> ORGANISM: Artificial Sequence
<220> FEATURE:
<223> OTHER INFORMATION: synthetic randomized sequence
<220> FEATURE:
<221> NAME/KEY: modified_base
<222> LOCATION: (21)...(28)
<223> OTHER INFORMATION: n = g, a, c or t

<400> SEQUENCE: 340
cttgggcacg cgtccattaa naaggagnaa ttaagc 36

<210> SEQ ID NO 341
<211> LENGTH: 36
<212> TYPE: DNA
<213> ORGANISM: Artificial Sequence
<220> FEATURE:
<223> OTHER INFORMATION: synthetic randomized sequence
<220> FEATURE:
<221> NAME/KEY: modified_base
<222> LOCATION: (20)...(29)
<223> OTHER INFORMATION: n = g, a, c or t

<400> SEQUENCE: 341
cttgggcacg cgtccattan taaggaggna ttaagc 36

<210> SEQ ID NO 342
<211> LENGTH: 34
<212> TYPE: DNA
<213> ORGANISM: Artificial Sequence
<220> FEATURE:
<223> OTHER INFORMATION: synthetic weak ribosome binding site (RBS)
(SBa_000507)

<400> SEQUENCE: 342
tatccaaacc agtagctcaa ttggagtcgt ctat 34

<210> SEQ ID NO 343
<211> LENGTH: 123
<212> TYPE: DNA
<213> ORGANISM: Artificial Sequence
<220> FEATURE:
<223> OTHER INFORMATION: synthetic N-terminal degradation tag
(SBa_000509)

<400> SEQUENCE: 343
ttgtttatca agcctgcgga tctccgcgaa attgtgactt ttccgctatt tagcgatctt 60
gttcagtgtg gctttccttc accggcagca gattacgttg aacagcgcat cgatctgggt 120
ggc 123

<210> SEQ ID NO 344
<211> LENGTH: 41
<212> TYPE: DNA

-continued

```
<213> ORGANISM: Artificial Sequence
<220> FEATURE:
<223> OTHER INFORMATION: synthetic Enterobacteria phage T7 terminator
      seed sequence
<220> FEATURE:
<221> NAME/KEY: modified_base
<222> LOCATION: (3)...(16)
<223> OTHER INFORMATION: n = g, a, c or t

<400> SEQUENCE: 344

tannnaaccs swwssnssss tcwwwcgsss ssswwssgtt t                    41


<210> SEQ ID NO 345
<211> LENGTH: 15
<212> TYPE: DNA
<213> ORGANISM: Artificial Sequence
<220> FEATURE:
<223> OTHER INFORMATION: synthetic replacement sequence for 15bp
      upstream of start codon
<220> FEATURE:
<221> NAME/KEY: modified_base
<222> LOCATION: (1)...(15)
<223> OTHER INFORMATION: n = g, a, c or t

<400> SEQUENCE: 345

nnnaggaggn nnnnn                                                 15
```

SYNTHETIC GENE CLUSTERS

CROSS-REFERENCE TO RELATED PATENT APPLICATIONS

The present application is a Continuation of U.S. application Ser. No. 14/126,307, filed Jun. 14, 2012, which is a US National Stage (371) of International Application No. PCT/US2012/042502, filed Jun. 14, 2012, which claims benefit of priority to U.S. Provisional Patent Application No. 61/497,781, filed Jun. 16, 2011, each of which is incorporated by reference.

STATEMENT AS TO RIGHTS TO INVENTIONS MADE UNDER FEDERALLY SPONSORED RESEARCH AND DEVELOPMENT

This invention was made with government support under grant nos. CFF0943385 and EEC0540879 awarded by the National Science Foundation and grant no. R01 AI067699, awarded by the National Institutes of Health. The government has certain rights in the invention.

BACKGROUND OF THE INVENTION

Genetically programming cells require sensors to receive information, circuits to process the inputs, and actuators to link the circuit output to a cellular response (Andrianantoandro E, et al., *Mol Syst Biol* 2 (2006); Chin J W *Curr Opin Struct Biol* 16: 551-556 (2006); Voigt C A *Curr Opin Biotech* 17: 548-557 (2006); Tan C, *Mol Biosyst* 3: 343-353 (2007)). In this paradigm, sensing, signal integration, and actuation are encoded by distinct 'devices' comprised of genes and regulatory elements (Knight T K, Sussman G J *Unconventional Models of Computation* 257-272 (1997); Endy D *Nature* 438: 449-453 (2005)). These devices communicate with one another through changes in gene expression and activity. For example, when a sensor is stimulated, this may lead to the activation of a promoter, which then acts as the input to a circuit.

BRIEF SUMMARY OF THE INVENTION

Embodiments of the present invention provide a polynucleotide comprising a synthetic operon, wherein the operon comprises at least two coding sequences under the control of a heterologous transcriptional regulatory sequence, wherein each coding sequence is operably linked to a heterologous ribosome binding site (RBS). In some embodiments, the coding sequences are from the same native operon and the heterologous RBSs regulate translation of the coding sequences in a ratio that is substantially similar to the ratio of native translation from the native operon. In some embodiments, the coding sequences are from different native operons and the heterologous RBSs regulate translation of the coding sequences in a ratio that is substantially similar to the ratio of native translation from the native operon. In some embodiments, the coding sequences are from the same native operon and the coding sequences in the operon comprise one or more altered codon compared to the native operon. In some embodiments, codons of one or more coding sequence have been selected for maximal distance from codon usage of a corresponding coding sequence in the native operon.

In some embodiments, at least two coding sequences encode different proteins encoded by the *Klebsiella pneumoniae* nif gene cluster. In some embodiments, the proteins are selected from the group consisting of nifJ, nifH, nifD, nifK, nifY, nifE, nifN, nifU, nifS, nifV, nifW, nifZ, niM, nifF, nifB, and nifQ (e.g., wherein the coding sequences are substantially identical to those listed in FIG. 18). In some embodiments, the operon comprises coding sequences for *Klebsiella pneumoniae* nifH, nifD, nifK, and nifY. In some embodiments, the operon comprises coding sequences for *Klebsiella pneumoniae* nifE and nifN. In some embodiments, the operon comprises coding sequences for *Klebsiella pneumoniae* nifU, nifS, nifV, nifW, nifZ, and nifM. In some embodiments, the operon comprises coding sequences for *Klebsiella pneumoniae* nifB and nifQ.

In some embodiments, at least two coding sequences encode different proteins of the *Salmonella typhimurium* Type III secretion system. In some embodiments, the proteins are selected from the group consisting of PrgH, PrgI, PrgJ, PrgK, OrgA, OrgB, InvA, InvC, InvE, InvF, InvG, InvI, InvJ, SpaO, SpaP, SpaQ, SpaR, and SpaS (e.g., wherein the coding sequences are substantially identical to those listed in FIG. 24). In some embodiments, the operon comprises coding sequences for *Salmonella typhimurium* PrgH, PrgI, PrgJ, PrgK, OrgA, and OrgB. In some embodiments, the operon comprises coding sequences for *Salmonella typhimurium* InvA, InvC, InvE, InvF, InvG, InvI, InvJ, SpaO, SpaP, SpaQ, SpaR, and SpaS.

Embodiments of the present invention also provide for a host cell (optionally isolated) comprising a polynucleotide as described above or elsewhere herein. In some embodiments, the host cell is a prokaryotic or eukaryotic cell (including but not limited to a mammalian or plant or fungal cell).

Embodiments of the present invention also provide a system comprising a set of two or more different synthetic operons, the two or more operons each comprising at least two coding sequences under the control of a heterologous transcriptional regulatory sequence, wherein each coding sequence is operably linked to a heterologous ribosome binding site (RBS), wherein the transcriptional regulatory sequence of each operon in the set is controlled by the same transcriptional activator or repressor polypeptide(s).

In some embodiments, the system further comprises an expression cassette comprising a promoter operably linked to a polynucleotide encoding the transcriptional activator or repressor polypeptide(s). In some embodiments, the promoter of the expression cassette is an inducible promoter. In some embodiments, the polynucleotide in the expression cassette encodes a transcriptional repressor. In some embodiments, the polynucleotide in the expression cassette encodes a transcriptional activator. In some embodiments, the transcriptional activator is an RNA polymerase (RNAP). In some embodiments, the RNAP is T7 RNAP or is substantially similar to T7 RNAP.

In some embodiments, the transcriptional regulatory sequences of at least two of the operons are different.

In some embodiments, the coding sequences in the operons are organized such that coding sequences having substantially similar native expression are grouped into the same operon. In some embodiments, the transcriptional regulatory sequence of at least two operons have different promoters that are differentially regulated by T7 RNA polymerase and wherein the different strength of the promoters correspond to the relative strength of native promoters of the coding sequences.

In some embodiments, the expression cassette and the synthetic operons are expressed in a cell. In some embodiments, the cell is from a different species than the species from which the native operon was isolated. In some embodiments, the cell is from the same species from which the native operon was isolated.

In some embodiments, the system encodes a nitrogenase. In some embodiments, the system comprises a first operon comprising coding sequences for *Klebsiella pneumoniae* nifH, nifD, nifK, and nifY; a second operon comprising coding sequences for *Klebsiella pneumoniae* nifE and nifN; a third operon comprising coding sequences for *Klebsiella pneumoniae* nifU, nifS, nifV, nifW, nifZ, and nifM; and a fourth operon comprising coding sequences for *Klebsiella pneumoniae* nifB and nifQ. In some embodiments, the first, second, third, and fourth operon comprising a T7 RNA polymerase (RNAP) promoter and the system further comprises an expression cassette comprising a promoter operably linked to a polynucleotide encoding an RNAP substantially identical to T7 RNA polymerase (RNAP).

In some embodiments, the system encodes a type III secretion system. In some embodiments, the type III secretion system is a *Salmonella typhimurium* type III secretion system. In some embodiments, the system comprises a first operon comprising coding sequences for *Salmonella typhimurium* PrgH, PrgI, PrgJ, PrgK, OrgA, and OrgB and a second operon comprising coding sequences for *Salmonella typhimurium* InvA, InvC, InvE, InvF, InvG, InvI, InvJ, SpaO, SpaP, SpaQ, SpaR, and SpaS.

Embodiments of the present invention also provide a method for replacing native regulation of a set of genes collectively associated with a function with synthetic regulation. In some embodiments, the method comprises providing coding sequences for a set of polypeptides encoded by genes collectively associated with a function; changing codon identity within at least one coding sequence, thereby removing at least one regulatory sequence within the coding sequence; organizing the coding sequences into one or more synthetic operon(s); operably linking one or more heterologous transcriptional regulatory sequence to the operon(s), thereby controlling the magnitude of gene expression from the operon(s); and expressing the one or more synthetic operon(s) in a cell under the control of a polypeptide that binds directly or indirectly to the heterologous transcriptional regulatory sequence.

In some embodiments, the polypeptide is heterologous to the cell.

In some embodiments, the providing comprises obtaining the gene nucleotide sequences and eliminating non-coding sequences.

In some embodiments, the set of genes is from a gene cluster. In some embodiments, the set of genes are from a prokaryote. In some embodiments, the genes are from a native operon.

In some embodiments, the at least one regulatory sequence is identified using computation. In some embodiments, the computation comprises searches of coding sequences for ribosome binding sites, terminators, and/or promoters.

In some embodiments, removing the at least one regulatory sequence comprises replacement of native codons in the coding sequence with non-native synonymous codons. In some embodiments, the removing comprises selecting non-native codons having maximal distance from codons of the native coding sequence. In some embodiments, the removing comprises selecting non-native codons for optimal expression in a host cell.

In some embodiments, the method further comprises identifying and removing one or more of transposon insertion sites, sites that promote recombination, sites for cleavage by restriction endonucleases, and sites that are methylated.

In some embodiments, the organizing comprises grouping coding sequences into operons based on substantially similar native expression level.

In some embodiments, the organizing comprises ordering coding sequences within operons such that the highest expressing gene (based on native expression) occurs first and the lowest expressing gene (based on native expression) occurs last. In some embodiments, organization is based on native temporal expression, function, ease of manipulation of DNA, and/or experimental design. In some embodiments, magnitude of expression of coding sequences substantially correspond to the ratio of proteins encoded by the coding sequences as measured in the native system. In some embodiments, magnitude of expression of coding sequences is determined by computation. In some embodiments, the computation comprises a numerical optimization algorithm.

In some embodiments, the numerical optimization algorithm a Nelder-Mead algorithm, a Newton's method, a quasi-Newton method, a conjugate gradient method, an interior point method, a gradient descent, a subgradient method, a ellipsoid method, a Frank-Wolfe method, an interpolation method and pattern search methods, or an ant colony model.

In some embodiments, the heterologous transcriptional regulatory sequence(s) comprise a T7 RNAP promoter(s).

In some embodiments, the heterologous transcriptional regulatory sequence(s) comprise an inducible promoter.

In some embodiments, the method further comprises operably linking a heterologous ribosomal binding site (RBS) to one or more coding sequence in the synthetic operon. In some embodiments, different RBSs are operably linked to different coding sequences. In some embodiments, the RBSs regulate translation of the coding sequences in a ratio that is substantially similar to the ratio of native translation from the native operon.

In some embodiments, the method further comprises operably linking a heterologous transcriptional terminator sequence to one or more coding sequence in the synthetic operon. In some embodiments, the terminators are T7 RNAP terminators. In some embodiments, terminators for different operons are different.

In some embodiments, the method further comprises operably linking a buffer sequences between two functional sequences in an operon wherein the functional sequences are selected from the group consisting of a promoter, ribosome binding site, coding sequence, and terminator. In some embodiments, the buffer sequence is selected from the group consisting of a random sequence, a UP-region of a promoter, an extended 5-UTR sequence, and a RNAase cleavage site.

In some embodiments, the operons are expressed from a plasmid. In some embodiments, the plasmid has a low copy origin of replication.

In some embodiments, the polypeptide that binds directly or indirectly to the heterologous transcriptional regulatory sequence is expressed from a control expression cassette, the expression cassette comprising a control promoter operably linked to a polynucleotide sequence encoding the polypeptide. In some embodiments, the expression cassette is contained in a control plasmid separate from a plasmid containing the operons. In some embodiments, the control promoter is an inducible promoter.

In some embodiments, the heterologous polypeptide comprises an RNA polymerase (RNAP). In some embodiments, the RNAP is T7 RNAP. In some embodiments, the expression cassette is an environmental sensor.

Embodiments of the invention also provide for a method for determining an experimentation point for controlling the magnitude of expression of two or more genes (e.g., within a synthetic operon). In some embodiments, the method comprises: receiving one or more input data points, wherein the input data points provide information about one or more regulatory elements and a system property; and determining, with a computer, a next data point using a computational method, wherein the next data point provides information about the one or more regulatory elements.

In some embodiments, the method further comprises using the next data point for further experimentation to optimize expression of the two or more genes. In some embodiments, the regulatory elements include, e.g., ribosomal binding sites and/or transcriptional regulatory elements.

In some embodiments, the computational method is a numerical analysis technique. In some embodiments, the numerical optimization method is the Nelder-Mead algorithm, the Newton's method, the quasi-Newton method, a conjugate gradient method, an interior point method, a gradient descent, a subgradient method, a ellipsoid method, the Frank-Wolfe method, an interpolation method and pattern search methods, or an ant colony model. In some embodiments, the numerical optimization method used to determine the next data point for further experimentation requires considering the reflection point, expansion point, or contraction point based on the one or more input data points.

In some embodiments, the computational method is a design of experiments (DoE) method.

Embodiments of the invention also provide for a computer program product comprising a tangible computer readable medium storing a plurality of instructions for controlling a processor to perform an operation for determining an experimentation point for controlling the magnitude of expression of two or more genes, the instructions comprising receiving one or more input data points, wherein the input data points provide information about one or more regulatory elements and a system property; and determining, with a computer, a next data point using a computational method, wherein the next data point provides information about the one or more regulatory elements.

DEFINITIONS

A recitation of "a", "an" or "the" is intended to mean "one or more" unless specifically indicated to the contrary.

A polynucleotide or polypeptide sequence is "heterologous to" an organism or a second sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is not naturally associated with the promoter (e.g. a T7 RNA polymerase promoter operably linked to a synthetic nif operon).

The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence. In the context of a ribosomal binding site (RBS) and coding sequences, the term refers to the functional linkage of the RBS to the coding sequence wherein the RBS recruits ribosomes for translation of the coding sequence on an RNA.

A "cognate pair" as used herein refers to a sequence-specific DNA binding polypeptide and a target DNA sequence that is bound by the particular sequence-specific DNA binding polypeptide. For sequence-specific DNA binding polypeptides that bind more than one target nucleic acid, the cognate pair can be formed with the sequence-specific DNA binding polypeptide and any one of the target DNA sequences the polypeptide binds.

"Orthogonal" transcriptional systems refer to systems (e.g., one, two, three, or more) of transcriptional regulatory elements comprising target DNA sequences regulated by their cognate sequence-specific DNA binding polypeptide such that the sequence-specific DNA binding polypeptides in the system do not have "cross-talk," i.e., the sequence-specific DNA binding polypeptides do not interfere or regulate transcriptional regulatory elements in the system other than the transcriptional regulatory elements containing the cognate target DNA sequence of the sequence-specific DNA binding polypeptide.

"Sequence-specific DNA binding polypeptides" refer to polypeptides that bind DNA in a nucleotide sequence specific manner. Exemplary sequence-specific DNA binding polypeptides include, but are not limited to transcription factors (e.g., transcriptional activators), RNA polymerases, and transcriptional repressors.

A "transcriptional activator" refers to a polypeptide, which when bound to a promoter sequence, activates or increases transcription of an RNA comprising the operably-linked coding sequence. In some embodiments, the transcriptional activator bound to a target sequence in a promoter can assist recruitment of RNA polymerase to the promoter. A "transcriptional repressor" refers to a polypeptide, which when bound to a promoter sequence, blocks or decreases transcription of an RNA comprising the operably-linked coding sequence. In some embodiments, the transcriptional repressor blocks recruitment of the RNA polymerase to the promoter or blocks the RNA polymerase's movement along the promoter.

The term "coding sequence" as used herein refers to a nucleotide sequence beginning at the codon for the first amino acid of an encoded protein and ending with the codon for the last amino acid and/or ending in a stop codon.

The term "host cell" refers to any cell capable of replicating and/or transcribing and/or translating a heterologous gene. Thus, a "host cell" refers to any prokaryotic cell (including but not limited to *E. coli*) or eukaryotic cell (including but not limited to yeast cells, mammalian cells, avian cells, amphibian cells, plant cells, fish cells, and insect cells), whether located in vitro or in vivo. For example, host cells may be located in a transgenic animal or transgenic plant. prokaryotic cell (including but not limited to *E. coli*) or eukaryotic cells (including but not limited to yeast cells, mammalian cells, avian cells, amphibian cells, plant cells, fish cells, and insect cells).

"Transcriptional regulatory elements" refer to any nucleotide sequence that influences transcription initiation and rate, or stability and/or mobility of a transcript product. Regulatory sequences include, but are not limited to, promoters, promoter control elements, protein binding sequences, 5' and 3' UTRs, transcriptional start sites, termination sequences, polyadenylation sequences, introns, etc. Such transcriptional regulatory sequences can be located either 5'-, 3'-, or within the coding region of the gene and can be either promote (positive regulatory element) or repress (negative regulatory element) gene transcription.

The term "nucleic acid" or "polynucleotide" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, and mRNA encoded by a gene.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds.

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the sequence is complementary to all or a portion of a reference polynucleotide sequence.

Examples of algorithms that are suitable for determining percent sequence identity and sequence similarity are the BLAST and BLAST 2.0 algorithms, which are described in Altschul et al., *Nucleic Acids Res.* 25:3389-3402 (1997), and Altschul et al., *J. Mol. Biol.* 215:403-410 (1990), respectively. Software for performing BLAST analyses is publicly available on the Web through the National Center for Biotechnology Information (ncbi.nlm.nih.gov). This algorithm involves first identifying high scoring sequence pairs (HSPs) by identifying short wordlength (W) in the query sequence, which either match or satisfy some positive-valued threshold score (T) when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff, *Proc. Natl. Acad. Sci. USA* 89:10915, (1989)) alignments (B) of 50, expectation (E) of 10, M=5, N=−4, and a comparison of both strands.

The BLAST algorithm also performs a statistical analysis of the similarity between two sequences (see, e.g., Karlin and Altschul, *Proc. Natl. Acad. Sci. USA* 90:5873-5787, (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 25% sequence identity to a designated reference sequence. Alternatively, percent identity can be any integer from 25% to 100%, for example, at least: 25%, 30%, 35%, 40%, 45%, 50%, 55%, 60%, 65%, 70%, 75%, 80%, 85%, 90%, 95%, or 99% compared to a reference sequence using the programs described herein; preferably BLAST using standard parameters, as described below. One of skill will recognize that the percent identity values above can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 40%. Percent identity of polypeptides can be any integer from 40% to 100%, for example, at least 40%, 45%, 50%, 55%, 60%, 65%, 70%, 75%, 80%, 85%, 90%, 95%, or 99%. In some embodiments, polypeptides that are "substantially similar" share sequences as noted above except that residue positions that are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Exemplary conservative amino acids substitution groups are: valine-leucine-isoleucine, phenylalanine-tyrosine, lysine-arginine, alanine-valine, aspartic acid-glutamic acid, and asparagine-glutamine.

BRIEF DESCRIPTION OF THE DRAWINGS

FIG. 3 illustrates a library of wild-type (SEQ ID NO:157) and mutant T7 promoters (SEQ ID NOS:158-163) and their strength to control gene expression. T7 promoter seed sequence=SEQ ID NO:156.

FIG. 4 illustrates strengths of T7 promoters to control nifE and nifN genes in selected mutant strains.

FIG. 5 illustrates the nitrogen fixation in the Reflection strain and the initial strains.

FIG. 10 illustrates the multiple clones used to identify the synthetic ribosome binding site that best matched the native ribosome binding site.

FIG. 12 lists the errors in the fully synthetic operons.

FIG. 14 shows a table of the control of the synthetic operons in the system.

FIG. 18 shows DNA sequences for native genes (SEQ ID NOS:1, 3, 5, 7, 9, 11, 13, 15, 17, 19, 21, 23, 25, 27, 29 and 31) and synthetic genes (SEQ ID NOS:2, 4, 6, 8, 10, 12, 14, 16, 18, 20, 22, 24, 26, 28, 30, and 32), as well as the percent common nucleotide and codon identities between each pair.

FIG. 19 shows the names and sequences of parts of the synthetic controller (SEQ ID NOS:33-51).

FIG. 20 lists the names, sequences and strengths of each components of the full cluster (SEQ ID NOS:52-118).

FIG. 22 depicts schematics of the inv-spa and prg-org operons and the plasmids used.

FIG. 23 shows a western blot of secreted protein expressed from the synthetic prg-org operon in Δprg-org knock-out strain.

FIG. 24 shows the synthetic RBS and synthetic operon sequences of the T3SS (SEQ ID NOS:119-155).

FIGS. 27A-27C illustrates the robustness of the nitrogen fixation pathway to changes in the expression of component proteins. FIG. 27A The pathway for nitrogenase maturation is shown and proteins are coloured by function (FIG. 26). The metal clusters are synthesized by the biosynthetic pathway (23, 24). Nitrogen fixation catalyzed by the matured nitrogenase is shown with its in vivo electron transport chain. FIG. 27B The tolerance of nitrogenase activity to changes in the expression of component proteins are shown. Activity is measured via an acetylene reduction assay and the % compared to wild-type *K. oxytoca* is presented. Wild-type operons are expressed from a $P_{tac}$ promoter on a low copy plasmid. The promoter activity is calculated as the output of the $P_{tac}$ promoter at a given concentration of IPTG and compared to a constitutive promoter. The effect of not including NifY (−Y) and NifX (−X) are shown in red. FIG. 27C The comparison of the strength of wild-type (black) and synthetic (white) ribosome binding sites (RBSs) is shown. The RBSs were measured through an in-frame transcriptional fusion (−60 to +90) with mRFP. The strength is measured as the geometric average from a distribution of cells measured by flow cytometry. The synthetic RBSs of nifF and nifQ are not intended to match the wild-type measurement. Error bars represent the standard deviation of at least three experiments performed on different days.

FIG. 28A Nitrogenase activity is shown as a function of promoter strength for each refactored operon in respective *K. oxytoca* knockout strains (ΔnifHDKTY, ΔnifENX, ΔnifJ ΔnifBQ, ΔnifF, and ΔnifUSVWZM). Vertical dashed lines indicate strength of the mutant T7 promoter that controls each operon in the complete refactored gene cluster. FIG. 28B A controller plasmid decouples operon expression from the inducible promoter. A T7 RNAP variant (T7*) was designed to reduce toxicity. A set of 4 mutated T7 promoters were used to control the expression of each operon (part numbers and sequences for mutants 1-4 are listed in the Materials and Methods section). $P_{tac}$ activity under 1 mM IPTG induction is indicated by a dashed horizontal line. FIG. 28C Nitrogenase activity is compared for each refactored operon under the control of the $P_{tac}$ promoter at the optimal IPTG concentration (black) and the controller (part D) with 1 mM IPTG and expression controlled by different T7 promoters (white). The T7 promoters used are WT for operons HDKY, EN and J; promoter 2 for operons BQ and USVWZM; and promoter 3 for F. Error bars represent the standard deviation of at least three experiments performed on different days.

FIG. 30A Nitrogenase activity for the three controllers are shown: IPTG-inducible, aTc-inducible, and IPTG ANDN aTc logic. The gas chromatography trace is shown for each as well as the calculated percent of wild-type activity, (7.4%±2.4%, 7.2%±1.7% and 6.6%±1.7% respectively). Standard deviation is calculated using data from at least two experiments performed on different days. FIG. 30B $^{15}N$ incorporation into cell biomass is shown. Nitrogen fixation from $N_2$ gas by the refactored gene cluster was traced using $^{15}N_2$ and measured using isotope ratio mass spectronomy (IRMS). Data are represented as the fraction of cellular nitrogen that is $^{15}N$. The standard deviation represents two experiments performed on different days. FIG. 30C The effect of ammonia on regulation of nitrogenase expression is shown. Acetylene reduction traces shown with (red) and without (blue) addition of 17.5 mM ammonium acetate for wild type cells (left) and cells bearing synthetic nif system (right). The synthetic system was induced by Controller #1 using 1 mM IPTG and exhibited nitrogenase activity of 1.1%±0.5% and 6.1%±0.4% with and without ammonium acetate respectively. FIG. 30D T7* RNAP expression of Controller #1 corresponding to Part C is shown. Strains carrying Controller #1 and a RFP reporter plasmid were characterized under 1 mM IPTG induction with or without addition of ammonium acetate.

FIG. 32 depicts a table of construction and verification of all *K. oxytoca* nif gene deletion mutants (SEQ ID NOS:164-177).

FIGS. 33A-33B shows promoter characterization using Relative Expression Units. FIG. 33A Conversion of arbitrary units into Relative Expression Units (REU). Promoters were characterized using mRFP1 fluorescent reporter protein in N155 (Measured Promoters). Data were first normalized by the fluorescence of N110 (Internal Standard) and then scaled by the fluorescence of N155(J23100) to account for RBS differences between N155 and N110 (RBS Adjustment). To directly compare our measurements to expression levels of the Kelly et al. standards, we further multiplied by the ratio of N110 fluorescence to the fluorescence of a Kelly standard plasmid expressing mRFP1 (RFP Promoter Standard). A final conversion factor is applied to compare all measurements to the Kelly et al. J23101-EGFP promoter standard based on a strong linear correlation of promoter strength (RPU) between constructs expressing mRFP and EGFP. Solid and dashed boxes were drawn to indicate which plasmids were measured at different facilities. Asterisked and non-asterisked units were measured in different facilities and correspond to the conversion factors directly above. FIG. 33B Promoter characterization for $P_{tac}$ promoter (left) and $P_{tet}$ promoter (right). The promoter strengths of $P_{tac}$ promoter and $P_{tet}$ promoter were measured under varied concentrations of inducers (IPTG or aTc). The strengths of T7 promoters (WT and mutants, FIG. 28B) are shown as horizontal dotted lines.

FIG. 34A The process is shown for the identification of problem sequences within a refactored operon. After design and synthesis, the problematic DNA is crossed with wild-type to create a chimeric library, which is screened. This is done iteratively to reduce the size of the problematic region until the specific errors are identified. FIG. 34B The debugging process led to the correction of RBS strengths (red arrows), the recoded sequence of nifH, and numerous nucleotide errors found in the sequenced cluster in the database. Amino acid mutations to correct errors in the synthetic sequence are shown.

FIG. 35 depicts a table of DNA sequence errors in nif cluster sequence X13303.1.

FIG. 38 depicts a table of DNA sequences of synthetic parts (SEQ ID NOS:178-238).

DETAILED DESCRIPTION

I. Introduction

Figure 1:
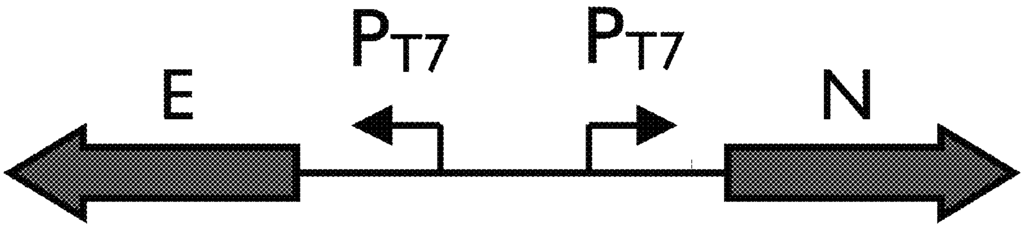
FIG. 1 depicts a scheme illustrating nifE and nifN genes under the control of unique T7 promoters.

The present invention relates to gene cluster engineering. It has been discovered how to recombinantly and computationally manipulate and select native gene cluster coding sequences and heterologous regulatory sequences such that the coding sequences are under control of heterologous regulation and produce the functional product of the gene cluster (e.g., a native operon). By eliminating native regulatory elements outside of, and within, coding sequences of gene clusters, and subsequently adding synthetic regulatory systems, the functional products of complex genetic operons and other gene clusters can be controlled and/or moved to heterologous cells, including cells of different species other than the species from which the native genes were derived.

As demonstrated below, the inventors have re-engineered the *Klebsiella oxytoca* Nif gene cluster as well as a *Salmo-*

*nella* Type III protein secretion system, thereby generating functional products (e.g., nitrogen fixing enzymes and peptide secretion complexes, respectively) under control of a heterologous regulatory system. Once re-engineered, the synthetic gene clusters can be controlled by genetic circuits or other inducible regulatory systems, thereby controlling the products' expression as desired.

II. Generation of Synthetic Gene Clusters

It is believed that the methods described herein can be used and adapted to re-engineer regulation of essentially any operon or other gene cluster. Generally, the native operons or gene clusters to be engineered will have the same functional product in the native host. For example, in some embodiments, at least a majority of the gene products within the native operon or gene cluster to be re-engineered will each function to produce a specific product or function of the native host. Functional products can include, for example, multi-component enzymes, membrane-associated complexes, including but not limited to complexes that transport biological molecules across membranes, or other biologically active complexes. For example, in some embodiments, the functional products are, e.g., a Type III protein secretion system, a bacterial microcompartment, a gas vesicle, a magnetosome, a cellulosome, an alkane degradation pathway, a nitrogen fixation complex, a polybiphenyl degradation complex, a pathway for biosynthesis of Poly (3-hydroxbutyrate), nonribosomal peptide biosynthesis enzymes, polyketide biosynthesis gene cluster products, a terpenoid biosynthesis pathway, an oligosaccharide biosynthesis pathway, an indolocarbazole biosynthesis pathway, a photosynthetic light harvesting complex, a stressosome, or a quorum sensing cluster. See, Fischbach and Voigt, *Biotechnol. J.,* 5:1277-1296 (2010), which is incorporated by reference, for a detailed description and examples of each.

Native operons or gene clusters used in embodiments of the present invention can be derived (originated) from prokaryotes or eukaryotes.

As used herein, "native" is intended to refer to the host cell or host genome from which an operon or gene cluster is originally derived (e.g., as the operon is found in nature). Thus, "native expression" of an operon refers to the specific expression levels and patterns of a set of genes in an operon or gene cluster in a native host.

An operon refers to a unit of DNA comprising multiple separate coding sequences under the control of a single promoter. The separate coding sequences are typically expressed within a single RNA molecule and subsequently translated separately, e.g., with varying translation levels due to the strength of ribosomal binding sites (RBSs) associated with the particular coding sequences. Operons are most typically found in prokaryotic cells.

Gene clusters refer to sets of genes having a common function or function product. Genes are typically found within physical proximity to each other within genomic DNA (e.g., within one centiMorgan (cM)). Gene clusters can occur in prokaryotic or eukaryotic cells.

A. Coding Sequences

Once a native operon or gene cluster has been identified for re-engineering, the coding sequences to be re-engineered can be identified. Generally, it will be desirable to start with only the coding sequences from the native operon or gene cluster, thereby removing native promoters and other non-coding regulatory sequences. Depending on the function of the various gene products of the native operon or gene cluster, in some embodiments all of the coding sequences of a native operon or gene cluster are re-engineered.

Alternatively, one or more coding sequences can be omitted from the re-engineering process. For example, it may be known that one or more of the gene products in a native operon or gene cluster do not contribute to the function product of the operon or may not be necessary for generation of the operon's or cluster's product. For example, as described in the examples below, in re-engineering the Nif operon, the nifT gene had no known function and notably it was known that elimination of nifT did not to significantly affect the ultimate function of the operon, i.e., nitrogen fixation. Thus, nifT was not included in the re-engineering process.

In some embodiments, the operon or gene cluster will include coding sequences for regulatory proteins that regulate expression or activity of one or more of the other products of the operon or gene cluster. In such embodiments, it can be desirable to omit such regulatory proteins from the re-engineering process because synthetic regulation will be employed instead. For example, as described in the examples below, in re-engineering the nif operon, nifL and nifA were known to act as regulatory genes for the nif operon and thus were omitted so that synthetic regulation could be instead used.

Once the set of gene products to be re-engineered has been identified, one can start with the native coding sequence, or the amino acid sequences of the gene products. For example, in some embodiments, the amino acid sequences of the gene products can be used to produce a synthetic coding sequence for expression in the host cell in which the re-engineered products are to be ultimately expressed.

In some embodiments, the native coding sequences of the set of gene products to be re-engineered are used as a starting point. In this case, in some embodiments, sequences not essential to production of the gene products is eliminated. For example, ribosome binding sites, terminators, or promoters within the coding sequences can be eliminated. In some embodiments, the nucleotide sequences of the coding sequences are analyzed using an algorithm (i.e., in a computer) to identify ribosome binding sites, terminators, or promoters within the sequence(s).

Nonessential regulatory sequences within the coding sequences can be reduced or eliminated by altering the codons of the native coding sequence(s). Regulatory sequences comprising codons can be disrupted, for example, by changing the codons to synonymous codons (i.e., encoding the same amino acid) thereby leaving the encoded amino acid sequence intact while changing the coding sequence. One or more codons of one or more coding sequences can be altered.

In some embodiments, at least 5%, 10%, 15%, 20% or more codons of one or more native coding sequence to be inserted into a synthetic operon are replaced. In some embodiments, at least 5%, 10%, 15%, 20%, 30%, 40%, 50% or more codons of each of the native coding sequences to be inserted into a synthetic operon are replaced.

In some embodiments, replacement codons can be selected, for example, to be significantly divergent from the native codons. The codon changes can result in codon optimization for the host cell, i.e., the cell in which the polynucleotide is to be expressed for testing and/or for ultimate expression. Methods of codon optimization are known (e.g., Sivaraman et al., *Nucleic Acids Res.* 36:e16 (2008); Mirzahoseini, et al., *Cell Journal* (Yakhteh) 12(4): 453 Winter 2011; U.S. Pat. No. 6,114,148) and can include reference to commonly used codons for a particular host cell. In some embodiments, one or more codon is randomized, i.e., a native codon is replaced with a random codon encoding the same amino acid. This latter approach can help to remove any cis-acting sequences involved in the native regulation of the polypeptide. In some embodiments, codons are selected to create a DNA sequence that is maximally distant from the native sequence. In some embodiments, an algorithm is used to eliminate transcriptionally functional sequences in a gene encoding the polypeptide. For example, in some embodiments, ribosome binding sites, transcriptional regulatory elements, terminators, or other DNA sequences bound by proteins are removed from the native coding sequence. Notably, the functional sequences removed can be functional in the native species (from which the sequence was originally derived), in the heterologous host cell, or both. In some embodiments, optimizing comprises removal of sequences in the native coding sequence that are functional for heterologous transcriptional activators or repressors to be used to regulate the synthetic operons to be generated.

Generation of synthetic coding sequences, as well as the remaining portions of the synthetic operon, in many cases will be performed de novo from synthetic oligonucleotides. Thus, in some embodiments, codons are selected to create a DNA sequence that does not generate difficulties for oligonucleotide production or combination. Thus, in some embodiments, codon sequences are avoided that would result in generation of oligonucleotides that form hairpins.

In some embodiments, as noted above, codon alteration will depend on the host cell used. Host cells can be any prokaryotic cell (including but not limited to *E. coli*) or eukaryotic cell (including but not limited to yeast cells, mammalian cells, avian cells, amphibian cells, plant cells, fish cells, and insect cells).

Nonessential regulatory sequences within native sequences can be identified, in some embodiments, using an algorithm performed by a processor executing instructions encoded on a computer-readable storage medium. For example, in some embodiments, ribosome binding sites are identified using a thermodynamic model that calculates the free energy of the ribosome binding to mRNA. In some embodiments, promoters are identified with an algorithm using a position weighted matrix. In some embodiments, transcriptional terminators are identified by an algorithm that identifies hairpins and/or poly-A tracks within sequences. In some embodiments, an algorithm identifies other transcriptionally functional sequences, including but not limited to transposon insertion sites, sites that promote recombination, sites for cleavage by restriction endonucleases, and/or sequences that are methylated.

In view of the alterations described above, in some embodiments, a coding sequence in a synthetic operon of the invention is less than 90, 85, 80, 75, or 70% identical to the native coding sequence. In some embodiments, the coding sequence encodes a protein sequence that is identical to the native protein or is at least 80, 85, 90 or 95% identical to the native protein. In some embodiments, less than 70%, 60%, or 50% of codons in one, two or more coding sequences in a synthetic operon are identical to the codons in the native coding sequence.

B. Organizing Coding Sequences into Synthetic Operons

Once coding sequences have been selected (e.g., and substantially "cleaned" of native or spurious regulatory sequences), the coding sequences are organized into one or more synthetic operon(s). Organization of the synthetic operon(s) includes insertion of various heterologous transcriptional and translational sequences between, before, and/or after the coding sequences so that expression of each coding sequence is controlled as desired. Thus, for example, 5' promoter sequences can be selected to drive expression of an operon RNA comprising the coding sequences of the operon. Selection of one or more terminator of appropriate strength will also affect expression levels. Moreover, the order of the coding sequences within a synthetic operon and/or selection of RBSs for the coding sequences allows for control of relative translation rates of each coding sequence, thereby allowing several levels of control for absolute and relative levels of the final protein products.

Because each synthetic operon can have its own promoter, different synthetic operons can be expressed at different strengths. Thus, in some embodiments, coding sequences are organized into different operons based on the relative native expression levels. Said another way, in some embodiments, coding sequences are organized into operons by grouping coding sequences expressed at substantially the same native level in a particular synthetic operon.

Moreover, because coding sequences at the 5' (front) end of an RNA can be expressed at a higher level than coding sequences further 3', in some embodiments, coding sequences are ordered within a synthetic operon such that the highest expressing coding sequence (in the native context) occurs first and the lowest expressing gene occurs last. In some embodiments, organization of genes within operons is based on native temporal expression, function, ease of manipulation of DNA, and/or experimental design.

In designing the transcriptional (e.g., promoters) and translational (e.g., RBSs) controls of the synthetic operons, the ratio of proteins measured in the native system can be considered. Thus, in some embodiments, two or more coding sequences that are expressed in a native context at substantially the same level and/or that are desirably expressed in an approximately 1:1 ratio to achieve functionality (e.g., where two or more members are part of a functional complex in a 1:1 ratio) are placed in proximity to each other within a synthetic operon. "Proximity" will generally mean that coding sequences are adjacent to each other in the synthetic operon.

In some embodiments, relative expression levels of coding sequences within and, in some embodiments, between synthetic operons is determined by testing one or more test operons for desired expression and/or desired functionality and then improving expression based on the initial results. While this method can be performed in a "trial and error" basis, in some embodiments, a numerical optimization method is employed to guide selection of regulatory elements in order to alter gene expression and to improve desired system properties. Such methods, for example, can be performed by a processor executing instructions encoded on a computer-readable storage medium (discussed further below). Exemplary numerical optimization methods include but are not limited to, a Nelder-Mead algorithm, a Newton's method, a quasi-Newton method, a conjugate gradient method, an interior point method, a gradient descent, a subgradient method, a ellipsoid method, a Frank-Wolfe method, an interpolation method and pattern search methods, or an ant colony model. In some embodiments, a computational design of experiments (DoE) method is employed to alter gene expression and to improve desired system properties in the synthetic operons.

Transcriptional regulatory elements, ribosomal binding sites, terminators, and other sequences affecting transcription or translation can be selected from existing collections of such sequences, and/or can be generated by screening of libraries generated by design or by random mutation. Exemplary regulatory sequences include cis-acting nucleotide sequences bound by a sequence-specific DNA binding polypeptide, e.g., a transcriptional activator or a transcriptional repressor. Exemplary transcriptional activators include, but are not limited to, sigma factors, RNA polymerases (RNAPs) and chaperone-assisted activators. In some embodiments, the transcriptional activator/cis-acting sequence cognate pair will be orthogonal to the host cell. Said another way, the regulatory sequence will not be bound by other host cells proteins except for the heterologous transcriptional activator that binds the cis-acting sequence.

i. Sigma Factors

In some embodiments, the sequence-specific DNA binding polypeptide is a sigma (a) factor and the regulatory sequence of the synthetic operon comprises the sigma factor's cognate cis-acting nucleotide sequenc. Sigma factors recruit RNA polymerase (RNAP) to specific promoter sequences to initiate transcription. The σ 70 family consist of 4 groups: Group 1 are the housekeeping σs and are essential; groups 2-4 are alternative σs that direct cellular transcription for specialized needs (Gruber and Gross, *Annu. Rev. Microbiol.,* 57:441-466 (2003)). Group 4 σs (also known as ECF σs; extracytoplasmic function) constitute the largest and most diverse group of σs, and have been classified into 43 subgroups (Staron et al., *Mol Microbiol* 74(3): 557-81 (2009)).

In some embodiments, the set of sequence-specific DNA-binding polypeptides comprise multiple sigma factors. In some embodiments, the set comprises sigma factors from Group 1, Group 2, Group 3, and/or Group 4 Sigma factors. The ECF subgroup of Group 4 is thought to recognize different promoter sequences, making these σs particularly useful for constructing orthogonal σ-promoter systems. However, it will be appreciated that any group of sigma factors can be used according to the methods of the embodiments of the invention to develop cognate pairs.

TABLE 1

| Group Nr[a] | ID[b] | GI[c] | SPECIES[d] | CLASS[d] | PHYLUM[d] |
|---|---|---|---|---|---|
| ECF01 | >3473 | 109899616 | *Pseudoalteromonas atlantica* T6c | Gammaproteobacteria | Proteobacteria |
| ECF01 | >4085 | 114562024 | *Shewanella frigidimarina* NCIMB 400 | Gammaproteobacteria | Proteobacteria |
| ECF02 | >2817 | 16130498 | *Escherichia coli* K12 | Gammaproteobacteria | Proteobacteria |
| ECF02 | >915 | 119774011 | *Shewanella amazonensis* SB2B | Gammaproteobacteria | Proteobacteria |
| ECF03 | >1198 | 29350055 | *Bacteroides thetaiotaomicron* VPI-5482 | | Bacteroidetes |
| ECF03 | >1244 | 34541012 | *Porphyromonas gingivalis* W83 | | Bacteroidetes |
| ECF04 | >1609 | 21673117 | *Chlorobium tepidum* TLS | | Chlorobi |
| ECF04 | >1617 | 68549683 | *Pelodictyon phaeoclathratiforme* BU-1 | | Chlorobi |
| ECF05 | >965 | 28868416 | *Pseudomonas syringae* pv. tomato str. DC3000 | Gammaproteobacteria | Proteobacteria |
| ECF05 | >1054 | 67154316 | *Azotobacter vinelandii* AvOP | Gammaproteobacteria | Proteobacteria |
| ECF06 | >3576 | 15595669 | *Pseudomonas aeruginosa* PAO1 | Gammaproteobacteria | Proteobacteria |
| ECF06 | >853 | 26987094 | *Pseudomonas putida* KT2440 | Gammaproteobacteria | Proteobacteria |
| ECF07 | >980 | 67154823 | *Azotobacter vinelandii* AvOP | Gammaproteobacteria | Proteobacteria |
| ECF07 | >1134 | 15598606 | *Pseudomonas aeruginosa* PAO1 | Gammaproteobacteria | Proteobacteria |
| ECF08 | >3580 | 15595872 | *Pseudomonas aeruginosa* PAO1 | Gammaproteobacteria | Proteobacteria |
| ECF08 | >3627 | 70730114 | *Pseudomonas fluorescens* Pf-5 | Gammaproteobacteria | Proteobacteria |
| ECF09 | >3581 | 15597622 | *Pseudomonas aeruginosa* PAO1 | Gammaproteobacteria | Proteobacteria |
| ECF09 | >1009 | 70730971 | *Pseudomonas fluorescens* Pf-5 | Gammaproteobacteria | Proteobacteria |
| ECF10 | >3486 | 77360766 | *Pseudoalteromonas haloplanktis* TAC125 | Gammaproteobacteria | Proteobacteria |
| ECF10 | >2914 | 88706154 | gamma proteobacterium KT 71 | Gammaproteobacteria | Proteobacteria |
| ECF11 | >3726 | 28868260 | *Pseudomonas syringae* pv. tomato str. DC3000 | Gammaproteobacteria | Proteobacteria |
| ECF11 | >987 | 28899132 | *Vibrio parahaemolyticus* RIMD 2210633 | Gammaproteobacteria | Proteobacteria |
| ECF12 | >807 | 86158800 | *Anaeromyxobacter dehalogenans* 2CP-C | Deltaproteobacteria | Proteobacteria |
| ECF12 | >808 | 108762328 | *Myxococcus xanthus* DK 1622 | Deltaproteobacteria | Proteobacteria |
| ECF13 | >1146 | 33152898 | *Haemophilus ducreyi* 35000HP | Gammaproteobacteria | Proteobacteria |
| ECF13 | >1025 | 37524103 | *Photorhabdus luminescens* subsp. *laumondii* TTO1 | Gammaproteobacteria | Proteobacteria |
| ECF14 | >3200 | 15608361 | *Mycobacterium tuberculosis* H37Rv | | Actinobacteria |
| ECF14 | >1324 | 21223516 | *Streptomyces coelicolor* A3(2) | | Actinobacteria |
| ECF15 | >436 | 77464848 | *Rhodobacter sphaeroides* 2.4.1 | Alphaproteobacteria | Proteobacteria |
| ECF15 | >524 | 16127705 | *Caulobacter crescentus* CB15 | Alphaproteobacteria | Proteobacteria |
| ECF16 | >3622 | 104782321 | *Pseudomonas entomophila* L48 | Gammaproteobacteria | Proteobacteria |
| ECF16 | >973 | 161378140 | *Pseudomonas putida* KT2440 | Gammaproteobacteria | Proteobacteria |
| ECF17 | >1691 | 15607875 | *Mycobacterium tuberculosis* H37Rv | | Actinobacteria |
| ECF17 | >1458 | 21221399 | *Streptomyces coelicolor* A3(2) | | Actinobacteria |
| ECF18 | >4451 | 21230791 | *Xanthomonas campestris* pv. *campestris* str. ATCC 33913 | Gammaproteobacteria | Proteobacteria |
| ECF18 | >4438 | 21242133 | *Xanthomonas axonopodis* pv. *citri* str. 306 | Gammaproteobacteria | Proteobacteria |
| ECF19 | >3197 | 15607586 | *Mycobacterium tuberculosis* H37Rv | | Actinobacteria |
| ECF19 | >1315 | 21219164 | *Streptomyces coelicolor* A3(2) | | Actinobacteria |
| ECF20 | >992 | 70731405 | *Pseudomonas fluorescens* Pf-5 | Gammaproteobacteria | Proteobacteria |
| ECF20 | >2913 | 88706222 | gamma proteobacterium KT 71 | Gammaproteobacteria | Proteobacteria |
| ECF21 | >1280 | 29350128 | *Bacteroides thetaiotaomicron* VPI-5482 | | Bacteroidetes |
| ECF21 | >2825 | 89889680 | Flavobacteria bacterium BBFL7 | | Bacteroidetes |
| ECF22 | >4450 | 21232074 | *Xanthomonas campestris* pv. *campestris* str. ATCC 33913 | Gammaproteobacteria | Proteobacteria |
| ECF22 | >1147 | 21243541 | *Xanthomonas axonopodis* pv. *citri* str. 306 | Gammaproteobacteria | Proteobacteria |
| ECF23 | >231 | 15895043 | *Clostridium acetobutylicum* ATCC 824 | | Firmicutes |
| ECF23 | >1851 | 30261806 | *Bacillus anthracis* str. Ames | | Firmicutes |
| ECF24 | >69 | 16079737 | *Bacillus subtilis* subsp. *subtilis* str. 168 | | Firmicutes |
| ECF24 | >1034 | 32470052 | *Escherichia coli* | Gammaproteobacteria | Proteobacteria |
| ECF25 | >1645 | 170078575 | *Synechococcus* sp. PCC 7002 | | Cyanobacteria |
| ECF25 | >1643 | 17230772 | *Nostoc* sp. PCC 7120 | | Cyanobacteria |
| ECF26 | >4464 | 58581966 | *Xanthomonas oryzae* pv. *oryzae* KACC10331 | Gammaproteobacteria | Proteobacteria |

TABLE 1-continued

| Group Nr[a] | ID[b] | GI[c] | SPECIES[d] | CLASS[d] | PHYLUM[d] |
|---|---|---|---|---|---|
| ECF26 | >837 | 77459110 | *Pseudomonas fluorescens* PfO-1 | Gammaproteobacteria | Proteobacteria |
| ECF27 | >4265 | 21222299 | *Streptomyces coelicolor* A3(2) | | Actinobacteria |
| ECF27 | >1331 | 31795084 | *Mycobacterium bovis* AF2122/97 | | Actinobacteria |
| ECF28 | >1088 | 114563849 | *Shewanella frigidimarina* NCIMB 400 | Gammaproteobacteria | Proteobacteria |
| ECF28 | >1040 | 15641058 | *Vibrio cholerae* O1 biovar eltor str. N16961 | Gammaproteobacteria | Proteobacteria |
| ECF29 | >371 | 13476734 | *Mesorhizobium loti* MAFF303099 | Alphaproteobacteria | Proteobacteria |
| ECF29 | >2688 | 71281387 | *Colwellia psychrerythraea* 34H | Gammaproteobacteria | Proteobacteria |
| ECF30 | >35 | 16079766 | *Bacillus subtilis* subsp. *subtilis* str. 168 | | Firmicutes |
| ECF30 | >83 | 18309341 | *Clostridium perfringens* str. 13 | | Firmicutes |
| ECF31 | >2963 | 85713274 | *Idiomarina baltica* OS145 | Gammaproteobacteria | Proteobacteria |
| ECF31 | >34 | 16080921 | *Bacillus subtilis* subsp. *subtilis* str. 168 | | Firmicutes |
| ECF32 | >1122 | 4581629 | *Erwinia amylovora* | Gammaproteobacteria | Proteobacteria |
| ECF32 | >3724 | 28868612 | *Pseudomonas syringae* pv. tomato str. DC3000 | Gammaproteobacteria | Proteobacteria |
| ECF33 | >375 | 27378153 | *Bradyrhizobium japonicum* USDA 110 | Alphaproteobacteria | Proteobacteria |
| ECF33 | >423 | 39934888 | *Rhodopseudomonas palustris* CGA009 | Alphaproteobacteria | Proteobacteria |
| ECF34 | >3302 | 77164965 | *Nitrosococcus oceani* ATCC 19707 | Gammaproteobacteria | Proteobacteria |
| ECF34 | >1384 | 21218750 | *Streptomyces coelicolor* A3(2) | | Actinobacteria |
| ECF35 | >3582 | 15598092 | *Pseudomonas aeruginosa* PAO1 | Gammaproteobacteria | Proteobacteria |
| ECF35 | >1119 | 24375055 | *Shewanella oneidensis* MR-1 | Gammaproteobacteria | Proteobacteria |
| ECF36 | >3196 | 15609206 | *Mycobacterium tuberculosis* H37Rv | | Actinobacteria |
| ECF36 | >1595 | 21219385 | *Streptomyces coelicolor* A3(2) | | Actinobacteria |
| ECF37 | >3390 | 89094252 | *Oceanospirillum* sp. MED92 | Gammaproteobacteria | Proteobacteria |
| ECF37 | >2513 | 83718468 | *Burkholderia thailandensis* E264 | Betaproteobacteria | Proteobacteria |
| ECF38 | >1322 | 21222029 | *Streptomyces coelicolor* A3(2) | | Actinobacteria |
| ECF38 | >1442 | 152967344 | *Kineococcus radiotolerans* SRS30216 | | Actinobacteria |
| ECF39 | >1438 | 21223369 | *Streptomyces coelicolor* A3(2) | | Actinobacteria |
| ECF39 | >2973 | 84494624 | *Janibacter* sp. HTCC2649 | | Actinobacteria |
| ECF40 | >3198 | 15610550 | *Mycobacterium tuberculosis* H37Rv | | Actinobacteria |
| ECF40 | >1380 | 62389491 | *Corynebacterium glutamicum* ATCC 13032 | | Actinobacteria |
| ECF41 | >491 | 16127496 | *Caulobacter crescentus* CB15 | Alphaproteobacteria | Proteobacteria |
| ECF41 | >1141 | 77459658 | *Pseudomonas fluorescens* PfO-1 | Gammaproteobacteria | Proteobacteria |
| ECF42 | >3583 | 15596548 | *Pseudomonas aeruginosa* PAO1 | Gammaproteobacteria | Proteobacteria |
| ECF42 | >4454 | 77747962 | *Xanthomonas campestris* pv. *campestris* str. ATCC 33913 | Gammaproteobacteria | Proteobacteria |
| ECF43 | >4437 | 21244845 | *Xanthomonas axonopodis* pv. *citri* str. 306 | Gammaproteobacteria | Proteobacteria |
| ECF43 | >3477 | 109897287 | *Pseudoalteromonas atlantica* T6c | Gammaproteobacteria | Proteobacteria |

In addition to native sigma factors, chimeric or other variant sigma factors can also be used in the method of the invention. For example, in some embodiments, one or more sigma factor are submitted to mutation to generate library of sigma factor variants and the resulting library can be screen for novel DNA binding activities.

In some embodiments, chimeric sigma factors formed from portions of two or more sigma factors can be used. Accordingly, embodiments of the invention provide for generating a library of polynucleotides encoding chimeric sigma factors, wherein the chimeric sigma factors comprise a domain from at least two different sigma factors, wherein each of the domains bind to the −10 or −35 region of a regulatory element; and expressing chimeric sigma factors from the library of polynucleotides, thereby generating a library of chimeric sigma factors. For example, in some embodiments, chimeric sigma factors are generated comprising a "Region 2" from a first sigma factor and a "Region 4" from a second sigma factor, thereby generating chimeric sigma factors with novel DNA binding activities. "Region 2" of sigma factors is a conserved domain that recognizes −10 regions of promoters. "Region 4" is a conserved domain of sigma factors that recognizes −35 regions of promoters. It will be appreciated that chimeric sigma factors can be generated from any two native sigma factors that bind different target DNA sequences (e.g., different promoter sequences). It has been found that chimeric sigma factors formed from the ECF2 and ECF11 subgroups have unique DNA binding activities useful for generating orthogonal sets as described herein. Exemplary chimeric sigma factors include, but are not limited to, ECF11_ECF02 (containing amino acids 1-106 from ECF02_2817 and 122-202 from ECF11_3726) and ECF02_ECF11 (containing amino acids 1-121 from ECF11_3726 and 107-191 from ECF02_2817).

The ECF11_ECF02 amino acid sequence is as follows (SEQ ID NO: 239):

```
  1 MRITASLRTFCHLSTPHSDSTTSRLWIDEVTAVARQRDRDSFM
    RIYDHFAPRLLRYLTGL

 61 NVPEGQAEELVQEVLLKLWHKAESEDPSKASLGTWLFRIARNL
    YIDSVRKDRGWVQVQNS

121 LEQLERLEAISNPENLMLSEELRQIVERTIESLPEDLRMAITL
    RELDGLSYEEIAAIMDC

181 PVGTVRSRIFRAREAIDNKVQPLIRR*
```

The ECF02_ECF11 amino acid sequence is as follows (SEQ ID NO: 240):

```
  1 MSEQLTDQVLVERVQKGDQKAFNLLVVRYQHKVASLVSRYVPS
    GDVPDVVQEAFIKAYRA

 61 LDSFRGDSAFYTWLYRIAVNTAKNYLVAQGRRPPSSDVDAIEA
    ENFEQLERLEAPVDRTL

121 DYSQRQEQQLNSAIQNLPTDQAKVLRMSYFEALSHREISERLD
    MPLGTVKSCLRLAFQKL

181 RSRIEES*
```

ii. RNA Polymerases

In some embodiments, the sequence-specific DNA-binding polypeptide is a polypeptide having DNA binding activity and that is a variant of the T7 RNA polymerase (RNAP) and the RNAP's cognate cis-acting sequence (e.g., a promoter recognized by the RNAP) is operably linked to the synthetic operon to control the operon's expression. The T7 RNAP amino acid sequence (SEQ ID NO:241) is as follows:

```
  1  mntiniaknd  fsdielaaip  fntladhyge  rlareqlale
     hesyemgear  frkmferqlk

 61  agevadnaaa  kplittllpk  miarindwfe  evkakrgkrp
     tafqflqeik  peavayitik

121  ttlacltsad  nttvqavasa  igraiedear  fgrirdleak
     hfkknveeql  nkrvghvykk

181  afmqvveadm  lskgllggea  wsswhkedsi  hvgvrcieml
     iestgmvslh  rqnagvvgqd

241  setielapey  aeaiatraga  lagispmfqp  cvvppkpwtg
     itgggywang  rrplalvrth

301  skkalmryed  vympevykai  niaqntawki  nkkvlavanv
     itkwkhcpve  dipaiereel

361  pmkpedidmn  pealtawkra  aaavyrkdka  rksrrislef
     mleqankfan  hkaiwfpynm

421  dwrgrvyays  mfnpqgndmt  kglltlakgk  pigkegyywl
     kihgancagv  dkvpfperik

481  fieenhenim  acaksplent  wwaeqdspfc  flafcfeyag
     vqhhglsync  slplafdgsc

541  sgiqhfsaml  rdevggravn  llpsetvqdi  ygivakkvne
     ilqadaingt  dnevvtvtde

601  ntgeisekvk  lgtkalagqw  laygvtrsvt  krsvmtlayg
     skefgfrqqv  ledtiqpaid

661  sgkglmftqp  nqaagymakl  iwesvsvtvv  aaveamnwlk
     saakllaaev  kdkktgeilr

721  krcavhwvtp  dgfpvwqeyk  kpiqtrinlm  flgqfrlqpt
     intnkdseid  ahkqesgiap

781  nfvhsqdgsh  lrktvvwahe  kygiesfali  hdsfgtipad
     aanlfkavre  tmvdtyescd

841  vladfydqfa  dqlhesqldk  mpalpakgnl  nlrdilesdf
     afa
```

The T7 RNAP promoter has also been characterized (see, e.g., Rong et al., *Proc. Natl. Acad. Sci. USA*, 95(2):515-519 (1998)) and is well known.

Methods have been discovered for generating orthogonal pairs of RNAP variants and target promoter variants. Due to toxicity of expression of native T7 RNAP, a series of mutations and modifications can be designed such that a library of RNAP variants can be expressed and tested for activity in cells without excessive toxicity. Accordingly, embodiments of the invention provide for one or more of the following modifications (and thus, for example, an embodiment of the invention provides for host cells comprising expression cassettes, or nucleic acids comprising expression cassettes, wherein the expression cassette encodes a RNAP variant substantially identical to T7 RNAP, wherein the expression cassette comprises one or more of the following):

Expression of the T7 RNAP variant can be expressed from a low copy plasmid. Expression of the RNAP can be controlled by a separately encoded protein from a separate vector, thereby blocking expression of the RNAP until a second vector is added to the cells promoting RNAP expression;

Translational control: a GTG start codon; weak ribosomal binding sites, and/or random DNA spacers to insulate RNAP expression can be used;

A molecular tag to promote rapid degradation of the RNAP. For example, an Lon N-terminal tag will result in rapid degradation of the tagged RNAP by the Lon protease system.

A mutated RNAP active site (e.g., within amino acids 625-655 of T7 RNAP). For example, it ha been discovered that a mutation of the position corresponding to amino acid 632 (R632) of T7 RNAP can be mutated to reduce the RNAP's activity. In some embodiments, the RNAP contains a mutation corresponding to R632S.

Moreover, a variety of mutant T7 promoters have been discovered that can be used in a genetic circuit. Thus, in some embodiments, the regulatory sequence of a synthetic operon comprises a mutant sequence as set forth in the table below (SEQ ID NOS:156-163).

| Promoter Name | Sequence TAATACGACTCACTANNNNNAGA | Strength (2009.10.02 to 2009.10.09) |
|---|---|---|
| WT | TAATACGACTCACTATAGGGAGA | 5263 |
| Mut1 | TAATACGACTCACTACAGGCAGA | 365 |
| Mut2 | TAATACGACTCACTAGAGAGAGA | 366 |
| Mut3 | TAATACGACTCACTAATGGGAGA | 577 |
| Mut4 | TAATACGACTCACTATAGGTAGA | 1614 |
| Mut5 | TAATACGACTCACTAAAGGGAGA | 1018 |
| Mut6 | TAATACGACTCACTATTGGGAGA | 3216 |

A number of different stem loop structures that function as terminators for T7 RNAP have also been discovered. See, Table directly below (SEQ ID NOS:242-253). Accordingly, an embodiment of the invention provides for a synthetic operon comprising a promoter functional to a native T7 RNAP or an RNAP substantially identical thereto, wherein the operably linked polynucleotide comprises a terminator selected from the table directly below. Terminators with different sequences can be selected for different transcupts to avoid homologous recombination.

| Termi-nator Name | Sequence TANNNNAACCSSWWSSSSSSTCWWW WCGSSSSSWWSGGTTTTTTGT | Strength (2009.12.16 Assay) |
|---|---|---|
| 52 | TATAAACGGGGGGCTAGGGGTTTTTT GT | 107 |
| 23 | TACTCGAACCCCTAGCCCGCTCTTATC GGGCGGCTAGGGGTTTTTTGT | 714 |
| 72 | TAGCAGAACCGCTAACGGGGGCGAAG GGGTTTTTTGT | 1051 |
| 48 | TACTCGAACCCCTAGCCCGCTCTTATC GGGCGGCTAGGGGTTTTTTGT | 1131 |
| 1 | TACATATCGGGGGGGTAGGGGTTTTTT GT | 1297 |
| 2 | TACATATCGGGGGGGTAGGGGTTTTTT GT | 1333 |
| WT | TAGCATAACCCCTTGGGGCCTCTAAAC GGGTCTTGAGGGGTTTTTTGT | 1395 |
| 31 | TACCCTAACCCCTTCCCCGGTCAATCG GGGCGGATGGGGTTTTTTGT | 1586 |

-continued

| Terminator Name | Sequence TANNNNAACCSSWWSSSSSSTCWWW WCGSSSSSWWSGGTTTTTTGT | Strength (2009.12.16 Assay) |
|---|---|---|
| 58 | TAGACCAACCCCTTGCGGCCTCAATCG GGGGGGATGGGGTTTTTTGT | 1608 |
| 25 | TACTCTAACCCCATCGGCCGTCTTAGG GGTTTTTTGT | 1609 |
| 17 | TACCTCAACCCCTTCCGCCCTCATATC GCGGGGCATGCGGTTTTTTGT | 1887 |

In some embodiments, RNAP variants can be designed comprising an altered specificity loop (corresponding to positions between 745 and 761). Thus in some embodiments, an RNAP is provided that is identical or substantially identical to T7 or T3 RNAP but has a Loop Sequence selected from those in the tables directly below between positions 745 and 761. Loop Sequences=SEQ ID NOS:254, 255, 257 and 259. Promoter Sequences=SEQ ID NOS:157, 256, 258 and 260.

A

| RNAP Family | Scaffold | RNAP Plasmid | Promoter Plasmid | Loop Sequence | Promoter Sequence |
|---|---|---|---|---|---|
| T7 | N249 | N249 | N155 | VWQEYKKPIQTRLNLMFLGQFRLQPTINTNKDSEI DAHK | TAATACGACTCACTATA GGGAGA |
| T3 | N115 | N377:115 | N352 | VWQEYKKPIQKRLDMIFLGQFRLQPTINTNKDSEI DAHK | TAATAACCCTCACTATA GGGAGA |
| K1F | N115 | N421:115 | N353 | VWQEYKKPIQTRLNLMFLGSFNLQPTVNTNKDSEI DAHK | TAATAACTATCACTATA GGGAGA |
| N4 | N77 | W78 | W74 | VWQEYKKPIQTRIDCVILGTHRMALTINTNKDSEID AHK | TAATAACCCACACTATA GGGAGA |

B

| | T7 promoter | T3 promoter | K1F promoter | N4 promoter |
|---|---|---|---|---|
| T7 RNAP | 2177 | 24 | 17 | 14 |
| T3 RNAP | 83 | 1062 | 14 | 14 |
| K1F RNAP | 45 | 26 | 463 | 13 |
| N4 RNAP | 51 | 147 | 46 | 2616 |

iii. Activators Requiring Chaperones

In some embodiments, the set of sequence-specific DNA-binding polypeptides comprise polypeptides having DNA binding activity and that require a separate chaperone protein to bind the sequence-specific DNA-binding polypeptide for the sequence-specific DNA-binding polypeptide to be active. Exemplary transcriptional activators requiring a chaperone for activity include, but are not limited to activator is substantially similar to InvF from *Salmonella typhimurium*, MxiE from *Shigella flexneri*, and ExsA from *Pseudomonas aeruginosa*. These listed activators require binding of SicA from *Salmonella typhimurium, IpgC from Shigella flexneri*, or ExsC from *Pseudomonas aeruginosa*, respectively, for activation.

Sequence information for the above components are provides as follows (SEQ ID NOS:260-273):

| Name | Type | DNA sequence encoding the named polypeptide | Optional Mutation |
|---|---|---|---|
| sicA | Gene | atggattatcaaaataatgtcagcgaagaacgtgttgcggaaatgatttgggatgccgttagtgaag<br>gcgccacgctaaaagacgttcatgggatccctcaagatatgatggacggtttatatgctcatgctta<br>tgagttttataaccagggacgactggatgaagctgagacgttctttcgtt**t**cttatgcatttatgatttt<br>tacaatcccgattacaccatgggactggcggcagtatgccaactgaaaaaacaatttcagaaagc<br>atgtgacctttatgcagtagcgtttacgttacttaaaaatgattatcgccccgtttttttaccgggcagt<br>gtcaattattaatgcgtaaggcagcaaaagccagacagtgttttgaacttgtcaatgaacgtactga<br>agatgagtctctgcgggcaaaagcgttggtctatctggaggcgctaaaaacggcggagacagag<br>cagcacagtgaacaagaaaaggaataa | |
| sicA* | Mutant sicA | atggattatcaaaataatgtcagcgaagaacgtgttgcggaaatgatttgggatgccgttagtgaag<br>gcgccacgctaaaagacgttcatgggatccctcaagatatgatggacggtttatatgctcatgctta<br>tgagttttataaccagggacgactggatgaagctgagacgttctttcgtt**a**cttatgcatttatgattt<br>ttacaatcccgattacaccatgggactggcggcagtatgccaactgaaaaaacaatttcagaaagc<br>atgtgacctttatgcagtagcgtttacgttacttaaaaatgattatcgccccgtttttttaccgggcagt<br>gtcaattattaatgcgtaaggcagcaaaagccagacagtgttttgaacttgtcaatgaacgtactga<br>agatgagtctctgcgggcaaaagcgttggtctatctggaggcgctaaaaacggcggagacagag<br>cagcacagtgaacaagaaaaggaataa | The large "t" of the sicA sequence above was mutated to "a" by error-prone PCR. This mutation was made to reduce cross talk between SicA and MxiE. |
| invF | Gene with new start codon | atgctaaatacgcaggaagtacttaaagaaggagagaagcggaaaatccgcagcccggaagca<br>tggtttatacagacgtgttccgcgcaaaagctgcatat**atg**tcattttctgaaagccgacacaatga<br>aaattgcctgattcaggaaggcgcgctgctttttttgcgagcaggccgttgtcgcaccagtatcagg<br>agacctggtttttcgaccgttaaaaattgaagtactcagcaaattactggcatttatcgatggcgcag<br>gattagtggacacgacatatgctgaatccgataaatgggttttgctgagtcctgagtttcgcgctattt<br>ggcaagatcgtaaacgctgcgagtactggtttttgcagcaaattattacgccttctccggccttcaat<br>aaggtactggcgctgttacgaaaaagcgagagttactggttggttggctatttactcgctcagtcaa<br>ccagcggcaacacgatgagaatgctgggagaagactatggcgtttcttatacccattttcgtcgttt<br>gtgcagcagagcgttgggcggaaaagcgaagagtgaattacgaaactggcgtatggcgcaatc<br>gctgctgaatagtgtagaaggccacgagaacatcacccaattagccgttaatcatggttactcatc<br>gccttcacatttttctagtgagatcaaagagctgatcggcgtttcgccgcggaaattatcaaatattat<br>tcaattggcagacaaatga | The accepted start codon (the large "atg") was determined to be incorrect and a correct upstream start codon was found. |
| psicA | Promoter | ccacaagaaacgaggtacggcattgagccgcgtaaggcagtagcgatgtattcattgggcgttttt<br>tgaatgttcactaaccaccgtcggggtttaataactgcatcagataaacgcagtcgttaagttctaca<br>aagtcggtgacagataacaggagtaagta | |
| ipgC | Gene | atgtctttaaatatcaccgaaaatgaaagcatctctactgcagtaattgatgcaattaactctggcgct<br>acactgaaagatattaatgcaattcctgatgatatgatggatgacatttattcatatgcttatgactttta<br>caacaaaggaagaatagaggaagctgaagttttcttcaggtttttatgtatatacgacttttacaatgt<br>agactacattatgggactcgcagctatttatcagataaaagaacagttccaacaagcagcagacct<br>ttatgctgtcgcttttgcattaggaaaaaatgactatacaccagtattccatactggacaatgtcagct<br>tcggttgaaagccccttaaaagctaaagagtgcttcgaactcgtaattcaacacagcaatgatga<br>aaaattaaaaataaaagcacaatcatacttggacgcaattcaggatatcaaggagtaa | |
| mxiE | Gene with codon optimization | **a**tgagtaaatataaaggcctgaacaccagcaacatgttctacatctacagctctggtcatgaacc<br>ggtgaacgttgaactggtgaaagataaagaacgtaacatcatcgaactggcaccggcgtggaaa<br>gg**ctttttcttt**gtgcgtaaccagaacatcaaattcagcgataacgttaactaccactacc<br>gcttcaacatcaactcttgcgcaaaattcctggcgttttgggattattttagcggcgccctggttgaac<br>attctcacgcagaaaaatgcatccatttctaccacgaaaacgatctgcgtgatagctgtaatacgga<br>atctatgctggataaactgatgctgcgcttcatttttagtagcgatcagaacgtgtctaatgccctggc | The wide type gene has "ttttttttt" in this enlarged sequence region. One more "t" was added to make "tttttttttt" and then the entire gene was |

-continued

| Name | Type | DNA sequence encoding the named polypeptide | Optional Mutation |
|---|---|---|---|
| | | aatgatccgtatgaccgaaagttatcatctggttctgtacctgctgcgtacgattgaaaaagaaaaa<br>gaagtgcgcatcaaaagcctgaccgaacactatggcgtttctgaagcgtactttcgtagtctgtgtc<br>gcaaagcgctgggtgccaaagtgaaagaacagctgaacacgtggcgcctggtgaatggcctgc<br>tggatgttttcctgcataaccagaccattacgagcgcggccatgaacaatggttatgcgtctaccag<br>tcacttcagcaatgaaattaaaacgcgtctgggctttagtgcccgcgaactgagcaacatcaccttc<br>ctggtgaagaaaattaatgaaaaaatctaa | codon optimized by GenScript. The additional "t" was added to make this ORF in-frame. In addition, the wide-type gene starts with "g" and this synthetic gene starts with "a." |
| pipaH9.8 | Promoter | gcgaaaatgacatcaaaaacgccattaacctgatgttctggggaatataaatgtcaggctagggtc<br>aaaaatcgtggcgttgacaaaatggctgcgttacgtcattgagcatatccaggactggccggcaa<br>accgggtacgcgatctgttgccttggaaagttgatctgacctctcagtaaatatcaatacggttctga<br>cgagccgcttaccgttcaaatatgaagtacgatgtttaactaaccgaaaaacaagaacaatacggt<br>gcaaacaggccattcacggttaactgaaacagtatcgtttttttacagccaattttgtttatccttatta**t**<br>**a**ataaaaaagtgct | |
| pipaH9.8* | Promoter with mutation | gcgaaaatgacatcaaaaacgccattaacctgatgttctggggaatataaatgtcaggctagggtc<br>aaaaatcgtggcgttgacaaaatggctgcgttacgtcattgagcatatccaggactggccggcaa<br>accgggtacgcgatctgttgccttggaaagttgatctgacctctcagtaaatatcaatacggttctga<br>cgagccgcttaccgttcaaatatgaagtacgatgtttaactaaccgaaaaacaagaacaatacggt<br>gcaaacaggccattcacggttaactgaaacagtatcgtttttttacagccaattttgtttatccttatta<br>**ag**ataaaaaagtgct | The enlarged "ta" above of pipaH9.8 was mutated to "ag" by saturation mutagenesis. This mutation was made to reduce leaky expression of pipaH9.8. |
| exsC | Gene | atggatttaacgagcaaggtcaaccgactgcttgccgagttcgcaggccgtatcggtttgccttcc<br>ctgtccctcgacgaggagggcatggcgagcctcctgttcgacgaacaggtgggcgtcaccctgt<br>tgctgctcgccgagcgcgagcgtctgttgctggaggccgatgtggcgggcatcgatgtgctggg<br>cgaggggatattcgccagctcgccagcttcaaccgccattggcaccgtttcgatctgcatttcggc<br>ttcgacgagctgaccggcaaggtccagttgtatgcgcagattctcgcagcgcaactgaccctcga<br>atgcttcgaggcgaccttggccaatctgctcgatcacgccgagttctggcagcgcctgctgccgt<br>gcgacagtgatcgcgaggcggtcgctgcggtcggcatgagggtttga | |
| exsD | Gene | atggagcaggaagacgataagcagtactcccgagaagcggtgttcgctggcaggcgggtatcc<br>gtggtgggctcggacgcccgctcgcggggtcgggtgccgggttacgcatcgagcagtttgtatc<br>gtgagtccggaatcatcagtgcgcggcaactggcgttgctgcagcggatgctgccgcgcctgcg<br>gctggagcaactgttccgctgcgagtggttgcagcagcgcctggcgcgcggcctggcgctggg<br>gcgcgaagaggtgcggcagattctcctctgcgcggcgcaggacgacgacggctggtgctccga<br>actgggcgaccgggtcaacctcgccgtgccgcagtcgatgatcgactgggtcctgctgccggtc<br>tatggctggtgggaaagcctgctcgaccaggcgatccccggctggcgcctgtcgctggtggagc<br>tggagacccagtcccggcaactgcgagtcaagtccgaattctggtcccgcgtggccgagctgga<br>gccggagcaggcccgcgaggaactggccagggtcgccaagtgccaggcgcgcacccagga<br>acaggtggccgaactggccggcaagctggagacggcttcggcactggcgaagagcgcctggc<br>cgaactggcagcggggcatggcgacgctgctcgccagcggcgggctggccggcttcgagccg<br>atccccgaggtcctcgaatgcctctggcaacctctctgccggctggacgacgacgtcggcgcgg<br>cggacgccgtccaggcctggctgcacgaacgcaacctgtgccaggcacaggatcacttctactg<br>gcagagctga | |
| exsA | Gene | atgcaaggagccaaatctcaggccgaaagcagataacgtcagtcattggaacattccaactacg<br>aatacagggtaaacaaggaagagggcgtatatgactgctcgagggcgaactgaccgtccagga<br>catcgattccactattgcctggcgcctggcgagagcattcgtccgccgcggaagctatgtcgtaa | |

-continued

| Name | Type | DNA sequence encoding the named polypeptide | Optional Mutation |
|---|---|---|---|
| | | gtaccaagggaaaggacagccgaatactctggattccattatctgcccagtactacaaggcttcgt<br>ccagcgcttcggcgcgctgagagtgaagtcgagcgagcgacgagcccgtgccgggcatcatc<br>gcgttcgctgccacgcctctgctggccggagcgtcaaggggttgaaggaattgcttgtgcatgag<br>catccgccgatgctcgcctgcctgaagatcgaggagagctgatgctcacgcgttcagtccgcag<br>gggccgctgctgatgtcggtcctgcggcaactgagcaaccggcatgtcgagcgtctgcagctatt<br>catggagaagcactacctcaacgagtggaagctgtccgacactcccgcgagacggcatgggg<br>ctgaccaccacaaggagctgacggcagtgtctatggggatcgccgcgcgcctggatcagcga<br>gcggagaatcctctatgcccatcagagctgctcaacagcgacatgagcatcgtcgacatcgccat<br>ggaggcgggcttaccagtcagtcctatacacccagagctatcgccgccgtacggctgcacgcc<br>gagccgctcgcggcaggggaaggacgaatgccgggctaaaaataactga | |
| pexsD | Promoter | gaaggacgaatgccgggctaaaaataactgacgttattgaaagcccggtagcggctgcatgagt<br>agaatcggcccaaat | |
| pexsC | Promoter | gatgtggctatacttaaaagaaaagtctctcagtgacaaaagcgatgcatagcccggtgctagca<br>tgcgctgagcttt | |
| rfp | Gene | atggcacctccgaagacgttatcaaagagacatgcgtacaaagttcgtatggaaggaccgttaa<br>cggtcacgagacgaaatcgaaggtgaaggtgaaggtcgtccgtacgaaggtacgcagaccgct<br>aaactgaaagttaccaaaggtggtccgctgccgacgcagggacatcctgtccccgcagaccag<br>tacggaccaaagcttacgttaaacacccggctgacatcccggactacctgaaactgtccacccg<br>gaaggatcaaatgggaacgtgttatgaacttcgaagacggtggtgagttaccgttacccaggact<br>cctccctgcaagacggtgagttcatctacaaagttaaactgcgtggtactaacttcccgtccgacg<br>gtccggttatgcagaaaaaaaccatgggagggaagcaccaccgaacgtatgtacccggaagac<br>ggtgctctgaaaggtgaaatcaaaatgcgtctgaaactgaaagacggtggtcactacgacgctga<br>agttaaaaccacctacatggctaaaaaaccggttcagctgccgggtgcttacaaaaccgacatca<br>aactggacatcacctcccacaacgaagactacaccatcgttgaacagtacgaacgtgctgaaggt<br>cgtcactccaccggtgctgcagcaaacgacgaaaactacgcttaa | |

C. Controlling Operon Expression

As noted above, the one or more synthetic operons are controlled by regulatory elements responsive to a sequence-specific DNA binding polypeptide (e.g., a transcriptional activator). Where more than one operon is used, it can be desirable that each operon be responsive to the same transcriptional activator, albeit with a different regulatory sequence that controls the "strength" of expression of a particular operon. As noted above, in some embodiments, the transcriptional activator is a T7 RNAP or a variant thereof.

Expression of the sequence-specific DNA binding polypeptide can be controlled on a separate expression cassette, the expression cassette comprising a promoter operably linked to a polynucleotide encoding the sequence-specific DNA binding polypeptide. In some embodiments, the promoter is inducible, thereby imparting control of expression of the operon based on the inducer. Exemplary inducible promoters (with inducer in parentheses) include, e.g., Ptac (IPTG), Ptrc (IPTG), Pbad (arabinose), Ptet (aTc), Plux (AI-1). Alternatively, in some embodiments, the promoter is constitutive.

In some embodiments, additional "buffer" nucleotide sequences are inserted between promoters and ribosomal binding sites, between coding sequences and terminators, and/or between coding sequences and a subsequent ribosomal binding site. These sequences act as "buffers" in that they reduce or eliminate regulatory cross-talk between different coding sequences. In some embodiments, the spacer forms a stem loop, is a native sequence from a metabolic pathway, or is from a 5'-UTR, e.g., obtained from a phage. In some embodiments, the stem loop is a ribozyme. In some embodiments, the ribozyme is RiboJ. In some embodiments, the buffer sequence is selected from sequences of a given length with nucleotides selected at random. In some embodiments, the buffer sequence is a UP-region of a promoters. UP regions can positively influence promoter strength and are generally centered at position −50 of a promoter (as measured from the start of transcription). See, e.g., Estrem, et al., *PNAS,* 95 (11): 9761-9766 (1988). In some embodiments, the buffer sequence is an extended 5-UTR sequence.

Exemplary buffer sequences include those listed in the table below (SEQ ID NOS:274-333, respectively):

| Sources | Sequences |
|---|---|
| T5 phage | agttcgatgagagcgataaccctctacaaataattttgtttaa |
| T5 phage | ataaattgataaacaaaaacctctacaaataattttgtttaa |
| T5 phage | ataaatttgagagaggagttcctctacaaataattttgtttaa |
| T5 phage | attaaagaggagaaattaaccctctacaaataattttgtttaa |
| T5 phage | aaacctaatggatcgaccttcctctacaaataattttgtttaa |
| T7 phage | atcgagagggacacggcgacctctacaaataattttgtttaa |
| T7 phage | gctaggtaacactagcagccctctacaaataattttgtttaa |
| T7 phage | atgaaacgacagtgagtcacctctacaaataattttgtttaa |
| T7 phage | agggagaccacaacggtttccctctacaaataattttgtttaa |
| High-transcription escape | attaaaaaacctgctaggatcctctacaaataattttgtttaa |
| High-transcription escape | ataaaggaaaacggtcaggtcctctacaaataattttgtttaa |
| High-transcription escape | ataggttaaaagcctgtcatcctctacaaataattttgtttaa |
| Carbon utilization | acaataaaaaatcatttacatgtttcctctacaaataattttgtttaa |
| Carbon utilization | agaagcagcgcgcaaaaatcagctgcctctacaaataattttgtttaa |
| Carbon utilization | atgagttcatttcagacaggcaaatcctctacaaataattttgtttaa |
| Carbon utilization | aacttgcagttatttactgtgattacctctacaaataattttgtttaa |
| Carbon utilization | agccacaaaaaaagtcatgttggttcctctacaaataattttgtttaa |
| Carbon utilization | acacagtcacttatcttttagttaaaaggtcctctacaaataattttgtttaa |
| Anti-escaping sequences | atccggaatcctcttcccggcctctacaaataattttgtttaa |
| | aacaaaataaaaaggagtcgctcaccctctacaaataattttgtttaa |
| T5 phage | agttcgatgagagcgataacagttccagattcaggaactataa |
| T5 phage | ataaattgataaacaaaaaagttccagattcaggaactataa |
| T5 phage | ataaatttgagagaggagttagttccagattcaggaactataa |
| T5 phage | attaaagaggagaaattaacagttccagattcaggaactataa |

-continued

| Sources | Sequences |
|---|---|
| T5 phage | aaacctaatggatcgaccttagttccagattcaggaactataa |
| T7 phage | atcgagagggacacggcgaagttccagattcaggaactataa |
| T7 phage | gctaggtaacactagcagcagttccagattcaggaactataa |
| T7 phage | atgaaacgacagtgagtcaagttccagattcaggaactataa |
| T7 phage | agggagaccacaacggtttcagttccagattcaggaactataa |
| High-transcription escape | attaaaaaacctgctaggatagttccagattcaggaactataa |
| High-transcription escape | ataaaggaaaacggtcaggtagttccagattcaggaactataa |
| High-transcription escape | ataggttaaaagcctgtcatagttccagattcaggaactataa |
| Carbon utilization | acaataaaaaatcatttacatgtttagttccagattcaggaactataa |
| Carbon utilization | agaagcagcgcgcaaaaatcagctgagttccagattcaggaactataa |
| Carbon utilization | atgagttcatttcagacaggcaaatagttccagattcaggaactataa |
| Carbon utilization | aacttgcagttatttactgtgattaagttccagattcaggaactataa |
| Carbon utilization | agccacaaaaaaagtcatgttggttagttccagattcaggaactataa |
| Carbon utilization | acacagtcacttatcUttagttaaaaggtagttccagattcaggaactataa |
| Anti-escaping sequences | atccggaatcctcttcccggagttccagattcaggaactataa |
| | aacaaaataaaaaggagtcgctcacagttccagattcaggaactataa |
| Stem loops | gatcaccaggggggatcccccggtgaaggat |
| Stem loops | gatcgcccaccggcagctgccggtgggcgatcaaggat |
| Stem loops | gatcatcggtagagttaatattgagcagatcccccggtgaaggat |
| Stem loops | attgatctggttattaaaggtaatcgggtcatttta |
| Stem loops | gttctccacgggtgggatgagcccctcgtggtggaaatgcg |
| Stem loops | agcatgaggtaaagtgtcatgcaccaa |
| Stem loops | acgtcgacttatctcgagtgagatattgttgacggtac |
| Stem loops | acgtcgacttatctcgagtgagataagttgacggtac |
| Stem loops | acgtcgacttatctcgagactgcagttcaatagagatattgttgacggtac |
| Stem loops (Ribozyme) | gactgtcaccggatgtgctaccggtctgatgagtccgtgaggacgaaacag |
| Stem loops | gatcaccaggggggatcccccggtgaaggatcctctacaaataattttgtttaa |
| Stem loops | Gatcgcccaccggcagctgccggtgggcgatcaaggatcctctacaaataatt ttgtttaa |
| Stem loops | gatcatcggtagagttaatattgagcagatcccccggtgaaggatcctctacaaa taattttgtttaa |
| Stem loops | attgatctggttattaaaggtaatcgggtcattnacctctacaaataattagataa |
| Stem loops | Gttctccacgggtgggatgagcccctcgtggtggaaatgcgcctctacaaataa ttttgtttaa |
| Stem loops | agcatgaggtaaagtgtcatgcaccaacctctacaaataattagataa |
| Stem loops | Acgtcgacttatctcgagtgagatattgttgacggtaccctctacaaataattagt ttaa |

-continued

| Sources | Sequences |
|---|---|
| Stem loops | Acgtcgacttatctcgagtgagataagttgacggtaccctctacaaataattttgtt taa |
| Stem loops | acgtcgacttatctcgagactgcagttcaatagagatattgttgacggtaccctct acaaataattttgtttaa |
| Stem loops (Ribozyme) | gactgtcaccggatgtgctaccggtctgatgagtccgtgaggacgaaacagcc tctacaaataattttgataa |

The synthetic operons and/or the expression cassette for expressing the sequence-specific DNA binding polypeptide can be carried on one or more plasmids, e.g., in a cell. In some embodiments, the operon and the expression cassette are on different plasmids. In some embodiments, the expression cassette plasmid and/or operon plasmid(s) are low copy plasmids. Low copy plasmids can include, for example, an origin of replication selected from PSC101, PSC101*, F-plasmid, R6K, or IncW.

III. Synthetic Operons

Embodiments of the present invention also provide for synthetic operons, for example as generated by the methods described herein.

IV. Systems of Synthetic Operons

Embodiments of the invention also provide for systems comprising synthetic operons and one or more controlling expression cassettes, wherein the expression cassette encodes a sequence-specific DNA binding polypeptide controlling expression of the synthetic operon(s). In some embodiments, the controlling expression cassette(s) are genetic circuits. For example, the expression cassettes can be designed to act as logic gates, pulse generators, oscillators, switches, or memory devices. In some embodiments, the controlling expression cassette are linked to a promoter such that the expression cassette functions as an environmental sensor. In some embodiments, the environmental sensor is an oxygen, temperature, touch, osmotic stress, membrane stress, or redox sensor.

As explained above, in some embodiments, the expression cassette encodes T7 RNAP or a functional variant thereof. In some embodiments, the T7 RNAP is the output of the genetic circuit(s).

The operons and expression cassettes can be expressed in a cell. Thus in some embodiments, a cell contains the systems of the invention. Any type of host cell can comprise the system.

V. Computation

In some aspects, the invention utilizes a computer program product that determines experimental values for controlling the magnitude of expression of two or more genes. This may be used for example to optimize a system property (e.g. nitrogen fixation levels). In one embodiment, the program code receives one or more input data points, wherein the input data points provide information about one or more regulatory elements and a system property. It then uses a computational method to determine a next data point. In one aspect, the computational method may be a design of experiments (DoE) method.

In some embodiments, the program code-generated next data point can then be used for further experimentation, e.g., to see if the suggested next data point results in optimized expression level for two or more genes, leading to an improvement in a desired system property. In one aspect, the generation of next data points is repeated until a desired system property level is obtained. In another aspect, the next data points are iteratively generated until the magnitude of expression of two or more genes reaches a desired level.

In some embodiments, the computer program code may use a computational method that employ numerical analysis or optimization algorithms. In some aspects, the numerical optimization methods may use the is the Nelder-Mead algorithm, the Newton's method, the quasi-Newton method, the conjugate gradient method, an interior point method, a gradient descent, a subgradient method, a ellipsoid method, the Frank-Wolfe method, an interpolation method and pattern search methods, or an ant colony model.

In one specific embodiment, the computer program to generate the next data point for experimentation uses the Nelder-Mead algorithm. The computer-implemented method will receive one or more input data points and calculate the reflection point, expansion point or contraction point to computationally determine the next data point to experiment with, based on the input data points.

In one implementation of the Nelder-Mead algorithm, the program code will take the received input data points as the simplex vertices of an n-dimensional space, having n+1 simplex vertices. Then the objective function will be evaluated for each vertex of the simplex, and the algorithm uses this information to propose a sequence of new coordinates for evaluation. New coordinates will be determined by the computer code according to the following algorithmic logic:

1. Order the simplex vertices: $f(x_1) \le f(x_2) \le \ldots \le f(x_{n+1})$
2. Calculate $x_0$, the center of gravity of all points except $x_{n+1}$.
3. Calculate a Reflection coordinate: $x_r = x_0 + \alpha(x_0 - x_{n+1})$
4. Calculate an Expansion coordinate: $x_e = x_0 + r(x_0 - x_{n+1})$
5. Calculate a Contraction coordinate: $x_c = x_{n+1} + \rho(x_0 - x_{n+1})$
6. Calculate Reduction coordinates: $x_i = x_1 + \sigma(x_i - x_1)$ for all $i \in \{2, \ldots, n+1\}$ The objective function is evaluated at these points and used to determine a new simplex according to the following criteria:

1. If the Reflection, Expansion or Contraction coordinates are better than the worst simplex point, $x_{n+1}$, define a new simplex by replacing the worst simplex point with the best of the three (Reflection, Expansion or Contraction).
2. Otherwise, define a new simplex by combining the best simplex point with the Reduction coordinates.

In one embodiment, a computer program product is provided comprising a tangible computer readable medium storing a plurality of instructions for controlling a processor to perform an operation for determining an experimentation point for controlling the magnitude of expression of two or more genes, the instructions comprising receiving one or more input data points, wherein the input data points provide information about one or more regulatory elements and a system property; and determining, with a computer, a next data point using a computational method, wherein the next data point provides information about the one or more regulatory elements.

Figure 25:
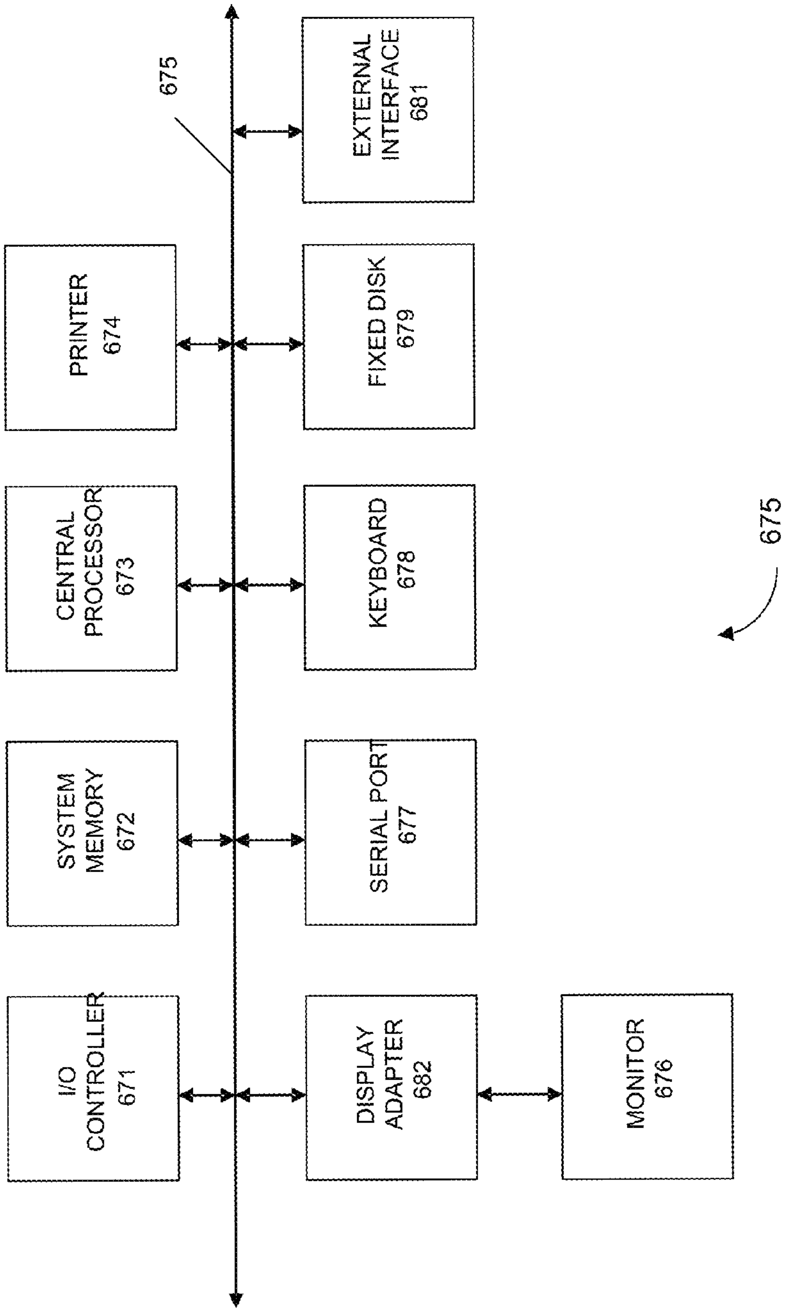
FIG. 25 shows a block diagram of a computer system.

FIG. 25 shows a block diagram of an example computer system 600 usable with system and methods according to embodiments of the present invention. The computer system 600 can be used to run the program code for various method claims according to embodiments of the present invention.

Any of the computer systems mentioned herein may utilize any suitable number of subsystems. Examples of such subsystems are shown in FIG. 25 in computer apparatus 600. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 25 are interconnected via a system bus 675. Additional subsystems such as a printer 674, keyboard 678, fixed disk 679, monitor 676, which is coupled to display adapter 682, and others are shown. Peripherals and input/output (I/O) devices, which couple to I/O controller 671, can be connected to the computer system by any number of means known in the art, such as serial port 677. For example, serial port 677 or external interface 681 can be used to connect computer system 600 to a wide area network such as the Internet, a mouse input device, or a scanner. The interconnection via system bus 675 allows the central processor 673 to communicate with each subsystem and to control the execution of instructions from system memory 672 or the fixed disk 679, as well as the exchange of information between subsystems. The system memory 672 and/or the fixed disk 679 may embody a computer readable medium. Any of the values mentioned herein can be output from one component to another component and can be output to the user.

A computer system can include a plurality of the same components or subsystems, e.g., connected together by external interface 681 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware and/or using computer software in a modular or integrated manner. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer program product (e.g. a hard drive, a CD, or an entire computer system), and may be present on or within different computer program products within a system or network. A computer system may include a monitor, printer, or other suitable display for providing any of the results mentioned herein to a user.

Any of the methods described herein may be totally or partially performed with a computer system including a processor, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The specific details of particular embodiments may be combined in any suitable manner or varied from those shown and described herein without departing from the spirit and scope of embodiments of the invention.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

EXAMPLES

The following examples are offered to illustrate, but not to limit the claimed invention.

Example 1: Use of the Nelder-Mead Method to Optimize Efficiency of Operon Discovery This examples illustrates how to recombinant and computationally manipulate and select native gene cluster coding sequences and heterologous regulatory sequences. We have termed this process "refactoring", which comprises optimization of multiple genes, regulation of the gene cluster, and establishment of the genetic context for the biological circuit. Refactoring complex gene clusters and engineering metabolic pathways requires numerous iterations between design, construction and evaluation in order to improve a desired system property, e.g. higher product titers, lower toxicity, or improved nitrogen fixation.

One common way to affect these properties is to modify gene expression levels within the system, even if the direct relationship between gene expression and the system property is unknown. Making quantitative changes to gene expression can be achieved through the use of regulatory elements, e.g. promoters and ribosome binding sites, that exhibit rationally predictable behavior.

It is possible to utilize numerical optimization methods to guide selection of regulatory elements in order to alter gene expression and to improve desired system properties. One relevant algorithm is the Nelder-Mead method, a nonlinear optimization algorithm that minimizes an objective function in multidimensional space. We use the Nelder-Mead method to optimize a system property where each dimension in algorithmic space corresponds to expression of a gene in the engineered system. Points in this space represent a particular combination of expression levels for the genes in the system. As a result, each point may be considered a uniquely engineered strain. The algorithm is used to suggest new coordinates in space that improve the system property. New strains can be engineered by modifying regulatory elements to attain the suggested levels of gene expression. After evaluating the performance of the new strains, the algorithm can be used to predict subsequent modifications. This process iterates until the system property has been improved a desired amount.

The Nelder-Mead method relies on the concept of a simplex, which is an object in N dimensional space having N+1 vertices. The objective function is evaluated at each vertex of the simplex, and the algorithm uses this information to propose a sequence of new coordinates for evaluation. New coordinates are proposed according to the following process:

1. Order the simplex vertices: $f(x_1) \leq f(x_2) \leq \ldots \leq f(x_{n+1})$
2. Calculate $x_0$, the center of gravity of all points except $x_{n+1}$.
3. Calculate a Reflection coordinate: $x_r = x_0 + \alpha(x_0 - x_{n+1})$
4. Calculate an Expansion coordinate: $x_e = x_0 + r(x_0 - x_{n+1})$
5. Calculate a Contraction coordinate: $x_c = x_{n+1} + \rho(x_0 - x_{n+1})$
6. Calculate Reduction coordinates: $x_i = x_1 + \sigma(x_i - x_1)$ for all $i \in \{2, \ldots, n+1\}$ The objective function is evaluated at these points and used to determine a new simplex according to the following criteria:

1. If the Reflection, Expansion or Contraction coordinates are better than the worst simplex point, $x_{n+1}$, define a new simplex by replacing the worst simplex point with the best of the three (Reflection, Expansion or Contraction).
2. Otherwise, define a new simplex by combining the best simplex point with the Reduction coordinates.

Figure 2:
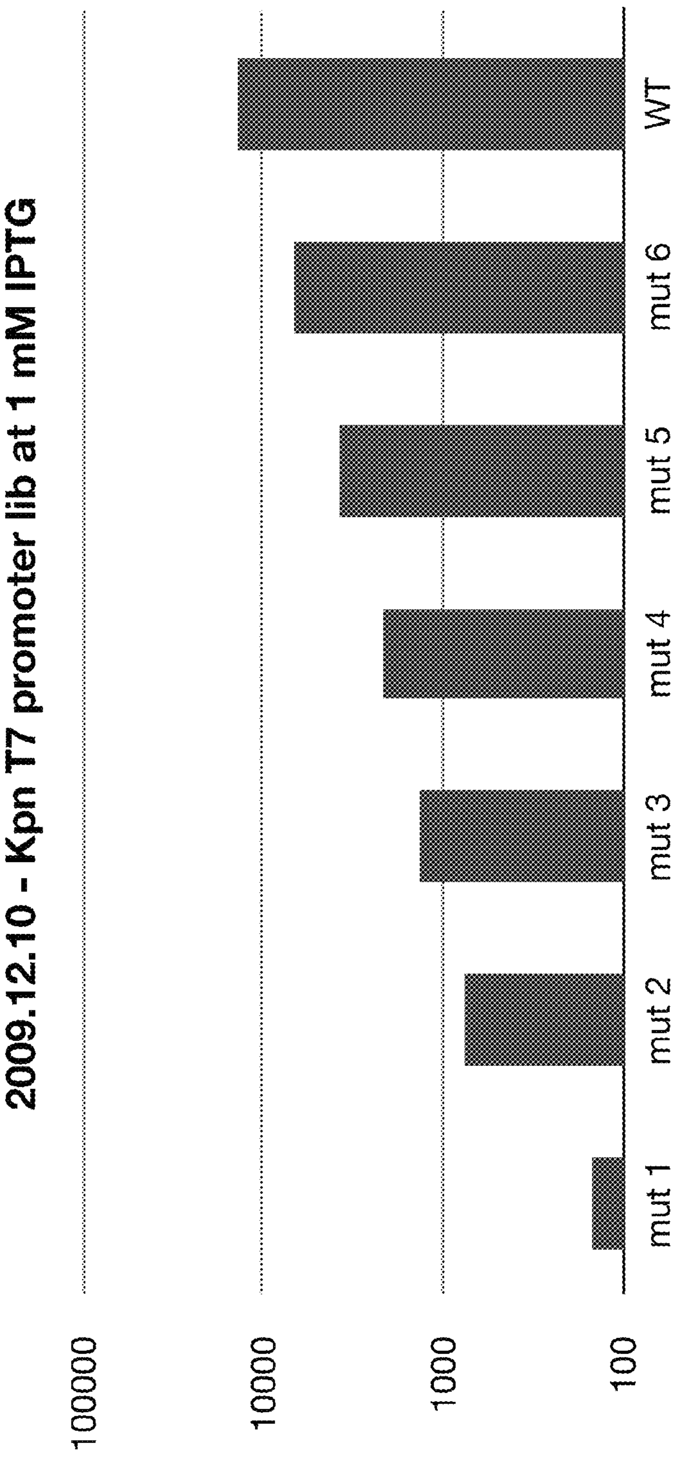
FIG. 2 illustrates the quantitatively measurement of the capacity of the synthetic operon to complement a nifEN knockout strain and recover the ability to fix nitrogen.

These steps constitute an iteration of the algorithm. The newly defined simplex becomes the seed for generating new coordinates during the next iteration of the algorithm. Iterations typically continue until one of the coordinates in the simplex crosses a desired threshold for objective function evaluation. We have optimized the performance of a nitrogen fixation operon by varying the selection of promoters that control expression of individual genes. We initially refactored the nifEN operon so that each gene was expressed under the control of a unique T7 promoter (FIG. 1). To assess the impact of refactoring the nifEN operon, we quantitatively measured the capacity of the synthetic operon to complement a nifEN knockout strain and recover the ability to fix nitrogen (FIG. 2). Our refactored system showed limited ability to fix nitrogen (20% of wild-type activity).

Figure 4A:
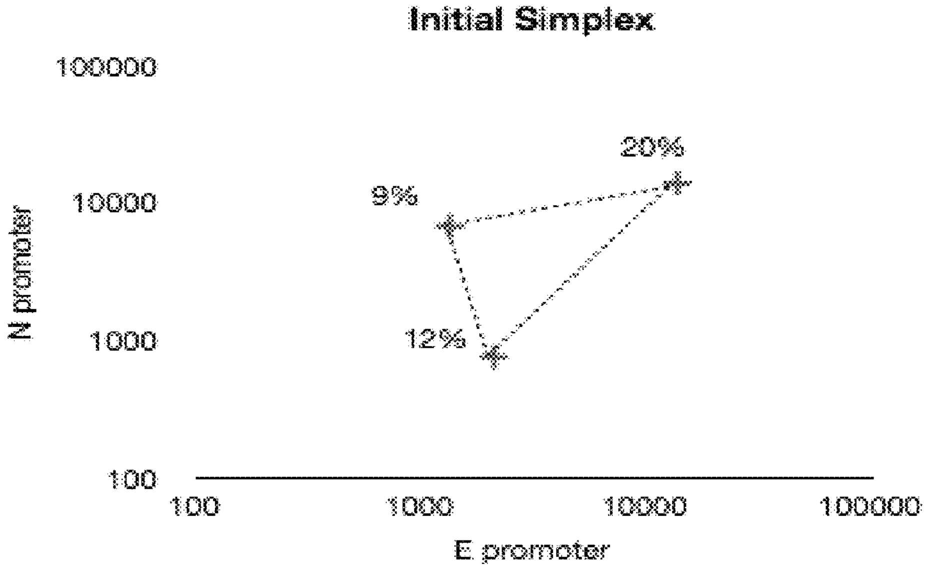
FIG. 4A depicts strengths of three strains.
Figure 4B:
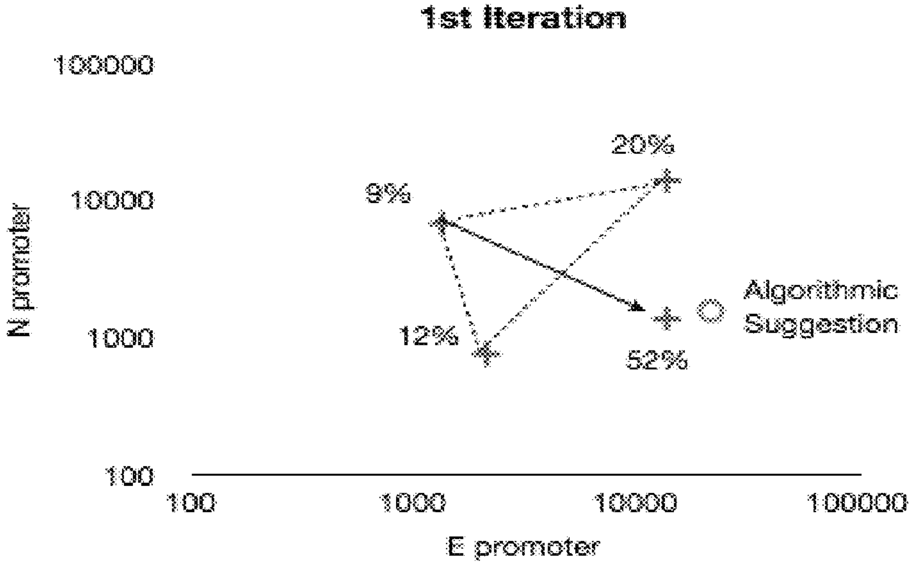
FIG. 4B depicts the calculated Reflection coordinates.
Figure 6:
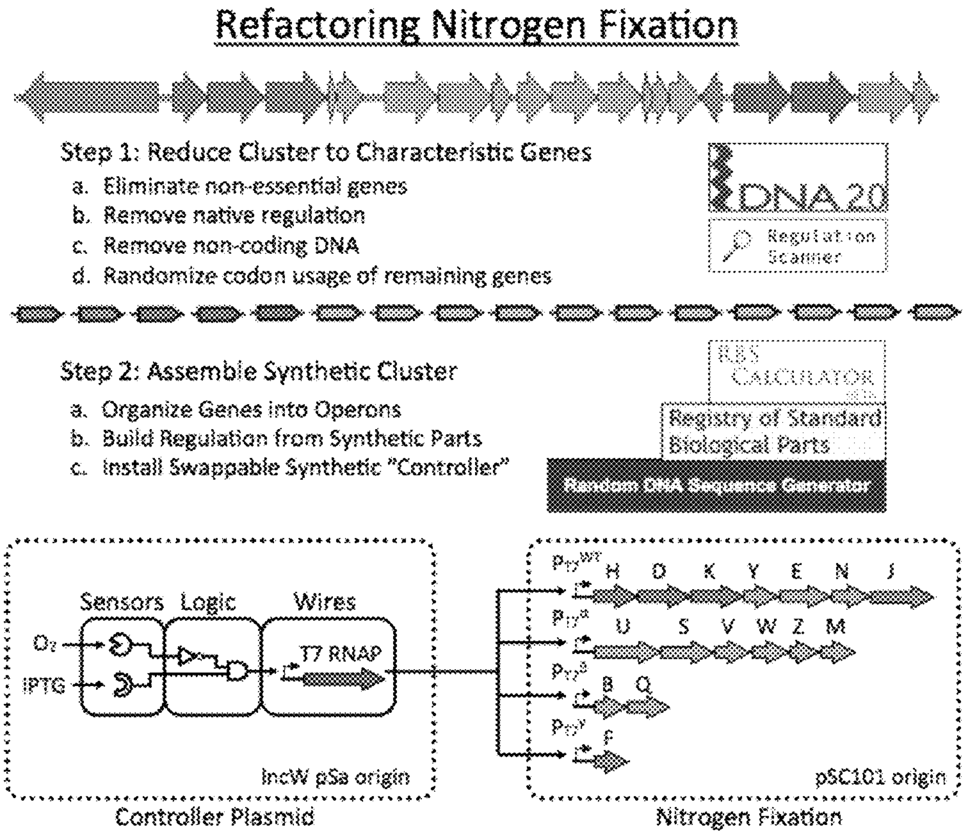
FIG. 6 illustrates the method of refactoring nitrogen fixation.

We subsequently applied the Nelder-Mead method to optimize nifE and nifN gene expression with the goal of improving nitrogen fixation rates. Our algorithmic space consisted of two dimensions, nifE and nifN expression. Our coordinate system was scaled to the strength of the promoters controlling these genes. To enable varied levels of gene expression, we generated and characterized a library of mutant T7 promoters (FIG. 3). Our library covers three order of magnitude of gene expression (This is the same library that is described in U.S. Provisional Patent Application No. 61/493,733. Here, it is characterized for behavior in *Klebsiella oxytoca*). We then randomly selected mutants from the library of T7 promoters to generate two additional strains with rationally altered levels of nifE and nifN expression. The strength of T7 promoters used in these three strains defined our initial simplex. We evaluated nitrogen fixation for each strain in the simplex (strain 1: 20%, strain 2: 9%, strain 3: 12%) and used the algorithm to calculate Reflection coordinates (FIG. 4). To construct the strain that matched the Reflection coordinates, we chose promoters from our library nearest to the coordinates in strength. We evaluated nitrogen fixation in this Reflection strain and found that it significantly outperformed (52%) our initial strains (FIG. 5).

Our improved strain had surprising results and surpassed expectations, and performed sufficiently for downstream applications. To reach higher levels of gene expression, stronger promoters can be engineered and used in the methods of the invention. Alternatively, complimentary changes to multiple regulatory elements, e.g., the promoter and ribosome binding site for a given gene, can be used to achieve desired expression levels. This involves describing the strengths of each type of element in common units of expression. This example demonstrates that new strains can be engineered by modifying regulatory elements to attain the desired levels of gene expression. The example also illustrates the use of numerical optimization methods, such as, but not limited to the Nelder-Mead method, to guide selection of regulatory elements in order to alter gene expression and to improve desired system properties.

Example 2: Refactoring Nitrogen Fixation

This example demonstrates the method of refactoring the nitrogen fixation gene cluster. The method includes steps that comprise: 1) removing host regulation and implement synthetic, orthogonal regulation; 2) tracking the contribution of each regulatory part to gene cluster function; 3) promoting modularity and integration with synthetic circuits; and 4) creating a platform amenable to rational optimization. In certain embodiments, the method of refactoring nitrogen fixation comprises reducing cluster to characteristic genes and assembling synthetic cluster.

Figure 7:
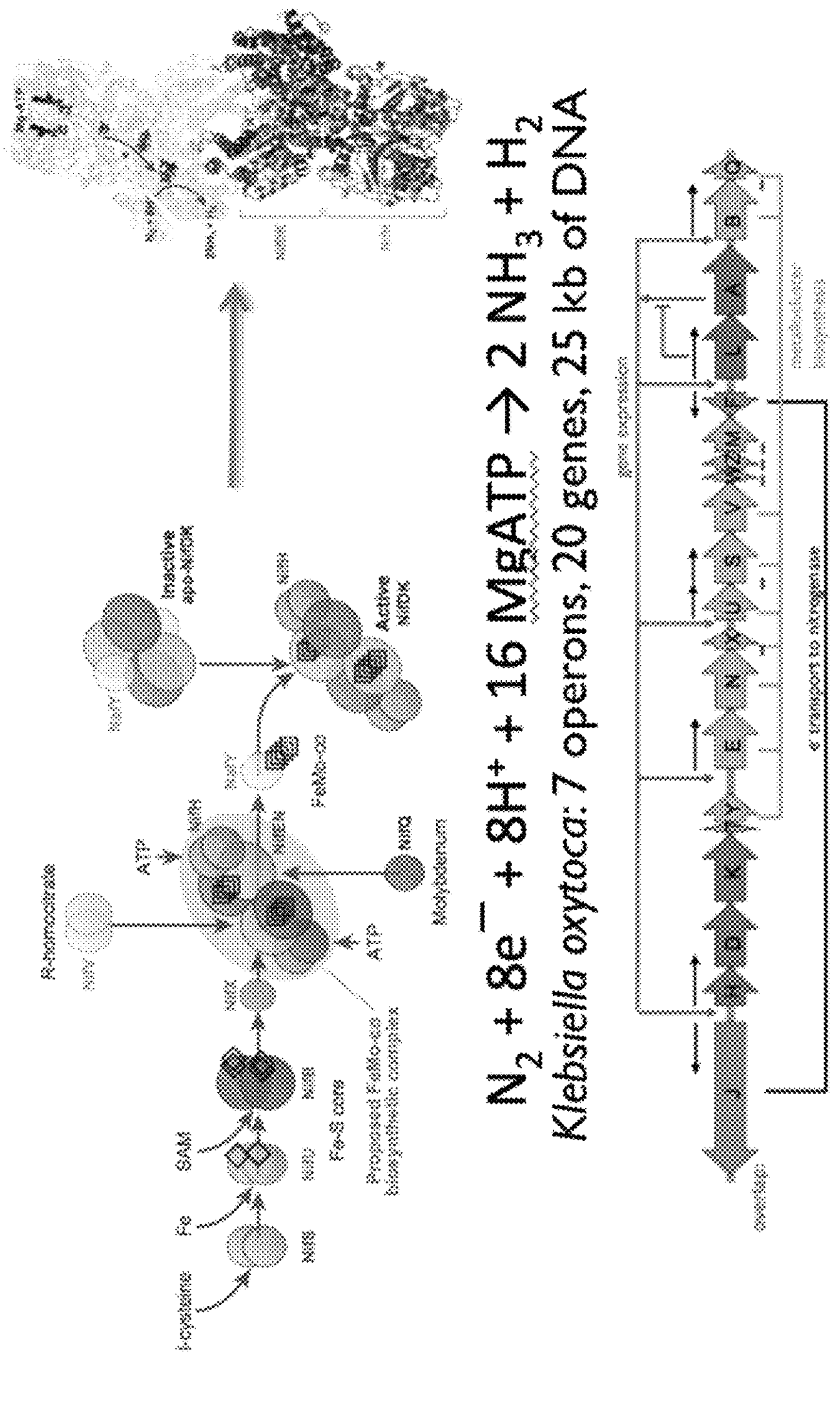
FIG. 7 illustrates the nif gene cluster from *Klebsiella oxytoca*.

The nif gene cluster from *Klebsiella oxytoca* has been one of the primary models for study of the nitrogenase enzyme (FIG. 7; see, Rubio and Ludden, Maturation of Nitrogenase: a Biochemical Puzzle, *J. Bacteriology,* 2005). It is a concise gene cluster, encompassing 20 genes in 7 operons within 25 kb of DNA. The nitrogenase enzyme is composed of two major units, Component I and Component II, that interact to facilitate the reduction of multiply bonded gases like $N_2$. Within the enzyme complex, multiple Fe—S clusters are responsible for active site chemistry and electron transfer to the active site. The majority of the genes in the gene cluster are involved in Fe—S cluster biosynthesis, chaperoning and insertion into the final enzyme complex.

Nearly every nif gene produces a protein with a function known to be essential to nitrogenase assembly or function (see, Simon, Homer and Roberts, Perturbation of nifT expression in *Klebsiella pneumoniae* has limited effect on nitrogen fixation, *J. Bacteriology,* 1996 and Gosink, Franklin and Roberts, The product of the *Klebsiella pneumoniae* nifX gene is a negative regulator of the nitrogen fixation (nif) regulon, *J Bacteriology,* 1990). Two genes, nifL and nifA, encode the master regulatory proteins. The nifT gene has no known function, and eliminating it has little effect on nitrogen fixation. Additionally, while elimination of nifX has minor effect on nitrogen fixation, its overexpression detrimentally reduces enzyme activity. For these reasons, we chose to eliminate nifL, nifA, nifT and nifX from our refactored gene cluster.

We designed synthetic genes by codon randomizing the DNA encoding each amino acid sequence. Protein coding sequences were based on the sequence deposited in the NCBI database (X13303; see, Arnold et al., Nucleotide sequence of a 24,206-base-pair DNA fragment carrying the entire nitrogen fixation gene cluster of *Klebsiella pneumoniae*. JMB, 1988). Codon selection was performed by DNA2.0 using an internal algorithm and two guiding criteria. We specified that our genes express reasonably well in both *E. coli* and *Klebsiella*. Also, we specified that our codon usage be as divergent as possible from the codon usage in the native gene. While designing synthetic genes, we scanned each proposed sequence for a list of undesired features and rejected any in which a feature was found. The feature list includes restriction enzyme recognition sites, transposon recognition sites, repetitive sequences, sigma 54 and sigma 70 promoters, cryptic ribosome binding sites, and rho independent terminators. FIG. 18 shows DNA sequences for native genes and synthetic genes, as well as the percent common nucleotide and codon identities between each pair.

Figure 8:
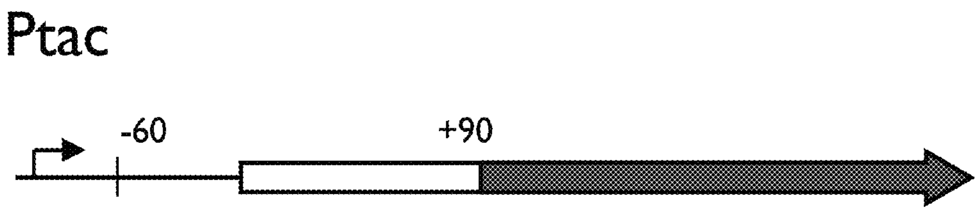
FIG. 8 depicts a scheme of a fluorescent reporter plasmid in which the 150 bp surrounding a gene's start codon (from −60 to +90) was fused to the mRFP gene and expressed under the control of the Ptac promoter.
Figure 9:
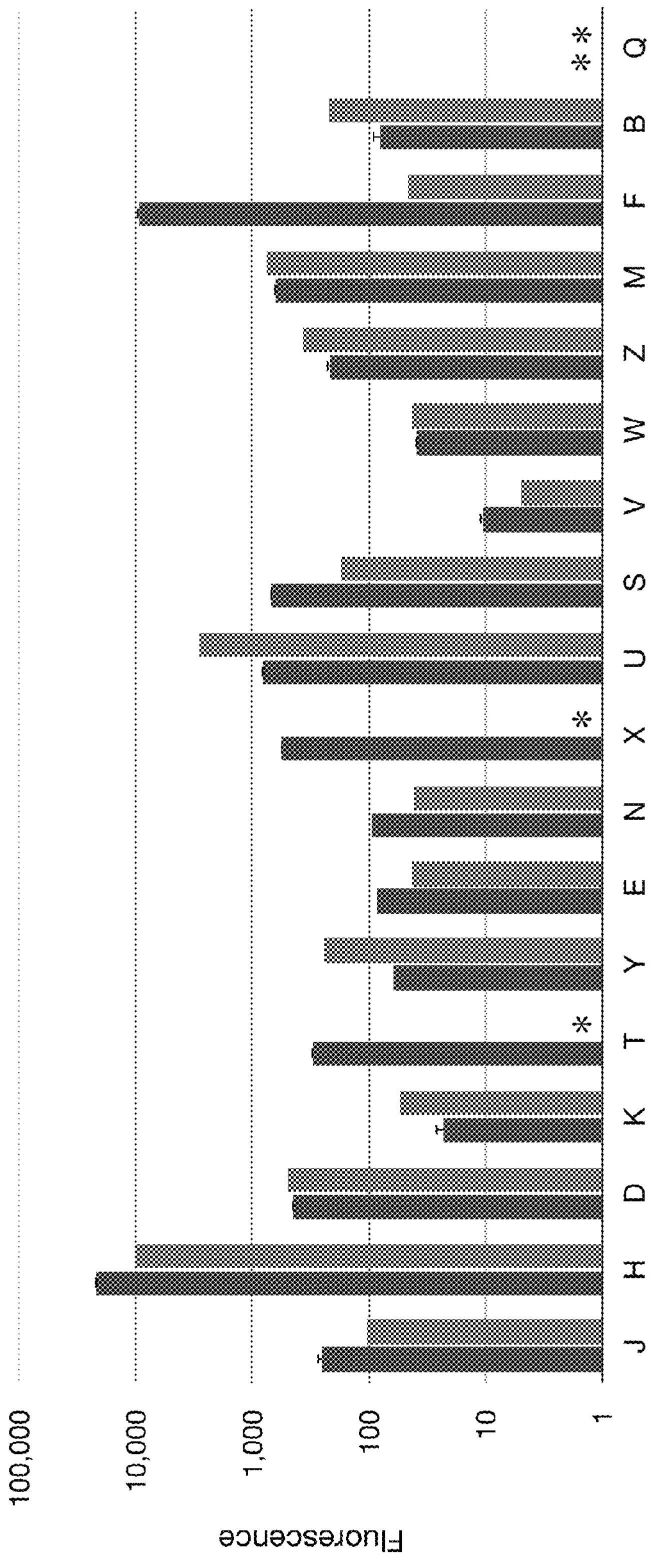
FIG. 9 illustrates the measured fluorescence by flow cytometry.

Synthetic ribosome binding sites were chosen to match the strength of each corresponding native ribosome binding site. To characterize the strength of a given native ribosome binding site, we constructed a fluorescent reporter plasmid in which the 150 bp surrounding a gene's start codon (from −60 to +90) were fused to the mRFP gene (FIG. 8). The chimera was expressed under control of the Ptac promoter, and fluorescence was measured via flow cytometry (FIG. 9). To generate synthetic ribosome binding sites, we constructed a library of reporter plasmids using 150 bp (−60 to +90) of a synthetic expression cassette. Briefly, a synthetic expression cassette consisted of a random DNA spacer, a degenerate sequence encoding an RBS library, and the coding sequence for each synthetic gene. We screened multiple clones to identify the synthetic ribosome binding site that best matched the native ribosome binding site (FIG. 10).

We constructed synthetic operons that consisted of the same genes as the native operons. This strategy enabled us to knock out a native operon from *Klebsiella* and complement the deletion using the synthetic counterpart.

Each synthetic operon consisted of a Ptac promoter followed by synthetic gene expression cassettes (random DNA spacer, synthetic rbs, synthetic coding sequence) and a transcription terminator. The random DNA spacer serves to insulate the expression of each synthetic coding sequence from preceding cassettes. Each synthetic operon was scanned to remove unintended regulatory sequences (similar to the process used during synthetic gene design and synthesis).

Figure 11:
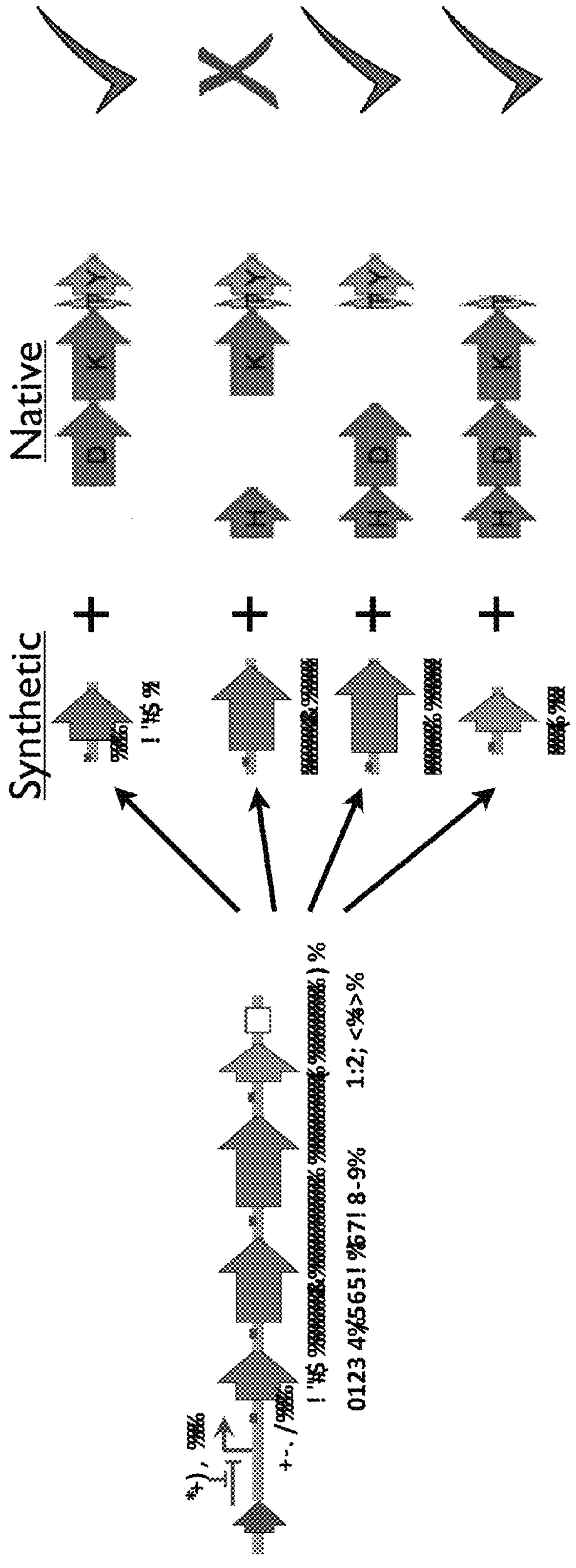
FIG. 11 illustrates the chimeric operons.

In two cases, we encountered synthetic operons that showed no functional complementation in the corresponding knockout strain (nifHDKTY and nifUSVWZM). To debug the synthetic operons, we broke the operon into constituent gene expression cassettes. We then constructed chimeric operons, wherein some cassettes had synthetic components and other cassettes were native genes and their ribosome binding sites (FIG. 11). This strategy enabled us to test each chimeric operon for functional complementation and quickly identify the problematic synthetic expression cassettes. With further analysis of problematic expression cassettes, we were able to diagnose and correct errors in the fully synthetic operons. FIG. 12 illustrates a list of errors in the two operons.

Figure 13:
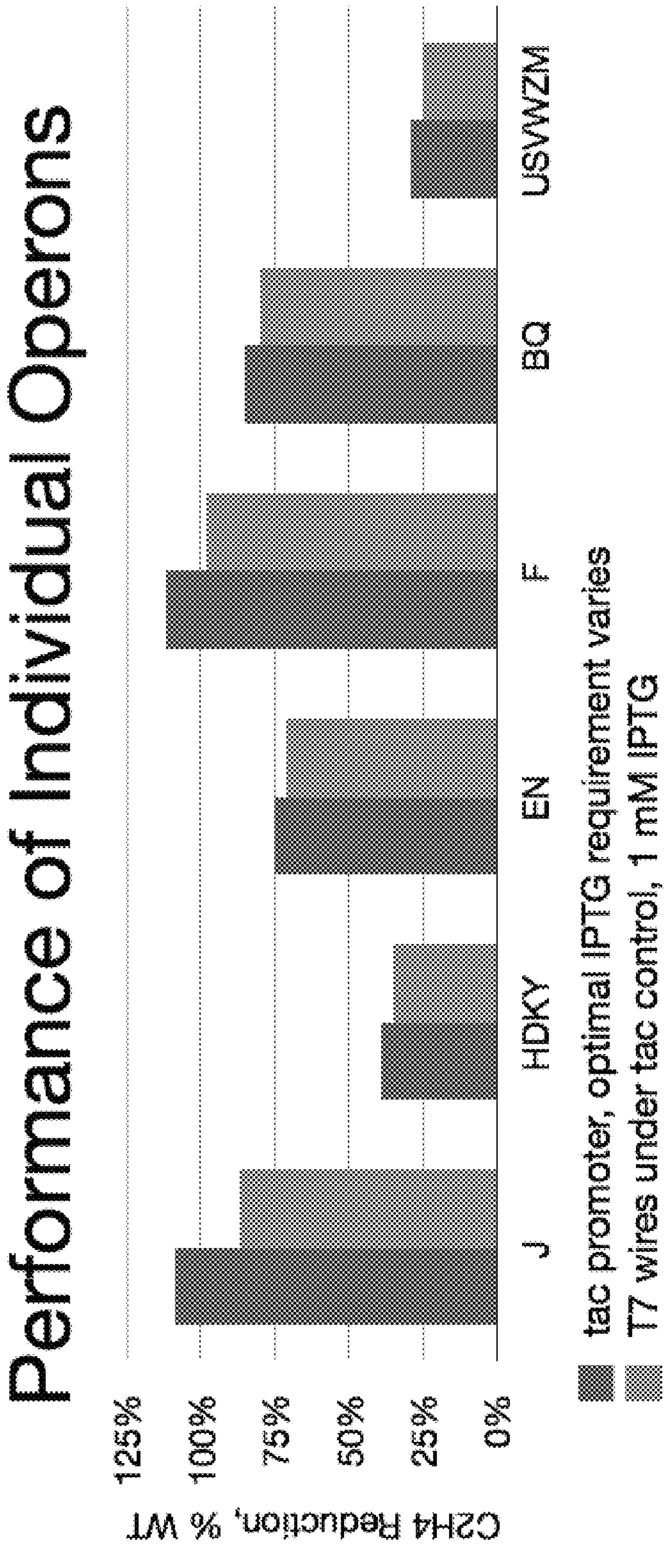
FIG. 13 shows that each synthetic operon required different levels of IPTG concentration for optimal function. It also shows the performance of individual operons in the T7 Wires system under Ptac promoter control.

Each synthetic operon was initially designed to be controlled by a Ptac inducible promoter. By titrating IPTG concentration, we could precisely specify promoter strength and corresponding synthetic operon expression. This enabled us to vary expression level to identify optimal operon function. We found that each synthetic operon required different levels of IPTG concentration for optimal function (FIG. 13).

We utilized the T7 Wires system to decouple the Ptac promoter from each synthetic operon. By inserting the wire between the promoter and transcriptional unit, we achieved two significant milestones. First, we gained the ability to modulate the transcriptional signal through the use of various mutant T7 promoters. This allowed us to shift optimal operon function to a single inducer concentration by selecting corresponding mutant T7 promoters. Second, we modularized control of the synthetic operon (FIG. 14). That is, any genetic circuit can control the synthetic operon provided that it can produce the necessary T7 RNAP concentration to drive each wire.

Figure 15:
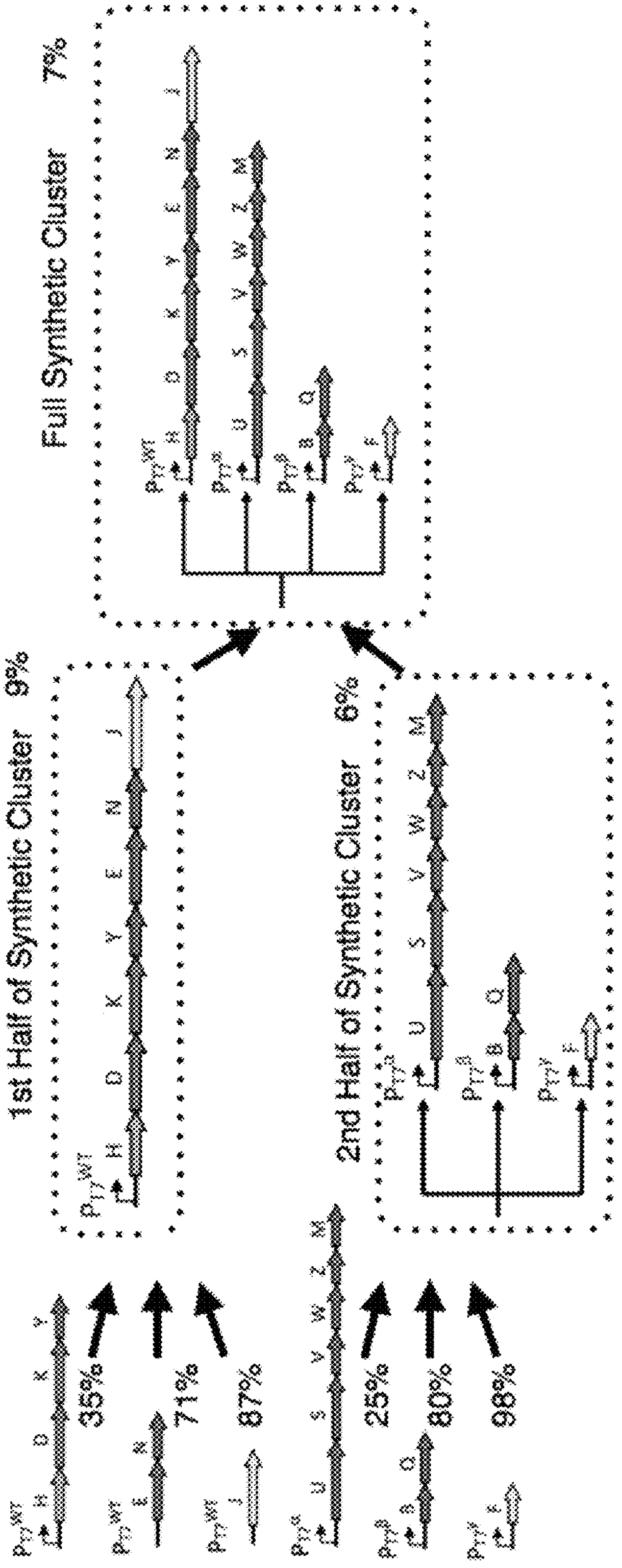
FIG. 15 shows nitrogen fixation from a full synthetic cluster expressed in a complete nif knockout strain.

We adopted a hierarchical approach to assembling individual operons into a fully synthetic cluster. First, we assembled three operons into half clusters (nifJ-nifHDKY-nifEN and nifUSVWZM-nifF-nifBQ) and demonstrated the ability of each synthetic half cluster to complement function in a corresponding knockout strain. Next, we combined the two half clusters into a full synthetic cluster and demonstrated nitrogen fixation in a complete nif knockout strain (FIG. 15).

Figure 16:
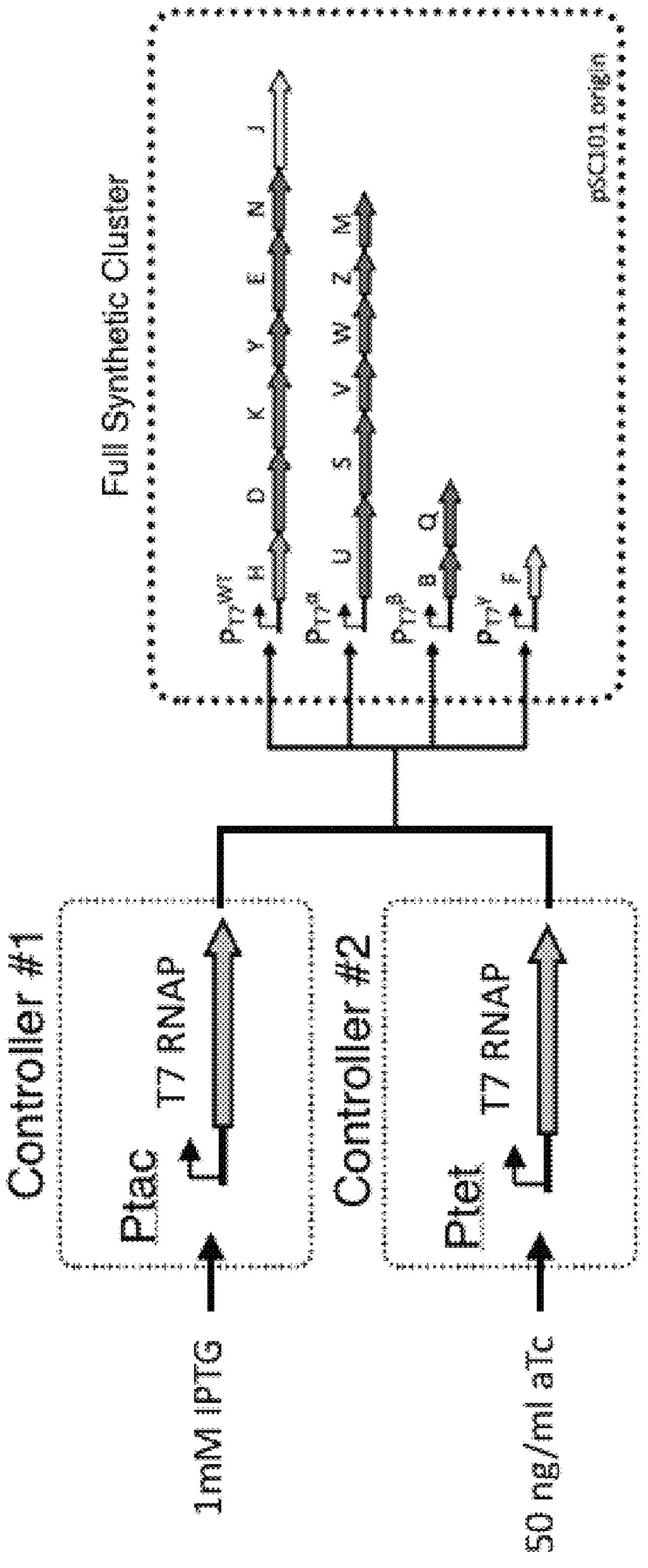
FIG. 16 illustrates the use of either controller #1 or controller #2 to produce the same performance from the full synthetic cluster.

We have shown that the use of T7 Wires produces a modular synthetic gene cluster. We have demonstrated that the use of either controller #1 or controller #2 produces the same functional performance from the synthetic cluster (FIG. 16). In controller #1, T7 RNAP is under control of the Ptac promoter. In controller #2, T7 RNAP is under control of the Ptet promoter.

Figure 17:
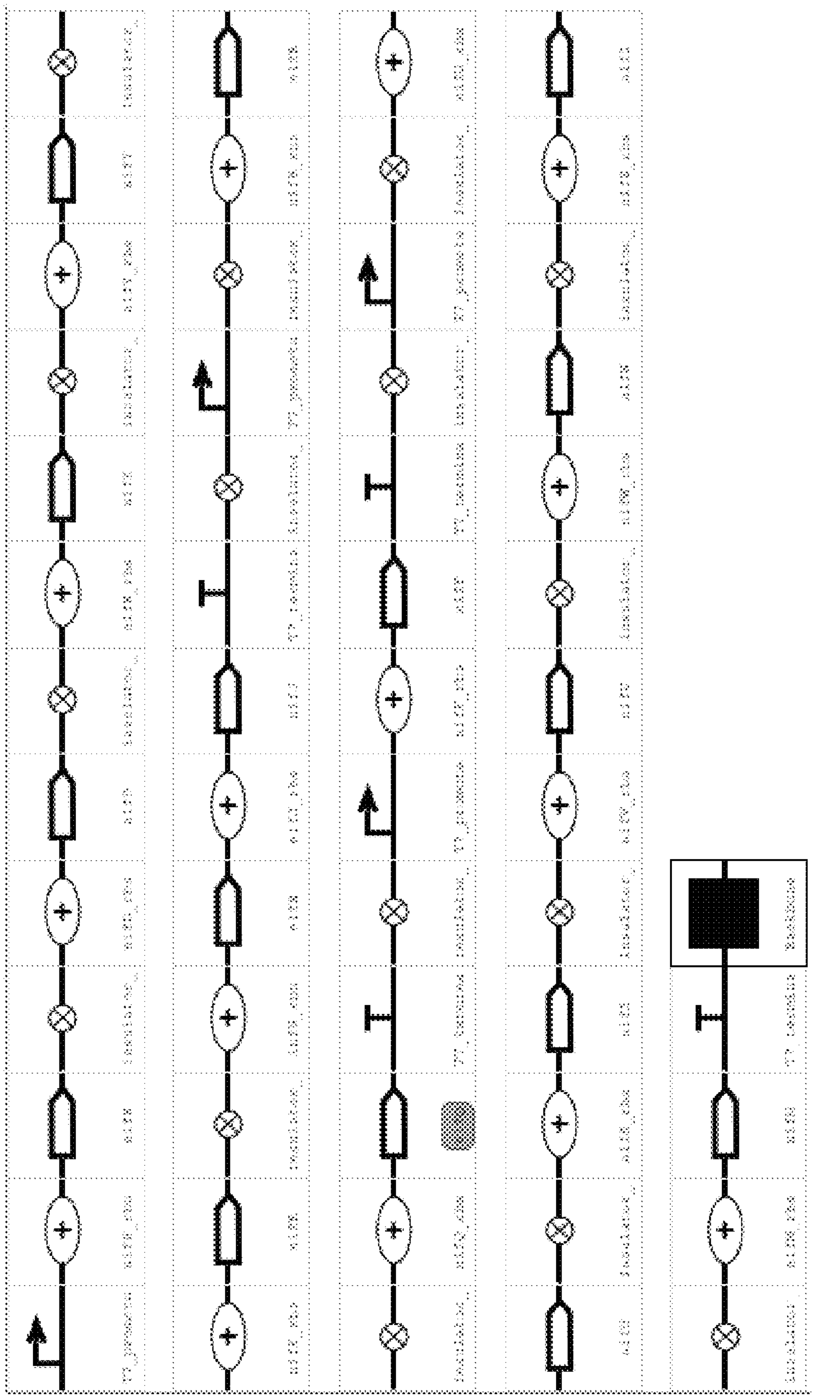
FIG. 17 depicts a detailed schematic of the full synthetic cluster.

FIG. 17 shows a schematic of the full biological cluster, with each part detailed. FIG. 19 shows the parts list of the synthetic controllers. FIG. 20 shows names, sequences and strengths of each component of the full cluster.

We have further demonstrated that complex genetic circuits can be used to produce functional performance of the synthetic gene cluster. We constructed a genetic circuit encoding the logic "A and not B" and used this circuit to control T7 RNAP. In this circuit, the "A and not B" logic corresponds to the presence or absence of the inducers, IPTG and aTc, such that the cell computes "IPTG and not aTc." The circuit was constructed by modifying controller #1 to include the cIrepressor binding sites OR1 and OR2 in the Ptac promoter to produce controller #3. Additionally, plasmid pNOR1020 (see, e.g., Tamsir and Voigt *Nature* 469:212-215 (2011)) encodes the repressor cI under control of the Ptet promoter. When pNOR1020 and controller #3 are co-transformed, they produce the logic circuit "IPTG and not aTc."

```
Ptac controller #1 promoter sequence (SEQ ID NO:
334):
tattctgaaatgagctgttgacaattaatcatcggctcgtataatgtgtg
gaattgtgagcggataacaatt

Controller #3 promoter sequence (SEQ ID NO: 335):
tattaacaccgtgcgtgttgacagctatacctctggcggttataatgcta
gcggaattgtgagcggataacaatt
```

| Input | Expected Logic Output | Synthetic Nitrogen Fixation Performance (% WT) |
|---|---|---|
| No inducer | 0 | <0.5% |
| 1 mM IPTG | 1 | 9% |
| 50 ng/ml aTc | 0 | <0.5% |
| 1 mM IPTG and 50 ng/ml aTc | 0 | <0.5% |

In this experiment, we also included controller #1 as a performance reference. Under inducing conditions (1 mM IPTG), controller #1 exhibits 12% of WT fixation.

Example 3: Refactoring the Bacterial Type III Secretion System (T3SS)

This example illustrates the use of the method described herein to completely refactor the Bacterial type III secretion system (T3SS). This example also illustrates that the refactored synthetic operons of T3SS are controllable and function independently of all native control and regulation.

Bacterial type III secretion systems (T3SS) are valuable because, unlike conventionally used Sec and Tat pathways, they translocate polypeptides through both inner and outer membranes. This enables the delivery of protein directly to culture media, which can be one of the critical requirements in engineered bacterial technology. For example, toxic proteins can be removed from the cytoplasm without being allowed in the periplasm and functional enzymes (e.g., cellulases) which need to work outside the cell, can be delivered directly into the media.

However, the difficulty with utilizing T3SS in engineered bacterial systems is twofold. T3SS generally exist in pathogenic bacteria which utilize these mechanisms for invasion of host cells. Thus, T3SS are very tightly regulated in the cell and are difficult to control independently. Because of this, we chose to use methods of the present invention to completely refactor T3SS and test the function of the refactored operons in knockout cells.

The term "refactoring" refers to a process that involves optimization of multiple genes, regulation of a gene cluster, and establishment of the genetic context for a biological circuit. Refactoring complex gene clusters and engineering biological pathways requires numerous iterations between design, construction and evaluation in order to improve a desired system property. Briefly, refactoring includes breaking down a biological system into its component parts and rebuilding it synthetically. It also involves removing all native control and regulation of the biological system in order to replace it with a mechanism that provides independent control.

This example illustrates a method of recoding 18 genes of the bacterial type III secretion systems. The term "recoding" refers to a method of removing or replacing sequence of a gene in order to reduce or eliminate any native regulation elements, while also preserving the protein sequence encoded by the gene. The genes of the type III secretion system were recoded using an algorithm provided by DNA2.0 (Menlo Park, Calif.) in which individual codons of each gene are re-selected such that the gene encodes the same protein, but with maximum dissimilarity with the native sequence.

The 18 genes are arranged in two bacterial operons. Each gene is a recoded version of a native gene from *Salmonella typhimurium*. Each gene is coupled to a synthetic ribosome binding site (RBS) sequence that sets an appropriate expression level for each individual gene. Details of the synthetic RBS selection are described below. The operons can be induced with any desired promoter. In this example, simple inducible promoters are used. The recoded T3SS operons can be attached to any genetic control circuit as needed.

To select a synthetic RBS sequence that best matches the native expression level of each of the 18 genes of the bacterial type III secretion systems, we measured the expression of each gene in the natural system. We cloned the 36-base region upstream on the start codon, along with the 36-bases of coding region fused to an RFP (Red Fluorescent Protein). This was cloned into a plasmid with a constitutive promoter.

This construct was transformed into *Salmonella typhimurium* SL1344 and grown overnight at 37° C. in PI-1 inducing media (LB with 17 g/L NaCl). The culture was subcultured into fresh inducing media to an $OD_{260}$ of 0.025, grown for 2 hours at 37° C. until cells reached log-phase. Fluorescence was measured on a cytometer. The geometric mean of RFP fluorescence across at least 10,000 cells was used as the measure of protein expression.

To find ribosomal binding sequences to test, we utilized the Ribosome Binding Site Calculator (voigtlab.ucsf.edu/software), identified known RBS sequences from the Registry of Standard Biological Parts (partsregistry.org/Main_Page), and generated a series of randomized sequences. The randomized sequences comprise the following formats:

```
                                    (SEQ ID NO: 336)
CTTGGGCACGCGTCCATTAANNAGGANNAATTAAGC;

                                    (SEQ ID NO: 337)
TGGGCACGCGTCCATTAANNAGGANNAATTATTAGC;

                                    (SEQ ID NO: 338)
TACTTGGGCACGCGTCCATTAANNAGGANNAATAGC;

                                    (SEQ ID NO: 339)
CTTGGGCACGCGTCCATTAANAAGGAGNAATTAAGC;

                                    (SEQ ID NO: 340)
CTTGGGCACGCGTCCATTANTAAGGAGGNATTAAGC.
```

Figure 21:
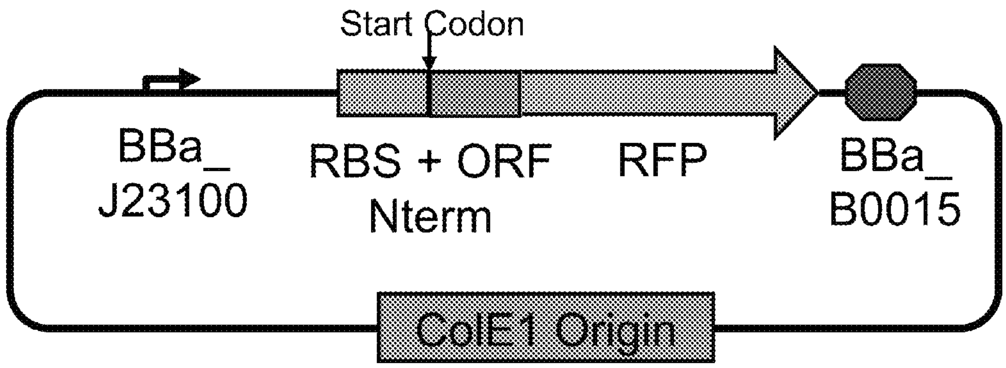
FIG. 21 shows a diagram of the RBS test vector.

All RBS sequences were cloned into the RBS test vector (FIG. 21) along with the first 36 bases of the synthetic gene they were generated to drive. We followed the same experimental procedure used to measure the expression of each gene in the natural system. Of the randomized RBS, 12-48 colonies of each randomized sequence was tested. The synthetic construct that best matched the native expression level was selected and sequenced. This sequence was then used in the construction of the refactored operons.

Two operons were assembled. The first, "prg-org" contains 6 genes, and the second "inv-spa" contains 13 genes.

Figure 22A:
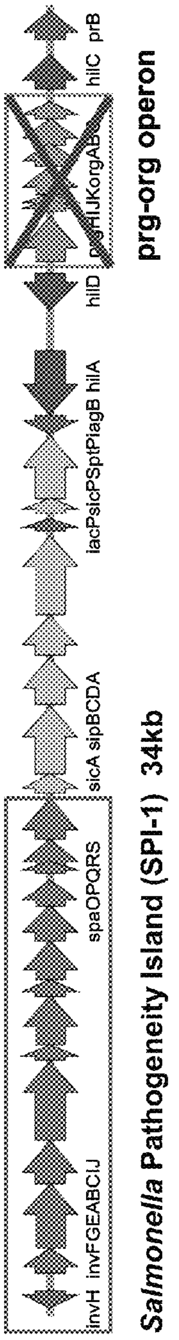
FIG. 22A shows a schematic of Δprg-org *Salmonella* SL1344 knock-out strain. The inv-spa and prg-org operons are boxed.
Figure 22B:
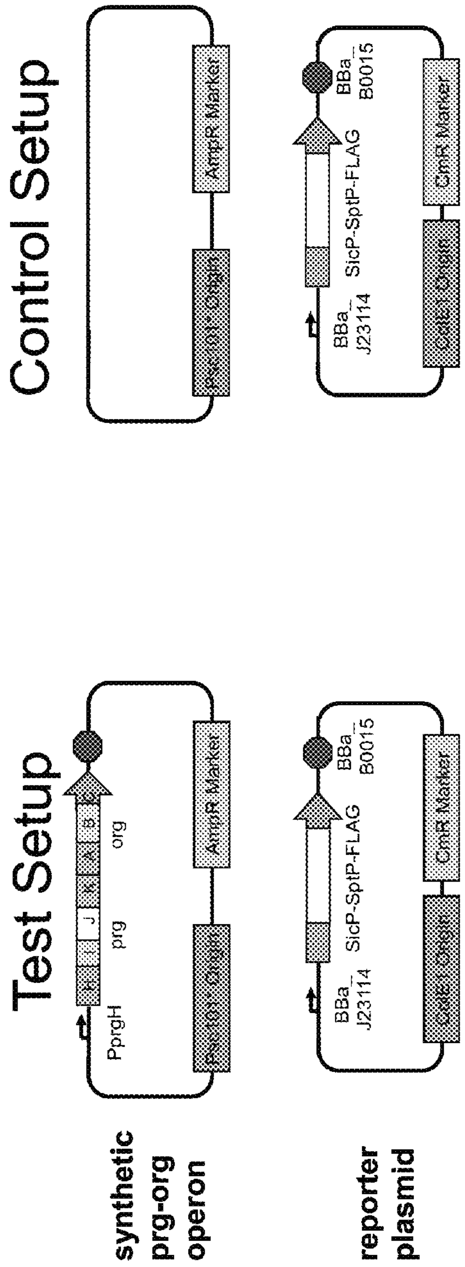
FIG. 22B shows a schematic of the prg-org operon test vector and reporter plasmid. The control plasmid and reporter plasmid are on the right.

These genes are allocated to each operon in the same manner as in the wild-type system. However, the order of genes in each operon is arranged on the basis of measured expression level from strongest to weakest. Operons were assembled by placing the selected synthetic RBS in front of its corresponding synthetic gene sequence. Restriction enzyme binding sites were added between genes or pairs of genes in order to facilitate future manipulation. The entire sequence was synthesized by DNA2.0. The synthetic operon was cloned into a low-copy test vector and placed under the control of an inducible promoter (e.g., pTac or pBad—IPTG or Arabinose induction). A reporter plasmid was created containing a native *Salmonella* secretable effector protein which was fused to a FLAG epitope tag for identification. This reporter was placed under a strong constitutive promoter. FIG. 22B shows a schematic of the prg-org operon test vector and a reporter plasmid.

Figure 23A:
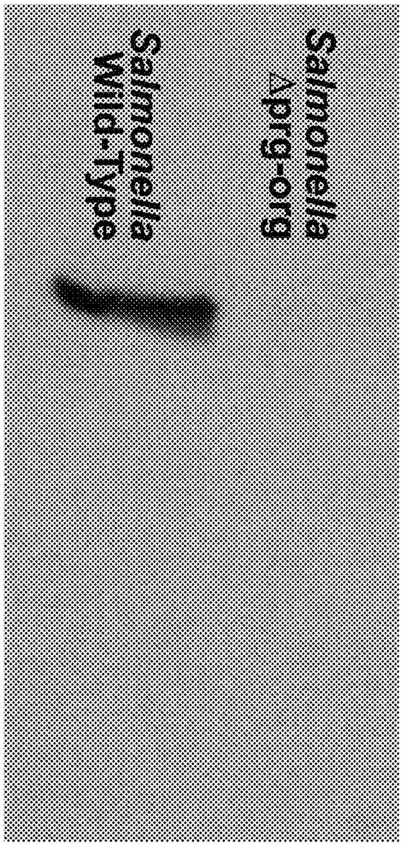
FIG. 23A shows that the Δprg-org knock-out strain does not express the prg-org operon.

We also generated two operon knockout (prg-org and inv-spa) *Salmonella* SL1344 cell lines using the method described in Datsenko, Wanner, *Proc. Natl. Acad. U.S.A.,* 2000. FIG. 22A shows a schematic of Δprg-org *Salmonella* SL1344 knock-out strain. The inv-spa and prg-org operons are boxed. FIG. 23A shows that the Δprg-org knock-out strain does not express the prg-org operon.

The test plasmid (or the control plasmid) and the reporter plasmid were transformed into the appropriate knockout strain. The strains were grown from colony overnight in low-salt media (LB with 5 g/L NaCl) at 37° C. The cultures were subcultured to an $OD_{260}$ of 0.025 in fresh low-salt media and grown for 2 hours. The cultures were diluted 1:10 into high-salt, inducting media (LB with 17 g/L of NaCl) in 50 mL unbaffled flasks and grown for 6-8 hours. 1 mL of each culture was spun down at 3000×g for 5 minutes, then the supernatant filtered through a 0.2 uM filter. This culture was then run on an SDS-PAGE gel and a western blot performed with an anti-FLAG antibody.

Figure 23B:
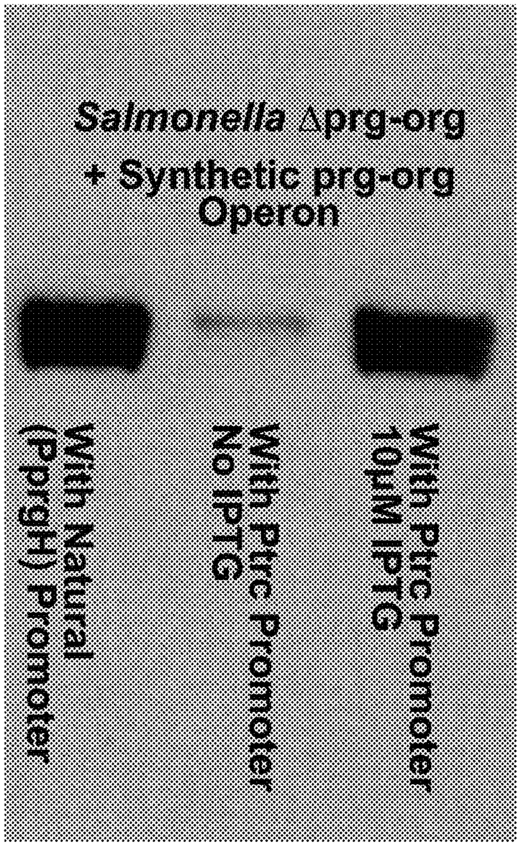
FIG. 23B shows that the synthetic refactored prg-org operon in *Salmonella* Δprg-org cells can be controlled by the addition of IPTG.

FIG. 23B shows that the synthetic refactored prg-org operon in *Salmonella* Δprg-org cells can be controlled by the addition of IPTG. The level of expression is comparable to that generated from the natural PprgH promoter.

Example 4: Refactoring Nitrogen Fixation Gene Cluster from *Klebsiella oxytoca*

Bacterial genes associated with a single trait are often grouped in a contiguous unit of the genome known as a gene cluster. It is difficult to genetically manipulate many gene clusters due to complex, redundant, and integrated host regulation. We have developed a systematic approach to completely specify the genetics of a gene cluster by rebuilding it from the bottom-up using only synthetic, well-characterized parts. This process removes all native regulation, including that which is undiscovered. First, all non-coding DNA, regulatory proteins, and non-essential genes are removed. The codons of essential genes are changed to create a DNA sequence as divergent as possible from the wild-type gene. Recoded genes are computationally scanned to eliminate internal regulation. They are organized into operons and placed under the control of synthetic parts (promoters, ribosome binding sites, and terminators) that are functionally separated by insulator parts. Finally, a controller consisting of genetic sensors and circuits regulates the conditions and dynamics of gene expression. We applied this approach to an agriculturally relevant gene cluster from *Klebsiella oxytoca* encoding the nitrogen fixation pathway for converting atmospheric $N_2$ to ammonia. The native gene cluster consists of 20 genes in 7 operons and is encoded in 23.5 kb of DNA. We constructed a refactored gene cluster that shares little DNA sequence identity with wild-type and for which the function of every genetic part is defined. This work demonstrates the potential for synthetic biology tools to rewrite the genetics encoding complex biological functions to facilitate access, engineering, and transferability.

Introduction

Many functions of interest for biotechnology are encoded in gene clusters, including metabolic pathways, nanomachines, nutrient scavenging mechanisms, and energy generators (1). Clusters typically contain internal regulation that is embedded in the global regulatory network of the organism. Promoters and 5'-UTRs are complex and integrate many regulatory inputs (2, 3). Regulation is highly redundant; for example, containing embedded feedforward and feedback loops (4). Regulation can also be internal to genes, including promoters, pause sites, and small RNAs (5, 6). Further, genes often physically overlap and regions of DNA can have multiple functions (7). The redundancy and extent of this regulation makes it difficult to manipulate a gene cluster to break its control by native environmental stimuli, optimize its function, or transfer it between organisms. As a consequence, many clusters are cryptic, meaning that laboratory conditions cannot be identified in which they are active (8).

Gene clusters have been controlled from the top-down by manipulating the native regulation or adding synthetic regulation in an otherwise wild-type background (9). For example, either knocking out a repressor or overexpressing an activator has turned on clusters encoding biosynthetic pathways (10-14). When the cluster is a single operon, it has been shown that a promoter can be inserted upstream to induce expression (15). The entire echinomycin biosynthetic cluster was transferred into *E. coli* by placing each native gene under the control of a synthetic promoter (16).

Figure 26:
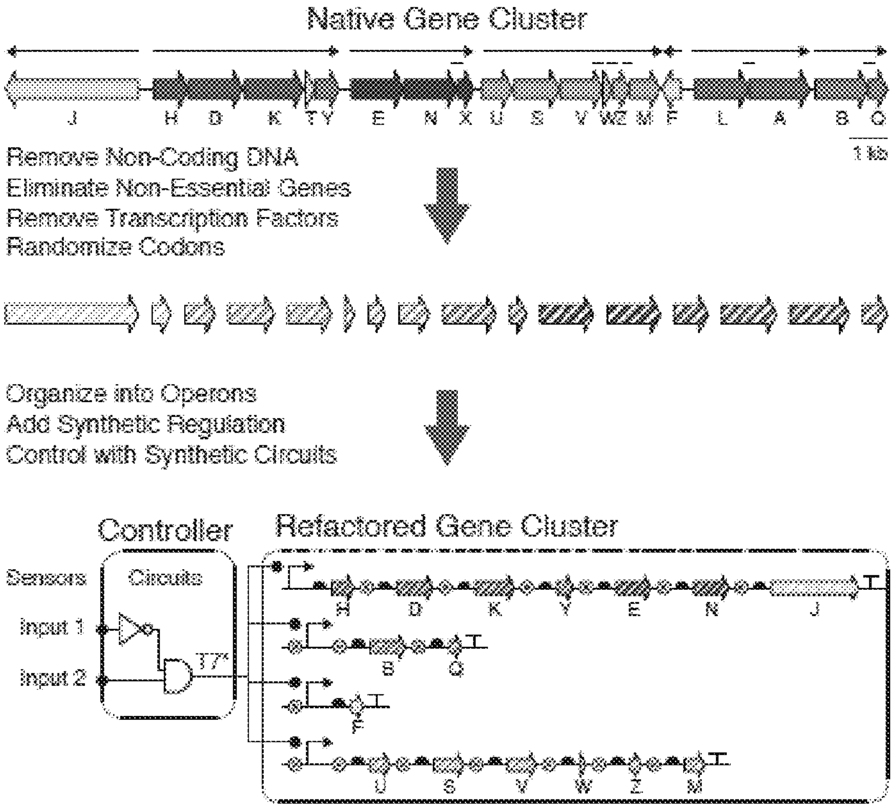
FIG. 26 illustrates the process of refactoring a gene cluster. The wild-type *K. oxytoca* nitrogen fixation gene cluster is shown at top. The genes are colored by function: blue (nitrogenase), green (co-factor biosynthesis, shading corresponds to operons), yellow (e-transport), and grey (unknown). The thin arrows show the length and orientation of the seven operons and a horizontal bar indicates overlapping genes. The recoded genes are shown as dashed lines. The symbols used to define the refactored cluster and controller are defined in FIGS. 29 and 30, respectively

In engineering, one approach to reduce the complexity of a system is to "refactor" it, a term borrowed from software development where the code underlying a program is rewritten to achieve some goal (e.g., stability) without changing functionality (17). This term was first applied to genetics to describe the top-down simplification of a phage genome by redesigning known genetic elements to be individually changeable by standard restriction digest (18). Here, we use it to refer to a comprehensive bottom-up process to systematically eliminate the native regulation of a gene cluster and replace it with synthetic genetic parts and circuits (FIG. 26). The end product is a version of the gene cluster whose DNA sequence has been rewritten, but it encodes the same function. The design process occurs on the computer, and then the resulting DNA sequence is constructed using DNA synthesis (19). The first step of the process is to remove all non-coding DNA, and regulatory genes. Next, each essential gene is recoded by selecting codons that produce a DNA sequence that is as distant as possible from the wild-type sequence. The intent is to introduce mutations throughout the gene to eliminate internal regulation (including that which is undiscovered), such as operators, promoters, mRNA secondary structure, pause sites, methylation sites, and codon regulation. Recoded sequences are further scanned by computational methods to identify putative functional sequences, which are then removed. The recoded genes are organized into artificial operons and the expression levels are controlled by synthetic ribosome binding sites (RBSs), and insulator sequences physically separate the genes. The end result is a refactored gene cluster whose native regulation has been removed and has been organized into a set of discrete, well-characterized genetic parts.

Once the native regulation has been removed, synthetic regulation can be added back to control the dynamics and conditions under which the cluster is expressed. Constructing such regulation has been a major thrust of synthetic biology and involves the design of genetic sensors and circuits and understanding how to connect them to form programs (20). In our design, we genetically separate the sensing/circuitry from the refactored pathway by carrying them on different low copy plasmids (FIG. 26). The plasmid containing the sensors and circuits is referred to as the "controller" and the output of the circuits lead to the expression of an engineered T7 polymerase (T7*). The refactored cluster is under the control of T7 promoters. One advantage of this organization is that T7 polymerase is orthogonal to native transcription and the T7 promoters are tightly off in the absence of the controller. In addition, changing the regulation is simplified to swapping the controller for one that contains different sensors and circuits, so long as the dynamic range of T7* is fixed.

As a demonstration, we have applied this process to refactor the gene cluster encoding nitrogen fixation in *Klebsiella oxytoca* (21). Nitrogen fixation is the conversion of atmospheric $N_2$ to ammonia ($NH_3$), so that it can enter metabolism (22). Industrial nitrogen fixation through the Haber-Bosch process is used to produce fertilizer. Many microorganisms fix nitrogen and the necessary genes typically occur together in a gene cluster, including the nitrogenase subunits, the metallocluster biosynthetic enzymes and chaperones, e-transport, and regulators (FIG. 27A) (23, 24). The gene cluster from *K. oxytoca* has been a model system for studying nitrogen fixation and consists of 20 genes encoded in 23.5 kb of DNA (FIG. 26, top) (25). The biosynthesis of nitrogenase is tightly regulated by a two-layer transcriptional cascade in response to fixed nitrogen, oxygen, and temperature (26). The complete cluster has been transferred to *E. coli*, thus demonstrating that it has all of the genes necessary for nitrogen fixation (27). The encoding of this function is complex, many of the genes overlap, the operons are oriented in opposite directions, and there are many putative hidden regulatory elements, including internal promoters and hairpins (25). The purpose of refactoring is to reorganize the cluster, simplify its regulation, and assign a concrete function to each genetic part.

Results

Tolerance of the Native Gene Cluster to Changes in Expression

Prior to refactoring a cluster, a robustness analysis is performed to determine the tolerances of a gene or set of genes to changes in expression level (FIG. 27B). This informs the grouping of genes into operons and the selection of synthetic parts to obtain desired expression levels. In the wild-type background, genes are knocked out and complemented under inducible control. The tolerance is obtained by measuring nitrogenase activity as a function of the activity of the inducible promoter.

Nitrogenase function is notably sensitive to expression changes and each tolerance has a clear optimum (FIG. 27B). The chaperone NifY is required to achieve full activity and broadens the tolerance to changes in expression level. NifT did not have an effect on activity, as observed previously (28), and it is frequently absent from homologous clusters (29). The genes controlling electron transport (nifJ and nifF) need to be expressed at low levels, and activity falls rapidly as expression increases. The optima for genes participating in the metal cluster biosynthetic pathways vary. The nifUSVWZM operon, which encodes proteins for early Fe—S cluster formation and proteins for component maturation, needs to be expressed at low levels, whereas nifBQ, encoding proteins for FeMo-co core synthesis and molybdenum integration, need to be expressed 10-fold higher. NifEN is tolerant to varied expression levels. However, activity is lost with the inclusion of nifX, which has been characterized as a negative regulator (30). The native cluster also includes the regulatory proteins NifL and NifA, which integrate environmental signals (26). The genes nifT, nifX, and nifLA are not included in the refactored cluster.

The Complete Refactored Gene Cluster

Figures 28A, 28B, 28C:
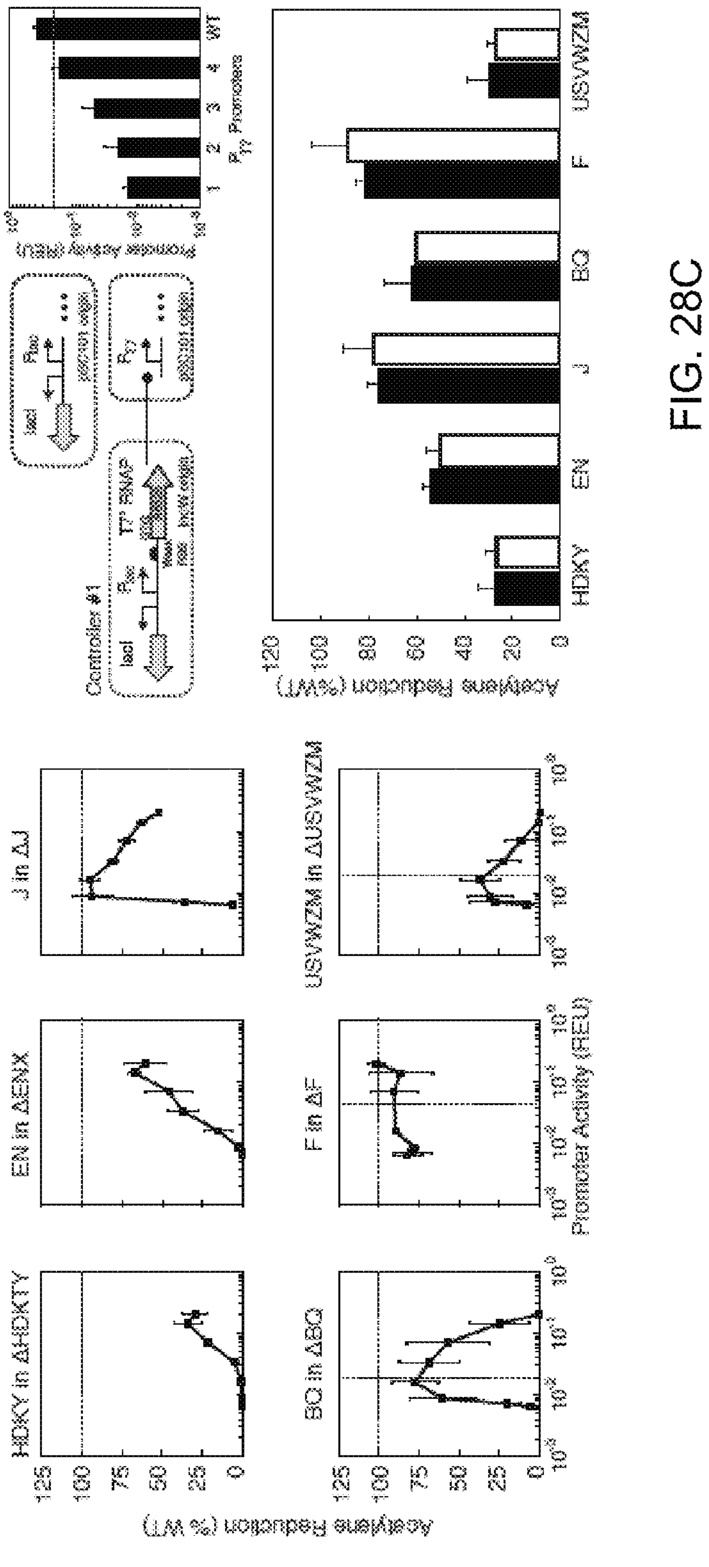
FIGS. 28A-28C illustrates converting to T7* RNAP Control.

The nitrogenase activities of the refactored operons were measured as a function of the IPTG-inducible $P_{tac}$ promoter (FIG. 28A). Each operon has a different optimum. To combine the operons, the $P_{tac}$ promoters were replaced with T7 promoters that have a strength close to the measured optimum (FIG. 28B and Materials and Methods section). The nitrogenase genes (nifHDK) are highly expressed in *Klebsiella* under fixing conditions (up to 10% of cell protein) (31), so the strongest promoter was used to control this operon (T7.WT, 0.38 REU) (32). A long operon was built to include the nifEN and nifJ genes, where the lower expression required for nifJ was achieved through transcriptional attenuation. The nifF gene was encoded separately under the control of a medium strength promoter (T7.3, 0.045 REU). Finally, the nifUSVWZM and nifBQ operons were controlled by weak promoters (T7.2, 0.019 REU). Each of the individual refactored operons under the control of a T7 promoter was able to recover the activity observed from the $P_{tac}$ promoter and corresponding optimal IPTG concentration (FIG. 28C).

Figure 29:
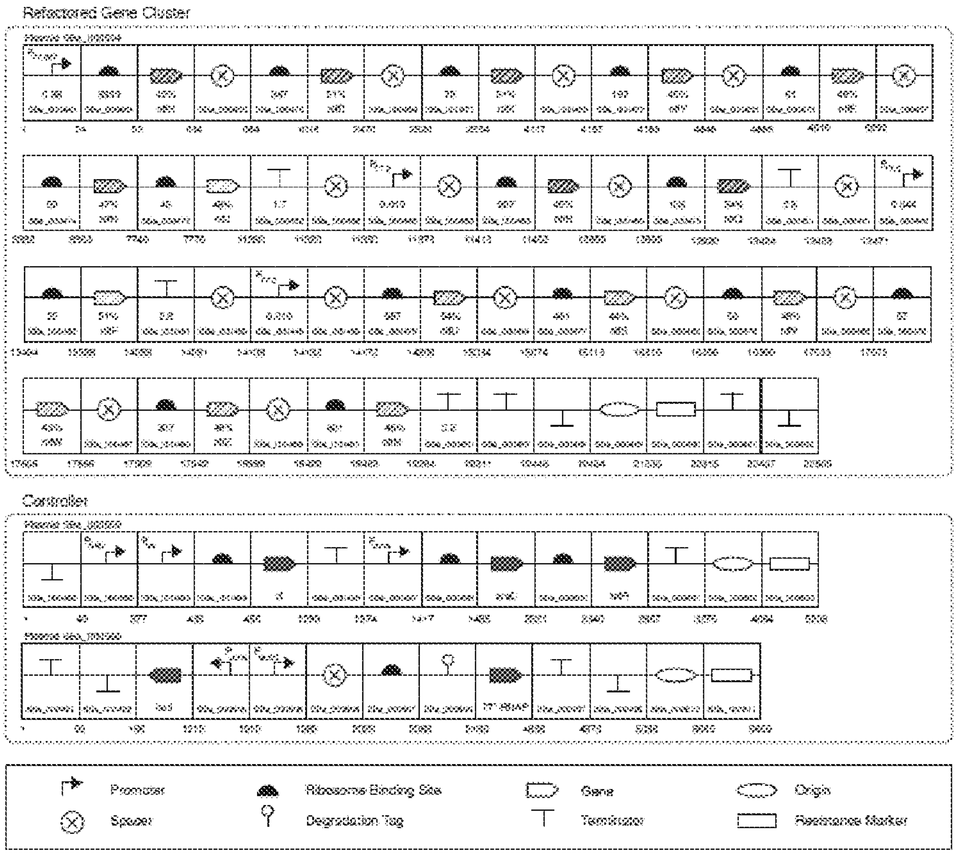
FIG. 29 shows a comprehensive schematic for the complete refactored gene cluster and controller. Each of the 89 parts is represented according to the SBOL visual standard (sbolstandard.org), and the SynBERC Registry part number (registry.synberc.org) and part activity are shown. The T7 promoter strengths are measured with red fluorescent protein (mRFP) and reported in REU (see, Materials and Methods). Terminator strengths are measured in a reporter plasmid and reported as the fold-reduction in mRFP expression when compared to a reporter without a terminator. The RBS strength is reported in as arbitrary units of expression from the induced $P_{tac}$ promoter (1 mM IPTG) and a fusion gene between the first 90 nucleotides of the gene and red fluorescent protein. The nucleotide numbers for the plasmids containing the refactored cluster and controller are shown. The codon identity of each recoded gene as compared to wild-type is shown as a percent.
Figures 30A, 30B, 30C, 30D:
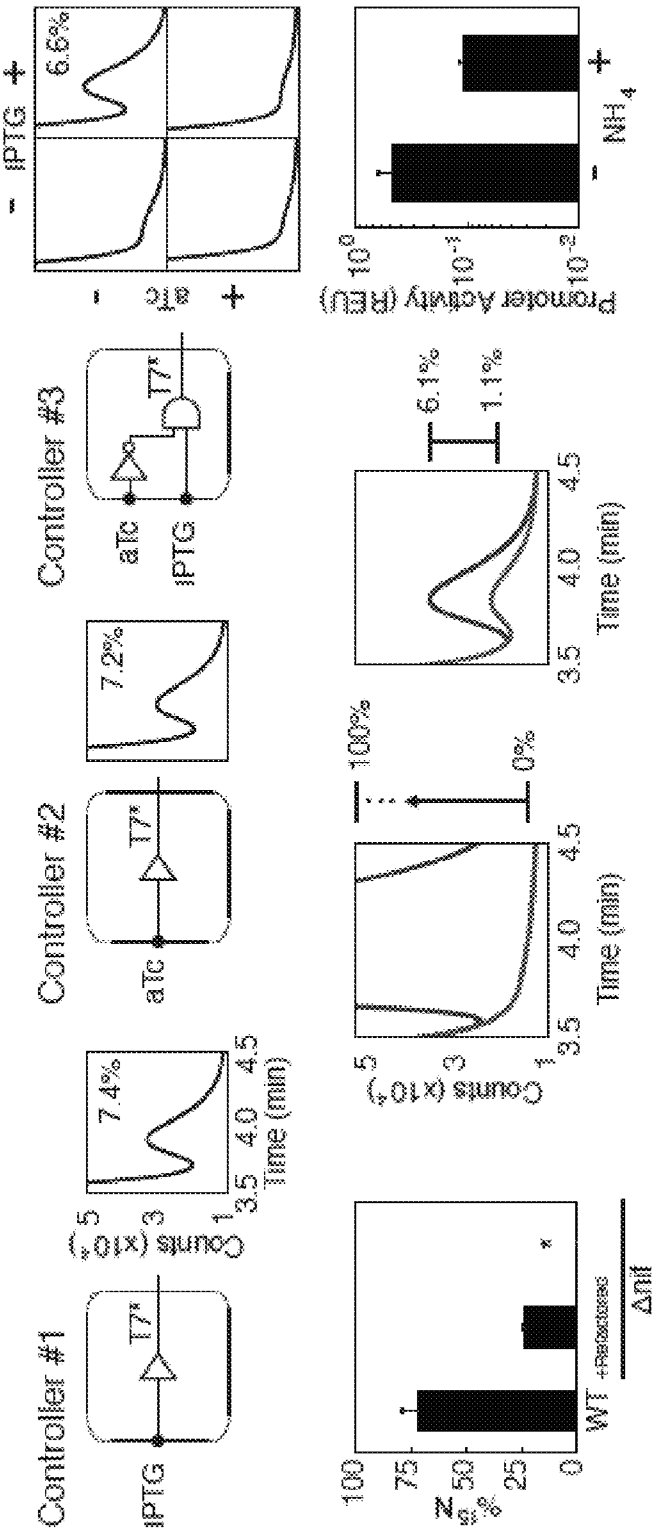
FIGS. 30A-30D shows the regulation of the complete refactored gene cluster.

Transitioning the control to T7* and T7 promoters facilitates the assembly of the complete cluster from refactored operons. We first assembled half-clusters using Gibson Assembly (33) and verified their function in strains with the corresponding genes deleted. The first half-cluster consisted of the nifHDKYENJ operon. The second half-cluster was assembled from the nifBQ, nifF, and nifUSVWZM operons. The half-clusters were able to recover 18%±0.7% and 26%±8.4% of wild-type activity, respectively. The full synthetic cluster was assembled from both half-clusters (FIG. 29), and its activity measured in a strain where the full cluster is deleted. The synthetic gene cluster recovers nitrogenase activity at 7.4%±2.4% of the wild-type (FIG. 30A). Strains carrying the synthetic gene cluster utilized ambient $N_2$ as a nitrogen source, growing 3.5-fold slower than the wild-type strain (FIG. 37) and incorporating $^{15}N$-labelled nitrogen into 24%±1.4% of their cellular nitrogen content, as measured by isotope ratio mass spectronomy (IRMS) (FIG. 30B).

The complete refactored cluster consists of 89 genetic parts, including a controller, and the function of each part is defined and characterized. Therefore, the genetics of the refactored system are complete and defined by the schematic in FIG. 29. However, the process of simplification and modularization reduces activity (18). This is an expected outcome of refactoring a highly evolved system.

Swapping Controllers to Change Regulation

The separation of the controller and the refactored cluster simplifies changing the regulation of the system. This can be achieved by transforming a different controller plasmid, as long as the dynamic range of the T7* RNAP expression is preserved. To demonstrate this, we constructed two additional controllers (FIG. 30A). Controller #2 changes the chemical that induces the system by placing the expression of T7* RNAP under the control of the aTc-inducible $P_{tet}$ promoter. When induced, Controller #2 produces nitrogenase activity identical to Controller #1 (7.2%±1.7%). The controller can also serve as a platform to encode genetic circuits to control regulatory dynamics or to integrate multiple sensors. To this end, Controller #3 contains two inducible systems (IPTG and aTc) and an ANDN gate (34, 35). In the presence of IPTG and the absence of aTc, nitrogen fixation is 6.6%±1.7% of wild-type activity. These controllers represent the simplicity by which the regulation of the refactored cluster can be changed.

In addition to making it possible to add new regulation, the process of refactoring eliminates the native regulation of the cluster. This is demonstrated through the decoupling of nitrogenase activity from the environmental signals that normally regulate its activity. For example, ammonia is a negative regulator that limits overproduction of fixed nitrogen (26). In the presence of 17.5 mM ammonia, no nitrogenase activity is observed for the wild-type cluster (FIG. 30C). In contrast, the refactored gene cluster maintains activity in the presence of ammonia (1.1%±0.5%). Interestingly, this 7-fold reduction of activity is not due to residual regulation present in the system. Rather, it occurs because the addition of ammonia to the media reduces the output of the controller by 4.5-fold (FIG. 30C). In theory, this could be fixed by increasing the expression level of T7* RNAP, but it speaks to the need to create genetic circuits that are robust to environmental context.

Discussion

The objective of refactoring is to facilitate the forward engineering of multi-gene systems encoded by complex genetics. Native gene clusters are the product of evolutionary processes; thus, they exhibit high redundancy, efficiency of information coding, and layers of regulation that rely on different biochemical mechanisms (36-38). These characteristics inhibit the quantitative alteration of function by part substitution, because the effect can become embedded in a web of interactions. Here, modularizing the cluster, physically separating and insulating the parts, and simplifying its regulation have guided the selection and analysis of part substitutions. The information gleaned from screening the permutations in a refactored system can be cleanly fed back into the design cycle.

The refactored cluster can also serve as a platform for addressing questions in basic biology. First, it allows for the impact of regulatory interactions to be quantified in isolation. For example, in the natural system, one feedback loop could be embedded in many other regulatory loops. Systematically removing such regulation provides a clean reference system (potentially less active and robust than wild-type) from which improvements can be quantified as a result of adding back regulation. It also serves as a basis for comparison of radically different regulatory programs or organizational principles; for example, to determine the importance of temporal control of gene expression (4, 39) or the need for genes to be encoded with a particular operon structure (40, 41). Second, the process of reconstruction and debugging is a discovery mechanism that is likely to reveal novel genetics and regulatory modes. In this work, the improvement from 0% to 7% revealed only minor changes: misannotations in genes and improper expression levels. However, the debugging process itself is blind to the mechanism—it simply identifies problematic regions of DNA.

One of the immediate applications of refactoring is in the access of gene clusters from genomic sequence information. This could be necessary either because the cluster is silent, meaning that it that cannot be activated in the laboratory, or because the desired cluster is from a metagenomic sample or information database and the physical DNA is unavailable (42). There are have been many elegant methods to activate a gene cluster, including the placement of inducible promoters upstream of the natural operons and the division of the cluster into individual cistrons, which can then be reassembled (43). With advances in DNA synthesis technology, it is possible to construct entire gene clusters with complete control over the identity of every nucleotide in the design. This capability eliminates the reliance on the natural physical DNA for construction and enables the simultaneous redesign of components in the complete system. Fully harnessing this technology will require the marriage of computational methods to select parts and scan designs, characterized part libaries, and methods to reduce their context dependence.

Material and Methods

Strains and Media

*E. coli* strain S17-1 was used for construction and propagation of all plasmids used in *Klebsiella oxytoca* knockout mutant construction. *K. oxytoca* strain M5al (Paul Ludden, UC Berkeley) and mutants derived from M5al were used for nitrogen fixation experiments. Luria-Bertani (LB)-Lennox was used for strain propagation. All assays were carried out in minimal medium containing (per liter) 25 g of $Na_2HPO_4$, 3 g of $KH_2PO_4$, 0.25 g of $MgSO_4.7H_2O$, 1 g of NaCl, 0.1 g of $CaCl_2.2H_2O$, 2.9 mg of $FeCl_3$, 0.25 mg of $Na_2MoO_4.2H_2O$, and 20 g of sucrose. Growth media is defined as minimal media supplemented with 6 ml (per liter) of 22% $NH_4Ac$. Derepression media is defined as minimal media supplemented with 1.5 ml (per liter) of 10% serine. The antibiotics used were 34.4 μg $ml^{-1}$ Cm, 100 μg $ml^{-1}$ Spec, 50 μg $ml^{-1}$ Kan, and/or 100 m $ml^{-1}$ Amp.

Codon Randomization

Initial gene sequences were proposed by DNA2.0 to maximize Hamming distance from the native sequence while seeking an optimal balance between *K. oxytoca* codon usage and *E. coli* codon preferences experimentally determined by the company (44). Rare codons (<5% occurrence in *K. oxytoca*) were avoided, and mRNA structure in the translation initiation region was suppressed. Known sequence motifs, including restriction sites, transposon recognition sites, Shine-Dalgarno sequences and transcriptional terminators, were removed by the DNA2.0 algorithm.

Elimination of Undesired Regulation

Each synthetic operon was scanned prior to DNA synthesis to identify and remove undesired regulation. Multiple types of regulation were identified using publicly available software. The RBS Calculator was used (Reverse Engineering, 16S RNA: ACCTCCTTA) to identify ribosome binding sites throughout the proposed DNA sequence of the operon (45). The Prokaryotic Promoter Prediction server was used to identify putative σ70 promoter sites (e-value cutoff of 5, sigma.hmm database) (46). The PromScan algorithm was used to identify putative σ54 promoter sites using default options (47). TransTermHP software was used with default parameters to identify terminator sequences in both the forward and reverse directions (48). RBSs greater than 50 AU and all identified promoters and terminators were considered significant.

Nitrogenase Activity Assay

In vivo nitrogenase activity is determined by acetylene reduction as previously described (49). For *K. oxytoca* whole-cell nitrogenase activity assay, cells harboring the appropriate plasmids were incubated in 5 ml of growth media (supplemented with antibiotics, 30° C., 250 r.p.m.) in 50 ml conical tubes for 14 hours. The cultures were diluted into 2 ml derepression media (supplemented with antibiotics and inducers) to a final $OD_{600}$ of 0.5 in 14 ml bottles, and bottles were sealed with rubber stoppers (Sigma Z564702).

Headspace in the bottles was repeatedly evacuated and flushed with $N_2$ past a copper catalyst trap using a vacuum manifold. After incubating the cultures for 5.5 hours at 30° C., 250 r.p.m, headspace was replaced by 1 atmosphere Ar. Acetylene was generated from $CaC_2$ using a Burris bottle, and 1 ml was injected into each bottle to start the reaction. Cultures were incubated for 1 hour at 30° C., 250 r.p.m before the assay was stopped by injection of 300 μl of 4M NaOH solution into each bottle. To quantify ethylene production, 50 μl of culture headspace was withdrawn through the rubber stopper with a gas tight syringe and manually injected into a HP 5890 gas chromatograph. Nitrogenase activity is reported as a percentage of wild-type activity. Briefly, ethylene production by strains was quantified by integrating area under the peak using HP Chemstation software and dividing ethylene production of experimental strains by the ethylene production of a wild type control included in each assay.

$N_2$-Dependent Growth and $^{15}N_2$ Incorporation Assay

Nitrogen fixation by synthetic nif cluster in *K. oxytoca* is further demonstrated by $N_2$-dependent growth and $^{15}N_2$ incorporation. Cells are diluted as described in the acetylene reduction assay. The headspace of the bottles is replaced by normal $N_2$ gas or by stable isotope nitrogen, $^{15}N_2$ ($^{15}N$ atom 99.9%, Icon Isotopes, Cat#: IN 5501). After incubating the cultures for 36 hours at 30° C., 250 r.p.m, $N_2$-dependent growth of the cells is determined by measuring optical density at 600 nm (OD600). To do the $^{15}N_2$ incorporation assay, the $^{15}N$-enriched cells with corresponding control cultures under normal nitrogen gas are collected by centrifugation, the cell pellets are dried in a laboratory oven at 100° C. for 12 hours. The dried pellets are analysis for $^{15}N/^{14}N$ ratio at the Center for Stable Isotope Biogeochemistry at the University of California, Berkeley using the Finnigan MAT Delta plus Isotope Ratio Mass Spectrometer.

*K. oxytoca* Knockout Strains

All *K. oxytoca* mutants are constructed from M5al by allele exchange using suicide plasmid pDS132 carrying the corresponding nif gene deletion (pDS132 was graciously provided by the Paul Ludden lab at UC Berkeley as a gift from Dr. Dominique Schneider at Université Joseph Fourier) (49). We made a slight modification to a previously published protocol (50). Here, a kanamycin resistance cassette was cloned into the suicide plasmid upstream of the left homologous exchange fragment. These operon deletions in nif gene cluster span the promoter and the complete amino acid coding sequences except when specifically designated. All mutants were verified by DNA sequencing of the PCR product of the corresponding gene region to confirm physical DNA deletion and by whole-cell acetylene reduction assay to confirm the lack of nitrogenase activity.

Promoter Characterization

As described in this example, the output of promoters is reported as relative expression units (REU). This is simply a linear factor that is multiplied by the arbitrary units measured by the flow cytometer. The objective of normalizing to REU is to standardize measurements between labs and projects. The linear factor is $1.66\times10^{-5}$ and the division by this number back converts to the raw arbitrary units. This number was calculated to be a proxy to the RPU (relative promoter units) reported by Kelly and co-workers (51). Our original standardized measurements were made prior to the Kelly paper and involved a different reference promoter, fluorescent protein (mRFP), RBS, and plasmid backbone. Because of these differences, one cannot calculate RPU as defined by Kelly, et al. Instead, a series of plasmids was made (FIG. 33A) to estimate the relative expression of reporter protein from experimental constructs compared the standard construct in Kelly, et al. Conversion factors between constructs were measured and multiplied to obtain the linear factor above. We renamed the unit to REU (relative expression units) because it is intended to be a simple normalization of fluorescent units (akin to a fluorescent bead) and not a direct measurement of the activity of a promoter (e.g., the polymerase flux).

Cells were grown as in the Acetylene Reduction Assay with two modifications. The initial flush of headspace with $N_2$ was not performed, and the assay was halted after the 5.5 hour incubation. To halt the assay, 10 μl of cells were transferred from each bottle to a 96-well plate containing phosphate buffered saline supplemented with 2 mg $ml^{-1}$ kanamycin. Fluorescence data was collected using a BD Biosciences LSRII flow cytometer. Data were gated by forward and side scatter, and each data set consisted of at least 10,000 cells. FlowJo was used to calculate the geometric means of the fluorescence distributions. The autofluorescence value of *K. oxytoca* cells harboring no plasmid was subtracted from these values to give the values reported in this study. The strengths of T7 promoter mutants were characterized by swapping them in place of the $P_{tac}$ promoter in plasmid N149 (SBa_000516), co-transforming with Controller #1 (plasmid N249), and measuring fluorescence via flow cytometry under 1 mM IPTG induction.

To replace the $P_{tac}$ promoter by a T7 promoter in each synthetic operon, we followed a simple process. First, we identified the IPTG concentration corresponding to the maximal functional activity of each synthetic operon. Second, we translated this IPTG concentration into REU based on characterization of the $P_{tac}$ promoter (FIG. 33B, left). Third, we selected the T7 mutant promoter with the closest strength in REU. For the synthetic nifF operon, we observed broad, robust fixation under the $P_{tac}$ promoter. We found that T7 mut 3 produced inducible functional activity with a maximum at 1 mM IPTG induction of the T7 RNAP. For the synthetic nifJ operon, our method suggests that we use a weak T7 mutant promoter. However, we found that a WT T7 promoter produced inducible activity with a maximum at 1 mM IPTG. We attribute this deviation to a change in RBS strength due to contextual differences between $P_{tac}$ and the T7 promoter.

Debugging Synthetic Operons

Figure 34A:
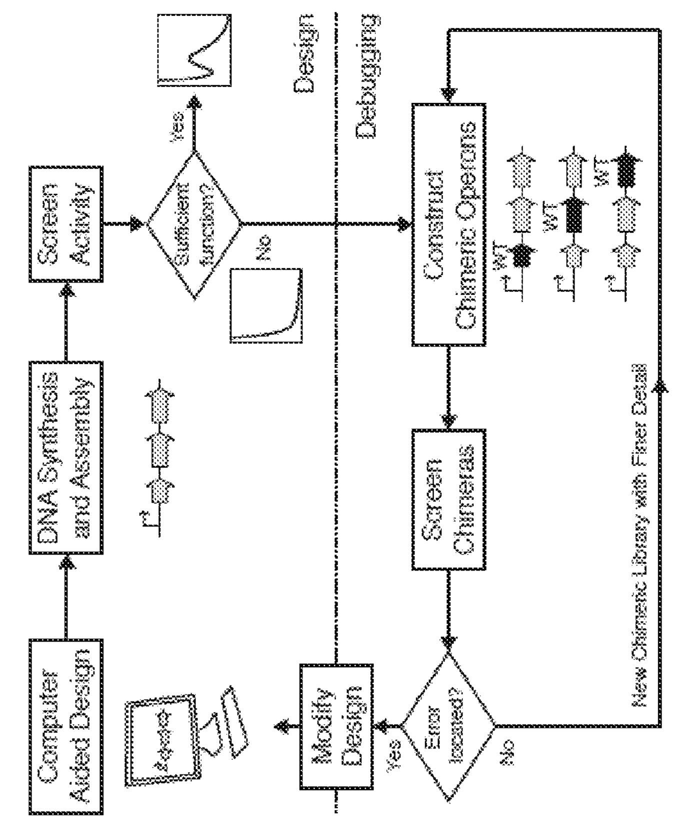
FIGS. 34A-34B illustrates debugging of the refactored operons.
Figure 34B:
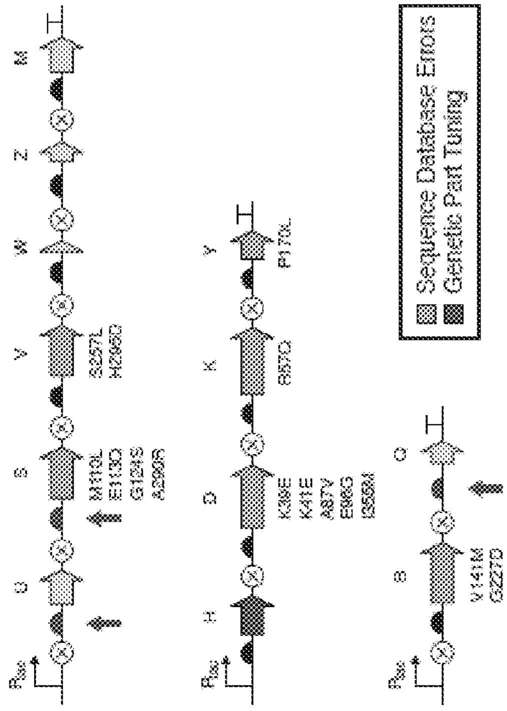
Figure 36:
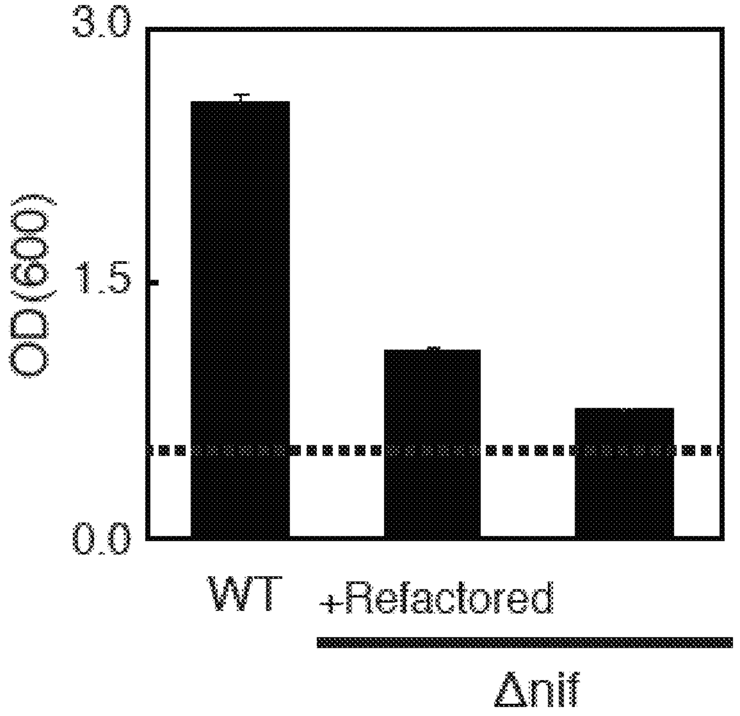
FIG. 36 shows cell growth supported by nitrogen fixation. The dotted line indicates initial seeding density of OD600 0.5. Wild-type *Klebsiella* grew to an OD600 2.57±0.07 after 36 hours of incubation in depression conditions. Eliminating the full nif cluster severely inhibited cell growth (Δnif, OD600 0.76±0.02). Complementing the knockout strain with the refactored cluster and Controller #1 under 1 mM IPTG induction yielded growth of OD600 1.10±0.03.

Some of the initial designs for refactored operons showed little or no activity. When this occurs, it is challenging to identify the problem because so many genetic changes have been made simultaneously to the extent that there is almost no DNA identity with the wild-type sequence. To rapidly identify the problem, a debugging method was developed that can be generalized when refactoring different functions (FIG. 34A). Chimeric operons are created by replacing a wild-type region of DNA with its synthetic counterpart. The function of each chimera in this library is assessed to identify which region of synthetic DNA caused a loss of activity. New chimeras are then be constructed with increasingly fine-resolution changes between synthetic and wild-type DNA. This approach "zooms in" on the problematic region of DNA, which can then be fixed. The most common problem is due to errors in the reference DNA sequence (Genbank, X13303.1) (52). Refactored genes were designed using only the amino acid sequence information from the database; thus, they were sensitive to sequencing errors leading to missense mutations that reduced or eliminated activity. Indeed, 18 such mutations were identified and confirmed by carefully resequencing the wild-type cluster (FIG. 35). Fifteen of the 18 mutations occurred in refactored operons that required debugging and were corrected (FIG. 34B). This demonstrates the challenge of reconstituting biological functions using only database information and DNA synthesis (55).

Figure 37:
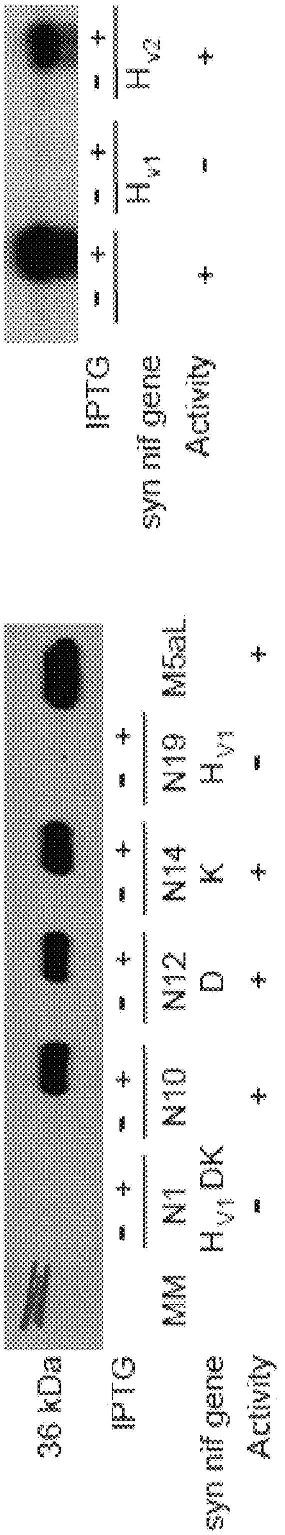
FIG. 37 shows expression of synthetic synthetic nifH variants. Western blot assay to detect the expression of synthetic $nifH_{v1}$ (left) and synthetic synthetic $nifH_{v2}$ (right). All constructs bore $P_{tac}$-nifHDK with the synthetic gene indicated. Cultures were induced with 50 μM IPTG.

Modifying synthetic RBS strength was also important to debugging. The function of the synthetic nifUSVWZM operon was significantly improved by changing RBSs to match a 1:1 ratio of NifU:NifS. The initial selection of RBSs led to an observed 10:1 ratio in their respective RBS strengths. After debugging, nifU and nifS RBS strength was better balanced (1.25:1) and this improved activity. For one RBS, the measurement method proved to be inaccurate. We found the measured strength of the wild-type nifQ RBS was extremely low (FIG. 27C), and the synthetic nifBQ operon showed low activity when the synthetic nifQ RBS was matched to the measured strength. In contrast, the robustness analysis showed a requirement for high expression level of the nifBQ operon (FIG. 27B). Thus, a strong synthetic RBS near the strength of the nifB RBS was used and significantly improved nifBQ operon activity. In one case, our initial recoded nifH gene did not express well using either wild-type or synthetic regulation (FIG. 37). We designed a new synthetic gene, requiring that it diverge in DNA sequence from both the native and first synthetic DNA sequences and found that the new synthetic gene both expressed well and recovered activity.

Growth by Nitrogen Fixation

Cells capable of nitrogen fixation should exhibit measurable growth on media that lacks nitrogen by utilizing atmospheric $N_2$ as a source of nitrogen. Conversely, cells incapable of nitrogen fixation should not grow on nitrogen-free media.

In parallel to the $^{15}N_2$ incorporation assay, we monitored strain growth under nitrogen-limited media conditions and 100% $^{15}N_2$ atmosphere (Methods, $N_2$-dependent Growth Assay). Cells were grown on derepression media as used in the Nitrogenase Activity Assay. Depression media is not strictly nitrogen-free, containing 1.43 mM serine in order to promote ribosomal RNA production and hasten nitrogenase biosynthesis (54).

Strains containing Controller #1 and the refactored gene cluster grew nearly 30% as much as wild-type strains. In contrast, minimal growth was observed in Δnif strains, consistent with the limited nitrogen available from serine and cell lysis products (55). FIG. 37 illustrates cell growth supported by nitrogen fixation.

Western Blot Assay for Synthetic nifH Expression

The first synthetic nifHDK did not exhibit nitrogenase activity under induction ranging from 0 to 1 mM IPTG, and the nifH gene (synthetic $nifH_{v1}$) was identified as a problematic part using the debugging protocol shown in FIG. 34. However there was no mutation found. Western blots were further used to confirm problematic synthetic nifH expression.

A western blot for NifH protein in FIG. 37 (left) showed that wild type nifH expressed well with either synthetic nifD or nifK (construct N10, N12, N14), whereas synthetic $nifH_{v1}$ was not expressed regardless of the context of nifDK (construct N1 and N19). A second synthetic nifH (synthetic $nifH_{v2}$) was used to replace synthetic $nifH_{v1}$. The western blot in FIG. 37 (right) showed the synthetic $nifH_{v2}$ (construct N38) expressed well.

Samples for western blots were prepared by boiling collected *K. oxytoca* cells in SDS-PAGE loading buffer and run on 12% SDS-Polyacrylamide gels (Lonza Biosciences). Proteins on the gels were transferred to PVDF membranes (BioRad Cat#: 162-0177) using Trans-Blot SD Semi-Dry Transfer Cell (BioRad Cat#:#170-3940). Blocking the membrane and Antibody binding were performed using SNAP i.d. Protein Detection System (Millipore Cat#WBAVDBA). The membranes were blocked by TBST-1% BSA (TBS-Tween20). The anti-NifH and anti-NifDK antibodies (kindly provided by Paul Ludden Lab at UC-Berkeley) were used as the primary antibodies. The anti-NifH antibody was a universal anti-NifH made against a mixture of purified NifH proteins from *Azotobacter vinelandii, Clostridium pasteurianum, Rhodospirillum rubrum*, and *K. oxytoca*. The anti-NifDK antibody was made against purified NifDK protein from *Azotobacter vinelandii*. The anti-NifH and anti-NifDK antibodies were used at 1:500 and 1:2000 respectively. The secondary antibody (Goat anti-Rabbit IgG-HRP, Sigam Cat#: A0545) was used at 1:10,000. Development was done using an enhanced chemiluminescent substrate for HRP (Pierce Cat#: 32209) and captured on film (Kodak: Cat#: 178-8207).

Construction of Plasmids and Parts

Plasmids were designed in silico. Synthetic parts (promoters, RBS, terminators and insulators) were combined with the initial synthetic gene sequences proposed by DNA2.0 in ApE (A Plasmid Editor) and GeneDesigner (56) to create synthetic operons. Synthetic operons were computationally scanned to eliminate unintended regulation (Methods, “Elimination of Undesired Regulation”), and parts containing such regulation were replaced. This reiterative process continued until the synthetic operons included only designed regulation.

Physical DNA was constructed using standard manipulation techniques. Assembly methods followed published protocols and included BioBrick (57), Megawhop (58), Phusion Site-Directed Mutagenesis or Gibson Assembly methods (59). We found that Gibson Assembly was the most efficient DNA assembly method, except when making small (<10 bp) changes in plasmids under 10 kb in size. We noted assembly failures were infrequent, more common in assemblies above 15 kbp, and linked to the presence of homology within ~500 bp of part termini. In these cases, we observed annealing of unexpected parts to create non-intended junctions.

Plasmid pIncW (pSa, SpR) was generated from pEXT21 (pSa, SpR) by deletion of osa, nucl, the Tn21 integrase gene, and ORF18 (60). Plasmid pSB4C5 (pSC101, CmR) was obtained from the Registry of Standard Biological parts and serves as the base vector for wild-type complementation, RBS characterization, and synthetic operons (57). Plasmid N58 (pSC101, CmR) was generated by inserting the $P_{tac}$ cassette (SynBERC Registry, SBa_000561) between the BioBrick prefix and BioBrick suffix of pSB4C5. Plasmid N292 (SBa_000566) was generated by inserting a terminator characterization cassette between the BioBrick prefix and BrioBrick suffix of pSB4C5. The cassette consists of the PT7 promoter, RBS (SBa_000498), GFP, the wild-type T7 terminator, RBS D103 (SBa_000563) from Salis et. al. (13), and mRFP (SBa_000484). Plasmid N149 (SBa_000516) was constructed by inserting the $P_{tac}$ promoter cassette (SBa_000563), RBS D103 (SBa_000563) from Salis et. al. (13), and mRFP (SBa_000484) between the BioBrick prefix and BioBrick suffix of pSB4C5. Plasmid N505 (SBa_000517) was constructed by inserting the $P_{tet}$ promoter cassette (SBa_000562), RBS D103 (SBa_000563), and mRFP (SBa_000484) between the BioBrick prefix and BioBrick suffix of pSB4C5. Plasmid N110 (SBa_000564) was constructed by inserting a constitutive promoter (SBa_000565), a strong RBS (SBa_000475), and mRFP (SBa_000484) between the BioBrick prefix and BioBrick suffix of pSB4C5. Plasmid N573 (SBa_000559) was constructed by inserting the AmpR resistance marker in pNOR1020 (14).

Figure 31:
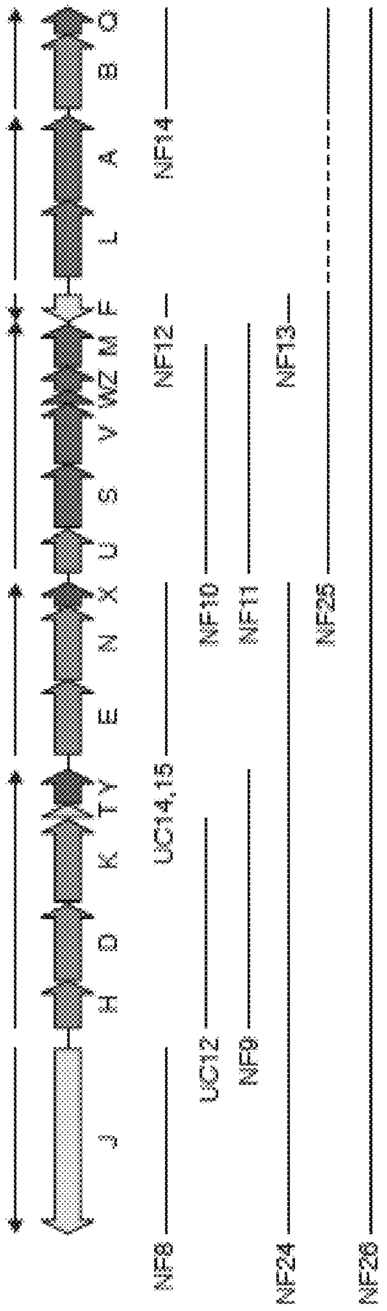
FIG. 31 shows the nif operon deletions used in this study. The solid lines show the region of deleted nif operons. The dashed line in NF25 shows the retained nifLA operon.

It has been shown that the multicopy expression of some nitrogen fixation genes can eliminate nitrogenase maturation and function (i.e., multicopy inhibition) (63, 64). An additional uncertainty is that the replacement of the native promoter with an inducible promoter could disrupt their function. To examine these effects, we constructed plasmids to complement the activities of the knockout strains (FIG. 31) and tested their activity under inducible control. These plasmids are also the basis for the experiments to quantify the robustness to changes in expression (FIG. 27).

Complementation plasmids were constructed by inserting the DNA encoding each wild-type operon between the Ptac promoter and BioBrick suffix of plasmid N58 (pSC101, CmR). One exception was plasmid Nif18 which was constructed by cloning the nifHDKTY operon into the multicloning site of pEXT21 (60). Wild-type operon sequences were defined by published transcription initiation sites (65).

Wild-type RBS characterization vectors were constructed by inserting the region from −60 bp to +90 bp for each native gene and mRFP (SBa_000484) between the Ptac cassette (SBa_000561) and the BioBrick suffix of plasmid N58 (pSC101, CmR). The native gene sequence from +1 bp to +90 bp formed an in-frame fusion with mRFP. In cases where the gene transcript does not extend to −60 bp, a shorter cassette was cloned into N58. RBS strength was characterized using the Promoter Characterization Assay described herein.

Synthetic RBSs of sufficient length to capture the full ribosome footprint (~35 bp) were generated with the RBS Calculator (61). The strength of each was measured using a synthetic RBS characterization vector. These vectors were constructed similar to the wild-type RBS characterization vectors using −60 bp to +90 bp of the designed synthetic gene. This region includes part of a buffer sequence, the synthetic RBS, and the region from +1 bp to +90 bp of the synthetic gene. If the synthetic and wild-type RBSs differed by more than 3-fold in expression, new RBS sequences were generated and screened. Insulator parts consisting of ~50 bp of random DNA precede each synthetic RBS (66).

Synthetic operons were cloned into the pSB4C5 (pSC101, CmR) backbone between the BioBrick prefix and BioBrick suffix.

Synthetic Part Generation

T7* RNA Polymerase: The T7 RNA polymerase was modified to be non-toxic to both *Klebsiella* and *E. coli* at high expression levels. The RNAP was expressed from a low-copy origin (pSa) under control of a weak RBS (SBa_000507, TATCCAAACCAGTAGCTCAATTGGAGTCGTCTAT (SEQ ID NO:341)) and N-terminal degradation tag (SBa_000509, TTGTTTATCAAGCCTGCGGATCTCCGCGAAATTGTGACTTTTCCGCTATTTAGCGA TCTTGTTCAGTGTGGCTTTCCTTCACCGGCAGCAGATTACGTTGAACAGCGCATC GATCTGGGTGGC (SEQ ID NO:342)). The start codon was changed from ATG to GTG, and the active site contained a mutation (R632S).

T7 promoters: T7 promoters were generated from a random library. The T7 promoter seed sequence was TAATACGACTCACTANNNNNAGA (SEQ ID NO:156). For the sequences of individual promoters, see FIG. 38.

T7 terminators: T7 terminators were generated from a random library and inserted into the terminator characterization vector N292 (SBa_000566). The T7 terminator seed sequence was TANNNAACCSSWWSSNSSSSTCWWWCGSSSSSSWWSSGTTT (SEQ ID NO:343). Terminator plasmids were co-transformed with plasmid N249 and characterized (Methods, Fluorescence Characterization) under 1 mM IPTG induction of T7* RNAP. RFP expression was measured for each terminator, and data are reported as the fold reduction in measured fluorescence when compared to a derivative of N292 carrying no terminator. For the sequences of individual terminators, see FIG. 38

Ribosome binding sites: The RBS Calculator was used to generate an RBS that matched the measured strength of the wild-type RBS. In three cases, synthetic RBSs were selected from existing parts (SBa_000475 for nifJ and nifQ, and SBa_000469 for nifH). In cases where the strength of the initial synthetic RBS differed from the WT RBS by more than 3-fold (nifV, nifZ, and nifM), a library of synthetic RBS was constructed by replacing the 15 bp upstream of the start codon with NNNAGGAGGNNNNNN (SEQ ID NO:344). We screened mutants in each library to identify synthetic RBSs within three fold of the WT RBS strength. Ribosome binding site strength is reported in arbitrary fluorescence units measured using the fluorescence characterization assay.

Insulator sequences (spacer sequences): Insulator sequences were generated using the Random DNA Generator using a random GC content of 50% (66).

ANDN Logic: We constructed a genetic circuit encoding the logic A ANDN B and used this circuit to control T7* RNAP in Controller #3. In this circuit, the A ANDN B logic corresponds to the presence or absence of the inducers, IPTG and aTc, such that the cell computes IPTG ANDN aTc. The circuit was constructed by modifying the Ptac promoter in Controller #1 (SBa_000520) to include the cI repressor binding sites OR1 and OR2 to produce plasmid N639 (SBa_000560). Additionally, plasmid pNOR1020 encodes the repressor cI under control of the Ptet promoter (62). We modified pNOR1020 by changing the resistance marker to confer ampicillin resistance to produce N573 (SBa_000559). When N639 and N573 are co-transformed, they produce the logic circuit IPTG ANDN aTc.

Figure 39:
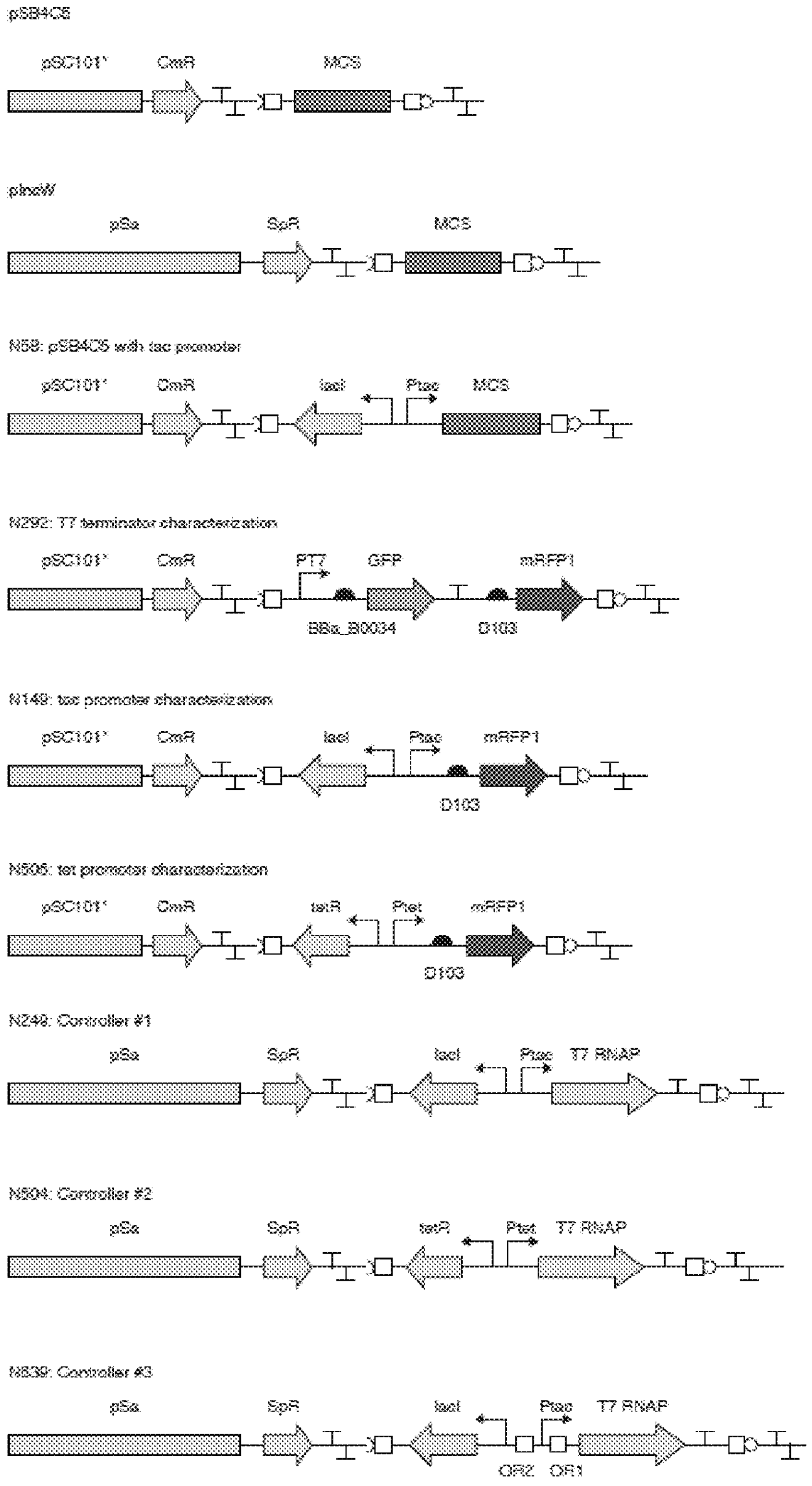
FIG. 39 shows maps of key plasmids. SBOL graphical notation is used to describe genetic parts: the BioBrick prefix and suffix are open squares, and terminators are in the shape of a T.

Ptac (SBa_000512) sequence (SEQ ID NO:334): tattctgaaatgagctgttgacaattaatcatcggctcgtataatgtgtggaattgtgagcggataacaatt Ptac plus OR1 and OR2 (SBa_000506) sequence (SEQ ID NO:335): tattaacaccgtgcgtgttgacagctatacctctggcggttataatgctagcggaattgtgagcggataacaatt FIG. 39 illustrates maps for key plasmids.

The nif gene cluster in *K. oxytoca* Ma5L was re-sequenced from PCR fragments. The re-sequenced DNA sequence was compared to the reference sequence from Genbank, X13303.1 (52). Sequence differences are listed in FIG. 35. The nucleotide locations are numbered relative to X13303.1. Amino acid mutations to correct errors in the X13303.1 record are shown (Impact).

REFERENCES

1. Fischbach M, Voigt, C. A. (2010) Prokaryotic gene clusters: A rich toolbox for synthetic biology. *Biotechnol. J.* 5:1277-1296.
2. Ishihama A (2010) Prokaryotic genome regulation: multifactor promoters, multitarget regulators and hierarchic networks. *FEMS Microbiol Rev* 34(5):628-645.
3. Mandal M & Breaker R R (2004) Gene regulation by riboswitches. *Nat Rev Mol Cell Biol* 5(6):451-463.
4. Temme K, et al. (2008) Induction and relaxation dynamics of the regulatory network controlling the type III secretion system encoded within *Salmonella* pathogenicity island 1. *J Mol Biol* 377(1):47-61.

5. Georg J & Hess W R (2011) cis-antisense RNA, another level of gene regulation in bacteria. *Microbiol Mol Biol Rev* 75(2):286-300.
6. Guell M, Yus E, Lluch-Senar M, & Serrano L (2011) Bacterial transcriptomics: what is beyond the RNA horizome? *Nature reviews. Microbiology* 9(9):658-669.
7. Johnson Z I & Chisholm S W (2004) Properties of overlapping genes are conserved across microbial genomes. *Genome Res* 14(11):2268-2272.
8. Zazopoulos E, et al. (2003) A genomics-guided approach for discovering and expressing cryptic metabolic pathways. *Nat Biotechnol* 21(2):187-190.
9. Medema M H, Breitling R, Bovenberg R, & Takano E (2011) Exploiting plug-and-play synthetic biology for drug discovery and production in microorganisms. *Nature reviews. Microbiology* 9(2): 131-137.
10. Gottelt M, Koi, S., Gomez-Escribano, J. P., Bibb, M., Takano, E. (2010) Deletion of a regulatory gene within the cpk gene cluster reveals novel antibacterial activity in Steptomyces coelicolor A3(2). *Microbiology* 156:2343-2353.
11. Lombo F, Brana, A. F., Mendez, C., Salas, J. A. (1999) The mithramycin gene cluster of Steptomyces argillaceus contains a positive regulatory gene and two repeated DNA sequences that are located at both ends of the cluster. *J. Bacteriol.* 181:642-647.
12. Medema M H, Bretiling, R., Takano, E. (2011) Synthetic biology in Steptomyces bacteria. *Methods Enzymol* 497: 485-502.
13. Pickens L B, Tang, Y., Chooi, Y-H. (2011) Metabolic engineering for the production of natural products. *Annu. Rev. Chem. Biomol. Eng.* 2:1-26.
14. Smanski M J, Peterson, R. M., Raj ski, S. R., Shen, B. (2009) Engineered *Streptomyces platensis* strains that overproduce antibiotics platensimycin and platencin. *Antimicrob. Agents Chemother.* 53:1299-12304.
15. Biggins J B, Liu, X., Feng, Z., Brady, S. F. (2011) Metabolites from the induced expression of crypic single operons found in the genome of *Burkolderia pseudomallei. JACS* 133:1638-1641.
16. Watanabe K, Hotta, K., Praseuth, A. P., Koketsu, K., Migita, A., Boddy, C. N., Wang, C. C. C., Oguri, H., Oikawa, H. (2006) Total biosynthesis of antitumor nonribosomal peptides in *Escherichia coli. Nature Chemical Biology*:1-6.
17. Fowler M & Beck K (1999) *Refactoring: improving the design of existing code* (Addison-Wesley, Reading, Mass.) pp xx1, 431 p.
18. Chan L Y, Kosuri S, & Endy D (2005) Refactoring bacteriophage T7. *Mol Syst Biol* 1:2005 0018.
19. Czar M J, Anderson J C, Bader J S, & Peccoud J (2009) Gene synthesis demystified. *Trends Biotechnol* 27(2):63-72.
20. Purnick P E & Weiss R (2009) The second wave of synthetic biology: from modules to systems. *Nat Rev Mol Cell Biol* 10(6):410-422.
21. Stacey G S, Burris R H, & Evans H J (1992) *Biological nitrogen fixation* (Chapman & Hall, New York) pp xii, 943 p.
22. Burris R H (1991) Nitrogenases. *J Biol Chem* 266(15): 9339-9342.
23. Hu Y, Fay A W, Lee C C, Yoshizawa J, & Ribbe M W (2008) Assembly of nitrogenase MoFe protein. *Biochemistry* 47(13):3973-3981.
24. Rubio L M & Ludden P W (2005) Maturation of nitrogenase: a biochemical puzzle. *J Bacteriol* 187(2): 405-414.
25. Arnold W, Rump A, Klipp W, Priefer U B, & Puhler A (1988) Nucleotide sequence of a 24,206-base-pair DNA fragment carrying the entire nitrogen fixation gene cluster of *Klebsiella pneumoniae. J Mol Biol* 203(3):715-738.
26. Dixon R & Kahn D (2004) Genetic regulation of biological nitrogen fixation. *Nat Rev Microbiol* 2(8):621-631.
27. Dixon R A & Postgate J R (1972) Genetic transfer of nitrogen fixation from *Klebsiella pneumoniae* to *Escherichia coli. Nature* 237(5350):102-103.
28. Simon H M, Homer M J, & Roberts G P (1996) Perturbation of nifT expression in *Klebsiella pneumoniae* has limited effect on nitrogen fixation. *J Bacteriol* 178 (10):2975-2977.
29. Fani R, Gallo R, & Lio P (2000) Molecular evolution of nitrogen fixation: the evolutionary history of the nifD, nifK, nifE, and nifN genes. *J Mol Evol* 51(1):1-11.
30. Gosink M M, Franklin N M, & Roberts G P (1990) The product of the *Klebsiella pneumoniae* nifX gene is a negative regulator of the nitrogen fixation (nif) regulon. *J Bacteriol* 172(3):1441-1447.
31. Orme-Johnson W H (1985) Molecular basis of biological nitrogen fixation. *Annu Rev Biophys Biophys Chem* 14:419-459.
32. Kelly J R, et al. (2009) Measuring the activity of BioBrick promoters using an in vivo reference standard. *J Biol Eng* 3:4.
33. Gibson D G, et al. (2009) Enzymatic assembly of DNA molecules up to several hundred kilobases. *Nat Methods* 6(5):343-345.
34. Yokobayashi Y, Weiss R, & Arnold F H (2002) Directed evolution of a genetic circuit. *Proc Natl Acad Sci USA* 99(26):16587-16591.
35. Tamsir A, Tabor J J, & Voigt C A (2011) Robust multicellular computing using genetically encoded NOR gates and chemical 'wires'. *Nature* 469(7329):212-215.
36. Alon U (2007) *An introduction to systems biology: design principles of biological circuits* (Chapman & Hall/CRC, Boca Raton, Fla.) pp xvi, 301 p., 304 p. of plates.
37. Kitano H (2002) Systems biology: a brief overview. *Science* 295(5560):1662-1664.
38. Palsson B (2006) *Systems biology: properties of reconstructed networks* (Cambridge University Press, Cambridge; New York) pp xii, 322 p.
39. Kalir S, et al. (2001) Ordering genes in a flagella pathway by analysis of expression kinetics from living bacteria. *Science* 292(5524):2080-2083.
40. Zaslaver A, Mayo A, Ronen M, & Alon U (2006) Optimal gene partition into operons correlates with gene functional order. *Phys Biol* 3(3):183-189.
41. Kovacs K, Hurst L D, & Papp B (2009) Stochasticity in protein levels drives colinearity of gene order in metabolic operons of *Escherichia coli. PLoS Biol* 7(5): e1000115.
42. Wenzel S C & Muller R (2005) Recent developments towards the heterologous expression of complex bacterial natural product biosynthetic pathways. *Curr Opin Biotechnol* 16(6):594-606.
43. Welch M, et al. (2009) Design parameters to control synthetic gene expression in *Escherichia coli. PLoS One* 4(9):e7002.
44. Salis H M, Mirsky E A, & Voigt C A (2009) Automated design of synthetic ribosome binding sites to control protein expression. *Nat Biotechnol* 27(10):946-950.
45. Zomer A L (2011) PPP: Perform Promoter Prediction.
46. Studholme D (2011) PromScan.

47. Kingsford C L, Ayanbule K, & Salzberg S L (2007) Rapid, accurate, computational discovery of Rho-independent transcription terminators illuminates their relationship to DNA uptake. *Genome Biol* 8(2):R22.
48. Stewart W D, Fitzgerald G P, & Burris R H (1967) In situ studies on nitrogen fixation with the acetylene reduction technique. *Science* 158(3800):536.
49. Philippe N, Alcaraz J P, Coursange E, Geiselmann J, & Schneider D (2004) Improvement of pCVD442, a suicide plasmid for gene allele exchange in bacteria. *Plasmid* 51(3):246-255.
50. Zhao D, Curatti L, & Rubio L M (2007) Evidence for nifU and nifS participation in the biosynthesis of the iron-molybdenum cofactor of nitrogenase. *J Biol Chem* 282(51):37016-37025.
51. Kelly J R, et al. (2009) Measuring the activity of BioBrick promoters using an in vivo reference standard. *J Biol Eng* 3:4.
52. Arnold W, Rump A, Klipp W, Priefer U B, & Puhler A (1988) Nucleotide sequence of a 24,206-base-pair DNA fragment carrying the entire nitrogen fixation gene cluster of *Klebsiella pneumoniae. J Mol Biol* 203(3):715-738.
53. Bayer T S, et al. (2009) Synthesis of Methyl Halides from Biomass Using Engineered Microbes. *J Am Chem Soc* 131(18):6508-6515.
54. Jacob G S, Schaefer J, Garbow J R, & Stejskal E O (1987) Solid-state NMR studies of *Klebsiella pneumoniae* grown under nitrogen-fixing conditions. *J Biol Chem* 262(1):254-259.
55. Mason C A & Hamer G (1987) Cryptic Growth in *Klebsiella-Pneumoniae. Appl Microbiol Biol* 25(6):577-584.
56. Villalobos A, Ness J E, Gustafsson C, Minshull J, & Govindarajan S (2006) Gene Designer: a synthetic biology tool for constructing artificial DNA segments. *BMC Bioinformatics* 7:285.
57. Shetty R P, Endy D, & Knight T F, Jr. (2008) Engineering BioBrick vectors from BioBrick parts. *J Biol Eng* 2:5.
58. Miyazaki K (2003) Creating random mutagenesis libraries by megaprimer PCR of whole plasmid (MEGAWHOP). *Methods Mol Biol* 231:23-28.
59. Gibson D G, et al. (2009) Enzymatic assembly of DNA molecules up to several hundred kilobases. *Nat Methods* 6(5):343-345.
60. Dykxhoorn D M, St Pierre R, & Linn T (1996) A set of compatible tac promoter expression vectors. *Gene* 177(1-2):133-136.
61. Salis H M, Mirsky E A, & Voigt C A (2009) Automated design of synthetic ribosome binding sites to control protein expression. *Nat Biotechnol* 27(10):946-950.
62. Tamsir A, Tabor J J, & Voigt C A (2011) Robust multicellular computing using genetically encoded NOR gates and chemical 'wires'. *Nature* 469(7329):212-215.
63. Buck M & Cannon W (1987) Frameshifts close to the *Klebsiella pneumoniae* nifH promoter prevent multicopy inhibition by hybrid nifH plasmids. *Mol Gen Genet* 207 (2-3):492-498.
64. Riedel G E, Brown S E, & Ausubel F M (1983) Nitrogen fixation by *Klebsiella pneumoniae* is inhibited by certain multicopy hybrid nif plasmids. *J Bacteriol* 153(1):45-56.
65. Beynon J, Cannon M, Buchanan-Wollaston V, & Cannon F (1983) The nif promoters of *Klebsiella pneumoniae* have a characteristic primary structure. *Cell* 34(2):665-671.
66. Maduro M (2011) Random DNA Generator, faculty.ucr.edu/~mmaduro/random.htm.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A bacterial nitrogen reduction expression system comprising nucleic acids encoding:

at least one operon comprising a plurality of coding sequences for a set of polypeptides encoded by genes collectively associated with nitrogen fixation within a cell, wherein at least one of the plurality of coding sequences comprises at least one non-native codon;

a heterologous promoter region that directs expression of the at least one operon; and a heterologous transcriptional controller coding sequence that encodes a protein that directs expression of the at least one operon of the expression system, wherein the protein binds directly or indirectly to the heterologous promoter region.

2. The bacterial nitrogen reduction expression system of claim 1, wherein the genes collectively associated with nitrogen fixation within a cell are selected from the group consisting of: nifJ, nifH, nifD, nifK, nifY, nifE, nifN, nifU, nifS, nifV, nifW, nifZ, nifM, nifB, and nifQ.

3. The bacterial nitrogen reduction expression system of claim 1, wherein the heterologous promoter of the one or more of the coding sequences causes the one or more coding sequences to be expressed at an expression level which is associated with maximal nitrogenase activity.

4. The bacterial nitrogen reduction expression system of claim 1, wherein the heterologous promoter region is a promoter which does not natively regulate a gene associated with nitrogen fixation.

5. A bacterial nitrogen reduction expression system comprising nucleic acids encoding:

at least one operon comprising a plurality of coding sequences for a set of polypeptides encoded by genes collectively associated with nitrogen fixation within a cell, wherein at least one of the plurality of coding sequences comprises at least one non-native codon;

a heterologous promoter region that directs expression of the at least one operon, wherein the heterologous promoter region is from the same species as the genes collectively associated with nitrogen fixation; and a transcriptional controller coding sequence that encodes a protein that directs expression of the at least one operon of the expression system, wherein the protein binds directly or indirectly to the heterologous promoter region, and wherein the transcriptional controller does not regulate the genes collectively associated with nitrogen fixation under native regulation.

6. The bacterial nitrogen reduction expression system of claim 5, wherein the genes collectively associated with nitrogen fixation within a cell are selected from the group consisting of: nifH, nifD, nifK, nifY, nifE, nifN, nifU, nifS, nifV, nifW, nifZ, nifM, nifB, and nifQ.

7. The bacterial nitrogen reduction expression system of claim 5, wherein the coding sequences have been modified to reduce a predicted RNA secondary structure.

8. The bacterial nitrogen reduction expression system of claim 5, wherein the heterologous promoter of the at least one operon causes a coding sequence of the operon to be expressed at an expression level which is associated with maximal nitrogenase activity.

9. The bacterial nitrogen reduction expression system of claim 5, wherein the heterologous promoter of the operon causes two or more coding sequences to be expressed at an expression level which causes maximal nitrogenase activity.

10. The bacterial nitrogen reduction expression system of claim 5, wherein the heterologous promoter causes each coding sequence of the operon to be expressed at an expression level which causes maximal nitrogenase activity.

11. The bacterial nitrogen reduction expression system of claim 5, wherein the heterologous promoter causes each coding sequence of the operon to be expressed at an expression level which is associated with maximal nitrogenase activity.

12. A bacterial nitrogen reduction expression system comprising nucleic acids encoding:

at least one operon comprising a plurality of coding sequences for a set of polypeptides encoded by genes collectively associated with nitrogen fixation within a cell, wherein at least one of the plurality of regulatory coding sequences has been synonymously mutated to remove internal regulation;

a genetically engineered promoter region that directs expression of the at least one operon; and a transcriptional controller coding sequence that encodes a protein that directs expression of the at least one operon of the expression system, wherein the protein binds directly or indirectly to the heterologous promoter region, and wherein the transcriptional controller does not regulate the genes collectively associated with nitrogen fixation under native regulation.

13. The bacterial nitrogen reduction expression system of claim 12, wherein the coding sequences have been modified to reduce a predicted RNA secondary structure.

14. The bacterial nitrogen reduction expression system of claim 12, wherein the genes collectively associated with nitrogen fixation within a cell are selected from the group consisting of: nifH, nifD, nifK, nifY, nifE, nifN, nifU, nifS, nifV, nifW, nifZ, nifM, nifB, and nifQ.

15. The bacterial nitrogen reduction expression system of claim 12, wherein the heterologous promoter of the at least one operon causes a coding sequence of the operon to be expressed at an expression level which is associated with maximal nitrogenase activity.

16. The bacterial nitrogen reduction expression system of claim 12, wherein the heterologous promoter of the operon causes two or more coding sequences to be expressed at an expression level which is associated with maximal nitrogenase activity.

* * * * *